(12) United States Patent
Cheng et al.

(10) Patent No.: US 9,845,322 B2
(45) Date of Patent: Dec. 19, 2017

(54) TETRAHYDROPYRIDOPYRIMIDINES AND TETRAHYDROPYRIDOPYRIDINES FOR THE TREATMENT AND PROPHYLAXIS OF HEPATITIS B VIRUS INFECTION

(71) Applicant: Hoffmann-La Roche Inc., Little Falls, NJ (US)

(72) Inventors: Zhanling Cheng, Shanghai (CN); Xingchun Han, Shanghai (CN); Min Jiang, Shanghai (CN); Jianhua Wang, Shanghai (CN); Min Wang, Shanghai (CN); Yongguang Wang, Shanghai (CN); Song Yang, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/144,996

(22) Filed: May 3, 2016

(65) Prior Publication Data

US 2016/0326167 A1    Nov. 10, 2016

(51) Int. Cl.
*C07D 471/04* (2006.01)

(52) U.S. Cl.
CPC ................... *C07D 471/04* (2013.01)

(58) Field of Classification Search
CPC .................................. C07D 471/04
See application file for complete search history.

(56) References Cited

U.S. PATENT DOCUMENTS 3,983,122 A   9/1976 Lundberg et al.

FOREIGN PATENT DOCUMENTS

| CN | 1 456 556 A | 11/2003 |
|---|---|---|
| CN | 102 516 339 A | 6/2012 |
| CN | 103450184 A | 12/2013 |
| EP | 0563732 A1 | 3/1993 |
| JP | S60197684 A | 7/1985 |
| WO | 02/064574 A2 | 8/2002 |
| WO | 2013/049352 A2 | 4/2013 |
| WO | 2015/113990 A1 | 8/2015 |
| WO | 2015/173164 A1 | 11/2015 |
| WO | 2016/071215 A1 | 5/2016 |
| WO | 2016/107832 A1 | 7/2016 |
| WO | 2016/128335 A1 | 8/2016 |

OTHER PUBLICATIONS

Acs et al., Proc Natl Acad Sci USA 84:4641-4644 ( 1987).
Ansel et al. Pharmaceutical Dosage Forms and Drug Delivery Systems, ( 2004).
Ansel et al., "Pharmaceutical Dosage Forms and Drug Delivery Systems" 6th Ed.:456-457 ( 1995).
Bastin et al., "Salt Selection and Optimisation Procedures for Pharmaceutical New Chemical Entities" Organic Process Research & Development 4:427-435 ( 2000).
Belloni et al., "IFN-α inhibits HBV transcription and replication in cell culture and in humanized mice by targeting the epigenetic regulation of the nuclear cccDNa minichromosome" J Clin Invest 122(2):529-537 (Feb. 2012).
Buster et al., "Peginterferon alpha-2b is safe and effective in HBeAg-Positive chronic hepatitis B patients with advanced fibrosis" Hepatology 46:388-394 ( 2007).
CAS Registry Database, XP002736278, Jun. 9, 2008.
Fecik et al., "Chiral DNA gyrase inhibitors. 3. Probing the chiral preference of the active site of DNA gyrase. Synthesis of 10-fluoro-6-methyl-6,7-dihydro-9-piperazinyl-2H-benzo[a]quinolizin-20-one-3-carboxylic acid analogues" J Med Chem 48:1229-1236 (2005).
Fisicaro et al., "Antiviral intrahepatic T-cell responses can be restored by blocking programmed death-1 pathway in chronic hepatits B" Gastroenterology 138:682-693 ( 2010).
Geng Ca et al., "Small-molecule inhibitors for the treatment of hepatitis B virus documented in patents" Mini Reviews in Medicinal Chemistry 13(5):749-776 (Apr. 1, 2013).
Gennaro et al. Remington: The Science and Practice of Pharmacy (Press), Philadelphia:Lippincott, Williams & Wilkins, ( 2000).
ISR and Written Opinion for PCT/EP2016/059718.
Janssen et al., "Pegylated interferon alfa-2b alone or in combination with lamivudine for HBeAg-positive chronic hepatitis B: a randomised trial" LANCET 365:123-129 (Jan. 8, 2005).
Kondo et al., "Hepatitis B surface antigen could contribute to the immunopathogenesis of hepatitis B virus infection" ISRN Gastroenterology (Article ID 935295), 2013.
Kondo et al., "Recovery of functional cytotoxic T lymphocytes during lamivudine therapy by acquiring muti-specificity" J Med Virol 74:425-433 ( 2004).
Kumar et al., "Hepatitis B virus regulatory HBx protein binds to adaptor protein IPS-1 and inhibits the activation of beta interferon" J Virol 85(2):987-995 (Jan. 2011).
Lambert et al., "Posttranslational N-glycosylation of the hepatitis B virus large envelope protein" Virol J 4( Suppl 1-9):45 (May 2007).
Locarnini, S., "Molecular virology and the development of resistant mutants: implications for therapy" Semin Liver Dis 25( Suppl 1):9-19 ( 2005).
Mao et al., "Indoleamine 2,3-dioxygenase mediates the antiviral effect of gagamma interferon against hepatitis B virus in human hepatocyte-derived cells" J Virol 85(2):1048-1057 (Jan. 2011).

(Continued)

Primary Examiner — Bruck Kifle

(57) ABSTRACT

The present invention provides novel compounds having the general formula:

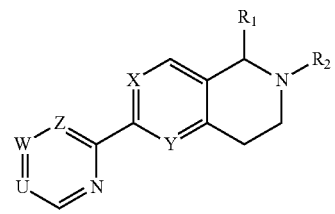

wherein $R^1$, $R^2$, U, W, X, Y and Z are as described herein, compositions including the compounds and methods of using the compounds.

46 Claims, No Drawings

(56) References Cited

OTHER PUBLICATIONS

Mao et al., "Inhibition of hepatitis B virus replication by the host zinc finger antiviral protein" PLoS Pathogens 9(7 Suppl 1-18):e1003494 (Jul. 2013).

Marcellin et al., "Peginterferon alfa-2a alone, lamivudine alone, and the two in combination in patients with HBeAg-negative chronic hepatitis B" New E J Med 351(12):1206-1217 (Sep. 16, 2004).

Nayersina et al., "HLA A2 restricted cytotoxic T lymphocyte responses to multiple hepatitis B surface antigen epitopes during hepatitis B virus infection" J Immunol 150:4659-4671 (May 15, 1993).

Op den Brouw et al., "Hepatitis B virus surface antigen impairs myeloid dendritic cell function: a possible immune escape mechanism of hepatitis B virus" Immunol 126:280-290 ( 2008).

Quasdorff et al., "Control of hepatitis B virus at the level of transcription" J Viral Hepatitis 17:527-536 ( 2010).

Rowe, R. Handbook of Pharmaceutical Excipients Chicago:Pharmaceutical Press, ( 2005).

Schulze et al., "Hepatitis B virus infection initiates with a large surface protein-dependent binding to heparan sulfate proteoglycans" Hepatology 46:1759-1768 ( 2007).

Shi et al., "Hepatitis B virus suppresses the functional interaction between natural killer cells and plasmacytoid dendritic cells" J Viral Hepatitis 19:e26-e33 ( 2012).

Wieland et al., "Stealth and cunning: hepatitis B and hepatitis C viruses" J Virol 79(15):9369-9380 (Aug. 2005).

Woltman et al., "Hepatitis B virus lacks immune activating capacity, but actively inhibits plasmacytoid dendritic cell function" PLoS ONE 6(1 Suppl 1-14):e15324 (Jan. 2011).

Yan et al., "Molecular determinants of hepatitis B and D virus entry restriction in mouse sodium taurocholate cotransporting polypeptide" J Virol 87(14):7977-7991 (Jul. 2013).

Ying-Rui Wu et al., "Two New Quaternary Alkaloids and Anti-Hepatitis B Virus Active Constituents from Corydalis saxicola" Planta Med 73:787-791 ( 2007).

TETRAHYDROPYRIDOPYRIMIDINES AND TETRAHYDROPYRIDOPYRIDINES FOR THE TREATMENT AND PROPHYLAXIS OF HEPATITIS B VIRUS INFECTION

The present invention relates to organic compounds useful for therapy and/or prophylaxis in a mammal, and in particular to HBsAg (HBV Surface antigen) inhibitors and HBV DNA production inhibitors useful for treating HBV infection.

FIELD OF THE INVENTION

The present invention relates to novel tetrahydropyridopyrimidines and tetrahydropyridopyridines having pharmaceutical activity, their manufacture, pharmaceutical compositions containing them and their potential use as medicaments.

The present invention relates to compounds of formula I

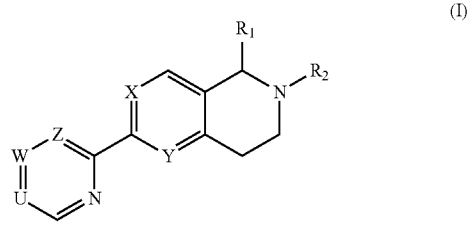

(I)

wherein $R^1$, $R^2$, U, W, X, Y and Z are as described below, or to pharmaceutically acceptable salts, or enantiomers, or diastereomers thereof.

The hepatitis B virus (HBV) is an enveloped, partially double-stranded DNA virus. The compact 3.2 kb HBV genome consists of four overlapping open reading frames (ORF), which encode for the core, polymerase (Pol), envelope and X-proteins. The Pol ORF is the longest and the envelope ORF is located within it, while the X and core ORFs overlap with the Pol ORF. The lifecycle of HBV has two main events: 1) generation of closed circular DNA (cccDNA) from relaxed circular (RC DNA), and 2) reverse transcription of pregenomic RNA (pgRNA) to produce RC DNA. Prior to the infection of host cells, the HBV genome exists within the virion as RC DNA. It has been determined that HBV virions are able to gain entry into host cells by non-specifically binding to the negatively charged proteoglycans present on the surface of human hepatocytes (Schulze, A., P. Gripon & S. Urban. *Hepatology*, 46, (2007), 1759-68) and via the specific binding of HBV surface antigens (HBsAg) to the hepatocyte sodium-taurocholate cotransporting polypeptide (NTCP) receptor (Yan, H. et al. *J Virol*, 87, (2013), 7977-91). Once the virion has entered the cell, the viral cores and the encapsidated RC DNA are transported by host factors, via a nuclear localization signal, into the nucleus through the Impβ/Impα nuclear transport receptors. Inside the nucleus, host DNA repair enzymes convert the RC DNA into cccDNA. cccDNA acts as the template for all viral mRNAs and as such, is responsible for HBV persistence in infected individuals. The transcripts produced from cccDNA are grouped into two categories; Pregenomic RNA (pgRNA) and subgenomic RNA. Subgenomic transcripts encode for the three envelopes (L, M and S) and X proteins, and pgRNA encodes for Pre-Core, Core, and Pol proteins (Quasdorff, M. & U. Protzer. *J Viral Hepat*, 17, (2010), 527-36). Inhibition of HBV gene expression or HBV RNA synthesis leads to the inhibition of HBV viral replication and antigens production (Mao, R. et al. *PLoS Pathog*, 9, (2013), e1003494; Mao, R. et al. *J Virol*, 85, (2011), 1048-57). For instance, IFN-α was shown to inhibit HBV replication and viral HBsAg production by decreasing the transcription of pgRNA and subgenomic RNA from the HBV covalently closed circular DNA (cccDNA) minichromosome. (Belloni, L. et al. *J Clin Invest*, 122, (2012), 529-37; Mao, R. et al. *J Virol*, 85, (2011), 1048-57). All HBV viral mRNAs are capped and polyadenylated, and then exported to the cytoplasm for translation. In the cytoplasm, the assembly of new virons is initiated and nascent pgRNA is packaged with viral Pol so that reverse transcription of pgRNA, via a single stranded DNA intermediate, into RC DNA can commence. The mature nucleocapsids containing RC DNA are enveloped with cellular lipids and viral L, M, and S proteins and then the infectious HBV particles are then released by budding at the intracellular membrane (Locarnini, S. *Semin Liver Dis*, (2005), 25 Suppl 1, 9-19). Interestingly, non-infectious particles are also produced that greatly outnumber the infectious virions. These empty, enveloped particles (L, M and S) are referred to as subviral particles. Importantly, since subviral particles share the same envelope proteins and as infectious particles, it has been surmised that they act as decoys to the host immune system and have been used for HBV vaccines. The S, M, and L envelope proteins are expressed from a single ORF that contains three different start codons. All three proteins share a 226aa sequence, the S-domain, at their C-termini. M and L have additional pre-S domains, Pre-S2 and Pre-S2 and Pre-S1, respectively. However, it is the S-domain that has the HBsAg epitope (Lambert, C. & R. Prange. *Virol J*, (2007), 4, 45).

The control of viral infection needs a tight surveillance of the host innate immune system which could respond within minutes to hours after infection to impact on the initial growth of the virus and limit the development of a chronic and persistent infection. Despite the available current treatments based on IFN and nucleos(t)ide analogues, the Hepatitis B virus (HBV) infection remains a major health problem worldwide which concerns an estimated 350 million chronic carriers who have a higher risk of liver cirrhosis and hepatocellular carcinoma.

The secretion of antiviral cytokines in response to HBV infection by the hepatocytes and/or the intra-hepatic immune cells plays a central role in the viral clearance of infected liver. However, chronically infected patients only display a weak immune response due to various escape strategies adopted by the virus to counteract the host cell recognition systems and the subsequent antiviral responses.

Many observations showed that several HBV viral proteins could counteract the initial host cellular response by interfering with the viral recognition signaling system and subsequently the interferon (IFN) antiviral activity. Among these, the excessive secretion of HBV empty subviral particles (SVPs, HBsAg) may participate to the maintenance of the immunological tolerant state observed in chronically infected patients (CHB). The persistent exposure to HBsAg and other viral antigens can lead to HBV-specific T-cell deletion or to progressive functional impairment (Kondo et al. *Journal of Immunology* (1993), 150, 4659-4671; Kondo et al. *Journal of Medical Virology* (2004), 74, 425-433; Fisicaro et al. *Gastroenterology*, (2010), 138, 682-93;). Moreover HBsAg has been reported to suppress the function of immune cells such as monocytes, dendritic cells (DCs) and natural killer (NK) cells by direct interaction (Op den Brouw et al. *Immunology*, (2009b), 126, 280-9; Woltman et al. *PLoS One*, (2011), 6, e15324; Shi et al. *J Viral Hepat.* (2012), 19, e26-33; Kondo et al. *ISRN Gastoroenterology*, (2013), Article ID 935295).

HBsAg quantification is a significant biomarker for prognosis and treatment response in chronic hepatitis B. However the achievement of HBsAg loss and seroconversion is rarely observed in chronically infected patients but remains the ultimate goal of therapy. Current therapy such as Nucleos(t)ide analogues are molecules that inhibit HBV DNA synthesis but are not directed at reducing HBsAg level. Nucleos(t)ide analogs, even with prolonged therapy, have demonstrated rates of HBsAg clearance comparable to those observed naturally (between −1%-2%) (Janssen et al. *Lancet*, (2005), 365, 123-9; Marcellin et al. *N. Engl. J Med.*, (2004), 351, 1206-17; Buster et al. *Hepatology*, (2007), 46, 388-94). Therefore, there is an unmet medical need to target HBsAg for HBV treatment (Wieland, S. F. & F. V. Chisari. *J Virol*, (2005), 79, 9369-80; Kumar et al. *J Virol*, (2011), 85, 987-95; Woltman et al. *PLoS One*, (2011), 6, e15324; Op den Brouw et al. *Immunology*, (2009b), 126, 280-9).

SUMMARY OF THE INVENTION

Objects of the present invention are novel compounds of formula I, their manufacture, medicaments based on a compound in accordance with the invention and their production as well as the use of compounds of formula I as HBV inhibitors and for the treatment or prophylaxis of HBV infection. The compounds of formula I show superior anti-HBV activity.

The present invention relates to a compound of formula I

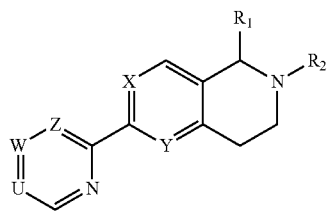

wherein $R^1$ is $C_{1-6}$alkyl, $C_{3-7}$cycloalkyl, halo$C_{1-6}$alkyl, hydroxy$C_{1-6}$alkyl, nitro$C_{1-6}$alkyl, $C_{1-6}$alkoxycarbonyl $C_{1-6}$alkyl, carboxy$C_{1-6}$alkyl, di($C_{1-6}$alkoxycarbonyl)methylenyl, cyano$C_{1-6}$alkyl, $C_{3-7}$cycloalkyl$C_{1-6}$alkyl, phenyl$C_{1-6}$alkyl, $C_{1-6}$alkylsulfanyl$C_{1-6}$alkyl, $C_{1-6}$alkylsufonyl$C_{1-6}$alkyl, amino$C_{1-6}$alkyl, $C_{1-6}$alkylcarbonylamino$C_{1-6}$alkyl, $C_{1-6}$alkylsufonylamino$C_{1-6}$alkyl, $C_{1-6}$alkoxycarbonyl amino$C_{1-6}$alkyl, aminocarbonyl $C_{1-6}$alkyl, di$C_{1-6}$alkylaminocarbonyl$C_{1-6}$alkyl, monocyclic heterocycloalkyl$C_{1-6}$alkyl or imidazolyl$C_{1-6}$alkyl;

$R^2$ is aryl or heteroaryl, said aryl or heteroaryl being unsubstituted, or substituted by one, two, three or four substituents independently selected from $C_{1-6}$alkyl, $C_{3-7}$cycloalkyl, halogen, halo$C_{1-6}$alkyl, cyano, nitro, hydroxy, halo$C_{1-6}$alkoxy, —O—$C_xH_{2x}$—$R^3$, —O—$C_yH_{2y}$—NHR$^6$, —NR$^9$R$^{10}$, —SO$_2$—R$^{11}$, —SO$_2$—NR$^{12}$R$^{13}$, carboxy, $C_{1-6}$alkoxycarbonyl, —C(=O)—NR$^{12}$R$^{13}$, aryl, heteroaryl, monocyclic heterocycloalkyl and —O—monocyclic heterocycloalkyl; wherein monocyclic heterocycloalkyl is unsubstituted or substituted by $C_{1-6}$alkyl, $C_{3-7}$cycloalkyl, $C_{1-6}$alkylcarbonyl, $C_{1-6}$alkylsufonyl or $C_{1-6}$alkoxycarbonyl;

$R^3$ is hydrogen; $C_{3-7}$cycloalkyl; halo$C_{3-7}$cycloalkyl; hydroxy; hydroxy$C_{1-6}$alkyl$C_{3-7}$cycloalkyl; $C_{1-6}$alkoxy; monocyclic heterocycloalkyl; monocyclic heterocycloalkyl substituted by $C_{1-6}$alkyl, $C_{1-6}$alkylcarbonyl, $C_{1-6}$alkylsufonyl, $C_{3-7}$cycloalkyl or $C_{1-6}$alkoxycarbonyl; —C(=O)—R$^4$; $C_{1-6}$alkylsulfinyl; —SO$_2$—R$^5$; —C(NHR$^7$)—C(=O)—R$^8$; carboxy$C_{1-6}$alkoxy or aminocarbonyl$C_{1-6}$alkoxy; wherein $R^4$ is hydroxy, $C_{1-6}$alkoxy, amino, $C_{1-6}$alkylamino, di$C_{1-6}$alkylamino, tetrahydrofuranylamino, pyrrolidinyl or morpholinyl;

$R^5$ is $C_{1-6}$alkyl, $C_{3-7}$cycloalkyl, hydroxy, amino, $C_{1-6}$alkylamino or di$C_{1-6}$alkylamino;

$R^7$ is hydrogen or $C_{1-6}$alkoxycarbonyl;

$R^8$ is hydroxy or $C_{1-6}$alkoxy;

$R^6$ is hydrogen, $C_{1-6}$alkylcarbonyl, halo$C_{1-6}$alkylcarbonyl, $C_{1-6}$alkoxycarbonyl, $C_{1-6}$alkylsulfonyl, $C_{3-7}$cycloalkylsulfonyl or $C_{1-6}$alkoxy$C_{1-6}$alkylsulfonyl;

$R^9$ and $R^{10}$ are independently selected from hydrogen, $C_{1-6}$alkyl, $C_{3-7}$cycloalkyl, $C_{1-6}$alkylcarbonyl, $C_{1-6}$alkylsulfonyl, $C_{3-7}$cycloalkylcarbonyl and $C_{3-7}$cycloalkylsulfonyl; or $R^9$ and $R^{10}$ together with the nitrogen to which they are attached form monocyclic heterocycloalkyl;

$R^{11}$ is $C_{1-6}$alkyl, halo$C_{1-6}$alkyl, $C_{3-7}$cycloalkyl, halo$C_{3-7}$cycloalkyl, hydroxy$C_{1-6}$alkyl, $C_{1-6}$alkoxy$C_{1-6}$alkyl, halo$C_{1-6}$alkoxy$C_{1-6}$alkyl, $C_{3-7}$cycloalkyl$C_{1-6}$alkyl, amino$C_{1-6}$alkyl, $C_{1-6}$alkylamino$C_{1-6}$alkyl, di$C_{1-6}$alkylamino$C_{1-6}$alkyl, $C_{1-6}$alkylcarbonylamino$C_{1-6}$alkyl, $C_{1-6}$alkylsulfonylamino$C_{1-6}$alkyl, $C_{1-6}$alkoxycarbonylamino$C_{1-6}$alkyl, $C_{1-6}$alkylsulfenyl$C_{1-6}$alkyl, $C_{1-6}$alkylsulfanyl$C_{1-6}$alkyl or $C_{1-6}$alkylsulfonyl$C_{1-6}$alkyl;

$R^{12}$ and $R^{13}$ are independently selected from hydrogen, $C_{1-6}$alkyl, $C_{1-6}$alkoxy$C_{1-6}$alkyl, halo$C_{1-6}$alkyl, $C_{3-7}$cycloalkyl and halo$C_{3-7}$cycloalkyl; or $R^{12}$ and $R^{13}$ together with the nitrogen to which they are attached form monocyclic heterocycloalkyl;

x is 1, 2, 3, 4, 5, 6, 7 or 8;
y is 1, 2, 3, 4, 5, 6, 7 or 8;
U, W and Z are independently selected from CH and N;
one of X and Y is N, and the other one is CH or N;
or pharmaceutically acceptable salts, or enantiomers, or diastereomers thereof.

DETAILED DESCRIPTION OF THE INVENTION

Definitions

As used herein, the term "$C_{1-6}$alkyl" alone or in combination signifies a saturated, linear- or branched chain alkyl group containing 1 to 6, particularly 1 to 4 carbon atoms, for example methyl, ethyl, propyl, isopropyl, 1-butyl, 2-butyl, tert-butyl and the like. Particular "$C_{1-6}$alkyl" groups are methyl, ethyl, isopropyl and tert-butyl.

The term "$C_{3-7}$cycloalkyl", alone or in combination, refers to a saturated carbon ring containing from 3 to 7 carbon atoms, particularly from 3 to 6 carbon atoms, for example, cyclopropyl, cyclobutyl, cyclopentyl, cyclohexyl, cycloheptyl and the like. Particular "$C_{3-7}$cycloalkyl" groups are cyclopropyl, cyclobutyl, cyclopentyl and cyclohexyl.

The term "$C_{1-6}$alkoxy" alone or in combination signifies a group $C_{1-6}$alkyl-O—, wherein the "$C_{1-6}$alkyl" is as defined above; for example methoxy, ethoxy, propoxy, iso-propoxy, n-butoxy, iso-butoxy, 2-butoxy, tert-butoxy, pentoxy, hexyloxy and the like. Particular "C$_{1-6}$alkoxy" groups are methoxy, ethoxy and propoxy.

The term "halogen" means fluorine, chlorine, bromine or iodine.

The term "haloC$_{1-6}$alkyl" denotes a C$_{1-6}$alkyl group wherein at least one of the hydrogen atoms of the C$_{1-6}$alkyl group has been replaced by same or different halogen atoms, particularly fluoro atoms. Examples of haloC$_{1-6}$alkyl include monofluoro-, difluoro- or trifluoro-methyl, -ethyl or -propyl, for example 3,3,3-trifluoropropyl, 3,3-difluoropropyl, 2-fluoroethyl, 2,2-difluoroethyl, 2,2,2-trifluoroethyl, fluoromethyl, difluoromethyl or trifluoromethyl. Particular "haloC$_{1-6}$alkyl" group is difluoromethyl or trifluoromethyl.

The term "haloC$_{1-6}$alkoxy" denotes a C$_{1-6}$alkoxy group wherein at least one of the hydrogen atoms of the C$_{1-6}$alkoxy group has been replaced by same or different halogen atoms, particularly fluoro atoms. Examples of haloC$_{1-6}$alkoxyl include monofluoro-, difluoro- or trifluoromethoxy, -ethoxy or -propoxy, for example fluoropropoxy, difluoropropoxy, trifluoropropoxy, fluoroethoxy, difluoroethoxy, trifluoroethoxy, fluoromethoxy, difluoromethoxy or trifluoromethoxy. Particular "haloC$_{1-6}$alkoxy" group is 3-fluoropropoxy, 3,3-difluoropropoxy, 3,3,3-trifluoropropoxy, 2-fluoroethoxy, 2,2-difluoroethoxy, 2,2,2-trifluoroethoxy, fluoromethoxy, difluoromethoxy or trifluoromethoxy.

The term "haloC$_{3-7}$cycloalkyl" denotes a C$_{3-7}$cycloalkyl group wherein at least one of the hydrogen atoms of the C$_{3-7}$cycloalkyl group has been replaced by same or different halogen atoms, particularly fluoro atoms. Examples of haloC$_{3-7}$cycloalkyl include monofluoro- or difluoro-cyclopropyl, -cyclobutyl, -cyclopentyl or -cyclohexyl, for example fluorocyclopropyl, difluorocyclopropyl, fluocyclobutyl, difluocyclobutyl, fluocyclopentyl, difluocyclopentyl, fluocyclohexyl or difluocyclohexyl. Particular "haloC$_{1-6}$alkyl" group is difluorocyclopropyl.

The term "amino" denotes a group of the formula —NR'R" wherein R' and R" are independently hydrogen, C$_{1-6}$alkyl, C$_{1-6}$alkoxy, C$_{3-7}$cycloalkyl, heteroC$_{3-7}$cycloalkyl, aryl or heteroaryl.

Alternatively, R' and R", together with the nitrogen to which they are attached, can form a heteroC$_{3-7}$cycloalkyl.

The term "carbonyl" alone or in combination refers to the group —C(O)—.

The term "cyano" alone or in combination refers to the group —CN.

The term "C$_{1-6}$alkylsulfinyl" denotes a group —SO—C$_{1-6}$alkyl, wherein C$_{1-6}$alkyl group is defined above. Examples of C$_{1-6}$alkylsulfinyl include methylsulfinyl and ethylsulfinyl.

The term "C$_{1-6}$alkylsulfonyl" denotes a group —SO$_2$—C$_{1-6}$alkyl, wherein C$_{1-6}$alkyl group is defined above. Examples of C$_{1-6}$alkylsulfonyl include methylsulfonyl and ethylsulfonyl.

The term "monocyclic heterocycloalkyl" is a monovalent saturated or partly unsaturated monocyclic ring system of 4 to 7 ring atoms, comprising 1, 2, or 3 ring heteroatoms selected from N, O and S, the remaining ring atoms being carbon. Examples for monocyclic heterocycloalkyl are aziridinyl, oxiranyl, azetidinyl, oxetanyl, pyrrolidinyl, 2-oxo-pyrrolidinyl, tetrahydrofuranyl, thietanyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, 2-oxo-morpholinyl, 2-oxo-piperazinyl, thiomorpholinyl, 1,1-dioxo-thiomorpholin-4-yl, 1,1-dioxothiolanyl, 1,1-dioxothietanyl, oxoimidazolidinyl, azepanyl, diazepanyl, homopiperazinyl, or oxazepanyl. Particular "monocyclic heterocycloalkyl" groups are azetidinyl, oxetanyl, thietanyl, tetrahydrofuranyl, tetrahydropyranyl, 1,1-dioxothietanyl, 1,1-dioxothiolanyl, morpholinyl, pyrrolidinyl, piperidinyl, piperazinyl, oxoimidazolidinyl, 2-oxo-pyrrolidinyl, 2-oxo-morpholinyl and 2-oxo-piperazinyl. More particularly, "monocyclic heterocycloalkyl" groups are azetidinyl, pyrrolidinyl, morpholinyl, oxomorpholinyl, piperidinyl, piperazinyl and oxopiperazinyl.

The term "aryl" denotes a monovalent aromatic carbocyclic mono- or bicyclic ring system comprising 6 to 10 carbon ring atoms. Examples of aryl moieties include phenyl and naphthyl, Particular "aryl" is phenyl.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl. Particular "heteroaryl" are pyridinyl and pyrimidinyl.

The term "enantiomer" denotes two stereoisomers of a compound which are non-superimposable mirror images of one another.

The term "diastereomer" denotes a stereoisomer with two or more centers of chirality and whose molecules are not mirror images of one another. Diastereomers have different physical properties, e.g. melting points, boiling points, spectral properties, and reactivities.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J., et al., Organic Process Research & Development 2000, 4, 427-435. Particular are the sodium salts of the compounds of formula I. Compounds of the general formula I which contain one or several chiral centers can either be present as racemates, diastereomeric mixtures, or optically active single isomers. The racemates can be separated according to known methods into the enantiomers. Particularly, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

Inhibitor of HBsAg

The present invention provides (i) a compound having the general formula I:

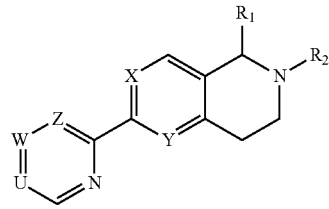

(I)

wherein
$R^1$ is $C_{1-6}$alkyl, $C_{3-7}$cycloalkyl, halo$C_{1-6}$alkyl, hydroxy$C_{1-6}$alkyl, nitro$C_{1-6}$alkyl, $C_{1-6}$alkoxycarbonyl$C_{1-6}$alkyl, carboxy$C_{1-6}$alkyl, di($C_{1-6}$alkoxycarbonyl)methylenyl, cyano$C_{1-6}$alkyl, $C_{3-7}$cycloalkyl$C_{1-6}$alkyl, phenyl$C_{1-6}$alkyl, $C_{1-6}$alkylsulfanyl$C_{1-6}$alkyl, $C_{1-6}$alkylsufonyl$C_{1-6}$alkyl, amino$C_{1-6}$alkyl, $C_{1-6}$alkylcarbonylamino$C_{1-6}$alkyl, $C_{1-6}$alkylsufonylamino$C_{1-6}$alkyl, $C_{1-6}$alkoxycarbonyl amino$C_{1-6}$alkyl, aminocarbonyl $C_{1-6}$alkyl, di$C_{1-6}$alkylaminocarbonyl$C_{1-6}$alkyl, monocyclic heterocycloalkyl$C_{1-6}$alkyl or imidazolyl$C_{1-6}$alkyl;

$R^2$ is aryl or heteroaryl, said aryl or heteroaryl being unsubstituted, or substituted by one, two, three or four substituents independently selected from $C_{1-6}$alkyl, $C_{3-7}$cycloalkyl, halogen, halo$C_{1-6}$alkyl, cyano, nitro, hydroxy, halo$C_{1-6}$alkoxy, —O—$C_xH_{2x}$—$R^3$, —O—$C_yH_{2y}$—NH$R^6$, —N$R^9R^{10}$, —$SO_2$—$R^{11}$, —$SO_2$—N$R^{12}R^{13}$, carboxy, $C_{1-6}$alkoxycarbonyl, —C(=O)—N$R^{12}R^{13}$, aryl, heteroaryl, monocyclic heterocycloalkyl and —O-monocyclic heterocycloalkyl; wherein monocyclic heterocycloalkyl is unsubstituted or substituted by $C_{1-6}$alkyl, $C_{3-7}$cycloalkyl, $C_{1-6}$alkylcarbonyl, $C_{1-6}$alkylsufonyl or $C_{1-6}$alkoxycarbonyl;

$R^3$ is hydrogen; $C_{3-7}$cycloalkyl; halo$C_{3-7}$cycloalkyl; hydroxy; hydroxy$C_{1-6}$alkyl$C_{3-7}$cycloalkyl; $C_{1-6}$alkoxy; monocyclic heterocycloalkyl; monocyclic heterocycloalkyl substituted by $C_{1-6}$alkyl, $C_{1-6}$alkylcarbonyl, $C_{1-6}$alkylsufonyl, $C_{3-7}$cycloalkyl or $C_{1-6}$alkoxycarbonyl; —C(═O)—$R^4$; $C_{1-6}$alkylsulfinyl; —$SO_2$—$R^5$; —C($NHR^7$)—C(═O)—$R^8$; carboxy$C_{1-6}$alkoxy or aminocarbonyl$C_{1-6}$alkoxy; wherein $R^4$ is hydroxy, $C_{1-6}$alkoxy, amino, $C_{1-6}$alkylamino, di$C_{1-6}$alkylamino, tetrahydrofuranylamino, pyrrolidinyl or morpholinyl;

$R^5$ is $C_{1-6}$alkyl, $C_{3-7}$cycloalkyl, hydroxy, amino, $C_{1-6}$alkylamino or di$C_{1-6}$alkylamino;

$R^7$ is hydrogen or $C_{1-6}$alkoxycarbonyl;

$R^8$ is hydroxy or $C_{1-6}$alkoxy;

$R^6$ is hydrogen, $C_{1-6}$alkylcarbonyl, halo$C_{1-6}$alkylcarbonyl, $C_{1-6}$alkoxycarbonyl, $C_{1-6}$alkylsulfonyl, $C_{3-7}$cycloalkylsulfonyl or $C_{1-6}$alkoxy$C_{1-6}$alkylsulfonyl;

$R^9$ and $R^{10}$ are independently selected from hydrogen, $C_{1-6}$alkyl, $C_{3-7}$cycloalkyl, $C_{1-6}$alkylcarbonyl, $C_{1-6}$alkylsulfonyl, $C_{3-7}$cycloalkylcarbonyl and $C_{3-7}$cycloalkylsulfonyl; or $R^9$ and $R^{10}$ together with the nitrogen to which they are attached form monocyclic heterocycloalkyl;

$R^{11}$ is $C_{1-6}$alkyl, halo$C_{1-6}$alkyl, $C_{3-7}$cycloalkyl, halo$C_{3-7}$cycloalkyl, hydroxy$C_{1-6}$alkyl, $C_{1-6}$alkoxy $C_{1-6}$alkyl, halo$C_{1-6}$alkoxy$C_{1-6}$alkyl, $C_{3-7}$cycloalkyl $C_{1-6}$alkyl, amino$C_{1-6}$alkyl, $C_{1-6}$alkylamino$C_{1-6}$alkyl, di$C_{1-6}$alkylamino$C_{1-6}$alkyl, $C_{1-6}$alkylcarbonylamino$C_{1-6}$alkyl, $C_{1-6}$alkylsulfonylamino$C_{1-6}$alkyl, $C_{1-6}$alkoxycarbonylamino$C_{1-6}$alkyl, $C_{1-6}$alkylsulfenyl$C_{1-6}$alkyl, $C_{1-6}$alkylsulfanyl$C_{1-6}$alkyl or $C_{1-6}$alkylsulfonyl$C_{1-6}$alkyl;

$R^{12}$ and $R^{13}$ are independently selected from hydrogen, $C_{1-6}$alkyl, $C_{1-6}$alkoxy$C_{1-6}$alkyl, halo$C_{1-6}$alkyl, $C_{3-7}$cycloalkyl and halo$C_{3-7}$cycloalkyl; or $R^{12}$ and $R^{13}$ together with the nitrogen to which they are attached form monocyclic heterocycloalkyl;

x is 1, 2, 3, 4, 5, 6, 7 or 8;

y is 1, 2, 3, 4, 5, 6, 7 or 8;

U, W and Z are independently selected from CH and N;

one of X and Y is N, and the other one is CH or N;

or pharmaceutically acceptable salts, or enantiomers, or diastereomers thereof.

A further embodiment of the present invention is (ii) a compound of formula I, wherein $R^1$ is $C_{1-6}$alkyl, $C_{3-7}$cycloalkyl, hydroxy$C_{1-6}$alkyl, $C_{1-6}$alkoxycarbonyl$C_{1-6}$alkyl or carboxy$C_{1-6}$alkyl;

$R^2$ is phenyl substituted by one, two, three or four groups independently selected from $C_{1-6}$alkyl, $C_{3-7}$cycloalkyl, halogen, halo$C_{1-6}$alkyl, cyano, nitro, hydroxy, halo$C_{1-6}$alkoxy, tetrahydrofuranyloxy, —O—$C_xH_{2x}$—$R^3$, —O—$C_yH_{2y}$—$NHR^6$, —$SO_2$—$R^{11}$, —$SO_2$—$NR^{12}R^{13}$, carboxy, $C_{1-6}$alkoxycarbonyl and —C(═O)—$NR^{12}R^{13}$; pyridinyl substituted by one, two or three groups independently selected from halogen, $C_{1-6}$alkyl, halo$C_{1-6}$alkoxy, tetrahydropyranyloxy, —O—$C_xH_{2x}$—$R^3$ and $NR^9R^{10}$; or pyrimidinyl substituted by $C_{1-6}$alkyl and di$C_{1-6}$alkylamino; wherein $R^3$ is hydrogen, $C_{3-7}$cycloalkyl, halo$C_{3-7}$cycloalkyl, hydroxy, hydroxy$C_{1-6}$alkyl$C_{3-7}$cycloalkyl, $C_{1-6}$alkoxy, oxetanyl, tetrahydrofuranyl, tetrahydropyranyl, thietanyl, 1,1-dioxothietanyl, 1,1-dioxothiolanyl, morpholinyl, oxopyrrolidinyl, oxomorpholinyl, oxopiperazinyl, $C_{1-6}$alkoxycarbonyloxopiperazinyl, oxoimidazolidinyl, $C_{1-6}$alkylpiperazinyl, $C_{1-6}$alkylcarbonylpiperazinyl, $C_{1-6}$alkylsulfonylpiperazinyl, $C_{1-6}$alkoxycarbonylpiperazinyl, azetidinyl, $C_{1-6}$alkylcarbonylazetidinyl, $C_{1-6}$alkylsulfonylazetidinyl, $C_{1-6}$alkoxycarbonylazetidinyl, —C(═O)—$R^4$, $C_{1-6}$alkylsulfinyl, —$SO_2$—$R^5$, —C($NHR^7$)—C(═O)—$R^8$, carboxy$C_{1-6}$alkoxy or aminocarbonyl$C_{1-6}$alkoxy; wherein $R^4$ is hydroxy, $C_{1-6}$alkoxy, amino, $C_{1-6}$alkylamino, di$C_{1-6}$alkylamino, tetrahydrofuranylamino, pyrrolidinyl or morpholinyl;

$R^5$ is $C_{1-6}$alkyl, hydroxy or amino;

$R^7$ is hydrogen or $C_{1-6}$alkoxycarbonyl;

$R^8$ is hydroxy or $C_{1-6}$alkoxy;

$R^6$ is hydrogen, $C_{1-6}$alkylcarbonyl, halo$C_{1-6}$alkylcarbonyl, $C_{1-6}$alkoxycarbonyl, $C_{1-6}$alkylsulfonyl, $C_{3-7}$cycloalkylsulfonyl or $C_{1-6}$alkoxy$C_{1-6}$alkylsulfonyl;

$R^9$ and $R^{10}$ are independently selected from hydrogen, $C_{1-6}$alkyl and $C_{1-6}$alkylsulfonyl; or $R^9$ and $R^{10}$ together with the nitrogen to which they are attached form pyrrolidinyl, morpholinyl, piperidinyl, piperazinyl and oxopiperazinyl;

$R^{11}$ is $C_{1-6}$alkyl or $C_{1-6}$alkoxy$C_{1-6}$alkyl;

$R^{12}$ and $R^{13}$ are independently selected from hydrogen, $C_{1-6}$alkyl and $C_{1-6}$alkoxy$C_{1-6}$alkyl;

x is 1, 2, 3, 4, 5, 6, 7 or 8;

y is 1, 2, 3, 4, 5, 6, 7 or 8;

U is CH;

W is CH;

Z is CH or N;

X is N;

Y is N;

or pharmaceutically acceptable salts, or enantiomers, or diastereomers thereof.

Another embodiment of the present invention is (iii) a compound of formula I, wherein, $R^1$ is $C_{1-6}$alkyl;

$R^2$ is phenyl substituted by one, two, three or four groups independently selected from $C_{1-6}$alkyl, $C_{3-7}$cycloalkyl, halogen, halo$C_{1-6}$alkyl, cyano, hydroxy, halo$C_{1-6}$alkoxy, tetrahydrofuranyloxy, —O—$C_xH_{2x}$—$R^3$, —O—$C_yH_{2y}$—$NHR^6$, —$SO_2$—$R^{11}$, —$SO_2$—$NR^{12}R^{13}$, carboxy, $C_{1-6}$alkoxycarbonyl and —C(=O)—$NR^{12}R^{13}$; pyridinyl substituted by one, two or three groups independently selected from halogen, $C_{1-6}$alkyl, halo$C_{1-6}$alkoxy, tetrahydropyranyloxy, —O—$C_xH_{2x}$—$R^3$ and $NR^9R^{10}$; or pyrimidinyl substituted by $C_{1-6}$alkyl and di$C_{1-6}$alkylamino; wherein $R^3$ is hydrogen, $C_{3-7}$cycloalkyl, halo$C_{3-7}$cycloalkyl, hydroxy$C_{1-6}$alkyl$C_{3-7}$cycloalkyl, oxetanyl, tetrahydrofuranyl, tetrahydropyranyl, thietanyl, 1,1-dioxothietanyl, 1,1-dioxothiolanyl, oxopyrrolidinyl, oxomorpholinyl, oxopiperazinyl, $C_{1-6}$alkoxycarbonyloxopiperazinyl, oxoimidazolidinyl, $C_{1-6}$alkylpiperazinyl, $C_{1-6}$alkylcarbonylpiperazinyl, $C_{1-6}$alkylsulfonylpiperazinyl, $C_{1-6}$alkoxycarbonylpiperazinyl, azetidinyl, $C_{1-6}$alkylcarbonylazetidinyl, $C_{1-6}$alkylsulfonylazetidinyl, $C_{1-6}$alkoxycarbonylazetidinyl, —C(=O)—$R^4$, $C_{1-6}$alkylsulfinyl, —$SO_2$—$R^5$, —C(NHR$^7$)—C(=O)—$R^8$, carboxy$C_{1-6}$alkoxy or aminocarbonyl$C_{1-6}$alkoxy; wherein $R^4$ is hydroxy, $C_{1-6}$alkoxy, amino, $C_{1-6}$alkylamino, tetrahydrofuranylamino, or morpholinyl;

$R^5$ is $C_{1-6}$alkyl, hydroxy or amino;

$R^7$ is hydrogen or $C_{1-6}$alkoxycarbonyl;

$R^8$ is hydroxy or $C_{1-6}$alkoxy;

$R^6$ is hydrogen, $C_{1-6}$alkylcarbonyl, halo$C_{1-6}$alkylcarbonyl, $C_{1-6}$alkoxycarbonyl, $C_{3-7}$cycloalkylsulfonyl or $C_{1-6}$alkoxy$C_{1-6}$alkylsulfonyl;

$R^9$ and $R^{10}$ are independently selected from hydrogen, $C_{1-6}$alkyl and $C_{1-6}$alkylsulfonyl; or $R^9$ and $R^{10}$ together with the nitrogen to which they are attached form pyrrolidinyl, morpholinyl, piperazinyl and oxopiperazinyl;

$R^{11}$ is $C_{1-6}$alkoxy$C_{1-6}$alkyl;

$R^{12}$ and $R^{13}$ are independently selected from hydrogen, $C_{1-6}$alkyl and $C_{1-6}$alkoxy$C_{1-6}$alkyl;

x is 1, 2, 3, 4, 5, 6, 7 or 8;

y is 1, 2, 3, 4, 5, 6, 7 or 8;

U is CH;

W is CH;

Z is N;

X is N;

Y is N;

or pharmaceutically acceptable salts, or enantiomers, or diastereomers thereof.

A further embodiment of the present invention is (iv) a compound of formula I, or pharmaceutically acceptable salts, or enantiomers, or diastereomers thereof, wherein $R^1$ is methyl, and all remaining substituents have the significances given herein before.

Another embodiment of the present invention is (v) a compound of formula I, wherein, $R^1$ is $C_{1-6}$alkyl;

$R^2$ is phenyl substituted by one, two, three or four groups independently selected from $C_{1-6}$alkyl, $C_{3-7}$cycloalkyl, halogen, halo$C_{1-6}$alkyl, cyano, hydroxy, halo$C_{1-6}$alkoxy, tetrahydrofuranyloxy, —O—$C_xH_{2x}$—$R^3$, —O—$C_yH_{2y}$—$NHR^6$, —$SO_2$—$R^{11}$, —$SO_2$—$NR^{12}R^{13}$, carboxy, $C_{1-6}$alkoxycarbonyl and —C(=O)—$NR^{12}R^{13}$;

$R^3$ is hydrogen, $C_{3-7}$cycloalkyl, halo$C_{3-7}$cycloalkyl, hydroxy$C_{1-6}$alkyl$C_{3-7}$cycloalkyl, oxetanyl, tetrahydrofuranyl, tetrahydropyranyl, thietanyl, 1,1-dioxothietanyl, 1,1-dioxothiolanyl, oxopyrrolidinyl, oxomorpholinyl, oxopiperazinyl, $C_{1-6}$alkoxycarbonyloxopiperazinyl, oxoimidazolidinyl, $C_{1-6}$alkylpiperazinyl, $C_{1-6}$alkylcarbonylpiperazinyl, $C_{1-6}$alkylsulfonylpiperazinyl, $C_{1-6}$alkoxycarbonylpiperazinyl, azetidinyl, $C_{1-6}$alkylcarbonylazetidinyl, $C_{1-6}$alkylsulfonylazetidinyl, $C_{1-6}$alkoxycarbonylazetidinyl, —C(=O)—$R^4$, $C_{1-6}$alkylsulfinyl, —$SO_2$—$R^5$ or —C(NHR$^7$)—C(=O)—$R^8$; wherein $R^4$ is hydroxy, $C_{1-6}$alkoxy, amino, $C_{1-6}$alkylamino, tetrahydrofuranylamino, or morpholinyl;

$R^5$ is $C_{1-6}$alkyl, hydroxy or amino;

$R^7$ is hydrogen or $C_{1-6}$alkoxycarbonyl;

$R^8$ is hydroxy or $C_{1-6}$alkoxy;

$R^6$ is hydrogen, $C_{1-6}$alkylcarbonyl, halo$C_{1-6}$alkylcarbonyl, $C_{1-6}$alkoxycarbonyl, $C_{3-7}$cycloalkylsulfonyl or $C_{1-6}$alkoxy$C_{1-6}$alkylsulfonyl;

$R^{11}$ is $C_{1-6}$alkoxy$C_{1-6}$alkyl;

$R^{12}$ and $R^{13}$ are independently selected from hydrogen, $C_{1-6}$alkyl and $C_{1-6}$alkoxy$C_{1-6}$alkyl;

x is 1, 2, 3, 4, 5 or 6;

y is 1, 2, 3, 4, 5, 6, 7 or 8;

U is CH;

W is CH;

Z is N;

X is N;

Y is N;

or pharmaceutically acceptable salts, or enantiomers, or diastereomers thereof.

A further embodiment of the present invention is (vi) a compound of formula I, wherein $R^1$ is methyl;

$R^2$ is phenyl substituted by one, two, three or four groups independently selected from methyl, cyclopropyl, fluoro, chloro, iodo, trifluoromethyl, cyano, hydroxy, methoxy, difluoroethoxy, difluoromethoxy, trifluoroethoxy, trifluoromethoxy, cyclopropylmethoxy, difluorocyclopropylmethoxy, hydroxymethylcyclopropylmethoxy, oxetanylethoxy, oxetanylmethoxy, tetrahydrofuranylethoxy, tetrahydrofuranylmethoxy, tetrahydropyranylmethoxy, thietanylmethoxy, (1,1-dioxothietanyl)methoxy, (1,1-dioxothiolanyl)methoxy, oxopyrrolidinylpropoxy, oxomorpholinylpropoxy, oxopiperazinylpropoxy, (tert-butoxycarbonyloxopiperazinyl)propoxy, oxoimidazolidinylpropoxy, methylpiperazinylpropoxy, acetylpiperazinylpropoxy, methyl sulfonylpiperazinylpropoxy, (tert-butoxycarbonylpiperazinyl)propoxy, azetidinylethoxy, acetylazetidinylethoxy, methyl sulfonylazetidinylethoxy, (tert-butoxycarbonylazetidinyl)ethoxy, (tert-butoxycarbonylazetidinyl)methoxy, carboxybutoxy, carboxyethoxy, carboxyhexyloxy, carboxymethoxy, carboxypropoxy, methoxycarbonylbutoxy, ethoxycarbonylhexyloxy, aminocarbonylbutoxy, aminocarbonylhexyloxy, aminocarbonylmethoxy, aminocarbonylpropoxy, methylaminocarbonylpropoxy, tetrahydrofuranylaminocarbonylmethoxy, morpholinylcarbonylmethoxy, methyl sulfinylpropoxy, methyl sulfonylpropoxy, sulfopropoxy, aminosulfonylpropoxy, amino-carboxy-propoxy, (tert-butoxycarbonylamino)-carboxy-propoxy, (tert-butoxycarbonylamino)-(methoxycarbonyl)-propoxy, aminopropoxy, aminopentoxy, aminohexyloxy, aminooctyloxy, methylcarbonylaminopropoxy, chloropropylcarbonylaminopropoxy, (tert-butoxycarbonylamino)hexyloxy, (tert-butoxycarbonylamino)octyloxy, (tert-butoxycarbonylamino)pentoxy, (tert-butoxycarbonylamino)propoxy, cyclopropylsulfonylaminopropoxy, methoxyethylsulfonylaminopropoxy, methoxypropylsulfonyl, methoxypropylaminosulfonyl, N-methoxypropyl-N-methyl-aminosulfonyl, carboxy, methoxycarbonyl, methoxypropylaminocarbonyl, N-methoxypropyl-N-methyl-aminocarbonyl and tetrahydrofuranyloxy;

U is CH;
W is CH;
Z is N;
X is N;
Y is N;
or pharmaceutically acceptable salts, or enantiomers, or diastereomers thereof, A further embodiment of the present invention is (vii) a compound of formula I, or pharmaceutically acceptable salts, or enantiomers, or diastereomers thereof, wherein $R^2$ is phenyl substituted by one, two or three groups independently selected from halogen, $C_{1-6}$alkoxy, halo$C_{1-6}$alkoxy, $C_{3-7}$cycloalkyl$C_{1-6}$alkoxy and halo$C_{3-7}$cycloalkyl$C_{1-6}$alkoxy; and all remaining substituents have the significances given herein before.

A further embodiment of the present invention is (viii) a compound of formula I, or pharmaceutically acceptable salts, or enantiomers, or diastereomers thereof, wherein $R^2$ is phenyl substituted by one, two or three groups independently selected from fluoro, chloro, methoxy, difluoroethoxy, trifluoroethoxy, cyclopropylmethoxy and difluorocyclopropylmethoxy; and all remaining substituents have the significances given herein before.

Another embodiment of the present invention is (ix) a compound of formula I, wherein
$R^1$ is $C_{1-6}$alkyl;
$R^2$ is phenyl substituted by two or three groups independently selected from halogen, cyano, halo$C_{1-6}$alkoxy, —O—$C_xH_{2x}$—$R^3$ and —O—$C_yH_{2y}$—$NHR^6$;
  $R^3$ is hydrogen, $C_{3-7}$cycloalkyl, halo$C_{3-7}$cycloalkyl, oxetanyl, tetrahydrofuranyl, tetrahydropyranyl, $C_{1-6}$alkylsulfonylazetidinyl, aminocarbonyl or $C_{1-6}$alkylsulfonyl;
  $R^6$ is hydrogen or $C_{1-6}$alkoxycarbonyl;
  x is 1, 2, 3, 4, 5 or 6;
  y is 1, 2, 3, 4, 5 or 6;
U is CH;
W is CH;
Z is N;
X is N;
Y is N;
or pharmaceutically acceptable salts, or enantiomers, or diastereomers thereof.

A further embodiment of the present invention is (x) a compound of formula I, wherein
$R^1$ is methyl;
$R^2$ is phenyl substituted by two or three groups independently selected from fluoro, chloro, cyano, methoxy, difluoroethoxy, trifluoroethoxy, cyclopropylmethoxy, difluorocyclopropylmethoxy, methylsulfonylpropoxy, aminocarbonylmethoxy, oxetanylmethoxy, oxetanylethoxy, tetrahydrofuranylmethoxy, tetrahydropyranylmethoxy, methylsulfonylazetidinylethoxy, aminohexyloxy and (tert-butoxycarbonylamino)propoxy;
U is CH;
W is CH;
Z is N;
X is N;
Y is N;
or pharmaceutically acceptable salts, or enantiomers, or diastereomers thereof.

Another embodiment of the present invention is (xi) a compound of formula I, wherein
$R^1$ is $C_{1-6}$alkyl;
$R^2$ is pyridinyl substituted by one, two or three groups independently selected from halogen, $C_{1-6}$alkyl, halo$C_{1-6}$alkoxy, tetrahydropyranyloxy, —O—$C_xH_{2x}$—$R^3$ and $NR^9R^{10}$;
  $R^3$ is hydrogen, $C_{3-7}$cycloalkyl, thietanyl, tetrahydrofuranyl, tetrahydropyranyl, oxomorpholinyl, 1,1-dioxo-thietanyl, $C_{1-6}$alkylcarbonylazetidinyl, $C_{1-6}$alkylsulfonylazetidinyl, —C(=O)—$R^4$, carboxy$C_{1-6}$alkoxy or aminocarbonyl$C_{1-6}$alkoxy; wherein
    $R^4$ is hydroxy, $C_{1-6}$alkoxy or amino;
  $R^9$ and $R^{10}$ are independently selected from hydrogen, $C_{1-6}$alkyl and $C_{1-6}$alkylsulfonyl; or
  $R^9$ and $R^{10}$ together with the nitrogen to which they are attached form pyrrolidinyl, morpholinyl, piperazinyl and oxopiperazinyl;
  x is 1, 2, 3, 4, 5, 6, 7 or 8;
U is CH;
W is CH;
Z is N;
X is N;
Y is N;
or pharmaceutically acceptable salts, or enantiomers, or diastereomers thereof.

A further embodiment of the present invention is (xii) a compound of formula I, wherein
$R^1$ is methyl;
$R^2$ is pyridinyl substituted by one, two or three groups independently selected from fluoro, chloro, iodo, methoxy, methyl, difluoroethoxy, tetrahydropyranyloxy, cyclopropylmethoxy, thietanylmethoxy, tetrahydrofuranylmethoxy, tetrahydropyranylmethoxy, oxomorpholinylpropoxy, (1,1-dioxo-thietanyl)methoxy, acetylazetidinylmethoxy, methyl sulfonylazetidinylmethoxy, carboxybutoxy, carboxyheptyloxy, carboxyhexyloxy, carboxypentyloxy, carboxypropoxy, methoxycarbonylheptyloxy, aminocarbonylbutoxy, aminocarbonylheptyloxy, aminocarbonylhexyloxy, aminocarbonylmethoxy, aminocarbonylpentyloxy, aminocarbonylpropoxy, carboxymethoxypropoxy, aminocarbonylmethoxypropoxy, amino, methylamino, dimethylamino, methylsulfonylamino, pyrrolidinyl, morpholinyl, piperazinyl and oxopiperazinyl;
U is CH;
W is CH;
Z is N;
X is N;
Y is N;
or pharmaceutically acceptable salts, or enantiomers, or diastereomers thereof.

A further embodiment of the present invention is (xiii) a compound of formula I, or pharmaceutically acceptable salts, or enantiomers, or diastereomers thereof, wherein $R^2$ is pyridinyl substituted by one, two or three groups independently selected from halogen, $C_{1-6}$alkoxy, halo$C_{1-6}$alkoxy, $C_{1-6}$alkylamino, di$C_{1-6}$alkylamino, pyrrolidinyl and oxopiperazinyl.

Another further embodiment of the present invention is (xiv) a compound of formula I, or pharmaceutically acceptable salts, or enantiomers, or diastereomers thereof, wherein $R^2$ is pyridinyl substituted by one, two or three groups independently selected from fluoro, chloro, methoxy, difluoroethoxy, methylamino, dimethylamino, pyrrolidinyl and oxopiperazinyl.

Another embodiment of the present invention is (xv) a compound of formula I, wherein $R^1$ is $C_{1-6}$alkyl;

$R^2$ is pyridinyl substituted by two or three groups independently selected from halogen, haloC$_{1-6}$alkoxy, —O—C$_x$H$_{2x}$—R$^3$ and NR$^9$R$^{10}$;

$R^3$ is hydrogen, tetrahydrofuranyl, tetrahydropyranyl, oxomorpholinyl or aminocarbonyl;

$R^9$ and $R^{10}$ are independently selected from hydrogen and $C_{1-6}$alkyl; or $R^9$ and $R^{10}$ together with the nitrogen to which they are attached form pyrrolidinyl and oxopiperazinyl;

x is 1, 2, 3, 4, 5 or 6;

U is CH;

W is CH;

Z is N;

X is N;

Y is N;

or pharmaceutically acceptable salts, or enantiomers, or diastereomers thereof.

A further embodiment of the present invention is (xvi) a compound of formula I, wherein $R^1$ is methyl;

$R^2$ is pyridinyl substituted by two or three groups independently selected from fluoro, chloro, methoxy, difluoroethoxy, tetrahydrofuranylmethoxy, tetrahydropyranylmethoxy, oxomorpholinylpropoxy, aminocarbonylhexyloxy, methylamino, dimethylamino, pyrrolidinyl and oxopiperazinyl;

U is CH;

W is CH;

Z is N;

X is N;

Y is N;

or pharmaceutically acceptable salts, or enantiomers, or diastereomers thereof.

Another embodiment of the present invention is (xvii) a compound of formula I, wherein $R^1$ is $C_{1-6}$alkyl, $C_{3-7}$cycloalkyl, hydroxyC$_{1-6}$alkyl, $C_{1-6}$alkoxycarbonylC$_{1-6}$alkyl, or carboxyC$_{1-6}$alkyl;

$R^2$ is phenyl substituted by one, two or three groups independently selected from halogen, nitro, C$_{1-6}$alkylsulfonyl, —O—C$_x$H$_{2x}$—R$^3$ and —O—C$_y$H$_{2y}$—NHR$^6$; or pyridinyl substituted by two groups independently selected from halogen, haloC$_{1-6}$alkoxy, —O—C$_x$H$_{2x}$—R$^3$ and NR$^9$R$^{10}$; wherein $R^3$ is hydrogen, C$_{3-7}$cycloalkyl, hydroxy, C$_{1-6}$alkoxy, tetrahydrofuranyl, tetrahydropyranyl, morpholinyl, —C(=O)—R$^4$, —SO$_2$—R$^5$ or aminocarbonyl C$_{1-6}$alkoxy; wherein $R^4$ is hydroxy, C$_{1-6}$alkoxy, amino, diC$_{1-6}$alkylamino or pyrrolidinyl;

$R^5$ is C$_{1-6}$alkyl;

$R^6$ is hydrogen or C$_{1-6}$alkylsulfonyl;

$R^9$ and $R^{10}$ are C$_{1-6}$alkyl; or $R^9$ and $R^{10}$ together with the nitrogen to which they are attached form pyrrolidinyl, morpholinyl, piperidinyl and oxopiperazinyl;

x is 1, 2, 3, 4, 5 or 6;

y is 1, 2, 3, 4, 5 or 6;

U is CH;

W is CH;

Z is CH;

X is N;

Y is N;

or pharmaceutically acceptable salts, or enantiomers, or diastereomers thereof.

Another embodiment of the present invention is (xviii) a compound of formula I, or pharmaceutically acceptable salts, or enantiomers, or diastereomers thereof, wherein $R^1$ is $C_{1-6}$alkyl, and all remaining substituents have the significances given herein before.

A further embodiment of the present invention is (xix) a compound of formula I, or pharmaceutically acceptable salts, or enantiomers, or diastereomers thereof, wherein $R^1$ is methyl, and all remaining substituents have the significances given herein before.

Another embodiment of the present invention is (xx) a compound of formula I, or pharmaceutically acceptable salts, or enantiomers, or diastereomers thereof, wherein $R^2$ is phenyl substituted by one, two or three groups independently selected from halogen and C$_{1-6}$alkoxy; or pyridinyl substituted by two groups independently selected from halogen, diC$_{1-6}$alkylamino, pyrrolidinyl, and oxopiperazinyl; and all remaining substituents have the significances given herein before.

A further embodiment of the present invention is (xxi) a compound of formula I, or pharmaceutically acceptable salts, or enantiomers, or diastereomers thereof, wherein $R^2$ is phenyl substituted by one, two or three groups independently selected from fluoro and methoxy; or pyridinyl substituted by two groups independently selected from fluoro, dimethylamio, pyrrolidinyl and oxopiperazinyl; and all remaining substituents have the significances given herein before.

Another embodiment of the present invention is (xxii) a compound of formula I, wherein $R^1$ is C$_{1-6}$alkyl, C$_{3-7}$cycloalkyl, haloC$_{1-6}$alkyl, hydroxyC$_{1-6}$alkyl, nitroC$_{1-6}$alkyl, C$_{1-6}$alkoxycarbonylC$_{1-6}$alkyl, carboxyC$_{1-6}$alkyl, di(C$_{1-6}$alkoxycarbonyl)methylenyl, cyanoC$_{1-6}$alkyl, C$_{3-7}$cycloalkylC$_{1-6}$alkyl, phenylC$_{1-6}$alkyl, C$_{1-6}$alkylsufanylC$_{1-6}$alkyl, C$_{1-6}$alkylsufonylC$_{1-6}$alkyl, aminoC$_{1-6}$alkyl, C$_{1-6}$alkylcarbonylaminoC$_{1-6}$alkyl, C$_{1-6}$alkylsufonylaminoC$_{1-6}$alkyl, C$_{1-6}$alkoxycarbonyl aminoC$_{1-6}$alkyl, aminocarbonylC$_{1-6}$alkyl, diC$_{1-6}$alkylaminocarbonylC$_{1-6}$alkyl, monocyclic heterocycloalkylC$_{1-6}$alkyl or imidazolyl C$_{1-6}$alkyl;

$R^2$ is aryl or heteroaryl, said aryl or heteroaryl being unsubstituted, or substituted by one to four substituents independently selected from C$_{1-6}$alkyl, C$_{3-7}$cycloalkyl, halogen, haloC$_{1-6}$alkyl, cyano, nitro, hydroxy, —O—C$_x$H$_{2x}$—R$^3$, —O—C$_y$H$_{2y}$—NHR$^6$, NR$^9$R$^{10}$, SO$_2$R$^{11}$, SO$_2$NR$^{12}$R$^{13}$, carboxy, —C(=O)—C$_{1-6}$alkoxy, —C(=O)—NR$^{12}$R$^{13}$, haloC$_{1-6}$alkoxy, aryl, heteroaryl and monocyclic heterocycloalkyl; wherein monocyclic heterocycloalkyl is unsubstituted or substituted by C$_{1-6}$alkyl, C$_{3-7}$cycloalkyl, C$_{1-6}$alkylcarbonyl, C$_{1-6}$alkylsufonyl or C$_{1-6}$alkoxycarbonyl;

$R^3$ is hydrogen; C$_{3-7}$cycloalkyl; haloC$_{3-7}$cycloalkyl; hydroxy; hydroxyC$_{1-6}$alkylC$_{3-7}$cycloalkyl; C$_{1-6}$alkoxy; monocyclic heterocycloalkyl; monocyclic heterocycloalkyl substituted by C$_{1-6}$alkyl, C$_{1-6}$alkylcarbonyl, C$_{1-6}$alkylsufonyl, C$_{3-7}$cycloalkyl or C$_{1-6}$alkoxycarbonyl; —C(=O)R$^4$; C$_{1-6}$alkylsulfanyl; —SO$_2$R$^5$ or —C(NHR$^7$)—C(=O)R$^8$; wherein $R^4$ is hydroxy, C$_{1-6}$alkoxy, amino, C$_{1-6}$alkylamino, diC$_{1-6}$alkylamino, tetrahydrofuranylamino, pyrrolyl or morpholinyl;

$R^5$ is C$_{1-6}$alkyl, C$_{3-7}$cycloalkyl, hydroxy, amino, C$_{1-6}$alkylamino or diC$_{1-6}$alkylamino;

$R^7$ is hydrogen or $C_{1-6}$alkoxycarbonyl;
$R^8$ is hydroxy or $C_{1-6}$alkoxy;
$R^6$ is hydrogen, $C_{1-6}$alkylcarbonyl, halo$C_{1-6}$alkylcarbonyl, $C_{1-6}$alkoxycarbonyl, $C_{1-6}$alkylsulfonyl, $C_{3-7}$cycloalkylsulfonyl or $C_{1-6}$alkoxy$C_{1-6}$alkylsulfonyl;
$R^9$ and $R^{10}$ are independently selected from hydrogen, $C_{1-6}$alkyl, $C_{3-7}$cycloalkyl, $C_{1-6}$alkylcarbonyl, $C_{1-6}$alkylsulfonyl, $C_{3-7}$cycloalkylcarbonyl and $C_{3-7}$cycloalkylsulfonyl; or
$R^9$ and $R^{10}$ together with the nitrogen to which they are attached form monocyclic heterocycloalkyl;
$R^{11}$ is $C_{1-6}$alkyl, halo$C_{1-6}$alkyl, $C_{3-7}$cycloalkyl halo$C_{3-7}$cycloalkyl, hydroxy$C_{1-6}$alkyl, $C_{1-6}$alkoxy $C_{1-6}$alkyl, halo$C_{1-6}$alkoxy$C_{1-6}$alkyl, $C_{3-7}$cycloalkyl $C_{1-6}$alkyl, amino$C_{1-6}$alkyl, $C_{1-6}$alkylamino$C_{1-6}$alkyl, di$C_{1-6}$alkylamino$C_{1-6}$alkyl, $C_{1-6}$alkylcarbonylamino$C_{1-6}$alkyl, $C_{1-6}$alkylsulfonylamino$C_{1-6}$alkyl, $C_{1-6}$alkoxycarbonylamino$C_{1-6}$alkyl, $C_{1-6}$alkylsulfenyl$C_{1-6}$alkyl, $C_{1-6}$alkylsulfanyl$C_{1-6}$alkyl or $C_{1-6}$alkylsulfonyl$C_{1-6}$alkyl;
$R^{12}$ and $R^{13}$ are independently selected from hydrogen, $C_{1-6}$alkyl, halo$C_{1-6}$alkyl, $C_{3-7}$cycloalkyl and halo$C_{3-7}$cycloalkyl; or
$R^{12}$ and $R^{13}$ together with the nitrogen to which they are attached form monocyclic heterocycloalkyl;
x is 1-6;
y is 1-8;
U, W and Z are independently selected from CH and N;
one of X and Y is N, and the other one is CH or N;
or pharmaceutically acceptable salts, or enantiomers, or diastereomer thereof.

A further embodiment of the present invention is (xxiii) a compound of formula I, or pharmaceutically acceptable salts, or enantiomers, or diastereomer thereof, wherein
$R^2$ is phenyl, pyridinyl, thienyl or furanyl, said phenyl, pyridinyl, thienyl or furanyl being unsubstituted, or substituted by one, to four substituents independently selected from $C_{1-6}$alkyl, $C_{3-7}$cycloalkyl, halogen, halo$C_{1-6}$alkyl, cyano, nitro, hydroxy, —O—$C_xH_{2x}$—$R^3$, —O—$C_yH_{2y}$—NHR$^6$, NR$^9$R$^{10}$, SO$_2$R$^{11}$, SO$_2$NR$^{12}$R$^{13}$, carboxy, —C(=O)—$C_{1-6}$alkoxy, —C(=O)—NR$^{12}$R$^{13}$, halo$C_{1-6}$alkoxy, aryl, heteroaryl and monocyclic heterocycloalkyl; wherein
monocyclic heterocycloalkyl is unsubstituted or substituted by $C_{1-6}$alkyl, $C_{1-6}$alkylcarbonyl, $C_{1-6}$alkylsufonyl, $C_{3-7}$ cycloalkyl or $C_{1-6}$alkoxycarbonyl;
$R^3$ is hydrogen; $C_{3-7}$cycloalkyl; halo$C_{3-7}$cycloalkyl; hydroxy; hydroxy$C_{1-6}$alkyl$C_{3-7}$cycloalkyl; $C_{1-6}$alkoxy; monocyclic heterocycloalkyl; monocyclic heterocycloalkyl substituted by $C_{1-6}$alkyl, $C_{1-6}$alkylcarbonyl, $C_{1-6}$alkylsufonyl, $C_{3-7}$cycloalkyl or $C_{1-6}$alkoxycarbonyl; —C(=O)R$^4$; $C_{1-6}$alkylsulfanyl; —SO$_2$R$^5$ or —C(NHR$^7$)—C(=O)R$^8$; wherein
$R^4$ is hydroxy, $C_{1-6}$alkoxy, amino, $C_{1-6}$alkylamino, di$C_{1-6}$alkylamino, tetrahydrofuranylamino, pyrrolyl or morpholinyl;
$R^5$ is $C_{1-6}$alkyl, $C_{3-7}$cycloalkyl, hydroxy, amino, $C_{1-6}$alkylamino or di$C_{1-6}$alkylamino;
$R^7$ is hydrogen or $C_{1-6}$alkoxycarbonyl;
$R^8$ is hydroxy or $C_{1-6}$alkoxy;
$R^6$ is hydrogen, $C_{1-6}$alkylcarbonyl, halo$C_{1-6}$alkylcarbonyl, $C_{1-6}$alkoxycarbonyl, $C_{1-6}$alkylsulfonyl, $C_{3-7}$cycloalkylsulfonyl or $C_{1-6}$alkoxy$C_{1-6}$alkylsulfonyl;
$R^9$ and $R^{10}$ are independently selected from hydrogen, $C_{1-6}$alkyl, $C_{3-7}$cycloalkyl, $C_{1-6}$alkylcarbonyl, $C_{1-6}$alkylsulfonyl, $C_{3-7}$cycloalkylcarbonyl and $C_{3-7}$cycloalkylsulfonyl; or
$R^9$ and $R^{10}$ together with the nitrogen to which they are attached form monocyclic heterocycloalkyl;
$R^{11}$ is $C_{1-6}$alkyl, halo$C_{1-6}$alkyl, $C_{3-7}$cycloalkyl, halo$C_{3-7}$cycloalkyl, hydroxy$C_{1-6}$alkyl, $C_{1-6}$alkoxy $C_{1-6}$alkyl, halo$C_{1-6}$alkoxy$C_{1-6}$alkyl, $C_{3-7}$cycloalkyl $C_{1-6}$alkyl, amino$C_{1-6}$alkyl, $C_{1-6}$alkylamino$C_{1-6}$alkyl, di$C_{1-6}$alkylamino$C_{1-6}$alkyl, $C_{1-6}$alkylcarbonylamino$C_{1-6}$alkyl, $C_{1-6}$alkylsulfonylamino$C_{1-6}$alkyl, $C_{1-6}$alkoxycarbonylamino$C_{1-6}$alkyl, $C_{1-6}$alkylsulfenyl$C_{1-6}$alkyl, $C_{1-6}$alkylsulfanyl$C_{1-6}$alkyl or $C_{1-6}$alkylsulfonyl$C_{1-6}$alkyl;
$R^{12}$ and $R^{13}$ are independently selected from hydrogen, $C_{1-6}$alkyl, halo$C_{1-6}$alkyl, $C_{3-7}$cycloalkyl and halo$C_{3-7}$cycloalkyl; or
$R^{12}$ and $R^{13}$ together with the nitrogen to which they are attached form monocyclic heterocycloalkyl;
x is 1-6;
y is 1-8;
and all remaining substituents have the significances given in embodiment (xxii).

Another embodiment of the present invention is (xxiv) a compound of formula I, wherein,
$R^1$ is $C_{1-6}$alkyl, $C_{3-7}$cycloalkyl, hydroxy$C_{1-6}$alkyl, nitro$C_{1-6}$alkyl, $C_{1-6}$alkoxycarbonyl$C_{1-6}$alkyl, carboxy $C_{1-6}$alkyl or di($C_{1-6}$alkoxycarbonyl)methylenyl;
$R^2$ is phenyl substituted by one to four groups independently selected from $C_{1-6}$alkyl, $C_{3-7}$cycloalkyl, halogen, halo$C_{1-6}$alkyl, cyano, nitro, hydroxy, $C_{1-6}$alkylsulfonyl, halo$C_{1-6}$alkoxy, tetrahydrofuranyloxy, pyridinyl, —O—$C_xH_{2x}$—R$^3$ and —O—$C_yH_{2y}$—NHR$^6$; or pyridinyl substituted by one, two or three groups independently selected from halogen and $C_{1-6}$alkoxy; wherein
$R^3$ is hydrogen, $C_{3-7}$cycloalkyl, halo$C_{3-7}$cycloalkyl, hydroxy, hydroxy$C_{1-6}$alkyl$C_{3-7}$cycloalkyl, $C_{1-6}$alkoxy, oxetanyl, tetrahydrofuranyl, tetrahydropyranyl, thietanyl, 1,1-dioxothietanyl, 1,1-dioxothiolanyl, morpholinyl, oxopyrrolidinyl, oxomorpholinyl, oxopiperazinyl, $C_{1-6}$alkoxycarbonyloxopiperazinyl, oxoimidazolidinyl, $C_{1-6}$alkylpiperazinyl, $C_{1-6}$alkylcarbonylpiperazinyl, $C_{1-6}$alkylsulfonylpiperazinyl, $C_{1-6}$alkoxycarbonylpiperazinyl, azetidinyl, $C_{1-6}$alkylcarbonylazetidinyl, $C_{1-6}$alkylsulfonylazetidinyl, $C_{1-6}$alkoxycarbonylazetidinyl, —C(=O)R$^4$, $C_{1-6}$alkylsulfanyl, —SO$_2$R$^5$ or —C(NHR$^7$)—C(=O)R$^8$; wherein
$R^4$ is hydroxy, $C_{1-6}$alkoxy, amino, $C_{1-6}$alkylamino, di$C_{1-6}$alkylamino, tetrahydrofuranylamino, pyrrolyl or morpholinyl;
$R^5$ is $C_{1-6}$alkyl, hydroxy or amino;
$R^7$ is hydrogen or $C_{1-6}$alkoxycarbonyl;
$R^8$ is hydroxy or $C_{1-6}$alkoxy;
$R^6$ is hydrogen, $C_{1-6}$alkylcarbonyl, halo$C_{1-6}$alkylcarbonyl, $C_{1-6}$alkoxycarbonyl, $C_{1-6}$alkylsulfonyl, $C_{3-7}$cycloalkylsulfonyl or $C_{1-6}$alkoxy$C_{1-6}$alkylsulfonyl;
x is 1-6;
y is 1-8;
U is CH;
W is CH;
Z is CH or N;
X is N;
Y is N or CH;
or pharmaceutically acceptable salts, or enantiomers, or diastereomer thereof.

Another embodiment of the present invention is (xxv) a compound of formula I, wherein $R^1$ is $C_{1-6}$alkyl;

$R^2$ is phenyl substituted by one to four groups independently selected from $C_{1-6}$alkyl, $C_{3-7}$cycloalkyl, halogen, halo$C_{1-6}$alkyl, cyano, hydroxy, halo$C_{1-6}$alkoxy, tetrahydrofuranyloxy, pyridinyl, —O—$C_xH_{2x}$—$R^3$ and —O—$C_yH_{2y}$—$NHR^6$; or pyridinyl substituted by one, two or three groups independently selected from halogen and $C_{1-6}$alkoxy; wherein $R^3$ is hydrogen, $C_{3-7}$cycloalkyl, halo$C_{3-7}$cycloalkyl, hydroxy$C_{1-6}$alkyl$C_{3-7}$cycloalkyl, oxetanyl, tetrahydrofuranyl, tetrahydropyranyl, thietanyl, 1,1-dioxothietanyl, 1,1-dioxothiolanyl, oxopyrrolidinyl, oxomorpholinyl, oxopiperazinyl, $C_{1-6}$alkoxycarbonyloxopiperazinyl, oxoimidazolidinyl, $C_{1-6}$alkylpiperazinyl, $C_{1-6}$alkylcarbonylpiperazinyl, $C_{1-6}$alkylsulfonylpiperazinyl, $C_{1-6}$alkoxycarbonylpiperazinyl, azetidinyl, $C_{1-6}$alkylcarbonylazetidinyl, $C_{1-6}$alkylsulfonylazetidinyl, $C_{1-6}$alkoxycarbonylazetidinyl, —C(=O)$R^4$, $C_{1-6}$alkylsulfanyl, —SO$_2R^5$ or —C(NHR$^7$)—C(=O)$R^8$; wherein $R^4$ is hydroxy, $C_{1-6}$alkoxy, amino, $C_{1-6}$alkylamino, tetrahydrofuranylamino, or morpholinyl;

$R^5$ is $C_{1-6}$alkyl, hydroxy or amino;

$R^7$ is hydrogen or $C_{1-6}$alkoxycarbonyl;

$R^8$ is hydroxy or $C_{1-6}$alkoxy;

$R^6$ is hydrogen, $C_{1-6}$alkylcarbonyl, halo$C_{1-6}$alkylcarbonyl, $C_{1-6}$alkoxycarbonyl, $C_{3-7}$cycloalkylsulfonyl or $C_{1-6}$alkoxy$C_{1-6}$alkylsulfonyl;

x is 1-6;

y is 1-8;

U is CH;

W is CH;

Z is N;

X is N;

Y is N or CH;

or pharmaceutically acceptable salts, or enantiomers, or diastereomer thereof.

A further embodiment of the present invention is (xxvi) a compound of formula I, or pharmaceutically acceptable salts, or enantiomers, or diastereomer thereof, wherein $R^1$ is methyl, and all remaining substituents have the significances given herein before.

A further embodiment of the present invention is (xxvii) a compound of formula I, or pharmaceutically acceptable salts, or enantiomers, or diastereomer thereof, wherein $R^2$ is phenyl substituted by one, two or three groups independently selected from halogen, $C_{1-6}$alkoxy, halo$C_{1-6}$alkoxy, $C_{3-7}$cycloalkyl$C_{1-6}$alkoxy and halo$C_{3-7}$cycloalkyl$C_{1-6}$alkoxy; or pyridinyl substituted by one, two or three groups independently selected from halogen and $C_{1-6}$alkoxy, and all remaining substituents have the significances given herein before.

A further embodiment of the present invention is (xxviii) a compound of formula I, or pharmaceutically acceptable salts, or enantiomers, or diastereomer thereof, wherein $R^2$ is phenyl substituted by one, two or three groups independently selected from fluoro, chloro, methoxy, difluoroethoxy, trifluoroethoxy, cyclopropylmethoxy and difluorocyclopropylmethoxy; or pyridinyl substituted by one, two or three groups independently selected from fluoro, chloro and methoxy, and all remaining substituents have the significances given herein before.

Another embodiment of the present invention is (xxix) a compound of formula I, wherein $R^1$ is $C_{1-6}$alkyl;

$R^2$ is phenyl substituted by two or three groups independently selected from halogen, cyano, halo$C_{1-6}$alkoxy, —O—$C_xH_{2x}$—$R^3$ and —O—$C_yH_{2y}$—$NHR^6$; or pyridinyl substituted by two groups independently selected from halogen and $C_{1-6}$alkoxy; wherein $R^3$ is hydrogen, $C_{3-7}$cycloalkyl, halo$C_{3-7}$cycloalkyl, oxetanyl, tetrahydrofuranyl, tetrahydropyranyl, $C_{1-6}$alkylsulfonylazetidinyl, —C(=O)$R^4$ or —SO$_2R^5$; wherein $R^4$ is amino;

$R^5$ is $C_{1-6}$alkyl;

$R^6$ is hydrogen or $C_{1-6}$alkoxycarbonyl;

x is 1-6;

y is 1-6;

U is CH;

W is CH;

Z is N;

X is N;

Y is N or CH;

or pharmaceutically acceptable salts, or enantiomers, or diastereomer thereof.

A further embodiment of the present invention is (xxx) a compound of formula I, wherein $R^1$ is methyl;

$R^2$ is phenyl substituted by two or three groups independently selected from fluoro, chloro, cyano, methoxy, difluoroethoxy, trifluoroethoxy, cyclopropylmethoxy, difluorocyclopropylmethoxy, methylsulfonylpropoxy, aminocarbonylmethoxy, aminohexyloxy, tert-butoxycarbonylaminopropoxy, oxetanylmethoxy, oxetanylethoxy, tetrahydrofuranylmethoxy, tetrahydropyranylmethoxy and methyl sulfonylazetidinylethoxy; or pyridinyl substituted by two groups independently selected from fluoro, chloro and methoxy;

U is CH;

W is CH;

Z is N;

X is N;

Y is N or CH;

or pharmaceutically acceptable salts, or enantiomers, or diastereomer thereof.

Another embodiment of the present invention is (xxxi) a compound of formula I, wherein $R^1$ is $C_{1-6}$alkyl, $C_{3-7}$cycloalkyl, hydroxy$C_{1-6}$alkyl, nitro$C_{1-6}$alkyl, $C_{1-6}$alkoxycarbonyl$C_{1-6}$alkyl, carboxy $C_{1-6}$alkyl or di($C_{1-6}$alkoxycarbonyl)methylenyl;

$R^2$ is phenyl substituted by one, two or three groups independently selected from halogen, nitro, $C_{1-6}$alkylsulfonyl, —O—$C_xH_{2x}$—$R^3$ and —O—$C_yH_{2y}$—$NHR^6$; wherein $R^3$ is hydrogen, hydroxy, $C_{1-6}$alkoxy, morpholinyl, —C(=O)$R^4$ or —SO$_2R^5$; wherein $R^4$ is hydroxy, $C_{1-6}$alkoxy, amino, di$C_{1-6}$alkylamino or pyrrolyl;

$R^5$ is $C_{1-6}$alkyl;

$R^6$ is hydrogen or $C_{1-6}$alkylsulfonyl;

x is 1-6;

y is 1-6;

U is CH;

W is CH;

Z is CH;

X is N;

Y is N;

or pharmaceutically acceptable salts, or enantiomers, or diastereomer thereof.

Another embodiment of the present invention is (xxxii) a compound of formula I, or pharmaceutically acceptable salts, or enantiomers, or diastereomer thereof, wherein $R^1$ is $C_{1-6}$alkyl, and all remaining substituents have the significances given herein before.

A further embodiment of the present invention is (xxxiii) a compound of formula I, or pharmaceutically acceptable salts, or enantiomers, or diastereomer thereof, wherein $R^1$ is methyl, and all remaining substituents have the significances given herein before.

Another embodiment of the present invention is (xxxiv) a compound of formula I, or pharmaceutically acceptable salts, or enantiomers, or diastereomer thereof, wherein $R^2$ is phenyl substituted by one, two or three groups independently selected from halogen and $C_{1-6}$alkoxy, and all remaining substituents have the significances given herein before.

A further embodiment of the present invention is (xxxv) a compound of formula I, or pharmaceutically acceptable salts, or enantiomers, or diastereomer thereof, wherein $R^2$ is phenyl substituted by one, two or three groups independently selected from fluoro and methoxy, and all remaining substituents have the significances given herein before.

Another embodiment of the present invention is (xxxvi) a compound of formula I, wherein
$R^1$ is $C_{1-6}$alkyl, $C_{3-7}$cycloalkyl, halo$C_{1-6}$alkyl, hydroxy$C_{1-6}$alkyl, nitro$C_{1-6}$alkyl, $C_{1-6}$alkoxycarbonyl$C_{1-6}$alkyl, carboxy$C_{1-6}$alkyl, di($C_{1-6}$alkoxycarbonyl)methylenyl, cyano$C_{1-6}$alkyl, $C_{3-7}$cycloalkyl$C_{1-6}$alkyl, phenyl$C_{1-6}$alkyl, $C_{1-6}$alkylsulfanyl$C_{1-6}$alkyl, $C_{1-6}$alkylsulfonyl$C_{1-6}$alkyl, amino$C_{1-6}$alkyl, $C_{1-6}$alkylcarbonylamino$C_{1-6}$alkyl, $C_{1-6}$alkylsufonylamino$C_{1-6}$alkyl, $C_{1-6}$alkoxycarbonyl amino$C_{1-6}$alkyl, aminocarbonyl $C_{1-6}$alkyl, di$C_{1-6}$alkylaminocarbonyl$C_{1-6}$alkyl, monocyclic heterocycloalkyl$C_{1-6}$alkyl or imidazolyl$C_{1-6}$alkyl;
$R^2$ is aryl or heteroaryl, said aryl or heteroaryl being unsubstituted, or substituted by one to four substituents independently selected from $C_{1-6}$alkyl, $C_{3-7}$cycloalkyl, halogen, halo$C_{1-6}$alkyl, cyano, nitro, hydroxy, amino, $C_{1-6}$alkylsulfonyl, halo$C_{1-6}$alkoxy, —O—$C_xH_{2x}$—$R^3$ and —O—$C_yH_{2y}$—NHR$^6$; wherein
$R^3$ is hydrogen, $C_{3-7}$cycloalkyl, halo$C_{3-7}$cycloalkyl, hydroxy, hydroxy$C_{1-6}$alkyl$C_{3-7}$cycloalkyl, $C_{1-6}$alkoxy, monocyclic heterocycloalkyl, monocyclic heterocycloalkyl substituted by $C_{1-6}$alkoxycarbonyl, —C(=O)$R^4$ or —SO$_2R^5$; wherein
$R^4$ is hydroxy, $C_{1-6}$alkoxy, amino, $C_{1-6}$alkylamino, di$C_{1-6}$alkylamino, tetrahydrofuranylamino, pyrrolyl or morpholinyl;
$R^5$ is $C_{1-6}$alkyl, hydroxy, amino, $C_{1-6}$alkylamino or di$C_{1-6}$alkylamino;
$R^6$ is hydrogen, $C_{1-6}$alkylcarbonyl, halo$C_{1-6}$alkylcarbonyl, $C_{1-6}$alkoxycarbonyl, $C_{1-6}$alkylsulfonyl, $C_{3-7}$cycloalkylsulfonyl or $C_{1-6}$alkoxy$C_{1-6}$alkylsulfonyl;
x is 1-6;
y is 1-8;
U, W and Z are independently selected from CH and N;
one of X and Y is N, and the other one is CH or N;
or pharmaceutically acceptable salts, or enantiomers, or diastereomer thereof.

Another embodiment of present invention is (xxxvii) a compound of formula I, wherein
$R^1$ is $C_{1-6}$alkyl, $C_{3-7}$cycloalkyl, halo$C_{1-6}$alkyl, hydroxy$C_{1-6}$alkyl, nitro$C_{1-6}$alkyl, $C_{1-6}$alkoxycarbonyl$C_{1-6}$alkyl, carboxy$C_{1-6}$alkyl, di($C_{1-6}$alkoxycarbonyl)methylenyl, cyano$C_{1-6}$alkyl, $C_{3-7}$cycloalkyl$C_{1-6}$alkyl, phenyl$C_{1-6}$alkyl, $C_{1-6}$alkylsulfanyl$C_{1-6}$alkyl, $C_{1-6}$alkylsufonyl$C_{1-6}$alkyl, amino$C_{1-6}$alkyl, $C_{1-6}$alkylcarbonylamino$C_{1-6}$alkyl, $C_{1-6}$alkylsufonylamino$C_{1-6}$alkyl, $C_{1-6}$alkoxycarbonyl amino$C_{1-6}$alkyl, aminocarbonyl $C_{1-6}$alkyl, di$C_{1-6}$alkylaminocarbonyl$C_{1-6}$alkyl, monocyclic heterocycloalkyl$C_{1-6}$alkyl or imidazolyl$C_{1-6}$alkyl;
$R^2$ is phenyl, pyridinyl, thienyl or furanyl, said phenyl, pyridinyl, thienyl or furanyl being unsubstituted, or substituted by one, to four substituents independently selected from $C_{1-6}$alkyl, $C_{3-7}$cycloalkyl, halogen, halo$C_{1-6}$alkyl, cyano, nitro, hydroxy, amino, $C_{1-6}$alkylsulfonyl, halo$C_{1-6}$alkoxy, —O—$C_xH_{2x}$—$R^3$ and —O—$C_yH_{2y}$—NHR$^6$; wherein
$R^3$ is hydrogen, $C_{3-7}$cycloalkyl, halo$C_{3-7}$cycloalkyl, hydroxy, hydroxy$C_{1-6}$alkyl$C_{3-7}$cycloalkyl, $C_{1-6}$alkoxy, monocyclic heterocycloalkyl, monocyclic heterocycloalkyl substituted by $C_{1-6}$alkoxycarbonyl, —C(=O)$R^4$ or —SO$_2R^5$; wherein
$R^4$ is hydroxy, $C_{1-6}$alkoxy, amino, $C_{1-6}$alkylamino, di$C_{1-6}$alkylamino, tetrahydrofuranylamino, pyrrolyl or morpholinyl;
$R^5$ is $C_{1-6}$alkyl, hydroxy, amino, $C_{1-6}$alkylamino or di$C_{1-6}$alkylamino;
$R^6$ is hydrogen, $C_{1-6}$alkylcarbonyl, halo$C_{1-6}$alkylcarbonyl, $C_{1-6}$alkoxycarbonyl, $C_{1-6}$alkylsulfonyl, $C_{3-7}$cycloalkylsulfonyl or $C_{1-6}$alkoxy$C_{1-6}$alkylsulfonyl;
x is 1-6;
y is 1-8;
U, W and Z are independently selected from CH and N;
one of X and Y is N, and the other one is CH or N;
or pharmaceutically acceptable salts, or enantiomers, or diastereomer thereof.

Another embodiment of present invention is (xxxviii) a compound of formula I, wherein
$R^1$ is $C_{1-6}$alkyl, $C_{3-7}$cycloalkyl, hydroxy$C_{1-6}$alkyl, nitro$C_{1-6}$alkyl, $C_{1-6}$alkoxycarbonyl$C_{1-6}$alkyl, carboxy$C_{1-6}$alkyl or di($C_{1-6}$alkoxycarbonyl)methylenyl;
$R^2$ is phenyl substituted by one, two or three groups independently selected from halogen, halo$C_{1-6}$alkyl, cyano, nitro, hydroxy, $C_{1-6}$alkylsulfonyl, halo$C_{1-6}$alkoxy, —O—$C_xH_{2x}$—$R^3$ and —O—$C_yH_{2y}$—NHR$^6$; wherein
$R^3$ is hydrogen, $C_{3-7}$cycloalkyl, halo$C_{3-7}$cycloalkyl, hydroxy, hydroxy$C_{1-6}$alkyl$C_{3-7}$cycloalkyl, $C_{1-6}$alkoxy, oxetanyl, tetrahydrofuranyl, tetrahydropyranyl, 1,1-dioxothiolanyl, morpholinyl, oxopyrrolidinyl, oxomorpholinyl, oxopiperazinyl, $C_{1-6}$alkoxycarbonyloxopiperazinyl, —C(=O)$R^4$ or —SO$_2R^5$; wherein
$R^4$ is hydroxy, $C_{1-6}$alkoxy, amino, $C_{1-6}$alkylamino, di$C_{1-6}$alkylamino, tetrahydrofuranylamino, pyrrolyl or morpholinyl;
$R^5$ is $C_{1-6}$alkyl, hydroxy or amino;
$R^6$ is hydrogen, $C_{1-6}$alkylcarbonyl, halo$C_{1-6}$alkylcarbonyl, $C_{1-6}$alkoxycarbonyl, $C_{1-6}$alkylsulfonyl, $C_{3-7}$cycloalkylsulfonyl or $C_{1-6}$alkoxy$C_{1-6}$alkylsulfonyl;
x is 1-6;
y is 1-8;
U is CH;
W is CH;
Z is CH or N;
X is N;
Y is N;
or pharmaceutically acceptable salts, or enantiomers, or diastereomer thereof.

A further embodiment of present invention is (xxxix) a compound of formula I, wherein
$R^1$ is methyl, ethyl, propyl, cyclopropyl, hydroxyethyl, nitromethyl, ethoxycarbonylmethyl, carboxymethyl or di(methoxycarbonyl)methylenyl;
$R^2$ is phenyl substituted by one, two or three groups independently selected from fluoro, chloro, trifluoromethyl, cyano, nitro, hydroxy, methylsulfonyl, difluoromethoxy, difluoroethoxy, trifluoroethoxy, methoxy, cyclopropylmethoxy, difluorocyclopropylmethoxy, hydroxybutoxy, hydroxypentoxy, hydroxymethyl cyclopropylmethoxy, methoxyethoxy, oxetanylmethoxy, oxetanylethoxy, tetrahydrofuranylmethoxy, tetrahydropyranylmethoxy, 1,1-dioxothiolanylmethoxy, morpholinylpropoxy, oxopyrrolidinylpropoxy, oxomorpholinylpropoxy, oxopiperazinylpropoxy, tert-butoxycarbonyloxopiperazinylpropoxy, carboxymethoxy, carboxyethoxy, carboxypropoxy, carboxybutoxy, carboxyhexyloxy, methoxycarbonylmethoxy, methoxycarbonylbutoxy, ethoxycarbonylhexyloxy, aminocarbonylmethoxy, aminocarbonylpropoxy, aminocarbonylbutoxy, aminocarbonylhexyloxy, methylaminocarbonylpropoxy, dimethylaminocarbonylmethoxy, tetrahydrofuranylaminocarbonylmethoxy, pyrrolylcarbonylmethoxy, morpholinylcarbonylmethoxy, methylsulfonylethoxy, methylsulfonylpropoxy, sulfopropoxy, aminosulfonylpropoxy, aminopropoxy, aminopentoxy, aminohexyloxy, aminooctyloxy, methylcarbonylaminopropoxy, chloropropylcarbonylaminopropoxy, tert-butoxycarbonylaminopropoxy, tert-butoxycarbonylaminopentoxy, tert-butoxycarbonylaminohexyloxy, tert-butoxycarbonylaminoctyloxy, methyl sulfonylaminopropoxy, cyclopropylsulfonylaminopropoxy and methoxyethyl sulfonylaminopropoxy;

U is CH;
W is CH;
Z is CH or N;
X is N;
Y is N;

or pharmaceutically acceptable salts, or enantiomers, or diastereomer thereof.

Another embodiment of present invention is (xl) a compound of formula I, wherein $R^1$ is $C_{1-6}$alkyl;
$R^2$ is phenyl substituted by one, two or three groups independently selected from halogen, halo$C_{1-6}$alkyl, cyano, hydroxy, halo$C_{1-6}$alkoxy, —O—$C_xH_{2x}$—$R^3$ and —O—$C_yH_{2y}$—$NHR^6$; wherein
$R^3$ is hydrogen, $C_{3-7}$cycloalkyl, halo$C_{3-7}$cycloalkyl, hydroxy$C_{1-6}$alkyl$C_{3-7}$cycloalkyl, oxetanyl, tetrahydrofuranyl, tetrahydropyranyl, 1,1-dioxothiolanyl, oxopyrrolidinyl, oxomorpholinyl, oxopiperazinyl, $C_{1-6}$alkoxycarbonyloxopiperazinyl, —C(=O)$R^4$ or —SO$_2R^5$; wherein
$R^4$ is hydroxy, $C_{1-6}$alkoxy, amino, $C_{1-6}$alkylamino, tetrahydrofuranylamino, or morpholinyl;
$R^5$ is $C_{1-6}$alkyl, hydroxy or amino;
$R^6$ is hydrogen, $C_{1-6}$alkylcarbonyl, halo$C_{1-6}$alkylcarbonyl, $C_{1-6}$alkoxycarbonyl, $C_{3-7}$cycloalkylsulfonyl or $C_{1-6}$alkoxy$C_{1-6}$alkylsulfonyl;
x is 1-6;
y is 1-8;
U is CH;
W is CH;
Z is N;
X is N;
Y is N;

or pharmaceutically acceptable salts, or enantiomers, or diastereomer thereof.

A further embodiment of present invention is (xli) a compound of formula I, wherein $R^1$ is methyl;
$R^2$ is phenyl substituted by one, two or three groups independently selected from fluoro, chloro, trifluoromethyl, cyano, hydroxy, difluoromethoxy, difluoroethoxy, trifluoroethoxy, methoxy, cyclopropylmethoxy, difluorocyclopropylmethoxy, hydroxymethylcyclopropylmethoxy, oxetanylmethoxy, oxetanylethoxy, tetrahydrofuranylmethoxy, tetrahydropyranylmethoxy, 1,1-dioxothiolanylmethoxy, oxopyrrolidinylpropoxy, oxomorpholinylpropoxy, oxopiperazinylpropoxy, tert-butoxycarbonyloxopiperazinylpropoxy, carboxymethoxy, carboxyethoxy, carboxypropoxy, carboxybutoxy, carboxyhexyloxy, methoxycarbonylbutoxy, ethoxycarbonylhexyloxy, aminocarbonylmethoxy, aminocarbonylpropoxy, aminocarbonylbutoxy, aminocarbonylhexyloxy, methylaminocarbonylpropoxy, tetrahydrofuranylaminocarbonylmethoxy, morpholinylcarbonylmethoxy, methylsulfonylpropoxy, sulfopropoxy, aminosulfonylpropoxy, aminopropoxy, aminopentoxy, aminohexyloxy, aminooctyloxy, methylcarbonylaminopropoxy, chloropropylcarbonylaminopropoxy, tert-butoxycarbonyl aminopropoxy, tert-butoxycarbonylaminopentoxy, tert-butoxycarbonylaminohexyloxy, tert-butoxycarbonylaminoctyloxy, cyclopropylsulfonylaminopropoxy and methoxyethyl sulfonylaminopropoxy;

U is CH;
W is CH;
Z is N;
X is N;
Y is N;

or pharmaceutically acceptable salts, or enantiomers, or diastereomer thereof.

A further embodiment of present invention is (xlii) a compound of formula I or pharmaceutically acceptable salts, or enantiomers, or diastereomer thereof, wherein $R^1$ is methyl, and all remaining substituents have the significances given herein before.

Another embodiment of present invention is (xliii) a compound of formula I or pharmaceutically acceptable salts, or enantiomers, or diastereomer thereof, wherein $R^2$ is phenyl substituted by one, two or three groups independently selected from halogen, halo$C_{1-6}$alkyl, cyano, hydroxy, halo$C_{1-6}$alkoxy, —O—$C_xH_{2x}$—$R^3$ and —O—$C_yH_{2y}$—$NHR^6$; wherein $R^3$ is hydrogen, $C_{3-7}$cycloalkyl, halo$C_{3-7}$cycloalkyl, hydroxy$C_{1-6}$alkyl$C_{3-7}$cycloalkyl, oxetanyl, tetrahydrofuranyl, tetrahydropyranyl, 1,1-dioxothiolanyl, oxopyrrolidinyl, oxomorpholinyl, —C(=O)$R^4$ or —SO$_2R^5$; wherein $R^4$ is hydroxy, $C_{1-6}$alkoxy, amino, $C_{1-6}$alkylamino or tetrahydrofuranylamino; $R^5$ is $C_{1-6}$alkyl or amino; $R^6$ is hydrogen, $C_{1-6}$alkylcarbonyl, $C_{1-6}$alkoxycarbonyl, $C_{3-7}$cycloalkylsulfonyl or $C_{1-6}$alkoxy$C_{1-6}$alkylsulfonyl; x is 1-6; y is 1-8; and all remaining substituents have the significances given herein before.

A further embodiment of present invention is (xliv) a compound of formula I or pharmaceutically acceptable salts, or enantiomers, or diastereomer thereof, wherein $R^2$ is phenyl substituted by one, two or three groups independently selected from fluoro, chloro, trifluoromethyl, cyano, hydroxy, difluoromethoxy, difluoroethoxy, trifluoroethoxy, methoxy, cyclopropylmethoxy, difluorocyclopropylmethoxy, hydroxymethylcyclopropylmethoxy, oxetanylmethoxy, oxetanylethoxy, tetrahydrofuranylmethoxy, tetrahydropyranylmethoxy, 1,1-dioxothiolanylmethoxy, oxopyrrolidinylpropoxy, oxomorpholinylpropoxy, carboxyhexyl, ethoxycarbonylhexyloxyl, aminocarbonylmethoxy, aminocarbonylpropoxy, aminocarbonylbutoxy, methylaminocarbonylpropoxy, tetrahydrofuranylaminocarbonylmethoxy, methylsulfonylpropoxy, aminosulfonylpropoxy, aminopentoxy, aminohexyloxy, aminooctyloxy, methylcarbonylaminopropoxy, tert-butoxycarbonylaminopropoxy, tert-butoxycarbonylaminopentoxy, tert-butoxycarbonylaminohexyloxy, tert-butoxycarbonylaminoctyloxy, cyclopropylsulfonylaminopropoxy and methoxyethylsulfonylaminopropoxy; and all remaining substituents have the significances given herein before.

Another embodiment of present invention is (xlv) a compound of formula I, wherein
$R^1$ is $C_{1-6}$alkyl, $C_{3-7}$cycloalkyl, hydroxy$C_{1-6}$alkyl, nitro$C_{1-6}$alkyl, $C_{1-6}$alkoxycarbonyl$C_{1-6}$alkyl, carboxy$C_{1-6}$alkyl or di($C_{1-6}$alkoxycarbonyl)methylenyl;
$R^2$ is phenyl substituted by one, two or three groups independently selected from halogen, nitro, $C_{1-6}$alkylsulfonyl, —O—$C_xH_{2x}$—$R^3$ and —O—$C_yH_{2y}$—$NHR^6$; wherein
  $R^3$ is hydrogen, hydroxy, $C_{1-6}$alkoxy, morpholinyl, —C(=O)$R^4$ or —SO$_2$$R^5$; wherein
    $R^4$ is hydroxy, $C_{1-6}$alkoxy, amino, di$C_{1-6}$alkylamino or pyrrolyl;
    $R^5$ is $C_{1-6}$alkyl;
  $R^6$ is hydrogen or $C_{1-6}$alkylsulfonyl;
  x is 1-6;
  y is 1-6;
U is CH;
W is CH;
Z is CH;
X is N;
Y is N;
or pharmaceutically acceptable salts, or enantiomers, or diastereomer thereof.

A further embodiment of present invention is (xlvi) a compound of formula I, wherein
$R^1$ is methyl, ethyl, propyl, cyclopropyl, hydroxyethyl, nitromethyl, ethoxycarbonylmethyl, carboxymethyl or di(methoxycarbonyl)methylenyl;
$R^2$ is phenyl substituted by one, two or three groups independently selected from fluoro, nitro, methylsulfonyl, methoxy, hydroxybutoxy, hydroxypentoxy, methoxyethoxy, morpholinylpropoxy, carboxyethoxy, methoxycarbonylmethoxy, aminocarbonylmethoxy, dimethylaminocarbonylmethoxy, pyrrolylcarbonylmethoxy, methylsulfonylethoxy, methyl sulfonylpropoxy, aminopropoxy and methylsulfonylaminopropoxy;
U is CH;
W is CH;
Z is CH;
X is N;
Y is N;
or pharmaceutically acceptable salts, or enantiomers, or diastereomer thereof.

Particular compounds of formula I according to the invention are the following:
5-methyl-6-(4-nitrophenyl)-2-(2-pyridyl)-7,8-dihydro-5H-pyrido[4,3-d]pyrimidine;
(+)-5-methyl-6-(4-nitrophenyl)-2-(2-pyridyl)-7,8-dihydro-5H-pyrido[4,3-d]pyrimidine;
(−)-5-methyl-6-(4-nitrophenyl)-2-(2-pyridyl)-7,8-dihydro-5H-pyrido[4,3-d]pyrimidine;
5-ethyl-6-(4-methylsulfonylphenyl)-2-(2-pyridyl)-7,8-dihydro-5H-pyrido[4,3-d]pyrimidine;
6-(3,4-difluoro-5-methoxy-phenyl)-5-methyl-2-(2-pyridyl)-7,8-dihydro-5H-pyrido[4,3-d]pyrimidine;
(+)-6-(3,4-difluoro-5-methoxy-phenyl)-5-methyl-2-(2-pyridyl)-7,8-dihydro-5H-pyrido[4,3-d]pyrimidine;
(−)-6-(3,4-difluoro-5-methoxy-phenyl)-5-methyl-2-(2-pyridyl)-7,8-dihydro-5H-pyrido[4,3-d]pyrimidine;
dimethyl 2-[6-(4-methyl sulfonylphenyl)-2-(2-pyridyl)-7,8-dihydro-5H-pyrido[4,3-d]pyrimidin-5-yl]propanedioate;
6-(3,4-difluoro-5-methoxy-phenyl)-5-ethyl-2-(2-pyridyl)-7,8-dihydro-5H-pyrido[4,3-d]pyrimidine;
(+)-6-(3,4-difluoro-5-methoxy-phenyl)-5-ethyl-2-(2-pyridyl)-7,8-dihydro-5H-pyrido[4,3-d]pyrimidine;
(−)-6-(3,4-difluoro-5-methoxy-phenyl)-5-ethyl-2-(2-pyridyl)-7,8-dihydro-5H-pyrido[4,3-d]pyrimidine;
6-(3,4-difluoro-5-methoxy-phenyl)-5-propyl-2-(2-pyridyl)-7,8-dihydro-5H-pyrido[4,3-d]pyrimidine;
(+)-6-(3,4-difluoro-5-methoxy-phenyl)-5-propyl-2-(2-pyridyl)-7,8-dihydro-5H-pyrido[4,3-d]pyrimidine;
(−)-6-(3,4-difluoro-5-methoxy-phenyl)-5-propyl-2-(2-pyridyl)-7,8-dihydro-5H-pyrido[4,3-d]pyrimidine;
6-(3,4-difluoro-5-methoxy-phenyl)-5-methyl-2-pyrimidin-2-yl-7,8-dihydro-5H-pyrido[4,3-d]pyrimidine;
(+)-6-(3,4-difluoro-5-methoxy-phenyl)-5-methyl-2-pyrimidin-2-yl-7,8-dihydro-5H-pyrido[4,3-d]pyrimidine;
(−)-6-(3,4-difluoro-5-methoxy-phenyl)-5-methyl-2-pyrimidin-2-yl-7,8-dihydro-5H-pyrido[4,3-d]pyrimidine;
5-cyclopropyl-6-(3,4-difluoro-5-methoxy-phenyl)-2-(2-pyridyl)-7,8-dihydro-5H-pyrido[4,3-d]pyrimidine;
6-[3,4-difluoro-5-(2-methoxyethoxy)phenyl]-5-methyl-2-(2-pyridyl)-7,8-dihydro-5H-pyrido[4,3-d]pyrimidine;
(+)-6-[3,4-difluoro-5-(2-methoxyethoxy)phenyl]-5-methyl-2-(2-pyridyl)-7,8-dihydro-5H-pyrido[4,3-d]pyrimidine;
(−)-6-[3,4-difluoro-5-(2-methoxyethoxy)phenyl]-5-methyl-2-(2-pyridyl)-7,8-dihydro-5H-pyrido[4,3-d]pyrimidine;
2-fluoro-6-methoxy-4-(5-methyl-2-pyrimidin-2-yl-7,8-dihydro-5H-pyrido[4,3-d]pyrimidin-6-yl)benzonitrile;
5-methyl-6-(4-methylsulfonylphenyl)-2-(2-pyridyl)-7,8-dihydro-5H-pyrido[4,3-d]pyrimidine;
4-[2,3-difluoro-5-[5-methyl-2-(2-pyridyl)-7,8-dihydro-5H-pyrido[4,3-d]pyrimidin-6-yl]phenoxy]butan-1-ol;
5-[2,3-difluoro-5-[5-methyl-2-(2-pyridyl)-7,8-dihydro-5H-pyrido[4,3-d]pyrimidin-6-yl]phenoxy]pentan-1-ol;
6-[3,4-difluoro-5-(2-methylsulfonylethoxy)phenyl]-5-methyl-2-(2-pyridyl)-7,8-dihydro-5H-pyrido[4,3-d]pyrimidine;
methyl 2-[2,3-difluoro-5-[5-methyl-2-(2-pyridyl)-7,8-dihydro-5H-pyrido[4,3-d]pyrimidin-6-yl]phenoxy]acetate;
2-[2,3-difluoro-5-[5-methyl-2-(2-pyridyl)-7,8-dihydro-5H-pyrido[4,3-d]pyrimidin-6-yl]phenoxy]acetic acid;
2-[2,3-difluoro-5-[5-methyl-2-(2-pyridyl)-7,8-dihydro-5H-pyrido[4,3-d]pyrimidin-6-yl]phenoxy]acetamide;
2-[2,3-difluoro-5-[5-methyl-2-(2-pyridyl)-7,8-dihydro-5H-pyrido[4,3-d]pyrimidin-6-yl]phenoxy]-N,N-dimethyl-acetamide;
2-[2,3-difluoro-5-[5-methyl-2-(2-pyridyl)-7,8-dihydro-5H-pyrido[4,3-d]pyrimidin-6-yl]phenoxy]-1-pyrrolidin-1-yl-ethanone;
4-[3-[2,3-difluoro-5-[5-methyl-2-(2-pyridyl)-7,8-dihydro-5H-pyrido[4,3-d]pyrimidin-6-yl]phenoxy]propyl]morpholine;
6-[3,4-difluoro-5-(3-methylsulfonylpropoxy)phenyl]-5-methyl-2-(2-pyridyl)-7,8-dihydro-5H-pyrido[4,3-d]pyrimidine;
3-[2,3-difluoro-5-[5-methyl-2-(2-pyridyl)-7,8-dihydro-5H-pyrido[4,3-d]pyrimidin-6-yl]phenoxy]propan-1-amine;
N-[3-[2,3-difluoro-5-[5-methyl-2-(2-pyridyl)-7,8-dihydro-5H-pyrido[4,3-d]pyrimidin-6-yl]phenoxy]propyl]methanesulfonamide;
ethyl 2-[6-(3,4-difluoro-5-methoxy-phenyl)-2-(2-pyridyl)-7,8-dihydro-5H-pyrido[4,3-d]pyrimidin-5-yl]acetate;
2-[6-(3,4-difluoro-5-methoxy-phenyl)-2-(2-pyridyl)-7,8-dihydro-5H-pyrido[4,3-d]pyrimidin-5-yl]acetic acid;
2-[6-(3,4-difluoro-5-methoxy-phenyl)-2-(2-pyridyl)-7,8-dihydro-5H-pyrido[4,3-d]pyrimidin-5-yl]ethanol;
6-(3,4-difluoro-5-methoxy-phenyl)-5-(nitromethyl)-2-(2-pyridyl)-7,8-dihydro-5H-pyrido[4,3-d]pyrimidine;

6-(4-chloro-3-fluoro-5-methoxy-phenyl)-5-methyl-2-pyrimidin-2-yl-7,8-dihydro-5H-pyrido[4,3-d]pyrimidine;
6-(3-chloro-4-fluoro-5-methoxy-phenyl)-5-methyl-2-pyrimidin-2-yl-7,8-dihydro-5H-pyrido[4,3-d]pyrimidine;
(+)-6-(3-chloro-4-fluoro-5-methoxy-phenyl)-5-methyl-2-pyrimidin-2-yl-7,8-dihydro-5H-pyrido[4,3-d]pyrimidine;
(−)-6-(3-chloro-4-fluoro-5-methoxy-phenyl)-5-methyl-2-pyrimidin-2-yl-7,8-dihydro-5H-pyrido[4,3-d]pyrimidine;
2,3-difluoro-5-(5-methyl-2-pyrimidin-2-yl-7,8-dihydro-5H-pyrido[4,3-d]pyrimidin-6-yl)phenol;
2,3-difluoro-5-[(5R)-5-methyl-2-pyrimidin-2-yl-7,8-dihydro-5H-pyrido[4,3-d]pyrimidin-6-yl]phenol;
2,3-difluoro-5-[(5 S)-5-methyl-2-pyrimidin-2-yl-7,8-dihydro-5H-pyrido[4,3-d]pyrimidin-6-yl]phenol;
6-[3,4-difluoro-5-(3-methylsulfonylpropoxy)phenyl]-5-methyl-2-pyrimidin-2-yl-7,8-dihydro-5H-pyrido[4,3-d]pyrimidine;
(+)-6-[3,4-difluoro-5-(3-methylsulfonylpropoxy)phenyl]-5-methyl-2-pyrimidin-2-yl-7,8-dihydro-5H-pyrido[4,3-d]pyrimidine;
(−)-6-[3,4-difluoro-5-(3-methylsulfonylpropoxy)phenyl]-5-methyl-2-pyrimidin-2-yl-7,8-dihydro-5H-pyrido[4,3-d]pyrimidine;
4-[2,3-difluoro-5-(5-methyl-2-pyrimidin-2-yl-7,8-dihydro-5H-pyrido[4,3-d]pyrimidin-6-yl)phenoxy]butanoic acid;
3-[2,3-difluoro-5-(5-methyl-2-pyrimidin-2-yl-7,8-dihydro-5H-pyrido[4,3-d]pyrimidin-6-yl)phenoxy]propanoic acid;
4-[2,3-difluoro-5-(5-methyl-2-pyrimidin-2-yl-7,8-dihydro-5H-pyrido[4,3-d]pyrimidin-6-yl)phenoxy]butanamide;
4-[2,3-difluoro-5-(5-methyl-2-pyrimidin-2-yl-7,8-dihydro-5H-pyrido[4,3-d]pyrimidin-6-yl)phenoxy]-N-methyl-butanamide;
tert-butyl N-[8-[2,3-difluoro-5-(5-methyl-2-pyrimidin-2-yl-7,8-dihydro-5H-pyrido[4,3-d]pyrimidin-6-yl)phenoxy]octyl]carbamate;
8-[2,3-difluoro-5-(5-methyl-2-pyrimidin-2-yl-7,8-dihydro-5H-pyrido[4,3-d]pyrimidin-6-yl)phenoxy]octan-1-amine;
tert-butyl N-[5-[2,3-difluoro-5-(5-methyl-2-pyrimidin-2-yl-7,8-dihydro-5H-pyrido[4,3-d]pyrimidin-6-yl)phenoxy]pentyl]carbamate;
5-[2,3-difluoro-5-(5-methyl-2-pyrimidin-2-yl-7,8-dihydro-5H-pyrido[4,3-d]pyrimidin-6-yl)phenoxy]pentan-1-amine;
tert-butyl N-[6-[2,3-difluoro-5-(5-methyl-2-pyrimidin-2-yl-7,8-dihydro-5H-pyrido[4,3-d]pyrimidin-6-yl)phenoxy]hexyl]carbamate;
6-[2,3-difluoro-5-(5-methyl-2-pyrimidin-2-yl-7,8-dihydro-5H-pyrido[4,3-d]pyrimidin-6-yl)phenoxy]hexan-1-amine;
(−)-6-[2,3-difluoro-5-[5-methyl-2-pyrimidin-2-yl-7,8-dihydro-5H-pyrido[4,3-d]pyrimidin-6-yl]phenoxy]hexan-1-amine;
(+)-6-[2,3-difluoro-5-[5-methyl-2-pyrimidin-2-yl-7,8-dihydro-5H-pyrido[4,3-d]pyrimidin-6-yl]phenoxy]hexan-1-amine;
methyl 5-[2,3-difluoro-5-(5-methyl-2-pyrimidin-2-yl-7,8-dihydro-5H-pyrido[4,3-d]pyrimidin-6-yl)phenoxy]pentanoate;
5-[2,3-difluoro-5-(5-methyl-2-pyrimidin-2-yl-7,8-dihydro-5H-pyrido[4,3-d]pyrimidin-6-yl)phenoxy]pentanoic acid;
5-[2,3-difluoro-5-(5-methyl-2-pyrimidin-2-yl-7,8-dihydro-5H-pyrido[4,3-d]pyrimidin-6-yl)phenoxy]pentanamide;
2-[2,3-difluoro-5-(5-methyl-2-pyrimidin-2-yl-7,8-dihydro-5H-pyrido[4,3-d]pyrimidin-6-yl)phenoxy]acetic acid;
2-[2,3-difluoro-5-(5-methyl-2-pyrimidin-2-yl-7,8-dihydro-5H-pyrido[4,3-d]pyrimidin-6-yl)phenoxy]acetamide;
(+)-2-[2,3-difluoro-5-[5-methyl-2-pyrimidin-2-yl-7,8-dihydro-5H-pyrido[4,3-d]pyrimidin-6-yl]phenoxy]acetamide;
(−)-2-[2,3-difluoro-5-[5-methyl-2-pyrimidin-2-yl-7,8-dihydro-5H-pyrido[4,3-d]pyrimidin-6-yl]phenoxy]acetamide;
6-[3,4-difluoro-5-(2,2,2-trifluoroethoxy)phenyl]-5-methyl-2-pyrimidin-2-yl-7,8-dihydro-5H-pyrido[4,3-d]pyrimidine;
6-[3-(2,2-difluoroethoxy)-4, 5-difluoro-phenyl]-5-methyl-2-pyrimidin-2-yl-7,8-dihydro-5H-pyrido[4,3-d]pyrimidine;
6-[3-(difluoromethoxy)-4, 5-difluoro-phenyl]-5-methyl-2-pyrimidin-2-yl-7,8-dihydro-5H-pyrido[4,3-d]pyrimidine;
6-(3-fluoro-5-methoxy-phenyl)-5-methyl-2-pyrimidin-2-yl-7,8-dihydro-5H-pyrido[4,3-d]pyrimidine;
(−)-6-(3-fluoro-5-methoxy-phenyl)-5-methyl-2-pyrimidin-2-yl-7,8-dihydro-5H-pyrido[4,3-d]pyrimidine;
(+)-6-(3-fluoro-5-methoxy-phenyl)-5-methyl-2-pyrimidin-2-yl-7,8-dihydro-5H-pyrido[4, 3-d]pyrimidine;
6-[3,4-difluoro-5-(tetrahydrofuran-3-ylmethoxy)phenyl]-5-methyl-2-pyrimidin-2-yl-7,8-dihydro-5H-pyrido[4,3-d]pyrimidine;
6-[3,4-difluoro-5-(oxetan-3-ylmethoxy)phenyl]-5-methyl-2-pyrimidin-2-yl-7,8-dihydro-5H-pyrido[4,3-d]pyrimidine;
[1-[[2,3-difluoro-5-(5-methyl-2-pyrimidin-2-yl-7,8-dihydro-5H-pyrido[4,3-d]pyrimidin-6-yl)phenoxy]methyl]cyclopropyl]methanol;
3-[2,3-difluoro-5-(5-methyl-2-pyrimidin-2-yl-7,8-dihydro-5H-pyrido[4,3-d]pyrimidin-6-yl)phenoxy]propane-1-sulfonic acid;
6-[3,4-difluoro-5-[2-(oxetan-3-yl)ethoxy]phenyl]-5-methyl-2-pyrimidin-2-yl-7,8-dihydro-5H-pyrido[4,3-d]pyrimidine;
4-[3-[2,3-difluoro-5-(5-methyl-2-pyrimidin-2-yl-7,8-dihydro-5H-pyrido[4,3-d]pyrimidin-6-yl)phenoxy]propyl]morpholin-3-one;
6-[3-fluoro-5-(trifluoromethyl)phenyl]-5-methyl-2-pyrimidin-2-yl-7,8-dihydro-5H-pyrido[4,3-d]pyrimidine;
6-[3-[(2,2-difluorocyclopropyl)methoxy]-5-fluoro-phenyl]-5-methyl-2-pyrimidin-2-yl-7,8-dihydro-5H-pyrido[4,3-d]pyrimidine;
2-[2,3-difluoro-5-(5-methyl-2-pyrimidin-2-yl-7,8-dihydro-5H-pyrido[4,3-d]pyrimidin-6-yl)phenoxy]-N-tetrahydrofuran-3-yl-acetamide;
2-[2,3-difluoro-5-(5-methyl-2-pyrimidin-2-yl-7,8-dihydro-5H-pyrido[4,3-d]pyrimidin-6-yl)phenoxy]-1-morpholino-ethanone;
ethyl 7-[2,3-difluoro-5-(5-methyl-2-pyrimidin-2-yl-7,8-dihydro-5H-pyrido[4,3-d]pyrimidin-6-yl)phenoxy]heptanoate;
7-[2,3-difluoro-5-(5-methyl-2-pyrimidin-2-yl-7,8-dihydro-5H-pyrido[4,3-d]pyrimidin-6-yl)phenoxy]heptanoic acid;
7-[2,3-difluoro-5-(5-methyl-2-pyrimidin-2-yl-7,8-dihydro-5H-pyrido[4,3-d]pyrimidin-6-yl)phenoxy]heptanamide;
6-[3-(cyclopropylmethoxy)-4, 5-difluoro-phenyl]-5-methyl-2-pyrimidin-2-yl-7,8-dihydro-5H-pyrido[4,3-d]pyrimidine;
6-[3,4-difluoro-5-(tetrahydropyran-4-ylmethoxy)phenyl]-5-methyl-2-pyrimidin-2-yl-7,8-dihydro-5H-pyrido[4,3-d]pyrimidine;
tert-butyl N-[3-[2,3-difluoro-5-(5-methyl-2-pyrimidin-2-yl-7,8-dihydro-5H-pyrido[4,3-d]pyrimidin-6-yl)phenoxy]propyl]carbamate;
3-[2,3-difluoro-5-(5-methyl-2-pyrimidin-2-yl-7,8-dihydro-5H-pyrido[4,3-d]pyrimidin-6-yl)phenoxy]propan-1-amine;

N-[3-[2,3-difluoro-5-(5-methyl-2-pyrimidin-2-yl-7,8-dihydro-5H-pyrido[4,3-d]pyrimidin-6-yl)phenoxy]propyl]acetamide;
N-[3-[2,3-difluoro-5-(5-methyl-2-pyrimidin-2-yl-7,8-dihydro-5H-pyrido[4,3-d]pyrimidin-6-yl)phenoxy]propyl]cyclopropanesulfonamide;
N-[3-[2,3-difluoro-5-(5-methyl-2-pyrimidin-2-yl-7,8-dihydro-5H-pyrido[4,3-d]pyrimidin-6-yl)phenoxy]propyl]-2-methoxy-ethanesulfonamide;
4-chloro-N-[3-[2,3-difluoro-5-(5-methyl-2-pyrimidin-2-yl-7,8-dihydro-5H-pyrido[4,3-d]pyrimidin-6-yl)phenoxy]propyl]butanamide;
1-[3-[2,3-difluoro-5-(5-methyl-2-pyrimidin-2-yl-7,8-dihydro-5H-pyrido[4,3-d]pyrimidin-6-yl)phenoxy]propyl]pyrrolidin-2-one;
3-[2,3-difluoro-5-(5-methyl-2-pyrimidin-2-yl-7,8-dihydro-5H-pyrido[4,3-d]pyrimidin-6-yl)phenoxy]propane-1-sulfonamide;
tert-butyl 4-[3-[2,3-difluoro-5-(5-methyl-2-pyrimidin-2-yl-7,8-dihydro-5H-pyrido[4,3-d]pyrimidin-6-yl)phenoxy]propyl]-3-oxo-piperazine-1-carboxylate;
1-[3-[2,3-difluoro-5-(5-methyl-2-pyrimidin-2-yl-7,8-dihydro-5H-pyrido[4,3-d]pyrimidin-6-yl)phenoxy]propyl]piperazin-2-one;
3-[[3-fluoro-5-(5-methyl-2-pyrimidin-2-yl-7,8-dihydro-5H-pyrido[4,3-d]pyrimidin-6-yl)phenoxy]methyl]thiolane 1,1-dioxide;
6-[3,4-difluoro-5-[3-(4-methylpiperazin-1-yl)propoxy]phenyl]-5-methyl-2-pyrimidin-2-yl-7,8-dihydro-5H-pyrido[4,3-d]pyrimidine;
methyl 2-(tert-butoxycarbonylamino)-4-[2,3-difluoro-5-(5-methyl-2-pyrimidin-2-yl-7,8-dihydro-5H-pyrido[4,3-d]pyrimidin-6-yl)phenoxy]butanoate;
2-(tert-butoxycarbonylamino)-4-[2,3-difluoro-5-(5-methyl-2-pyrimidin-2-yl-7,8-dihydro-5H-pyrido[4,3-d]pyrimidin-6-yl)phenoxy]butanoic acid;
2-amino-4-[2,3-difluoro-5-(5-methyl-2-pyrimidin-2-yl-7,8-dihydro-5H-pyrido[4,3-d]pyrimidin-6-yl)phenoxy]butanoic acid;
6-[3,4-difluoro-5-(2-tetrahydrofuran-2-ylethoxy)phenyl]-5-methyl-2-pyrimidin-2-yl-7,8-dihydro-5H-pyrido[4,3-d]pyrimidine;
6-[3,4-difluoro-5-(3-methylsulfinylpropoxy)phenyl]-5-methyl-2-pyrimidin-2-yl-7,8-dihydro-5H-pyrido[4,3-d]pyrimidine;
4-[3-[2,3-difluoro-5-(5-methyl-2-pyrimidin-2-yl-7,8-dihydro-5H-pyrido[4,3-d]pyrimidin-6-yl)phenoxy]propyl]piperazin-2-one;
tert-butyl 4-[3-[2,3-difluoro-5-(5-methyl-2-pyrimidin-2-yl-7,8-dihydro-5H-pyrido[4,3-d]pyrimidin-6-yl)phenoxy]propyl]piperazine-1-carboxylate;
1-[4-[3-[2,3-difluoro-5-(5-methyl-2-pyrimidin-2-yl-7,8-dihydro-5H-pyrido[4,3-d]pyrimidin-6-yl)phenoxy]propyl]piperazin-1-yl]ethanone;
6-[3,4-difluoro-5-[3-(4-methylsulfonylpiperazin-1-yl)propoxy]phenyl]-5-methyl-2-pyrimidin-2-yl-7,8-dihydro-5H-pyrido[4,3-d]pyrimidine;
6-(3-fluoro-4-iodo-5-methoxy-phenyl)-5-methyl-2-pyrimidin-2-yl-7,8-dihydro-5H-pyrido[4,3-d]pyrimidine;
6-[3-methoxy-5-(trifluoromethyl)phenyl]-5-methyl-2-pyrimidin-2-yl-7,8-dihydro-5H-pyrido[4,3-d]pyrimidine;
1-[3-[2,3-difluoro-5-(5-methyl-2-pyrimidin-2-yl-7,8-dihydro-5H-pyrido[4,3-d]pyrimidin-6-yl)phenoxy]propyl]imidazolidin-2-one;
6-[3,4-difluoro-5-(2-tetrahydrofuran-3-ylethoxy)phenyl]-5-methyl-2-pyrimidin-2-yl-7,8-dihydro-5H-pyrido[4,3-d]pyrimidine;
tert-butyl 3-[2-[2,3-difluoro-5-(5-methyl-2-pyrimidin-2-yl-7,8-dihydro-5H-pyrido[4,3-d]pyrimidin-6-yl)phenoxy]ethyl]azetidine-1-carboxylate;
6-[3-[2-(azetidin-3-yl)ethoxy]-4,5-difluoro-phenyl]-5-methyl-2-pyrimidin-2-yl-7,8-dihydro-5H-pyrido[4,3-d]pyrimidine;
1-[3-[2-[2,3-difluoro-5-(5-methyl-2-pyrimidin-2-yl-7,8-dihydro-5H-pyrido[4,3-d]pyrimidin-6-yl)phenoxy]ethyl]azetidin-1-yl]ethanone;
6-[3,4-difluoro-5-[2-(1-methylsulfonylazetidin-3-yl)ethoxy]phenyl]-5-methyl-2-pyrimidin-2-yl-7,8-dihydro-5H-pyrido[4,3-d]pyrimidine;
6-[3,4-difluoro-5-(thietan-3-ylmethoxy)phenyl]-5-methyl-2-pyrimidin-2-yl-7,8-dihydro-5H-pyrido[4,3-d]pyrimidine;
3-[[2,3-difluoro-5-(5-methyl-2-pyrimidin-2-yl-7,8-dihydro-5H-pyrido[4,3-d]pyrimidin-6-yl)phenoxy]methyl]thietane 1,1-dioxide;
6-(3,4-difluoro-5-tetrahydrofuran-3-yloxy-phenyl)-(5R/S)-methyl-2-pyrimidin-2-yl-7,8-dihydro-5H-pyrido[4,3-d]pyrimidine;
6-[3,4-difluoro-5-(tetrahydrofuran-2-ylmethoxy)phenyl]-(5R/S)-methyl-2-pyrimidin-2-yl-7,8-dihydro-5H-pyrido[4,3-d]pyrimidine;
(+)-6-(2,6-dichloro-3-fluoro-5-methoxy-phenyl)-5-methyl-2-pyrimidin-2-yl-7,8-dihydro-5H-pyrido[4,3-d]pyrimidine;
(+)-6-(2,4-dichloro-5-fluoro-3-methoxy-phenyl)-5-methyl-2-pyrimidin-2-yl-7,8-dihydro-5H-pyrido[4,3-d]pyrimidine;
(+)-6-(2,4-dichloro-3-fluoro-5-methoxy-phenyl)-5-methyl-2-pyrimidin-2-yl-7,8-dihydro-5H-pyrido[4,3-d]pyrimidine;
6-(6-chloro-4-methoxy-2-pyridyl)-5-methyl-2-(2-pyridyl)-7,8-dihydro-5H-pyrido[4,3-d]pyrimidine;
6-(6-fluoro-4-methoxy-2-pyridyl)-5-methyl-2-pyrimidin-2-yl-7,8-dihydro-5H-pyrido[4,3-d]pyrimidine;
6-(6-fluoro-5-iodo-4-methoxy-2-pyridyl)-5-methyl-2-pyrimidin-2-yl-7,8-dihydro-5H-pyrido[4,3-d]pyrimidine;
6-(2-fluoro-6-methoxy-4-pyridyl)-5-methyl-2-pyrimidin-2-yl-7,8-dihydro-5H-pyrido[4,3-d]pyrimidine;
(−)-6-(2-chloro-3-fluoro-5-methoxy-phenyl)-5-methyl-2-pyrimidin-2-yl-7,8-dihydro-5H-pyrido[4,3-d]pyrimidine;
(−)-6-(2-chloro-5-fluoro-3-methoxy-phenyl)-5-methyl-2-pyrimidin-2-yl-7,8-dihydro-5H-pyrido[4,3-d]pyrimidine;
tert-butyl 3-[[2,3-difluoro-5-(5-methyl-2-pyrimidin-2-yl-7,8-dihydro-5H-pyrido[4,3-d]pyrimidin-6-yl)phenoxy]methyl]azetidine-1-carboxylate;
6-[3-fluoro-5-(trifluoromethoxy)phenyl]-5-methyl-2-pyrimidin-2-yl-7,8-dihydro-5H-pyrido[4,3-d]pyrimidine;
6-(3-fluoro-5-methyl-phenyl)-5-methyl-2-pyrimidin-2-yl-7,8-dihydro-5H-pyrido[4,3-d]pyrimidine;
2-(3-fluoro-5-methoxy-phenyl)-1-methyl-6-pyrimidin-2-yl-3,4-dihydro-1H-2,7-naphthyridine;
2-[3-fluoro-5-methoxy-4-(4-pyridyl)phenyl]-1-methyl-6-pyrimidin-2-yl-3,4-dihydro-1H-2,7-naphthyridine;
6-(3-cyclopropyl-5-fluoro-phenyl)-5-methyl-2-pyrimidin-2-yl-7,8-dihydro-5H-pyrido[4,3-d]pyrimidine;
(−)-6-(6-fluoro-4-methoxy-2-pyridyl)-5-methyl-2-pyrimidin-2-yl-7,8-dihydro-5H-pyrido[4,3-d]pyrimidine;
(+)-6-(6-fluoro-4-methoxy-2-pyridyl)-5-methyl-2-pyrimidin-2-yl-7,8-dihydro-5H-pyrido[4,3-d]pyrimidine;
6-(4-chloro-6-methoxy-2-pyridyl)-5-methyl-2-pyrimidin-2-yl-7,8-dihydro-5H-pyrido[4,3-d]pyrimidine;
6-(2-chloro-6-methoxy-4-pyridyl)-5-methyl-2-pyrimidin-2-yl-7,8-dihydro-5H-pyrido[4,3-d]pyrimidine;

6-(4-fluoro-6-methoxy-2-pyridyl)-5-methyl-2-pyrimidin-2-yl-7,8-dihydro-5H-pyrido[4,3-d]pyrimidine;
6-[3-(2,2-difluoroethoxy)-5-fluoro-phenyl]-5-methyl-2-pyrimidin-2-yl-7,8-dihydro-5H-pyrido[4,3-d]pyrimidine;
6-[3-fluoro-5-(2,2,2-trifluoroethoxy)phenyl]-5-methyl-2-pyrimidin-2-yl-7,8-dihydro-5H-pyrido[4,3-d]pyrimidine;
6-[3-(cyclopropylmethoxy)-5-fluoro-phenyl]-5-methyl-2-pyrimidin-2-yl-7,8-dihydro-5H-pyrido[4,3-d]pyrimidine;
(−)-6-(5-chloro-6-fluoro-4-methoxy-2-pyridyl)-5-methyl-2-pyrimidin-2-yl-7,8-dihydro-5H-pyrido[4,3-d]pyrimidine;
(−)-6-(3-chloro-6-fluoro-4-methoxy-2-pyridyl)-5-methyl-2-pyrimidin-2-yl-7,8-dihydro-5H-pyrido[4,3-d]pyrimidine;
6-[6-(2,2-difluoroethoxy)-4-fluoro-2-pyridyl]-5-methyl-2-pyrimidin-2-yl-7,8-dihydro-5H-pyrido[4,3-d]pyrimidine;
6-[4-(2,2-difluoroethoxy)-6-fluoro-2-pyridyl]-5-methyl-2-pyrimidin-2-yl-7,8-dihydro-5H-pyrido[4,3-d]pyrimidine;
6-[2-(2,2-difluoroethoxy)-6-fluoro-4-pyridyl]-5-methyl-2-pyrimidin-2-yl-7,8-dihydro-5H-pyrido[4,3-d]pyrimidine;
6-[6-fluoro-4-(tetrahydropyran-4-ylmethoxy)-2-pyridyl]-5-methyl-2-pyrimidin-2-yl-7,8-dihydro-5H-pyrido[4,3-d]pyrimidine;
6-[4-(cyclopropylmethoxy)-6-fluoro-2-pyridyl]-5-methyl-2-pyrimidin-2-yl-7,8-dihydro-5H-pyrido[4,3-d]pyrimidine;
6-(6-fluoro-4-methoxy-2-pyridyl)-5-methyl-2-(2-pyridyl)-7,8-dihydro-5H-pyrido[4,3-d]pyrimidine;
6-[6-fluoro-4-(tetrahydrofuran-3-ylmethoxy)-2-pyridyl]-5-methyl-2-pyrimidin-2-yl-7,8-dihydro-5H-pyrido[4,3-d]pyrimidine;
(−)-7-[[2-fluoro-6-[5-methyl-2-pyrimidin-2-yl-7,8-dihydro-5H-pyrido[4,3-d]pyrimidin-6-yl]-4-pyridyl]oxy]heptanoic acid;
(−)-7-[[2-fluoro-6-[5-methyl-2-pyrimidin-2-yl-7,8-dihydro-5H-pyrido[4,3-d]pyrimidin-6-yl]-4-pyridyl]oxy]heptanamide;
(−)-5-[[2-fluoro-6-[5-methyl-2-pyrimidin-2-yl-7,8-dihydro-5H-pyrido[4,3-d]pyrimidin-6-yl]-4-pyridyl]oxy]pentanoic acid;
(−)-5-[[2-fluoro-6-[5-methyl-2-pyrimidin-2-yl-7,8-dihydro-5H-pyrido[4,3-d]pyrimidin-6-yl]-4-pyridyl]oxy]pentanamide;
6-[6-fluoro-4-[(1-methylsulfonylazetidin-3-yl)methoxy]-2-pyridyl]-5-methyl-2-pyrimidin-2-yl-7,8-dihydro-5H-pyrido[4,3-d]pyrimidine;
1-[3-[[2-fluoro-6-(5-methyl-2-pyrimidin-2-yl-7,8-dihydro-5H-pyrido[4,3-d]pyrimidin-6-yl)-4-pyridyl]oxymethyl]azetidin-1-yl]ethanone;
6-(4-methoxy-6-methyl-2-pyridyl)-5-methyl-2-pyrimidin-2-yl-7,8-dihydro-5H-pyrido[4,3-d]pyrimidine;
2-[3-[[2-fluoro-6-(5-methyl-2-pyrimidin-2-yl-7,8-dihydro-5H-pyrido[4,3-d]pyrimidin-6-yl)-4-pyridyl]oxy]propoxy]acetic acid;
2-[3-[[2-fluoro-6-(5-methyl-2-pyrimidin-2-yl-7,8-dihydro-5H-pyrido[4,3-d]pyrimidin-6-yl)-4-pyridyl]oxy]propoxy]acetamide;
(−)-6-[[2-fluoro-6-[5-methyl-2-pyrimidin-2-yl-7,8-dihydro-5H-pyrido[4,3-d]pyrimidin-6-yl]-4-pyridyl]oxy]hexanoic acid;
(−)-6-[[2-fluoro-6-[5-methyl-2-pyrimidin-2-yl-7,8-dihydro-5H-pyrido[4,3-d]pyrimidin-6-yl]-4-pyridyl]oxy]hexanamide;
6-[6-fluoro-4-(tetrahydrofuran-2-ylmethoxy)-2-pyridyl]-5-methyl-2-pyrimidin-2-yl-7,8-dihydro-5H-pyrido[4,3-d]pyrimidine;
methyl 8-[[2-fluoro-6-(5-methyl-2-pyrimidin-2-yl-7,8-dihydro-5H-pyrido[4,3-d]pyrimidin-6-yl)-4-pyridyl]oxy]octanoate;
8-[[2-fluoro-6-(5-methyl-2-pyrimidin-2-yl-7,8-dihydro-5H-pyrido[4,3-d]pyrimidin-6-yl)-4-pyridyl]oxy]octanoic acid;
8-[[2-fluoro-6-(5-methyl-2-pyrimidin-2-yl-7,8-dihydro-5H-pyrido[4,3-d]pyrimidin-6-yl)-4-pyridyl]oxy]octanamide;
6-[[2-fluoro-6-[5-methyl-2-(2-pyridyl)-7,8-dihydro-5H-pyrido[4,3-d]pyrimidin-6-yl]-4-pyridyl]oxy]hexanoic acid;
6-[[2-fluoro-6-[5-methyl-2-(2-pyridyl)-7,8-dihydro-5H-pyrido[4,3-d]pyrimidin-6-yl]-4-pyridyl]oxy]hexanamide;
6-(6-fluoro-4-tetrahydropyran-4-yloxy-2-pyridyl)-5-methyl-2-pyrimidin-2-yl-7,8-dihydro-5H-pyrido[4,3-d]pyrimidine;
6-(4-fluoro-6-tetrahydropyran-4-yloxy-2-pyridyl)-5-methyl-2-pyrimidin-2-yl-7,8-dihydro-5H-pyrido[4,3-d]pyrimidine;
2-[[2-fluoro-6-(5-methyl-2-pyrimidin-2-yl-7,8-dihydro-5H-pyrido[4,3-d]pyrimidin-6-yl)-4-pyridyl]oxy]acetamide;
methyl 3-fluoro-5-(5-methyl-2-pyrimidin-2-yl-7,8-dihydro-5H-pyrido[4,3-d]pyrimidin-6-yl)benzoate;
3-fluoro-5-(5-methyl-2-pyrimidin-2-yl-7,8-dihydro-5H-pyrido[4,3-d]pyrimidin-6-yl)benzoic acid;
3-fluoro-N-(3-methoxypropyl)-5-(5-methyl-2-pyrimidin-2-yl-7,8-dihydro-5H-pyrido[4,3-d]pyrimidin-6-yl)benzamide;
3-fluoro-N-(3-methoxypropyl)-N-methyl-5-(5-methyl-2-pyrimidin-2-yl-7,8-dihydro-5H-pyrido[4,3-d]pyrimidin-6-yl)benzamide;
7-[[2-fluoro-6-[5-methyl-2-(2-pyridyl)-7,8-dihydro-5H-pyrido[4,3-d]pyrimidin-6-yl]-4-pyridyl]oxy]heptanoic acid;
7-[[2-fluoro-6-[5-methyl-2-(2-pyridyl)-7,8-dihydro-5H-pyrido[4,3-d]pyrimidin-6-yl]-4-pyridyl]oxy]heptanamide;
(−)-4-[3-[[2-fluoro-6-[5-methyl-2-pyrimidin-2-yl-7,8-dihydro-5H-pyrido[4,3-d]pyrimidin-6-yl]-4-pyridyl]oxy]propyl]morpholin-3-one;
3-fluoro-N-(3-methoxypropyl)-5-(5-methyl-2-pyrimidin-2-yl-7,8-dihydro-5H-pyrido[4,3-d]pyrimidin-6-yl)benzenesulfonamide;
3-fluoro-N-(3-methoxypropyl)-N-methyl-5-(5-methyl-2-pyrimidin-2-yl-7,8-dihydro-5H-pyrido[4,3-d]pyrimidin-6-yl)benzenesulfonamide;
(−)-4-[[2-fluoro-6-[5-methyl-2-pyrimidin-2-yl-7,8-dihydro-5H-pyrido[4,3-d]pyrimidin-6-yl]-4-pyridyl]oxy]butanoic acid;
(−)-4-[[2-fluoro-6-[5-methyl-2-pyrimidin-2-yl-7,8-dihydro-5H-pyrido[4,3-d]pyrimidin-6-yl]-4-pyridyl]oxy]butanamide;
2-[3-[[2-fluoro-6-[5-methyl-2-(2-pyridyl)-7,8-dihydro-5H-pyrido[4,3-d]pyrimidin-6-yl]-4-pyridyl]oxy]propoxy]acetamide;
6-[3-fluoro-5-(3-methoxypropylsulfonyl)phenyl]-5-methyl-2-pyrimidin-2-yl-7,8-dihydro-5H-pyrido[4,3-d]pyrimidine;
6-[6-fluoro-4-(tetrahydrofuran-3-ylmethoxy)-2-pyridyl]-5-methyl-2-(2-pyridyl)-7,8-dihydro-5H-pyrido[4,3-d]pyrimidine;
6-[6-fluoro-4-(tetrahydrofuran-2-ylmethoxy)-2-pyridyl]-5-methyl-2-(2-pyridyl)-7,8-dihydro-5H-pyrido[4,3-d]pyrimidine;
6-[6-fluoro-4-(tetrahydropyran-4-ylmethoxy)-2-pyridyl]-5-methyl-2-(2-pyridyl)-7,8-dihydro-5H-pyrido[4,3-d]pyrimidine;
6-[4-(cyclopropylmethoxy)-6-fluoro-2-pyridyl]-5-methyl-2-(2-pyridyl)-7,8-dihydro-5H-pyrido[4,3-d]pyrimidine;

6-[4-(2,2-difluoroethoxy)-6-fluoro-2-pyridyl]-5-methyl-2-(2-pyridyl)-7,8-dihydro-5H-pyrido[4,3-d]pyrimidine;
6-[6-(2,2-difluoroethoxy)-4-fluoro-2-pyridyl]-5-methyl-2-(2-pyridyl)-7,8-dihydro-5H-pyrido[4,3-d]pyrimidine;
6-[6-fluoro-4-(thietan-3-ylmethoxy)-2-pyridyl]-5-methyl-2-(2-pyridyl)-7,8-dihydro-5H-pyrido[4,3-d]pyrimidine;
3-[[2-fluoro-6-(5-methyl-2-pyrimidin-2-yl-7,8-dihydro-5H-pyrido[4,3-d]pyrimidin-6-yl)-4-pyridyl]oxymethyl]thietane 1,1-dioxide;
2-fluoro-N,N-dimethyl-6-(5-methyl-2-pyrimidin-2-yl-7,8-dihydro-5H-pyrido[4,3-d]pyrimidin-6-yl)pyridin-4-amine;
4-fluoro-N,N-dimethyl-6-(5-methyl-2-pyrimidin-2-yl-7,8-dihydro-5H-pyrido[4,3-d]pyrimidin-6-yl)pyridin-2-amine;
6-(6-fluoro-4-pyrrolidin-1-yl-2-pyridyl)-5-methyl-2-pyrimidin-2-yl-7,8-dihydro-5H-pyrido[4,3-d]pyrimidine;
6-(4-fluoro-6-pyrrolidin-1-yl-2-pyridyl)-5-methyl-2-pyrimidin-2-yl-7,8-dihydro-5H-pyrido[4,3-d]pyrimidine;
(−)-6-(6-fluoro-4-pyrrolidin-1-yl-2-pyridyl)-5-methyl-2-pyrimidin-2-yl-7,8-dihydro-5H-pyrido[4,3-d]pyrimidine;
(+)-6-(6-fluoro-4-pyrrolidin-1-yl-2-pyridyl)-5-methyl-2-pyrimidin-2-yl-7,8-dihydro-5H-pyrido[4,3-d]pyrimidine;
4-[2-fluoro-6-(5-methyl-2-pyrimidin-2-yl-7,8-dihydro-5H-pyrido[4,3-d]pyrimidin-6-yl)-4-pyridyl]morpholine;
(−)-2-fluoro-N-methyl-6-[5-methyl-2-pyrimidin-2-yl-7,8-dihydro-5H-pyrido[4,3-d]pyrimidin-6-yl]pyridin-4-amine;
(+)-4-fluoro-N,N-dimethyl-6-[5-methyl-2-pyrimidin-2-yl-7,8-dihydro-5H-pyrido[4,3-d]pyrimidin-6-yl]pyridin-2-amine;
(−)-4-fluoro-N,N-dimethyl-6-[5-methyl-2-pyrimidin-2-yl-7,8-dihydro-5H-pyrido[4,3-d]pyrimidin-6-yl]pyridin-2-amine;
(+)-2-fluoro-N,N-dimethyl-6-[5-methyl-2-pyrimidin-2-yl-7,8-dihydro-5H-pyrido[4,3-d]pyrimidin-6-yl]pyridin-4-amine;
(−)-2-fluoro-N,N-dimethyl-6-[5-methyl-2-pyrimidin-2-yl-7,8-dihydro-5H-pyrido[4,3-d]pyrimidin-6-yl]pyridin-4-amine;
6-(6-fluoro-4-piperazin-1-yl-2-pyridyl)-5-methyl-2-pyrimidin-2-yl-7,8-dihydro-5H-pyrido[4,3-d]pyrimidine;
6-(4-fluoro-6-piperazin-1-yl-2-pyridyl)-5-methyl-2-pyrimidin-2-yl-7,8-dihydro-5H-pyrido[4,3-d]pyrimidine;
2-fluoro-6-(5-methyl-2-pyrimidin-2-yl-7,8-dihydro-5H-pyrido[4,3-d]pyrimidin-6-yl)pyridin-4-amine;
N-[2-fluoro-6-(5-methyl-2-pyrimidin-2-yl-7,8-dihydro-5H-pyrido[4,3-d]pyrimidin-6-yl)-4-pyridyl]methanesulfonamide;
N-[4-fluoro-6-(5-methyl-2-pyrimidin-2-yl-7,8-dihydro-5H-pyrido[4,3-d]pyrimidin-6-yl)-2-pyridyl]methanesulfonamide;
(−)-N,N,6-trimethyl-2-[5-methyl-2-pyrimidin-2-yl-7,8-dihydro-5H-pyrido[4,3-d]pyrimidin-6-yl]pyrimidin-4-amine;
4-[4-fluoro-6-(5-methyl-2-pyrimidin-2-yl-7,8-dihydro-5H-pyrido[4,3-d]pyrimidin-6-yl)-2-pyridyl]piperazin-2-one;
4-[2-fluoro-6-(5-methyl-2-pyrimidin-2-yl-7,8-dihydro-5H-pyrido[4,3-d]pyrimidin-6-yl)-4-pyridyl]piperazin-2-one;
2-fluoro-N,N-dimethyl-6-[5-methyl-2-(2-pyridyl)-7,8-dihydro-5H-pyrido[4,3-d]pyrimidin-6-yl]pyridin-4-amine;
4-fluoro-N,N-dimethyl-6-[5-methyl-2-(2-pyridyl)-7,8-dihydro-5H-pyrido[4,3-d]pyrimidin-6-yl]pyridin-2-amine;
6-[6-fluoro-4-(1-piperidyl)-2-pyridyl]-5-methyl-2-(2-pyridyl)-7,8-dihydro-5H-pyrido[4,3-d]pyrimidine;
6-[4-fluoro-6-(1-piperidyl)-2-pyridyl]-5-methyl-2-(2-pyridyl)-7,8-dihydro-5H-pyrido[4,3-d]pyrimidine;
4-[2-fluoro-6-[5-methyl-2-(2-pyridyl)-7,8-dihydro-5H-pyrido[4,3-d]pyrimidin-6-yl]-4-pyridyl]morpholine;
4-[4-fluoro-6-[5-methyl-2-(2-pyridyl)-7,8-dihydro-5H-pyrido[4,3-d]pyrimidin-6-yl]-2-pyridyl]morpholine;
4-[2-fluoro-6-[5-methyl-2-(2-pyridyl)-7,8-dihydro-5H-pyrido[4,3-d]pyrimidin-6-yl]-4-pyridyl]piperazin-2-one;
4-[4-fluoro-6-[5-methyl-2-(2-pyridyl)-7,8-dihydro-5H-pyrido[4,3-d]pyrimidin-6-yl]-2-pyridyl]piperazin-2-one;
6-(6-fluoro-4-pyrrolidin-1-yl-2-pyridyl)-5-methyl-2-(2-pyridyl)-7,8-dihydro-5H-pyrido[4,3-d]pyrimidine;
(−)-4-[4-fluoro-6-(5-methyl-2-pyrimidin-2-yl-7,8-dihydro-5H-pyrido[4,3-d]pyrimidin-6-yl)-2-pyridyl]piperazin-2-one;

or pharmaceutically acceptable salts, or enantiomers, or diastereomer thereof.

More particularly, the invention relates to the following compounds of formula I:
(−)-6-(3,4-difluoro-5-methoxy-phenyl)-5-methyl-2-(2-pyridyl)-7,8-dihydro-5H-pyrido[4,3-d]pyrimidine;
6-(3,4-difluoro-5-methoxy-phenyl)-5-methyl-2-pyrimidin-2-yl-7,8-dihydro-5H-pyrido[4,3-d]pyrimidine;
(−)-6-(3,4-difluoro-5-methoxy-phenyl)-5-methyl-2-pyrimidin-2-yl-7,8-dihydro-5H-pyrido[4,3-d]pyrimidine;
2-fluoro-6-methoxy-4-(5-methyl-2-pyrimidin-2-yl-7,8-dihydro-5H-pyrido[4,3-d]pyrimidin-6-yl)benzonitrile;
6-(3-chloro-4-fluoro-5-methoxy-phenyl)-5-methyl-2-pyrimidin-2-yl-7,8-dihydro-5H-pyrido[4,3-d]pyrimidine;
(−)-6-(3-chloro-4-fluoro-5-methoxy-phenyl)-5-methyl-2-pyrimidin-2-yl-7,8-dihydro-5H-pyrido[4,3-d]pyrimidine;
(−)-6-[3,4-difluoro-5-(3-methylsulfonylpropoxy)phenyl]-5-methyl-2-pyrimidin-2-yl-7,8-dihydro-5H-pyrido[4,3-d]pyrimidine;
(−)-6-[2,3-difluoro-5-[5-methyl-2-pyrimidin-2-yl-7,8-dihydro-5H-pyrido[4,3-d]pyrimidin-6-yl]phenoxy]hexan-1-amine;
(−)-2-[2,3-difluoro-5-[5-methyl-2-pyrimidin-2-yl-7,8-dihydro-5H-pyrido[4,3-d]pyrimidin-6-yl]phenoxy]acetamide;
6-[3,4-difluoro-5-(2,2,2-trifluoroethoxy)phenyl]-5-methyl-2-pyrimidin-2-yl-7,8-dihydro-5H-pyrido[4,3-d]pyrimidine;
6-[3-(2,2-difluoroethoxy)-4, 5-difluoro-phenyl]-5-methyl-2-pyrimidin-2-yl-7,8-dihydro-5H-pyrido[4,3-d]pyrimidine;
6-(3-fluoro-5-methoxy-phenyl)-5-methyl-2-pyrimidin-2-yl-7,8-dihydro-5H-pyrido[4,3-d]pyrimidine;
(−)-6-(3-fluoro-5-methoxy-phenyl)-5-methyl-2-pyrimidin-2-yl-7,8-dihydro-5H-pyrido[4,3-d]pyrimidine;
6-[3,4-difluoro-5-(tetrahydrofuran-3-ylmethoxy)phenyl]-5-methyl-2-pyrimidin-2-yl-7,8-dihydro-5H-pyrido[4,3-d]pyrimidine;
6-[3,4-difluoro-5-(oxetan-3-ylmethoxy)phenyl]-5-methyl-2-pyrimidin-2-yl-7,8-dihydro-5H-pyrido[4,3-d]pyrimidine;
6-[3,4-difluoro-5-[2-(oxetan-3-yl)ethoxy]phenyl]-5-methyl-2-pyrimidin-2-yl-7,8-dihydro-5H-pyrido[4,3-d]pyrimidine;
6-[3-[(2,2-difluorocyclopropyl)methoxy]-5-fluoro-phenyl]-5-methyl-2-pyrimidin-2-yl-7,8-dihydro-5H-pyrido[4,3-d]pyrimidine;
6-[3-(cyclopropylmethoxy)-4, 5-difluoro-phenyl]-5-methyl-2-pyrimidin-2-yl-7,8-dihydro-5H-pyrido[4,3-d]pyrimidine;
6-[3,4-difluoro-5-(tetrahydropyran-4-ylmethoxy)phenyl]-5-methyl-2-pyrimidin-2-yl-7,8-dihydro-5H-pyrido[4,3-d]pyrimidine;

tert-butyl N-[3-[2,3-difluoro-5-(5-methyl-2-pyrimidin-2-yl-7,8-dihydro-5H-pyrido[4,3-d]pyrimidin-6-yl)phenoxy]propyl]carbamate;
6-[3,4-difluoro-5-[2-(1-methylsulfonylazetidin-3-yl)ethoxy]phenyl]-5-methyl-2-pyrimidin-2-yl-7,8-dihydro-5H-pyrido[4,3-d]pyrimidine;
6-[3,4-difluoro-5-(tetrahydrofuran-2-ylmethoxy)phenyl]-(5R/S)-methyl-2-pyrimidin-2-yl-7,8-dihydro-5H-pyrido[4,3-d]pyrimidine;
6-(6-chloro-4-methoxy-2-pyridyl)-5-methyl-2-(2-pyridyl)-7,8-dihydro-5H-pyrido[4, 3-d]pyrimidine;
6-(6-fluoro-4-methoxy-2-pyridyl)-5-methyl-2-pyrimidin-2-yl-7,8-dihydro-5H-pyrido[4,3-d]pyrimidine;
6-(2-fluoro-6-methoxy-4-pyridyl)-5-methyl-2-pyrimidin-2-yl-7,8-dihydro-5H-pyrido[4,3-d]pyrimidine;
(−)-6-(2-chloro-5-fluoro-3-methoxy-phenyl)-5-methyl-2-pyrimidin-2-yl-7,8-dihydro-5H-pyrido[4,3-d]pyrimidine;
2-(3-fluoro-5-methoxy-phenyl)-1-methyl-6-pyrimidin-2-yl-3,4-dihydro-1H-2,7-naphthyridine;
(−)-6-(6-fluoro-4-methoxy-2-pyridyl)-5-methyl-2-pyrimidin-2-yl-7,8-dihydro-5H-pyrido[4,3-d]pyrimidine;
6-(4-chloro-6-methoxy-2-pyridyl)-5-methyl-2-pyrimidin-2-yl-7,8-dihydro-5H-pyrido[4,3-d]pyrimidine;
6-(4-fluoro-6-methoxy-2-pyridyl)-5-methyl-2-pyrimidin-2-yl-7,8-dihydro-5H-pyrido[4, 3-d]pyrimidine;
6-[3-(2,2-difluoroethoxy)-5-fluoro-phenyl]-5-methyl-2-pyrimidin-2-yl-7,8-dihydro-5H-pyrido[4,3-d]pyrimidine;
6-[3-(cyclopropylmethoxy)-5-fluoro-phenyl]-5-methyl-2-pyrimidin-2-yl-7,8-dihydro-5H-pyrido[4,3-d]pyrimidine;
(−)-6-(5-chloro-6-fluoro-4-methoxy-2-pyridyl)-5-methyl-2-pyrimidin-2-yl-7,8-dihydro-5H-pyrido[4,3-d]pyrimidine;
6-[6-(2,2-difluoroethoxy)-4-fluoro-2-pyridyl]-5-methyl-2-pyrimidin-2-yl-7,8-dihydro-5H-pyrido[4,3-d]pyrimidine;
6-[4-(2,2-difluoroethoxy)-6-fluoro-2-pyridyl]-5-methyl-2-pyrimidin-2-yl-7,8-dihydro-5H-pyrido[4,3-d]pyrimidine;
6-[6-fluoro-4-(tetrahydropyran-4-ylmethoxy)-2-pyridyl]-5-methyl-2-pyrimidin-2-yl-7,8-dihydro-5H-pyrido[4,3-d]pyrimidine;
6-[6-fluoro-4-(tetrahydrofuran-3-ylmethoxy)-2-pyridyl]-5-methyl-2-pyrimidin-2-yl-7,8-dihydro-5H-pyrido[4,3-d]pyrimidine;
(−)-7-[[2-fluoro-6-[5-methyl-2-pyrimidin-2-yl-7,8-dihydro-5H-pyrido[4,3-d]pyrimidin-6-yl]-4-pyridyl]oxy]heptanamide;
(−)-4-[3-[[2-fluoro-6-[5-methyl-2-pyrimidin-2-yl-7,8-dihydro-5H-pyrido[4,3-d]pyrimidin-6-yl]-4-pyridyl]oxy]propyl]morpholin-3-one;
2-fluoro-N,N-dimethyl-6-[5-methyl-2-pyrimidin-2-yl-7,8-dihydro-5H-pyrido[4,3-d]pyrimidin-6-yl]pyridin-4-amine;
(−)-6-(6-fluoro-4-pyrrolidin-1-yl-2-pyridyl)-5-methyl-2-pyrimidin-2-yl-7,8-dihydro-5H-pyrido[4,3-d]pyrimidine;
(−)-2-fluoro-N-methyl-6-[5-methyl-2-pyrimidin-2-yl-7,8-dihydro-5H-pyrido[4,3-d]pyrimidin-6-yl]pyridin-4-amine;
(−)-2-fluoro-N,N-dimethyl-6-[5-methyl-2-pyrimidin-2-yl-7,8-dihydro-5H-pyrido[4,3-d]pyrimidin-6-yl]pyridin-4-amine;
4-[4-fluoro-6-(5-methyl-2-pyrimidin-2-yl-7,8-dihydro-5H-pyrido[4,3-d]pyrimidin-6-yl)-2-pyridyl]piperazin-2-one;
4-[2-fluoro-6-(5-methyl-2-pyrimidin-2-yl-7,8-dihydro-5H-pyrido[4,3-d]pyrimidin-6-yl)-4-pyridyl]piperazin-2-one;
(−)-4-[4-fluoro-6-(5-methyl-2-pyrimidin-2-yl-7,8-dihydro-5H-pyrido[4,3-d]pyrimidin-6-yl)-2-pyridyl]piperazin-2-one;
or pharmaceutically acceptable salts, or enantiomers, or diastereomer thereof.

Synthesis

The compounds of the present invention can be prepared by any conventional means. Suitable processes for synthesizing these compounds as well as their starting materials are provided in the schemes below and in the examples. All substituents, in particular, $R^1$, $R^2$, U, W, X, Y and Z are as defined above unless otherwise indicated. Furthermore, and unless explicitly otherwise stated, all reactions, reaction conditions, abbreviations and symbols have the meanings well known to a person of ordinary skill in organic chemistry.

General Synthetic Route for Compound Ia (Scheme 1)

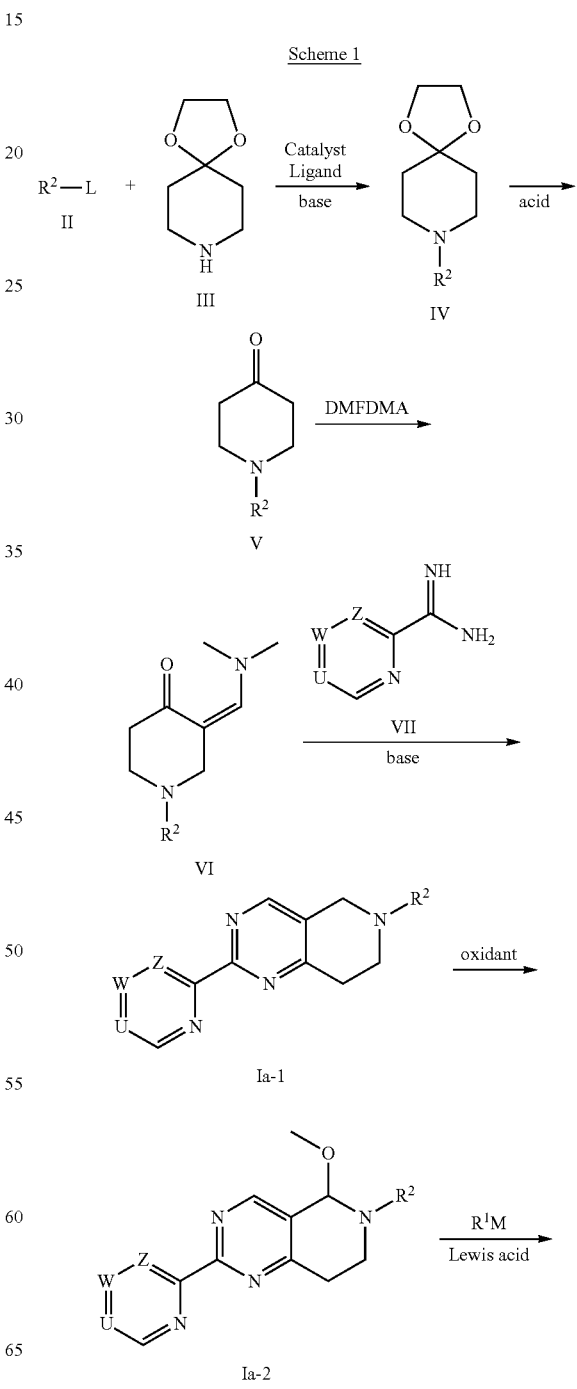

-continued

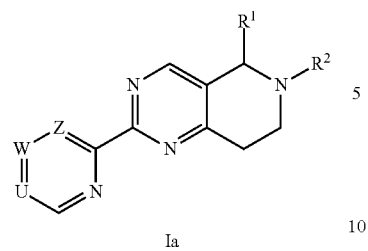

Ia

The compound of formula Ia can be prepared according to Scheme 1, wherein L is Cl, Br, I, —O—mesyl or —O-tosyl; M is H, Hg, Zn or Na.

Compound II is heated with compound III in the presence of a catalyst such as $Pd_2(dba)_3$ or $Pd(OAc)_2$, a ligand such as Ruphos, Sphos or BINAP, and a base such as $Cs_2CO_3$ or t-BuONa in a suitable solvent such as 1,4-dioxane or toluene, to afford compound IV. Deprotection of compound IV under an acidic condition affords compound V. Reaction of compound V with DMFDMA in the absence or presence of a suitable solvent such as DMF or acetonitrile generates intermediate VI. Compound Ia-1 can be obtained by cyclization of intermediate VI with compound VII in the presence of a base such as $K_2CO_3$, NaOMe or $Et_3N$, in a suitable solvent such as EtOH or MeOH. Oxidation of compound Ia-1 produces intermediate Ia-2. Compound Ia-2 reacts with nucleophile $R^1M$ in the presence of a Lewis acid such as $BF_3.Et_2O$ or $Sc(OTf)_3$ gives compound Ia.

General Synthetic Route for Compound Ib (Scheme 2)

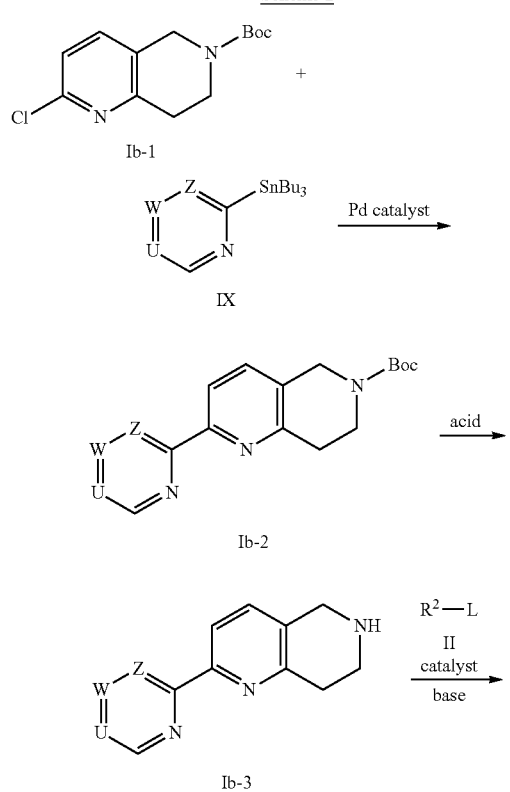

-continued

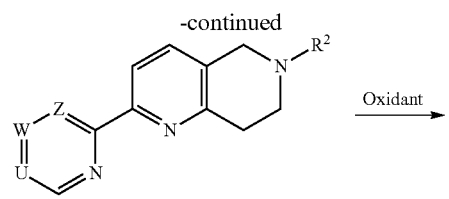

Ib-4

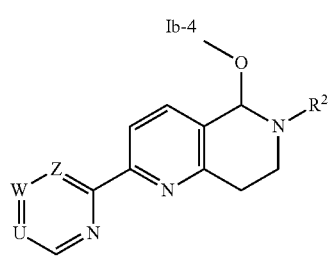

Ib-5

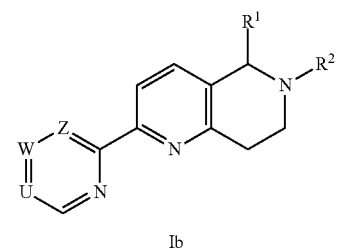

Ib

The compound of formula Ib can be prepared according to Scheme 2, wherein L is Cl, Br, I, —O-mesyl or —O-tosyl; M is H, Hg, Zn or Na.

Coupling of intermediate IX with intermediate Ib-1 in the presence of a catalyst such as $Pd(PPh_3)_4$, $Pd(dppf)Cl_2$ or $Pd_2(dba)_3$, in a suitable solvent such as 1,4-dioxane, $CHCl_3$ or THF can afford compound Ib-2. Removal of Boc protection under acidic condition affords compound Ib-3. Compound Ib-4 can be obtained by coupling of compound Ib-3 with compound II in the presence of a catalyst such as $Pd_2(dba)_3$ or $Pd(OAc)_2$ and a base such as $Cs_2CO_3$ or t-BuONa, in a suitable solvent such as 1,4-dioxane, DMF or DMA. Oxidation of compound Ib-4 produces intermediate Ib-5. Compound Ib-5 reacts with nucleophile $R^1M$ in the presence of Lewis acid such as $BF_3.Et_2O$ or $Sc(OTf)_3$ gives compound Ib.

General Synthetic Route for Compound Ic (Scheme 3)

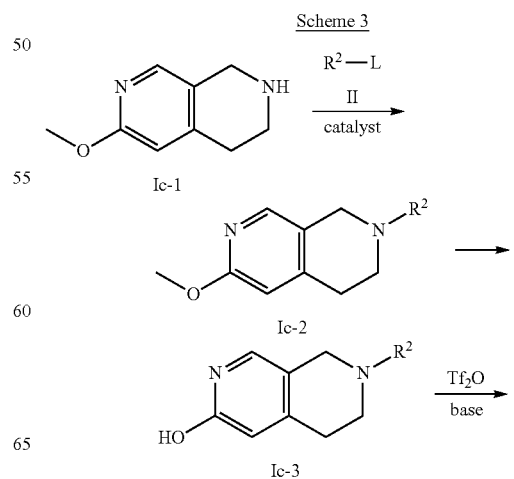

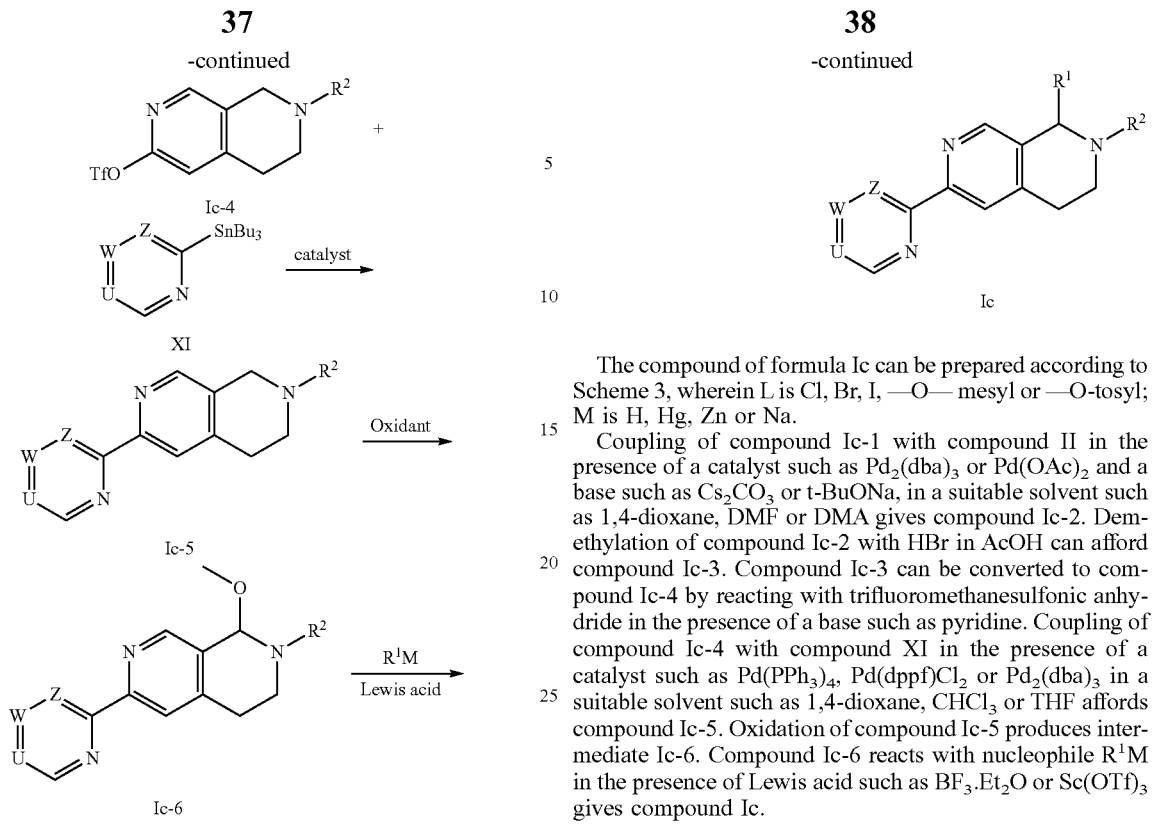

The compound of formula Ic can be prepared according to Scheme 3, wherein L is Cl, Br, I, —O— mesyl or —O-tosyl; M is H, Hg, Zn or Na.

Coupling of compound Ic-1 with compound II in the presence of a catalyst such as $Pd_2(dba)_3$ or $Pd(OAc)_2$ and a base such as $Cs_2CO_3$ or t-BuONa, in a suitable solvent such as 1,4-dioxane, DMF or DMA gives compound Ic-2. Demethylation of compound Ic-2 with HBr in AcOH can afford compound Ic-3. Compound Ic-3 can be converted to compound Ic-4 by reacting with trifluoromethanesulfonic anhydride in the presence of a base such as pyridine. Coupling of compound Ic-4 with compound XI in the presence of a catalyst such as $Pd(PPh_3)_4$, $Pd(dppf)Cl_2$ or $Pd_2(dba)_3$ in a suitable solvent such as 1,4-dioxane, $CHCl_3$ or THF affords compound Ic-5. Oxidation of compound Ic-5 produces intermediate Ic-6. Compound Ic-6 reacts with nucleophile $R^1M$ in the presence of Lewis acid such as $BF_3.Et_2O$ or $Sc(OTf)_3$ gives compound Ic.

General Synthetic Route for Compound Id (Scheme 4)

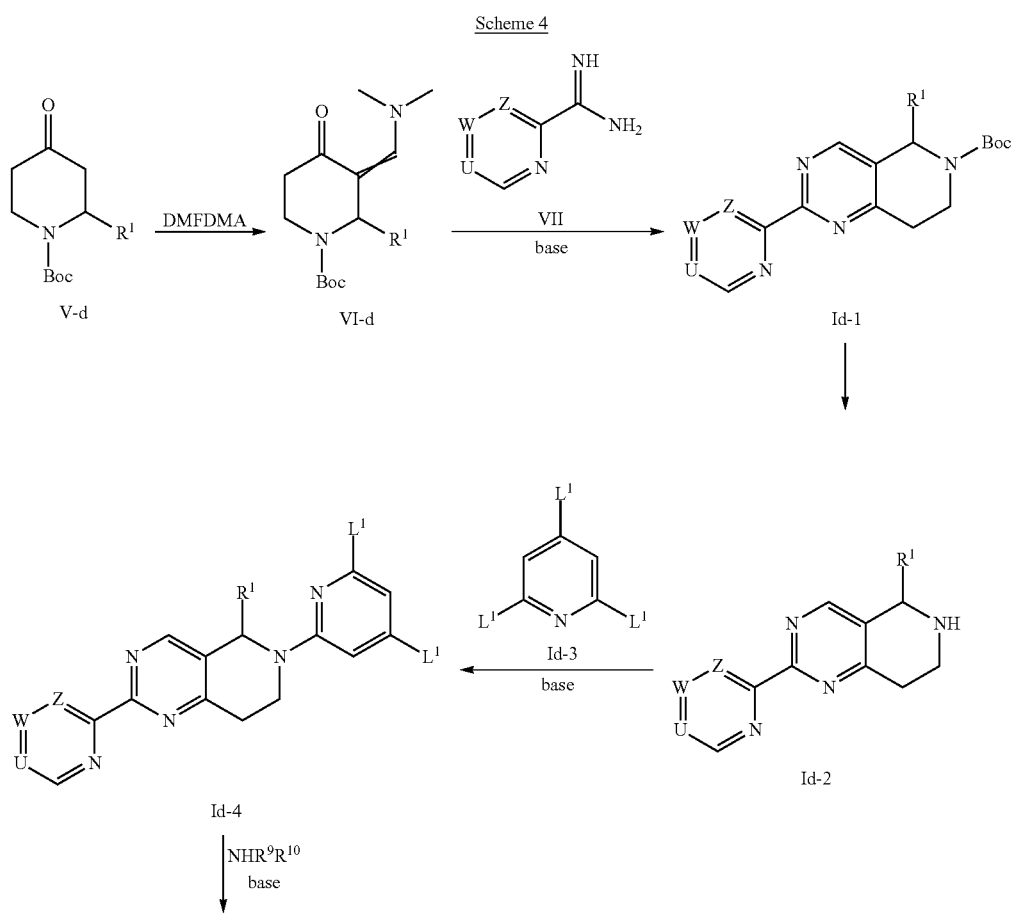

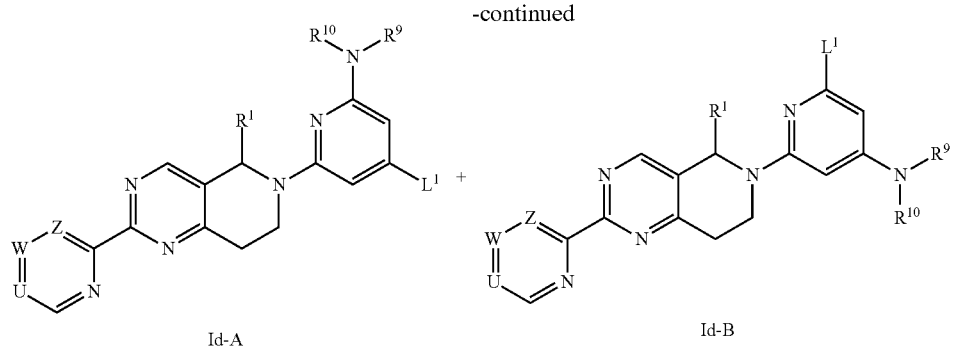

Id-A    Id-B

The compound of formula Id-A and Id-B can be prepared according to Scheme 4, wherein $L^1$ is F, Cl or Br.

Treatment of V-d with DMFDMA in the presence or absence of a suitable solvent such DMF and $CH_3CN$ produces intermediate VI-d. Cyclization of VI-d with compound VII affords compound Id-1. The reaction can be carried out in the presence of a suitable base such as NaOMe, $NaHCO_3$ or $K_2CO_3$ in a suitable solvent such MeOH or EtOH. Deprotection of Id-1 with acid such as HCl or TFA generates intermediate Id-2. Coupling of Id-2 with halopyridine Id-3 in the presence of a suitable base such as DIEA in a suitable solvent such as DMSO or NMP gives compound Id-4. Compound Id-A and Id-B can be afforded by reaction of compound Id-4 with amine $NHR^9R^{10}$ in the presence of a suitable base such as $K_2CO_3$ or DIEA in a suitable solvent such as NMP or DMSO.

General Synthetic Route for Compound Ia (Scheme 5)

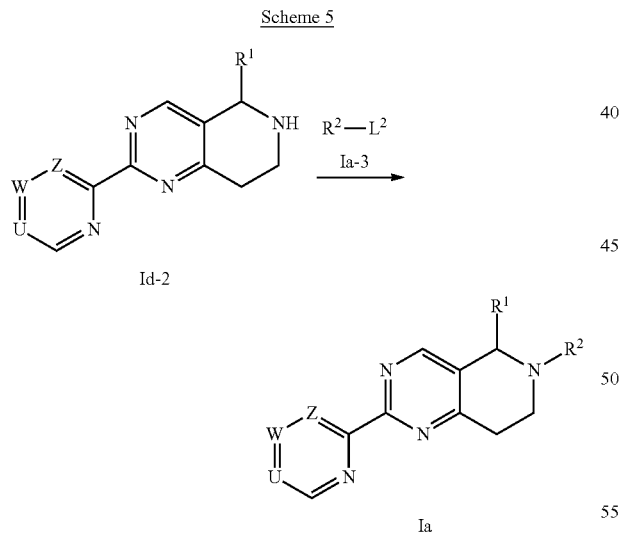

Scheme 5

The compound of formula Ia can also be prepared according to scheme 5, wherein $L^2$ is F, Cl or Br.

Coupling of intermediate Id-2 with intermediate Ia-3 in the presence or absence of a suitable base such as DIEA or $K_2CO_3$ in a suitable solvent such as DMSO or NMP affords compound Ia.

This invention also relates to a process for the preparation of a compound of formula I comprising one of the following steps:

(a) coupling of a compound of formula (A)

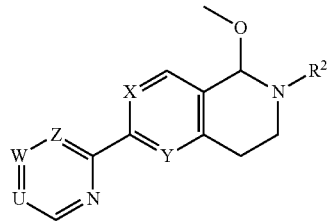

(A)

with a compound of formula (B)

$R^1M$    (B)

in the presence of a Lewis acid;

(b) coupling of a compound of formula (C)

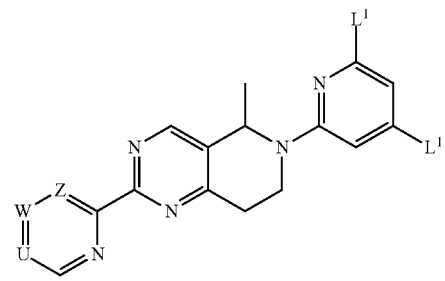

(C)

with a compound of formula (D)

$NHR^9R^{10}$    (D)

in the presence of a base;

(c) coupling of a compound of formula (E)

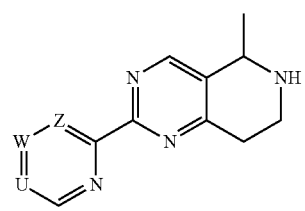

(E)

with a compound of formula (F)

$$R^2\text{-}L^2 \quad (F);$$

wherein $R^1$, $R^2$, U, W, X, Y and Z are defined as above; M is H, Mg, Zn or Na; $L^1$ is F, Cl or Br; and $L^2$ is F, Cl or Br.

In step (a), the Lewis acid can be for example $BF_3.Et_2O$ or $Sc(OTf)_3$;

In step (b), the base can be for example $K_2CO_3$ or DIEA;

In step (c), the reaction can be carried out in the presence of a base, and the base can be for example $K_2CO_3$ or DIEA. The reaction can also be carried out in the absence of a base.

A compound of formula I when manufactured according to the above process is also an object of the invention.

The compound of this invention also shows good safety and PK profile.

Pharmaceutical Compositions and Administration

The invention also relates to a compound of formula I for use as therapeutically active substance. Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compounds of formula (I) are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit HBsAg. For example, such amount may be below the amount that is toxic to normal cells, or the mammal as a whole.

In one example, the pharmaceutically effective amount of the compound of the invention administered parenterally per dose will be in the range of about 0.01 to 100 mg/kg, alternatively about 0.01 to 100 mg/kg of patient body weight per day, with the typical initial range of compound used being 0.3 to 15 mg/kg/day. In another embodiment, oral unit dosage forms, such as tablets and capsules, preferably contain from about 0.1 to about 1000 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 0.1 to 1000 mg of the compound of the invention compounded with about 0 to 2000 mg anhydrous lactose, about 0 to 2000 mg sodium croscarmellose, about 0 to 2000 mg polyvinylpyrrolidone (PVP) K30, and about 0 to 2000 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 0.1 to 1000 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of Formula I, or a stereoisomer or pharmaceutically acceptable salt thereof. In a further embodiment includes a pharmaceutical composition comprising a compound of Formula I, or a stereoisomer or pharmaceutically acceptable salt thereof, together with a pharmaceutically acceptable carrier or excipient.

The following example A and B illustrate typical compositions of the present invention, but serve merely as representative thereof.

Example A

A compound of formula I can be used in a manner known per se as the active ingredient for the production of tablets of the following composition:

|  | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula I can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

Indications and Methods of Treatment

The compounds of the invention can inhibit HBsAg production or secretion and inhibit HBV gene expression. Accordingly, the compounds of the invention are useful for the treatment or prophylaxis of HBV infection.

The invention relates to the use of a compound of formula I for the inhibition of HBsAg production or secretion.

The invention relates to the use of a compound of formula I for the inhibition of HBV DNA production.

The invention relates to the use of a compound of formula I for the inhibition of HBV gene expression.

The invention relates to the use of a compound of formula I for the treatment or prophylaxis of HBV infection.

The use of a compound of formula I for the preparation of medicaments useful in the treatment or prophylaxis diseases that are related to HBV infection is an object of the invention.

The invention relates in particular to the use of a compound of formula I for the preparation of a medicament for the treatment or prophylaxis of HBV infection.

Another embodiment includes a method for the treatment or prophylaxis of HBV infection, which method comprises administering an effective amount of a compound of Formula I, a stereoisomer, tautomer, prodrug, conjugates or pharmaceutically acceptable salt thereof.

EXAMPLES

The invention will be more fully understood by reference to the following examples. They should not, however, be construed as limiting the scope of the invention.

Abbreviations used herein are as follows:

μL: microliter
μm: micrometer
μM: micromoles per liter
(Boc)$_2$O: di-tert-butyl dicarbonate
BSA: bovine serum albumin
IC$_{50}$: the half maximal inhibitory concentration
LC/MS: liquid chromatography/mass spectrometry
M: molarity
MHz: megahertz
min: minute
hr(s): hour(s)
mM: millimoles per liter
Me$_3$SiCl: chlorotrimethylsilane
MS (ESI): mass spectroscopy (electron spray ionization)
nM: nanomoles per liter
NMR: nuclear magnetic resonance
obsd. observed
rt: room temperature
Pd/C: palladium on activated carbon
Pd(PPh$_3$)$_4$: tetrakis(triphenylphosphine)palladium(0)
Pd(dppf)Cl$_2$: [1,1'-bis(diphenylphosphino)ferrocene]dichloropalladium(II)
Pd$_2$(dba)$_3$: Tris(dibenzylideneacetone)dipalladium(0)
TFA: trifluoroacetic acid
δ: chemical shift
RuPhos: 2-dicyclohexylphosphino-2',6'-diisopropoxybiphenyl
BINAP: (2,2'-bis(diphenylphosphino)-1,1'-binaphthyl)
Sphos: 2-dicyclohexylphosphino-2',6'-dimethoxybiphenyl
Xphos 2-Dicyclohexylphosphino-2',4',6'-triisopropylbiphenyl
DMFDMA: N,N-dimethylformamide dimethyl acetal
t-BuONa: sodium tert-butoxide
DIEA: N,N-diisopropylethylamine
CDI: 1,1'-carbonyldiimidazole
DL-homoserine: DL-2-amino-4-hydroxybutyric acid
NMP: N-methyl-2-pyrrolidone
Tosyl-Cl: 4-Toluenesulfonyl chloride
m-CPBA meta-chloroperoxybenzoic acid General Experimental Conditions Intermediates and final compounds were purified by flash chromatography using one of the following instruments: i) Biotage SP1 system and the Quad 12/25 Cartridge module. ii) ISCO combi-flash chromatography instrument. Silica gel Brand and pore size: i) KP-SIL 60 Å, particle size: 40-60 μm; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using X Bridge™ Perp C$_{18}$ (5 μm, OBD™ 30×100 mm) column or SunFire™ Perp C$_{18}$ (5 μm, OBD™ 30×100 mm) column.

Chiral Separation was conducted on Thar 350 preparative SFC using ChiralPak AD-10u (200×50 mm I.D.) with mobile phase A for CO$_2$ and B for ethanol.

LC/MS spectra were obtained using an Acquity Ultra Performance LC-3100 Mass Detector or Acquity Ultra Performance LC-SQ Detector. Standard LC/MS conditions were as follows (running time 3 minutes):

Acidic condition: A: 0.1% formic acid in H$_2$O; B: 0.1% formic acid in acetonitrile;

Basic condition: A: 0.05% NH$_3$.H$_2$O in H$_2$O; B: acetonitrile;

Neutral condition: A: H$_2$O; B: acetonitrile.

Mass spectra (MS): generally only ions which indicate the parent mass are reported, and unless otherwise stated the mass ion quoted is the positive mass ion (M+H)$^+$.

The microwave assisted reactions were carried out in a Biotage Initiator Sixty or CEM Discover.

NMR Spectra were obtained using Bruker Avance 400 MHz.

Optical rotation was measured on an AUTOPOL® V automatic polarimeter.

All reactions involving air-sensitive reagents were performed under an argon atmosphere.

Reagents were used as received from commercial suppliers without further purification unless otherwise noted.

PREPARATIVE EXAMPLES

Example 1: 5-methyl-6-(4-nitrophenyl)-2-(2-pyridyl)-7,8-dihydro-5H-pyrido[4,3-d]pyrimidine

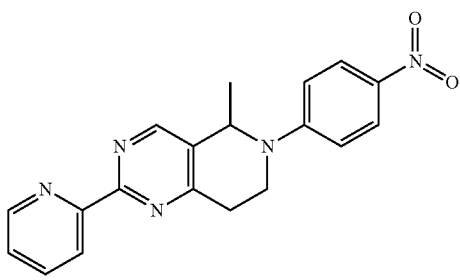 [SMILES: CC1c2cnc(-c3ccccn3)nc2CCN1c1ccc([N+](=O)[O-])cc1]

Step 1: Preparation of tert-butyl 5-methyl-2-(2-pyridyl)-7,8-dihydro-5H-pyrido[4,3-d]pyrimidine-6-carboxylate

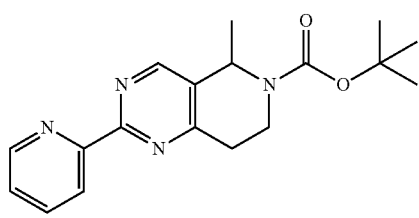 [SMILES: CC1c2cnc(-c3ccccn3)nc2CCN1C(=O)OC(C)(C)C]

To a solution of tert-butyl 2-methyl-4-oxo-piperidine-1-carboxylate (3.00 g, 14.1 mmol) in DMF (20 mL) was added DMFDMA (1.84 g, 15.47 mmol). The resulting mixture was heated at 90° C. with stirring overnight. After being cooled to rt, the resulting reaction mixture was concentrated in vacuo and the residue was dissolved in EtOH (50 mL). To the solution was added pyridine-2-carboxamidine hydrochloride (2.2 g, 14.1 mmol) and sodium methoxide (1.05 g, 19.4 mmol). After being heated at 100° C. with stirring overnight, the resulting mixture was cooled down to rt and concentrated in vacuo. The residue was diluted with water (15 mL) and then extracted with EA (30 mL) for three times. The combined organic layer was dried over anhydrous Na$_2$SO$_4$ and concentrated in vacuo to give crude tert-butyl 5-methyl-2-(2-pyridyl)-7,8-dihydro-5H-pyrido[4,3-d]pyrimidine-6-carboxylate (2.5 g) which was used in the next step directly without further purification.

Step 2: Preparation of 5-methyl-2-(2-pyridyl)-5,6,7,8-tetrahydropyrido[4,3-d]pyrimidine

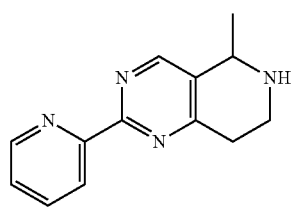 [SMILES: CC1NCCc2nc(-c3ccccn3)ncc21]

A mixture of crude tert-butyl 5-methyl-2-(2-pyridyl)-7,8-dihydro-5H-pyrido[4,3-d]pyrimidine-6-carboxylate and 2,2,2-trifluoroacetic acid (15 mL) in DCM (30 mL) was stirred at rt for 3 hrs. The resulting mixture was concentrated in vacuo to give crude 5-methyl-2-(2-pyridyl)-5,6,7,8-tetrahydropyrido[4,3d]pyrimidine as trifluoroacetic acid salt (2.6 g).

Step 3: Preparation of 5-methyl-6-(4-nitrophenyl)-2-(2-pyridyl)-7,8-dihydro-5H-pyrido[4,3-d]pyrimidine

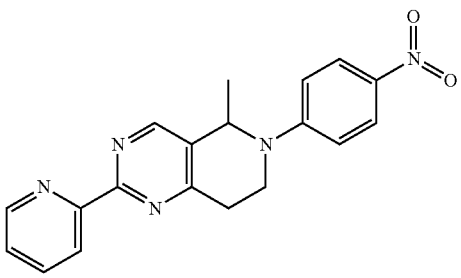 [SMILES: CC1c2cnc(-c3ccccn3)nc2CCN1c1ccc([N+](=O)[O-])cc1]

A mixture of 5-methyl-2-(2-pyridyl)-5,6,7,8-tetrahydropyrido[4,3-d]pyrimidine (1.0 g, 2.9 mmol, trifluoroacetic acid salt), 1-fluoro-4-nitro-benzene (1.24 g, 8.8 mmol) and potassium carbonate (2.43 g, 17.6 mmol) in DMSO (20 mL) was heated at 115° C. with stirring overnight. The mixture was filtered and the filtration was concentrated in vacuo. The residue was purified by prep-HPLC to give 5-methyl-6-(4-nitrophenyl)-2-(2-pyridyl)-7,8-dihydro-5H-pyrido[4,3-d]pyrimidine (15 mg) as a pale yellow solid. $^1$H NMR (400 MHz, CDCl$_3$) δ: 8.96-9.08 (m, 1H), 8.75-8.83 (m, 1H), 8.63-8.74 (m, 1H), 8.22 (d, 3H), 7.63-7.77 (m, 1H), 6.94 (d, 2H), 5.25 (d, 1H), 4.07-4.20 (m, 1H), 3.68 (m, 1H), 3.22-3.35 (m, 2H), 1.67 (d, 3H). MS obsd. (ESI$^+$) [(M+H)$^+$]: 348.

Example 2 and 3: (+)-5-methyl-6-(4-nitrophenyl)-2-(2-pyridyl)-7,8-dihydro-5H-pyrido[4,3-d]pyrimidine and (−)-5-methyl-6-(4-nitrophenyl)-2-(2-pyridyl)-7,8-dihydro-5H-pyrido[4,3-d]pyrimidine

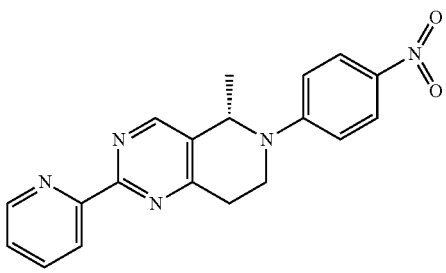

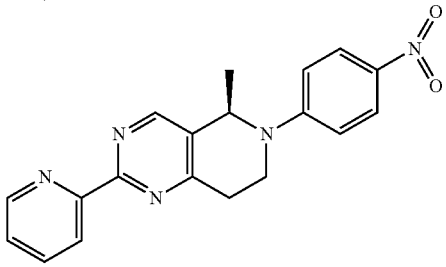

Separation of 5-methyl-6-(4-nitrophenyl)-2-(2-pyridyl)-7,8-dihydro-5H-pyrido[4,3-d]pyrimidine (32 mg, Example 1) by chiral HPLC gave (+)-5-methyl-6-(4-nitrophenyl)-2-(2-pyridyl)-7,8-dihydro-5H-pyrido[4,3-d]pyrimidine (5 mg) and (−)-5-methyl-6-(4-nitrophenyl)-2-(2-pyridyl)-7,8-dihydro-5H-pyrido[4,3-d]pyrimidine (4.5 mg) both as white solid.

Example 2: (+)-5-methyl-6-(4-nitrophenyl)-2-(2-pyridyl)-7,8-dihydro-5H-pyrido[4,3-d]pyrimidine, $^1$H NMR (400 MHz, CDCl$_3$) δ: 8.90 (d, 1H), 8.75 (s, 1H), 8.55 (d, 1H), 8.16-8.25 (m, 2H), 7.93 (m, 1H), 7.47 (m, 1H), 6.86-6.97 (m, 2H), 5.17-5.27 (m, 1H), 4.12 (m, 1H), 3.69 (m, 1H), 3.23-3.35 (m, 2H), 1.66 (d, 3H); MS obsd. (ESI+) [(M+H)$^+$]: 348.

Example 3: (−)-5-methyl-6-(4-nitrophenyl)-2-(2-pyridyl)-7,8-dihydro-5H-pyrido[4,3-d]pyrimidine, $^1$H NMR (400 MHz, CDCl$_3$) δ: 8.87 (br. s, 1H), 8.75 (br. s, 1H), 8.54 (d, 1H), 8.22 (d, 2H), 7.90 (m, 1H), 7.41-7.51 (m, 1H), 6.93 (d, 2H), 5.24 (m, 1H), 4.13 (m, 1H), 3.69 (m, 1H), 3.26-3.40 (m, 2H), 1.66 (d, 3H). MS obsd. (ESI$^+$) [(M+H)$^+$]: 348; $[a]_D^{20}$=−124.00° (0.05 g/100 mL, methanol).

Example 4: 5-ethyl-6-(4-methylsulfonylphenyl)-2-(2-pyridyl)-7,8-dihydro-5H-pyrido[4,3-d]pyrimidine

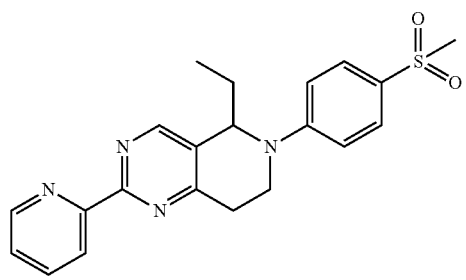 [SMILES: CCC1c2cnc(-c3ccccn3)nc2CCN1c1ccc(S(C)(=O)=O)cc1]

Step 1: Preparation of 8-(4-methylsulfonylphenyl)-1,4-dioxa-8-azaspiro[4.5]decane

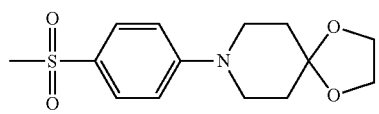 [SMILES: CS(=O)(=O)c1ccc(N2CCC3(CC2)OCCO3)cc1]

To a mixture of 1-bromo-4-methylsulfonyl-benzene (1.9 g, 8.12 mmol), 1,4-dioxa-8-azaspiro[4.5]decane (1.39 g, 9.74 mmol) and t-BuONa (1.56 g, 16.24 mmol) in dioxane (40 mL) was added Pd$_2$(dba)$_3$ (147 mg, 0.16 mmol) and Sphos (131 mg, 0.32 mmol) successively under N$_2$. The resulting mixture was heated at 100° C. with stirring overnight, then cooled down to rt, diluted with H$_2$O (20 mL) and extracted with EA (50 mL) for three times. The combined organic layer was washed with brine (50 mL), dried over anhydrous Na$_2$SO$_4$ and concentrated in vacuo to give crude 8-(4-methyl sulfonylphenyl)-1,4-dioxa-8-azaspiro[4.5]decane (2.2 g) which was used in next step directly without further purification.

Step 2: Preparation of 1-(4-methylsulfonylphenyl)piperidin-4-one

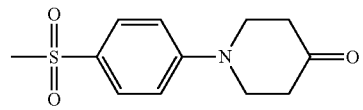 [SMILES: CS(=O)(=O)c1ccc(N2CCC(=O)CC2)cc1]

Crude 8-(4-methyl sulfonylphenyl)-1,4-dioxa-8-azaspiro[4.5]decane (2.2 g, 7.48 mmol) was treated with 44% formic acid (20 mL) at 90° C. for 8 hrs. The resulting mixture was concentrated in vacuo. The residue was diluted with saturated aqueous solution of NaHCO$_3$ (20 mL) and extracted with EA (50 mL) for three times. The combined organic layer was washed with brine (50 mL), dried over anhydrous Na$_2$SO$_4$ and concentrated in vacuo to give 1-(4-methylsulfonylphenyl)piperidin-4-one (1.64 g) as brown solid which was used in the next step directly without further purification.

Step 3: Preparation of 6-(4-methylsulfonylphenyl)-2-(2-pyridyl)-7,8-dihydro-5H-pyrido[4,3-d]pyrimidine

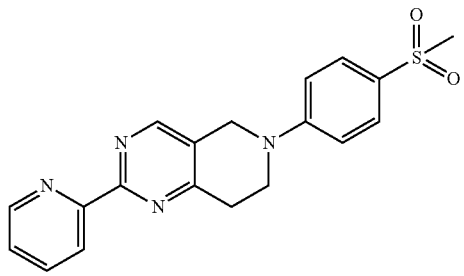 [SMILES: CS(=O)(=O)c1ccc(N2CCc3nc(-c4ccccn4)ncc3C2)cc1]

Crude 1-(4-methylsulfonylphenyl)piperidin-4-one (1.64 g, 6.75 mmol) was stirred with DMFDMA (10 mL) at 90° C. for 3 hrs. The resulting mixture was concentrated in vacuo. The residue was dissolved in EtOH (20 mL). To the solution was added pyridine-2-carboxamidine hydrochloride (1.06 g, 6.75 mmol) and K$_2$CO$_3$ (1.86 g, 13.5 mmol) successively. After being heated at 80° C. with stirring overnight, the resulting mixture was cooled down to rt and purified by prep-HPLC to give 6-(4-methylsulfonylphenyl)-2-(2-pyridyl)-7,8-dihydro-5H-pyrido[4,3-d]pyrimidine (1.0 g) as light yellow solid.

Step 4: Preparation of 5-methoxy-6-(4-methylsulfonylphenyl)-2-(2-pyridyl)-7,8-dihydro-5H-pyrido[4,3-d]pyrimidine

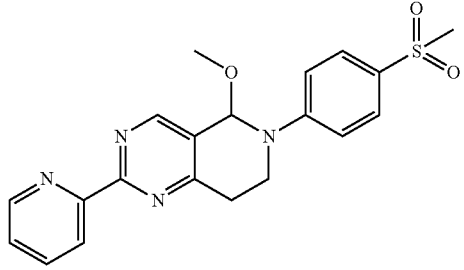

To a cooled solution of 6-(4-methylsulfonylphenyl)-2-(2-pyridyl)-7,8-dihydro-5H-pyrido[4,3-d]pyrimidine (160 mg, 0.44 mmol) in a mixed solvent of DCM (10 mL) and MeOH (2 mL) at −70° C. was added RuCl₃ hydrate (0.13 mmol) and NaIO₄ (282 mg in 3 mL H₂O, 1.32 mmol) successively. The cooling bath was removed and the reaction mixture was warmed naturally to rt. After the reaction was complete, the resulting mixture was quenched with saturated aqueous solution of Na₂S₂O₃ (20 mL) and extracted with EA (30 mL) for three times. The combined organic layer was dried over anhydrous Na₂SO₄ and concentrated in vacuo to give 5-methoxy-6-(4-methylsulfonylphenyl)-2-(2-pyridyl)-7,8-dihydro-5H-pyrido[4,3-d]pyrimidine as (160 mg) as dark foam which was used directly in the next step directly without further purification.

Step 5: Preparation of 5-ethyl-6-(4-methylsulfonyl-phenyl)-2-(2-pyridyl)-7,8-dihydro-5H-pyrido[4,3-d]pyrimidine

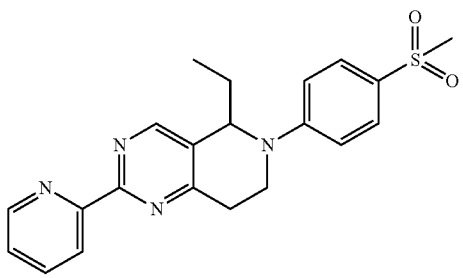 [SMILES: CCC1c2cnc(-c3ccccn3)nc2CCN1c1ccc(S(C)(=O)=O)cc1]

To a cooled solution of 5-methoxy-6-(4-methylsulfonyl-phenyl)-2-(2-pyridyl)-7,8-dihydro-5H-pyrido[4,3-d]pyrimidine (100 mg, 0.25 mmol) in THF (10 mL) at −70° C. was added BF₃.Et₂O (70 mg, 0.5 mmol). The mixture was stirred for 15 min at this temperature, and then to the reaction mixture was added EtMgBr (0.75 mL in THF, 1.0 M from Aldrich). After being warmed to rt and stirred at rt for 1 hr, the reaction mixture was diluted with saturated aqueous solution of NH₄Cl and extracted with EA (30 mL) for three times. The combined organic layer was dried over anhydrous Na₂SO₄ and concentrated in vacuo. The residue was purified by prep-HPLC to give 5-ethyl-6-(4-methyl sulfonylphenyl)-2-(2-pyridyl)-7,8-dihydro-5H-pyrido[4,3-d]pyrimidine (20 mg) as light yellow solid. ¹H NMR (400 MHz, CDCl₃) δ: 8.81-8.89 (m, 1H), 8.68 (s, 1H), 8.50 (d, 1H), 7.88 (t, 1H), 7.80 (d, 2H), 7.37-7.47 (m, 1H), 6.99 (d, 2H), 4.83-4.95 (m, 1H), 3.92-4.05 (m, 1H), 3.68-3.81 (m, 1H), 3.16-3.39 (m, 2H), 3.02 (s, 3H), 1.83-2.16 (m, 2H), 1.10 (t, 3H). MS obsd. (ESI⁺) [(M+H)⁺]: 395.

Example 5: 6-(3,4-difluoro-5-methoxy-phenyl)-5-methyl-2-(2-pyridyl)-7,8-dihydro-5H-pyrido[4,3-d]pyrimidine

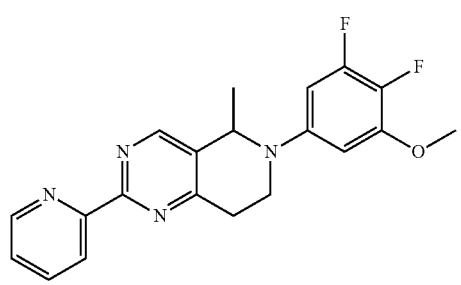 [SMILES: COc1cc(N2CCc3nc(-c4ccccn4)ncc3C2C)cc(F)c1F]

Step 1: Preparation of 8-(3,4-difluoro-5-methoxy-phenyl)-1,4-dioxa-8-azaspiro[4.5]decane

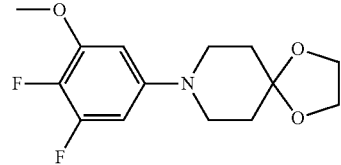 [SMILES: COc1cc(N2CCC3(CC2)OCCO3)cc(F)c1F]

To a mixture of 5-bromo-1,2-difluoro-3-methoxy-benzene (1.1 g, 4.93 mmol), 1,4-dioxa-8-azaspiro[4.5]decane (0.85 g, 5.92 mmol) and t-BuONa (0.95 g, 9.86 mmol) in 1,4-dioxane (10 mL) was added Pd₂(dba)₃ (92 mg, 0.10 mmol) and Ru-Phos (92 mg, 0.20 mmol) successively under N₂. After being heated at 100° C. with stirring overnight, the reaction mixture was cooled down to rt, diluted with water (20 mL) and extracted with EA (30 mL) for three times. The combined organic layer was washed with brine, dried over anhydrous Na₂SO₄ and concentrated in vacuo to give 8-(3,4-difluoro-5-methoxy-phenyl)-1,4-dioxa-8-azaspiro[4.5]decane (1.57 g) which was used in the next step directly without further purification.

Step 2: Preparation of 1-(3,4-difluoro-5-methoxy-phenyl)piperidin-4-one

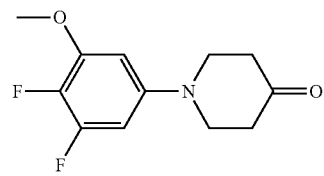 [SMILES: COc1cc(N2CCC(=O)CC2)cc(F)c1F]

A mixture of 8-(3,4-difluoro-5-methoxy-phenyl)-1,4-dioxa-8-azaspiro[4.5]decane (1.57 g, 5.51 mmol), H₂O (5 mL) and formic acid (5 mL) was heated at 90° C. with stirring overnight. The reaction mixture was concentrated in vacuo, diluted with saturated aqueous solution of NaHCO₃ and then extracted with EA (30 mL) for three times. The combined organic layer was washed with brine, dried over anhydrous Na₂SO₄, and concentrated in vacuo to give 1-(3,4-difluoro-5-methoxy-phenyl)piperidin-4-one (1.06 g) which was used in the next step directly without further purification.

Step 3: Preparation of 6-(3,4-difluoro-5-methoxy-phenyl)-2-(2-pyridyl)-7,8-dihydro-5H-pyrido[4,3-d]pyrimidine

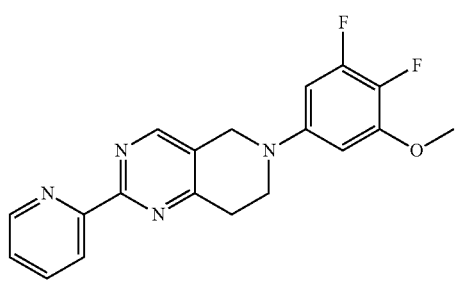

Crude 1-(3,4-difluoro-5-hydroxy-phenyl)piperidin-4-one (8.1 g, 33.75 mmol) was stirred in DMFDMA (30 mL) at 90° C. for 3 hrs. The resulting mixture was concentrated in vacuo and the residue was dissolved in EtOH (50 mL). To the solution was added pyridine-2-carboxamidine hydrochloride (5.3 g, 33.75 mmol) and $K_2CO_3$ (9.3 g, 67.5 mmol) successively. The resulting mixture was heated at 80° C. with stirring overnight, then cooled down to rt and purified by prep-HPLC to give 6-(3,4-difluoro-5-methoxy-phenyl)-2-(2-pyridyl)-7,8-dihydro-5H-pyrido[4,3-d]pyrimidine (5.0 g).

Step 4: Preparation of 6-(3,4-difluoro-5-methoxy-phenyl)-5-methoxy-2-(2-pyridyl)-7,8-dihydro-5H-pyrido[4,3-d]pyrimidine

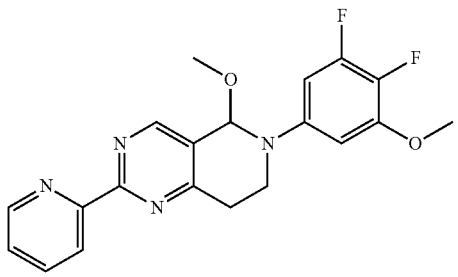 [SMILES: COc1cc(N2CCc3nc(-c4ccccn4)ncc3C2OC)cc(F)c1F]

To a stirred solution of 6-(3,4-difluoro-5-methoxy-phenyl)-2-(2-pyridyl)-7,8-dihydro-5H-pyrido[4,3-d]pyrimidine (400 mg, 1.13 mmol) in a mixed solvent of DCM (20 mL) and MeOH (4 mL) at −70° C. was added $RuCl_3$ hydrate (0.23 mmol) and $NaIO_4$ (725 mg in 10 mL $H_2O$, 3.39 mmol) successively. The cooling bath was removed. The reaction mixture was warmed to rt slowly and stirred at rt. After the reaction was completed, the resulting mixture was diluted with saturated aqueous solution of $Na_2S_2O_3$ (20 mL), and extracted with EA (50 mL) for three times. The combined organic layer was dried over anhydrous $Na_2SO_4$ and concentrated in vacuo to give 6-(3,4-difluoro-5-methoxy-phenyl)-5-methoxy-2-(2-pyridyl)-7,8-dihydro-5H-pyrido[4,3-d]pyrimidine (430 mg) dark foam which was used directly in the next step directly without further purification.

Step 5: Preparation of 6-(3,4-difluoro-5-methoxy-phenyl)-5-methyl-2-(2-pyridyl)-7,8-dihydro-5H-pyrido[4,3-d]pyrimidine

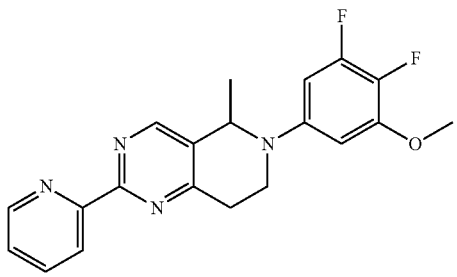

To a solution of 6-(3,4-difluoro-5-methoxy-phenyl)-5-methoxy-2-(2-pyridyl)-7,8-dihydro-5H-pyrido[4,3-d]pyrimidine (430 mg, 1.13 mmol) in THF (20 mL) at −70° C. was added $BF_3.Et_2O$ (320 mg, 2.26 mmol). The mixture was stirred at this temperature for 15 mins and to the reaction mixture was added MeMgBr (1.13 mL in THF, 3.0 M from Aldrich). After being warmed to rt and stirred at rt for 1 hr, the resulting mixture was diluted with saturated aqueous solution of $NH_4Cl$ and then extracted with EA (30 mL) for three times. The combined organic layer was dried over anhydrous $Na_2SO_4$ and concentrated in vacuo. The residue was purified by prep-HPLC to give 6-(3,4-difluoro-5-methoxy-phenyl)-5-methyl-2-(2-pyridyl)-7,8-dihydro-5H-pyrido[4,3-d]pyrimidine (200 mg) as light yellow solid. $^1H$ NMR (400 MHz, $CDCl_3$) δ: 8.79-8.87 (m, 1H), 8.66 (s, 1H), 8.43-8.53 (m, 1H), 7.80-7.88 (m, 1H), 7.34-7.42 (m, 1H), 6.30-6.38 (m, 2H), 4.84-4.99 (m, 1H), 3.89 (s, 3H), 3.63-3.75 (m, 1H), 3.41-3.55 (m, 1H), 3.09-3.30 (m, 2H), 1.41 (d, 3H). MS obsd. ($ESI^+$) [$(M+H)^+$]: 369.

Example 6 and 7: (−)-6-(3,4-difluoro-5-methoxy-phenyl)-5-methyl-2-(2-pyridyl)-7,8-dihydro-5H-pyrido[4,3-d]pyrimidine and (+)-6-(3,4-difluoro-5-methoxy-phenyl)-5-methyl-2-(2-pyridyl)-7,8-dihydro-5H-pyrido[4,3-d]pyrimidine

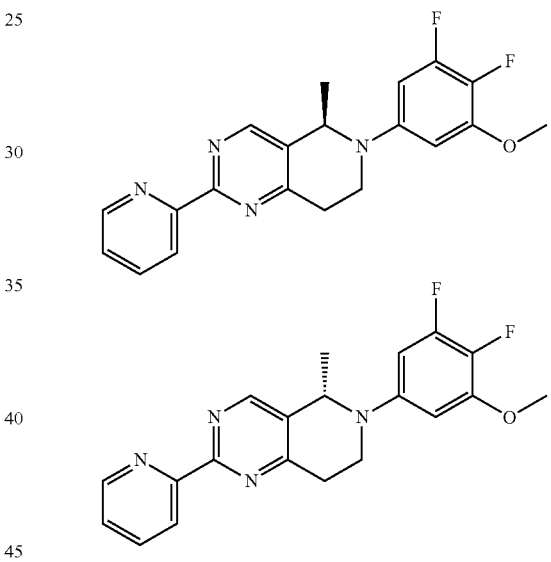

Separation of 6-(3,4-difluoro-5-methoxy-phenyl)-5-methyl-2-(2-pyridyl)-7,8-dihydro-5H-pyrido[4,3-d]pyrimidine (50 mg, Example 5) by chiral HPLC gave (−)-6-(3,4-difluoro-5-methoxy-phenyl)-5-methyl-2-(2-pyridyl)-7,8-dihydro-5H-pyrido[4,3-d]pyrimidine (15 mg) and (+)-6-(3,4-difluoro-5-methoxy-phenyl)-5-methyl-2-(2-pyridyl)-7,8-dihydro-5H-pyrido[4,3-d]pyrimidine (16 mg) both as yellow solid.

Example 6: (+)-6-(3,4-difluoro-5-methoxy-phenyl)-5-methyl-2-(2-pyridyl)-7,8-dihydro-5H-pyrido[4,3-d]pyrimidine: $^1H$ NMR (400 MHz, $CDCl_3$) δ: 8.78-8.92 (m, 1H), 8.69 (s, 1H), 8.45-8.57 (m, 1H), 7.83-7.91 (m, 1H), 7.36-7.48 (m, 1H), 6.32-6.41 (m, 2H), 4.87-5.01 (m, 1H), 3.92 (s, 3H), 3.66-3.78 (m, 1H), 3.44-3.56 (m, 1H), 3.09-3.35 (m, 2H), 1.44 (d, 3H). MS obsd. ($ESI^+$) [$(M+H)^+$]: 369.

Example 7: (−)-6-(3,4-difluoro-5-methoxy-phenyl)-5-methyl-2-(2-pyridyl)-7,8-dihydro-5H-pyrido[4,3-d]pyrimidine: $^1H$ NMR (400 MHz, $CDCl_3$) δ: 8.84-8.94 (m, 1H), 8.64-8.76 (m, 1H), 8.48-8.59 (m, 1H), 7.84-7.96 (m, 1H), 7.40-7.49 (m, 1H), 6.32-6.43 (m, 2H), 4.90-5.02 (m, 1H), 3.93 (s, 3H), 3.65-3.79 (m, 1H), 3.43-3.59 (m, 1H), 3.13-

3.36 (m, 2H), 1.45 (d, 3H). MS obsd. (ESI⁺) [(M+H)⁺]: 369, [a]$_D^{25}$=−53.333° (0.06 g/100 mL, MeOH).

Example 8: dimethyl 2-[6-(3,4-difluoro-5-methoxy-phenyl)-2-(2-pyridyl)-7,8-dihydro-5H-pyrido[4,3-d]pyrimidin-5-yl]propanedioate

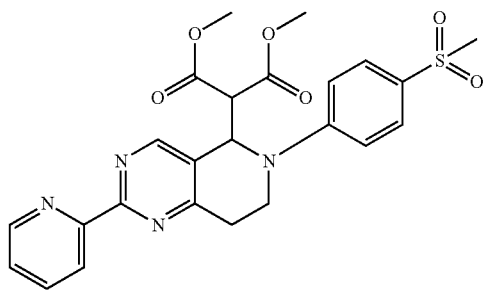 [SMILES: COC(=O)C(C(=O)OC)C1c2cnc(-c3ccccn3)nc2CCN1c1ccc(S(C)(=O)=O)cc1]

To a cooled solution of 5-methoxy-6-(4-methylsulfonyl-phenyl)-2-(2-pyridyl)-7,8-dihydro-5H-pyrido[4,3-d]pyrimidine (200 mg, 0.5 mmol) in THF (20 mL) at −70° C. was added BF₃.Et₂O (142 mg, 1.0 mmol). The mixture was stirred for 15 min at this temperature. Then to the mixture was added a solution of preformed sodium dimethylmalonate (100 mg dimethylmalonate treated with 30 mg of 60% NaH) in THF (2 mL). After being warmed to rt and stirred at rt for 1 hr, the resulting mixture was diluted with saturated aqueous solution of NH₄Cl and then extracted with EA (30 mL) for three times. The combined organic layer was dried over anhydrous Na₂SO₄ and concentrated in vacuo. The residue was purified by prep-HPLC to give dimethyl 2-[6-(3,4-difluoro-5-methoxy-phenyl)-2-(2-pyridyl)-7,8-dihydro-5H-pyrido[4,3-d]pyrimidin-5-yl]propanedioate (40 mg) as a yellow solid. ¹H NMR (400 MHz, CDCl₃) δ: 8.86-8.93 (m, 1H), 8.83 (s, 1H), 8.47-8.57 (m, 1H), 7.88-7.97 (m, 1H), 7.83 (d, 2H), 7.43-7.51 (m, 1H), 7.15 (d, 2H), 5.87-6.00 (m, 1H), 4.02-4.12 (m, 2H), 3.82-3.92 (m, 1H), 3.77 (s, 3H), 3.66 (s, 3H), 3.32-3.43 (m, 1H), 3.21-3.31 (m, 1H), 3.02 (s, 3H). MS obsd. (ESI⁺) [(M+H)⁺]: 497.

Example 9: 6-(3,4-difluoro-5-methoxy-phenyl)-5-ethyl-2-(2-pyridyl)-7,8-dihydro-5H-pyrido[4,3-d]pyrimidine

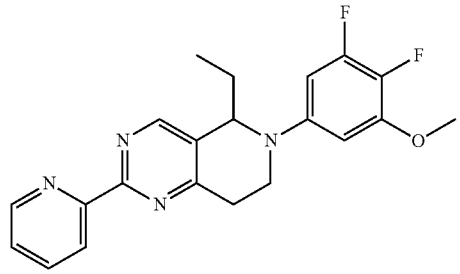 [SMILES: CCC1c2cnc(-c3ccccn3)nc2CCN1c1cc(F)c(F)c(OC)c1]

To a solution of 6-(3,4-difluoro-5-methoxy-phenyl)-5-methoxy-2-(2-pyridyl)-7,8-dihydro-5H-pyrido[4,3-d]pyrimidine (350 mg, 0.91 mmol) in THF (10 mL) at −78° C. was added BF₃.Et₂O (209 mg, 1.82 mmol). The mixture was stirred for 10 mins at this temperature and to the mixture was added EtMgBr (2.8 mL, 1.0 M in THF). After being warmed slowly to 15° C. and stirred at this temperature for 1 hr, the reaction mixture was diluted with H₂O and extracted with EA (30 mL) for three times. The combined organic layer was washed with brine, dried over anhydrous Na₂SO₄ and concentrated in vacuo. The residue was purified by prep-HPLC to give 6-(3,4-difluoro-5-methoxy-phenyl)-5-ethyl-2-(2-pyridyl)-7,8-dihydro-5H-pyrido[4,3-d]pyrimidine (10 mg) as light yellow solid. ¹H NMR (400 MHz, CDCl₃) δ: 1.04 (t, 3H), 1.76-1.85 (m, 1H), 1.95 (dt, 1H), 3.05-3.29 (m, 2H), 3.57-3.79 (m, 2H), 3.88 (s, 3H), 4.56 (t, 1H), 6.24-6.34 (m, 2H), 7.35-7.43 (m, 1H), 7.84 (t, 1H), 8.48 (d, 1H), 8.65 (s, 1H), 8.82 (d, 1H). MS obsd. (ESI⁺) [(M+H)⁺]: 383.

Example 10 and 11: (−)-6-(3,4-difluoro-5-methoxy-phenyl)-5-ethyl-2-(2-pyridyl)-7,8-dihydro-5H-pyrido[4,3-d]pyrimidine and (+)-6-(3,4-difluoro-5-methoxy-phenyl)-5-ethyl-2-(2-pyridyl)-7,8-dihydro-5H-pyrido[4,3-d]pyrimidine

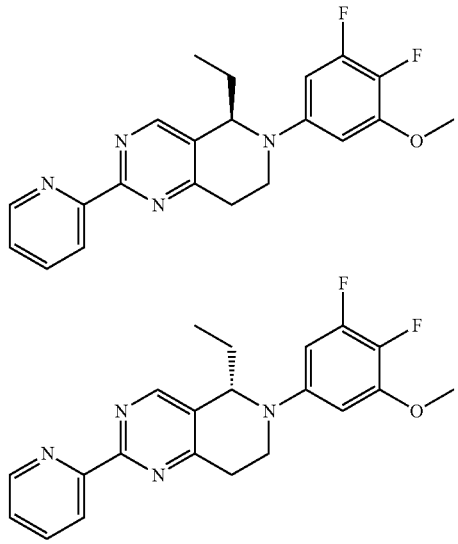

Separation of 6-(3,4-difluoro-5-methoxy-phenyl)-5-ethyl-2-(2-pyridyl)-7,8-dihydro-5H-pyrido[4,3-d]pyrimidine (30 mg Example 9) by chiral HPLC gave (−)-6-(3,4-difluoro-5-methoxy-phenyl)-5-ethyl-2-(2-pyridyl)-7,8-dihydro-5H-pyrido[4,3-d]pyrimidine (10 mg) and (+)-6-(3,4-difluoro-5-methoxy-phenyl)-5-ethyl-2-(2-pyridyl)-7,8-dihydro-5H-pyrido[4,3-d]pyrimidine (11 mg) both as yellow solid.

Example 10: (+)-6-(3,4-difluoro-5-methoxy-phenyl)-5-ethyl-2-(2-pyridyl)-7,8-dihydro-5H-pyrido[4,3-d]pyrimidine: ¹H NMR (400 MHz, CDCl₃) δ: 1.00-1.13 (m, 3H), 1.83 (dd, 1H), 1.96 (dt, 1H), 3.05-3.32 (m, 2H), 3.58-3.79 (m, 2H), 3.90 (s, 3H), 4.58 (d, 1H), 6.30 (d, 2H), 7.40 (brs, 1H), 7.86 (t, 1H), 8.49 (d, 1H), 8.66 (s, 1H), 8.83 (brs, 1H). MS obsd. (ESI⁺) [(M+H)⁺]: 383.

Example 11: (−)-6-(3,4-difluoro-5-methoxy-phenyl)-5-ethyl-2-(2-pyridyl)-7,8-dihydro-5H-pyrido[4,3-d]pyrimidine: ¹H NMR (400 MHz, CDCl₃) δ: 1.00-1.13 (m, 3H), 1.83 (dd, 1H), 1.96 (dt, 1H), 3.05-3.32 (m, 2H), 3.58-3.79 (m, 2H), 3.90 (s, 3H), 4.58 (d, 1H), 6.30 (d, 2H), 7.40 (brs, 1H), 7.86 (t, 1H), 8.49 (d, 1H), 8.66 (s, 1H), 8.83 (brs, 1H). MS obsd. (ESI⁺) [(M+H)⁺]: 383. [a]$_D^{25}$=−54.769° (0.065 g/100 mL, MeOH).

Example 12: 6-(3,4-difluoro-5-methoxy-phenyl)-5-propyl-2-(2-pyridyl)-7,8-dihydro-5H-pyrido[4,3-d]pyrimidine

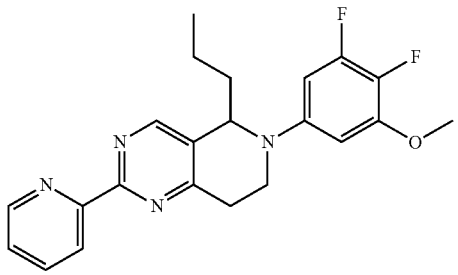 [SMILES: CCCC1c2cnc(-c3ccccn3)nc2CCN1c1cc(F)c(F)c(OC)c1]

To a solution of 6-(3,4-difluoro-5-methoxy-phenyl)-5-methoxy-2-(2-pyridyl)-7,8-dihydro-5H-pyrido[4,3-d]pyrimidine (160 mg, 0.42 mmol) in THF (5 mL) at −78° C. was added BF$_3$.Et$_2$O (70 mg, 1.82 mmol). The mixture was stirred at −78° C. for 10 mins and then to the resulting mixture was added n-PrMgBr (1.5 mmol, 2.0 M in diethyl ether). After being warmed to 15° C. slowly and stirred at 15° C. for 1 hr, the resulting mixture was diluted with H$_2$O and extracted with EA (30 mL) for three times. The combined organic layer was washed with brine, dried over anhydrous Na$_2$SO$_4$ and concentrated in vacuo. The residue was purified by prep-HPLC to give 6-(3,4-difluoro-5-methoxy-phenyl)-5-propyl-2-(2-pyridyl)-7,8-dihydro-5H-pyrido[4,3-d]pyrimidine (9 mg) as a pale yellow solid. $^1$H NMR (400 MHz, CDCl$_3$) δ: 0.98 (t, 3H) 1.40-1.56 (m, 2H) 1.74 (dd, 1H), 1.85-1.99 (m, 1H), 3.04-3.31 (m, 2H), 3.58-3.80 (m, 2H), 3.89 (s, 3H), 4.66 (t, 1H), 6.23-6.36 (m, 2H), 7.40 (dd, 1H), 7.86 (td, 1H), 8.48 (d, 1H), 8.65 (s, 1H), 8.84 (d, 1H). MS obsd. (ESI$^+$) [(M+H)$^+$]: 397.

Example 13 and 14: (−)-6-(3,4-difluoro-5-methoxy-phenyl)-5-propyl-2-(2-pyridyl)-7,8-dihydro-5H-pyrido[4,3-d]pyrimidine and (+)-6-(3,4-difluoro-5-methoxy-phenyl)-5-propyl-2-(2-pyridyl)-7,8-dihydro-5H-pyrido[4,3-d]pyrimidine

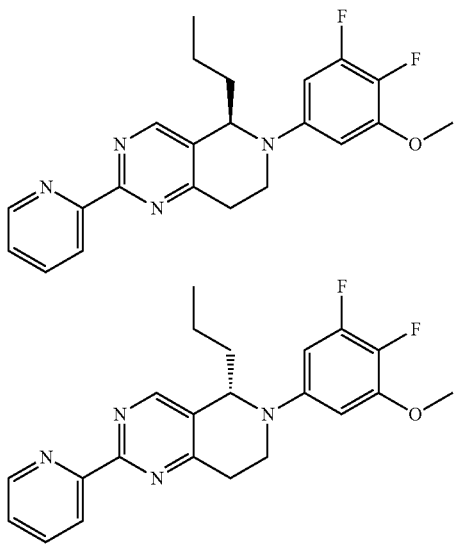

Separation of 6-(3,4-difluoro-5-methoxy-phenyl)-5-propyl-2-(2-pyridyl)-7,8-dihydro-5H-pyrido[4,3-d]pyrimidine (30 mg, Example 12) by chiral HPLC gave (−)-6-(3,4-difluoro-5-methoxy-phenyl)-5-propyl-2-(2-pyridyl)-7,8-dihydro-5H-pyrido[4,3-d]pyrimidine (12 mg) and (+)-6-(3,4-difluoro-5-methoxy-phenyl)-5-propyl-2-(2-pyridyl)-7,8-dihydro-5H-pyrido[4,3-d]pyrimidine (11 mg) both as yellow solid.

Example 13: (+)-6-(3,4-difluoro-5-methoxy-phenyl)-5-propyl-2-(2-pyridyl)-7,8-dihydro-5H-pyrido[4,3-d]pyrimidine: $^1$H NMR (400 MHz, CDCl$_3$) δ: 0.98 (t, 3H) 1.40-1.56 (m, 2H) 1.74 (m, 1H) 1.85-1.99 (m, 1H) 3.04-3.14 (m, 1H), 3.16-3.31 (m, 1H), 3.58-3.68 (m, 1H), 3.70-3.80 (m, 1H), 3.89 (s, 3H), 4.66 (t, 1H), 6.23-6.36 (m, 2H), 7.40 (dd, 1H) 7.86 (td, 1H) 8.48 (d, 1H), 8.65 (s, 1H), 8.84 (d, 1H). MS obsd. (ESI$^+$) [(M+H)$^+$]: 397.

Example 14: (−)-6-(3,4-difluoro-5-methoxy-phenyl)-5-propyl-2-(2-pyridyl)-7,8-dihydro-5H-pyrido[4,3-d]pyrimidine: $^1$H NMR (400 MHz, CDCl$_3$) δ: 0.98 (t, 3H) 1.40-1.56 (m, 2H) 1.74 (m, 1H) 1.85-1.99 (m, 1H) 3.04-3.14 (m, 1H), 3.16-3.31 (m, 1H), 3.58-3.68 (m, 1H), 3.70-3.80 (m, 1H), 3.89 (s, 3H), 4.66 (t, 1H), 6.23-6.36 (m, 2H), 7.40 (dd, 1H) 7.86 (td, 1H) 8.48 (d, 1H), 8.65 (s, 1H), 8.84 (d, 1H). MS obsd. (ESI$^+$) [(M+H)$^+$]: 397. $[a]_D^{25}$=−56.800° (0.05 g/100 mL, MeOH).

Example 15: 6-(3,4-difluoro-5-methoxy-phenyl)-5-methyl-2-pyrimidin-2-yl-7,8-dihydro-5H-pyrido[4,3-d]pyrimidine

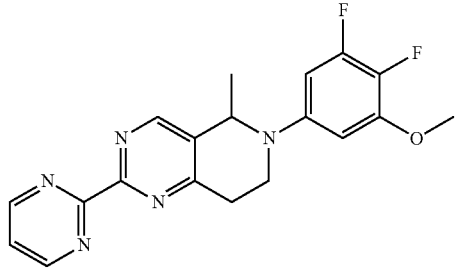

Step 1: Preparation of 6-(3,4-difluoro-5-methoxy-phenyl)-2-pyrimidin-2-yl-7,8-dihydro-5H-pyrido[4,3-d]pyrimidine

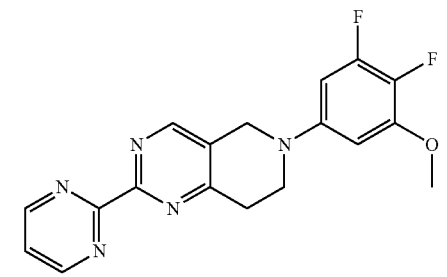 [SMILES: COc1cc(N2CCc3nc(-c4ncccn4)ncc3C2)cc(F)c1F]

A solution of 1-(3,4-difluoro-5-methoxy-phenyl)piperidin-4-one (0.39 g, 1.64 mmol) and DMFDMA (1 mL) in acetonitrile (9 mL) was stirred at 90° C. for 2 hrs. The reaction mixture was concentrated in vacuo and the residue was dissolved in EtOH (10 mL). To the solution was added pyrimidine-2-carboxamidine hydrochloride (260 mg, 1.64 mmol) and potassium carbonate (453 mg, 3.28 mmol) successively. After being heated at 90° C. with stirring overnight, the reaction mixture was cooled down to rt and purified by prep-HPLC to give 6-(3,4-difluoro-5-methoxyphenyl)-2-pyrimidin-2-yl-7,8-dihydro-5H-pyrido[4,3-d]pyrimidine (10 mg) as light yellow solid.

Step 2: Preparation of 6-(3,4-difluoro-5-methoxyphenyl)-5-methoxy-2-pyrimidin-2-yl-7,8-dihydro-5H-pyrido[4,3-d]pyrimidine

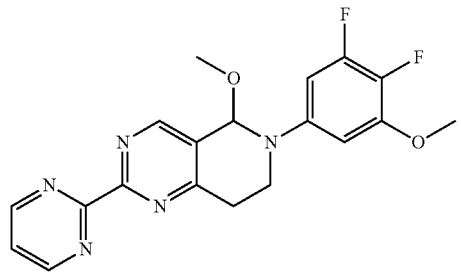 [SMILES: COc1cc(N2CCc3nc(-c4ncccn4)ncc3C2OC)cc(F)c1F]

To a stirred solution of 6-(3,4-difluoro-5-methoxy-phenyl)-2-pyrimidin-2-yl-7,8-dihydro-5H-pyrido[4,3-d]pyrimidine (1.7 g, 4.79 mmol) in a mixed solvent of DCM (40 mL) and MeOH (8 mL) at −70° C. was added RuCl$_3$ hydrate (1.44 mmol) and NaIO$_4$ (3.1 g in 30 mL H$_2$O, 14.37 mmol) successively. The cooling bath was removed. The reaction mixture was warmed to rt slowly and stirred at rt. After the reaction was complete, the reaction mixture was diluted with saturated aqueous solution of Na$_2$S$_2$O$_3$ (30 mL) and extracted with EA (50 mL) for three times. The combined organic layer was dried over anhydrous Na$_2$SO$_4$ and concentrated in vacuo to give 6-(3,4-difluoro-5-methoxy-phenyl)-5-methoxy-2-pyrimidin-2-yl-7,8-dihydro-5H-pyrido[4,3-d]pyrimidine (1800 mg) as dark foam which was used directly in the next step directly without further purification.

Step 3: Preparation of 6-(3,4-difluoro-5-methoxyphenyl)-5-methyl-2-pyrimidin-2-yl-7,8-dihydro-5H-pyrido[4,3-d]pyrimidine

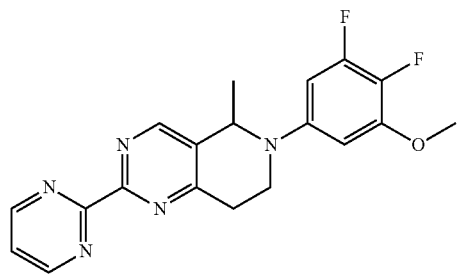 [SMILES: COc1cc(N2CCc3nc(-c4ncccn4)ncc3C2C)cc(F)c1F]

To a solution of 6-(3,4-difluoro-5-methoxy-phenyl)-5-methoxy-2-pyrimidin-2-yl-7,8-dihydro-5H-pyrido[4,3-d]pyrimidine (1.8 mg, 4.79 mmol) in THF (40 mL) at −70° C. was added BF$_3$.Et$_2$O (1360 mg, 9.58 mmol). The mixture was stirred for 15 mins at this temperature. To the resulting mixture was added MeMgBr (4.8 mL in THF, 3.0 M from Aldrich). After being warmed to rt and stirred at rt for 1 hr, the resulting mixture was diluted with saturated aqueous solution of NH$_4$Cl and extracted with EA (50 mL) for three times. The combined organic layer was dried over anhydrous Na$_2$SO$_4$ and concentrated in vacuo. The residue was purified by prep-HPLC to give 6-(3,4-difluoro-5-methoxyphenyl)-5-methyl-2-pyrimidin-2-yl-7,8-dihydro-5H-pyrido[4,3-d]pyrimidine (300 mg). $^1$H NMR (400 MHz, Methanol-d$_4$) δ: 9.05 (d, 2H), 8.83-8.92 (m, 1H), 7.62-7.71 (m, 1H), 6.48-6.63 (m, 2H), 5.17-5.30 (m, 1H), 3.80-3.98 (m, 4H), 3.50-3.62 (m, 1H), 3.10-3.28 (m, 2H), 1.48 (d, 3H). MS obsd. (ESI$^+$) [(M+H)$^+$]: 370.

Example 16 and 17: (−)-6-(3,4-difluoro-5-methoxyphenyl)-5-methyl-2-pyrimidin-2-yl-7,8-dihydro-5H-pyrido[4,3-d]pyrimidine and (+)-6-(3,4-difluoro-5-methoxy-phenyl)-5-methyl-2-pyrimidin-2-yl-7,8-dihydro-5H-pyrido[4,3-d]pyrimidine

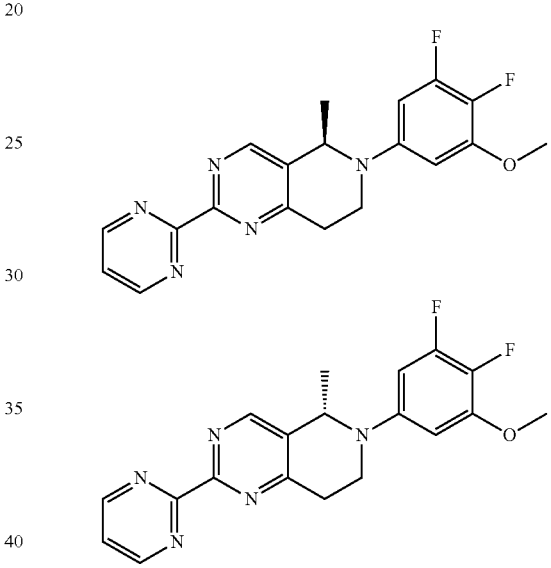

Separation of 6-(3,4-difluoro-5-methoxy-phenyl)-5-methyl-2-pyrimidin-2-yl-7,8-dihydro-5H-pyrido[4,3-d]pyrimidine (100 mg, Example 15) by chiral HPLC gave (−)-6-(3,4-difluoro-5-methoxy-phenyl)-5-methyl-2-pyrimidin-2-yl-7,8-dihydro-5H-pyrido[4,3-d]pyrimidine (40 mg) and (+)-6-(3,4-difluoro-5-methoxy-phenyl)-5-methyl-2-pyrimidin-2-yl-7,8-dihydro-5H-pyrido[4,3-d]pyrimidine (40 mg).

Example 16: (+)-6-(3,4-difluoro-5-methoxy-phenyl)-5-methyl-2-pyrimidin-2-yl-7,8-dihydro-5H-pyrido[4,3-d]pyrimidine: $^1$H NMR (400 MHz, CDCl$_3$) δ: 8.92-9.05 (m, 2H), 8.67-8.79 (m, 1H), 7.35-7.45 (m, 1H), 6.24-6.39 (m, 2H), 4.88-5.01 (m, 1H), 3.86 (d, 3H), 3.60-3.75 (m, 1H), 3.39-3.53 (m, 3H), 3.14-3.34 (m, 3H), 1.40 (t, 3H). MS obsd. (ESI$^+$) [(M+H)$^+$]: 370.

Example 17: (−)-6-(3,4-difluoro-5-methoxy-phenyl)-5-methyl-2-pyrimidin-2-yl-7,8-dihydro-5H-pyrido[4,3-d]pyrimidine: $^1$H NMR (400 MHz, CDCl$_3$) δ: 8.92-9.05 (m, 2H), 8.67-8.79 (m, 1H), 7.35-7.45 (m, 1H), 6.24-6.39 (m, 2H), 4.88-5.01 (m, 1H), 3.86 (d, 3H), 3.60-3.75 (m, 1H), 3.39-3.53 (m, 3H), 3.14-3.34 (m, 3H), 1.40 (t, 3H). MS obsd. (ESI$^+$) [(M+H)$^+$]: 370. [a]$_D^{20}$=−74.679° (0.086 g/100 mL, MeOH).

Example 18: 5-cyclopropyl-6-(3,4-difluoro-5-methoxy-phenyl)-2-pyrimidin-2-yl-7,8-dihydro-5H-pyrido[4,3-d]pyrimidine

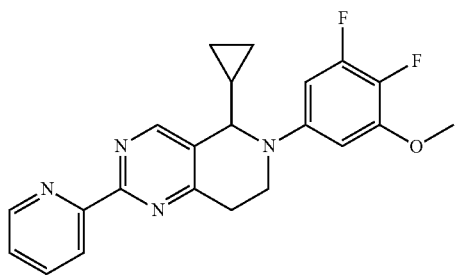 [SMILES: COc1cc(N2CCc3nc(-c4ccccn4)ncc3C2C2CC2)cc(F)c1F]

To a stirred solution of 6-(3,4-difluoro-5-methoxy-phenyl)-5-methoxy-2-(2-pyridyl)-7,8-dihydro-5H-pyrido[4,3-d]pyrimidine (300 mg, 0.78 mmol) in THF (20 mL) at −70° C. was added BF$_3$.Et$_2$O (180 mg, 1.56 mmol). The mixture was stirred for 15 min at this temperature followed by the addition of a solution of cyclopropylmagnesium bromide (3.9 mmol, 0.5 M) in THF. After being warmed to rt and stirred for 1 hr, the reaction mixture was diluted with saturated aqueous solution of NH$_4$Cl and extracted with EA (30 mL) for three times. The combined organic layer was dried over anhydrous Na$_2$SO$_4$ and concentrated in vacuo. The residue was purified by prep-HPLC to give 5-cyclopropyl-6-(3,4-difluoro-5-methoxy-phenyl)-2-pyrimidin-2-yl-7,8-dihydro-5H-pyrido[4,3-d]pyrimidine (40 mg) as light yellow solid. $^1$H NMR (400 MHz, CDCl$_3$) δ: 0.21-0.43 (m, 2H) 0.49-0.69 (m, 2H) 1.20-1.31 (m, 1H) 3.12-3.32 (m, 2H) 3.68-3.87 (m, 2H) 3.90 (s, 3H) 4.25 (d, 1H) 6.33-6.42 (m, 2H) 7.41 (dd, 1H) 7.87 (t, 1H) 8.50 (d, 1H) 8.72 (s, 1H) 8.85 (d, 1H). MS obsd. (ESI$^+$) [(M+H)$^+$]: 395.

Example 19: 6-[3,4-difluoro-5-(2-methoxyethoxy)phenyl]-5-methyl-2-(2-pyridyl)-7,8-dihydro-5H-pyrido[4,3-d]pyrimidine

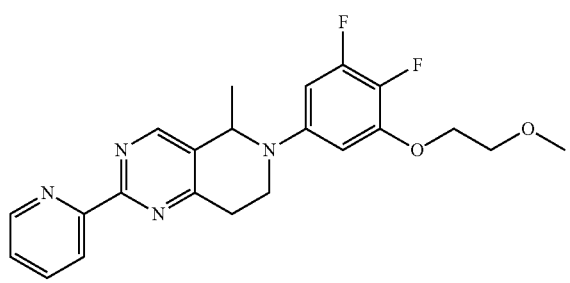 [SMILES: COCCOc1cc(N2CCc3nc(-c4ccccn4)ncc3C2C)cc(F)c1F]

Step 1: Preparation of 5-bromo-1,2-difluoro-3-(2-methoxyethoxy)benzene

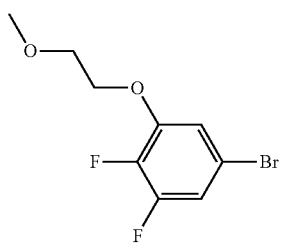

To a solution of 5-bromo-2,3-difluoro-phenol (25.0 g, 0.12 mol) in MeCN (200 mL) was added 1-bromo-2-methoxy-ethane (18.3 g, 0.132 mol) and Cs$_2$CO$_3$ (60.0 g, 0.18 mol). After being heated at 70° C. with stirring for 12 hrs, the resulting mixture was cooled down to rt and filtered. The filtrate was concentrated in vacuo to give 5-bromo-1,2-difluoro-3-(2-methoxyethoxy)benzene (30.0 g) as a yellow oil which was used in the next step directly without further purification.

Step 2: Preparation of 8-[3,4-difluoro-5-(2-methoxyethoxy)phenyl]-1,4-dioxa-8-azaspiro[4.5]decane

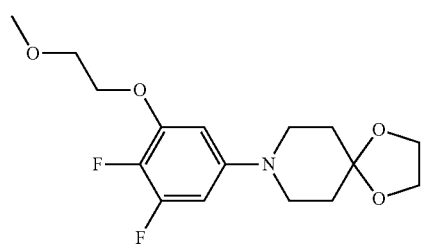 [SMILES: COCCOc1cc(N2CCC3(CC2)OCCO3)cc(F)c1F]

A mixture of 1,4-dioxa-8-azaspiro[4.5]decane (10.0 g, 69.89 mmol), 5-bromo-1,2-difluoro-3-(2-methoxyethoxy)benzene (24.25 g, 90.85 mmol), t-BuONa (10.1 g, 105 mmol), Ruphos (1.3 g) and Pd$_2$(dba)$_3$ (1.28 g) in dioxane (100 mL) was heated at 100° C. with stirring under N$_2$ for 16 hrs. The resulting mixture was cooled down to rt and filtered. The filtrate was concentrated in vacuo, diluted with DCM, washed with water, brine, dried over anhydrous Na$_2$SO$_4$ and concentrated in vacuo. The residue was purified by column to give 5-bromo-1,2-difluoro-3-(2-methoxyethoxy)benzene (12.0 g) as a yellow solid.

Step 3: Preparation of 1-[3,4-difluoro-5-(2-methoxyethoxy)phenyl]piperidin-4-one

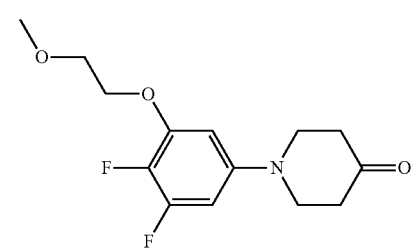 [SMILES: COCCOc1cc(N2CCC(=O)CC2)cc(F)c1F]

A mixture of 5-bromo-1,2-difluoro-3-(2-methoxyethoxy)benzene (11.0 g, 33.4 mmol), formic acid (50 mL) and H$_2$O (55 mL) was heated with stirring at 90° C. for 2 hrs. The resulting mixture was concentrated in vacuo and the residue was diluted with saturated aqueous solution of NaHCO$_3$. The resulting mixture was extracted with EA (100 mL) for three times. The combined organic layer was washed with brine, dried over anhydrous Na$_2$SO$_4$ and concentrated in vacuo. The residue was purified by column to give 1-[3,4-difluoro-5-(2-methoxyethoxy)phenyl]piperidin-4-one (4.82 g) as dark solid.

Step 4: Preparation of 6-[3,4-difluoro-5-(2-methoxyethoxy)phenyl]-2-(2-pyridyl)-7,8-dihydro-5H-pyrido[4,3-d]pyrimidine

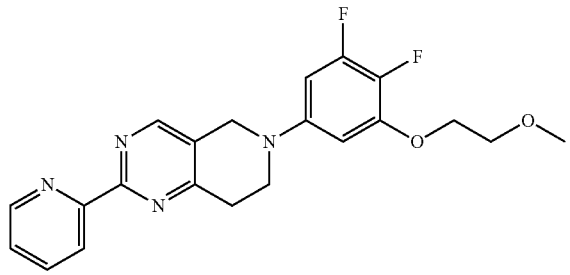 [SMILES: COCCOc1cc(N2CCc3nc(-c4ccccn4)ncc3C2)cc(F)c1F]

A mixture of 1-[3,4-difluoro-5-(2-methoxyethoxy)phenyl]piperidin-4-one (4.82 g, 16.9 mmol) and DMFDMF (50 mL) was heated at 120° C. with stirring for 4 hrs. The mixture was concentrated in vacuo and the residue was dissolved in MeOH (50 mL). To the solution was added pyridine-2-carboximidamide hydrochloride (2.35 g, 15 mmol), and K₂CO₃ (4.75 g, 33 mmol). After being heated at 60° C. with stirring for 16 hrs, the resulting mixture was cooled down to rt, diluted with saturated aqueous solution of NH₄Cl and extracted with EA (100 mL) for three times. The combined organic layer was washed with brine, dried over anhydrous Na₂SO₄ and concentrated in vacuo. The residue was purified by flash column to give 6-[3,4-difluoro-5-(2-methoxyethoxy)phenyl]-2-(2-pyridyl)-7,8-dihydro-5H-pyrido[4,3-d]pyrimidine (2.3 g) as a pale yellow solid.

Step 5: Preparation of 6-[3,4-difluoro-5-(2-methoxyethoxy)phenyl]-5-methoxy-2-(2-pyridyl)-7,8-dihydro-5H-pyrido[4,3-d]pyrimidine

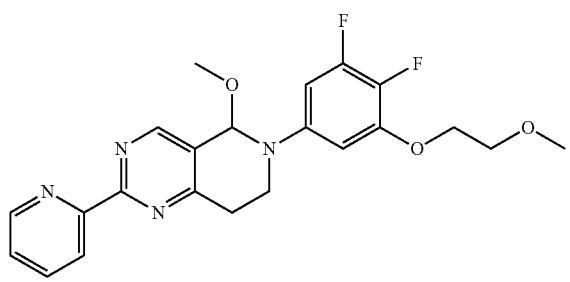 [SMILES: COCCOc1cc(N2CCc3nc(-c4ccccn4)ncc3C2OC)cc(F)c1F]

To a cooled solution of 6-[3,4-difluoro-5-(2-methoxyethoxy)phenyl]-5-methyl-2-(2-pyridyl)-7,8-dihydro-5H-pyrido[4,3-d]pyrimidine (2.2 g, 5.53 mmol) in dichloromethane (180 mL) and methanol (40 mL) at −70° C. was added RuCl₃ hydrate (1.66 mmol) followed by a solution of NaIO₄ (3.55 g, 16.58 mmol) in water (80 mL) slowly. The cooling bath was removed and the mixture was stirred at rt overnight. The reaction mixture was then diluted with saturated aqueous solution of Na₂S₂O₃ and extracted with EA (50 mL) for three times. The combined organic layer was dried over anhydrous Na₂SO₄ and concentrated in vacuo to give crude 6-[3,4-difluoro-5-(2-methoxyethoxy)phenyl]-5-methoxy-2-(2-pyridyl)-7,8-dihydro-5H-pyrido[4,3-d]pyrimidine (2.3 g) as a black oil.

Step 6: Preparation of 6-[3,4-difluoro-5-(2-methoxyethoxy)phenyl]-5-methyl-2-(2-pyridyl)-7,8-dihydro-5H-pyrido[4,3-d]pyrimidine

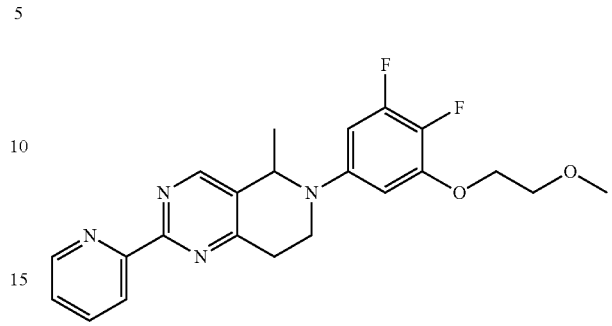

To a cooled solution of 6-[3,4-difluoro-5-(2-methoxyethoxy)phenyl]-5-methoxy-2-(2-pyridyl)-7,8-dihydro-5H-pyrido[4,3-d]pyrimidine (2.3 g, 5.4 mmol) in THF (30 mL) at −70° C. was added BF₃.Et₂O with stirring. The mixture was stirred for 10 mins followed by addition of CH₃MgCl (3.0 M in THF, 2.01 g, 27 mmol). The resulting mixture was slowly warmed to rt and stirred at rt. After the reaction was complete, the reaction mixture was diluted with H₂O and extracted with EA (50 mL) for three times. The combined organic layer was dried over anhydrous Na₂SO₄ and concentrated in vacuo. The residue was purified by prep-HPLC to give 6-[3,4-difluoro-5-(2-methoxyethoxy)phenyl]-5-methyl-2-(2-pyridyl)-7,8-dihydro-5H-pyrido[4,3-d]pyrimidine (1.05 g). $^1$H NMR (400 MHz, CDCl₃) δ: 8.82-8.90 (m, 1H), 8.67 (s, 1H), 8.51 (d, 1H), 7.87 (m, 1H), 7.41 (m, 1H), 6.33-6.47 (m, 2H), 4.92 (m, 1H), 4.17-4.28 (m, 2H), 3.75-3.83 (m, 2H), 3.70 (m, 1H), 3.42-3.52 (m, 4H), 3.11-3.33 (m, 2H), 1.43 (d, 3H); MS obsd. (ESI⁺) [(M+H)⁺]: 413.

Example 20 and 21: (+)-6-[3,4-difluoro-5-(2-methoxyethoxy)phenyl]-5-methyl-2-(2-pyridyl)-7,8-dihydro-5H-pyrido[4,3-d]pyrimidine and (−)-6-[3,4-difluoro-5-(2-methoxyethoxy)phenyl]-5-methyl-2-(2-pyridyl)-7,8-dihydro-5H-pyrido[4,3-d]pyrimidine

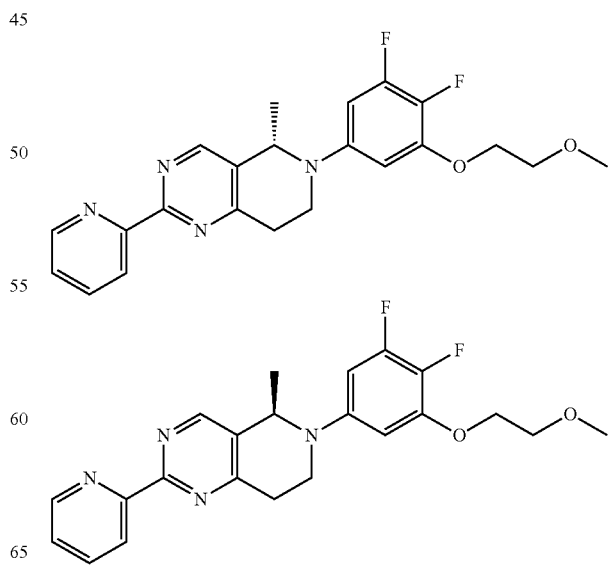

Separation of 6-[3,4-difluoro-5-(2-methoxyethoxy)phenyl]-5-methyl-2-(2-pyridyl)-7,8-dihydro-5H-pyrido[4,3-d]pyrimidine (1 g, Example 19) by chiral HPLC gave (+)-6-[3,4-difluoro-5-(2-methoxyethoxy)phenyl]-5-methyl-2-(2-pyridyl)-7,8-dihydro-5H-pyrido[4, 3-d]pyrimidine (278 mg) and (−)-6-[3,4-difluoro-5-(2-methoxyethoxy)phenyl]-5-methyl-2-(2-pyridyl)-7,8-dihydro-5H-pyrido[4,3-d]pyrimidine (275 mg) both as yellow solid.

Example 20: (+)-6-[3,4-difluoro-5-(2-methoxyethoxy)phenyl]-5-methyl-2-(2-pyridyl)-7,8-dihydro-5H-pyrido[4,3-d]pyrimidine, $^1$H NMR (400 MHz, CDCl$_3$) δ: 8.88 (d, 1H), 8.69 (s, 1H), 8.53 (d, 1H), 7.91 (m, 1H), 7.44 (m, 1H), 6.33-6.48 (m, 2H), 4.93 (m, 1H), 4.19-4.28 (m, 2H), 3.79 (m, 2H), 3.71 (m, 1H), 3.43-3.54 (m, 4H), 3.12-3.34 (m, 2H), 1.39-1.49 (m, 3H). MS obsd. (ESI$^+$) [(M+H)$^+$]: 413.

Example 21: (−)-6-[3,4-difluoro-5-(2-methoxyethoxy)phenyl]-5-methyl-2-(2-pyridyl)-7,8-dihydro-5H-pyrido[4,3-d]pyrimidine, $^1$H NMR (400 MHz, CDCl$_3$) δ: 8.88 (d, 1H), 8.69 (s, 1H), 8.53 (d, 1H), 7.91 (m, 1H), 7.44 (m, 1H), 6.33-6.48 (m, 2H), 4.93 (m, 1H), 4.19-4.28 (m, 2H), 3.79 (m, 2H), 3.71 (m, 1H), 3.43-3.54 (m, 4H), 3.12-3.34 (m, 2H), 1.39-1.49 (m, 3H); MS obsd. (ESI$^+$) [(M+H)$^+$]: 413. $[a]_D^{25}$=−64.00° (0.05 g/100 mL, methanol).

Example 22: 2-fluoro-6-methoxy-4-(5-methyl-2-pyrimidin-2-yl-7,8-dihydro-5H-pyrido[4,3-d]pyrimidin-6-yl)benzonitrile

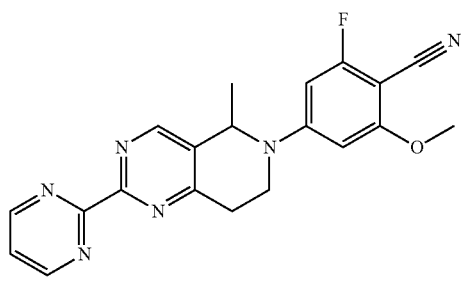 [SMILES: COc1cc(N2CCc3nc(-c4ncccn4)ncc3C2C)cc(F)c1C#N]

Step 1: Preparation of 4-bromo-2-fluoro-6-methoxy-benzonitrile

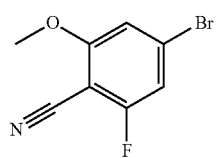

To a solution of 4-bromo-2,6-difluoro-benzonitrile (3.0 g, 13.8 mmol) in THF (40 mL) was added NaOMe (1.1 g, 20.7 mmol) at rt. The reaction mixture was stirred overnight at rt and purified by column to give 4-bromo-2-fluoro-6-methoxy-benzonitrile (700 mg).

Step 2: Preparation of 4-(1,4-dioxa-8-azaspiro[4.5]decan-8-yl)-2-fluoro-6-methoxy-benzonitrile

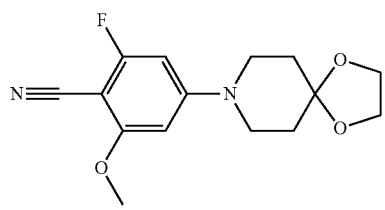 [SMILES: COc1cc(N2CCC3(CC2)OCCO3)cc(F)c1C#N]

To a mixture of 4-bromo-2-fluoro-6-methoxy-benzonitrile (700 mg, 1.75 mmol) and 1,4-dioxa-8-azaspiro[4.5]decane (276 mg, 1.93 mmol) in dioxane (15 mL) was added Cs$_2$CO$_3$ (1700 mg, 5.25 mmol). The mixture was degassed and charged with N$_2$. To the mixture was added Pd$_2$(dba)$_3$ (83 mg, 0.09 mmol) and Ruphos (84 mg, 0.18 mmol) successively. After being heated at 100° C. with stirring overnight, the reaction mixture was cooled down to rt, diluted with H$_2$O (30 mL) and extracted with EA (30 mL) for three times. The combined organic layer was washed with brine (30 mL), dried over anhydrous Na$_2$SO$_4$ and concentrated in vacuo to give crude 4-(1,4-dioxa-8-azaspiro[4.5]decan-8-yl)-2-fluoro-6-methoxy-benzonitrile (510 mg) as dark oil which was used in the next step directly without further purification.

Step 3: Preparation of 2-fluoro-6-methoxy-4-(4-oxo-1-piperidyl)benzonitrile

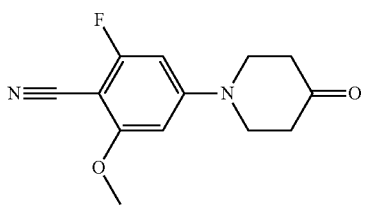 [SMILES: COc1cc(N2CCC(=O)CC2)cc(F)c1C#N]

A flask containing crude 4-(1,4-dioxa-8-azaspiro[4.5]decan-8-yl)-2-fluoro-6-methoxy-benzonitrile (510 mg, 1.75 mmol) was added 44% formic acid (10 mL) and the mixture was heated at 90° C. with stirring for 8 hrs. The reaction mixture was concentrated in vacuo. The residue was diluted with saturated aqueous solution of NaHCO$_3$ (20 mL) and extracted with EA (30 mL) for three times. The combined organic layer was washed with brine (50 mL), dried over anhydrous Na$_2$SO$_4$ and concentrated in vacuo to give 2-fluoro-6-methoxy-4-(4-oxo-1-piperidyl)benzonitrile (430 mg) as brown oil which was used in the next step directly without further purification.

Step 4: Preparation of 2-fluoro-6-methoxy-4-(2-pyrimidin-2-yl-7,8-dihydro-5H-pyrido[4,3-d]pyrimidin-6-yl)benzonitrile

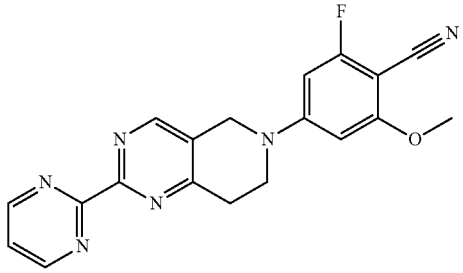 [SMILES: COc1cc(N2CCc3nc(-c4ncccn4)ncc3C2)cc(F)c1C#N]

A mixture of crude 2-fluoro-6-methoxy-4-(4-oxo-1-piperidyl)benzonitrile (430 mg, 1.75 mmol) and DMFDMA (10 mL) was heated at 90° C. with stirring for 3 hrs. The reaction mixture was concentrated in vacuo and the residue was dissolved in EtOH (20 mL). To the solution was added pyrimidine-2-carboxamidine hydrochloride (277 mg, 1.75 mmol) and $K_2CO_3$ (480 mg, 3.5 mmol) successively and the reaction mixture was heated at 80° C. with stirring overnight. The reaction mixture was cooled down to rt and purified by prep-HPLC to give 2-fluoro-6-methoxy-4-(2-pyrimidin-2-yl-7,8-dihydro-5H-pyrido[4,3-d]pyrimidin-6-yl)benzonitrile (50 mg) as yellow solid.

Step 5: Preparation of 2-fluoro-6-methoxy-4-(5-methoxy-2-pyrimidin-2-yl-7,8-dihydro-5H-pyrido[4,3-d]pyrimidin-6-yl)benzonitrile

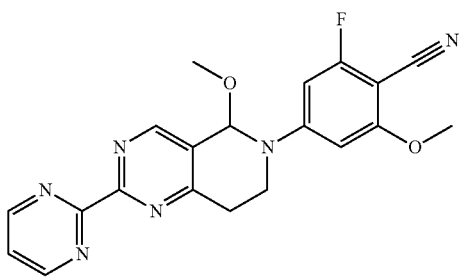 [SMILES: COc1cc(N2CCc3nc(-c4ncccn4)ncc3C2OC)cc(F)c1C#N]

To a stirred solution of 2-fluoro-6-methoxy-4-(2-pyrimidin-2-yl-7,8-dihydro-5H-pyrido[4,3-d]pyrimidin-6-yl)benzonitrile (400 mg, 1.1 mmol) in a mixed solvent of DCM (40 mL) and MeOH (8 mL) at −70° C. was added $RuCl_3$ hydrate (0.33 mmol) and $NaIO_4$ (706 mg in 5 mL $H_2O$, 3.3 mmol) successively. The cooling bath was removed and the reaction mixture was warmed to rt slowly and stirred at rt. After the reaction was complete, the reaction mixture was diluted with saturated aqueous solution of $Na_2S_2O_3$ (30 mL) and extracted with EA (50 mL) for three times. The combined organic layer was dried over anhydrous $Na_2SO_4$ and concentrated in vacuo to give 2-fluoro-6-methoxy-4-(5-methoxy-2-pyrimidin-2-yl-7,8-dihydro-5H-pyrido[4,3-d]pyrimidin-6-yl)benzonitrile (430 mg) black foam which was used directly in the next step directly without further purification.

Step 6: Preparation of 2-fluoro-6-methoxy-4-(5-methyl-2-pyrimidin-2-yl-7,8-dihydro-5H-pyrido[4,3-d]pyrimidin-6-yl)benzonitrile

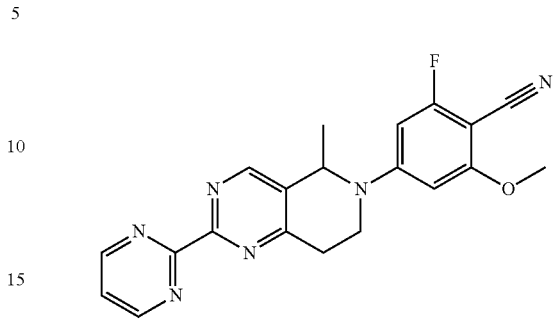

To a cooled solution of 2-fluoro-6-methoxy-4-(5-methoxy-2-pyrimidin-2-yl-7,8-dihydro-5H-pyrido[4,3-d]pyrimidin-6-yl)benzonitrile (430 mg, 1.1 mmol) in THF (20 mL) at −70° C. was added $BF_3.Et_2O$ (310 mg, 2.2 mmol). The mixture was stirred for 15 mins at this temperature followed by the addition of MeMgBr (1.1 mL in THF, 3.0 M from Aldrich). The reaction mixture was warmed to rt and stirred for 1 hr. the reaction mixture was diluted with saturated aqueous solution of $NH_4Cl$. and extracted with EA (30 mL) for three times. The combined organic layer was dried over anhydrous $Na_2SO_4$ and concentrated in vacuo. The residue was purified by prep-HPLC to give 2-fluoro-6-methoxy-4-(5-methyl-2-pyrimidin-2-yl-7,8-dihydro-5H-pyrido[4,3-d]pyrimidin-6-yl)benzonitrile (15 mg). $^1$H NMR (400 MHz, $CDCl_3$) δ: 9.0-9.12 (m, 2H), 8.77-8.92 (m, 1H), 7.48 (t, 1H), 6.26-6.37 (m, 1H), 6.17 (s, 1H), 5.06-5.24 (m, 1H), 3.97 (s, 4H), 3.59-3.73 (m, 1H), 3.30-3.41 (m, 2H), 1.65 (d, 3H). MS obsd. ($ESI^+$) [$(M+H)^+$]: 377.

Example 23: 5-methyl-6-(4-methylsulfonylphenyl)-2-(2-pyridyl)-7,8-dihydro-5H-pyrido[4,3-d]pyrimidine

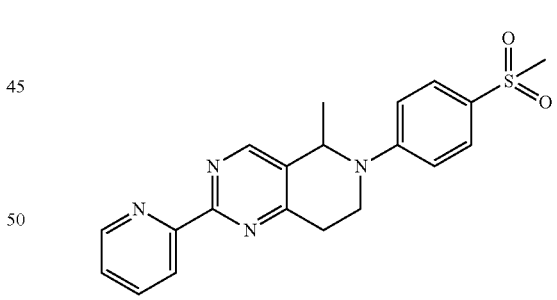

To a cooled solution of 5-methoxy-6-(4-methyl sulfonylphenyl)-2-(2-pyridyl)-7,8-dihydro-5H-pyrido[4,3-d]pyrimidine (160 mg, 0.4 mmol) in THF (10 mL) at −70° C. was added $BF_3.Et_2O$ (114 mg, 0.8 mmol). The mixture was stirred for 15 mins at this temperature followed by the addition of MeMgBr (0.4 mL in THF, 3.0 M from Aldrich). After being warmed to rt and stirred for 1 hr, the reaction mixture was diluted with saturated aqueous solution of $NH_4Cl$ and extracted with EA (30 mL) for three times. The combined organic layer was dried over anhydrous $Na_2SO_4$ and concentrated in vacuo. The residue was purified by prep-HPLC to give 5-methyl-6-(4-methyl sulfonylphenyl)-2-(2-pyridyl)-7,8-dihydro-5H-pyrido[4,3-d]pyrimidine (15 mg). $^1$H NMR (400 MHz, CDCl$_3$) δ: 8.86-8.92 (m, 1H), 8.74 (s, 1H), 8.55 (d, 1H), 7.89-7.97 (m, 1H), 7.84 (d, 2H), 7.42-7.52 (m, 1H), 7.02 (d, 2H), 5.13-5.26 (m, 1H), 4.00-4.15 (m, 1H), 3.57-3.71 (m, 1H), 3.19-3.39 (m, 2H), 3.04 (s, 3H), 1.62 (d, 3H). MS obsd. (ESI$^+$) [(M+H)$^+$]: 381.

Example 24: 4-[2,3-difluoro-5-[5-methyl-2-(2-pyridyl)-7,8-dihydro-5H-pyrido[4,3-d]pyrimidin-6-yl]phenoxy]butan-1-ol

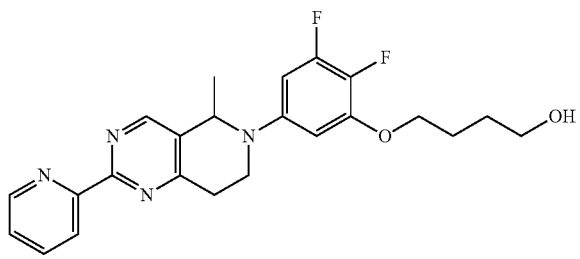 [SMILES: CC1c2cnc(-c3ccccn3)nc2CCN1c1cc(F)c(F)c(OCCCCO)c1]

Step 1: Preparation of 1-benzyloxy-5-bromo-2,3-difluoro-benzene

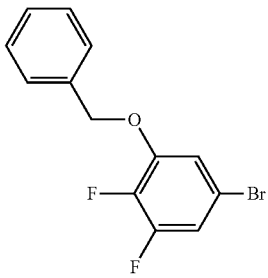 [SMILES: Fc1cc(Br)cc(OCc2ccccc2)c1F]

To a mixture of 5-bromo-2,3-difluorophenol (600.0 g, 2885.5 mmol) and Cs$_2$CO$_3$ (1410.0 g, 4327.5 mmol) in MeCN (6000 mL) was added BnBr (519.0 g, 3034.5 mmol). The mixture was heated at 50° C. with stirring for 16 hrs. The reaction mixture was filtered and the filtrate was concentrated in vacuo. The residue was diluted with EA (3000 mL), washed with brine (800 mL), dried over anhydrous Na$_2$SO$_4$ and concentrated in vacuo to give 1-benzyloxy-5-bromo-2,3-difluoro-benzene (820.0 g) as a pale yellow solid which was used directly in the next step directly without further purification.

Step 2: Preparation of 8-(3-benzyloxy-4,5-difluoro-phenyl)-1,4-dioxa-8-azaspiro[4.5]decane

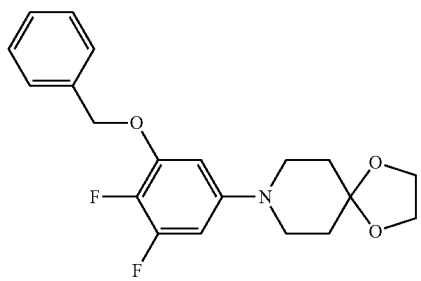 [SMILES: Fc1cc(N2CCC3(CC2)OCCO3)cc(OCc2ccccc2)c1F]

A mixture of 1,4-dioxa-8-azaspiro[4.5]decane hydrochloride (495.0 g, 2254.5 mmol), 1-benzyloxy-5-bromo-2,3-difluoro-benzene (741.9 g, 2480.1 mmol), t-BuONa (541.5 g, 5636.4 mmol), Ruphos (31.5 g, 67.65 mmol) and Pd$_2$(dba)$_3$ (41.4 g, 45.09 mmol) in dioxane (4050 mL) was degassed and heated at 100° C. with stirring under N$_2$ for 16 hrs. The reaction mixture was cooled down to rt and filtered. The filtrate was concentrated in vacuo. The residue was diluted with DCM (3000 mL), then washed with water (800 mL) and brine (600 mL), dried over anhydrous Na$_2$SO$_4$ and concentrated in vacuo. The residue was purified by column chromatography to give 8-(3-benzyloxy-4,5-difluoro-phenyl)-1,4-dioxa-8-azaspiro[4.5]decane (495.0 g) as a dark green solid.

Step 3: Preparation of 1-(3-benzyloxy-4,5-difluoro-phenyl)piperidin-4-one

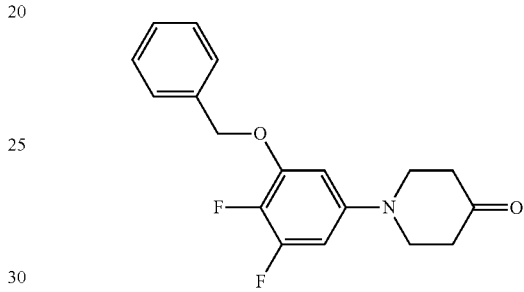

A mixture of 8-(3-benzyloxy-4,5-difluoro-phenyl)-1,4-dioxa-8-azaspiro[4.5]decane (495.0 g, 1369.8 mmol), formic acid (2400 mL) and H$_2$O (2400 mL) was heated at 90° C. with stirring for 2 hrs. The reaction mixture was concentrated in vacuo and the residue was diluted with DCM (3000 mL). The organic layer was washed with water (800 mL), saturated aqueous solution of Na$_2$CO$_3$ (500 mL) and brine (800 mL), dried over anhydrous Na$_2$SO$_4$ and concentrated in vacuo. The residue was purified by column chromatography to give 1-(3-benzyloxy-4,5-difluoro-phenyl)piperidin-4-one (366.0 g) as a pale yellow solid.

Step 4: Preparation of 6-(3-benzyloxy-4,5-difluoro-phenyl)-2-(2-pyridyl)-7,8-dihydro-5H-pyrido[4,3-d]pyrimidine

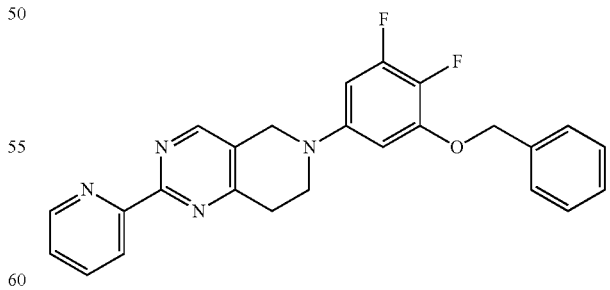

A mixture of 1-(3-benzyloxy-4,5-difluoro-phenyl)piperidin-4-one (25.0 g, 78.8 mmol) in DMFDMA (250 mL) was heated at 120° C. with stirring for 4 hrs. The reaction mixture was cooled down to rt and concentrated in vacuo. The residue was dissolved in MeOH (300 mL) and to the solution was added pyridine-2-carboxamidine hydrochloride (12.4 g, 78.8 mmol) and K₂CO₃ (27.2 g, 197 mmol). The resulting mixture was heated at 70° C. for 12 hrs. The mixture was cooled down to rt and concentrated in vacuo. The residue was purified on silica gel column to give 6-(3-benzyloxy-4,5-difluoro-phenyl)-2-(2-pyridyl)-7,8-dihydro-5H-pyrido[4,3-d]pyrimidine (15 g) as yellow solid.

Step 5: Preparation of 6-(3-benzyloxy-4,5-difluoro-phenyl)-5-methoxy-2-(2-pyridyl)-7,8-dihydro-5H-pyrido[4,3-d]pyrimidine

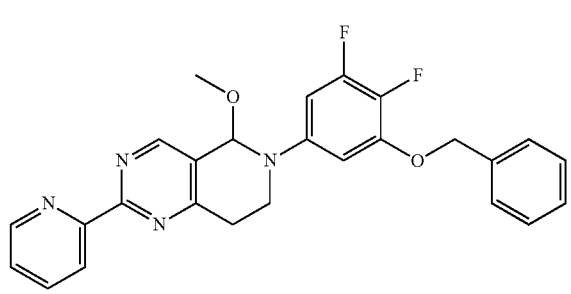 [SMILES: COC1c2cnc(-c3ccccn3)nc2CCN1c1cc(F)c(F)c(OCc2ccccc2)c1]

To a cooled solution of 6-(3-benzyloxy-4,5-difluoro-phenyl)-2-(2-pyridyl)-7,8-dihydro-5H-pyrido[4,3-d]pyrimidine (10.0 g, 23 mmol) in MeOH (150 mL) and DCM (850 mL) at −70° C. was added RuCl₃ hydrate (7.7 mmol) followed by a solution of NaIO₄ (14.9 g, 70 mmol) in H₂O (400 mL) slowly. The mixture was warmed up to 20° C. and stirred at 20° C. for 2 hrs. The mixture was diluted with saturated aqueous solution of Na₂S₂O₃ and extracted with EA (200 mL) for three times. The combined organic layers were dried over anhydrous Na₂SO₄ and concentrated in vacuo to give crude 6-(3-benzyloxy-4,5-difluoro-phenyl)-5-methoxy-2-(2-pyridyl)-7,8-dihydro-5H-pyrido[4,3-d]pyrimidine which was used in the next step directly without further purification.

Step 6: Preparation of 6-(3-benzyloxy-4,5-difluoro-phenyl)-5-methyl-2-(2-pyridyl)-7,8-dihydro-5H-pyrido[4,3-d]pyrimidine

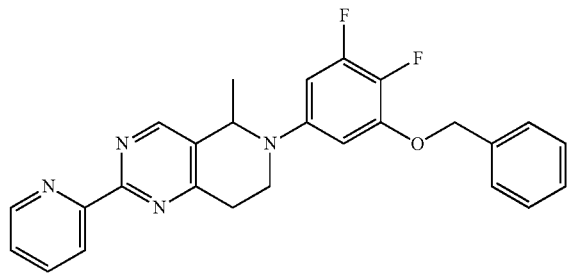 [SMILES: CC1c2cnc(-c3ccccn3)nc2CCN1c1cc(F)c(F)c(OCc2ccccc2)c1]

To a cooled and stirred solution of 6-(3-benzyloxy-4,5-difluoro-phenyl)-5-methoxy-2-(2-pyridyl)-7,8-dihydro-5H-pyrido[4,3-d]pyrimidine (10.6 g, 23 mmol) in THF (1.0 L) was added BF₃.Et₂O (10.6 g, 46 mmol) at −78° C. The mixture was stirred for 10 mins at −70° C. followed by the addition of MeMgBr (30 mL, 115 mmol, 3.0M) in THF. The mixture was slowly warmed up to rt and stirred for 2 hrs. The reaction was diluted with saturated aqueous solution of NH₄Cl and extracted with EA (300 mL) for three times. The combined organic phase was dried over anhydrous Na₂SO₄ and concentrated in vacuo. The residue was purified on silica gel column to give 6-(3-benzyloxy-4, 5-difluoro-phenyl)-5-methyl-2-(2-pyridyl)-7,8-dihydro-5H-pyrido[4,3-d]pyrimidine (3.5 g) as yellow solid.

Step 7: Preparation of 2,3-difluoro-5-[5-methyl-2-(2-pyridyl)-7,8-dihydro-5H-pyrido[4,3-d]pyrimidin-6-yl]phenol

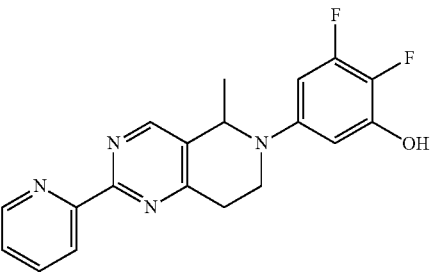 [SMILES: CC1c2cnc(-c3ccccn3)nc2CCN1c1cc(O)c(F)c(F)c1]

To a mixture of 6-(3-benzyloxy-4,5-difluoro-phenyl)-5-methyl-2-(2-pyridyl)-7,8-dihydro-5H-pyrido[4,3-d]pyrimidine (3.5 g, 7.9 mmol) and TFA (35 mL) was added thioanisole (18 mL) at rt. After being stirred at rt for 12 hrs, the resulting mixture was concentrated in vacuo and the residue was purified on silica gel column to give 2,3-difluoro-5-[5-methyl-2-(2-pyridyl)-7,8-dihydro-5H-pyrido[4,3-d]pyrimidin-6-yl]phenol (2.4 g) as yellow solid.

Step 8: Preparation of 4-[2,3-difluoro-5-[5-methyl-2-(2-pyridyl)-7,8-dihydro-5H-pyrido[4,3-d]pyrimidin-6-yl]phenoxy]butan-1-ol

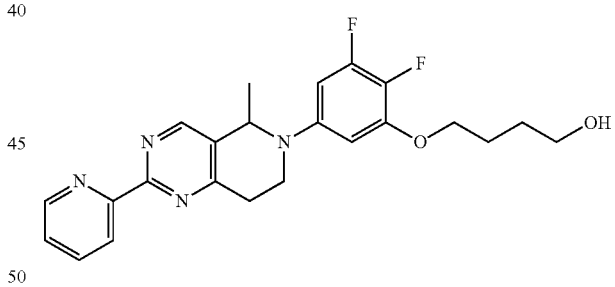

A mixture of 2,3-difluoro-5-[5-methyl-2-(2-pyridyl)-7,8-dihydro-5H-pyrido[4,3-d]pyrimidin-6-yl]phenol (100 mg, 0.282 mmol), 4-bromobutan-1-ol (216 mg, 1.412 mmol) and K₂CO₃ (194 mg, 1.412 mmol) in DMF (10 mL) was heated at 120° C. with stirring overnight. After being cooled to rt, the reaction mixture was diluted with H₂O (10 mL) and extracted with EA (30 mL) for three times. The combined organic layer was concentrated in vacuo and the residue was purified by prep-HPLC to give 4-[2,3-difluoro-5-[5-methyl-2-(2-pyridyl)-7,8-dihydro-5H-pyrido[4,3-d]pyrimidin-6-yl]phenoxy]butan-1-ol (3 mg). ¹H NMR (400 MHz, CDCl₃) δ: 8.84-8.90 (m, 1H), 8.70 (s, 1H), 8.53 (d, 1H), 7.91 (m, 1H), 7.45 (m, 1H), 6.34-6.46 (m, 2H), 4.94 (d, 1H), 4.12 (m, 2H), 3.77 (m, 3H), 3.42-3.56 (m, 1H), 3.21 (d, 2H), 1.90-2.01 (m, 2H), 1.70-1.85 (m, 2H), 1.45 (d, 3H); MS obsd. (ESI⁺) [(M+H)⁺]: 426.

Example 25: 5-[2,3-difluoro-5-[5-methyl-2-(2-pyridyl)-7,8-dihydro-5H-pyrido[4,3-d]pyrimidin-6-yl]phenoxy]pentan-1-ol

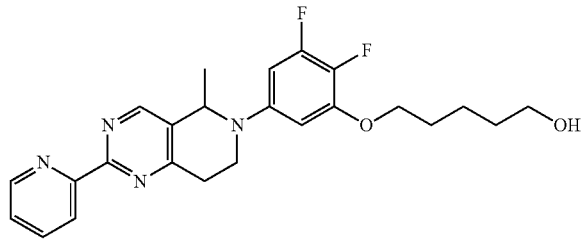 [SMILES: CC1c2cnc(-c3ccccn3)nc2CCN1c1cc(F)c(F)c(OCCCCCO)c1]

A mixture of 2,3-difluoro-5-[5-methyl-2-(2-pyridyl)-7,8-dihydro-5H-pyrido[4,3-d]pyrimidin-6-yl]phenol (50 mg, 0.141 mmol), 5-bromopentan-1-ol (118 mg, 0.706 mmol) and $Cs_2CO_3$ (138 mg, 0.424 mmol) in DMF (10 mL) was heated at 120° C. with stirring overnight. After being cooled to rt, the reaction mixture was diluted with $H_2O$ (10 mL) and extracted with EA (30 mL) for three times. The combined organic layer was concentrated in vacuo and the residue was purified by prep-HPLC to give 5-[2,3-difluoro-5-[5-methyl-2-(2-pyridyl)-7,8-dihydro-5H-pyrido[4,3-d]pyrimidin-6-yl]phenoxy]pentan-1-ol (17 mg) as yellow solid. $^1$H NMR (400 MHz, $CDCl_3$) δ: 8.86 (d, 1H), 8.69 (s, 1H), 8.51 (d, 1H), 7.89 (d, 1H), 7.39-7.47 (m, 1H), 6.36 (d, 2H), 4.93 (d, 1H), 4.07 (m, 2H), 3.71 (m, 3H), 3.44-3.55 (m, 1H), 3.12-3.33 (m, 2H), 1.86-1.94 (m, 2H), 1.54-1.72 (m, 4H), 1.44 (d, 3H); MS obsd. (ESI$^+$) [(M+H)$^+$]: 441.

Example 26: 6-[3,4-difluoro-5-(2-methylsulfonylethoxy)phenyl]-5-methyl-2-(2-pyridyl)-7,8-dihydro-5H-pyrido[4,3-d]pyrimidine

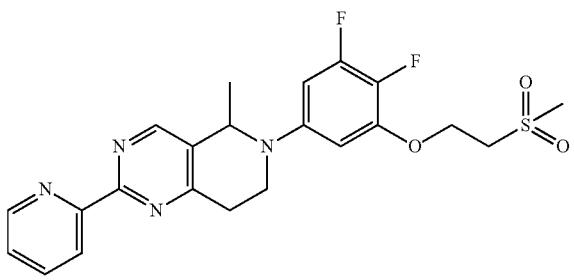 [SMILES: CC1c2cnc(-c3ccccn3)nc2CCN1c1cc(F)c(F)c(OCCS(C)(=O)=O)c1]

Step 1: Preparation of 6-[3,4-difluoro-5-(2-methylsulfanylethoxy)phenyl]-5-methyl-2-(2-pyridyl)-7,8-dihydro-5H-pyrido[4,3-d]pyrimidine

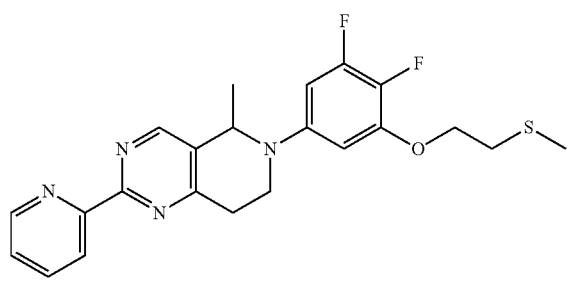 [SMILES: CSCCOc1cc(N2CCc3nc(-c4ccccn4)ncc3C2C)cc(F)c1F]

A mixture of 2,3-difluoro-5-[5-methyl-2-(2-pyridyl)-7,8-dihydro-5H-pyrido[4,3-d]pyrimidin-6-yl]phenol (50 mg, 0.141 mmol), 1-chloro-2-methylsulfanyl-ethane (46.61 mg, 0.424 mmol) and $K_2CO_3$ (58 mg, 0.424 mmol) in DMF (10 mL) was heated at 110° C. with stirring overnight. After being cooled to rt, the reaction mixture was diluted with $H_2O$ (10 mL) and extracted with EA (30 mL) for three times. The combined organic layer was concentrated in vacuo and the residue was used in the next step directly without further purification.

Step 2: Preparation of 6-[3,4-difluoro-5-(2-methylsulfonylethoxy)phenyl]-5-methyl-2-(2-pyridyl)-7,8-dihydro-5H-pyrido[4,3-d]pyrimidine

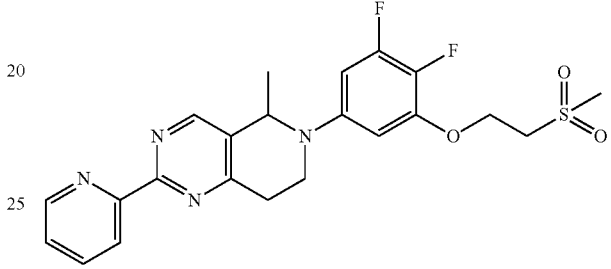

A mixture of 6-[3,4-difluoro-5-(2-methylsulfanylethoxy)phenyl]-5-methyl-2-(2-pyridyl)-7,8-dihydro-5H-pyrido[4,3-d]pyrimidine (60 mg, 0.14 mmol) and oxone (173 mg, 0.28 mmol) in DMF (5 mL) was stirred at rt for 3 hrs. The reaction mixture was diluted with $H_2O$ (10 mL) and extracted with EA (30 mL) for three times. The combined organic layer was concentrated in vacuo and the residue was purified by prep-HPLC to give 6-[3,4-difluoro-5-(2-methylsulfonylethoxy)phenyl]-5-methyl-2-(2-pyridyl)-7,8-dihydro-5H-pyrido[4,3-d]pyrimidine (1.2 mg). $^1$H NMR (400 MHz, $CDCl_3$) δ: 8.95 (br. s., 1H), 8.73 (s, 1H), 8.58 (d, 1H), 7.99 (m, 1H), 7.46-7.57 (m, 1H), 6.35-6.51 (m, 2H), 4.96 (m, 1H), 4.49-4.59 (m, 2H), 3.70-3.77 (m, 1H), 3.46-3.58 (m, 3H), 3.22-3.29 (m, 2H), 3.13-3.18 (m, 3H), 1.47 (d, 3H); MS obsd. (ESI$^+$) [(M+H)$^+$]: 461.

Example 27: methyl 2-[2,3-difluoro-5-[5-methyl-2-(2-pyridyl)-7,8-dihydro-5H-pyrido[4,3-d]pyrimidin-6-yl]phenoxy]acetate

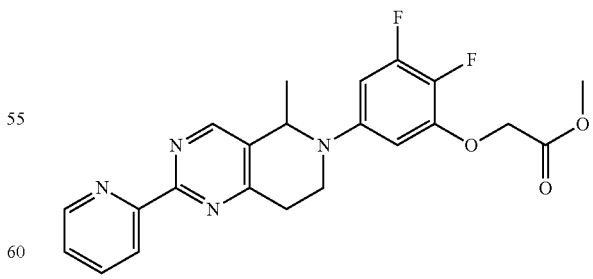

A mixture of 2,3-difluoro-5-[5-methyl-2-(2-pyridyl)-7,8-dihydro-5H-pyrido[4,3-d]pyrimidin-6-yl]phenol (500 mg, 1.412 mmol), methyl 2-bromoacetate (324 mg, 2.119 mmol) and $Cs_2CO_3$ (1.38 g, 4.237 mmol) in DMF (10 mL) was stirred at rt overnight. The reaction mixture was diluted with H₂O (10 mL) and extracted with EA (30 mL) for three times. The combined organic layer was dried over anhydrous Na₂SO₄ and concentrated in vacuo to give the crude product (400 mg). 50 mg of crude product was purified by prep-HPLC to give methyl 2-[2,3-difluoro-5-[5-methyl-2-(2-pyridyl)-7,8-dihydro-5H-pyrido[4,3-d]pyrimidin-6-yl]phenoxy]acetate (10 mg) as pale yellow solid. ¹H NMR (400 MHz, CDCl₃) δ: 8.85-8.94 (m, 1H), 8.66-8.73 (m, 1H), 8.49-8.59 (m, 1H), 7.92 (d, 1H), 7.43-7.51 (m, 1H), 6.41-6.51 (m, 1H), 6.38 (m, 1H), 4.87-4.97 (m, 1H), 4.75 (s, 2H), 3.83 (s, 3H), 3.66-3.76 (m, 1H), 3.50 (d, 1H), 3.18-3.32 (m, 2H), 1.45 (d, 3H); MS obsd. (ESI+) [(M+H)⁺]: 427.

Example 28: 2-[2,3-difluoro-5-[5-methyl-2-(2-pyridyl)-7,8-dihydro-5H-pyrido[4,3-d]pyrimidin-6-yl]phenoxy]acetic acid

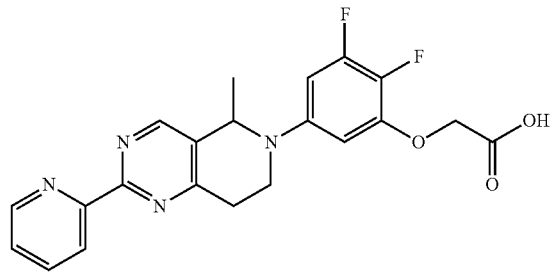 [SMILES: CC1c2cnc(-c3ccccn3)nc2CCN1c1cc(F)c(F)c(OCC(=O)O)c1]

A mixture of methyl 2-[2,3-difluoro-5-[5-methyl-2-(2-pyridyl)-7,8-dihydro-5H-pyrido[4,3-d]pyrimidin-6-yl]phenoxy]acetate (50 mg, 0.117 mmol) and NaOH (14 mg, 0.352 mg) in THF (1 mL), methanol (3 mL) and H₂O (0.5 mL) was stirred at rt for 3 hrs. Then the mixture was acidified with 2N hydrochloric acid and extracted with DCM (20 mL) for three times. The combined organic layer was washed with brine (10 mL), dried over anhydrous Na₂SO₄ and concentrated in vacuo. The residue was purified by prep-HPLC to give 2-[2,3-difluoro-5-[5-methyl-2-(2-pyridyl)-7,8-dihydro-5H-pyrido[4,3-d]pyrimidin-6-yl]phenoxy]acetic acid (4.5 mg) as pale yellow solid. ¹H NMR (400 MHz, CDCl₃) δ: 8.90 (d, 1H), 8.66 (s, 1H), 8.50 (d, 1H), 7.97 (m, 1H), 7.44-7.56 (m, 1H), 6.29-6.49 (m, 2H), 4.83-4.95 (m, 1H), 4.77 (s, 2H), 3.60-3.72 (m, 1H), 3.45 (m, 1H), 2.97-3.19 (m, 2H), 1.31-1.47 (m, 3H); MS obsd. (ESI⁺) [(M+H)⁺]: 413.

Example 29: 2-[2,3-difluoro-5-[5-methyl-2-(2-pyridyl)-7,8-dihydro-5H-pyrido[4,3-d]pyrimidin-6-yl]phenoxy]acetamide

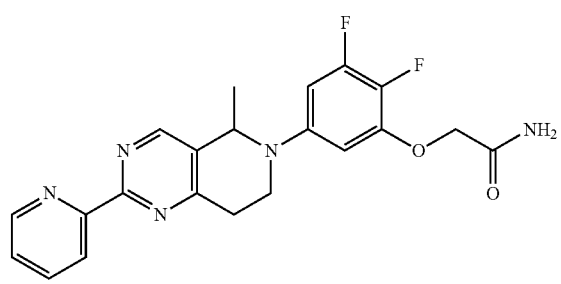 [SMILES: CC1c2cnc(-c3ccccn3)nc2CCN1c1cc(F)c(F)c(OCC(N)=O)c1]

A mixture of 2-[2,3-difluoro-5-[5-methyl-2-(2-pyridyl)-7,8-dihydro-5H-pyrido[4,3-d]pyrimidin-6-yl]phenoxy]acetic acid (100 mg, 0.243 mmol) and CDI (47 mg, 0.291 mmol) in DMF (5 mL) was stirred at rt for 2 hrs. Then to the reaction mixture was added NH₃ (7 mL, 14 mmol, 2.0 mol/L in isopropyl alcohol). After being stirred overnight, the resulting mixture was concentrated in vacuo. The residue was diluted with DCM (20 mL), washed with water, dried over anhydrous Na₂SO₄ and concentrated in vacuo. The residue was purified by prep-HPLC to give 2-[2,3-difluoro-5-[5-methyl-2-(2-pyridyl)-7,8-dihydro-5H-pyrido[4,3-d]pyrimidin-6-yl]phenoxy]acetamide (11 mg) as yellow solid. ¹H NMR (400 MHz, Methanol-d4) δ: 8.78 (s, 1H), 8.72-8.76 (m, 1H), 8.52 (d, 1H), 7.96-8.05 (m, 1H), 7.50-7.58 (m, 1H), 6.55-6.68 (m, 2H), 5.11-5.21 (m, 1H), 4.64 (s, 2H), 3.80-3.90 (m, 1H), 3.47-3.61 (m, 1H), 3.12 (d, 2H), 1.47 (d, 3H); MS obsd. (ESI⁺) [(M+H)⁺]: 412.

Example 30: 2-[2,3-difluoro-5-[5-methyl-2-(2-pyridyl)-7,8-dihydro-5H-pyrido[4,3-d]pyrimidin-6-yl]phenoxy]-N,N-dimethyl-acetamide

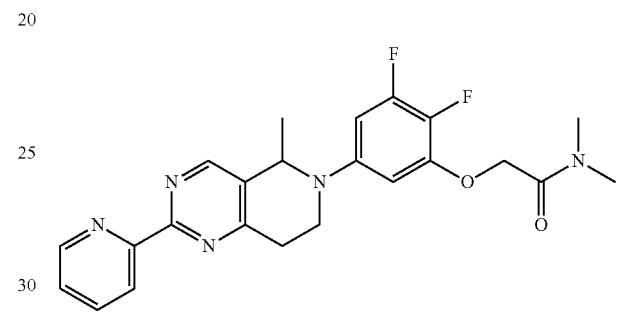

A mixture of 2-[2,3-difluoro-5-[5-methyl-2-(2-pyridyl)-7,8-dihydro-5H-pyrido[4,3-d]pyrimidin-6-yl]phenoxy]acetic acid (100 mg, 0.243 mmol) and CDI (47 mg, 0.291 mmol) in DMF (5 mL) was stirred at rt for 2 hrs. Then to the reaction mixture was added N-methylmethanamine (7 mL, 14 mmol, 2.0 M in methanol). After being stirred overnight, the mixture was concentrated in vacuo. The residue wad diluted with DCM (20 mL), washed with water, dried over anhydrous Na₂SO₄ and concentrated in vacuo. The residue was purified by prep-HPLC to give 2-[2,3-difluoro-5-[5-methyl-2-(2-pyridyl)-7,8-dihydro-5H-pyrido[4,3-d]pyrimidin-6-yl]phenoxy]-N,N-dimethyl-acetamide (7 mg) as yellow solid. ¹H NMR (400 MHz, Methanol-d₄) δ: 8.79 (s, 1H), 8.72-8.77 (m, 1H), 8.49-8.54 (m, 1H), 8.00 (d, 1H), 7.50-7.58 (m, 1H), 6.51-6.66 (m, 2H), 5.07-5.19 (m, 1H), 4.94 (s, 2H), 3.76-3.90 (m, 1H), 3.46-3.60 (m, 1H), 3.13 (s, 5H), 2.98 (s, 3H), 1.46 (d, 3H); MS obsd. (ESI⁺) [(M+H)⁺]: 440.

Example 31: 2-[2,3-difluoro-5-[5-methyl-2-(2-pyridyl)-7,8-dihydro-5H-pyrido[4,3-d]pyrimidin-6-yl]phenoxy]-1-pyrrolidin-1-yl-ethanone

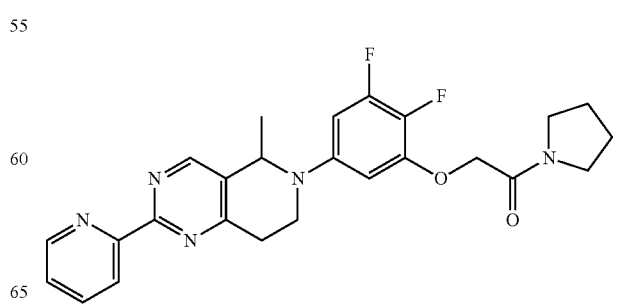

A mixture of 2-[2,3-difluoro-5-[5-methyl-2-(2-pyridyl)-7,8-dihydro-5H-pyrido[4,3-d]pyrimidin-6-yl]phenoxy]acetic acid (100 mg, 0.243 mmol) and CDI (47 mg, 0.291 mmol) in DMF (5 mL) was stirred at rt for 2 hrs. After being stirred overnight, the mixture was concentrated in vacuo. The residue was diluted with DCM (20 mL), washed with water, dried over anhydrous Na₂SO₄ and concentrated in vacuo. The residue was purified by prep-HPLC to give 2-[2,3-difluoro-5-[5-methyl-2-(2-pyridyl)-7,8-dihydro-5H-pyrido[4,3-d]pyrimidin-6-yl]phenoxy]-1-pyrrolidin-1-yl-ethanone (12 mg) as yellow solid. $^1$H NMR (400 MHz, Methanol-d₄) δ: 8.78 (s, 1H), 8.71-8.76 (m, 1H), 8.49-8.55 (m, 1H), 7.96-8.04 (m, 1H), 7.50-7.59 (m, 1H), 6.52-6.64 (m, 2H), 5.08-5.18 (m, 1H), 4.86 (s, 2H), 3.77-3.87 (m, 1H), 3.43-3.62 (m, 5H), 3.03-3.23 (m, 2H), 2.02 (m, 2H), 1.85-1.95 (m, 2H), 1.46 (d, 3H); MS obsd. (ESI⁺) [(M+H)⁺]: 466.

Example 32: 4-[3-[2,3-difluoro-5-[5-methyl-2-(2-pyridyl)-7,8-dihydro-5H-pyrido[4,3-d]pyrimidin-6-yl]phenoxy]propyl]morpholine

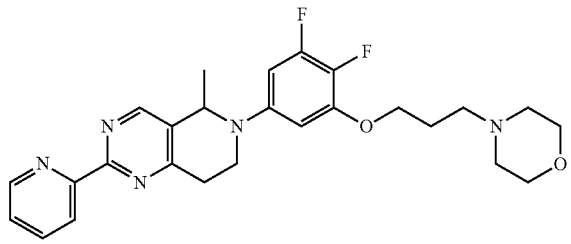 [SMILES: CC1c2cnc(-c3ccccn3)nc2CCN1c1cc(F)c(F)c(OCCCN2CCOCC2)c1]

A mixture of 2,3-difluoro-5-[5-methyl-2-(2-pyridyl)-7,8-dihydro-5H-pyrido[4,3-d]pyrimidin-6-yl]phenol (50 mg, 0.141 mmol), 4-(3-chloropropyl)morpholine (69 mg, 0.424 mmol) and K₂CO₃ (58 mg, 0.424 mmol) in DMF (5 mL) was heated at 110° C. with stirring overnight. After being cooled to rt, the reaction mixture was diluted with H₂O (10 mL) and extracted with EA (30 mL) for three times. The combined organic layer was concentrated in vacuo and the residue was purified by prep-HPLC to give 4-[3-[2,3-difluoro-5-[5-methyl-2-(2-pyridyl)-7,8-dihydro-5H-pyrido[4,3-d]pyrimidin-6-yl]phenoxy]propyl]morpholine (11 mg). $^1$H NMR (400 MHz, CDCl₃) δ: 8.81-8.89 (m, 1H), 8.69 (s, 1H), 8.49-8.55 (m, 1H), 7.83-7.94 (m, 1H), 7.38-7.46 (m, 1H), 6.33-6.45 (m, 2H), 4.89-5.00 (m, 1H), 4.14 (m, 2H), 3.65-3.83 (m, 5H), 3.44-3.56 (m, 1H), 3.20 (d, 2H), 2.51-2.72 (m, 6H), 2.00-2.12 (m, 2H), 1.44 (d, 3H); MS obsd. (ESI⁺) [(M+H)⁺]: 482.

Example 33: 6-[3,4-difluoro-5-(3-methylsulfonylpropoxy)phenyl]-5-methyl-2-(2-pyridyl)-7,8-dihydro-5H-pyrido[4,3-d]pyrimidine

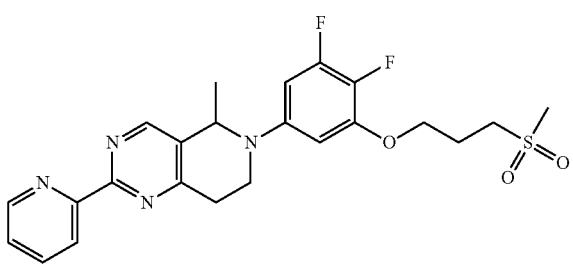

Step 1: Preparation of 3-methylsulfanylpropyl 4-methylbenzenesulfonate

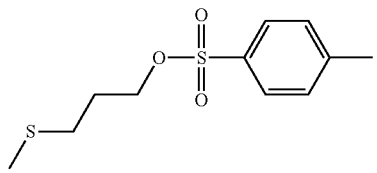

A mixture of 3-methylsulfanylpropan-1-ol (2 g, 18.8 mmol), DMAP (0.46 g, 3.77 mmol) and Et₃N (3.812 g, 37.7 mmol) in DCM (30 mL) was stirred at 0° C. for 30 mins. Then to the reaction mixture was added 4-toluene sulfonyl chloride (4.31 g, 22.6 mmol). After being stirred at rt overnight, the resulting mixture was washed with 1 N HCl, saturated aqueous solution of NaHCO₃ and water successively. The organic layer was dried over anhydrous Na₂SO₄ and concentrated in vacuo to give 3-methylsulfanylpropyl 4-methylbenzenesulfonate as pale yellow oil (4.5 g) which was used in the next step directly without further purification.

Step 2: Preparation of 6-[3,4-difluoro-5-(3-methylsulfanylpropoxy)phenyl]-5-methyl-2-(2-pyridyl)-7,8-dihydro-5H-pyrido[4,3-d]pyrimidine

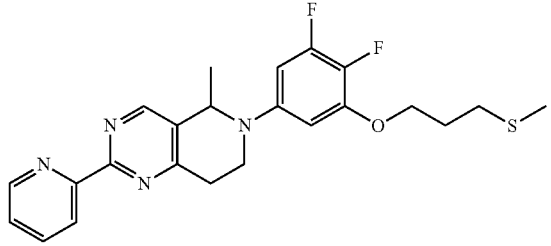 [SMILES: CSCCCOc1cc(N2CCc3nc(-c4ccccn4)ncc3C2C)cc(F)c1F]

A mixture of 2,3-difluoro-5-[5-methyl-2-(2-pyridyl)-7,8-dihydro-5H-pyrido[4,3-d]pyrimidin-6-yl]phenol (100 mg, 0.282 mmol), 3-methylsulfanylpropyl 4-methylbenzenesulfonate (147 mg, 0.565 mmol) and Cs₂CO₃ (275 mg, 0.847 mmol) in DMF (5 mL) was heated at 120° C. with stirring overnight. After being cooled to rt, the reaction mixture was diluted with H₂O (10 mL) and extracted with EA (30 mL) for three times. The combined organic layer was concentrated in vacuo and the residue was purified by flash column to give 6-[3,4-difluoro-5-(3-methylsulfanylpropoxy)phenyl]-5-methyl-2-(2-pyridyl)-7,8-dihydro-5H-pyrido[4,3-d]pyrimidine (50 mg) as a yellow solid.

Step 3: Preparation of 6-[3,4-difluoro-5-(3-methylsulfonylpropoxy)phenyl]-5-methyl-2-(2-pyridyl)-7,8-dihydro-5H-pyrido[4,3-d]pyrimidine

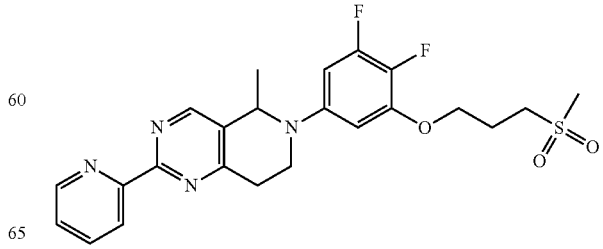

A mixture of 6-[3,4-difluoro-5-(3-methylsulfanylpropoxy)phenyl]-5-methyl-2-(2-pyridyl)-7,8-dihydro-5H-pyrido[4,3-d]pyrimidine (50 mg, 0.113 mmol) and oxone (139 mg, 0.226 mmol) in DMF (5 mL) was stirred at rt for 3 hrs. Then the reaction mixture was diluted with H$_2$O (5 mL) and extracted with EA (30 mL) for three times. The combined organic layer was concentrated in vacuo and the residue was purified by prep-HPLC to give 6-[3,4-difluoro-5-(3-methylsulfonylpropoxy)phenyl]-5-methyl-2-(2-pyridyl)-7,8-dihydro-5H-pyrido[4,3-d]pyrimidine (1.4 mg) as pale yellow solid. $^1$H NMR (400 MHz, CDCl$_3$) δ: 8.91-9.02 (m, 1H), 8.73 (s, 1H), 8.54-8.63 (m, 1H), 7.96-8.08 (m, 1H), 7.54 (br. s., 1H), 6.33-6.46 (m, 2H), 4.88-5.02 (m, 1H), 4.25 (s, 2H), 3.67-3.78 (m, 1H), 3.47-3.57 (m, 1H), 3.21-3.36 (m, 4H), 3.01 (s, 3H), 2.41 (m, 2H), 1.46 (d, 3H); MS obsd. (ESI$^+$) [(M+H)$^+$]: 475.

Example 34: 3-[2,3-difluoro-5-[5-methyl-2-(2-pyridyl)-7,8-dihydro-5H-pyrido[4,3-d]pyrimidin-6-yl]phenoxy]propan-1-amine

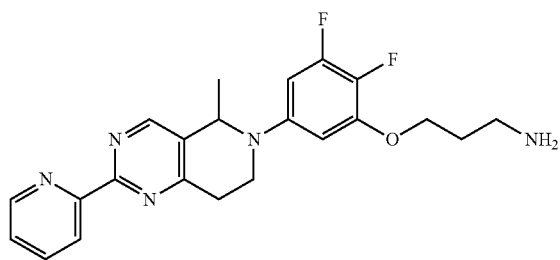 [SMILES: CC1c2cnc(-c3ccccn3)nc2CCN1c1cc(F)c(F)c(OCCCN)c1]

Step 1: Preparation of tert-butyl N-[3-[2,3-difluoro-5-[5-methyl-2-(2-pyridyl)-7,8-dihydro-5H-pyrido[4,3-d]pyrimidin-6-yl]phenoxy]propyl]carbamate

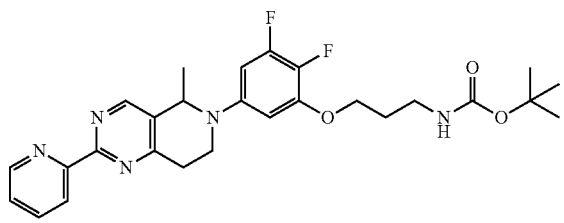 [SMILES: CC1c2cnc(-c3ccccn3)nc2CCN1c1cc(F)c(F)c(OCCCNC(=O)OC(C)(C)C)c1]

A mixture of 2,3-difluoro-5-[5-methyl-2-(2-pyridyl)-7,8-dihydro-5H-pyrido[4,3-d]pyrimidin-6-yl]phenol (100 mg, 0.282 mmol), tert-butyl N-(3-bromopropyl)carbamate (135 mg, 0.565 mmol) and K$_2$CO$_3$ (117 mg, 0.847 mmol) in DMF (10 mL) was heated at 100° C. with stirring overnight. After being cooled to rt, the reaction mixture was diluted with H$_2$O (10 mL) and exacted with EA (30 mL) for three times. The combined organic layer was dried over anhydrous Na$_2$SO$_4$ and concentrated in vacuo give crude tert-butyl N-[3-[2,3-difluoro-5-[5-methyl-2-(2-pyridyl)-7,8-dihydro-5H-pyrido[4,3-d]pyrimidin-6-yl]phenoxy]propyl]carbamate which was used in the next step directly without further purification.

Step 2: Preparation of 3-[2,3-difluoro-5-[5-methyl-2-(2-pyridyl)-7,8-dihydro-5H-pyrido[4,3-d]pyrimidin-6-yl]phenoxy]propan-1-amine

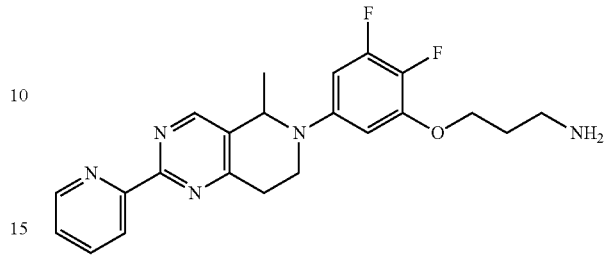

A mixture of the crude tert-butyl N-[3-[2,3-difluoro-5-[5-methyl-2-(2-pyridyl)-7,8-dihydro-5H-pyrido[4,3-d]pyrimidin-6-yl]phenoxy]propyl]carbamate and CF$_3$COOH (10 mL) in DCM (10 mL) was stirred at rt for 1 hr. Then the mixture was concentrated in vacuo. The residue was diluted with saturated aqueous solution of NaHCO$_3$ and extracted with DCM (20 mL) for three times. The combined organic layer was dried over anhydrous Na$_2$SO$_4$ and concentrated in vacuo. The residue was purified by prep-HPLC to give 3-[2,3-difluoro-5-[5-methyl-2-(2-pyridyl)-7,8-dihydro-5H-pyrido[4,3-d]pyrimidin-6-yl]phenoxy]propan-1-amine (4.5 mg) as yellow solid. $^1$H NMR (400 MHz, CDCl$_3$) δ: 8.86 (d, 1H), 8.70 (s, 1H), 8.52 (d, 1H), 7.88 (m, 1H), 7.37-7.47 (m, 1H), 6.20-6.46 (m, 2H), 4.89-4.99 (m, 1H), 4.11-4.25 (m, 2H), 3.65-3.79 (m, 1H), 3.45 (s, 2H), 3.05-3.32 (m, 3H), 2.01-2.11 (m, 2H), 1.47 (br. s., 3H); MS obsd. (ESI$^+$) [(M+H)$^+$]: 412.

Example 35: N-[3-[2,3-difluoro-5-[5-methyl-2-(2-pyridyl)-7,8-dihydro-5H-pyrido[4,3-d]pyrimidin-6-yl]phenoxy]propyl]methanesulfonamide

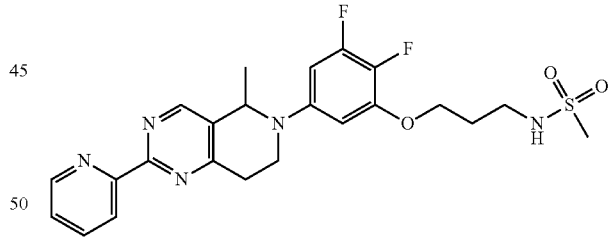

A mixture of 3-[2,3-difluoro-5-[5-methyl-2-(2-pyridyl)-7,8-dihydro-5H-pyrido[4,3-d]pyrimidin-6-yl]phenoxy]propan-1-amine (60 mg, 0.15 mmol), methylsulfonyl methanesulfonate (60 mg, 0.53 mmol) and pyridine (104 mg, 1.31 mmol) in DCM (10 mL) was stirred at 0° C. for 2 hrs and then at rt overnight. The mixture was concentrated in vacuo and the residue was purified by prep-HPLC to give N-[3-[2,3-difluoro-5-[5-methyl-2-(2-pyridyl)-7,8-dihydro-5H-pyrido[4,3-d]pyrimidin-6-yl]phenoxy]propyl]methanesulfonamide (2 mg) as yellow solid. $^1$H NMR (400 MHz, Methanol-d$_4$) δ: 8.80 (s, 1H), 8.71-8.77 (m, 1H), 8.49-8.56 (m, 1H), 7.97-8.05 (m, 1H), 7.51-7.59 (m, 1H), 6.49-6.65 (m, 2H), 5.12-5.23 (m, 1H), 4.15-4.27 (m, 2H), 3.79-3.93 (m, 1H), 3.45-3.60 (m, 1H), 3.31 (m, 2H), 3.18 (m, 1H), 3.06-3.15

(m, 1H), 2.95-2.99 (m, 3H), 1.90-2.15 (m, 2H), 1.46 (d, 3H); MS obsd. (ESI⁺) [(M+H)⁺]: 490.

Example 36: ethyl 2-[6-(3,4-difluoro-5-methoxy-phenyl)-2-(2-pyridyl)-7,8-dihydro-5H-pyrido[4,3-d]pyrimidin-5-yl]acetate

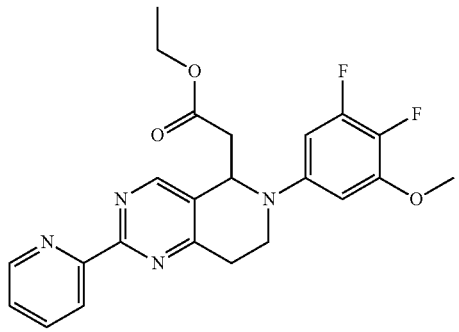 [SMILES: CCOC(=O)CC1c2cnc(-c3ccccn3)nc2CCN1c1cc(F)c(F)c(OC)c1]

Step 1: Preparation of 1-ethoxyvinyloxy(trimethyl)silane

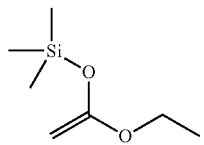

To a stirred solution of diisopropylamine (41.3 g, 409 mmol) in THF (300 mL) was added n-BuLi (150 mL, 375 mmol) at 0° C. After being stirred at 0° C. for 20 mins, the reaction mixture was cooled down to −70° C. and to the cooled mixture was added a solution of EA (30 g, 341 mmol) and chlorotrimethylsilane (44.1 g, 409 mmol) in THF (200 mL). The resulting mixture was warmed to rt and stirred at rt for 16 hrs. The mixture was filtered and the filtrate was concentrated in vacuo. The residue was dissolved in hexane (200 mL) and filtered. The filtrate was concentrated in vacuo and the residue was purified by distillation to give 1-ethoxyvinyloxy(trimethyl)silane (16.0 g) as colorless oil.

Step 2: Preparation of ethyl 2-[6-(3,4-difluoro-5-methoxy-phenyl)-2-(2-pyridyl)-7,8-dihydro-5H-pyrido[4,3-d]pyrimidin-5-yl]acetate

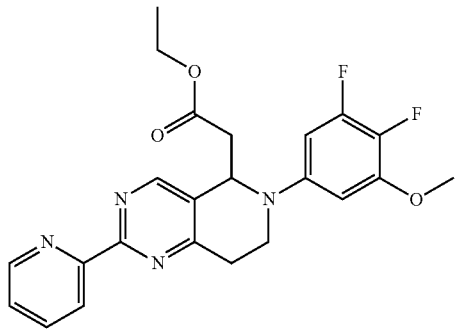 [SMILES: CCOC(=O)CC1c2cnc(-c3ccccn3)nc2CCN1c1cc(F)c(F)c(OC)c1]

To a cooled solution of 6-(3,4-difluoro-5-methoxy-phenyl)-5-methoxy-2-(2-pyridyl)-7,8-dihydro-5H-pyrido[4,3-d]pyrimidine (300 mg, 0.78 mmol) in MeCN (3 mL) was added a solution of Sc(OTf)₃ (384 mg, 0.13 mmol) in MeCN (3 mL) at 0° C. The mixture was stirred at 0° C. for 20 mins. Then to the resulting mixture was added 1-ethoxyvinyloxy(trimethyl)silane (1.25 g, 7.8 mmol) at 0° C. After being warmed to rt and stirred at rt for another 2 hrs, the resulting mixture was diluted with water (10 mL) and extracted with DCM (30 mL) for three times. The combined organic layer was washed with brine (30 mL), dried over anhydrous Na₂SO₄ and concentrated in vacuo. The residue was purified by prep-HPLC to give ethyl 2-[6-(3,4-difluoro-5-methoxy-phenyl)-2-(2-pyridyl)-7,8-dihydro-5H-pyrido[4,3-d]pyrimidin-5-yl]acetate (100 mg) as a brown solid. ¹H NMR (400 MHz, CDCl₃) δ: 9.39 (s, 1H), 8.83-8.94 (m, 2H), 8.54 (s, 1H), 8.04 (s, 1H), 6.38-6.53 (m, 2H), 5.41 (t, 1H), 4.18 (q, 2H), 3.94 (s, 3H), 3.75-3.83 (m, 1H), 3.55-3.68 (m, 1H), 3.25-3.52 (m, 2H), 2.90-3.01 (m, 1H), 2.38-2.62 (m, 1H), 1.26 (t, 3H). MS obsd. (ESI⁺) [(M+H)+]: 441.

Example 37: 2-[6-(3,4-difluoro-5-methoxy-phenyl)-2-(2-pyridyl)-7,8-dihydro-5H-pyrido[4,3-d]pyrimidin-5-yl]acetic acid

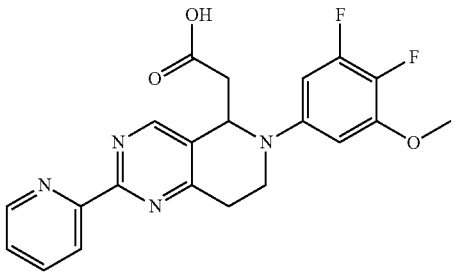 [SMILES: COc1cc(N2CCc3nc(-c4ccccn4)ncc3C2CC(=O)O)cc(F)c1F]

To a solution of ethyl 2-[6-(3,4-difluoro-5-methoxy-phenyl)-2-(2-pyridyl)-7,8-dihydro-5H-pyrido[4,3-d]pyrimidin-5-yl]acetate (50 mg, 0.11 mmol) in MeOH (1 mL) was added 2N NaOH (0.2 mL, 0.4 mmol). After being stirred at 25° C. for 16 hrs, the resulting mixture was concentrated in vacuo. The residue was acidified with 1N HCl and purified by prep-HPLC to give 2-[6-(3,4-difluoro-5-methoxy-phenyl)-2-(2-pyridyl)-7,8-dihydro-5H-pyrido[4,3-d]pyrimidin-5-yl]acetic acid (37.8 mg) as a red solid. ¹H NMR (400 MHz, Methanol-d₄) δ: 9.02-9.12 (m, 1H), 8.94 (s, 1H), 8.80-8.84 (m, 1H), 8.78-8.88 (m, 1H), 8.11-8.28 (m, 1H), 6.70 (d, 1H), 6.53-6.62 (m, 1H), 5.54 (t, 1H), 3.90-3.99 (m, 1H), 3.89 (s, 3H), 3.68-3.73 (m, 1H), 3.24-3.38 (m, 1H), 3.12-3.22 (m, 1H), 2.88-3.06 (m, 2H). MS obsd. (ESI⁺) [(M+H)⁺]: 413.

Example 38: 2-[6-(3,4-difluoro-5-methoxy-phenyl)-2-(2-pyridyl)-7,8-dihydro-5H-pyrido[4,3-d]pyrimidin-5-yl]ethanol

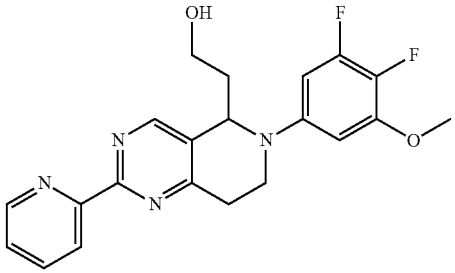 [SMILES: COc1cc(N2CCc3nc(-c4ccccn4)ncc3C2CCO)cc(F)c1F]

To a mixture of ethyl 2-[6-(3,4-difluoro-5-methoxy-phenyl)-2-(2-pyridyl)-7,8-dihydro-5H-pyrido[4,3-d]pyrimidin-5-yl]acetate (450 mg, 1.05 mmol) in THF (5 mL) was added LiAlH₄ (78 mg, 2.02 mmol) at −70° C. The mixture was stirred at 0° C. for 1 hr. The reaction was quenched by the addition of water (0.1 mL) and 15% NaOH (0.1 mL) at 0° C. The resulting mixture was diluted with THF (10 mL) and filtered. The filtrate was concentrated in vacuo and the residue was purified by prep-HPLC to give 2-[6-(3,4-difluoro-5-methoxy-phenyl)-2-(2-pyridyl)-7,8-dihydro-5H-pyrido[4,3-d]pyrimidin-5-yl]ethanol (70 mg) as a red solid. ¹H NMR (400 MHz, Methanol-d₄) δ: 9.02-9.12 (m, 1H), 8.93 (s, 1H), 8.80-8.84 (m, 1H), 8.78-8.88 (m, 1H), 8.21-8.28 (m, 1H), 6.68-6.74 (m, 1H), 6.53-6.62 (m, 1H), 5.21-5.29 (m, 1H), 3.99-4.02 (m, 1H), 3.91 (s, 3H), 3.63-3.75 (m, 3H), 3.32-3.35 (m, 1H), 3.08-3.14 (m, 1H), 2.20-2.27 (m, 1H), 2.01-2.11 (m, 1H). MS obsd. (ESI⁺) [(M+H)⁺]: 399.

Example 39: 6-(3,4-difluoro-5-methoxy-phenyl)-5-(nitromethyl)-2-(2-pyridyl)-7,8-dihydro-5H-pyrido[4,3-d]pyrimidine

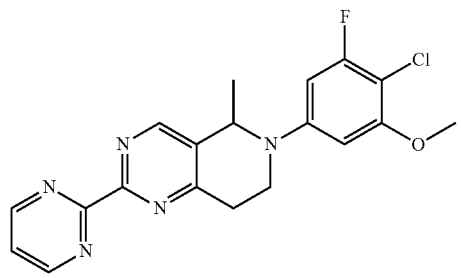

To a mixture of 6-(3,4-difluoro-5-methoxy-phenyl)-2-(2-pyridyl)-7,8-dihydro-5H-pyrido[4,3-d]pyrimidine (1 g, 2.82 mmol) and 4 Å MS (500 mg) in MeNO₂ (15 mL) was added PhI(OAc)₂ (2.72 g, 8.47 mmol). After being heated at 40° C. with stirring for 16 hrs, the resulting mixture was filtered and the filtrate was concentrated in vacuo. The residue was purified by prep-HPLC to give 6-(3,4-difluoro-5-methoxy-phenyl)-5-(nitromethyl)-2-(2-pyridyl)-7,8-dihydro-5H-pyrido[4,3-d]pyrimidine (40 mg) as a red solid. ¹H NMR (400 MHz, Methanol-d₄) δ: 9.06-9.11 (m, 2H), 8.91-8.96 (m, 1H), 8.81-8.88 (m, 1H), 8.21-8.28 (m, 1H), 6.68-6.74 (m, 1H), 6.53-6.62 (m, 1H), 5.93-5.98 (m, 1H), 4.87-5.21 (m, 2H), 3.99-4.02 (m, 1H), 3.91 (s, 3H), 3.75-3.83 (m, 1H), 3.10-3.15 (m, 1H), 3.08-3.09 (m, 1H). MS obsd. (ESI⁺) [(M+H)⁺]: 414.

Example 40: 6-(4-chloro-3-fluoro-5-methoxy-phenyl)-5-methyl-2-pyrimidin-2-yl-7,8-dihydro-5H-pyrido[4,3-d]pyrimidine Step 1: Preparation of 5-bromo-2-chloro-1-fluoro-3-methoxy-benzene

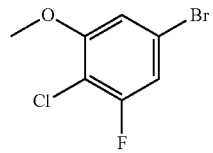

To a solution of 5-bromo-2-chloro-1,3-difluoro-benzene (7200 mg, 31.9 mmol) in MeOH (50 mL) was added NaOMe (5200 mg, 95.7 mmol) at rt. The reaction mixture was stirred overnight at rt and purified by column to give 5-bromo-2-chloro-1-fluoro-3-methoxy-benzene (5200 mg).

Step 2: Preparation of 8-(4-chloro-3-fluoro-5-methoxy-phenyl)-1,4-dioxa-8-azaspiro[4.5]decane

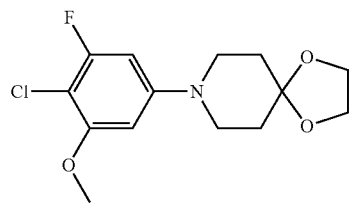 [SMILES: COc1cc(N2CCC3(CC2)OCCO3)cc(F)c1Cl]

To a mixture of 5-bromo-2-chloro-1,3-difluoro-3-methoxy-benzene (5200 mg, 21.85 mmol), 1,4-dioxa-8-azaspiro[4.5]decane (3440 mg, 24.04 mmol) and t-BuONa (4200 mg, 43.7 mmol) in dioxane (50 m) was added Pd(dba)₃ (1000 mg, 1.09 mmol) and Ruphos (1020 mg, 2.18 mmol) under N₂ successively. After being heated at 100° C. overnight, the resulting mixture was cooled down to rt, diluted with H₂O (50 mL) and extracted with EA (50 mL) for three times. The combined organic layer was washed with brine (50 mL), dried over anhydrous Na₂SO₄ and concentrated in vacuo to give crude 8-(4-chloro-3-fluoro-5-methoxy-phenyl)-1,4-dioxa-8-azaspiro[4.5]decane (800 mg) which was used in the next step directly without further purification.

Step 3: 1-(4-chloro-3-fluoro-5-methoxy-phenyl) piperidin-4-one

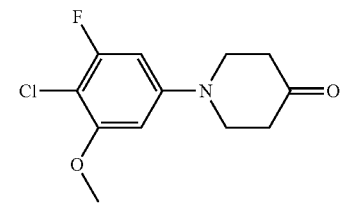 [SMILES: COc1cc(N2CCC(=O)CC2)cc(F)c1Cl]

To a flask containing crude 8-(4-chloro-3-fluoro-5-methoxy-phenyl)-1,4-dioxa-8-azaspiro[4.5]decane (800 mg, 2.65 mmol) was added 44% formic acid (10 mL). After being heated at 90° C. with stirring for 8 hrs, the resulting mixture was concentrated in vacuo. The residue was diluted with saturated NaHCO₃ (20 mL) and extracted with EA (30 mL) for three times. The combined organic layer was washed with brine (50 mL), dried over anhydrous Na₂SO₄ and concentrated in vacuo to give 1-(4-chloro-3-fluoro-5-methoxy-phenyl)piperidin-4-one (680 mg) as brown oil, which was used in the next step directly without further purification.

Step 4: Preparation of 6-(4-chloro-3-fluoro-5-methoxy-phenyl)-2-pyrimidin-2-yl-7,8-dihydro-5H-pyrido[4,3-d]pyrimidine

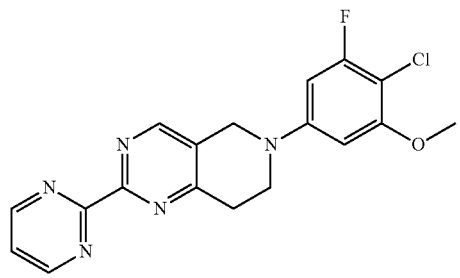 [SMILES: COc1cc(N2CCc3nc(-c4ncccn4)ncc3C2)cc(F)c1Cl]

A mixture of crude 1-(4-chloro-3-fluoro-5-methoxy-phenyl)piperidin-4-one (680 mg, 2.65 mmol) and DMFDMA (10 mL) was heated at 90° C. for 3 hrs. The reaction mixture was concentrated in vacuo and the residue was dissolved in EtOH (20 mL). To the solution was added pyrimidine-2-carboxamidine hydrochloride (420 mg, 2.65 mmol) and K₂CO₃ (730 mg, 5.3 mmol) successively. After being heated to 80° C. with stirring overnight, the reaction mixture was cooled down to rt and purified by prep-HPLC to give 6-(4-chloro-3-fluoro-5-methoxy-phenyl)-2-pyrimidin-2-yl-7,8-dihydro-5H-pyrido[4,3-d]pyrimidine (250 mg).

Step 5: Preparation of 6-(4-chloro-3-fluoro-5-methoxy-phenyl)-5-methoxy-2-pyrimidin-2-yl-7,8-dihydro-5H-pyrido[4,3-d]pyrimidine

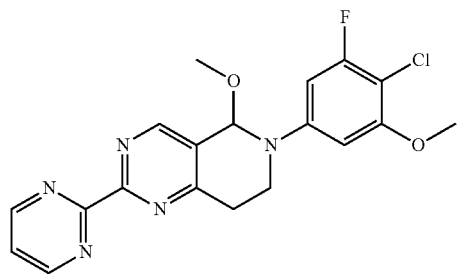

To a stirred solution of 6-(4-chloro-3-fluoro-5-methoxy-phenyl)-2-pyrimidin-2-yl-7,8-dihydro-5H-pyrido[4,3-d]pyrimidine (200 mg, 0.54 mmol) in a mixed solvent of DCM (10 mL) and MeOH (2 mL) at −70° C. was added RuCl₃ hydrate (0.16 mmol) and NaIO₄ (347 mg in 3 mL H₂O, 1.62 mmol) successively. The cooling bath was then removed. The reaction mixture was warmed to rt slowly and stirred at rt. After the reaction was complete, the resulting mixture was diluted with saturated aqueous solution of Na₂S₂O₃ and extracted with EA (30 mL) for three times. The combined organic layer was dried over Na₂SO₄ and concentrated in vacuo to give 6-(4-chloro-3-fluoro-5-methoxy-phenyl)-5-methoxy-2-pyrimidin-2-yl-7,8-dihydro-5H-pyrido[4, 3-d] pyrimidine (210 mg) as black foam which was used in the next step directly without further purification.

Step 6: Preparation of 6-(4-chloro-3-fluoro-5-methoxy-phenyl)-5-methyl-2-pyrimidin-2-yl-7,8-dihydro-5H-pyrido[4,3-d]pyrimidine

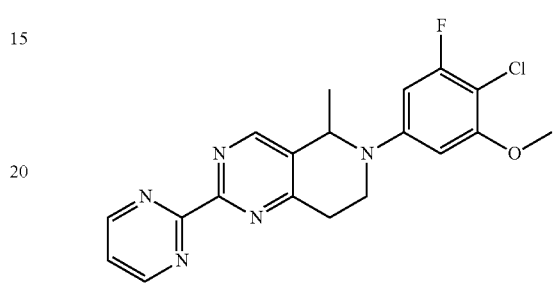

To a cooled solution of 6-(4-chloro-3-fluoro-5-methoxy-phenyl)-5-methoxy-2-pyrimidin-2-yl-7,8-dihydro-5H-pyrido[4,3-d]pyrimidine (210 mg, 0.54 mmol) in THF (20 mL) at −70° C. was added BF₃.Et₂O (140 mg, 1.1 mmol). The mixture was stirred at this temperature for 15 mins followed by the addition of MeMgBr (0.5 mL in THF, 3.0 M from Aldrich). After being warmed to rt and stirred for 1 hr, the reaction mixture was diluted with saturated aqueous solution of NH₄Cl and extracted with EA (30 mL) for three times. The combined organic layer was dried over anhydrous Na₂SO₄ and concentrated in vacuo. The residue was purified by prep-HPLC to give 6-(4-chloro-3-fluoro-5-methoxy-phenyl)-5-methyl-2-pyrimidin-2-yl-7,8-dihydro-5H-pyrido[4,3-d]pyrimidine (15 mg) as light yellow solid. $^1$H NMR (400 MHz, Methanol-$d_4$) δ: 8.99-9.12 (m, 2H), 8.76-8.88 (m, 1H), 7.61-7.75 (m, 1H), 6.80-6.96 (m, 2H), 4.72-4.82 (m, 1H), 3.85 (s, 3H), 3.60-3.73 (m, 1H), 3.43-3.56 (m, 1H), 3.07-3.25 (m, 2H), 1.40 (d, 3H). MS obsd. (ESI$^+$) [(M+H)$^+$]: 386.

Example 41: 6-(3-chloro-4-fluoro-5-methoxy-phenyl)-5-methyl-2-pyrimidin-2-yl-7,8-dihydro-5H-pyrido[4,3-d]pyrimidine

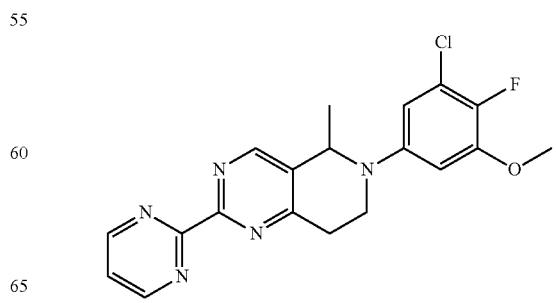

Step 1: Preparation of 8-(3-chloro-4-fluoro-5-methoxy-phenyl)-1,4-dioxa-8-azaspiro[4.5]decane

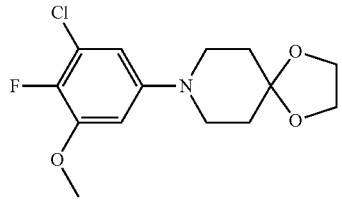

To a mixture of 5-bromo-1-chloro-2-fluoro-3-methoxy-benzene (1000 mg, 4.2 mmol), 1,4-dioxa-8-azaspiro[4.5]decane (660 mg, 4.6 mmol) and t-BuONa (800 mg, 8.4 mmol) in dioxane (20 mL) was added $Pd_2(dba)_3$ (184 mg, 0.2 mmol) and Ruphos (187 mg, 0.4 mmol) successively under $N_2$. After being heated at 100° C. with stirring overnight, the resulting mixture was cooled down to rt, diluted with $H_2O$ (50 mL) and extracted with EA (50 mL) for three times. The combined organic layer was washed with brine (50 mL), dried over anhydrous $Na_2SO_4$ and concentrated in vacuo to give crude 8-(3-chloro-4-fluoro-5-methoxy-phenyl)-1,4-dioxa-8-azaspiro[4.5]decane (500 mg) which was used in the next step directly without further purification.

Step 2: Preparation of 1-(3-chloro-4-fluoro-5-methoxy-phenyl)piperidin-4-one

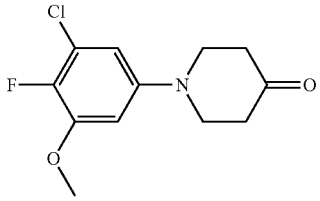

A mixture of crude 8-(3-chloro-4-fluoro-5-methoxy-phenyl)-1,4-dioxa-8-azaspiro[4.5]decane (500 mg, 1.66 mmol) and 44% formic acid (10 mL) was heated at 90° C. and stirred for 8 hrs. The resulting mixture was concentrated in vacuo. The residue was diluted with a saturated aqueous solution of $NaHCO_3$ (20 mL) and extracted with EA (30 mL) for three times. The combined organic layer was washed with brine (50 mL), dried over anhydrous $Na_2SO_4$ and concentrated in vacuo to give 1-(3-chloro-4-fluoro-5-methoxy-phenyl)piperidin-4-one (420 mg) as brown oil which was used in the next step directly without further purification.

Step 3: Preparation of 6-(3-chloro-4-fluoro-5-methoxy-phenyl)-2-pyrimidin-2-yl-7,8-dihydro-5H-pyrido[4,3-d]pyrimidine

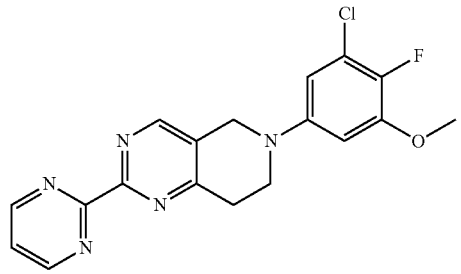

A mixture of crude 1-(3-chloro-4-fluoro-5-methoxy-phenyl)piperidin-4-one (420 mg, 1.66 mmol) and DMFDMA (10 mL) was heated at 90° C. with stirring for 3 hrs. The resulting mixture was concentrated in vacuo. The residue was dissolved in EtOH (20 mL). To the solution was added pyrimidine-2-carboxamidine hydrochloride (260 mg, 1.66 mmol) and $K_2CO_3$ (458 mg, 3.32 mmol) successively. After being heated at 80° C. with stirring overnight, the reaction mixture was cooled down to rt and purified by prep-HPLC to give 6-(3-chloro-4-fluoro-5-methoxy-phenyl)-2-pyrimidin-2-yl-7,8-dihydro-5H-pyrido[4,3-d]pyrimidine (300 mg) as brown solid.

Step 4: Preparation of 6-(3-chloro-4-fluoro-5-methoxy-phenyl)-5-methoxy-2-pyrimidin-2-yl-7,8-dihydro-5H-pyrido[4,3-d]pyrimidine

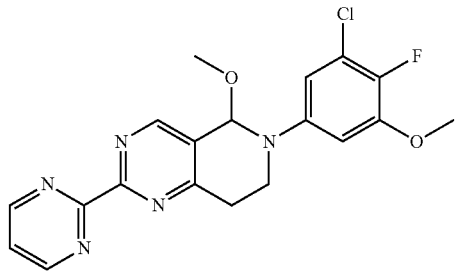 [SMILES: COc1cc(N2CCc3nc(-c4ncccn4)ncc3C2OC)cc(F)c1Cl]

To a cooled solution of 6-(3-chloro-4-fluoro-5-methoxy-phenyl)-2-pyrimidin-2-yl-7,8-dihydro-5H-pyrido[4,3-d]pyrimidine (300 mg, 0.8 mmol) in a mixed solvent of DCM (15 mL) and MeOH (3 mL) at −70° C. was added $RuCl_3$ hydrate (0.24 mmol) and $NaIO_4$ (514 mg in 5 mL $H_2O$, 2.4 mmol) successively. The cooling bath was removed. The reaction mixture was warmed to rt slowly and stirred at rt. After the reaction was complete, the resulting mixture was diluted with a saturated aqueous solution of $Na_2S_2O_3$ and extracted with EA (30 mL) for three times. The combined organic layer was dried and concentrated in vacuo to give 6-(3-chloro-4-fluoro-5-methoxy-phenyl)-5-methoxy-2-pyrimidin-2-yl-7,8-dihydro-5H-pyrido[4,3-d]pyrimidine (320 mg) as black foam which was used directly in the next step directly without further purification.

Step 4: Preparation of 6-(3-chloro-4-fluoro-5-methoxy-phenyl)-5-methyl-2-pyrimidin-2-yl-7,8-dihydro-5H-pyrido[4,3-d]pyrimidine

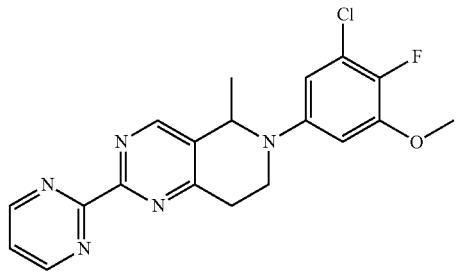

To a cooled solution of 6-(3-chloro-4-fluoro-5-methoxy-phenyl)-5-methoxy-2-pyrimidin-2-yl-7,8-dihydro-5H-pyrido[4,3-d]pyrimidine (320 mg, 0.8 mmol) in THF (20 mL) at −70° C. was added BF₃.Et₂O (220 mg, 1.6 mmol). The mixture was stirred for 15 min at −70° C. followed by the addition of MeMgBr (0.8 mL in THF, 3.0 M from Aldrich). After being warmed to rt and stirred at rt for 1 hr, the resulting mixture was diluted with a saturated aqueous solution of NH₄Cl and extracted with EA (30 mL) for three times. The combined organic layer was dried over Na₂SO₄ and concentrated in vacuo. The residue was purified by prep-HPLC to give 6-(3-chloro-4-fluoro-5-methoxy-phenyl)-5-methyl-2-pyrimidin-2-yl-7,8-dihydro-5H-pyrido[4,3-d]pyrimidine (100 mg) as yellow solid. ¹H NMR (400 MHz, DMSO-d₆) δ: 9.00 (d, 2H), 8.85 (s, 1H), 7.65 (t, 1H), 6.75-6.84 (m, 1H), 6.67-6.73 (m, 1H), 5.26-5.43 (m, 1H), 3.87-3.98 (m, 4H), 3.40-3.56 (m, 1H), 2.92-3.20 (m, 2H), 1.40 (d, 3H). MS obsd. (ESI⁺) [(M+H)⁺]: 386.

Example 42 and 43: (+)-6-(3-chloro-4-fluoro-5-methoxy-phenyl)-5-methyl-2-pyrimidin-2-yl-7,8-dihydro-5H-pyrido[4,3-d]pyrimidine and (−)-6-(3-chloro-4-fluoro-5-methoxy-phenyl)-5-methyl-2-pyrimidin-2-yl-7,8-dihydro-5H-pyrido[4,3-d]pyrimidine

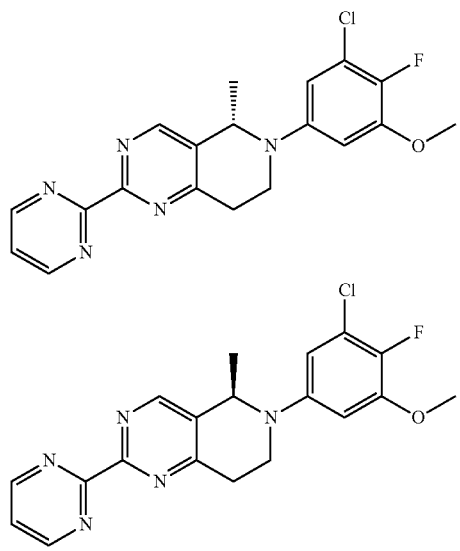

Separation of 6-(3-chloro-4-fluoro-5-methoxy-phenyl)-5-methyl-2-pyrimidin-2-yl-7,8-dihydro-5H-pyrido[4,3-d]pyrimidine (100 mg) by chiral HPLC gave (−)-6-(3-chloro-4-fluoro-5-methoxy-phenyl)-5-methyl-2-pyrimidin-2-yl-7,8-dihydro-5H-pyrido[4,3-d]pyrimidine (40 mg) and (+)-6-(3-chloro-4-fluoro-5-methoxy-phenyl)-5-methyl-2-pyrimidin-2-yl-7,8-dihydro-5H-pyrido[4,3-d]pyrimidine (45 mg) both as yellow solid.

Example 42: (+)-6-(3-chloro-4-fluoro-5-methoxy-phenyl)-5-methyl-2-pyrimidin-2-yl-7,8-dihydro-5H-pyrido[4,3-d]pyrimidine: ¹H NMR (400 MHz, Methanol-d₄) δ: 9.04 (d, 2H), 8.86 (s, 1H), 7.65 (t, 1H), 6.62-6.79 (m, 2H), 5.15-5.30 (m, 1H), 3.92 (s, 3H), 3.80-3.88 (m, 1H), 3.49-3.59 (m, 1H), 3.10-3.28 (m, 2H), 1.46 (d, 3H). MS obsd. (ESI⁺) [(M+H)⁺]: 386. [a]_D^{25}=+53.333° (0.105 g/100 mL, MeOH).

Example 43: (−)-6-(3-chloro-4-fluoro-5-methoxy-phenyl)-5-methyl-2-pyrimidin-2-yl-7,8-dihydro-5H-pyrido[4,3-d]pyrimidine: ¹H NMR (400 MHz, Methanol-d₄) δ: 9.04 (d, 2H), 8.86 (s, 1H), 7.65 (t, 1H), 6.63-6.78 (m, 2H), 5.17-5.31 (m, 1H), 3.91 (s, 3H), 3.79-3.88 (m, 1H), 3.48-3.59 (m, 1H), 3.11-3.25 (m, 2H), 1.40 (d, 3H). MS obsd. (ESI⁺) [(M+H)⁺]: 386.

Example 44: 2,3-difluoro-5-(5-methyl-2-pyrimidin-2-yl-7,8-dihydro-5H-pyrido[4,3-d]pyrimidin-6-yl) phenol

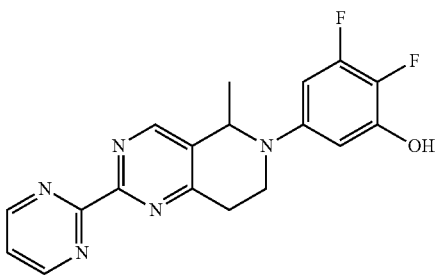 [SMILES: CC1c2cnc(-c3ncccn3)nc2CCN1c1cc(O)c(F)c(F)c1]

Step 1: Preparation of 6-(3-benzyloxy-4,5-difluoro-phenyl)-5-methyl-2-pyrimidin-2-yl-7,8-dihydro-5H-pyrido[4,3-d]pyrimidine

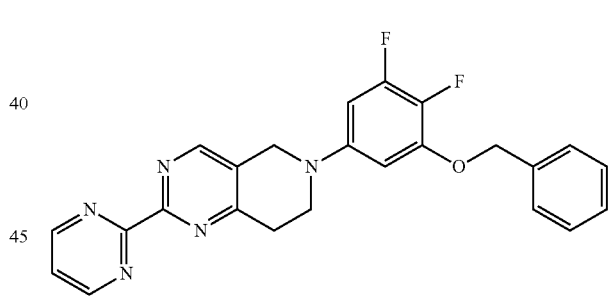

A mixture of 1-(3-benzyloxy-4,5-difluoro-phenyl)piperidin-4-one (366.0 g, 1153.2 mmol) and DMFDMA (3600 mL) was heated at 120° C. with stirring for 4 hrs. The reaction mixture was concentrated in vacuo and the residue was dissolved in MeOH (3900 mL). To the solution was added pyrimidine-2-carboxamidine hydrochloride (167.1 g, 1047.0 mmol) and K₂CO₃ (318.3 g, 2303.4 mmol). After being heated at 60° C. with stirring for 2 hrs, the reaction mixture was cooled down to rt and filtered. The filtrate was concentrated in vacuo and the residue was diluted with DCM (4000 mL). The organic mixture was washed with brine (1200 mL), dried over anhydrous Na₂SO₄ and concentrated in vacuo. The residue was purified by column chromatography on silica gel to give 6-(3-benzyloxy-4,5-difluoro-phenyl)-5-methyl-2-pyrimidin-2-yl-7,8-dihydro-5H-pyrido[4,3-d]pyrimidine (280.0 g) as a yellow solid.

Step 2: Preparation of 6-(3-benzyloxy-4,5-difluoro-phenyl)-5-methoxy-2-pyrimidin-2-yl-7,8-dihydro-5H-pyrido[4,3-d]pyrimidine

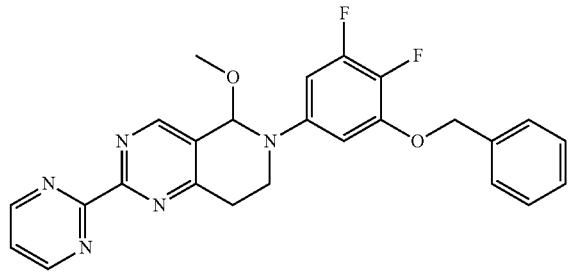 [SMILES: COC1c2cnc(-c3ncccn3)nc2CCN1c1cc(F)c(F)c(OCc2ccccc2)c1]

A solution of 6-(3-benzyloxy-4,5-difluoro-phenyl)-5-methyl-2-pyrimidin-2-yl-7,8-dihydro-5H-pyrido[4,3-d]pyrimidine (180.0 g, 417.24 mmol) in a mixed solvent of DCM (1500 mL) and MeOH (300 mL) was cooled to −78° C. with stirring. To the solution was added RuCl₃ hydrate (125.16 mmol) followed by an aqueous solution of NaIO₄ (267.72 g, 1251.72 mmol, 3000 mL H₂O) slowly. The mixture was stirred at −70° C. for 15 mins, then warmed to 15° C. and stirred for 16 hrs. The resulting reaction mixture was diluted with saturated aqueous solution of Na₂SO₄ and filtered. The filtrate was diluted with DCM (32000 mL), washed with brine (8000 mL), dried over anhydrous Na₂SO₄ and concentrated in vacuo to give crude 6-(3-benzyloxy-4,5-difluoro-phenyl)-5-methoxy-2-pyrimidin-2-yl-7,8-dihydro-5H-pyrido[4,3-d]pyrimidine (197.2 g) as a dark solid, which was used in the next step directly without further purification.

Step 3: Preparation of 6-(3-benzyloxy-4,5-difluoro-phenyl)-5-methyl-2-pyrimidin-2-yl-7,8-dihydro-5H-pyrido[4,3-d]pyrimidine

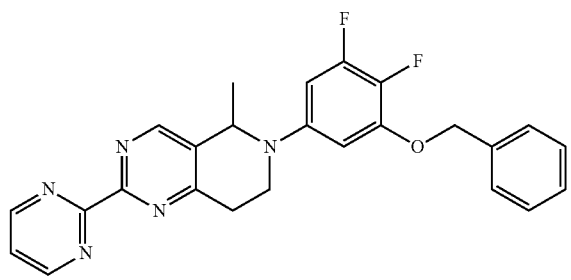 [SMILES: CC1c2cnc(-c3ncccn3)nc2CCN1c1cc(F)c(F)c(OCc2ccccc2)c1]

A solution of crude 6-(3-benzyloxy-4,5-difluoro-phenyl)-5-methoxy-2-pyrimidin-2-yl-7,8-dihydro-5H-pyrido[4,3-d]pyrimidine (197.2 g, 427.3 mmol) in THF (2000 mL) was cooled to −78° C. with stirring. To the solution was added BF₃.Et₂O (147.3 g, 1282.0 mmol) and the mixture was stirred for 30 mins. Then to the reaction mixture was added a solution of MeMgBr (570 mL, 1709.2 mmol, 3M) in THF slowly. After being warmed to 15° C. and stirred at 15° C. for 2 hrs, the resulting reaction mixture was diluted with saturated aqueous solution of NH₄Cl (150 mL) and DCM (6000 mL), washed with water (1000 mL) and brine (1000 mL), dried over anhydrous Na₂SO₄ and concentrated in vacuo. The residue was purified by column chromatography on silica gel to give 6-(3-benzyloxy-4,5-difluoro-phenyl)-5-methyl-2-pyrimidin-2-yl-7,8-dihydro-5H-pyrido[4,3-d]pyrimidine (80 g) as a dark solid.

Step 4: Preparation of 2,3-difluoro-5-(5-methyl-2-pyrimidin-2-yl-7,8-dihydro-5H-pyrido[4,3-d]pyrimidin-6-yl)phenol

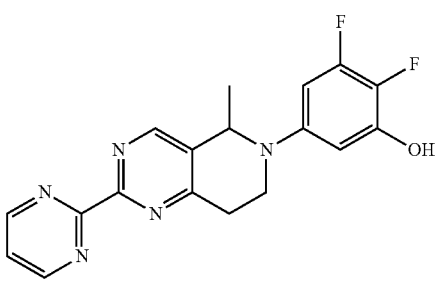 [SMILES: CC1c2cnc(-c3ncccn3)nc2CCN1c1cc(O)c(F)c(F)c1]

A mixture of 6-(3-benzyloxy-4,5-difluoro-phenyl)-5-methyl-2-pyrimidin-2-yl-7,8-dihydro-5H-pyrido[4,3-d]pyrimidine (65.8 g, 147.6 mmol) and solution of HBr in AcOH (1000 mL, 33 wt. %) was heated at 80° C. with stirring for 2 hrs. The reaction mixture was concentrated in vacuo. The residue was diluted with H₂O (300 mL), basified with 15% NaOH aqueous solution and washed with DCM (500 mL) for three times. The combined aqueous layer was then acidified with 1 N HCl aqueous solution and extracted with DCM (400 mL) for five times. The combined organic layer was dried over anhydrous Na₂SO₄ and concentrated in vacuo. The residue was purified by chromatography on silica gel to give 2,3-difluoro-5-(5-methyl-2-pyrimidin-2-yl-7,8-dihydro-5H-pyrido[4,3-d]pyrimidin-6-yl)phenol (11 g) as a yellowish solid. ¹H NMR (400 MHz, CDCl₃) δ: 9.04 (d, 2H), 8.77 (s, 1H), 7.45 (t, 1H), 6.25-6.44 (m, 2H), 5.61 (br. s, 1H), 4.96 (q, 1H), 3.68-3.77 (m, 1H), 3.44-3.53 (m, 1H), 3.16-3.34 (m, 2H), 1.47 (d, 3H). MS obsd. (ESI⁺) [(M+H)⁺]: 356.

Example 45 and 46: (−)-2,3-difluoro-5-(5-methyl-2-pyrimidin-2-yl-7,8-dihydro-5H-pyrido[4,3-d]pyrimidin-6-yl)phenol and (+)-2,3-difluoro-5-(5-methyl-2-pyrimidin-2-yl-7,8-dihydro-5H-pyrido[4,3-d]pyrimidin-6-yl)phenol

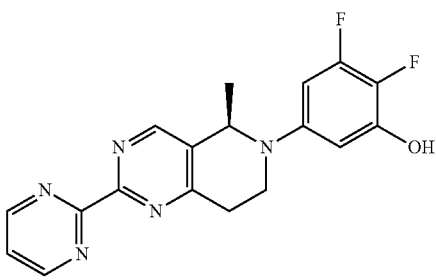

-continued

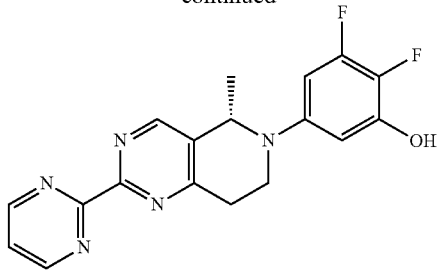

Separation of 2,3-difluoro-5-(5-methyl-2-pyrimidin-2-yl-7,8-dihydro-5H-pyrido[4,3-d]pyrimidin-6-yl)phenol (6 g, Example 44) by chiral HPLC gave (−)-2,3-difluoro-5(5-methyl-2-pyrimidin-2-yl-7,8-dihydro-5H-pyrido[4,3-d]pyrimidin-6-yl)phenol (2.7 g) and (+)-2,3-difluoro-5-(5-methyl-2-pyrimidin-2-yl-7,8-dihydro-5H-pyrido[4,3-d]pyrimidin-6-yl)phenol (2.6 g) both as grey solid.

Example 45: (−)-2,3-difluoro-5-(5-methyl-2-pyrimidin-2-yl-7,8-dihydro-5H-pyrido[4,3-d]pyrimidin-6-yl)phenol, $^1$H NMR (400 MHz, DMSO-d$_6$) δ: 1.40 (d, 3H), 2.89-3.16 (m, 2H), 3.38-3.50 (m, 1H), 3.71-3.83 (m, 1H), 5.05-5.20 (m, 1H), 6.32-6.44 (m, 1H), 6.47-6.61 (m, 1H), 7.59-7.69 (m, 1H), 8.86 (s, 1H), 9.00 (d, 2H), 10.09-10.27 (m, 1H). MS obsd. (ESI$^+$) [(M+H)$^+$]: 356. [a]$_D^{20}$=−40.00° (0.05 g/100 mL, methanol).

Example 46: (+)-2,3-difluoro-5-(5-methyl-2-pyrimidin-2-yl-7,8-dihydro-5H-pyrido[4,3-d]pyrimidin-6-yl)phenol, $^1$H NMR (400 MHz, CDCl$_3$) δ: 8.97-9.10 (m, 2H), 8.76 (s, 1H), 7.46 (m, 1H), 6.24-6.46 (m, 2H), 4.94 (m, 1H), 3.71 (m, 1H), 3.41-3.54 (m, 1H), 3.11-3.34 (m, 2H), 1.46 (d, 3H); MS obsd. (ESI$^+$) [(M+H)$^+$]: 356.

Example 47: 6-[3,4-difluoro-5-(3-methylsulfonylpropoxy)phenyl]-5-methyl-2-pyrimidin-2-yl-7,8-dihydro-5H-pyrido[4,3-d]pyrimidine

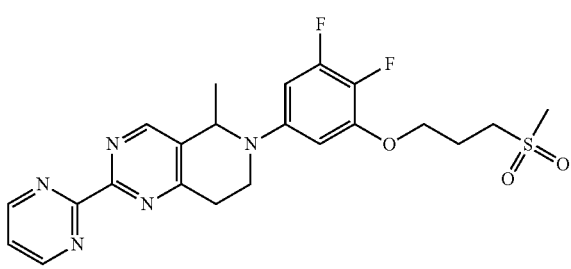 [SMILES: CC1c2cnc(-c3ncccn3)nc2CCN1c1cc(F)c(F)c(OCCCS(C)(=O)=O)c1]

Step 1: Preparation of 3-methylsulfonylpropyl 4-methylbenzenesulfonate

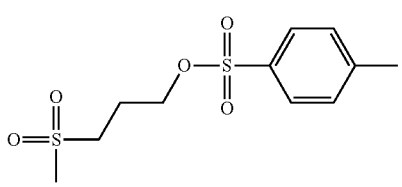 [SMILES: Cc1ccc(S(=O)(=O)OCCCS(C)(=O)=O)cc1]

To a solution of 3-methylsulfanylpropyl 4-methylbenzenesulfonate (2 g, 7.7 mmol) in methanol (50 mL) was added a solution of oxone (9.47 g, 15.4 mmol) in water (50 mL) dropwise at 0° C. After being warmed to rt and stirred at rt for 20 hrs, the mixture was filtered and the filtrate was extracted with EA (50 mL) for three times. The combined organic layer was washed with water, dried over anhydrous Na$_2$SO$_4$ and concentrated in vacuo to give 3-methylsulfonylpropyl 4-methylbenzenesulfonate as a white solid (1.95 g) which was used in the next step directly without further purification.

Step 2: Preparation of 6-[3,4-difluoro-5-(3-methylsulfonylpropoxy)phenyl]-5-methyl-2-pyrimidin-2-yl-7,8-dihydro-5H-pyrido[4,3-d]pyrimidine

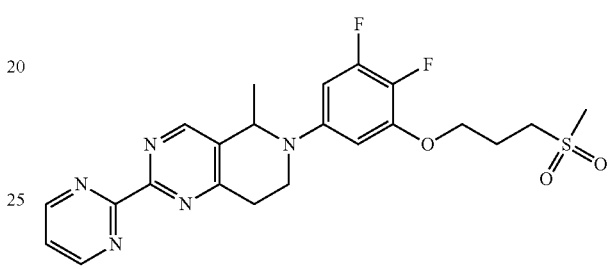

A mixture of 2,3-difluoro-5-(5-methyl-2-pyrimidin-2-yl-7,8-dihydro-5H-pyrido[4,3-d]pyrimidin-6-yl)phenol (400 mg, 1.13 mmol), 3-methylsulfonylpropyl 4-methylbenzenesulfonate (494 mg, 1.69 mmol) and K$_2$CO$_3$ (311 mg, 2.254 mmol) in DMF (10 mL) was heated at 110° C. overnight. After being cooled to rt, the reaction mixture was diluted with H$_2$O (10 mL) and extracted with DCM (30 mL) for three times. The combined organic layer was dried over anhydrous Na$_2$SO$_4$ and concentrated in vacuo. The residue was purified by prep-HPLC to give 6-[3,4-difluoro-5-(3-methylsulfonylpropoxy)phenyl]-5-methyl-2-pyrimidin-2-yl-7,8-dihydro-5H-pyrido[4,3-d]pyrimidine (107 mg) as yellow solid. $^1$H NMR (400 MHz, Methanol-d$_4$) δ: 9.05 (d, 2H), 8.84-8.90 (m, 1H), 7.62-7.71 (m, 1H), 6.53-6.66 (m, 2H), 5.16-5.30 (m, 1H), 4.22-4.32 (m, 2H), 3.81-3.93 (m, 1H), 3.49-3.62 (m, 1H), 3.34-3.39 (m, 2H), 3.11-3.28 (m, 2H), 3.05 (s, 3H), 2.28-2.39 (m, 2H), 1.48 (d, 3H); MS obsd. (ESI$^+$) [(M+H)$^+$]: 476.

Example 48 and 49: (+)-6-[3,4-difluoro-5-(3-methylsulfonylpropoxy)phenyl]-5-methyl-2-pyrimidin-2-yl-7,8-dihydro-5H-pyrido[4,3-d]pyrimidine and (−)-6-[3,4-difluoro-5-(3-methylsulfonylpropoxy)phenyl]-5-methyl-2-pyrimidin-2-yl-7,8-dihydro-5H-pyrido[4,3-d]pyrimidine

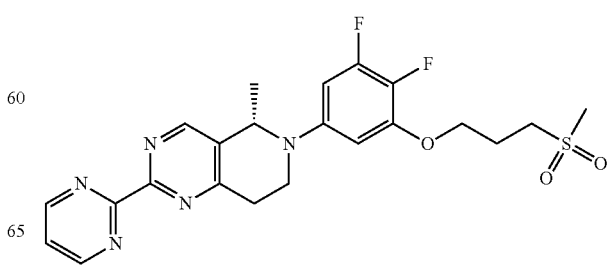

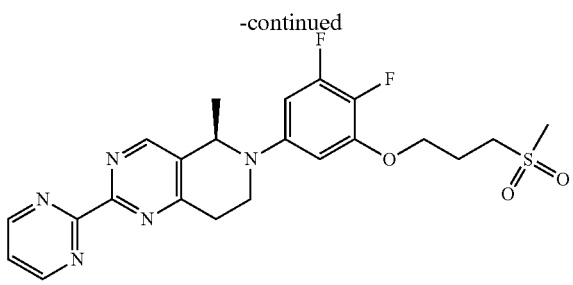

Separation of 6-[3,4-difluoro-5-(3-methylsulfonylpropoxy)phenyl]-5-methyl-2-pyrimidin-2-yl-7,8-dihydro-5H-pyrido[4,3-d]pyrimidine (100 mg, Example 47) by chiral HPLC gave (−)-6-[3,4-difluoro-5-(3-methylsulfonylpropoxy)phenyl]-5-methyl-2-pyrimidin-2-yl-7,8-dihydro-5H-pyrido[4,3-d]pyrimidine (16 mg) and (+)-6-[3,4-difluoro-5-(3-methylsulfonylpropoxy)phenyl]-5-methyl-2-pyrimidin-2-yl-7,8-dihydro-5H-pyrido[4,3-d]pyrimidine (16 mg) both as yellow solid.

Example 48: (+)-6-[3,4-difluoro-5-(3-methyl sulfonylpropoxy)phenyl]-5-methyl-2-pyrimidin-2-yl-7,8-dihydro-5H-pyrido[4,3-d]pyrimidine: $^1$H NMR (400 MHz, Methanol-$d_4$) δ: 9.05 (d, 2H), 8.84-8.91 (m, 1H), 7.63-7.70 (m, 1H), 6.53-6.68 (m, 2H), 5.19-5.29 (m, 1H), 4.22-4.34 (m, 2H), 3.83-3.94 (m, 1H), 3.50-3.62 (m, 1H), 3.35-3.40 (m, 2H), 3.16-3.27 (m, 2H), 3.05 (s, 3H), 2.29-2.38 (m, 2H), 1.46-1.52 (m, 3H); MS obsd. (ESI$^+$) [(M+H)$^+$]: 476; $[α]_D^{20}$=+56.00° (0.05 g/100 mL, methanol).

Example 49: (−)-6-[3,4-difluoro-5-(3-methylsulfonylpropoxy)phenyl]-5-methyl-2-pyrimidin-2-yl-7,8-dihydro-5H-pyrido[4,3-d]pyrimidine: $^1$H NMR (400 MHz, Methanol-$d_4$) δ: 9.05 (d, 2H), 8.84-8.91 (m, 1H), 7.63-7.70 (m, 1H), 6.53-6.68 (m, 2H), 5.19-5.29 (m, 1H), 4.22-4.34 (m, 2H), 3.83-3.94 (m, 1H), 3.50-3.62 (m, 1H), 3.35-3.40 (m, 2H), 3.16-3.27 (m, 2H), 3.05 (s, 3H), 2.29-2.38 (m, 2H), 1.46-1.52 (m, 3H); MS obsd. (ESI$^+$) [(M+H)$^+$]: 476.

Example 50: 4-[2,3-difluoro-5-(5-methyl-2-pyrimidin-2-yl-7,8-dihydro-5H-pyrido[4,3-d]pyrimidin-6-yl)phenoxy]butanoic acid

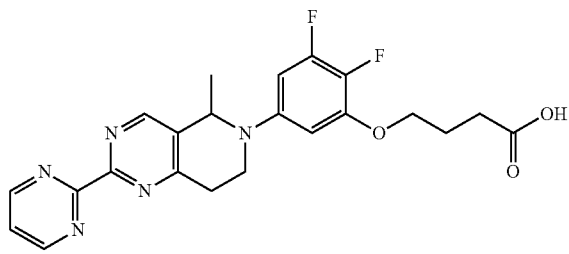 [SMILES: CC1c2cnc(-c3ncccn3)nc2CCN1c1cc(F)c(F)c(OCCCC(=O)O)c1]

Step 1: Preparation of ethyl 4-[2,3-difluoro-5-(5-methyl-2-pyrimidin-2-yl-7,8-dihydro-5H-pyrido[4,3-d]pyrimidin-6-yl)phenoxy]butanoate

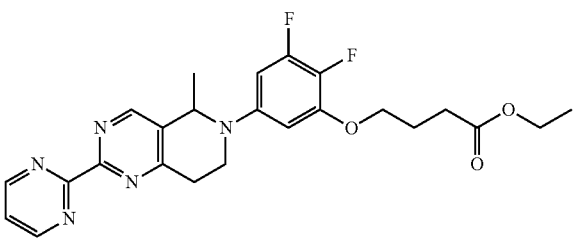 [SMILES: CCOC(=O)CCCOc1cc(N2CCc3nc(-c4ncccn4)ncc3C2C)cc(F)c1F]

A mixture of 2,3-difluoro-5-(5-methyl-2-pyrimidin-2-yl-7,8-dihydro-5H-pyrido[4,3-d]pyrimidin-6-yl)phenol (300 mg, 0.845 mmol), ethyl 4-bromobutanoate (330 mg, 1.69 mmol), KI (140 mg, 0.845 mmol) and $K_2CO_3$ (117 mg, 0.845 mmol) in DMF (10 mL) was heated to 110° C. with stirring overnight. After being cooled to rt, the reaction mixture was diluted with $H_2O$ (10 mL) and extracted with DCM (30 mL) for three times. The combined organic layer was dried over anhydrous $Na_2SO_4$ and concentrated in vacuo to give the crude ethyl 4-[2,3-difluoro-5-(5-methyl-2-pyrimidin-2-yl-7,8-dihydro-5H-pyrido[4,3-d]pyrimidin-6-yl)phenoxy]butanoate (300 mg) which was used in the next step directly without further purification.

Step 2: Preparation of 4-[2,3-difluoro-5-(5-methyl-2-pyrimidin-2-yl-7,8-dihydro-5H-pyrido[4,3-d]pyrimidin-6-yl)phenoxy]butanoic acid

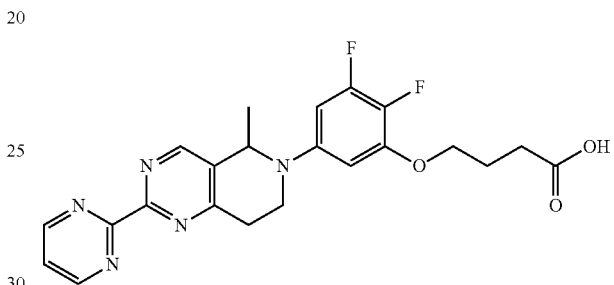

A mixture of crude ethyl 4-[2,3-difluoro-5-(5-methyl-2-pyrimidin-2-yl-7,8-dihydro-5H-pyrido[4,3-d]pyrimidin-6-yl)phenoxy]butanoate (200 mg, 0.426 mmol) and LiOH monohydrate (89 mg, 2.13 mmol) in THF (3 mL), methanol (5 mL) and $H_2O$ (1 mL) was stirred at rt for 3 hrs. The resulting mixture was acidified with 2N hydrochloric acid, and extracted with DCM (20 mL) for three times. The combined organic layer was washed with brine, dried over anhydrous $Na_2SO_4$ and concentrated in vacuo. The residue was purified by prep-HPLC to give 4-[2,3-difluoro-5-(5-methyl-2-pyrimidin-2-yl-7,8-dihydro-5H-pyrido[4,3-d]pyrimidin-6-yl)phenoxy]butanoic acid (15 mg) as light yellow solid. $^1$H NMR (400 MHz, Methanol-$d_4$) δ: 9.05 (d, 2H), 8.87 (s, 1H), 7.66 (s, 1H), 6.50-6.65 (m, 2H), 5.18-5.30 (m, 1H), 4.11-4.21 (m, 2H), 3.82-3.92 (m, 1H), 3.48-3.61 (m, 1H), 3.11-3.29 (m, 2H), 2.53 (s, 2H), 2.03-2.18 (m, 2H), 1.48 (d, 3H); MS obsd. (ESI$^+$) [(M+H)$^+$]: 442.

Example 51: 3-[2,3-difluoro-5-(5-methyl-2-pyrimidin-2-yl-7,8-dihydro-5H-pyrido[4,3-d]pyrimidin-6-yl)phenoxy]propanoic acid

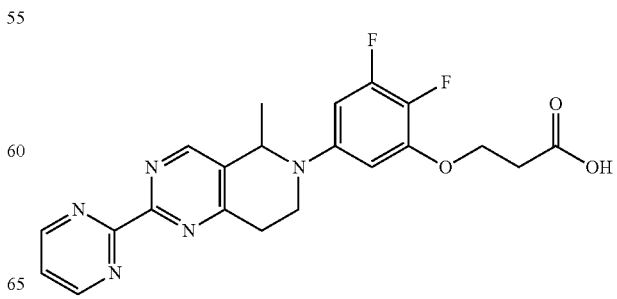

To the suspension of 2,3-difluoro-5-(5-methyl-2-pyrimidin-2-yl-7,8-dihydro-5H-pyrido[4,3-d]pyrimidin-6-yl)phenol (100 mg, 0.28 mmol), KI (47 mg, 0.28 mmol) and 3-bromopropanoic acid (43 mg, 0.28 mmol) in H$_2$O (3 mL) was added a solution of NaOH (24 mg) in H$_2$O (2 mL). After being heated at 110° C. with stirring overnight, the resulting reaction mixture was cooled to rt, acidified with 2N hydrochloric acid and extracted with DCM (20 mL) for three times. The combined organic layer was dried over anhydrous Na$_2$SO$_4$ and concentrated in vacuo. The residue was purified by prep-HPLC to give 3-[2,3-difluoro-5-(5-methyl-2-pyrimidin-2-yl-7,8-dihydro-5H-pyrido[4,3-d]pyrimidin-6-yl)phenoxy]propanoic acid (3 mg) as white solid. $^1$H NMR (400 MHz, Methanol-d$_4$) δ: 9.05 (d, 2H), 8.89 (s, 1H), 7.67 (s, 1H), 6.50-6.67 (m, 2H), 5.20-5.27 (m, 1H), 4.36 (d, 2H), 3.81-3.93 (m, 1H), 3.49-3.62 (m, 1H), 3.12-3.29 (m, 2H), 2.81 (m, 2H), 1.49 (d, 3H); MS obsd. (ESI$^+$) [(M+H)$^+$]: 428.

Example 52: 4-[2,3-difluoro-5-(5-methyl-2-pyrimidin-2-yl-7,8-dihydro-5H-pyrido[4,3-d]pyrimidin-6-yl)phenoxy]butanamide

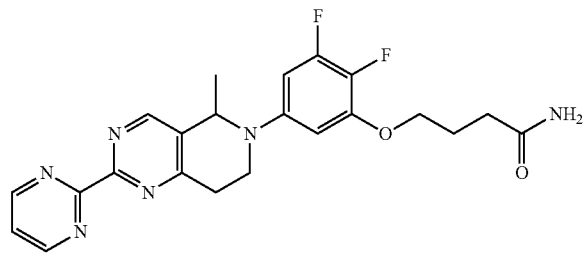 [SMILES: CC1c2cnc(-c3ncccn3)nc2CCN1c1cc(F)c(F)c(OCCCC(N)=O)c1]

A mixture of 4-[2,3-difluoro-5-(5-methyl-2-pyrimidin-2-yl-7,8-dihydro-5H-pyrido[4,3-d]pyrimidin-6-yl)phenoxy] butanoic acid (100 mg, 0.23 mmol) and CDI (44 mg, 0.272 mmol) in DMF (5 mL) was stirred at rt for 2 hrs. Then to the reaction mixture was added NH$_3$ (7 mL, 14 mmol, 2.0 mol/L in isopropyl alcohol). After being stirred overnight, the resulting mixture was concentrated in vacuo. The residue was diluted with DCM (20 mL), washed with water, dried over anhydrous Na$_2$SO$_4$ and concentrated in vacuo. The residue was purified by prep-HPLC to give 4-[2,3-difluoro-5-(5-methyl-2-pyrimidin-6-yl)phenoxy]butanamide (2.5 mg) as light yellow solid. $^1$H NMR (400 MHz, Methanol-d$_4$) δ: 9.05 (d, 2H), 8.88 (s, 1H), 7.61-7.72 (m, 1H), 6.50-6.67 (m, 2H), 5.18-5.30 (m, 1H), 4.08-4.22 (m, 2H), 3.80-3.94 (m, 1H), 3.48-3.63 (m, 1H), 3.10-3.29 (m, 2H), 2.46 (s, 2H), 2.04-2.21 (m, 2H), 1.48 (d, 3H); MS obsd. (ESI$^+$) [(M+H)$^+$]: 441.

Example 53: 4-[2,3-difluoro-5-(5-methyl-2-pyrimidin-2-yl-7,8-dihydro-5H-pyrido[4,3-d]pyrimidin-6-yl)phenoxy]-N-methyl-butanamide

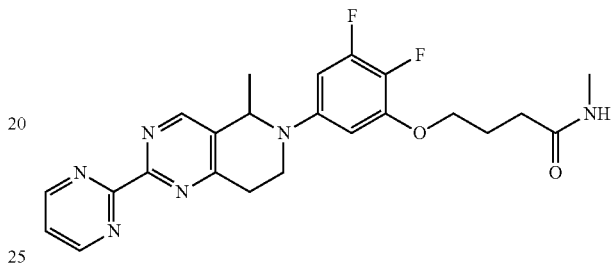

A mixture of 4-[2,3-difluoro-5-(5-methyl-2-pyrimidin-2-yl-7,8-dihydro-5H-pyrido[4,3-d]pyrimidin-6-yl)phenoxy] butanoic acid (150 mg, 0.34 mmol) and CDI (66 mg, 0.41 mmol) in DMF (5 mL) was stirred at rt for 2 hrs. Then to the reaction mixture was added methanamine (21 mg, 0.68 mmol). After being stirred overnight, the mixture was concentrated in vacuo. The residue was diluted with DCM (20 mL), washed with water, dried over anhydrous Na$_2$SO$_4$ and concentrated in vacuo. The residue was purified by prep-HPLC to give 4-[2,3-difluoro-5-(5-methyl-2-pyrimidin-2-yl-7,8-dihydro-5H-pyrido[4,3-d]pyrimidin-6-yl)phenoxy]-N-methyl-butanamide (30 mg) as light yellow solid. $^1$H NMR (400 MHz, MeO-d$_4$) δ: 9.05 (d, 2H), 8.88 (s, 1H), 7.66 (m, 1H), 6.58 (s, 2H), 5.23 (m, 1H), 4.05-4.20 (m, 2H), 3.78-3.94 (m, 1H), 3.47-3.60 (m, 1H), 3.04-3.29 (m, 2H), 2.74 (s, 3H), 2.37-2.52 (m, 2H), 2.05-2.20 (m, 2H), 1.47 (s, 3H); MS obsd. (ESI$^+$) [(M+H)$^+$]: 455.

Example 54: tert-butyl N-[8-[2,3-difluoro-5-(5-methyl-2-pyrimidin-2-yl-7,8-dihydro-5H-pyrido[4,3-d]pyrimidin-6-yl)phenoxy]octyl]carbamate

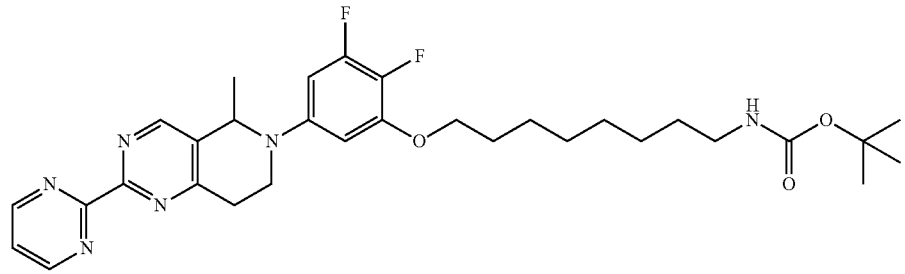 [SMILES: CC1c2cnc(-c3ncccn3)nc2CCN1c1cc(F)c(F)c(OCCCCCCCCNC(=O)OC(C)(C)C)c1]

Step 1: Preparation of 8-(tert-butoxycarbonylamino)octyl 4-methylbenzenesulfonate

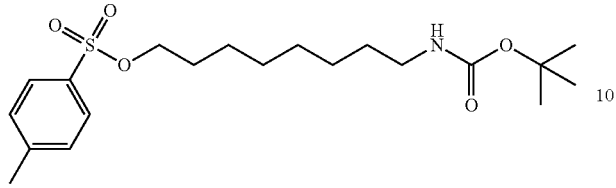

To a mixture of tert-butyl N-(8-hydroxyoctyl)carbamate (5.45 g, 22.26 mmol) and triethylamine (3.72 mL, 26.7 mmol) in DCM (200 mL) was added p-toluenesulfonyl chloride (5.09 g, 26.7 mmol) and DMAP (0.272 g, 2.226 mmol) at rt. After being stirred overnight, the mixture was concentrated in vacuo and the residue was purified by flash column to give 8-(tert-butoxycarbonylamino)octyl 4-methylbenzenesulfonate (4.1 g).

Step 2: Preparation of tert-butyl N-[8-[2,3-difluoro-5-(5-methyl-2-pyrimidin-2-yl-7,8-dihydro-5H-pyrido[4,3-d]pyrimidin-6-yl)phenoxy]octyl]carbamate

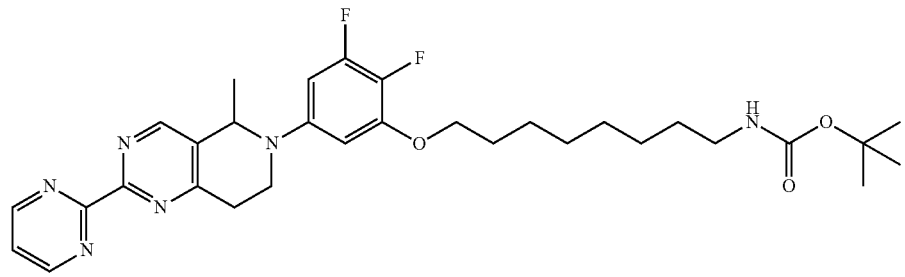 [SMILES: CC1c2cnc(-c3ncccn3)nc2CCN1c1cc(F)c(F)c(OCCCCCCCCNC(=O)OC(C)(C)C)c1]

A mixture of 2,3-difluoro-5-[5-methyl-2-(2-pyridyl)-7,8-dihydro-5H-pyrido[4,3-d]pyrimidin-6-yl]phenol (200 mg, 0.563 mmol), 8-(tert-butoxycarbonylamino)octyl 4-methylbenzenesulfonate (450 mg, 1.127 mmol) and $K_2CO_3$ (233 mg, 1.69 mmol) in DMF (10 mL) was heated at 100° C. with stirring overnight. After being cooled to rt, the reaction mixture was diluted with $H_2O$ (10 mL) and exacted with EA (30 mL) for three times. The combined organic layer was dried over anhydrous $Na_2SO_4$ and concentrated in vacuo to give crude product (240 mg). The crude product (100 mg) was purified by prep-HPLC to give tert-butyl N-[8-[2,3-difluoro-5-(5-methyl-2-pyrimidin-2-yl-7,8-dihydro-5H-pyrido[4,3-d]pyrimidin-6-yl)phenoxy]octyl]carbamate (48 mg) as yellow solid. $^1$H NMR (400 MHz, Methanol-$d_4$) δ: 9.00-9.09 (m, 2H), 8.87 (s, 1H), 7.66 (m, 1H), 6.42-6.61 (m, 2H), 5.22 (m, 1H), 4.01-4.16 (m, 2H), 3.80-3.93 (m, 1H), 3.46-3.63 (m, 1H), 3.08-3.28 (m, 2H), 3.04 (m, 2H), 1.75-1.88 (m, 2H), 1.25-1.57 (m, 22H); MS obsd. (ESI$^+$) [(M+H)$^+$]: 583.

Example 55: 8-[2,3-difluoro-5-(5-methyl-2-pyrimidin-2-yl-7,8-dihydro-5H-pyrido[4,3-d]pyrimidin-6-yl)phenoxy]octan-1-amine

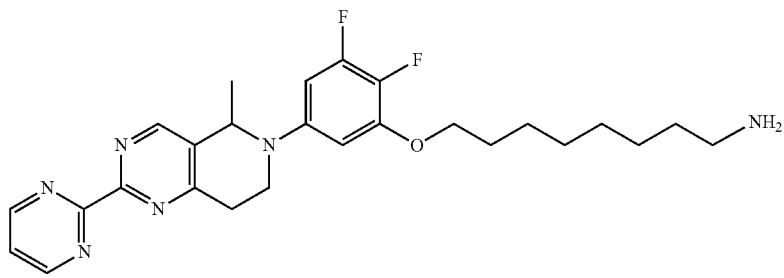 [SMILES: CC1c2cnc(-c3ncccn3)nc2CCN1c1cc(F)c(F)c(OCCCCCCCCN)c1]

A mixture of the crude tert-butyl N-[8-[2,3-difluoro-5-(5-methyl-2-pyrimidin-2-yl-7,8-dihydro-5H-pyrido[4,3-d]pyrimidin-6-yl)phenoxy]octyl]carbamate (140 mg) and CF₃COOH (10 mL) in DCM (10 mL) was stirred at rt for 1 hr. The reaction mixture was concentrated in vacuo. The residue was diluted with saturated aqueous solution of NaHCO₃, and extracted with DCM (20 mL) for three times. The combined organic layer was dried over anhydrous Na₂SO₄ and concentrated in vacuo. The residue was purified by prep-HPLC to give 8-[2,3-difluoro-5-(5-methyl-2-pyrimidin-2-yl-7,8-dihydro-5H-pyrido[4,3-d]pyrimidin-6-yl) phenoxy]octan-1-amine (20 mg) as yellow solid. $^1$H NMR (400 MHz, Methanol-d₄) δ: 9.06 (d, 2H), 8.88 (s, 1H), 7.67 (m, 1H), 6.44-6.62 (m, 2H), 5.22 (d, 1H), 4.11 (m, 2H), 3.78-3.95 (m, 1H), 3.57 (d, 1H), 3.09-3.27 (m, 2H), 2.88-3.00 (m, 2H), 1.77-1.90 (m, 2H), 1.61-1.74 (m, 2H), 1.30-1.60 (m, 11H); MS obsd. (ESI⁺) [(M+H)⁺]: 483.

Example 56: tert-butyl N-[5-[2,3-difluoro-5-(5-methyl-2-pyrimidin-2-yl-7,8-dihydro-5H-pyrido[4,3-d]pyrimidin-6-yl)phenoxy]pentyl]carbamate

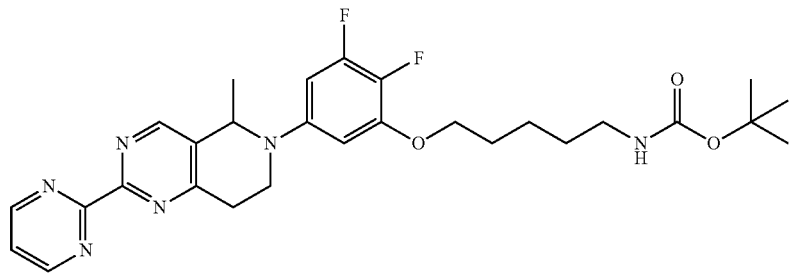 [SMILES: CC1c2cnc(-c3ncccn3)nc2CCN1c1cc(F)c(F)c(OCCCCCNC(=O)OC(C)(C)C)c1]

Step 1: Preparation of 5-(tert-butoxycarbonylamino)pentyl 4-methylbenzenesulfonate

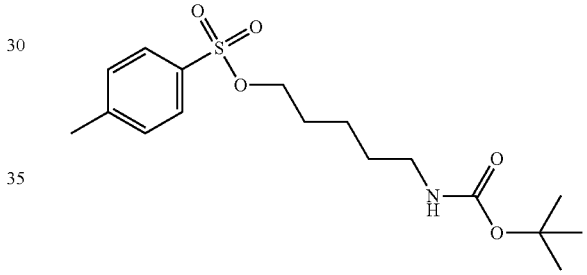

To a mixture of tert-butyl N-(5-hydroxypentyl)carbamate (4.52 g, 22.26 mmol) and triethylamine (3.72 mL, 26.7 mmol) in DCM (200 mL) at rt was added p-toluenesulfonyl chloride (5.09 g, 26.7 mmol) and DMAP (0.272 g, 2.226 mmol). After being stirred overnight, the reaction mixture was concentrated in vacuo and the residue was purified by flash column to give 5-(tert-butoxycarbonylamino)pentyl 4-methylbenzenesulfonate (4.2 g).

Step 2: Preparation of tert-butyl N-[5-[2,3-difluoro-5-(5-methyl-2-pyrimidin-2-yl-7,8-dihydro-5H-pyrido[4,3-d]pyrimidin-6-yl)phenoxy]pentyl]carbamate

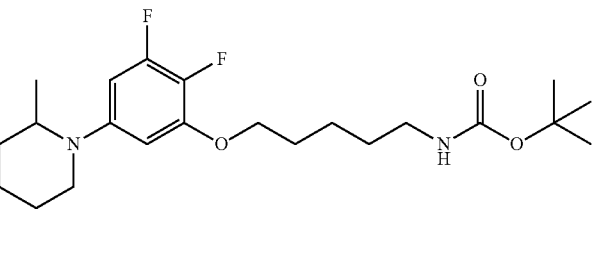

A mixture of 2,3-difluoro-5-[5-methyl-2-(2-pyridyl)-7,8-dihydro-5H-pyrido[4,3-d]pyrimidin-6-yl]phenol (200 mg, 0.563 mmol), 5-(tert-butoxycarbonylamino)hexyl 4-methylbenzenesulfonate (402 mg, 1.127 mmol) and K$_2$CO$_3$ (233 mg, 1.69 mmol) in DMF (10 mL) was heated at 100° C. with stirring overnight. After being cooled to rt, the reaction mixture was diluted with H$_2$O (10 mL) and exacted with EA (30 mL) for three times. The combined organic layer was dried over anhydrous Na$_2$SO$_4$ and concentrated in vacuo. The residue was purified by prep-HPLC to give tert-butyl N-[5-[2,3-difluoro-5-(5-methyl-2-pyrimidin-2-yl-7,8-dihydro-5H-pyrido[4,3-d]pyrimidin-6-yl)phenoxy]pentyl]carbamate (36 mg) as yellow solid. $^1$H NMR (400 MHz, Methanol-d$_4$) δ: 9.05 (d, 2H), 8.88 (s, 1H), 7.67 (m, 1H), 6.46-6.64 (m, 2H), 5.22 (m, 1H), 4.05-4.20 (m, 2H), 3.78-3.93 (m, 1H), 3.47-3.62 (m, 1H), 2.99-3.28 (m, 4H), 1.76-1.96 (m, 2H), 1.35-1.65 (m, 16H). MS obsd. (ESI$^+$) [(M+H)$^+$]: 541.

NaHCO$_3$ and extracted with DCM (20 mL) for three times. The combined organic layer was dried over anhydrous Na$_2$SO$_4$ and concentrated in vacuo. The residue was purified by prep-HPLC to give 5-[2,3-difluoro-5-(5-methyl-2-pyrimidin-2-yl-7,8-dihydro-5H-pyrido[4,3-d]pyrimidin-6-yl)phenoxy]pentan-1-amine (4.9 mg) as yellow solid. $^1$H NMR (400 MHz, Methanol-d$_4$) δ: 8.99-9.10 (m, 2H), 8.87 (s, 1H), 7.62-7.72 (m, 1H), 6.48-6.65 (m, 2H), 5.22 (m, 1H), 4.04-4.22 (m, 2H), 3.77-3.94 (m, 1H), 3.48-3.62 (m, 1H), 3.11-3.25 (m, 2H), 2.88 (m, 2H), 1.80-1.97 (m, 2H), 1.56-1.77 (m, 4H), 1.41-1.53 (m, 3H); MS obsd. (ESI$^+$) [(M+H)$^+$]: 441.

Example 58: tert-butyl N-[6-[2,3-difluoro-5-(5-methyl-2-pyrimidin-2-yl-7,8-dihydro-5H-pyrido[4,3-d]pyrimidin-6-yl)phenoxy]hexyl]carbamate

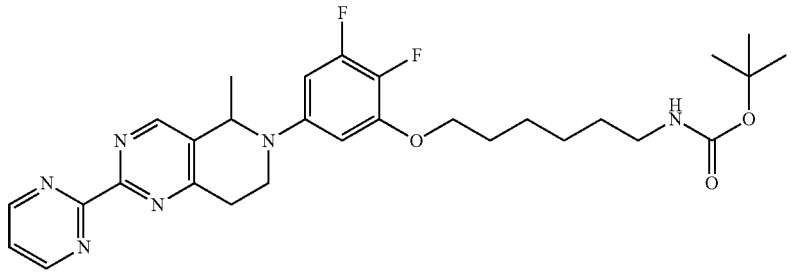

Example 57: 5-[2,3-difluoro-5-(5-methyl-2-pyrimidin-2-yl-7,8-dihydro-5H-pyrido[4,3-d]pyrimidin-6-yl)phenoxy]pentan-1-amine Step 1: Preparation of 6-(tert-butoxycarbonylamino)hexyl 4-methyl benzenesulfonate

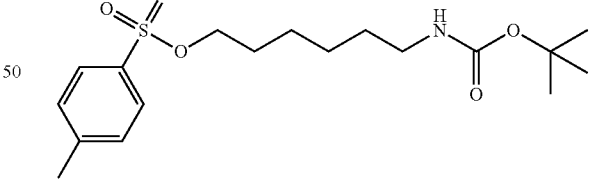

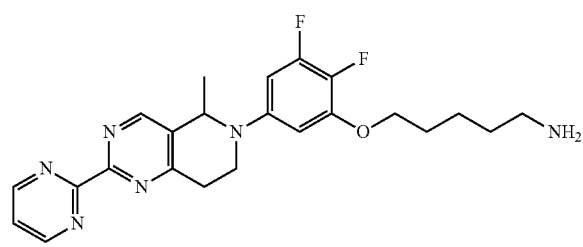 [SMILES: CC1c2cnc(-c3ncccn3)nc2CCN1c1cc(F)c(F)c(OCCCCCN)c1]

A mixture of the crude tert-butyl N-[5-[2,3-difluoro-5-(5-methyl-2-pyrimidin-2-yl-7,8-dihydro-5H-pyrido[4,3-d]pyrimidin-6-yl)phenoxy]pentyl]carbamate (140 mg) and CF$_3$COOH (10 mL) in DCM (10 mL) was stirred at rt for 1 hr. The resulting mixture was concentrated in vacuo. The residue was diluted with saturated aqueous solution of To a mixture of tert-butyl N-(6-hydroxyhexyl)carbamate (4.83 g, 22.26 mmol) and triethylamine (3.72 mL, 26.7 mmol) in DCM (200 mL) at rt was added p-toluenesulfonyl chloride (5.09 g, 26.7 mmol) and DMAP (0.27 g, 2.23 mmol). After being stirred overnight, the resulting mixture was concentrated in vacuo and the residue was purified by flash column to give 6-(tert-butoxycarbonylamino)hexyl 4-methylbenzenesulfonate (4.0 g).

Step 2: Preparation of tert-butyl N-[6-[2,3-difluoro-5-(5-methyl-2-pyrimidin-2-yl-7,8-dihydro-5H-pyrido[4,3-d]pyrimidin-6-yl)phenoxy]hexyl]carbamate

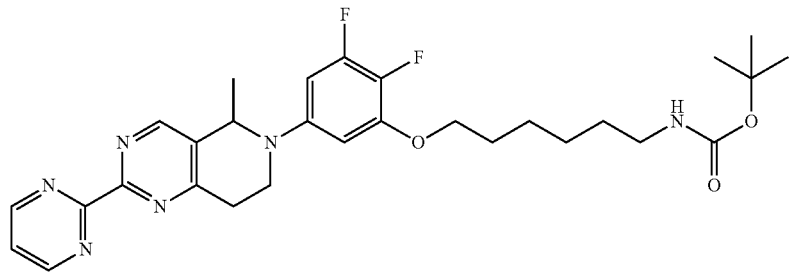 [SMILES: CC1c2cnc(-c3ncccn3)nc2CCN1c1cc(F)c(F)c(OCCCCCCNC(=O)OC(C)(C)C)c1]

A mixture of 2,3-difluoro-5-[5-methyl-2-(2-pyridyl)-7,8-dihydro-5H-pyrido[4,3-d]pyrimidin-6-yl]phenol (200 mg, 0.5 mmol), 6-(tert-butoxycarbonylamino)hexyl 4-methylbenzenesulfonate (418 mg, 1.1 mmol) and $K_2CO_3$ (233 mg, 1.7 mmol) in DMF (10 mL) was heated at 100° C. overnight. After being cooled to rt, the reaction mixture was diluted with $H_2O$ (10 mL) and extracted with EA (30 mL) for three times. The combined organic layer was dried over anhydrous $Na_2SO_4$ and concentrated in vacuo give crude tert-butyl N-[6-[2,3-difluoro-5-(5-methyl-2-pyrimidin-2-yl-7,8-dihydro-5H-pyrido[4,3-d]pyrimidin-6-yl)phenoxy]hexyl]carbamate (240 mg). The crude product (100 mg) was purified by prep-HPLC to give tert-butyl N-[6-[2,3-difluoro-5-(5-methyl-2-pyrimidin-2-yl-7,8-dihydro-5H-pyrido[4,3-d]pyrimidin-6-yl)phenoxy]hexyl]carbamate (54 mg) as yellow solid. $^1$H NMR (400 MHz, Methanol-$d_4$) δ: 9.05 (d, 2H), 8.83-8.90 (m, 1H), 7.67 (s, 1H), 6.46-6.61 (m, 2H), 5.14-5.30 (m, 1H), 4.10 (m, 2H), 3.78-3.92 (m, 1H), 3.47-3.62 (m, 1H), 3.11-3.30 (m, 2H), 2.99-3.11 (m, 2H), 1.75-1.90 (m, 2H), 1.44 (s, 18H); MS obsd. (ESI$^+$) [(M+H)$^+$]: 555.

Example 59: 6-[2,3-difluoro-5-(5-methyl-2-pyrimidin-2-yl-7,8-dihydro-5H-pyrido[4,3-d]pyrimidin-6-yl)phenoxy]hexan-1-amine A mixture of the crude tert-butyl N-[6-[2,3-difluoro-5-(5-methyl-2-pyrimidin-2-yl-7,8-dihydro-5H-pyrido[4,3-d]pyrimidin-6-yl)phenoxy]hexyl]carbamate (140 mg) and $CF_3COOH$ (10 mL) in DCM (10 mL) was stirred at rt for 1 hr. Then the mixture was concentrated in vacuo. The residue was diluted with saturated aqueous solution of $NaHCO_3$ and extracted with DCM (20 mL) for three times. The combined organic layer was dried over anhydrous $Na_2SO_4$ and concentrated in vacuo. The residue was purified by prep-HPLC to give 6-[2,3-difluoro-5-(5-methyl-2-pyrimidin-2-yl-7,8-dihydro-5H-pyrido[4,3-d]pyrimidin-6-yl)phenoxy]hexan-1-amine (15 mg) as yellow solid. $^1$H NMR (400 MHz, Methanol-$d_4$) δ: 9.05 (d, 2H), 8.87 (s, 1H), 7.61-7.74 (m, 1H), 6.49-6.63 (m, 2H), 5.15-5.27 (m, 1H), 4.05-4.18 (m, 2H), 3.76-3.92 (m, 1H), 3.48-3.64 (m, 1H), 3.10-3.24 (m, 2H), 2.69 (m, 2H), 1.78-1.90 (m, 2H), 1.36-1.62 (m, 9H). MS obsd. (ESI$^+$) [(M+H)$^+$]: 455.

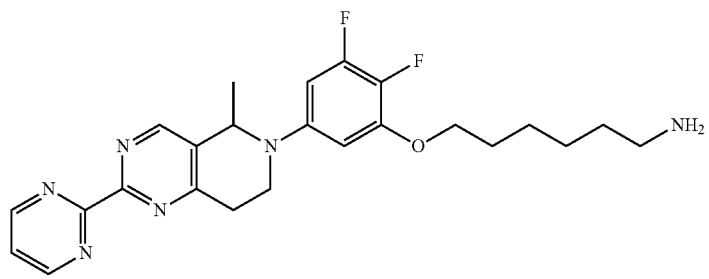 [SMILES: CC1c2cnc(-c3ncccn3)nc2CCN1c1cc(F)c(F)c(OCCCCCCN)c1]

Example 60 and 61: (−)-6-[2,3-difluoro-5-[5-methyl-2-pyrimidin-2-yl-7,8-dihydro-5H-pyrido[4,3-d]pyrimidin-6-yl]phenoxy]hexan-1-amine and (+)-6-[2,3-difluoro-5-[5-methyl-2-pyrimidin-2-yl-7,8-dihydro-5H-pyrido[4,3-d]pyrimidin-6-yl]phenoxy]hexan-1-amine

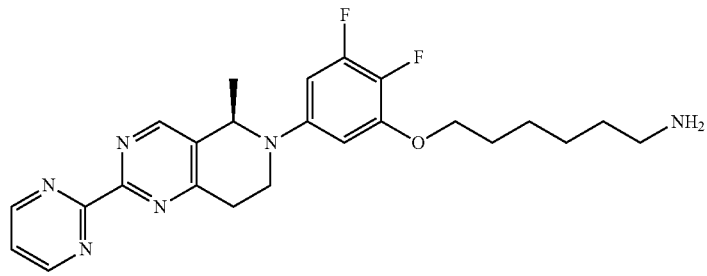

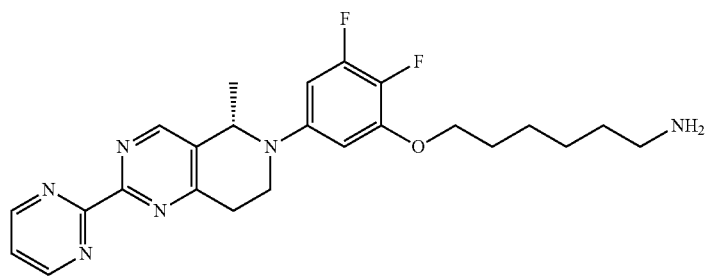

Separation of 6-[2,3-difluoro-5-(5-methyl-2-pyrimidin-2-yl-7,8-dihydro-5H-pyrido[4,3-d]pyrimidin-6-yl)phenoxy]hexan-1-amine (100 mg, Example 59) by chiral HPLC gave (−)-6-[2,3-difluoro-5-[5-methyl-2-pyrimidin-2-yl-7,8-dihydro-5H-pyrido[4,3-d]pyrimidin-6-yl]phenoxy]hexan-1-amine (42 mg) and (+)-6-[2,3-difluoro-5-(5-methyl-2-pyrimidin-2-yl-7,8-dihydro-5H-pyrido[4,3-d]pyrimidin-6-yl)phenoxy]hexan-1-amine (40 mg) both as yellow solid.

Example 60: (−)-6-[2,3-difluoro-5-(5-methyl-2-pyrimidin-2-yl-7,8-dihydro-5H-pyrido[4,3-d]pyrimidin-6-yl)phenoxy]hexan-1-amine, $^1$H NMR (400 MHz, CDCl$_3$) δ: 9.05 (d, 2H), 8.81 (s, 1H), 7.46 (s, 1H), 6.28-6.43 (m, 2H), 4.92-5.05 (m, 1H), 4.04 (m, 2H), 3.71 (d, 1H), 3.44-3.57 (m, 1H), 3.18-3.39 (m, 2H), 2.90 (m, 2H), 1.77-1.90 (m, 2H), 1.71 (br. s., 2H), 1.40-1.60 (m, 7H); MS obsd. (ESI$^+$) [(M+H)$^+$]: 455. [a]$_D^{20}$=−58.00° (0.05 g/100 mL, methanol).

Example 61: (+)-6-[2,3-difluoro-5-[(5 S)-5-methyl-2-pyrimidin-2-yl-7,8-dihydro-5H-pyrido[4,3-d]pyrimidin-6-yl]phenoxy]hexan-1-amine, $^1$H NMR (400 MHz, CDCl$_3$) δ: 9.04 (d, 2H), 8.81 (s, 1H), 7.46 (m, 1H), 6.30-6.45 (m, 2H), 5.00 (m, 1H), 4.02 (m, 2H), 3.73 (m, 1H), 3.44-3.60 (m, 1H), 3.20-3.38 (m, 2H), 2.84-3.01 (m, 2H), 1.63-1.89 (m, 4H), 1.45 (d, 7H); MS obsd. (ESI$^+$) [(M+H)$^+$]: 455. [a]$_D^{20}$=+62.00° (0.05%, methanol).

Example 62: methyl 5-[2,3-difluoro-5-(5-methyl-2-pyrimidin-2-yl-7,8-dihydro-5H-pyrido[4,3-d]pyrimidin-6-yl)phenoxy]pentanoate

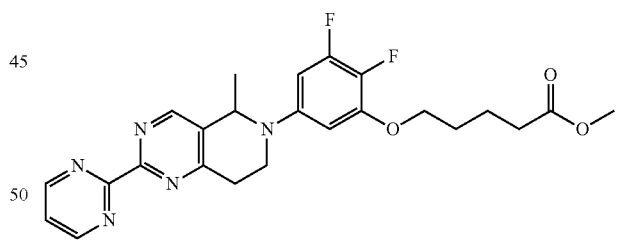

A mixture of 2,3-difluoro-5-(5-methyl-2-pyrimidin-2-yl-7,8-dihydro-5H-pyrido[4,3-d]pyrimidin-6-yl)phenol (200 mg, 0.563 mmol), methyl 5-bromopentanoate (220 mg, 1.127 mmol), KI (94 mg, 0.563 mmol) and K$_2$CO$_3$ (155 mg, 1.127 mmol) in DMF (10 mL) was heated at 100° C. with stirring overnight. After being cooled to rt, the reaction mixture was diluted with H$_2$O (10 mL) and exacted with DCM (30 mL) for three times. The combined organic layer was dried over anhydrous Na$_2$SO$_4$ and concentrated in vacuo to give the crude product (200 mg). The crude product (50 mg) was purified by prep-HPLC to give methyl 5-[2,3-difluoro-5-(5-methyl-2-pyrimidin-2-yl-7,8-dihydro-5H- pyrido[4,3-d]pyrimidin-6-yl)phenoxy]pentanoate (3 mg) as yellow solid. ¹H NMR (400 MHz, Methanol-d₄) δ: 9.05 (d, 2H), 8.88 (s, 1H), 7.67 (m, 1H), 6.48-6.66 (m, 2H), 5.23 (m, 1H), 4.63 (s, 2H), 4.13 (m, 2H), 3.80-3.95 (m, 1H), 3.49-3.60 (m, 2H), 3.14-3.24 (m, 2H), 2.46 (m, 2H), 1.73-1.90 (m, 4H), 1.48 (d, 3H); MS obsd. (ESI⁺) [(M+H)⁺]: 470.

Example 63: 5-[2,3-difluoro-5-(5-methyl-2-pyrimidin-2-yl-7,8-dihydro-5H-pyrido[4,3-d]pyrimidin-6-yl)phenoxy]pentanoic acid

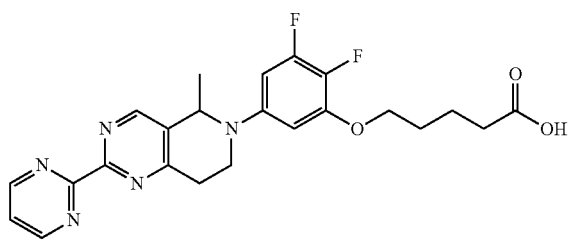 [SMILES: CC1c2cnc(-c3ncccn3)nc2CCN1c1cc(F)c(F)c(OCCCCC(=O)O)c1]

A mixture of methyl 5-[2,3-difluoro-5-(5-methyl-2-pyrimidin-2-yl-7,8-dihydro-5H-pyrido[4,3-d]pyrimidin-6-yl)phenoxy]pentanoate (150 mg, 0.432 mmol) and LiOH monohydrate (67 mg, 1.6 mmol) in THF (3 mL), methanol (5 mL) and H₂O (1 mL) was stirred at rt for 3 hrs. Then the mixture was acidified with 2 N HCl and extracted with DCM (20 mL) for three times. The combined organic layer was washed with brine, dried over anhydrous Na₂SO₄ and concentrated in vacuo. The residue was purified by prep-HPLC to give methyl 5-[2,3-difluoro-5-(5-methyl-2-pyrimidin-2-yl-7,8-dihydro-5H-pyrido[4,3-d]pyrimidin-6-yl)phenoxy]pentanoic acid (17 mg) as yellow solid. ¹H NMR (400 MHz, Methanol-d₄) δ: 9.05 (d, 2H), 8.87 (s, 1H), 7.66 (s, 1H), 6.47-6.65 (m, 2H), 5.16-5.28 (m, 1H), 4.13 (s, 2H), 3.78-3.93 (m, 1H), 3.48-3.65 (m, 1H), 3.08-3.28 (m, 2H), 2.41 (m, 2H), 1.73-1.95 (m, 4H), 1.47 (d, 3H); MS obsd. (ESI⁺) [(M+H)⁺]: 456.

Example 64: 5-[2,3-difluoro-5-(5-methyl-2-pyrimidin-2-yl-7,8-dihydro-5H-pyrido[4,3-d]pyrimidin-6-yl)phenoxy]pentanamide

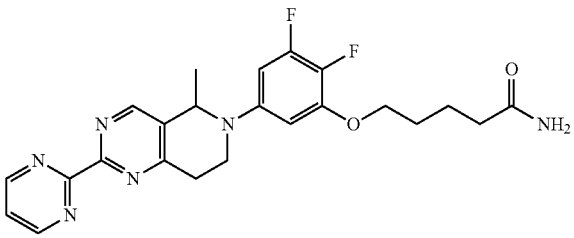 [SMILES: CC1c2cnc(-c3ncccn3)nc2CCN1c1cc(F)c(F)c(OCCCCC(N)=O)c1]

A mixture of methyl 5-[2,3-difluoro-5-(5-methyl-2-pyrimidin-2-yl-7,8-dihydro-5H-pyrido[4,3-d]pyrimidin-6-yl)phenoxy]pentanoic acid (70 mg, 0.154 mmol) and CDI (37 mg, 0.23 mmol) in DMF (5 mL) was stirred for at rt 2 hrs. Then to the reaction mixture was added NH₃ (7 mL, 14 mmol, 2.0 mol/L in isopropyl alcohol). After being stirred overnight, the resulting mixture was concentrated in vacuo. The residue was diluted with DCM (20 mL) and washed with water, dried over anhydrous Na₂SO₄ and concentrated in vacuo. The residue was purified by prep-HPLC to give 5-[2,3-difluoro-5-(5-methyl-2-pyrimidin-2-yl-7,8-dihydro-5H-pyrido[4,3-d]pyrimidin-6-yl)phenoxy]pentanamide (11 mg) as yellow solid. ¹H NMR (400 MHz, Methanol-d₄) δ: 9.05 (d, 2H), 8.88 (s, 1H), 7.67 (s, 1H), 6.48-6.64 (m, 2H), 5.22 (d, 1H), 4.13 (m, 2H), 3.80-3.94 (m, 1H), 3.49-3.62 (m, 1H), 3.10-3.25 (m, 2H), 2.26-2.38 (m, 2H), 1.78-1.90 (m, 4H), 1.42-1.53 (m, 3H); (ESI⁺) [(M+H)⁺]: 455.

Example 65: 2-[2,3-difluoro-5-(5-methyl-2-pyrimidin-2-yl-7,8-dihydro-5H-pyrido[4,3-d]pyrimidin-6-yl)phenoxy]acetic acid

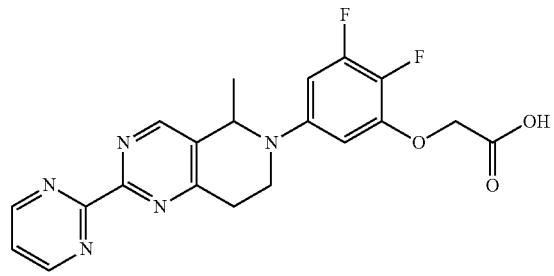 [SMILES: CC1c2cnc(-c3ncccn3)nc2CCN1c1cc(F)c(F)c(OCC(=O)O)c1]

Step 1: Preparation of methyl 2-[2,3-difluoro-5-(5-methyl-2-pyrimidin-2-yl-7,8-dihydro-5H-pyrido[4,3-d]pyrimidin-6-yl)phenoxy]acetate

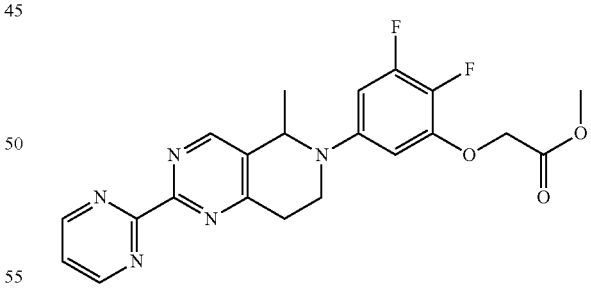

A mixture of 2,3-difluoro-5-(5-methyl-2-pyrimidin-2-yl-7,8-dihydro-5H-pyrido[4,3-d]pyrimidin-6-yl)phenol (350 mg, 0.986 mmol), methyl 2-bromoacetate (226 mg, 1.48 mmol) and K₂CO₃ (408 mg, 2.96 mmol) in DMF (10 mL) was stirred at rt overnight. The reaction mixture was diluted with H₂O (10 mL) and exacted with EA (30 mL) for three times. The combined organic layer was dried over anhydrous Na₂SO₄ and concentrated in vacuo to give the crude product (350 mg), which was used in the next step directly without further purification.

Step 2: Preparation of 2-[2,3-difluoro-5-(5-methyl-2-pyrimidin-2-yl-7,8-dihydro-5H-pyrido[4,3-d]pyrimidin-6-yl)phenoxy]acetic acid

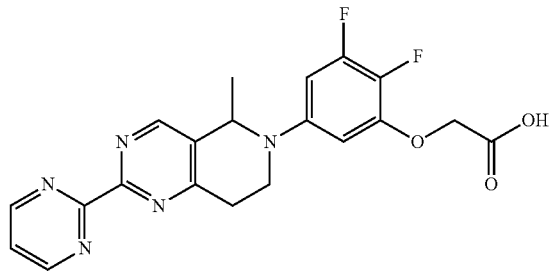 [SMILES: CC1c2cnc(-c3ncccn3)nc2CCN1c1cc(F)c(F)c(OCC(=O)O)c1]

A mixture of 2-[2,3-difluoro-5-(5-methyl-2-pyrimidin-2-yl-7,8-dihydro-5H-pyrido[4,3-d]pyrimidin-6-yl)phenoxy] acetic acid (350 mg, 0.82 mmol) and LiOH monohydrate (172 mg, 4.1 mmol) in THF (3 mL), MeOH (5 mL) and H$_2$O (1 mL) was stirred at rt overnight. Then the mixture was acidified with 1N HCl and extracted with DCM (20 mL) for three times. The combined organic layer was washed with brine (10 mL), dried over anhydrous Na$_2$SO$_4$ and concentrated in vacuo. The residue was purified by prep-HPLC to give 2-[2,3-difluoro-5-(5-methyl-2-pyrimidin-2-yl-7,8-dihydro-5H-pyrido[4,3-d]pyrimidin-6-yl)phenoxy]acetic acid (9 mg) as yellow solid. $^1$H NMR (400 MHz, Methanol-d$_4$) δ: 8.98-9.14 (m, 2H), 8.81-8.92 (m, 1H), 7.67 (m, 1H), 6.48-6.68 (m, 2H), 5.20 (m, 1H), 4.82 (s, 2H), 3.76-3.92 (m, 1H), 3.49-3.61 (m, 1H), 3.10-3.27 (m, 2H), 1.41-1.59 (m, 3H); MS obsd. (ESI$^+$) [(M+H)$^+$]: 414.

Example 66: 2-[2,3-difluoro-5-(5-methyl-2-pyrimidin-2-yl-7,8-dihydro-5H-pyrido[4,3-d]pyrimidin-6-yl)phenoxy]acetamide

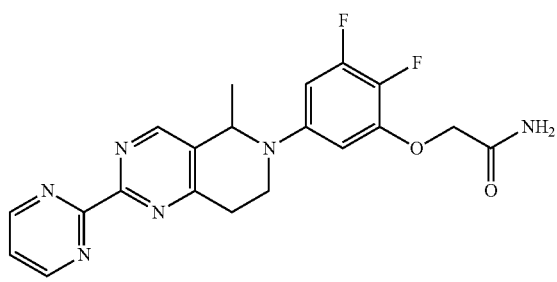

A mixture of 2-[2,3-difluoro-5-(5-methyl-2-pyrimidin-2-yl-7,8-dihydro-5H-pyrido[4,3-d]pyrimidin-6-yl)phenoxy] acetic acid (260 mg, 0.63 mmol) and CDI (153 mg, 0.94 mmol) in DMF (5 mL) was stirred for at rt 4 hrs. Then to the reaction mixture was added NH$_3$ (7 mL, 14 mmol, 2.0 mol/L in isopropyl alcohol). After being stirred overnight, the resulting mixture was concentrated in vacuo. The residue was diluted with DCM (20 mL), washed with water, dried over anhydrous Na$_2$SO$_4$ and concentrated in vacuo. The residue was purified by prep-HPLC to give 2-[2,3-difluoro-5-(5-methyl-2-pyrimidin-2-yl-7,8-dihydro-5H-pyrido[4,3-d]pyrimidin-6-yl)phenoxy]acetamide (12 mg) as yellow solid. $^1$H NMR (400 MHz, Methanol-d$_4$) δ: 9.01-9.10 (m, 2H), 8.87 (s, 1H), 7.66 (m, 1H), 6.56-6.73 (m, 2H), 5.16-5.28 (m, 1H), 4.60-4.69 (m, 2H), 3.88 (m, 1H), 3.48-3.64 (m, 1H), 3.11-3.30 (m, 2H), 1.41-1.59 (m, 3H); MS obsd. (ESI$^+$) [(M+H)$^+$]: 413.

Example 67 and 68: (+)-2-[2,3-difluoro-5-[5-methyl-2-pyrimidin-2-yl-7,8-dihydro-5H-pyrido[4,3-d]pyrimidin-6-yl]phenoxy]acetamide and (−)-2-[2,3-difluoro-5-[5-methyl-2-pyrimidin-2-yl-7,8-dihydro-5H-pyrido[4,3-d]pyrimidin-6-yl]phenoxy]acetamide

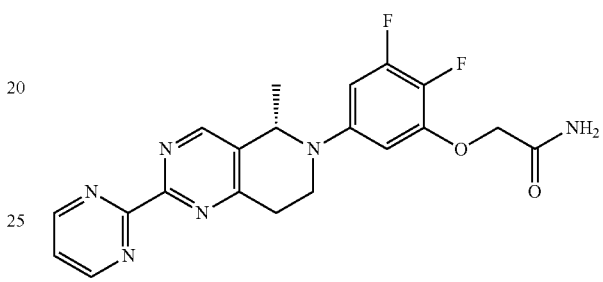

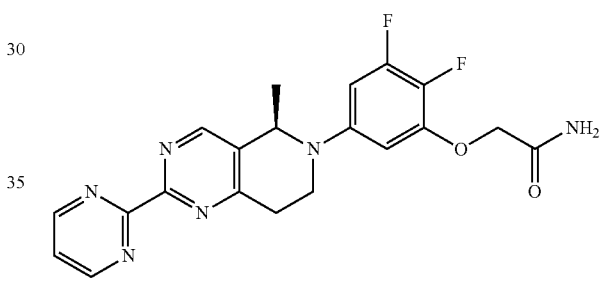

Separation of 2-[2,3-difluoro-5-(5-methyl-2-pyrimidin-2-yl-7,8-dihydro-5H-pyrido[4,3-d]pyrimidin-6-yl)phenoxy] acetamide (80 mg, Example 66) by chiral HPLC gave (+)-2-[2,3-difluoro-5-[5-methyl-2-pyrimidin-2-yl-7,8-dihydro-5H-pyrido[4,3-d]pyrimidin-6-yl]phenoxy]acetamide (10 mg) and (−)-2-[2,3-difluoro-5-[5-methyl-2-pyrimidin-2-yl-7,8-dihydro-5H-pyrido[4,3-d]pyrimidin-6-yl]phenoxy] acetamide (20 mg) both as yellow solid.

Example 67: (+)-2-[2,3-difluoro-5-[5-methyl-2-pyrimidin-2-yl-7,8-dihydro-5H-pyrido[4,3-d]pyrimidin-6-yl]phenoxy]acetamide: $^1$H NMR (400 MHz, Methanol-d$_4$) δ: 8.99-9.10 (m, 2H), 8.86 (s, 1H), 7.66 (m, 1H), 6.52-6.69 (m, 2H), 5.10-5.27 (m, 1H), 4.57-4.69 (m, 2H), 3.79-3.93 (m, 1H), 3.45-3.65 (m, 1H), 3.06-3.28 (m, 2H), 1.40-1.54 (m, 3H); MS obsd. (ESI$^+$) [(M+H)$^+$]: 413. [a]$_D^{20}$=+64.00° (0.05 g/100 mL, methanol)

Example 68: (−)-2-[2,3-difluoro-5-[5-methyl-2-pyrimidin-2-yl-7,8-dihydro-5H-pyrido[4,3-d]pyrimidin-6-yl]phenoxy]acetamide: $^1$H NMR (400 MHz, Methanol-d$_4$) δ: 9.04 (d, 2H), 8.85 (s, 1H), 7.65 (m, 1H), 6.60 (s, 2H), 5.20 (d, 1H), 4.64 (s, 2H), 3.77-3.92 (m, 1H), 3.46-3.63 (m, 1H), 3.05-3.28 (m, 2H), 1.48 (d, 3H); MS obsd. (ESI$^+$) [(M+H)$^+$]: 413.

Example 69: 6-[3,4-difluoro-5-(2,2,2-trifluoroethoxy)phenyl]-5-methyl-2-pyrimidin-2-yl-7,8-dihydro-5H-pyrido[4,3-d]pyrimidine

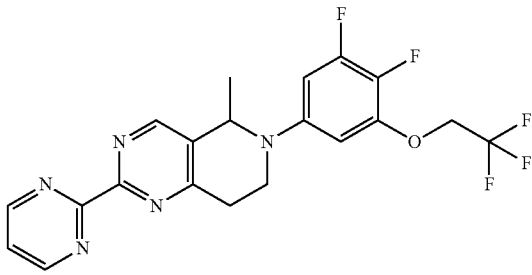 [SMILES: CC1c2cnc(-c3ncccn3)nc2CCN1c1cc(F)c(F)c(OCC(F)(F)F)c1]

A mixture of 2,3-difluoro-5-(5-methyl-2-pyrimidin-2-yl-7,8-dihydro-5H-pyrido[4,3-d]pyrimidin-6-yl)phenol (100 mg, 0.282 mmol), 1,1,1-trifluoro-2-iodo-ethane (118 mg, 0.56 mmol) and $Cs_2CO_3$ (275 mg, 0.845 mmol) in DMF (10 mL) was heated at 100° C. with stirring overnight. After being cooled to rt, the reaction mixture was diluted with $H_2O$ (10 mL) and extracted with DCM (30 mL) for three times. The combined organic layer was dried over anhydrous $Na_2SO_4$ and concentrated in vacuo. The residue was purified by prep-HPLC to give 6-[3,4-difluoro-5-(2,2,2-trifluoroethoxy)phenyl]-5-methyl-2-pyrimidin-2-yl-7,8-dihydro-5H-pyrido[4,3-d]pyrimidine (10 mg) as white solid. $^1H$ NMR (400 MHz, Methanol-$d_4$) δ: 9.05 (d, 2H), 8.87 (s, 1H), 7.67 (m, 1H), 6.60-6.78 (m, 2H), 5.26 (d, 1H), 4.59-4.78 (m, 2H), 3.85-3.97 (m, 1H), 3.47-3.64 (m, 1H), 3.09-3.29 (m, 2H), 1.39-1.54 (m, 3H); MS obsd. (ESI$^+$) [(M+H)$^+$]: 438.

Example 70: 6-[3-(2,2-difluoroethoxy)-4,5-difluorophenyl]-5-methyl-2-pyrimidin-2-yl-7,8-dihydro-5H-pyrido[4,3-d]pyrimidine

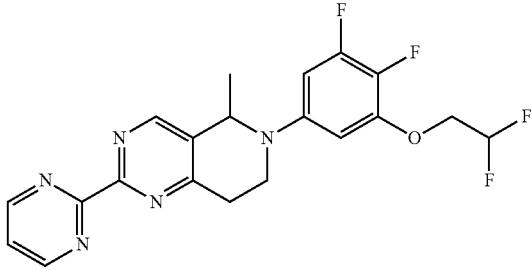 [SMILES: CC1c2cnc(-c3ncccn3)nc2CCN1c1cc(F)c(F)c(OCC(F)F)c1]

To a solution of 2,3-difluoro-5-(5-methyl-2-pyrimidin-2-yl-7,8-dihydro-5H-pyrido[4,3-d]pyrimidin-6-yl)phenol (49 mg, 138 μmol) in DMF (4 mL) was added $K_2CO_3$ (38 mg, 276 mol) and 2-bromo-1,1-difluoroethane (40 mg, 276 μmol). After being stirred at room temperature overnight, the reaction mixture was purified by prep-HPLC to give 6-(3-(2,2-difluoroethoxy)-4, 5-difluorophenyl)-5-methyl-2-(pyrimidin-2-yl)-5,6,7,8-tetrahydropyrido[4,3-d]pyrimidine (22 mg) as light yellow solid. $^1H$ NMR (400 MHz, DMSO-$d_6$) δ: 1.42 (d, 3H), 2.93-3.19 (m, 2H), 3.39-3.54 (m, 1H), 3.89-4.02 (m, 1H), 4.40-4.56 (m, 2H), 5.26-5.40 (m, 1H), 6.27-6.62 (m, 1H), 6.65-6.77 (m, 2H), 7.65 (t, 1H), 8.83 (s, 1H), 9.00 (d, 2H). MS obsd. (ESI$^+$) [(M+H)$^+$]: 420.

Example 71: 6-[3-(difluoromethoxy)-4,5-difluorophenyl]-5-methyl-2-pyrimidin-2-yl-7,8-dihydro-5H-pyrido[4,3-d]pyrimidine

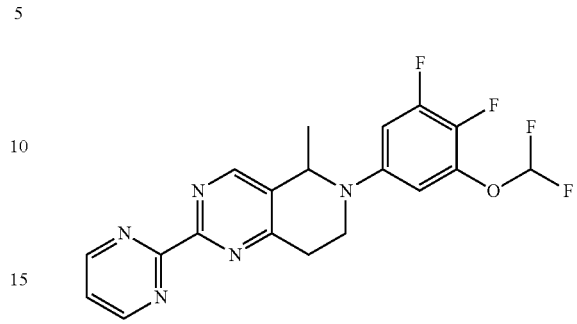

To a solution of 2,3-difluoro-5-(5-methyl-2-pyrimidin-2-yl-7,8-dihydro-5H-pyrido[4,3-d]pyrimidin-6-yl)phenol (38 mg, 107 μmol) in DMF (2 mL) was added potassium carbonate (15 mg, 107 μmol) and sodium 2-chloro-2,2-difluoroacetate (32 mg, 214 μmol). The resulting mixture was heated at 100° C. with stirring for 3 hrs. After the reaction was complete, the reaction mixture was purified by prep-HPLC to give 6-[3-(difluoromethoxy)-4,5-difluorophenyl]-5-methyl-2-pyrimidin-2-yl-7,8-dihydro-5H-pyrido[4,3-d]pyrimidine (25 mg) as light yellow solid. $^1H$ NMR (400 MHz, Methanol-$d_4$) δ: 1.26 (s, 1H), 1.52 (d, 3H), 2.64 (dt, 1H), 3.46-3.66 (m, 1H), 3.93 (dd, 1H), 5.26 (q, 1H), 6.74-6.80 (m, 1H), 6.90-6.97 (m, 1H), 7.67 (t, 1H), 8.89 (s, 1H), 9.06 (d, 2H). MS obsd. (ESI$^+$) [(M+H)$^+$]: 420.

Example 72: 6-(3-fluoro-5-methoxy-phenyl)-5-methyl-2-pyrimidin-2-yl-7,8-dihydro-5H-pyrido[4,3-d]pyrimidine

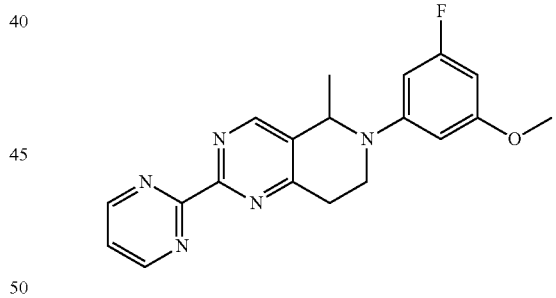

Step 1: Preparation of 8-(3-fluoro-5-methoxy-phenyl)-1,4-dioxa-8-azaspiro[4.5]decane

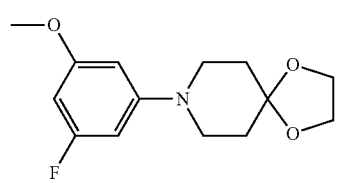 [SMILES: COc1cc(F)cc(N2CCC3(CC2)OCCO3)c1]

A mixture of 3-bromo-5-fluoroanisole (87.6 g, 0.49 mol), 1,4-dioxa-8-azaspiro[4.5]decane hydrochloride (100.0 g, 0.49 mol), t-BuONa (117.2 g, 1.22 mol), BINAP (12.1 g, 0.02 mol) and Pd$_2$(dba)$_3$ (8.9 g, 0.01 mol) in toluene (1.3 L) was heated at 100° C. with stirring under nitrogen for 16 hrs. The reaction mixture was cooled down to rt and filtered. The filtrate was diluted with DCM (3.0 L), and washed with H$_2$O (500 mL) and brine (200 mL). The organic layer was dried over anhydrous Na$_2$SO$_4$, concentrated in vacuo and purified by the flash column chromatography to give 8-(3-fluoro-5-methoxy-phenyl)-1,4-dioxa-8-azaspiro[4.5]decane (78.2 g) as a yellow oil.

Step 2: Preparation of 1-(3-fluoro-5-methoxy-phenyl)piperidin-4-one

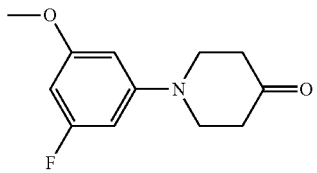

A mixture of 8-(3-fluoro-5-methoxy-phenyl)-1,4-dioxa-8-azaspiro[4.5]decane (78.2 g, 0.29 mol), formic acid (400 mL) and H$_2$O (400 mL) was heated at 90° C. with stirring for 3 hrs. The resulting mixture was concentrated in vacuo. The residue was diluted with DCM (1.0 L) and washed with a saturated aqueous solution of Na$_2$CO$_3$ (200 mL) and brine (200 mL). The organic phase was dried over anhydrous Na$_2$SO$_4$, and concentrated in vacuo. The residue was purified by the flash column chromatography to give 1-(3-fluoro-5-methoxy-phenyl)piperidin-4-one (42.0 g) as a yellow solid.

Step 3: Preparation of 6-(3-fluoro-5-methoxy-phenyl)-2-pyrimidin-2-yl-7,8-dihydro-5H-pyrido[4,3-d]pyrimidine

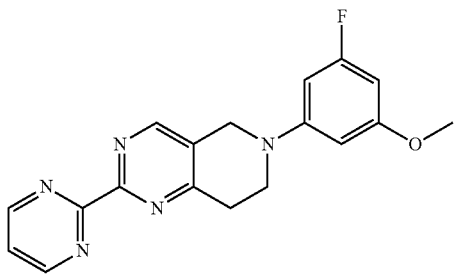

A mixture of 1-(3-fluoro-5-methoxy-phenyl)piperidin-4-one (42.0 g. 0.15 mol) and DMFDMA (400 mL) was heated at 120° C. with stirring for 4 hrs. The resulting mixture was concentrated in vacuo and the residue was dissolved in MeOH (700 mL). To the solution was added pyrimidine-2-carboximidamide hydrochloride (26.2 g, 0.17 mol) and K$_2$CO$_3$ (50.3 g, 0.36 mol). After being heated at 60° C. with stirring for 2 hrs, the reaction mixture was cooled down to rt and filtered. The filtrate was concentrated in vacuo. The residue was diluted with DCM (1.0 L), then washed H$_2$O (200 mL) and brine (200 mL), dried over anhydrous Na$_2$SO$_4$ and concentrated in vacuo. The residue was purified by the flash column chromatography to give 6-(3-fluoro-5-methoxy-phenyl)-2-pyrimidin-2-yl-7,8-dihydro-5H-pyrido[4,3-d]pyrimidine (30.8 g) as a light yellow solid.

Step 4: Preparation of 6-(3-fluoro-5-methoxy-phenyl)-5-methoxy-2-pyrimidin-2-yl-7,8-dihydro-5H-pyrido[4,3-d]pyrimidine

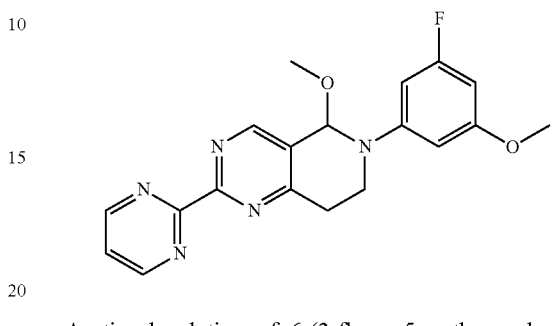

A stirred solution of 6-(3-fluoro-5-methoxy-phenyl)-2-pyrimidin-2-yl-7,8-dihydro-5H-pyrido[4,3-d]pyrimidine (3.0 g, 8.89 mmol) in DCM (300 mL) and MeOH (50 mL) was cooled to −70° C. To the cooled solution was added RuCl$_3$ hydrate (2.67 mmol) followed by a solution of NaIO$_4$ (5.7 g, 26.6 mmol) in H$_2$O (50 mL) slowly. After being stirred at −70° C. for 15 mins, the reaction mixture was warmed to 15° C. and stirred at 15° C. for 16 hrs, then diluted with saturated aqueous solution of Na$_2$SO$_3$ (50 mL) and filtered. The filtrate was extracted with EA (100 mL) for three times. The combined organic layer was dried over anhydrous Na$_2$SO$_4$ and concentrated in vacuo to give 6-(3-fluoro-5-methoxy-phenyl)-5-methoxy-2-pyrimidin-2-yl-7,8-dihydro-5H-pyrido[4,3-d]pyrimidine (1.5 g) as crude product, which was used in the next step directly without further purification.

Step 5: Preparation of 6-(3-fluoro-5-methoxy-phenyl)-5-methyl-2-pyrimidin-2-yl-7,8-dihydro-5H-pyrido[4,3-d]pyrimidine

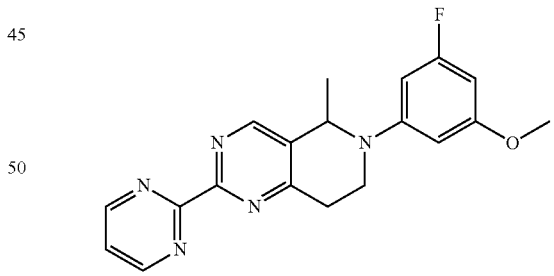

A stirred solution of 6-(3-fluoro-5-methoxy-phenyl)-5-methoxy-2-pyrimidin-2-yl-7,8-dihydro-5H-pyrido[4,3-d]pyrimidine (1.5 g, 4.08 mmol) in THF (75 mL) was cooled to −70° C. and then to the solution was added BF$_3$.Et$_2$O (1.41 g, 12.25 mmol) slowly. After the mixture was stirred at −70° C. for 10 mins, to the resulting mixture was added a solution of MeMgBr (6.8 mL, 20.41 mmol) in THF dropwise. After being stirred for 1 hr at −70° C., the resulting reaction mixture was diluted with a saturated aqueous solution of NH$_4$Cl (20 mL) and extracted with EA (30 mL) for three times. The combined organic layer was washed with brine (50 mL), dried over anhydrous Na$_2$SO$_4$ and concentrated in vacuo. The residue was purified by pre-HPLC to give 6-(3-fluoro-5-methoxy-phenyl)-5-methyl-2-pyrimidin-2-yl-7,8-dihydro-5H-pyrido[4,3-d]pyrimidine (70 mg) as a light yellow solid. ¹H NMR (400 MHz, Methanol-d₄) δ: 9.03 (d, 2H), 8.86 (s, 1H), 7.64 (t, 1H), 6.34-6.46 (m, 2H), 6.14 (dt, 1H), 5.25 (q, 1H), 3.89-3.98 (m, 1H), 3.78 (s, 3H), 3.54 (m, 1H), 3.07-3.27 (m, 2H), 1.50 (d, 3H). MS obsd. (ESI⁺) [(M+H)⁺]: 352.

Example 73 and 74: (−)-6-(3-fluoro-5-methoxy-phenyl)-5-methyl-2-pyrimidin-2-yl-7,8-dihydro-5H-pyrido[4,3-d]pyrimidine and (+)-6-(3-fluoro-5-methoxy-phenyl)-5-methyl-2-pyrimidin-2-yl-7,8-dihydro-5H-pyrido[4,3-d]pyrimidine

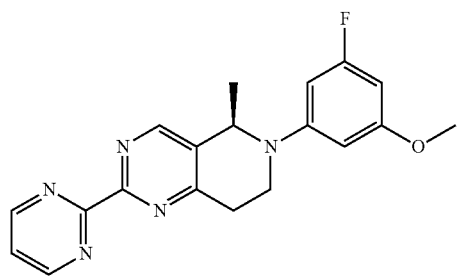

Separation of 6-(3-fluoro-5-methoxy-phenyl)-5-methyl-2-pyrimidin-2-yl-7,8-dihydro-5H-pyrido[4,3-d]pyrimidine (200 mg) by chiral HPLC gave (−)-6-(3-fluoro-5-methoxy-phenyl)-5-methyl-2-pyrimidin-2-yl-7,8-dihydro-5H-pyrido[4,3-d]pyrimidine (90 mg) and (+)-6-(3-fluoro-5-methoxy-phenyl)-5-methyl-2-pyrimidin-2-yl-7,8-dihydro-5H-pyrido[4,3-d]pyrimidine (90 mg) both as yellow solid.

Example 73: (−)-6-(3-fluoro-5-methoxy-phenyl)-5-methyl-2-pyrimidin-2-yl-7,8-dihydro-5H-pyrido[4,3-d]pyrimidine: ¹H NMR (400 MHz, Methanol-d₄) δ: 9.03 (d, 2H), 8.86 (s, 1H), 7.64 (t, 1H), 6.34-6.48 (m, 2H), 6.14 (dt, 1H), 5.25 (q, 1H), 3.89-4.00 (m, 1H), 3.78 (s, 3H), 3.49-3.61 (m, 1H), 3.08-3.27 (m, 2H), 1.45-1.54 (m, 3H). MS obsd. (ESI⁺) [(M+H)⁺]: 352. [α]$_D^{20}$=−72.448° (0.091 g/100 mL, methanol).

Example 74: (+)-6-(3-fluoro-5-methoxy-phenyl)-5-methyl-2-pyrimidin-2-yl-7,8-dihydro-5H-pyrido[4,3-d]pyrimidine: ¹H NMR (400 MHz, Methanol-d₄) δ: 9.03 (d, 2H), 8.86 (s, 1H), 7.64 (t, 1H), 6.34-6.47 (m, 2H), 6.14 (dt, 1H), 5.25 (q, 1H), 3.88-3.98 (m, 1H), 3.78 (s, 3H), 3.48-3.61 (m, 1H), 3.07-3.27 (m, 2H), 1.45-1.53 (m, 3H). MS obsd. (ESI⁺) [(M+H)⁺]: 352

Example 75: 6-[3,4-difluoro-5-(tetrahydrofuran-3-ylmethoxy)phenyl]-5-methyl-2-pyrimidin-2-yl-7,8-dihydro-5H-pyrido[4,3-d]pyrimidine

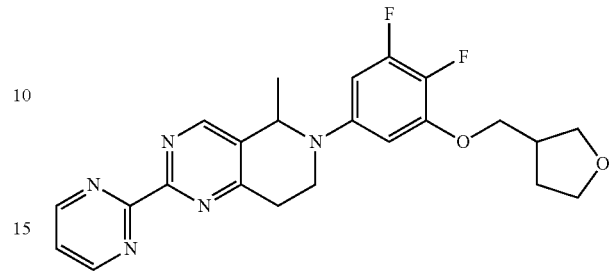

Step 1: Preparation of tetrahydrofuran-3-ylmethyl 4-methylbenzenesulfonate

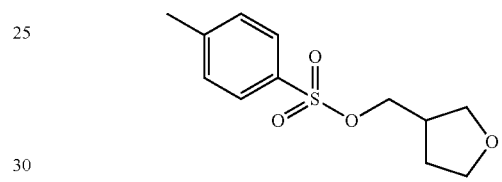

To a stirred solution of tetrahydro-3-furanmethanol (500 mg, 4.90 mmol) in DCM (5 mL) was added Et₃N (892 mg, 8.81 mmol) and DMAP (60 mg, 0.49 mmol). Then to the mixture was added a solution of 4-methylbenzenesulfonyl chloride (1.4 g, 7.34 mmol) in DCM (5 mL) dropwise. After being stirred at 15° C. for 16 hrs, the resulting mixture was diluted with DCM (50 mL), washed with H₂O (20 mL), 2 N HCl (20 mL) and brine (10 mL), then dried over anhydrous Na₂SO₄ and concentrated in vacuo to give tetrahydrofuran-3-ylmethyl 4-methylbenzenesulfonate (1.1 g) as a colorless oil, which was used in the next step directly without further purification.

Step 2: Preparation of 6-[3,4-difluoro-5-(tetrahydrofuran-3-ylmethoxy)phenyl]-5-methyl-2-pyrimidin-2-yl-7,8-dihydro-5H-pyrido[4,3-d]pyrimidine

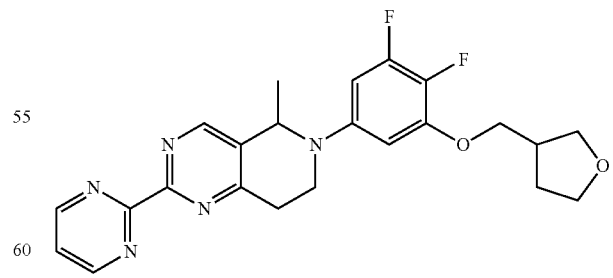

A mixture of 2,3-difluoro-5-(5-methyl-2-pyrimidin-2-yl-7,8-dihydro-5H-pyrido[4,3-d]pyrimidin-6-yl)phenol (100 mg, 0.28 mmol), tetrahydrofuran-3-ylmethyl 4-methylbenzenesulfonate (87 mg, 0.34 mmol) and Cs₂CO₃ (138 mg, 0.42 mmol) in DMF (3 mL) was heated at 80° C. with stirring for 12 hrs. After being cooled down to rt, the reaction mixture was diluted with EA (20 mL), washed with brine (10 mL), then dried over anhydrous Na$_2$SO$_4$ and concentrated in vacuo. The residue was purified by pre-HPLC to give 6-[3,4-difluoro-5-(tetrahydrofuran-3-ylmethoxy)phenyl]-5-methyl-2-pyrimidin-2-yl-7,8-dihydro-5H-pyrido[4,3-d]pyrimidine (15 mg) as a white solid. $^1$H NMR (400 MHz, CDCl$_3$) δ: 9.04 (d, 2H), 8.79 (s, 1H), 7.45 (s, 1H), 6.28-6.49 (m, 2H), 4.88-5.05 (m, 1H), 3.65-4.09 (m, 8H), 3.40-3.58 (m, 1H), 3.20-3.37 (m, 2H), 2.71-2.86 (m, 1H), 2.14 (s, 1H), 1.32-1.54 (m, 3H). MS obsd. (ESI$^+$) [(M+H)$^+$]: 440.

Example 76: 6-[3,4-difluoro-5-(oxetan-3-ylmethoxy)phenyl]-5-methyl-2-pyrimidin-2-yl-7,8-dihydro-5H-pyrido[4,3-d]pyrimidine

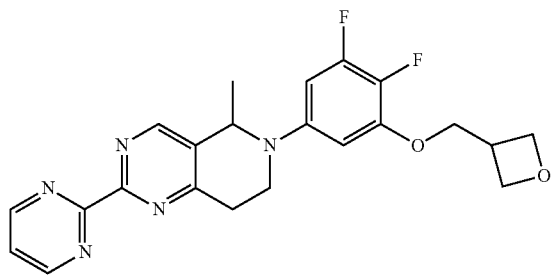 [SMILES: CC1c2cnc(-c3ncccn3)nc2CCN1c1cc(F)c(F)c(OCC2COC2)c1]

Step 1: Preparation of oxetan-3-ylmethyl 4-methylbenzenesulfonate

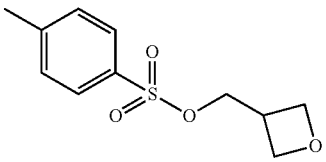 [SMILES: Cc1ccc(S(=O)(=O)OCC2COC2)cc1]

To a stirred solution of 3-oxetanemethanol (500 mg, 5.67 mmol) in DCM (5 mL) was added Et$_3$N (1.0 g, 10.2 mmol) and DMAP (70 mg, 0.57 mmol). Then to the mixture was added a solution of 4-methylbenzenesulfonyl chloride (1.6 g, 8.51 mmol) in DCM (5 mL) dropwise. After being stirred at 15° C. for 16 hrs, the resulting mixture was diluted with DCM (50 mL), washed with H$_2$O (20 mL), 2 N HCl (20 mL) and brine (10 mL), then dried over anhydrous Na$_2$SO$_4$ and concentrated in vacuo to give oxetan-3-ylmethyl 4-methylbenzenesulfonate (1.0 g) as a colorless oil which was used in the next step directly without further purification.

Step 2: Preparation of 6-[3,4-difluoro-5-(oxetan-3-ylmethoxy)phenyl]-5-methyl-2-pyrimidin-2-yl-7,8-dihydro-5H-pyrido[4,3-d]pyrimidine

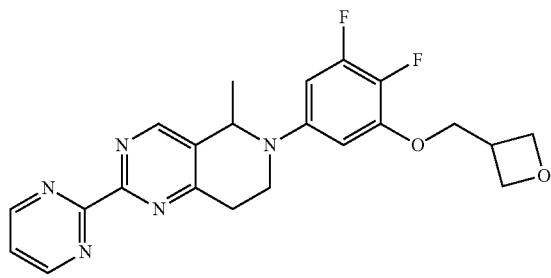 [SMILES: CC1c2cnc(-c3ncccn3)nc2CCN1c1cc(F)c(F)c(OCC2COC2)c1]

A mixture of 2,3-difluoro-5-(5-methyl-2-pyrimidin-2-yl-7,8-dihydro-5H-pyrido[4,3-d]pyrimidin-6-yl)phenol (100 mg, 0.28 mmol), oxetan-3-ylmethyl 4-methylbenzenesulfonate (82 mg, 0.34 mmol) and Cs$_2$CO$_3$ (138 mg, 0.42 mmol) in DMF (3 mL) was heated to 80° C. with stirring for 12 hrs. The reaction mixture was cooled down to rt and diluted with EA (20 mL). The organic phase was washed with brine (30 mL), dried over anhydrous Na$_2$SO$_4$ and concentrated in vacuo. The residue was purified by the prep-HPLC to give 6-[3,4-difluoro-5-(oxetan-3-ylmethoxy)phenyl]-5-methyl-2-pyrimidin-2-yl-7,8-dihydro-5H-pyrido[4,3-d]pyrimidine (69 mg) as a yellow solid. $^1$H NMR (400 MHz, CDCl$_3$) δ: 9.04 (d, 2H), 8.79 (s, 1H), 7.45 (t, 1H), 6.35-6.48 (m, 2H), 4.98 (q, 1H), 4.87-4.94 (m, 2H), 4.52-4.63 (m, 2H), 4.26-4.37 (m, 2H), 3.66-3.78 (m, 1H), 3.41-3.58 (m, 2H), 3.21-3.38 (m, 2H), 1.46 (d, 3H). MS obsd. (ESI$^+$) [(M+H)$^+$]: 426.

Example 77: [1-[[2,3-difluoro-5-(5-methyl-2-pyrimidin-2-yl-7,8-dihydro-5H-pyrido[4,3-d]pyrimidin-6-yl)phenoxy]methyl]cyclopropyl]methanol

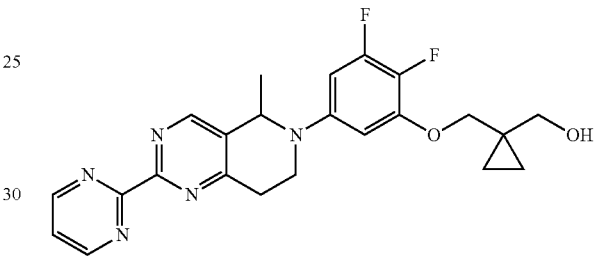

To a solution of 2,3-difluoro-5-(5-methyl-2-pyrimidin-2-yl-7,8-dihydro-5H-pyrido[4,3-d]pyrimidin-6-yl)phenol (100 mg, 0.28 mmol) in DCM (5 mL) was added 1,1-bis(hydroxymethyl)cyclopropane (86 mg, 0.84 mmol). After the mixture was stirred at rt for 5 mins, to the resulting mixture was added PPh$_3$ (221 mg, 0.84 mmol) and diethyl azodicarboxylate (147 mg, 0.84 mmol). After being stirred at rt for 4 hrs, the resulting reaction mixture was diluted with DCM (60 mL), washed with H$_2$O (30 mL) and brine (30 mL) successively, then dried over anhydrous Na$_2$SO$_4$ and concentrated in vacuo. The residue was purified by prep-HPLC to give [1-[[2,3-difluoro-5-(5-methyl-2-pyrimidin-2-yl-7,8-dihydro-5H-pyrido[4,3-d]pyrimidin-6-yl)phenoxy]methyl]cyclopropyl]methanol (19 mg) as a yellow solid. $^1$H NMR (400 MHz, DMSO-d$_6$) δ: 9.00 (d, 2H), 8.84 (s, 1H), 7.65 (m, 1H), 6.62 (m, 2H), 5.31 (m, 1H), 4.69 (br. s, 1H), 3.84-4.06 (m, 4H), 3.41 (br. s, 2H), 2.93-3.13 (m, 2H), 1.39 (m, 3H), 0.53 (d, 4H). MS obsd. (ESI$^+$) [(M+H$^+$)]: 440.

Example 78: 3-[2,3-difluoro-5-(5-methyl-2-pyrimidin-2-yl-7,8-dihydro-5H-pyrido[4,3-d]pyrimidin-6-yl)phenoxy]propane-1-sulfonic acid

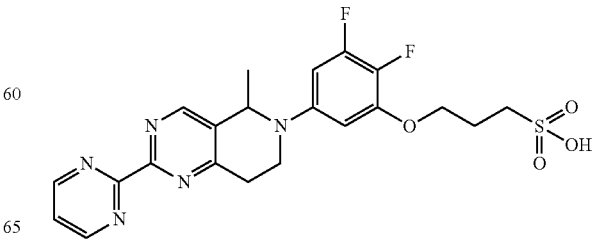

To a solution of 2,3-difluoro-5-(5-methyl-2-pyrimidin-2-yl-7,8-dihydro-5H-pyrido[4,3-d]pyrimidin-6-yl)phenol (50 mg, 0.14 mmol) in DMF (3 mL) was added 1,3-propanesultone (26 mg, 0.21 mmol) and $Cs_2CO_3$ (137 mg, 0.42 mmol). After being stirred at rt for 12 hrs, the resulting mixture was purified by prep-HPLC to give 3-[2,3-difluoro-5-(5-methyl-2-pyrimidin-2-yl-7,8-dihydro-5H-pyrido[4,3-d]pyrimidin-6-yl)phenoxy]propane-1-sulfonic acid (23 mg) as a yellow solid. $^1$H NMR (400 MHz, DMSO-$d_6$) δ: 8.93 (m, 2H), 8.77 (s, 1H), 7.62 (m, 1H), 6.53-6.66 (m, 2H), 5.01 (m, 1H), 4.19 (m, 2H), 3.61-3.78 (m, 1H), 3.41-3.58 (m, 1H), 2.97-3.16 (m, 4H), 2.09-2.23 (m, 2H), 1.33 (d, 3H). MS obsd. (ESI$^+$) [(M+H$^+$)]: 478.

Example 79: 6-[3,4-difluoro-5-[2-(oxetan-3-yl)ethoxy]phenyl]-5-methyl-2-pyrimidin-2-yl-7,8-dihydro-5H-pyrido[4,3-d]pyrimidine

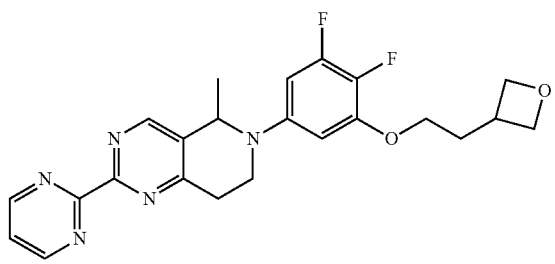 [SMILES: CC1c2cnc(-c3ncccn3)nc2CCN1c1cc(F)c(F)c(OCCC2COC2)c1]

Step 1: Preparation of 2-(oxetan-3-yl)ethyl 4-methylbenzenesulfonate

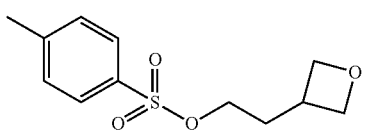 [SMILES: Cc1ccc(S(=O)(=O)OCCC2COC2)cc1]

To a stirred solution of 2-(oxetan-3-yl) ethanol (500 mg, 4.90 mmol) in DCM (5 mL) was added $Et_3N$ (892 mg, 8.81 mmol) followed by the addition of a solution of 4-methylbenzenesulfonyl chloride (1.1 g, 5.87 mmol) in DCM (10 mL) dropwise. After being stirred at rt for 16 hrs, the resulting mixture was diluted with DCM (100 mL), washed with saturated aqueous solution of $NaHCO_3$ (20 mL), 1.0 N HCl (20 mL) and brine (30 mL) successively, then dried over anhydrous $Na_2SO_4$ and concentrated in vacuo to give 2-(oxetan-3-yl)ethyl 4-methylbenzenesulfonate (1.01 g) as a colorless oil which was used in the next step directly without further purification.

Step 2: Preparation of 6-[3,4-difluoro-5-[2-(oxetan-3-yl)ethoxy]phenyl]-5-methyl-2-pyrimidin-2-yl-7,8-dihydro-5H-pyrido[4,3-d]pyrimidine

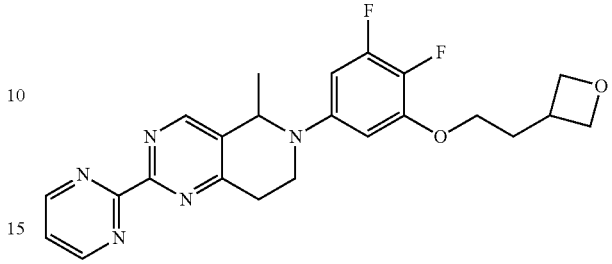

A mixture of 2,3-difluoro-5-(5-methyl-2-pyrimidin-2-yl-7,8-dihydro-5H-pyrido[4,3-d]pyrimidin-6-yl)phenol (100 mg, 0.28 mmol), 2-(oxetan-3-yl)ethyl 4-methylbenzenesulfonate (87 mg, 0.34 mmol) and $Cs_2CO_3$ (138 mg, 0.42 mmol) in DMF (3 mL) was heated at 80° C. with stirring for 12 hrs. After being cooled down to rt, the reaction mixture was diluted with EA (20 mL), washed with brine (10 mL) then dried over anhydrous $Na_2SO_4$ and concentrated in vacuo. The residue was purified by prep-HPLC to give 6-[3,4-difluoro-5-[2-(oxetan-3-yl)ethoxy]phenyl]-5-methyl-2-pyrimidin-2-yl-7,8-dihydro-5H-pyrido[4,3-d]pyrimidine (36 mg) as a yellow solid. $^1$H NMR (400 MHz, CDCl$_3$) δ: 9.04 (d, 2H), 8.79 (s, 1H), 7.42-7.48 (m, 1H), 6.39 (m, 1H), 6.32 (dd, 1H), 4.96 (q, 1H), 4.87 (dd, 2H), 4.53 (t, 2H), 4.03 (t, 2H), 3.65-3.78 (m, 1H), 3.43-3.57 (m, 1H), 3.20-3.37 (m, 3H), 2.18-2.27 (m, 2H), 1.45 (d, 3H). MS obsd. (ESI$^+$) [(M+H)$^+$]: 440.

Example 80: 6-[3,4-difluoro-5-[2-(oxetan-3-yl)ethoxy]phenyl]-5-methyl-2-pyrimidin-2-yl-7,8-dihydro-5H-pyrido[4,3-d]pyrimidine

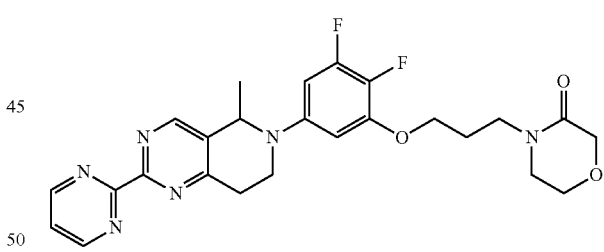

Step 1: Preparation of 4-(3-bromopropyl)morpholin-3-one

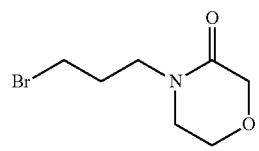 [SMILES: O=C1COCCN1CCCBr]

To a cooled solution of morpholin-3-one (2.0 g, 19.78 mmol) in DMF (20 mL) was added NaH (950 mg, 23.74 mmol, 60% wt) slowly at 0° C. The reaction mixture was warmed to rt and stirred at rt for 1.5 hrs. Then to the reaction mixture was added a solution of 1,3-dibromopropane (4.4 g, 21.76 mmol) in DMF (5 mL). After being stirred at rt for another 0.5 hr, the resulting reaction mixture was diluted with aqueous solution of NH$_4$Cl (30 mL) and extracted with EA (100 mL) for three times. The combined organic layer was washed with brine (150 mL), dried over anhydrous Na$_2$SO$_4$ and concentrated in vacuo. The residue was purified by chromatography on silica gel to give 4-(3-bromopropyl)-morpholin-3-one (1.5 g) as a colorless oil.

Step 2: Preparation of 6-[3,4-difluoro-5-[2-(oxetan-3-yl)ethoxy]phenyl]-5-methyl-2-pyrimidin-2-yl-7,8-dihydro-5H-pyrido[4,3-d]pyrimidine

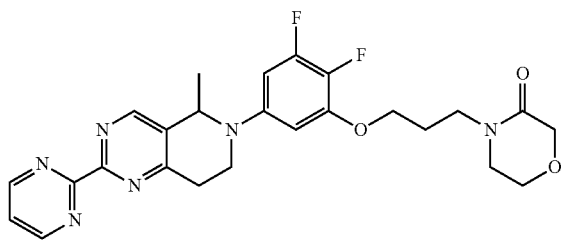 [SMILES: CC1c2cnc(-c3ncccn3)nc2CCN1c1cc(F)c(F)c(OCCCN2CCOCC2=O)c1]

To a solution of 4-(3-bromopropyl)morpholin-3-one (375 mg, 0.562 mmol) in DMF (4 mL) was added K$_2$CO$_3$ (58 mg, 0.422 mmol) and 2,3-difluoro-5-(5-methyl-2-pyrimidin-2-yl-7,8-dihydro-5H-pyrido[4,3-d]pyrimidin-6-yl)phenol (100 mg, 0.281 mmol). After being stirred at rt for 16 hrs, the reaction mixture was diluted with water (20 mL) and extracted with DCM (80 mL) twice. The combined organic layer was washed with brine (150 mL), dried over anhydrous Na$_2$SO$_4$ and concentrated in vacuo. The residue was purified by prep-HPLC to give 6-[3,4-difluoro-5-[2-(oxetan-3-yl)ethoxy]phenyl]-5-methyl-2-pyrimidin-2-yl-7,8-dihydro-5H-pyrido[4,3-d]pyrimidine (47 mg) as a pink solid. $^1$H NMR (400 MHz, CDCl$_3$) δ: 9.04 (d, 2H), 8.80 (s, 1H), 7.45 (t, 1H), 6.34-6.43 (m, 2H), 4.95-5.02 (m, 1H), 4.08-4.19 (m, 4H), 3.86-3.94 (m, 2H), 3.72 (d, 1H), 3.64 (t, 2H), 3.40-3.51 (m, 3H), 3.22-3.33 (m, 2H), 2.08-2.19 (m, 2H), 1.45 (d, 3H). MS obsd. (ESI$^+$) [(M+H)$^+$]: 497.

Example 81: 6-[3-fluoro-5-(trifluoromethyl)phenyl]-5-methyl-2-pyrimidin-2-yl-7,8-dihydro-5H-pyrido[4,3-d]pyrimidine

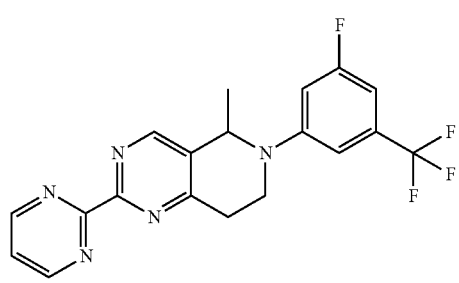 [SMILES: CC1c2cnc(-c3ncccn3)nc2CCN1c1cc(F)cc(C(F)(F)F)c1]

Step 1: Preparation of 8-[3-fluoro-5-(trifluoromethyl)phenyl]-1,4-dioxa-8-azaspiro[4.5]decane

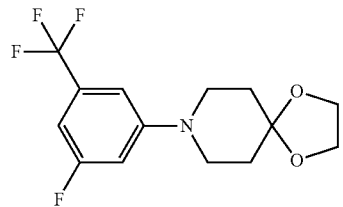 [SMILES: Fc1cc(N2CCC3(CC2)OCCO3)cc(C(F)(F)F)c1]

A mixture of 3-bromo-5-fluorobenzotrifluoride (15.0 g, 0.062 mol), 1,4-dioxa-8-azaspiro[4.5]decane hydrochloride (13.3 g, 0.074 mol), t-BuONa (14.8 g, 0.154 mol), BINAP (1.5 g, 0.002 mol) and Pd$_2$(dba)$_3$ (1.1 g, 0.001 mol) in toluene (200 mL) was heated at 100° C. with stirring under N$_2$ for 16 hrs. The resulting reaction mixture was cooled down to rt and filtered. The filtrate was diluted with DCM (1.0 L), washed with H$_2$O (200 mL) and brine (200 mL) successively, then dried over anhydrous Na$_2$SO$_4$ and concentrated in vacuo. The residue was purified by the flash column chromatography to give 8-[3-fluoro-5-(trifluoromethyl)phenyl]-1,4-dioxa-8-azaspiro[4.5]decane (14.6 g) as yellow oil.

Step 2: Preparation of 1-[3-fluoro-5-(trifluoromethyl)phenyl]piperidin-4-one

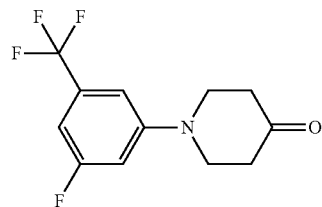 [SMILES: O=C1CCN(c2cc(F)cc(C(F)(F)F)c2)CC1]

A mixture of 8-[3-fluoro-5-(trifluoromethyl)phenyl]-1,4-dioxa-8-azaspiro[4.5]decane (12.6 g, 0.04 mol), formic acid (120 mL) and H$_2$O (120 mL) was heated at 90° C. with stirring for 2 hrs. The reaction mixture was concentrated in vacuo. The residue was diluted with DCM (500 mL), washed with saturated aqueous solution of Na$_2$CO$_3$ (100 mL, 2 times) and brine (100 mL) successively, then dried over anhydrous Na$_2$SO$_4$ and concentrated in vacuo. The residue was purified by the flash column chromatography to give 1-[3-fluoro-5-(trifluoromethyl)phenyl]piperidin-4-one (7.0 g) as a yellow solid.

Step 3: Preparation of 6-[3-fluoro-5-(trifluoromethyl)phenyl]-2-pyrimidin-2-yl-7,8-dihydro-5H-pyrido[4,3-d]pyrimidine

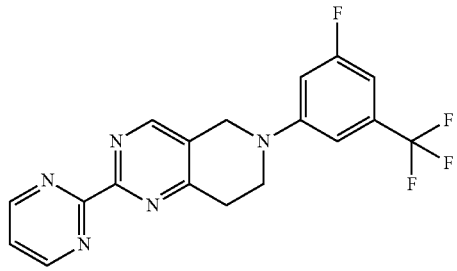 [SMILES: Fc1cc(N2CCc3nc(-c4ncccn4)ncc3C2)cc(C(F)(F)F)c1]

A mixture of 1-[3-fluoro-5-(trifluoromethyl)phenyl]piperidin-4-one (7.0 g. 0.026 mol) and DMFDMA (70 mL) was heated at 120° C. with stirring for 4 hrs. The reaction mixture was concentrated in vacuo and the residue was dissolved in MeOH (130 mL). To the solution was added pyrimidine-2-carboximidamide hydrochloride (5.1 g, 0.032 mol) and $K_2CO_3$ (9.3 g, 0.067 mol). The reaction mixture was heated at 60° C. with stirring under nitrogen for 2 hrs, then cooled down to rt and filtered. The filtrate was concentrated in vacuo. The residue was diluted with DCM (500 mL), washed with $H_2O$ (100 mL) and brine (200 mL), then dried over anhydrous $Na_2SO_4$ and concentrated in vacuo. The residue was purified by the flash column chromatography to give 6-[3-fluoro-5-(trifluoromethyl)phenyl]-2-pyrimidin-2-yl-7,8-dihydro-5H-pyrido[4,3-d]pyrimidine (4.7 g) as a light yellow solid.

Step 4: Preparation of 6-[3-fluoro-5-(trifluoromethyl)phenyl]-5-methoxy-2-pyrimidin-2-yl-7,8-dihydro-5H-pyrido[4,3-d]pyrimidine

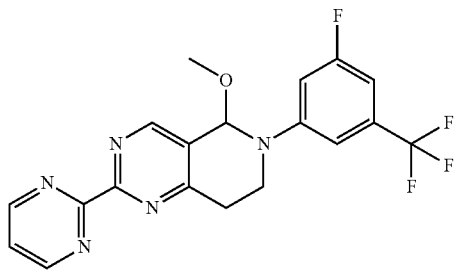 [SMILES: COC1c2cnc(-c3ncccn3)nc2CCN1c1cc(F)cc(C(F)(F)F)c1]

A stirred solution of 6-[3-fluoro-5-(trifluoromethyl)phenyl]-2-pyrimidin-2-yl-7,8-dihydro-5H-pyrido[4,3-d]pyrimidine (1.0 g, 2.66 mmol) in DCM (80 mL) and MeOH (20 mL) was cooled to −70° C. and to the cooled solution was added $RuCl_3$ hydrate (0.80 mmol) and a solution of $NaIO_4$ (1.71 g in 25 mL H2O) successively. After being warmed to rt and stirred at rt for 16 hrs, the resulting reaction mixture was diluted with saturated aqueous solution of $Na_2S_2O_3$ and filtered. The filtrate was diluted with DCM (100 mL), washed with brine (50 mL), then dried over anhydrous $Na_2SO_4$ and concentrated in vacuo to give 6-[3-fluoro-5-(trifluoromethyl)phenyl]-5-methoxy-2-pyrimidin-2-yl-7,8-dihydro-5H-pyrido[4,3-d]pyrimidine (1.0 g) which was used in the next step directly without further purification.

Step 5: Preparation of 6-[3-fluoro-5-(trifluoromethyl)phenyl]-5-methyl-2-pyrimidin-2-yl-7,8-dihydro-5H-pyrido[4,3-d]pyrimidine

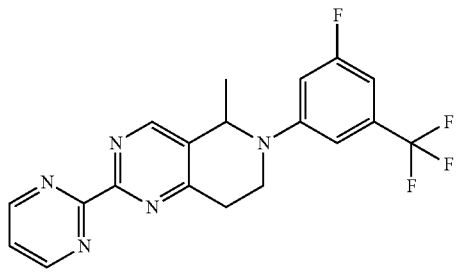 [SMILES: CC1c2cnc(-c3ncccn3)nc2CCN1c1cc(F)cc(C(F)(F)F)c1]

To a cooled solution of 6-[3-fluoro-5-(trifluoromethyl)phenyl]-5-methoxy-2-pyrimidin-2-yl-7,8-dihydro-5H-pyrido[4,3-d]pyrimidine (1.0 g, 2.47 mmol) in THF (50 mL) was added $BF_3.Et_2O$ (851 mg, 7.40 mmol) with stirring. After the resulting mixture was stirred at this temperature for additional 20 mins, to the mixture was added a solution of MeMgBr (2.5 mL, 7.40 mmol) in THF dropwise. After the addition, the reaction mixture was warmed up to 10° C. and stirred at 10° C. for 1 hr. The resulting mixture was diluted with saturated aqueous solution of $NH_4Cl$ (20 mL) and extracted with EA (30 mL) for three times. The combined organic phase was washed with brine (50 mL), dried over anhydrous $Na_2SO_4$ and concentrated in vacuo. The residue was purified by pre-HPLC to give 6-[3-fluoro-5-(trifluoromethyl)phenyl]-5-methyl-2-pyrimidin-2-yl-7,8-dihydro-5H-pyrido[4,3-d]pyrimidine (120 mg) as yellow solid. $^1$H NMR (400 MHz, Methanol-$d_4$) δ: 9.03 (d, 2H), 8.89 (s, 1H), 7.64 (t, 1H), 7.02-7.14 (m, 2H), 6.76 (d, 1H), 5.37 (q, 1H), 4.07 (m, 1H), 3.54-3.69 (m, 1H), 3.13-3.29 (m, 2H), 1.55 (d, 3H). MS obsd. (ESI$^+$) [(M+H)$^+$]: 390.

Example 82: 6-[3-[(2,2-difluorocyclopropyl)methoxy]-5-fluoro-phenyl]-5-methyl-2-pyrimidin-2-yl-7,8-dihydro-5H-pyrido[4,3-d]pyrimidine

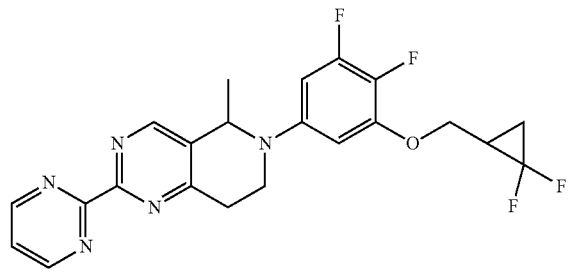 [SMILES: CC1c2cnc(-c3ncccn3)nc2CCN1c1cc(F)c(F)c(OCC2CC2(F)F)c1]

To a solution of 2,3-difluoro-5-(5-methyl-2-pyrimidin-2-yl-7,8-dihydro-5H-pyrido[4,3-d]pyrimidin-6-yl)phenol (70 mg, 0.20 mmol) in DMF (2 mL) was added 1-bromomethyl-2,2-difluorocyclopropane (51 mg, 0.30 mmol) and $Cs_2CO_3$ (192 mg, 0.59 mmol). After being stirred at rt for 12 hrs, the resulting reaction mixture was diluted with EA (60 mL), washed with $H_2O$ (30 mL) and brine (30 mL), then dried over anhydrous $Na_2SO_4$ and concentrated in vacuo. The residue was purified by prep-HPLC to afford 6-[3-[(2,2-difluorocyclopropyl)methoxy]-5-fluoro-phenyl]-5-methyl-2-pyrimidin-2-yl-7,8-dihydro-5H-pyrido[4,3-d]pyrimidine (44 mg) as yellow solid. $^1$H NMR (400 MHz, CDCl$_3$) δ: 9.04 (d, 2H), 8.78 (s, 1H), 7.44 (m, 1H), 6.42 (m, 1H), 6.32-6.39 (m, 1H), 4.96 (m, 1H), 4.05-4.22 (m, 2H), 3.65-3.78 (m, 1H), 3.43-3.55 (m, 1H) 3.19-3.38 (m, 2H), 2.02-2.19 (m, 1H), 1.56-1.68 (m, 1H), 1.45 (d, 3H), 1.21-1.37 (m, 1H). MS obsd. (ESI$^+$) [(M+H$^+$)]: 446.

Example 83: 2-[2,3-difluoro-5-(5-methyl-2-pyrimidin-2-yl-7,8-dihydro-5H-pyrido[4,3-d]pyrimidin-6-yl)phenoxy]-N-tetrahydrofuran-3-yl-acetamide

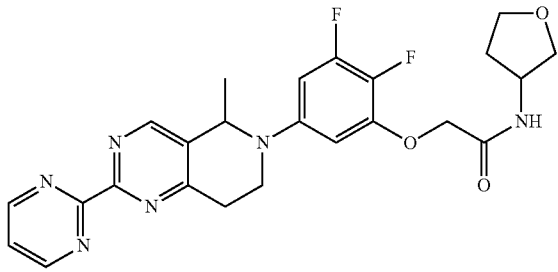 [SMILES: CC1c2cnc(-c3ncccn3)nc2CCN1c1cc(F)c(F)c(OCC(=O)NC2CCOC2)c1]

A mixture of 2-[2,3-difluoro-5-(5-methyl-2-pyrimidin-2-yl-7,8-dihydro-5H-pyrido[4,3-d]pyrimidin-6-yl)phenoxy]acetic acid (70 mg, 0.17 mmol) and CDI (33 mg, 0.2 mmol) in DMF (5 mL) was stirred for 3 hrs at rt. Then to the resulting mixture was added tetrahydrofuran-3-amine (44 mg, 0.5 mmol). After being stirred for 10 hrs, the reaction mixture was concentrated in vacuo. The residue was purified by prep-HPLC to give 2-[2,3-difluoro-5-(5-methyl-2-pyrimidin-2-yl-7,8-dihydro-5H-pyrido[4,3-d]pyrimidin-6-yl)phenoxy]-N-tetrahydrofuran-3-yl-acetamide (10 mg) as yellow solid. $^1$H NMR (400 MHz, CDCl$_3$) δ: 9.05 (d, 2H), 8.81 (s, 1H), 7.46 (m, 1H), 6.77-6.90 (m, 1H), 6.42-6.53 (m, 1H), 6.26-6.40 (m, 1H), 4.92-5.05 (m, 1H), 4.60-4.68 (m, 1H), 4.57 (s, 2H), 3.65-4.05 (m, 5H), 3.45-3.59 (m, 1H), 3.30 (d, 2H), 2.25-2.43 (m, 1H), 1.83-1.95 (m, 1H), 1.48 (d, 3H); MS obsd. (ESI$^+$) [(M+H)$^+$]: 483.

Example 84: 2-[2,3-difluoro-5-(5-methyl-2-pyrimidin-2-yl-7,8-dihydro-5H-pyrido[4,3-d]pyrimidin-6-yl)phenoxy]-1-morpholino-ethanone

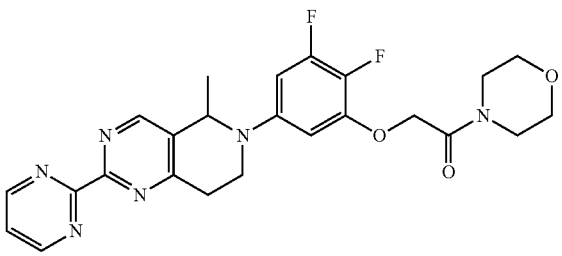 [SMILES: CC1c2cnc(-c3ncccn3)nc2CCN1c1cc(F)c(F)c(OCC(=O)N2CCOCC2)c1]

A mixture of CDI (32.9 mg, 0.2 mmol) and morpholine (44.3 mg, 0.5 mmol) in DMF (5 mL) was stirred for 3 hrs. Then to the resulting mixture was added 2-[2,3-difluoro-5-(5-methyl-2-pyrimidin-2-yl-7,8-dihydro-5H-pyrido[4,3-d]pyrimidin-6-yl)phenoxy]acetic acid (70 mg, 0.17 mmol). After being stirred for 10 hrs at rt, the resulting mixture was concentrated in vacuo. The residue was purified by prep-HPLC to give 2-[2,3-difluoro-5-(5-methyl-2-pyrimidin-2-yl-7,8-dihydro-5H-pyrido[4,3-d]pyrimidin-6-yl)phenoxy]-1-morpholino-ethanone (15 mg) as yellow solid. $^1$H NMR (400 MHz, CDCl$_3$) δ: 9.04 (d, 2H), 8.80 (s, 1H), 7.45 (s, 1H), 6.50-6.57 (m, 1H), 6.35-6.48 (m, 1H), 4.92-5.05 (m, 1H), 4.81 (s, 2H), 3.44-3.81 (m, 10H), 3.26 (s, 2H), 1.47 (d, 3H). MS obsd. (ESI$^+$) [(M+H)$^+$]: 483.

Example 85: ethyl 7-[2,3-difluoro-5-(5-methyl-2-pyrimidin-2-yl-7,8-dihydro-5H-pyrido[4,3-d]pyrimidin-6-yl)phenoxy]heptanoate

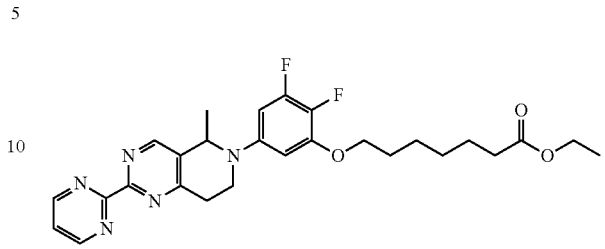

A mixture of 2,3-difluoro-5-(5-methyl-2-pyrimidin-2-yl-7,8-dihydro-5H-pyrido[4,3-d]pyrimidin-6-yl)phenol (400 mg, 1.13 mmol), ethyl 7-bromoheptanoate (400 mg, 1.69 mmol) and K$_2$CO$_3$ (467 mg, 3.38 mmol) in DMF (10 mL) was heated at 110° C. with stirring for 10 hrs. The reaction mixture was poured into 10 mL H$_2$O and extracted with DCM (20 mL) for three times. The combined organic layer was dried over anhydrous Na$_2$SO$_4$ and concentrated in vacuo. The residue was purified by flash chromatography to give ethyl 7-[2,3-difluoro-5-(5-methyl-2-pyrimidin-2-yl-7,8-dihydro-5H-pyrido[4,3-d]pyrimidin-6-yl)phenoxy]heptanoate (500 mg) as a light yellow solid. $^1$H NMR (400 MHz, CDCl$_3$) δ: 9.05 (d, 2H), 8.80 (s, 1H), 7.46 (m, 1H), 6.37 (d, 2H), 4.92-5.04 (m, 1H), 4.00-4.20 (m, 4H), 3.67-3.78 (m, 1H), 3.45-3.58 (m, 1H), 3.22-3.39 (m, 2H), 2.33 (m, 2H), 1.78-1.92 (m, 2H), 1.65-1.75 (m, 2H), 1.37-1.58 (m, 7H), 1.27 (m, 3H); MS obsd. (ESI$^+$) [(M+H)$^+$]: 512.

Example 86: 7-[2,3-difluoro-5-(5-methyl-2-pyrimidin-2-yl-7,8-dihydro-5H-pyrido[4,3-d]pyrimidin-6-yl)phenoxy]heptanoic acid

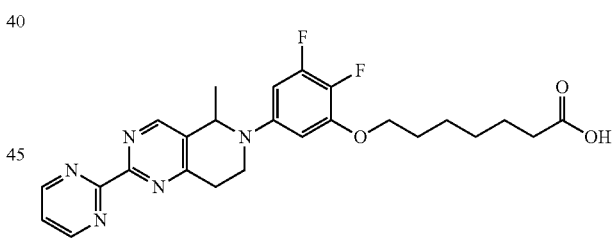

To a solution of ethyl 7-[2,3-difluoro-5-(5-methyl-2-pyrimidin-2-yl-7,8-dihydro-5H-pyrido[4,3-d]pyrimidin-6-yl)phenoxy]heptanoate (450 mg, 880 μmol) in THF (9 mL) and MeOH (15 mL) was added a solution of lithium hydroxide (105 mg, 4.4 mmol) in water (3 mL). After being stirred at rt for 10 hrs, the reaction mixture was acidified with 1.0 N HCl and then extracted with DCM (20 mL) for three times. The combined organic layer was dried over anhydrous Na$_2$SO$_4$ and concentrated in vacuo. The residue was purified by prep-HPLC to give 7-[2,3-difluoro-5-(5-methyl-2-pyrimidin-2-yl-7,8-dihydro-5H-pyrido[4,3-d]pyrimidin-6-yl)phenoxy]heptanoic acid (60 mg) as a yellow solid. $^1$H NMR (400 MHz, CDCl$_3$) δ: 9.05 (d, 2H), 8.81 (s, 1H), 7.46 (m, 1H), 6.30-6.46 (m, 2H), 4.97 (m, 1H), 4.05 (m, 2H), 3.73 (m, 1H), 3.45-3.59 (m, 1H), 3.20-3.39 (m, 2H), 2.39 (m, 2H), 1.84 (m, 2H), 1.69 (m, 2H), 1.37-1.60 (m, 7H); MS obsd. (ESI$^+$) [(M+H)$^+$]: 484.

Example 87: 7-[2,3-difluoro-5-(5-methyl-2-pyrimidin-2-yl-7,8-dihydro-5H-pyrido[4,3-d]pyrimidin-6-yl)phenoxy]heptanamide

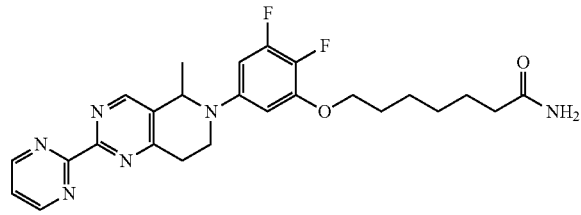 [SMILES: CC1c2cnc(-c3ncccn3)nc2CCN1c1cc(F)c(F)c(OCCCCCCC(N)=O)c1]

A mixture of 7-[2,3-difluoro-5-(5-methyl-2-pyrimidin-2-yl-7,8-dihydro-5H-pyrido[4,3-d]pyrimidin-6-yl)phenoxy]heptanoic acid (70 mg, 0.15 mmol) and CDI (28 mg, 0.17 mmol) in DMF (5 mL) was stirred for 3 hrs at rt. Then to the mixture was added NH$_3$ (0.4 mL, 0.8 mmol, 2.0 M in isopropyl alcohol) and the resulting mixture was stirred for 10 hrs at rt. The mixture was concentrated in vacuo and the residue was purified by prep-HPLC to give 7-[2,3-difluoro-5-(5-methyl-2-pyrimidin-2-yl-7,8-dihydro-5H-pyrido[4,3-d]pyrimidin-6-yl)phenoxy]heptanamide (18 mg) as a light yellow solid. $^1$H NMR (400 MHz, CDCl$_3$) δ: 9.04 (d, 2H), 8.79 (s, 1H), 7.45 (m, 1H), 6.31-6.46 (m, 2H), 5.53 (br. s., 2H), 4.97 (m, 1H), 3.97-4.12 (m, 2H), 3.64-3.80 (m, 1H), 3.42-3.59 (m, 1H), 3.16-3.39 (m, 2H), 2.25 (m, 2H), 1.77-1.90 (m, 2H), 1.69 (m, 2H), 1.36-1.59 (m, 7H); MS obsd. (ESI$^+$) [(M+H)$^+$]: 483.

Example 88: 6-[3-(cyclopropylmethoxy)-4,5-difluoro-phenyl]-5-methyl-2-pyrimidin-2-yl-7,8-dihydro-5H-pyrido[4,3-d]pyrimidine

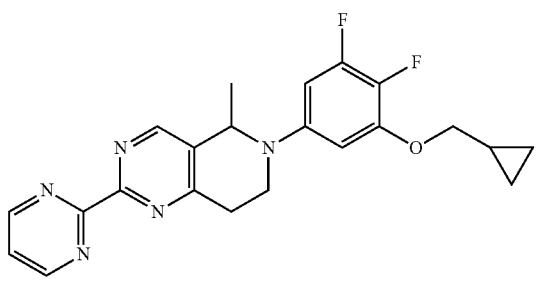 [SMILES: CC1c2cnc(-c3ncccn3)nc2CCN1c1cc(F)c(F)c(OCC2CC2)c1]

A mixture of 2,3-difluoro-5-(5-methyl-2-pyrimidin-2-yl-7,8-dihydro-5H-pyrido[4,3-d]pyrimidin-6-yl)phenol (70 mg, 0.197 mmol), (bromomethyl)cyclopropane (79.8 mg, 0.591 mmol), KI (32.7 mg, 0.197 mmol) and K$_2$CO$_3$ (81.7 mg, 0.591 mmol) in DMF (5 mL) was heated at 110° C. with stirring for 10 hrs. The resulting mixture was purified by prep-HPLC to give 6-[3-(cyclopropylmethoxy)-4,5-difluoro-phenyl]-5-methyl-2-pyrimidin-2-yl-7,8-dihydro-5H-pyrido[4,3-d]pyrimidine (30 mg) as a yellow solid. $^1$H NMR (400 MHz, CDCl$_3$) δ: 9.05 (d, 2H), 8.79 (s, 1H), 7.45 (m, 1H), 6.30-6.47 (m, 2H), 4.90-5.07 (m, 1H), 3.91 (d, 2H), 3.65-3.77 (m, 1H), 3.42-3.60 (m, 1H), 3.28 (s, 2H), 1.45 (d, 3H), 1.32 (s, 1H), 0.61-0.74 (m, 2H), 0.31-0.45 (m, 2H); MS obsd. (ESI$^+$) [(M+H)$^+$]: 410.

Example 89: 6-[3,4-difluoro-5-(tetrahydropyran-4-ylmethoxy)phenyl]-5-methyl-2-pyrimidin-2-yl-7,8-dihydro-5H-pyrido[4,3-d]pyrimidine

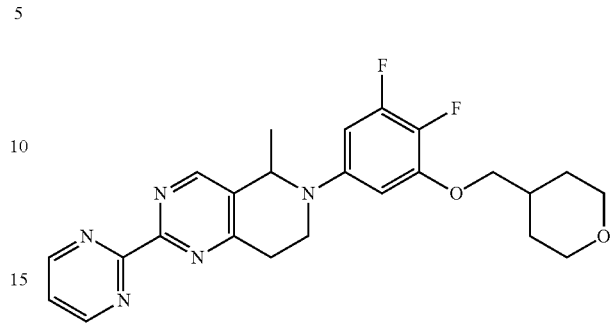

To a mixture of 2,3-difluoro-5-(5-methyl-2-pyrimidin-2-yl-7,8-dihydro-5H-pyrido[4,3-d]pyrimidin-6-yl)phenol (70 mg, 197 μmol) and potassium carbonate (55 mg, 394 μmol) in DMF (2 mL) was added 4-(bromomethyl)tetrahydro-2H-pyran (106 mg, 591 μmol). After being heated at 110° C. with stirring for 1 hr, the reaction mixture was cooled to room temperature and then filtered. The filtrate was purified by prep-HPLC to afford 6-[3,4-difluoro-5-(tetrahydropyran-4-ylmethoxy)phenyl]-5-methyl-2-pyrimidin-2-yl-7,8-dihydro-5H-pyrido[4,3-d]pyrimidine (28 mg) as a yellow solid. $^1$H NMR (400 MHz, CDCl$_3$) δ: 9.05 (m, 2H), 8.80 (s, 1H), 7.46 (t, 1H), 6.44-6.33 (m, 2H), 4.98 (q, 1H), 4.04 (dd, 2H), 3.89 (d, 2H), 3.78-3.68 (m, 1H), 3.56-3.42 (m, 3H), 3.38-3.25 (m, 2H), 2.20-2.08 (m, 1H), 1.86-1.76 (m, 2H), 1.55-1.42 (m, 2H), 1.46 (d, 3H). MS obsd. (ESI$^+$) [(M+H$^+$)]: 454.

Example 90: tert-butyl N-[3-[2,3-difluoro-5-(5-methyl-2-pyrimidin-2-yl-7,8-dihydro-5H-pyrido[4,3-d]pyrimidin-6-yl)phenoxy]propyl]carbamate

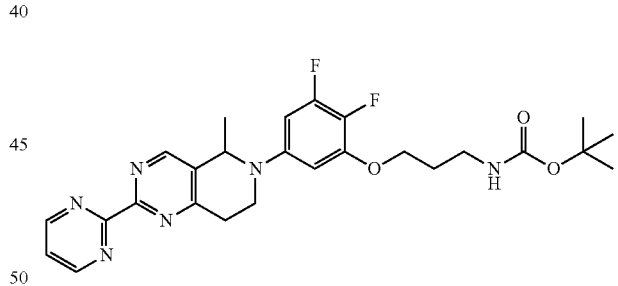

To a mixture of 2,3-difluoro-5-(5-methyl-2-pyrimidin-2-yl-7,8-dihydro-5H-pyrido[4,3-d]pyrimidin-6-yl)phenol (888 mg, 2.5 mmol) and potassium carbonate (691 mg, 5 mmol) in DMF (10 mL) was added tert-butyl (3-bromopropyl)-carbamate (1.19 g, 5 mmol). After being heated at 110° C. with stirring overnight, The reaction mixture was cooled to room temperature, then diluted with water and extracted with EA (50 mL) for three times. The combined organic layer was washed with brine, dried over anhydrous Na$_2$SO$_4$ and concentrated to give crude product (1.59 g) as dark brown oil. 160 mg of crude product was purified by prep-HPLC to afford tert-butyl N-[3-[2,3-difluoro-5-(5-methyl-2-pyrimidin-2-yl-7,8-dihydro-5H-pyrido[4,3-d]pyrimidin-6-yl)phenoxy]propyl]carbamate (125 mg) as a yellow solid. $^1$H NMR (400 MHz, CDCl$_3$) δ: 9.05 (m, 2H), 8.80 (s, 1H), 7.46 (t, 1H), 6.44-6.36 (m, 2H), 4.99 (q, 1H), 4.85 (br. s, 1H), 4.13 (t, 2H), 3.73 (ddd, 1H), 3.50 (ddd, 1H), 3.42-3.34 (m, 2H), 3.34-3.27 (m, 2H), 2.04 (quin, 2H), 1.48-1.44 (m, 12H). MS obsd. (ESI⁺) [(M+H⁺)]: 513.

Example 91: 3-[2,3-difluoro-5-(5-methyl-2-pyrimidin-2-yl-7,8-dihydro-5H-pyrido[4,3-d]pyrimidin-6-yl)phenoxy]propan-1-amine

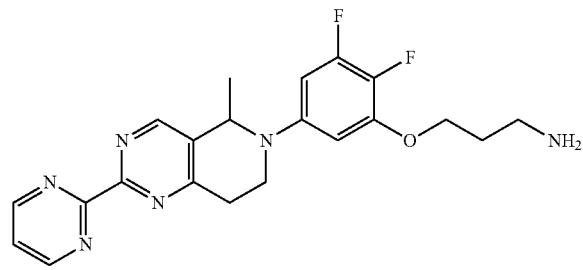 [SMILES: CC1c2cnc(-c3ncccn3)nc2CCN1c1cc(F)c(F)c(OCCCN)c1]

To a solution of HCl in EtOAc (30 mL, 30 mmol) was added tert-butyl N-[3-[2,3-difluoro-5-(5-methyl-2-pyrimidin-2-yl-7,8-dihydro-5H-pyrido[4,3-d]pyrimidin-6-yl)phenoxy]propyl]-carbamate (1.15 g, 2.25 mmol). After being stirred at rt for 2 hrs, the resulting mixture was concentrated in vacuo to give the crude product (1.23 g) as a brown solid. 130 mg of the brown solid was purified by prep-HPLC to afford 3-[2,3-difluoro-5-(5-methyl-2-pyrimidin-2-yl-7,8-dihydro-5H-pyrido[4,3-d]pyrimidin-6-yl)phenoxy]propan-1-amine (12 mg) as a yellow solid. ¹H NMR (400 MHz, CDCl₃) δ: 9.05 (s, 1H), 9.04 (s, 1H), 8.85 (s, 1H), 7.45 (t, 1H), 6.46-6.26 (m, 2H), 5.04 (d, 1H), 4.18 (m, 2H), 3.75-3.65 (m, 1H), 3.54-3.41 (m, 1H), 3.38-3.15 (m, 4H), 2.30-2.15 (m, 2H), 1.44 (d, 3H). MS obsd. (ESI⁺) [(M+H⁺)]: 413.

Example 92: N-[3-[2,3-difluoro-5-(5-methyl-2-pyrimidin-2-yl-7,8-dihydro-5H-pyrido[4,3-d]pyrimidin-6-yl)phenoxy]propyl]acetamide

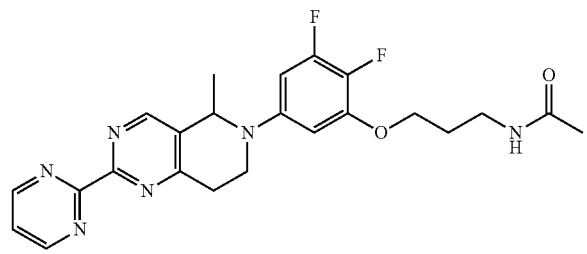 [SMILES: CC(=O)NCCCOc1cc(N2CCc3nc(-c4ncccn4)ncc3C2C)cc(F)c1F]

To a solution of 3-[2,3-difluoro-5-(5-methyl-2-pyrimidin-2-yl-7,8-dihydro-5H-pyrido[4,3-d]pyrimidin-6-yl)phenoxy]propan-1-amine hydrochloride (120 mg, 0.2 mmol) and DIEA (78 mg, 600 μmol) in DCM (2 mL) was added acetyl chloride (19 mg, 240 μmol) at 0° C. and the resulting mixture was stirred at rt for 4 hrs and then partitioned between DCM and water. The separated aqueous layer was extracted with DCM (20 mL) for three times. The combined organic layer was washed with brine, dried over anhydrous Na₂SO₄ and concentrated in vacuo. The residue was purified by prep-HPLC to afford N-[3-[2,3-difluoro-5-(5-methyl-2-pyrimidin-2-yl-7,8-dihydro-5H-pyrido[4,3-d]pyrimidin-6-yl)phenoxy]propyl]-acetamide (4 mg) as a yellow solid. ¹H NMR (400 MHz, CDCl₃) δ: 9.06 (m, 2H), 8.81 (s, 1H), 7.46 (t, 1H), 6.45-6.35 (m, 2H), 4.99 (q, 1H), 4.17 (t, 2H), 3.79-3.70 (m, 1H), 3.57-3.48 (m, 3H), 3.34-3.27 (m, 2H), 2.07 (quin, 2H), 2.02 (s, 3H), 1.48 (d, 3H). MS obsd. (ESI⁺) [(M+H⁺)]: 455.

Example 93: N-[3-[2,3-difluoro-5-(5-methyl-2-pyrimidin-2-yl-7,8-dihydro-5H-pyrido[4,3-d]pyrimidin-6-yl)phenoxy]propyl]cyclopropanesulfonamide

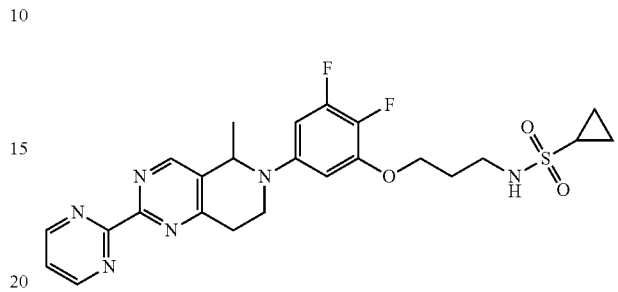

To a solution of 3-[2,3-difluoro-5-(5-methyl-2-pyrimidin-2-yl-7,8-dihydro-5H-pyrido[4,3-d]pyrimidin-6-yl)phenoxy]propan-1-amine hydrochloride (120 mg, 0.2 mmol) and DIEA (78 mg, 600 μmol) in DCM (2 mL) was added cyclopropanesulfonyl chloride (34 mg, 240 μmol) at 0° C. The resulting mixture was stirred at rt for 4 hrs and then partitioned between DCM and water. The separated aqueous layer was extracted with DCM (20 mL) for three times and the combined organic layer was washed with brine, dried over anhydrous Na₂SO₄ and concentrated in vacuo. The residue was purified by prep-HPLC to afford N-[3-[2,3-difluoro-5-(5-methyl-2-pyrimidin-2-yl-7,8-dihydro-5H-pyrido[4,3-d]pyrimidin-6-yl)phenoxy]propyl]cyclopropanesulfonamide (7 mg) as a yellow solid. ¹H NMR (400 MHz, CDCl₃) δ: 9.08 (m, 2H), 8.90 (s, 1H), 7.50 (t, 1H), 6.64 (br. s., 1H), 6.50 (ddd, 1H), 5.07 (q, 1H), 4.25 (t, 2H), 3.79 (td, 1H), 3.65-3.56 (m, 1H), 3.44 (t, 2H), 3.42-3.36 (m, 2H), 3.34-3.26 (m, 1H), 2.47 (tt, 1H), 2.13 (quin, 2H), 1.52 (d, 3H), 1.25-1.17 (m, 2H), 1.02 (dd, 2H). MS obsd. (ESI⁺) [(M+H⁺)]: 517.

Example 94: N-[3-[2,3-difluoro-5-(5-methyl-2-pyrimidin-2-yl-7,8-dihydro-5H-pyrido[4,3-d]pyrimidin-6-yl)phenoxy]propyl]-2-methoxy-ethanesulfonamide

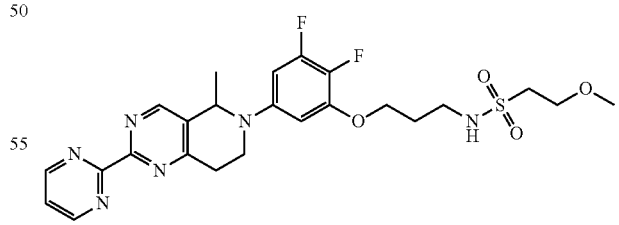

To a solution of 3-[2,3-difluoro-5-(5-methyl-2-pyrimidin-2-yl-7,8-dihydro-5H-pyrido[4,3-d]pyrimidin-6-yl)phenoxy]propan-1-amine hydrochloride (120 mg, 0.2 mmol) and DIEA (155 mg, 1.2 mmol) in DMF (2 mL) was added 2-methoxyethanesulfonyl chloride (76.1 mg, 480 mol) at 0° C. The resulting mixture was stirred at rt for 2 hrs and then partitioned between DCM and water. The separated aqueous layer was extracted with DCM (20 mL) for three times. The combined organic layer was washed with brine, dried over anhydrous Na$_2$SO$_4$ and concentrated in vacuo. The crude was purified by prep-HPLC to afford N-[3-[2,3-difluoro-5-(5-methyl-2-pyrimidin-2-yl-7,8-dihydro-5H-pyrido[4,3-d]pyrimidin-6-yl)phenoxy]propyl]-2-methoxy-ethanesulfonamide (8 mg) as a yellow solid. $^1$H NMR (400 MHz, CDCl$_3$) δ: 9.06 (m, 2H), 8.82 (s, 1H), 7.46 (t, 1H), 6.46-6.36 (m, 2H), 5.01 (q, 1H), 4.66 (t, 1H), 4.20 (t, 2H), 3.83 (t, 2H), 3.78-3.71 (m, 1H), 3.56-3.48 (m, 1H), 3.41-3.35 (m, 2H), 3.37 (s, 3H), 3.34-3.28 (m, 4H), 2.12 (quin, 2H), 1.47 (d, 3H). MS obsd. (ESI$^+$) [(M+H$^+$)]: 535.

Example 95: 4-chloro-N-[3-[2,3-difluoro-5-(5-methyl-2-pyrimidin-2-yl-7,8-dihydro-5H-pyrido[4,3-d]pyrimidin-6-yl)phenoxy]propyl]butanamide

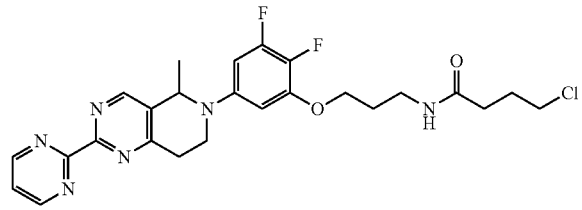 [SMILES: CC1c2cnc(-c3ncccn3)nc2CCN1c1cc(F)c(F)c(OCCCNC(=O)CCCCl)c1]

To a solution of 3-[2,3-difluoro-5-(5-methyl-2-pyrimidin-2-yl-7,8-dihydro-5H-pyrido[4,3-d]pyrimidin-6-yl)phenoxy]propan-1-amine hydrochloride (239 mg, 0.4 mmol) and DIEA (310 mg, 2.4 mmol) in DMF (3 mL) was added 4-chlorobutanoyl chloride (135 mg, 960 μmol) at 0° C. The resulting mixture was stirred at rt for 2 hrs and then partitioned between DCM and water. The separated aqueous layer was extracted with DCM (20 mL) for three times. The combined organic layer was washed with brine, dried over anhydrous Na$_2$SO$_4$ and concentrated in vacuo to give the crude product (300 mg). 150 mg of the crude product was purified by prep-HPLC to afford 4-chloro-N-[3-[2,3-difluoro-5-(5-methyl-2-pyrimidin-2-yl-7,8-dihydro-5H-pyrido[4,3-d]pyrimidin-6-yl)phenoxy]propyl]butanamide (5 mg) as a yellow solid. $^1$H NMR (400 MHz, CDCl$_3$) δ: 8.99-8.90 (m, 2H), 8.76 (s, 1H), 7.50 (s, 1H), 7.45-7.40 (m, 1H), 6.43-6.28 (m, 2H), 5.05 (d, 1H), 4.16-4.07 (m, 2H), 3.77-3.65 (m, 1H), 3.46-3.36 (m, 1H), 3.22-2.75 (m, 8H), 2.24-2.10 (m, 2H), 1.42-1.30 (m, 3H), 1.17 (s, 2H). MS obsd. (ESI$^+$) [(M+H$^+$)]: 517.

Example 96: 1-[3-[2,3-difluoro-5-(5-methyl-2-pyrimidin-2-yl-7,8-dihydro-5H-pyrido[4,3-d]pyrimidin-6-yl)phenoxy]propyl]pyrrolidin-2-one

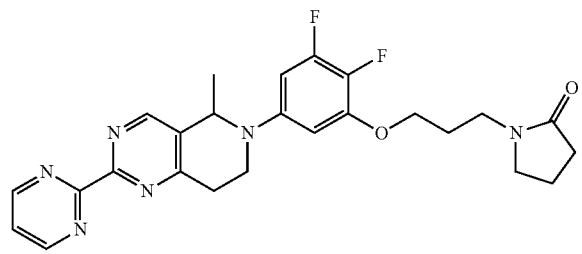 [SMILES: CC1c2cnc(-c3ncccn3)nc2CCN1c1cc(F)c(F)c(OCCCN2CCCC2=O)c1]

To a solution of 4-chloro-N-[3-[2,3-difluoro-5-(5-methyl-2-pyrimidin-2-yl-7,8-dihydro-5H-pyrido[4,3-d]pyrimidin-6-yl)phenoxy]propyl]butanamide (148 mg, 200 μmol) in DMF (3 mL) was added potassium tert-butoxide (67.3 mg, 600 μmol) at 0° C. After being stirred at rt overnight, the resulting reaction mixture was purified by prep-HPLC to afford 1-[3-[2,3-difluoro-5-(5-methyl-2-pyrimidin-2-yl-7,8-dihydro-5H-pyrido[4,3-d]pyrimidin-6-yl)phenoxy]propyl]pyrrolidin-2-one (5.7 mg) as a yellow solid. $^1$H NMR (400 MHz, CDCl$_3$) δ: 9.06 (s, 1H), 9.05 (s, 1H), 8.81 (s, 1H), 7.46 (t, 1H), 6.44-6.35 (m, 2H), 5.00 (q, 1H), 4.10 (t, 2H), 3.77-3.70 (m, 1H), 3.50 (m, 5H), 3.33-3.26 (m, 2H), 2.40 (t, 2H), 2.15-2.00 (m, 5H), 1.47 (d, 3H). MS obsd. (ESI$^+$) [(M+H$^+$)]: 481.

Example 97: 3-[2,3-difluoro-5-(5-methyl-2-pyrimidin-2-yl-7,8-dihydro-5H-pyrido[4,3-d]pyrimidin-6-yl)phenoxy]propane-1-sulfonamide

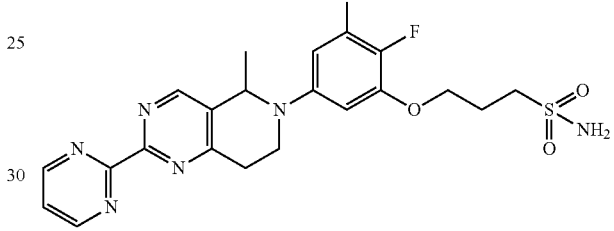

Step 1: Preparation of 3-[2,3-difluoro-5-(5-methyl-2-pyrimidin-2-yl-7,8-dihydro-5H-pyrido[4,3-d]pyrimidin-6-yl)phenoxy]propane-1-sulfonyl chloride

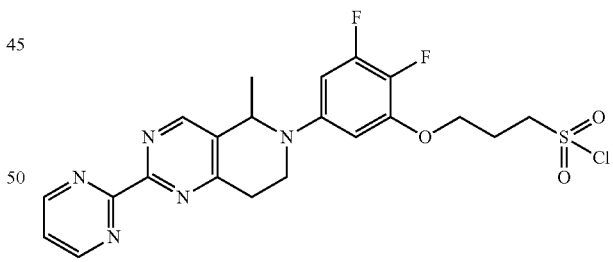

To a solution of 3-[2,3-difluoro-5-(5-methyl-2-pyrimidin-2-yl-7,8-dihydro-5H-pyrido[4,3-d]pyrimidin-6-yl)phenoxy]propane-1-sulfonic acid (80 mg, 0.17 mmol) in MeCN (2 mL) was added POCl$_3$ (128 mg, 0.84 mmol). After being heated at 85° C. with stirring for 6 hrs, the reaction mixture was cooled down to rt, diluted with DCM (60 mL), washed with H$_2$O (30 mL) and brine (30 mL), then dried over anhydrous Na$_2$SO$_4$ and concentrated in vacuo to afford crude 3-[2,3-difluoro-5-(5-methyl-2-pyrimidin-2-yl-7,8-dihydro-5H-pyrido[4,3-d]pyrimidin-6-yl)phenoxy]propane-1-sulfonyl chloride (50 mg) as yellow oil which was used directly in the next step without further purification.

Step 2: Preparation of 3-[2,3-difluoro-5-(5-methyl-2-pyrimidin-2-yl-7,8-dihydro-5H-pyrido[4,3-d]pyrimidin-6-yl)phenoxy]propane-1-sulfonamide

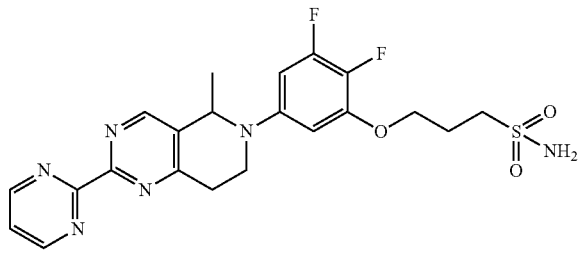 [SMILES: CC1c2cnc(-c3ncccn3)nc2CCN1c1cc(F)c(F)c(OCCCS(N)(=O)=O)c1]

To a mixture of 3-[2,3-difluoro-5-(5-methyl-2-pyrimidin-2-yl-7,8-dihydro-5H-pyrido[4,3-d]pyrimidin-6-yl)phenoxy]propane-1-sulfonyl chloride (50 mg, 0.10 mmol) in THF (1 mL) was added NH$_4$OH (1 mL) dropwise at 0° C. After being stirred for 12 hrs at rt, the reaction mixture was concentrated in vacuo and the residue was purified by prep-HPLC to afford 3-[2,3-difluoro-5-(5-methyl-2-pyrimidin-2-yl-7,8-dihydro-5H-pyrido[4,3-d]pyrimidin-6-yl)phenoxy]propane-1-sulfonamide (13 mg) as yellow solid. $^1$H NMR (400 MHz, CDCl$_3$) δ: 9.04 (d, 2H), 8.79 (s, 1H), 7.45 (M, 1H), 6.30-6.46 (m, 2H), 4.97 (m, 1H), 4.78 (br. s, 2H), 4.23 (m, 2H), 3.73 (d, 1H), 3.45-3.59 (m, 1H), 3.35-3.44 (m, 2H), 3.18-3.34 (m, 2H), 2.39 (m, 2H), 1.46 (d, 3H). MS obsd. (ESI$^+$) [(M+H$^+$)]: 477.

Example 98: tert-butyl 4-[3-[2,3-difluoro-5-(5-methyl-2-pyrimidin-2-yl-7,8-dihydro-5H-pyrido[4,3-d]pyrimidin-6-yl)phenoxy]propyl]-3-oxo-piperazine-1-carboxylate

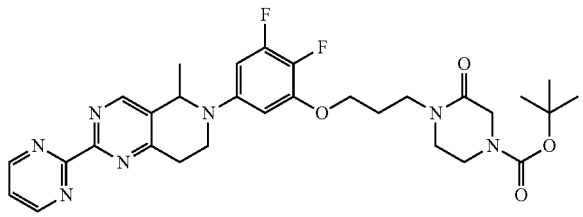 [SMILES: CC1c2cnc(-c3ncccn3)nc2CCN1c1cc(F)c(F)c(OCCCN2CCN(C(=O)OC(C)(C)C)CC2=O)c1]

Step 1: Preparation of tert-butyl 4-(3-bromopropyl)-3-oxo-piperazine-1-carboxylate

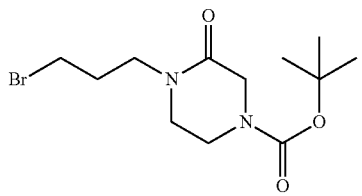 [SMILES: CC(C)(C)OC(=O)N1CCN(CCCBr)C(=O)C1]

To a cooled solution of tert-butyl 3-oxopiperazine-1-carboxylate (1.0 g, 4.99 mmol) in DMF (10 mL) was added NaH (240 mg, 5.99 mmol, 60% wt) at 0° C. slowly. The resulting mixture was warmed to rt and stirred for 90 mins. Then to the reaction mixture was added a solution of 1,3-dibromopropane (1.1 g, 5.49 mmol) in DMF (5 mL). After being stirred at rt for another 30 mins, the reaction mixture was diluted with saturated aqueous solution of NH$_4$Cl (30 mL) and extracted with EA (150 mL) for three times. The combined organic layer was washed with brine (200 mL), dried over anhydrous Na$_2$SO$_4$ and concentrated in vacuo. The residue was purified by chromatography on silica gel to give tert-butyl 4-(3-bromopropyl)-3-oxo-piperazine-1-carboxylate (600 mg) as a yellow oil.

Step 2: Preparation of tert-butyl 4-[3-[2,3-difluoro-5-(5-methyl-2-pyrimidin-2-yl-7,8-dihydro-5H-pyrido[4,3-d]pyrimidin-6-yl)phenoxy]propyl]-3-oxo-piperazine-1-carboxylate

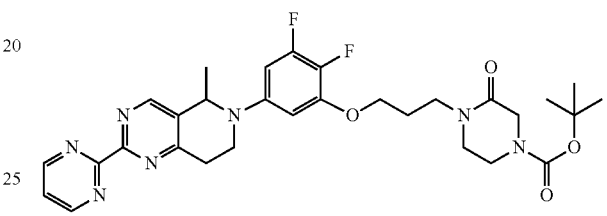

To a solution of tert-butyl 4-(3-bromopropyl)-3-oxo-piperazine-1-carboxylate (250 mg, 1.126 mmol) in DMF (5 mL) was added K$_2$CO$_3$ (117 mg, 0.847 mmol) and 2,3-difluoro-5-(5-methyl-2-pyrimidin-2-yl-7,8-dihydro-5H-pyrido[4,3-d]pyrimidin-6-yl)phenol (200 mg, 0.563 mmol). After being stirred at rt for 16 hrs, the reaction mixture was diluted with water (50 mL) and extracted with DCM (100 mL) twice. The combined organic phase was washed with brine (200 mL), dried over anhydrous Na$_2$SO$_4$ and concentrated in vacuo. The residue was purified by prep-HPLC to give tert-butyl 4-[3-[2,3-difluoro-5-(5-methyl-2-pyrimidin-2-yl-7,8-dihydro-5H-pyrido[4,3-d]pyrimidin-6-yl)phenoxy]propyl]-3-oxo-piperazine-1-carboxylate (161 mg) as a pale yellow solid. $^1$H NMR (400 MHz, CDCl$_3$) δ: 9.04 (d, 2H), 8.79 (s, 1H), 7.44 (br. s, 1H), 6.37 (d, 2H), 4.98 (d, 1H), 4.01-4.20 (m, 4H), 3.58-3.78 (m, 5H), 3.38-3.54 (m, 3H), 3.20-3.36 (m, 2H), 2.06-2.19 (m, 2H), 1.32-1.57 (m, 12H). MS obsd. (ESI$^+$) [(M+H)$^+$]: 596.

Example 99: 1-[3-[2,3-difluoro-5-(5-methyl-2-pyrimidin-2-yl-7,8-dihydro-5H-pyrido[4,3-d]pyrimidin-6-yl)phenoxy]propyl]piperazin-2-one

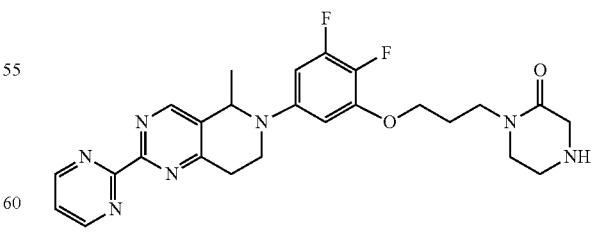

A solution of tert-butyl 4-[3-[2,3-difluoro-5-(5-methyl-2-pyrimidin-2-yl-7,8-dihydro-5H-pyrido[4,3-d]pyrimidin-6-yl)phenoxy]propyl]-3-oxo-piperazine-1-carboxylate (140 mg, 0.235 mmol, Example 98) was stirred with a 1.0 N HCl in EA (20 mL) at rt for 16 hrs. The reaction mixture was concentrated in vacuo and the residue was purified by prep-HPLC to give 1-[3-[2,3-difluoro-5-(5-methyl-2-pyrimidin-2-yl-7,8-dihydro-5H-pyrido[4,3-d]pyrimidin-6-yl)phenoxy]propyl]-piperazin-2-one (25 mg) as a pale yellow solid. $^1$H NMR (400 MHz, DMSO-d$_6$) δ: 10.18 (br. s, 2H), 9.01 (d, 2H), 8.90 (br. s, 1H), 7.67 (br. s, 1H), 6.59-6.76 (m, 2H), 5.42 (d, 1H), 4.18 (d, 2H), 3.86-4.01 (m, 1H), 3.34-3.65 (m, 9H), 2.94-3.19 (m, 2H), 1.93-2.03 (m, 2H), 1.40 (d, 3H). MS obsd. (ESI$^+$) [(M+H)$^+$]: 496.

Example 100: 3-[[3-fluoro-5-(5-methyl-2-pyrimidin-2-yl-7,8-dihydro-5H-pyrido[4,3-d]pyrimidin-6-yl)phenoxy]methyl]thiolane 1,1-dioxide

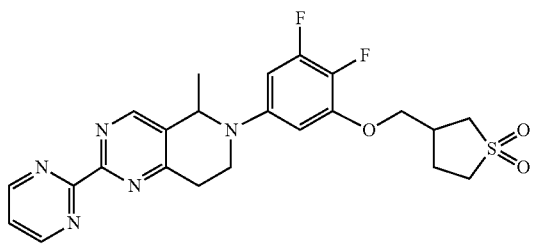 [SMILES: CC1c2cnc(-c3ncccn3)nc2CCN1c1cc(F)c(F)c(OCC2CCS(=O)(=O)C2)c1]

Step 1: Preparation of 3-(p-tolylsulfonylmethyl)thiolane 1,1-dioxide

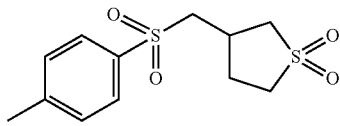 [SMILES: Cc1ccc(S(=O)(=O)CC2CCS(=O)(=O)C2)cc1]

To a stirred solution of (1, 1-dioxidotetrahydro-3-thienyl)-methanol (200 mg, 1.33 mmol) in DCM (5 mL) was added Et$_3$N (202 mg, 2.00 mmol) followed by addition of a solution of 4-methylbenzenesulfonyl chloride (305 mg, 1.60 mmol) in DCM (3 mL) dropwise. After being stirred at rt for 16 hrs, the resulting mixture was diluted with DCM (20 mL), and then washed with H$_2$O (10 mL), aqueous HCl (10 mL, 2.0 M) and brine (10 mL) successively. The organic phase was dried over anhydrous Na$_2$SO$_4$ and concentrated in vacuo to give 3-(p-tolylsulfonylmethyl)thiolane 1,1-dioxide (200 mg) as colorless oil.

Step 2: Preparation of 3-[[3-fluoro-5-(5-methyl-2-pyrimidin-2-yl-7,8-dihydro-5H-pyrido[4,3-d]pyrimidin-6-yl)phenoxy]methyl]thiolane 1,1-dioxide

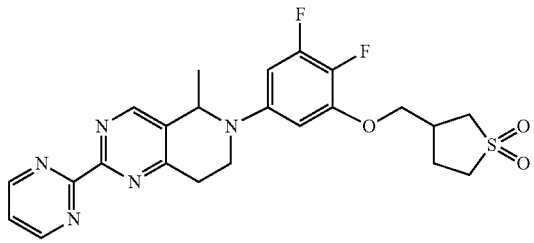 [SMILES: CC1c2cnc(-c3ncccn3)nc2CCN1c1cc(F)c(F)c(OCC2CCS(=O)(=O)C2)c1]

A mixture of 2,3-difluoro-5-(5-methyl-2-pyrimidin-2-yl-7,8-dihydro-5H-pyrido[4,3-d]pyrimidin-6-yl)phenol (150 mg, 0.42 mmol), 3-(p-tolylsulfonylmethyl)-thiolane-1,1-dioxide (200 mg, 0.66 mmol) and Cs$_2$CO$_3$ (344 mg, 1.06 mmol) in DMF (5 mL) was heated at 80° C. with stirring for 12 hrs. The reaction mixture was cooled down to rt and diluted with EA (20 mL). The organic phase was washed with brine (10 mL), dried over anhydrous Na$_2$SO$_4$ and concentrated in vacuo. The residue was purified by the pre-HPLC to give 3-[[3-fluoro-5-(5-methyl-2-pyrimidin-2-yl-7,8-dihydro-5H-pyrido[4,3-d]pyrimidin-6-yl)phenoxy]methyl]thiolane 1,1-dioxide (33 mg) as a yellow solid. $^1$H NMR (400 MHz, CDCl$_3$) δ: 9.04 (d, 2H), 8.79 (s, 1H), 7.45 (t, 1H), 6.44 (m, 1H), 6.34 (dd, 2.26 Hz, 1H), 4.97 (q, 1H), 4.05-4.19 (m, 2H), 3.67-3.79 (m, 1H), 3.45-3.58 (m, 1H), 3.22-3.39 (m, 4H), 2.92-3.19 (m, 3H), 2.39-2.54 (m, 1H), 2.08-2.27 (m, 1H), 1.46 (d, 3H). MS obsd. (ESI$^+$) [(M+H)$^+$]: 488.

Example 101: 6-[3,4-difluoro-5-[3-(4-methylpiperazin-1-yl)propoxy]phenyl]-5-methyl-2-pyrimidin-2-yl-7,8-dihydro-5H-pyrido[4,3-d]pyrimidine

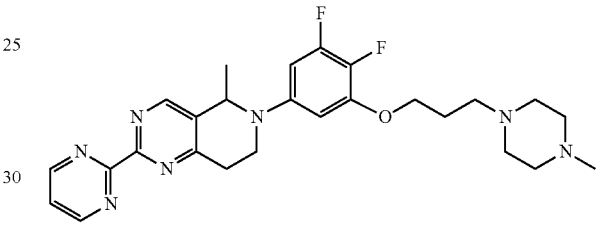

A mixture of 2,3-difluoro-5-(5-methyl-2-pyrimidin-2-yl-7,8-dihydro-5H-pyrido[4,3-d]pyrimidin-6-yl)phenol (100 mg, 281 μmol), 1-(3-chloropropyl)-4-methylpiperazine (149 mg, 844 μmol), KI (46.7 mg, 281 μmol) and K$_2$CO$_3$ (117 mg, 844 μmol) in DMF (10 mL) was heated with stirring at 110° C. for 10 hrs. Then the resulting reaction mixture was concentrated in vacuo and the residue was purified by prep-HPLC to give 6-[3,4-difluoro-5-[3-(4-methylpiperazin-1-yl)propoxy]phenyl]-5-methyl-2-pyrimidin-2-yl-7,8-dihydro-5H-pyrido[4,3-d]pyrimidine (20 mg) as light yellow solid. $^1$H NMR (400 MHz, Methanol-d$_4$) δ: 9.06 (d, 2H), 8.88 (s, 1H), 7.67 (s, 1H), 6.48-6.66 (m, 2H), 5.16-5.29 (m, 1H), 4.13-4.23 (m, 2H), 3.81-3.94 (m, 1H), 3.48-3.67 (m, 2H), 3.12-3.28 (m, 2H), 2.61-2.95 (m, 9H), 2.50 (s, 3H), 1.96-2.13 (m, 2H), 1.48 (d, 3H). MS obsd. (ESI$^+$) [(M+H)$^+$]: 496.

Example 102: methyl 2-(tert-butoxycarbonylamino)-4-[2,3-difluoro-5-(5-methyl-2-pyrimidin-2-yl-7,8-dihydro-5H-pyrido[4,3-d]pyrimidin-6-yl)phenoxy]butanoate

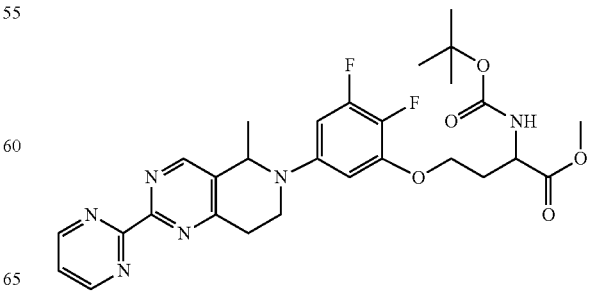

Step 1: Preparation of 2-(tert-butoxycarbonylamino)-4-hydroxy-butanoic acid

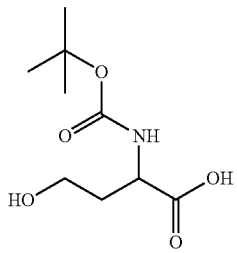

A mixture of DL-homoserine (2.0 g, 16.79 mmol, DIEA (4.3 g, 33.58 mmol) and Boc₂O (4.0 g, 18.47 mmol) in acetone (50 mL) and H₂O (50 mL) was stirred at 30° C. for 12 hrs. The resulting reaction mixture was concentrated in vacuo to give crude 2-(tert-butoxycarbonylamino)-4-hydroxy-butanoic acid (4.0 g) as yellow oil which was used directly in the next step without further purification.

Step 2: Preparation of methyl 2-(tert-butoxycarbonylamino)-4-hydroxy-butanoate

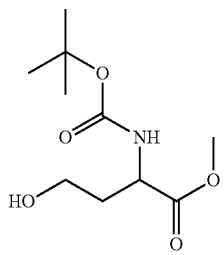 [SMILES: COC(=O)C(CCO)NC(=O)OC(C)(C)C]

To a stirred solution of crude 2-(tert-butoxycarbonylamino)-4-hydroxy-butanoic acid (4.0 g, 0.02 mol) in DMF (50 mL) was added CH₃I (5.82 g, 0.04 mol) slowly. The reaction mixture was stirred at 30° C. for 12 hrs, then diluted with EA (200 mL), and washed with HCl (1.0 M, 50 mL) and brine (50 mL). The organic phase was dried over anhydrous Na₂SO₄ and concentrated in vacuo to give methyl 2-(tert-butoxycarbonylamino)-4-hydroxy-butanoate (3.5 g) as yellow oil which was used directly in the next step without further purification.

Step 3: Preparation of methyl 2-(tert-butoxycarbonylamino)-4-methylsulfonyloxy-butanoate

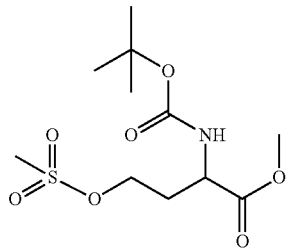 [SMILES: COC(=O)C(CCOS(C)(=O)=O)NC(=O)OC(C)(C)C]

To a stirred solution of methyl 2-(tert-butoxycarbonylamino)-4-hydroxy-butanoate (500 mg, 2.14 mmol) and Et₃N (282 mg, 2.79 mmol) in DCM (10 mL) was added methanesulfonyl chloride (230 mg, 2.01 mmol) slowly at −15° C. Then the reaction mixture was warmed up to 0° C. and stirred for 1 hr. The reaction was quenched by addition of saturated aqueous NH₄Cl solution. The resulting mixture was extracted with DCM (30 mL) for three times. The organic phases were combined, washed with HCl (20 mL, 1.0 M) and brine (30 mL), dried over anhydrous Na₂SO₄, and concentrated in vacuo to give methyl 2-(tert-butoxycarbonylamino)-4-methylsulfonyloxy-butanoate (450 mg) as a white solid which was used directly in the next step without further purification.

Step 4: Preparation of methyl 2-(tert-butoxycarbonylamino)-4-[2,3-difluoro-5-(5-methyl-2-pyrimidin-2-yl-7,8-dihydro-5H-pyrido[4,3-d]pyrimidin-6-yl)phenoxy]butanoate

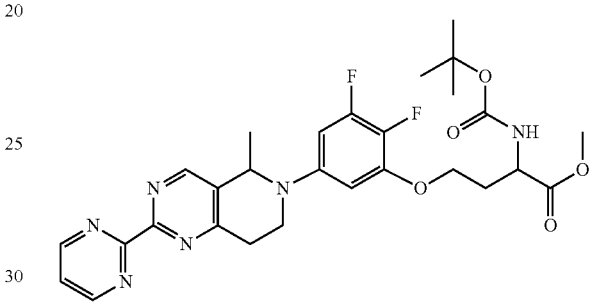

A mixture of 2,3-difluoro-5-(5-methyl-2-pyrimidin-2-yl-7,8-dihydro-5H-pyrido[4,3-d]pyrimidin-6-yl)phenol (500 mg, 1.41 mmol), methyl 2-(tert-butoxycarbonylamino)-4-methylsulfonyloxy-butanoate (450 mg, 1.44 mmol) and K₂CO₃ (350 mg, 2.53 mmol) in DMF (10 mL) was stirred at 15° C. for 16 hrs. The reaction mixture was diluted with EA (100 mL) and washed with brine (60 mL). The organic phase was dried over anhydrous Na₂SO₄ and concentrated in vacuo. The residue was purified by prep-HPLC to give methyl 2-(tert-butoxycarbonylamino)-4-[2,3-difluoro-5-(5-methyl-2-pyrimidin-2-yl-7,8-dihydro-5H-pyrido[4,3-d]pyrimidin-6-yl)phenoxy]butanoate (310 mg) as a yellow solid. ¹H NMR (400 MHz, CDCl₃) δ: 9.04 (d, 2H), 8.79 (s, 1H), 7.45 (t, 1H), 6.32-6.44 (m, 2H), 5.40 (s, 0.5H), 4.98 (q, 1H), 4.54 (s, 0.5H), 4.06-4.22 (m, 2H), 3.79 (s, 3H), 3.66-3.76 (m, 1H), 3.43-3.55 (m, 1H), 3.17-3.39 (m, 2H), 2.04-2.32 (m, 2H), 1.42-1.47 (m, 12H). MS obsd. (ESI⁺) [(M+H)⁺]: 571.

Example 103: 2-(tert-butoxycarbonylamino)-4-[2,3-difluoro-5-(5-methyl-2-pyrimidin-2-yl-7,8-dihydro-5H-pyrido[4,3-d]pyrimidin-6-yl)phenoxy]butanoic acid

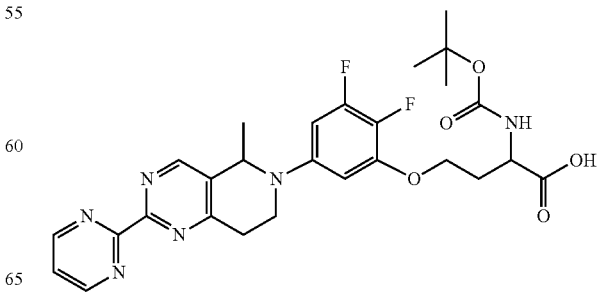

To a solution of methyl 2-(tert-butoxycarbonylamino)-4-[2,3-difluoro-5-(5-methyl-2-pyrimidin-2-yl-7,8-dihydro-5H-pyrido[4,3-d]pyrimidin-6-yl)phenoxy]butanoate (120 mg, 0.21 mmol) in THF (2 mL) was added an aqueous solution of LiOH (0.6 mL, 1.0 M) and the reaction mixture was stirred at 15° C. for 16 hrs. The resulting reaction mixture was acidified to pH 3-4 with HCl (1.0 M), and then concentrated in vacuo. The residue was purified by prep-HPLC to give 2-(tert-butoxycarbonylamino)-4-[2,3-difluoro-5-(5-methyl-2-pyrimidin-2-yl-7,8-dihydro-5H-pyrido[4,3-d]pyrimidin-6-yl)phenoxy]butanoic acid (40 mg) as a white solid. $^1$H NMR (400 MHz, Methanol-d$_4$) δ: 9.04 (d, 2H), 8.86 (s, 1H), 7.65 (t, 1H), 6.49-6.63 (m, 2H), 5.16-5.26 (m, 1H), 4.38 (s, 1H), 4.14-4.23 (m, 2H), 3.80-3.89 (m, 1H), 3.48-3.59 (m, 1H), 3.13-3.28 (m, 2H), 2.39-2.38 (m, 1H), 2.11-2.06 (m, 1H), 1.46 (d, 3H), 1.42 (s, 9H). MS obsd. (ESI$^+$) [(M+H)$^+$]: 557.

Example 104: 2-amino-4-[2,3-difluoro-5-(5-methyl-2-pyrimidin-2-yl-7,8-dihydro-5H-pyrido[4,3-d]pyrimidin-6-yl)phenoxy]butanoic acid

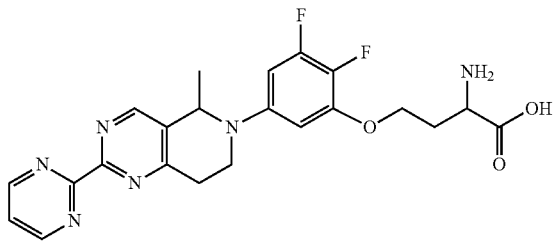 [SMILES: CC1c2cnc(-c3ncccn3)nc2CCN1c1cc(F)c(F)c(OCCC(N)C(=O)O)c1]

A mixture of 2-(tert-butoxycarbonylamino)-4-[2,3-difluoro-5-(5-methyl-2-pyrimidin-2-yl-7,8-dihydro-5H-pyrido[4,3-d]pyrimidin-6-yl)phenoxy]butanoic acid (29 mg, 0.052 mmol) and a solution of HCl in 1, 4-dioxane (1 mL, 4.0 M) was stirred at 15° C. for 16 hrs. The resulting reaction mixture was concentrated in vacuo and the residue was purified by prep-HPLC to give 2-amino-4-[2,3-difluoro-5-(5-methyl-2-pyrimidin-2-yl-7,8-dihydro-5H-pyrido[4,3-d]pyrimidin-6-yl)phenoxy]butanoic acid (7 mg) as a white solid. $^1$H NMR (400 MHz, Methanol-d$_4$) δ: 9.04 (d, 2H), 8.86 (s, 1H), 7.65 (t, 1H), 6.62-6.58 (m, 2H), 5.25-5.23 (m, 1H), 4.63 (s, 1H), 4.33-4.13 (m, 2H), 3.86-3.83 (m, 1H), 3.37-3.33 (m, 1H), 3.23-3.20 (m, 2H), 2.34-2.31 (m, 1H), 2.06-2.03 (m, 1H), 1.47 (d, 3H). MS obsd. (ESI$^+$) [(M+H)$^+$]: 457.

Example 105: 6-[3,4-difluoro-5-(2-tetrahydrofuran-2-ylethoxy)phenyl]-5-methyl-2-pyrimidin-2-yl-7,8-dihydro-5H-pyrido[4,3-d]pyrimidine

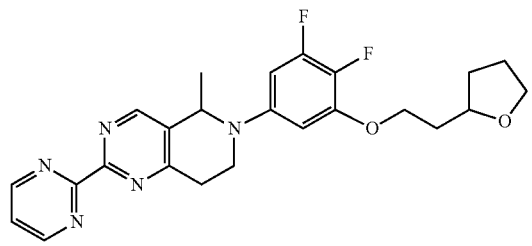 [SMILES: CC1c2cnc(-c3ncccn3)nc2CCN1c1cc(F)c(F)c(OCCC2CCCO2)c1]

Step 1: Preparation of 2-tetrahydrofuran-2-ylethanol

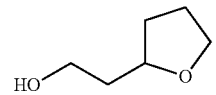

A solution of tetrahydrofuran-2-acetic acid ethyl ester (1.0 g, 6.32 mmol in THF (10 mL) was cooled to 0° C. and to the cooled solution was added LiAlH$_4$ (480 mg, 12.64 mmol) slowly. The resulting mixture was stirred at 15° C. for 2 hrs. The reaction was quenched by addition of water (20 mL). The resulting mixture was extracted with EA (100 mL) twice. The organic layers were combined, washed with brine (80 mL), dried over anhydrous Na$_2$SO$_4$ and concentrated in vacuo to give crude 2-tetrahydrofuran-2-ylethanol (650 mg) as colorless oil, which was used directly in the next step without further purification.

Step 2: Preparation of 2-tetrahydrofuran-2-ylethyl 4-methylbenzenesulfonate

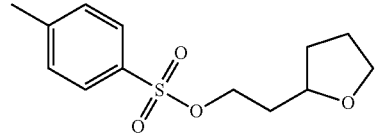 [SMILES: Cc1ccc(S(=O)(=O)OCCC2CCCO2)cc1]

To a solution of 2-tetrahydrofuran-2-ylethanol (650 mg, 5.596 mmol) in DCM (8 mL) was added Et$_3$N (1.13 g, 11.19 mmol) and tosyl chloride (853 mg, 4.48 mmol). The reaction mixture was stirred at 15° C. for 16 hrs. The resulting mixture was diluted with DCM (300 mL), washed with water (80 mL) and brine (100 mL), dried over anhydrous Na$_2$SO$_4$ and then concentrated in vacuo. The residue was purified by column chromatography on silica gel to give 2-tetrahydrofuran-2-ylethyl 4-methylbenzenesulfonate (290 mg) as yellow oil.

Step 3: Preparation of 6-[3,4-difluoro-5-(2-tetrahydrofuran-2-ylethoxy)phenyl]-5-methyl-2-pyrimidin-2-yl-7,8-dihydro-5H-pyrido[4,3-d]pyrimidine

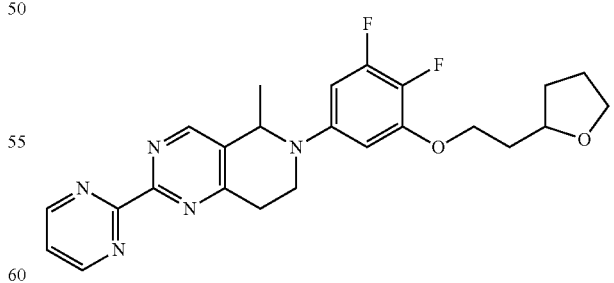

A mixture of 2-tetrahydrofuran-2-ylethyl 4-methylbenzenesulfonate (100 mg, 0.281 mmol, 2,3-difluoro-5-(5-methyl-2-pyrimidin-2-yl-7,8-dihydro-5H-pyrido[4,3-d]pyrimidin-6-yl)phenol (114 mg, 0.422 mmol) and Cs$_2$CO$_3$ (57 mg, 0.422 mmol) in DMF (3 mL) was heated with stirring at 80° C. for 12 hrs. The resulting reaction mixture was diluted with EA (100 mL), washed with water (50 mL) and brine (100 mL), dried over with anhydrous Na$_2$SO$_4$ and concentrated in vacuo. The residue was purified by prep-HPLC to give 6-[3,4-difluoro-5-(2-tetrahydrofuran-2-ylethoxy)phenyl]-5-methyl-2-pyrimidin-2-yl-7,8-dihydro-5H-pyrido[4,3-d]pyrimidine (45 mg) as a yellow solid. $^1$H NMR (400 MHz, CDCl$_3$) δ: 9.04 (d, 2H), 8.78 (s, 1H), 7.44 (t, 1H), 6.29-6.46 (m, 2H), 4.97 (q, 1H), 4.12-4.23 (m, 2H), 4.00-4.11 (m, 1H), 3.89 (q, 1H), 3.67-3.81 (m, 2H), 3.42-3.53 (m, 1H), 3.19-3.37 (m, 2H), 1.89-2.13 (m, 5H), 1.51-1.64 (m, 1H), 1.43 (d, 3H). MS obsd. (ESI$^+$) [(M+H)$^+$]: 454.

Example 106: 6-[3,4-difluoro-5-(3-methylsulfinylpropoxy)phenyl]-5-methyl-2-pyrimidin-2-yl-7,8-dihydro-5H-pyrido[4,3-d]pyrimidine

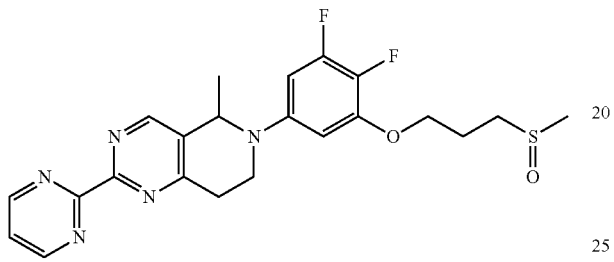

Step 1: preparation of 3-methylsulfanylpropyl 4-methylbenzenesulfonate

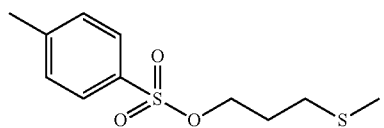

To a stirred mixture of 3-methylthiopropanol (5.0 g, 47.1 mmol) and DCM (50 mL) was added Et$_3$N (9.5 g, 94.2 mmol) followed by addition of a solution of tosyl chloride (7.2 g, 37.7 mmol) in DCM (20 mL) drop wise at 0° C. Then the reaction mixture was stirred for 12 hrs at 20° C., then diluted with DCM (200 mL), and washed with 2 N NaOH (50 mL), water (50 mL) and brine (50 mL) successively. The organic layer was dried over anhydrous Na$_2$SO$_4$ and concentrated in vacuo to give colorless oil, which was purified by the flash column to afford 3-methylsulfanylpropyl 4-methylbenzenesulfonate (7.0 g) as colorless oil.

Step 2: Preparation of 6-[3,4-difluoro-5-(3-methylsulfanylpropoxy)phenyl]-5-methyl-2-pyrimidin-2-yl-7,8-dihydro-5H-pyrido[4,3-d]pyrimidine

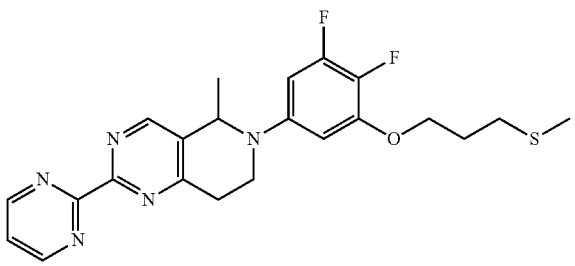

To a solution of 2,3-difluoro-5-(5-methyl-2-pyrimidin-2-yl-7,8-dihydro-5H-pyrido[4,3-d]pyrimidin-6-yl)phenol (100 mg, 0.28 mmol) in DMF (2 mL) was added 3-methylsulfanylpropyl 4-methylbenzenesulfonate (88 mg, 0.34 mmol) and Cs$_2$CO$_3$ (183 mg, 0.56 mmol). The mixture was stirred at 20° C. for 12 hrs. The mixture was diluted with EA (50 mL) and washed with water (30 mL) and brine (30 mL). The organic layer was dried over anhydrous Na$_2$SO$_4$ and concentrated in vacuo to give crude product as brown oil. It was purified by the flash column to afford of 6-[3,4-difluoro-5-(3-methylsulfanylpropoxy)phenyl]-5-methyl-2-pyrimidin-2-yl-7,8-dihydro-5H-pyrido[4,3-d]pyrimidine (40 mg) as brown oil.

Step 3: Preparation of 6-[3,4-difluoro-5-(3-methylsulfinylpropoxy)phenyl]-5-methyl-2-pyrimidin-2-yl-7,8-dihydro-5H-pyrido[4,3-d]pyrimidine

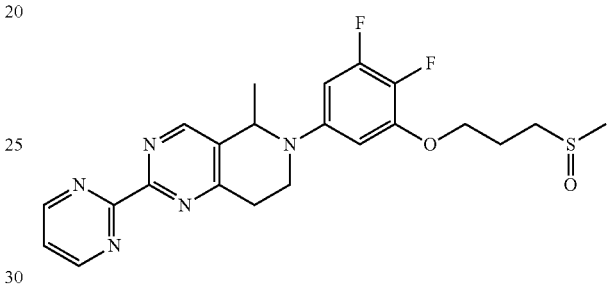

To a mixture of 6-[3,4-difluoro-5-(3-methylsulfanylpropoxy)phenyl]-5-methyl-2-pyrimidin-2-yl-7,8-dihydro-5H-pyrido[4,3-d]pyrimidine (35 mg, 0.079 mmol) in MeOH (1 mL) and H$_2$O (1 mL) was added oxone (24 mg, 0.039 mmol) at 0° C. The reaction mixture was stirred for 12 hrs at 20° C., then diluted with DCM (60 mL), and washed with aq. Na$_2$SO$_3$ (20 mL) and brine (30 mL). The organic layer was dried over anhydrous Na$_2$SO$_4$ and concentrated in vacuo. The residue was purified by prep-HPLC to afford 6-[3,4-difluoro-5-(3-methylsulfinylpropoxy)phenyl]-5-methyl-2-pyrimidin-2-yl-7,8-dihydro-5H-pyrido[4,3-d]pyrimidine (7.6 mg) as yellow solid. $^1$H NMR (400 MHz, CDCl$_3$) δ: 9.03 (d, 2H), 8.79 (s, 1H), 7.44 (m, 1H), 6.27-6.48 (m, 2H), 4.98 (m, 1H), 4.09-4.34 (m, 2H), 3.63-3.81 (m, 1H), 3.41-3.57 (m, 1H), 3.17-3.39 (m, 2H), 2.81-3.07 (m, 2H), 2.64 (s, 3H), 2.34 (t, 2H), 1.45 (d, 3H). MS obsd. (ESI$^+$) [(M+H$^+$)]: 460.

Example 107: 4-[3-[2,3-difluoro-5-(5-methyl-2-pyrimidin-2-yl-7,8-dihydro-5H-pyrido[4,3-d]pyrimidin-6-yl)phenoxy]propyl]piperazin-2-one

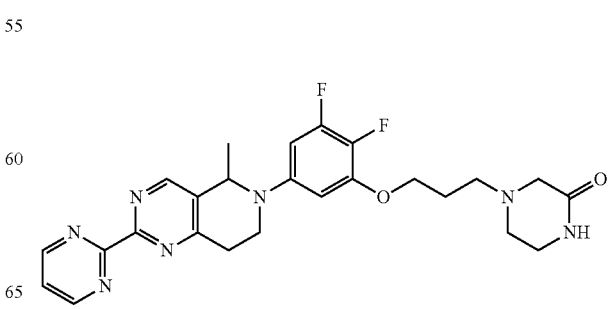

Step 1: Preparation of 6-[3-(3-bromopropoxy)-4,5-difluoro-phenyl]-5-methyl-2-pyrimidin-2-yl-7,8-dihydro-5H-pyrido[4,3-d]pyrimidine

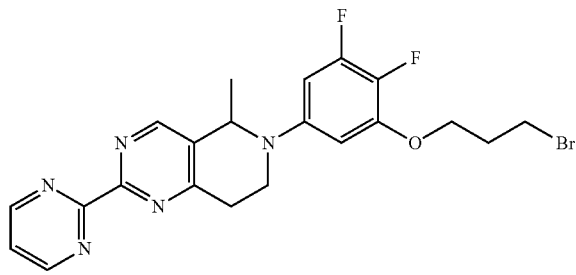 [SMILES: CC1c2cnc(-c3ncccn3)nc2CCN1c1cc(F)c(F)c(OCCCBr)c1]

A mixture of 2,3-difluoro-5-(5-methyl-2-pyrimidin-2-yl-7,8-dihydro-5H-pyrido[4,3-d]pyrimidin-6-yl)phenol (100 mg, 0.282 mmol), 1,3-dibromopropane (70 mg, 0.338 mmol) and K$_2$CO$_3$ (60 mg, 0.423 mmol) in DMF (3 mL) was stirred at 15° C. for 16 hrs. The resulting reaction mixture was diluted with H$_2$O (50 mL) and extracted with DCM (100 mL) twice. The organic layer was washed with brine (30 mL), dried over with anhydrous Na$_2$SO$_4$ and concentrated in vacuo. The residue was purified by flash column to give 6-[3-(3-bromopropoxy)-4,5-difluoro-phenyl]-5-methyl-2-pyrimidin-2-yl-7,8-dihydro-5H-pyrido[4,3-d]pyrimidine (110 mg) as a red solid.

Step 2: Preparation of 4-[3-[2,3-difluoro-5-(5-methyl-2-pyrimidin-2-yl-7,8-dihydro-5H-pyrido[4,3-d]pyrimidin-6-yl)phenoxy]propyl]piperazin-2-one

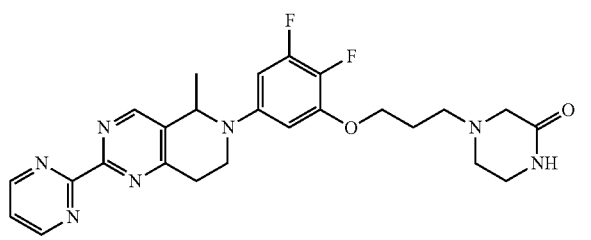 [SMILES: CC1c2cnc(-c3ncccn3)nc2CCN1c1cc(F)c(F)c(OCCCN2CCNC(=O)C2)c1]

A mixture of 6-[3-(3-bromopropoxy)-4,5-difluoro-phenyl]-5-methyl-2-pyrimidin-2-yl-7,8-dihydro-5H-pyrido[4,3-d]pyrimidine (100 mg, 0.210 mmol), piperazin-2-one (42 mg, 0.420 mmol) and K$_2$CO$_3$ (46 mg, 0.315 mmol) in DMF (3 mL) was stirred at 15° C. for 16 hrs. The resulting reaction mixture was diluted with water (20 mL) and extracted with EA (100 mL) for three times. The organic layers were combined, washed with brine (80 mL), dried over with anhydrous Na$_2$SO$_4$ and concentrated in vacuo. The residue was purified by prep-HPLC to give 4-[3-[2,3-difluoro-5-(5-methyl-2-pyrimidin-2-yl-7,8-dihydro-5H-pyrido[4,3-d]pyrimidin-6-yl)phenoxy]propyl]piperazin-2-one (5 mg) as a brown solid. $^1$H NMR (400 MHz, CDCl$_3$) δ: 9.05 (d, 2H), 8.80 (s, 1H), 7.45 (t, 1H), 6.34-6.43 (m, 2H), 6.22 (br. s, 1H), 4.97 (q, 1H), 4.13 (t, 2H), 3.72 (dd, 1H), 3.45-3.55 (m, 1H), 3.34-3.43 (m, 2H), 3.24-3.35 (m, 2H), 3.19 (s, 2H), 2.62-2.76 (m, 4H), 1.99-2.05 (m, 2H), 1.45 (d, 3H). MS obsd. (ESI$^+$) [(M+H)$^+$]: 496.

Example 108: tert-butyl 4-[3-[2,3-difluoro-5-(5-methyl-2-pyrimidin-2-yl-7,8-dihydro-5H-pyrido[4,3-d]pyrimidin-6-yl)phenoxy]propyl]piperazine-1-carboxylate

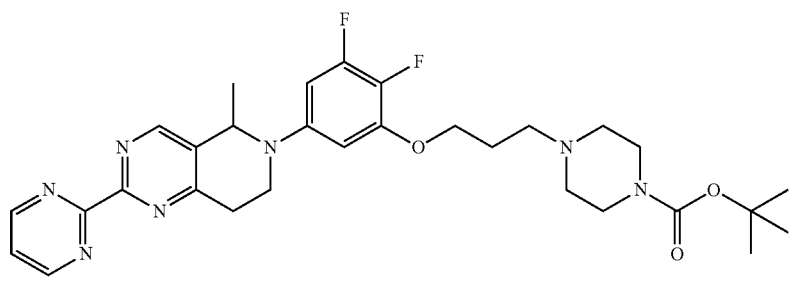 [SMILES: CC1c2cnc(-c3ncccn3)nc2CCN1c1cc(F)c(F)c(OCCCN2CCN(C(=O)OC(C)(C)C)CC2)c1]

A mixture of 2,3-difluoro-5-(5-methyl-2-pyrimidin-2-yl-7,8-dihydro-5H-pyrido[4,3-d]pyrimidin-6-yl)phenol (400 mg, 1.13 mmol), tert-butyl 4-(3-chloropropyl)-piperazine-1-carboxylate (887 mg, 3.38 mmol), KI (187 mg, 1.13 mmol) and K$_2$CO$_3$ (467 mg, 3.38 mmol) in DMF (10 ml) was heated with stirring at 110° C. for 10 hrs. The resulting mixture was concentrated in vacuo and the residue was purified by flash column to give a white solid (200 mg). The white solid was further purified by prep-HPLC to give tert-butyl 4-[3-[2,3-difluoro-5-(5-methyl-2-pyrimidin-2-yl-7,8-dihydro-5H-pyrido[4,3-d]pyrimidin-6-yl)phenoxy]propyl]piperazine-1-carboxylate (43 mg). $^1$H NMR (400 MHz, CDCl3) δ: 9.05 (d, 2H), 8.79 (s, 1H), 7.39-7.52 (m, 1H), 6.33-6.47 (m, 2H), 4.90-5.03 (m, 1H), 4.06-4.17 (m, 2H), 3.67-3.78 (m, 1H), 3.39-3.58 (m, 5H), 3.20-3.38 (m, 2H), 2.50-2.62 (m, 2H), 2.35-2.49 (m, 4H), 1.94-2.09 (m, 2H), 1.38-1.54 (m, 12H). MS obsd. (ESI$^+$) [(M+H)$^+$]: 582.

Example 109: 1-[4-[3-[2,3-difluoro-5-(5-methyl-2-pyrimidin-2-yl-7,8-dihydro-5H-pyrido[4,3-d]pyrimidin-6-yl)phenoxy]propyl]piperazin-1-yl]ethanone

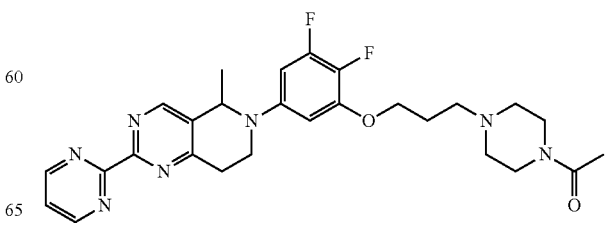

Step 1: Preparation of 6-[3,4-difluoro-5-(3-piperazin-1-ylpropoxy)phenyl]-5-methyl-2-pyrimidin-2-yl-7,8-dihydro-5H-pyrido[4,3-d]pyrimidine hydrochloride

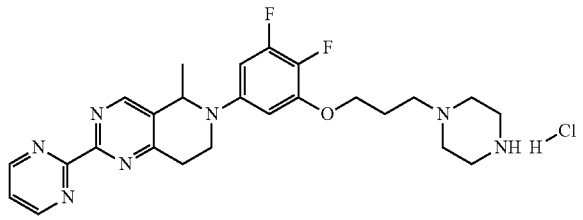

A mixture of tert-butyl 4-[3-[2,3-difluoro-5-(5-methyl-2-pyrimidin-2-yl-7,8-dihydro-5H-pyrido[4,3-d]pyrimidin-6-yl)phenoxy]propyl]piperazine-1-carboxylate (589 mg, 1.01 mmol) and a solution of HCl in 1,4-dioxane (1.3 M) (13 mL, 13 mmol) was stirred for 10 mins and then concentrated in vacuo to give 6-[3,4-difluoro-5-(3-piperazin-1-ylpropoxy)phenyl]-5-methyl-2-pyrimidin-2-yl-7,8-dihydro-5H-pyrido[4,3-d]pyrimidine hydrochloride as a yellow solid (450 mg).

Step 2: Preparation of 1-[4-[3-[2,3-difluoro-5-(5-methyl-2-pyrimidin-2-yl-7,8-dihydro-5H-pyrido[4,3-d]pyrimidin-6-yl)phenoxy]propyl]piperazin-1-yl]ethanone

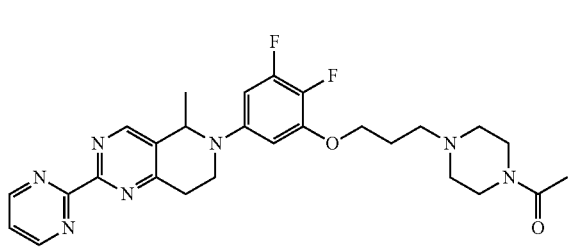 [SMILES: CC(=O)N1CCN(CCCOc2cc(N3CCc4nc(-c5ncccn5)ncc4C3C)cc(F)c2F)CC1]

A mixture of 6-[3,4-difluoro-5-(3-piperazin-1-ylpropoxy)phenyl]-5-methyl-2-pyrimidin-2-yl-7,8-dihydro-5H-pyrido[4,3-d]pyrimidine hydrochloride (100 mg, 193 μmol), acetic anhydride (106 mg, 1.04 mmol) and pyridine (45.8 mg, 579 μmol) in DCM (10 ml) was stirred at room temperature overnight. Then the resulting mixture was concentrated in vacuo. The residue was purified by prep-HPLC to give 1-[4-[3-[2,3-difluoro-5-(5-methyl-2-pyrimidin-2-yl-7,8-dihydro-5H-pyrido[4,3-d]pyrimidin-6-yl)phenoxy]propyl]piperazin-1-yl]ethanone (3.6 mg). $^1$H NMR (400 MHz, CDCl$_3$) δ: 9.05 (d, 2H), 8.79 (s, 1H), 7.46 (s, 1H), 6.38 (d, 2H), 4.89-5.05 (m, 1H), 4.04-4.20 (m, 2H), 3.60-3.80 (m, 3H), 3.41-3.60 (m, 3H), 3.18-3.37 (m, 2H), 2.39-2.73 (m, 6H), 1.89-2.19 (m, 5H), 1.46 (d, 3H). MS obsd. (ESI$^+$) [(M+H)$^+$]: 524.

Example 110: 6-[3,4-difluoro-5-[3-(4-methylsulfonylpiperazin-1-yl)propoxy]phenyl]-5-methyl-2-pyrimidin-2-yl-7,8-dihydro-5H-pyrido[4,3-d]pyrimidine

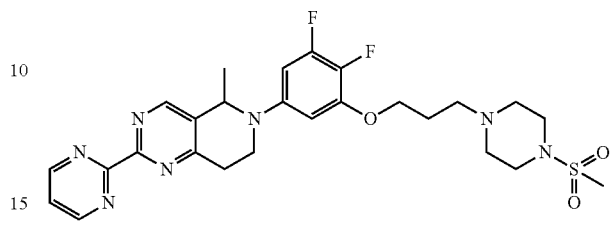

A mixture of 6-[3,4-difluoro-5-(3-piperazin-1-ylpropoxy)phenyl]-5-methyl-2-pyrimidin-2-yl-7,8-dihydro-5H-pyrido[4,3-d]pyrimidine hydrochloride (100 mg, 193 μmol), methanesulfonic anhydride (33.6 mg, 193 μmol) and pyridine (45.8 mg, 579 μmol) in DCM (10 mL) was stirred at rt overnight. The resulting reaction mixture was poured into H$_2$O (10 mL) and extracted with DCM (25 mL) twice. The organic layers were combined, dried over Na$_2$SO$_4$ and concentrated in vacuo. The residue was purified by prep-HPLC to give 6-[3,4-difluoro-5-[3-(4-methylsulfonylpiperazin-1-yl)propoxy]phenyl]-5-methyl-2-pyrimidin-2-yl-7,8-dihydro-5H-pyrido[4,3-d]pyrimidine (8 mg). $^1$H NMR (400 MHz, CDCl$_3$) δ: 9.06 (d, 2H), 8.80 (s, 1H), 7.46 (s, 1H), 6.31-6.47 (m, 2H), 4.86-5.05 (m, 1H), 4.13 (s, 2H), 3.62-3.77 (m, 1H), 3.45-3.61 (m, 1H), 3.22-3.42 (m, 6H), 2.81 (s, 9H), 1.96-2.15 (m, 2H), 1.36-1.52 (m, 3H). MS obsd. (ESI$^+$) [(M+H)$^+$]: 560.

Example 111: 6-(3-fluoro-4-iodo-5-methoxy-phenyl)-5-methyl-2-pyrimidin-2-yl-7,8-dihydro-5H-pyrido[4,3-d]pyrimidine

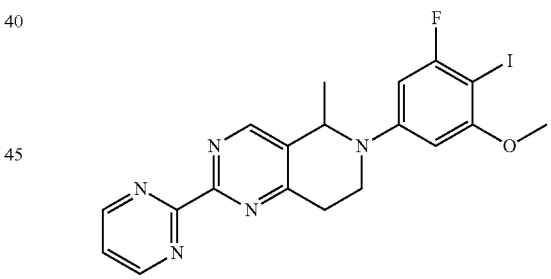

Step 1: Preparation of 6-(3-fluoro-4-iodo-5-methoxy-phenyl)-5-methoxy-2-pyrimidin-2-yl-7,8-dihydro-5H-pyrido[4,3-d]pyrimidine

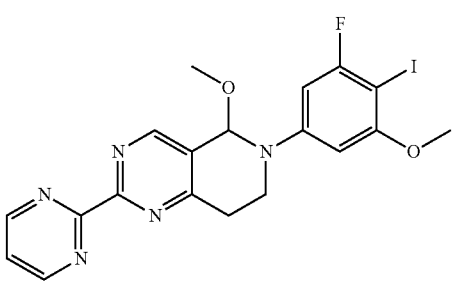

To a solution of 6-(3-fluoro-4-iodo-5-methoxy-phenyl)-2-pyrimidin-2-yl-7,8-dihydro-5H-pyrido[4,3-d]pyrimidine (2.0 g, 5.93 mmol) in DCM (135 mL) and MeOH (25 mL) was added ruthenium(III) chloride hydrate (401 mg, 1.78 mmol) and a solution of sodium period ate (3.8 g, 17.79 mmol) in H₂O (40 mL) successively at −70° C. The cooling bath was removed and the reaction mixture was warmed naturally to 15° C. and stirred at this temperature for 48 hrs. After the reaction was quenched with saturated aqueous Na₂SO₃ solution, the resulting mixture was diluted with H₂O (50 mL) and extracted with DCM (50 mL) for three times. The organic layers were washed brine (30 mL), dried over Na₂SO₄ and concentrated in vacuo to get 6-(3-fluoro-4-iodo-5-methoxy-phenyl)-5-methoxy-2-pyrimidin-2-yl-7,8-dihydro-5H-pyrido[4,3-d]pyrimidine (2.0 g, crude) as black solid which was used directly in the next step without any further purification.

Step 2: Preparation of 6-(3-fluoro-4-iodo-5-methoxy-phenyl)-5-methyl-2-pyrimidin-2-yl-7,8-dihydro-5H-pyrido[4,3-d]pyrimidine

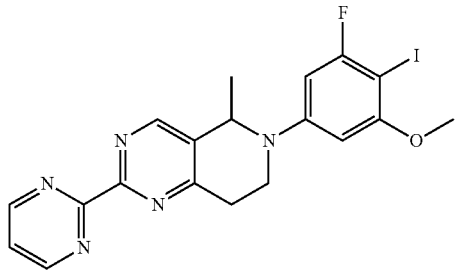

A stirred solution of 6-(3-fluoro-4-iodo-5-methoxy-phenyl)-5-methoxy-2-pyrimidin-2-yl-7,8-dihydro-5H-pyrido[4,3-d]pyrimidine (2.0 g, 5.4 mmol) in THF (100 mL) was cooled to −70° C. To the solution was added BF₃.Et₂O (2.3 g, 16.3 mmol) followed by a solution of MeMgBr (5.4 mL, 16.3 mmol) in Et₂O. The resulting reaction mixture was warmed up to 0° C. and stirred for 1 hr. The reaction was quenched by addition of saturated aqueous NH₄Cl (20 mL) solution and the resulting mixture was extracted with EA (30 mL) for three times. The organic layers were washed with brine (50 mL), dried over anhydrous Na₂SO₄ and concentrated in vacuo. The residue was purified by prep-HPLC to give 6-(3-fluoro-4-iodo-5-methoxy-phenyl)-5-methoxy-2-pyrimidin-2-yl-7,8-dihydro-5H-pyrido[4,3-d]pyrimidine (63 mg) as a white solid. ¹H NMR (400 MHz, CDCl₃) δ: 9.04 (d, 2H), 8.81 (s, 1H), 7.45 (t, 1H), 6.39 (dd, 1H), 6.27 (d, 1H), 5.09 (q, 1H), 3.92 (s, 3H), 3.79-3.91 (m, 1H), 3.56 (ddd, 1H), 3.23-3.40 (m, 2H), 1.52 (d, 3H). MS obsd. (ESI⁺) [(M+H)⁺]: 478.

Example 112: 6-[3-methoxy-5-(trifluoromethyl)phenyl]-5-methyl-2-pyrimidin-2-yl-7,8-dihydro-5H-pyrido[4,3-d]pyrimidine

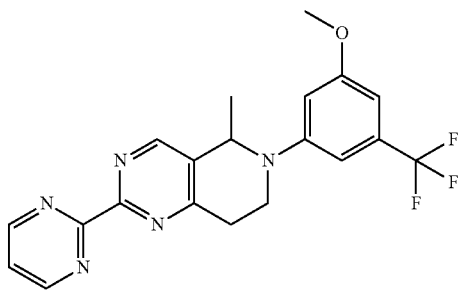 [SMILES: COc1cc(N2CCc3nc(-c4ncccn4)ncc3C2C)cc(C(F)(F)F)c1]

Step 1: Preparation of 1-bromo-3-methoxy-5-(trifluoromethyl)benzene

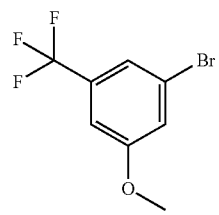

A mixture of 3-(tert-butyl)-5-methylphenol (1.5 g, 9.13 mmol), iodomethane (1.43 g, 10 mmol) and K₂CO₃ (1.89 g, 13.7 mmol) in acetone (20 mL) was heated with stirring at 60° C. for 3 hrs. Then the resulting mixture was cooled down to rt and filtered. The filtrate was concentrated in vacuo to give crude 1-bromo-3-methoxy-5-(trifluoromethyl)benzene (1.98 g) which was used directly in the next step without any further purification.

Step 2: Preparation of 8-[3-methoxy-5-(trifluoromethyl)phenyl]-1,4-dioxa-8-azaspiro[4.5]decane

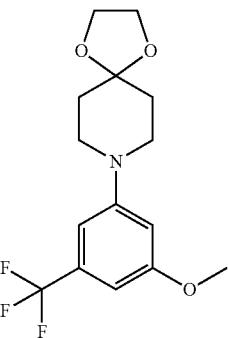 [SMILES: COc1cc(N2CCC3(CC2)OCCO3)cc(C(F)(F)F)c1]

To a mixture of 1-bromo-3-methoxy-5-(trifluoromethyl)benzene (500 mg, 1.96 mmol), 1,4-dioxa-8-azaspiro[4.5]decane (281 mg, 1.96 mmol) and sodium tert-butoxide (377 mg, 3.92 mmol) in dioxane (10 mL) was added Pd₂(dba)₃ (71.8 mg, 78.4 μmol) and Ruphos (18.3 mg, 39.2 μmol) under N₂. The resulting mixture was then heated with stirring at 100° C. overnight. After being cooled down to rt, the resulting mixture was diluted with H₂O (10 mL) and extracted with EA (30 mL) for three times. The organic layers were combined, dried over anhydrous Na₂SO₄ and concentrated in vacuo to give crude 8-(3-methoxy-5-(trifluoromethyl)phenyl)-1,4-dioxa-8-azaspiro[4.5]decane (650 mg) which was used in the next step directly without an further purification.

Step 3: Preparation of 1-[3-methoxy-5-(trifluoromethyl)phenyl]piperidin-4-one

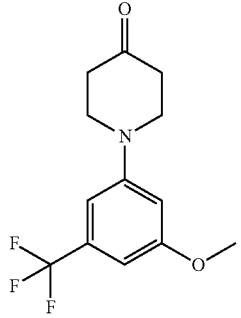 [SMILES: COc1cc(N2CCC(=O)CC2)cc(C(F)(F)F)c1]

To a flask containing 8-(3-methoxy-5-(trifluoromethyl) phenyl)-1,4-dioxa-8-azaspiro[4.5]decane (600 mg, 1.89 mmol) was added formic acid (7 mL) and H₂O (7 mL). The resulting mixture was heated with stirring at 100° C. for 2 hrs, and then concentrated in vacuo. The residue was diluted with saturated aqueous NaHCO₃ solution and then extracted with EA (30 mL) for three times. The organic layers were combined and concentrated in vacuo to give crude 1-[3-methoxy-5-(trifluoromethyl)phenyl]piperidin-4-one (530 mg) which was used in the next step directly without any further purification.

Step 4: Preparation of 6-[3-methoxy-5-(trifluoromethyl)phenyl]-2-pyrimidin-2-yl-7,8-dihydro-5H-pyrido[4,3-d]pyrimidine

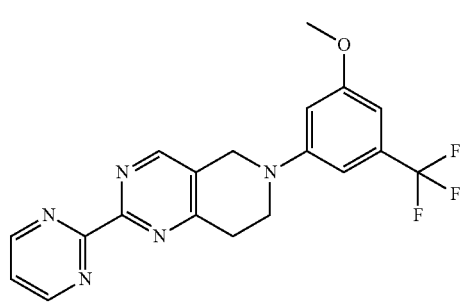 [SMILES: COc1cc(N2CCc3nc(-c4ncccn4)ncc3C2)cc(C(F)(F)F)c1]

A mixture of 1-(3-methoxy-5-(trifluoromethyl)phenyl)piperidin-4-one (600 mg, 2.2 mmol) and DMFDMA (3 mL) was heated with stirring at 90° C. for 2 hrs. The resulting mixture was concentrated in vacuo and the residue was dissolved in EtOH (20 mL). To the solution was added pyrimidine-2-carboximidamide hydrochloride (348 mg, 2.2 mmol) and potassium carbonate (607 mg, 4.39 mmol). The resulting mixture was heated with stirring at 90° C. for 1 hr, then cooled down to rt and purified by flash column to give 6-[3-methoxy-5-(trifluoromethyl)phenyl]-2-pyrimidin-2-yl-7,8-dihydro-5H-pyrido[4,3-d]pyrimidine (400 mg).

Step 5: Preparation of 5-methoxy-6-[3-methoxy-5-(trifluoromethyl)phenyl]-2-pyrimidin-2-yl-7,8-dihydro-5H-pyrido[4,3-d]pyrimidine

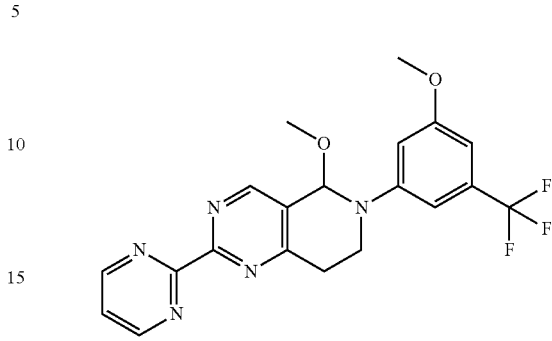

A solution of 6-[3-methoxy-5-(trifluoromethyl)phenyl]-2-pyrimidin-2-yl-7,8-dihydro-5H-pyrido[4,3-d]pyrimidine (0.32 g, 826 µmol) in THF (5 mL) and MeOH (5 mL) was cooled to −78° C. Then to the cooled solution was added RuCl₃ hydrate (34.3 mg, 165 µmol) and a solution of NaIO₄ (353 mg, 1.65 mmol) in water (5 mL) successively. The resulting mixture was warmed to rt and stirred for 3 hrs. The reaction was quenched with aqueous sodium thiosulfate and the resulting mixture was extracted with EA (20 mL) for three times. The organic layers were combined, washed with brine, dried over anhydrous Na₂SO₄ and concentrated in vacuo to give crude 5-methoxy-6-[3-methoxy-5-(trifluoromethyl)phenyl]-2-pyrimidin-2-yl-7,8-dihydro-5H-pyrido[4,3-d]pyrimidine (0.43 g) which was used in the next step without any further purification.

Step 6: Preparation of 6-[3-methoxy-5-(trifluoromethyl)phenyl]-5-methyl-2-pyrimidin-2-yl-7,8-dihydro-5H-pyrido[4,3-d]pyrimidine

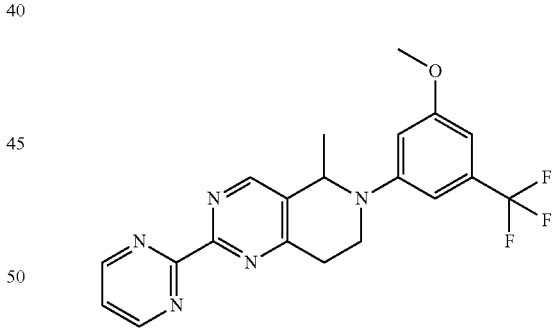

A mixture of 5-methoxy-6-[3-methoxy-5-(trifluoromethyl)phenyl]-2-pyrimidin-2-yl-7,8-dihydro-5H-pyrido[4,3-d]pyrimidine (0.43 g, 1.03 mmol) in THF (10 mL) was cooled to −78° C. To the cooled solution was added boron-trifluoride diethyl etherate (439 mg, 3.09 mmol) and a solution of MeMgBr (1.1 mL, 3.3 mmol) successively. After the reaction was complete monitoring by LC/MS, the reaction was quenched with water and the resulting mixture was extracted with EA (20 mL) for three times. The organic layers were combined, washed with brine, dried over anhydrous Na₂SO₄ and concentrated in vacuo. The residue was purified by prep-HPLC to give 6-[3-methoxy-5-(trifluoromethyl)phenyl]-5-methyl-2-(2-pyridyl)-7,8-dihydro-5H-pyrido[4,3-d]pyrimidine (15 mg) as light yellow solid. ¹H NMR (400 MHz, CDCl₃) δ: 1.54 (d, 3H), 3.23-3.41 (m, 2H), 3.53-3.64 (m, 1H), 3.86 (s, 3H), 3.89-3.98 (m, 1H), 5.14 (d, 1H), 6.59-6.68 (m, 2H), 6.79-6.86 (m, 1H), 7.41-7.50 (m, 1H), 8.74-8.88 (m, 1H), 8.99-9.11 (m, 2H). MS obsd. (ESI⁺) [(M+H)⁺]: 402.

Example 113: 1-[3-[2,3-difluoro-5-(5-methyl-2-pyrimidin-2-yl-7,8-dihydro-5H-pyrido[4,3-d]pyrimidin-6-yl)phenoxy]propyl]imidazolidin-2-one

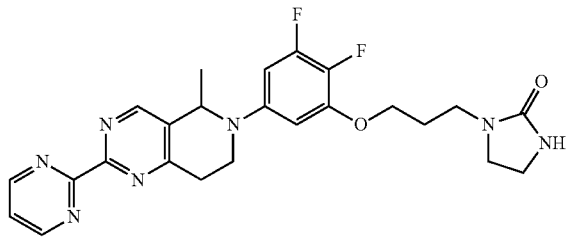 [SMILES: CC1c2cnc(-c3ncccn3)nc2CCN1c1cc(F)c(F)c(OCCCN2CCNC2=O)c1]

Step 1: Preparation of 6-[3-(3-chloropropoxy)-4,5-difluoro-phenyl]-5-methyl-2-pyrimidin-2-yl-7,8-dihydro-5H-pyrido[4,3-d]pyrimidine

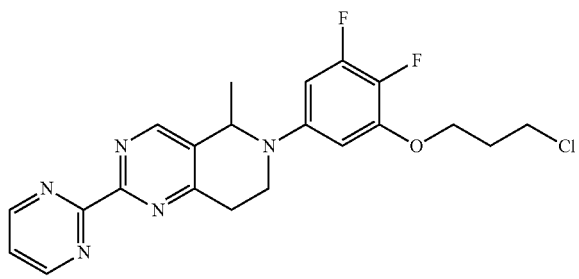 [SMILES: CC1c2cnc(-c3ncccn3)nc2CCN1c1cc(F)c(F)c(OCCCCl)c1]

A mixture of 2,3-difluoro-5-(5-methyl-2-pyrimidin-2-yl-7,8-dihydro-5H-pyrido[4,3-d]pyrimidin-6-yl)phenol (200 mg, 563 μmol), K₂CO₃ (156 mg, 1.13 mmol) and 1-bromo-3-chloropropane (97.5 mg, 619 mol) in DMF (5 ml) was stirred overnight at rt. The resulting reaction mixture was diluted with H₂O (5 mL), and then extracted with DCM (20 mL) twice. The organic layers were combined and concentrated in vacuo. The residue was purified by flash chromatography to give 6-[3-(3-chloropropoxy)-4,5-difluoro-phenyl]-5-methyl-2-pyrimidin-2-yl-7,8-dihydro-5H-pyrido[4,3-d]pyrimidine (200 mg) as a light brown solid.

Step 2: Preparation of 1-[3-[2,3-difluoro-5-(5-methyl-2-pyrimidin-2-yl-7,8-dihydro-5H-pyrido[4,3-d]pyrimidin-6-yl)phenoxy]propyl]imidazolidin-2-one

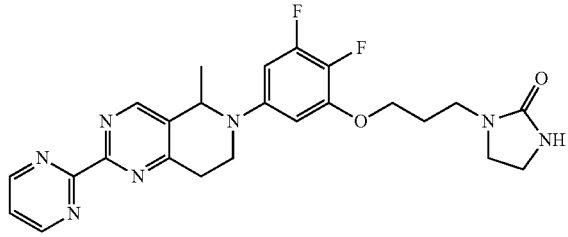 [SMILES: CC1c2cnc(-c3ncccn3)nc2CCN1c1cc(F)c(F)c(OCCCN2CCNC2=O)c1]

A mixture of 6-[3-(3-chloropropoxy)-4,5-difluoro-phenyl]-5-methyl-2-pyrimidin-2-yl-7,8-dihydro-5H-pyrido[4,3-d]pyrimidine (160 mg, 370 μmol), imidazolidin-2-one (128 mg, 1.48 mmol) and sodium tert-butoxide (214 mg, 2.22 mmol) in DMF (10 ml) was heated with stirring at 100° C. for 10 hrs. After being cooled to room temperature, the resulting reaction mixture was poured into H₂O (10 mL) and extracted with DCM (20 mL) twice. The organic layers were combined and concentrated in vacuo. The residue was purified by prep-HPLC to give 1-[3-[2,3-difluoro-5-(5-methyl-2-pyrimidin-2-yl-7,8-dihydro-5H-pyrido[4,3-d]pyrimidin-6-yl)phenoxy]propyl]imidazolidin-2-one as a yellow solid (57 mg). ¹H NMR (400 MHz, CDCl3) δ: 9.04 (d, 2H), 8.81 (s, 1H), 7.40-7.49 (m, 1H), 6.31-6.45 (m, 2H), 4.91-5.08 (m, 1H), 4.46-4.60 (m, 1H), 4.11 (s, 2H), 3.68-3.80 (m, 1H), 3.46-3.54 (m, 3H), 3.34-3.46 (m, 4H), 3.21-3.32 (m, 2H), 2.08 (s, 2H), 1.45 (d, 3H). MS obsd. (ESI⁺) [(M+H)⁺]:482.

Example 114: 6-[3,4-difluoro-5-(2-tetrahydrofuran-3-ylethoxy)phenyl]-5-methyl-2-pyrimidin-2-yl-7,8-dihydro-5H-pyrido[4,3-d]pyrimidine

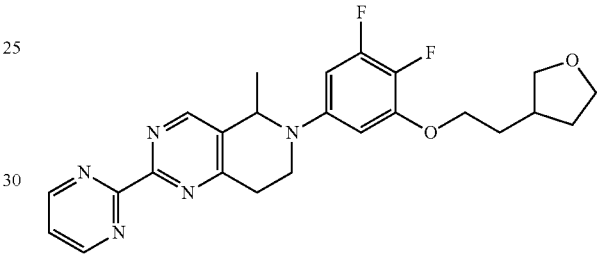

A mixture of 2,3-difluoro-5-(5-methyl-2-pyrimidin-2-yl-7,8-dihydro-5H-pyrido[4,3-d]pyrimidin-6-yl)phenol (100 mg, 0.28 mmol), 3-(2-bromoethyl)tetrahydrofuran (60 mg, 0.34 mmol) and K₂CO₃ (70 mg, 0.51 mmol) in DMF (2 mL) was stirred at 15° C. for 12 hrs. The resulting reaction mixture was diluted with H₂O (10 mL) and extracted with EA (20 mL) for three times. The organic layers were washed with brine (10 mL), dried over anhydrous Na₂SO₄ and concentrated in vacuo. The residue was purified by prep-HPLC to give 6-[3,4-difluoro-5-(2-tetrahydrofuran-3-ylethoxy)phenyl]-5-methyl-2-pyrimidin-2-yl-7,8-dihydro-5H-pyrido[4,3-d]pyrimidine (38 mg) as a yellow solid. ¹H NMR (400 MHz, CDCl₃) δ: 9.04 (d, 2H), 8.78 (s, 1H), 7.44 (t, 1H), 6.29-6.46 (m, 2H), 4.96 (q, 1H), 4.03-4.13 (m, 2H), 3.98 (t, 1H), 3.89 (td, 1H), 3.67-3.82 (m, 2H), 3.42-3.55 (m, 2H), 3.19-3.37 (m, 2H), 2.44 (m, 1H), 2.09-2.20 (m, 1H), 1.84-2.02 (m, 2H), 1.56-1.70 (m, 1H), 1.45 (d, 3H). MS obsd. (ESI⁺) [(M+H)⁺]: 454.

Example 115: tert-butyl 3-[2-[2,3-difluoro-5-(5-methyl-2-pyrimidin-2-yl-7,8-dihydro-5H-pyrido[4,3-d]pyrimidin-6-yl)phenoxy]ethyl]azetidine-1-carboxylate

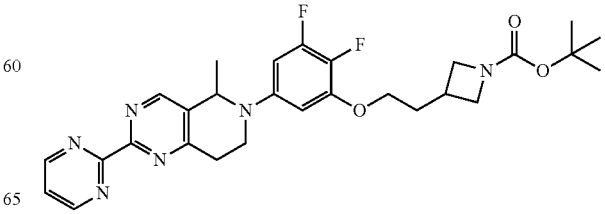

Step 1: Preparation of tert-butyl 3-[2-(p-tolylsulfonyloxy)ethyl]azetidine-1-carboxylate

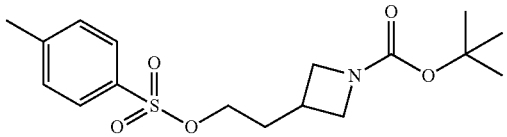 [SMILES: Cc1ccc(S(=O)(=O)OCCC2CN(C(=O)OC(C)(C)C)C2)cc1]

To a stirred solution of tert-butyl 3-(2-hydroxyethyl)azetidine-1-carboxylate (100 mg, 0.50 mmol) in DCM (2 mL) was added Et₃N (75 mg, 0.75 mmol). Then to the resulting mixture was added a solution of tosyl chloride (85 mg, 0.45 mmol) in DCM (1 mL) drop wise. After being stirred at 15° C. for 16 hrs, the resulting mixture was diluted with DCM (30 mL), and then washed with H₂O (10 mL), aqueous HCl (10 mL, 2.0 M) and brine (10 mL) successively. The organic layer was dried over anhydrous Na₂SO₄ and concentrated in vacuo to give tert-butyl 3-[2-(p-tolyl sulfonyloxy)ethyl]azetidine-1-carboxylate (130 mg, crude) as light yellow oil which was used directly in the next step without any further purification.

Step 2: Preparation of tert-butyl 3-[2-[2,3-difluoro-5-(5-methyl-2-pyrimidin-2-yl-7,8-dihydro-5H-pyrido[4,3-d]pyrimidin-6-yl)phenoxy]ethyl]azetidine-1-carboxylate

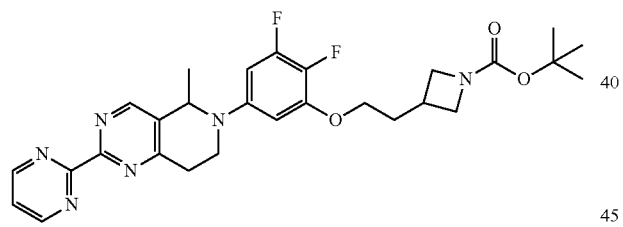

A mixture of 2,3-difluoro-5-(5-methyl-2-pyrimidin-2-yl-7,8-dihydro-5H-pyrido[4,3-d]pyrimidin-6-yl)phenol (87 mg, 0.24 mmol), tert-butyl 3-[2-(p-tolylsulfonyloxy)-ethyl]azetidine-1-carboxylate (130 mg, 0.29 mmol) and K₂CO₃ (67 mg, 0.49 mmol) in DMF (3 mL) was heated with stirring at 60° C. for 12 hrs. The resulting reaction mixture was cooled to rt, diluted with H₂O (5 mL) and extracted with EA (10 mL) for three times. The organic layers were combined, washed with brine (10 mL), dried over anhydrous Na₂SO₄ and concentrated in vacuo. The residue was purified by prep-HPLC to give tert-butyl 3-[2-[2,3-difluoro-5-(5-methyl-2-pyrimidin-2-yl-7,8-dihydro-5H-pyrido[4,3-d]pyrimidin-6-yl)phenoxy]ethyl]azetidine-1-carboxylate (21 mg) as a white solid. ¹H NMR (400 MHz, CDCl₃) δ: 9.05 (d, 2H), 8.79 (s, 1H), 7.45 (t, 1H), 6.27-6.45 (m, 2H), 4.96 (q, 1H), 3.99-4.14 (m, 4H), 3.63-3.77 (m, 3H), 3.42-3.56 (m, 1H), 3.18-3.38 (m, 2H), 2.71-2.86 (m, 1H), 2.08-2.18 (m, 2H), 1.41-1.48 (m, 12H). MS obsd. (ESI⁺) [(M+H)⁺]: 539.

Example 116: 6-[3-[2-(azetidin-3-yl)ethoxy]-4,5-difluoro-phenyl]-5-methyl-2-pyrimidin-2-yl-7,8-dihydro-5H-pyrido[4,3-d]pyrimidine

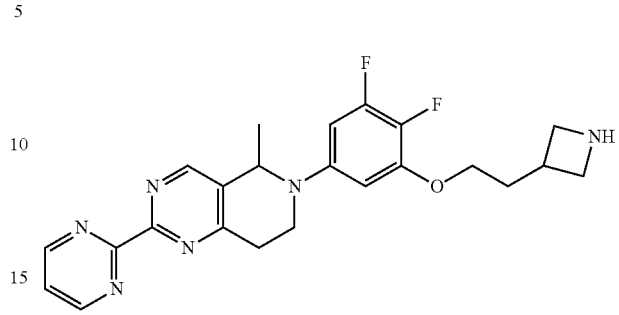

A mixture of tert-butyl 3-[2-[2,3-difluoro-5-(5-methyl-2-pyrimidin-2-yl-7,8-dihydro-5H-pyrido[4,3-d]pyrimidin-6-yl)phenoxy]ethyl]azetidine-1-carboxylate (495 mg, 0.71 mmol) and a solution of HCl in 1, 4-dioxane (5 mL, 4.0 M) was stirred at 15° C. for 12 hrs. The resulting mixture was concentrated in vacuo and the residue was purified by prep-HPLC to give 6-[3-[2-(azetidin-3-yl)ethoxy]-4, 5-difluoro-phenyl]-5-methyl-2-pyrimidin-2-yl-7,8-dihydro-5H-pyrido[4,3-d]pyrimidine (34 mg) as a yellow solid. ¹H NMR (400 MHz, Methanol-d₄) δ: 9.04 (d, 2H), 8.85 (s, 1H), 7.65 (t, 1H), 6.47-6.62 (m, 2H), 5.13-5.27 (m, 1H), 4.09-4.22 (m, 4H), 3.95-4.05 (m, 2H), 3.80-3.91 (m, 1H), 3.47-3.59 (m, 1H), 3.08-3.28 (m, 3H), 2.12-2.24 (m, 2H), 1.46 (d, 3H). MS obsd. (ESI⁺) [(M+H)⁺]: 439.

Example 117: 1-[3-[2-[2,3-difluoro-5-(5-methyl-2-pyrimidin-2-yl-7,8-dihydro-5H-pyrido[4,3-d]pyrimidin-6-yl)phenoxy]ethyl]azetidin-1-yl]ethanone

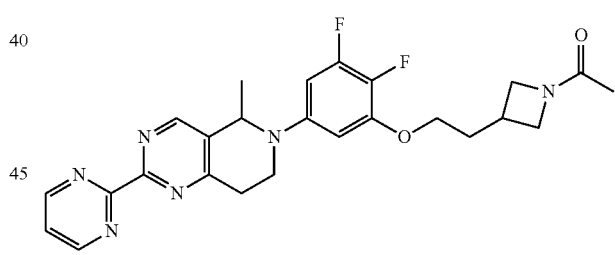

A stirred solution of 6-[3-[2-(azetidin-3-yl)ethoxy]-4,5-difluoro-phenyl]-5-methyl-2-pyrimidin-2-yl-7,8-dihydro-5H-pyrido[4,3-d]pyrimidine (200 mg, 0.46 mmol) and Et₃N (138 mg, 1.37 mmol) in DCM (4 mL) was cooled to 0° C. and to the cooled solution was added acetyl chloride (43 mg, 0.55 mmol) slowly. Then the resulting mixture was warmed up to 15° C. and stirred for 16 hrs. The resulting reaction mixture was quenched by addition of H₂O and extracted with DCM (10 mL) for three times. The organic layers were combined, washed with brine (10 mL), dried over anhydrous Na₂SO₄ and concentrated in vacuo. The residue was purified by prep-HPLC to give 1-[3-[2-[2,3-difluoro-5-(5-methyl-2-pyrimidin-2-yl-7,8-dihydro-5H-pyrido[4,3-d]pyrimidin-6-yl)phenoxy]ethyl]azetidin-1-yl]ethanone (14 mg) as a yellow solid. ¹H NMR (400 MHz, CDCl₃) δ: 9.03 (d, 2H), 8.78 (s, 1H), 7.39-7.48 (m, 1H), 6.38 (ddd, 1H), 6.32 (dd, 1H), 4.96 (q, 1H), 4.29 (t, 1H), 4.16 (t, 1H), 3.99-4.13 (m, 2H), 3.87-3.95 (m, 1H), 3.66-3.78 (m, 2H), 3.42-3.54 (m, 1H), 3.19-3.37 (m, 2H), 2.78-2.93 (m, 1H), 2.05-2.22 (m, 2H), 1.86 (s, 3H), 1.38-1.50 (m, 3H). MS obsd. (ESI$^+$) [(M+H)$^+$]: 481.

Example 118: 6-[3,4-difluoro-5-[2-(1-methylsulfonylazetidin-3-yl)ethoxy]phenyl]-5-methyl-2-pyrimidin-2-yl-7,8-dihydro-5H-pyrido[4,3-d]pyrimidine

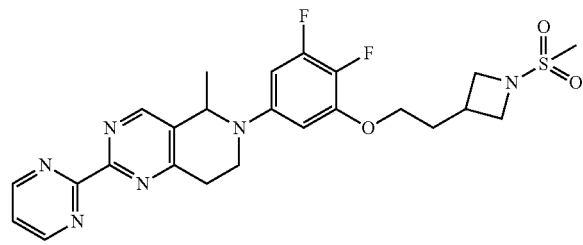 [SMILES: CC1c2cnc(-c3ncccn3)nc2CCN1c1cc(F)c(F)c(OCCC2CN(S(C)(=O)=O)C2)c1]

To a stirred solution of 6-[3-[2-(azetidin-3-yl)ethoxy]-4,5-difluoro-phenyl]-5-methyl-2-pyrimidin-2-yl-7,8-dihydro-5H-pyrido[4,3-d]pyrimidine (260 mg, 0.55 mmol) and Et$_3$N (166 mg, 1.64 mmol) in DCM (5 mL) was added methanesulfonyl chloride (94 mg, 0.82 mmol) slowly at 0° C. Then the resulting mixture was warmed up to 15° C., and stirred for 0.5 hr. The reaction was quenched by addition of H$_2$O (5 mL) and extracted with DCM (10 mL) for three times. The organic layers were combined, washed with saturated aqueous NaHCO$_3$ (15 mL) and brine (20 mL), dried over anhydrous Na$_2$SO$_4$ and concentrated in vacuo. The residue was purified by prep-HPLC to afford 6-[3,4-difluoro-5-[2-(1-methylsulfonylazetidin-3-yl)ethoxy]phenyl]-5-methyl-2-pyrimidin-2-yl-7,8-dihydro-5H-pyrido[4,3-d]pyrimidine (10 mg) as a white solid. $^1$H NMR (400 MHz, CDCl$_3$) δ: 9.05 (d, 2H), 8.75-8.83 (m, 1H), 7.45 (t, 1H), 6.28-6.48 (m, 2H), 4.91-5.02 (m, 1H), 4.01-4.12 (m, 4H), 3.74-3.84 (m, 2H), 3.71-3.73 (m, 1H), 3.44-3.55 (m, 1H), 3.23-3.36 (m, 2H), 2.84-2.94 (m, 4H), 2.11-2.20 (m, 2H), 1.42-1.49 (m, 3H). MS obsd. (ESI$^+$) [(M+H)$^+$]: 517.

Example 119: 6-[3,4-difluoro-5-(thietan-3-ylmethoxy)phenyl]-5-methyl-2-pyrimidin-2-yl-7,8-dihydro-5H-pyrido[4,3-d]pyrimidine

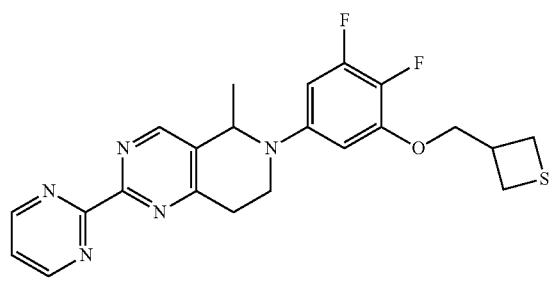 [SMILES: CC1c2cnc(-c3ncccn3)nc2CCN1c1cc(F)c(F)c(OCC2CSC2)c1]

Step 1: Preparation of thietane-3-carbonitrile

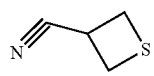

To a solution of 2-(chloromethyl)thiirane (15.0 g, 138.1 mmol) in THF (60 mL) was added a solution of KCN (14.2 g, 218.4 mmol) in water (60 mL). After being heated with stirring at 50° C. for 16 hrs, the resulting mixture was diluted with EA (500 mL), washed with water (100 mL) and brine (100 mL), dried over Na$_2$SO$_4$ and concentrated in vacuo to give crude thietane-3-carbonitrile (8.2 g) as dark oil which was used directly in the next step without any further purification.

Step 2: Preparation of thietane-3-carboxylic acid

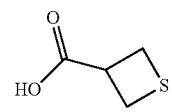

A mixture of thietane-3-carbonitrile (7.2 g, 72.7 mmol) and 10% NaOH (120 mL) was heated with stirring at 100° C. for 16 hrs. The resulting mixture was acidified with 3N HCl to pH=1 and extracted with EA (200 mL). The organic layer was washed with brine (50 mL), dried over anhydrous Na$_2$SO$_4$ and concentrated in vacuo to give thietane-3-carboxylic acid (3.2 g) as a dark solid, which was used directly in the next step without any further purification.

Step 3: Preparation of thietan-3-ylmethanol

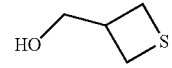

To a solution of thietane-3-carboxylic acid (1.0 g, 8.47 mmol) in THF (12 mL) was added LiAlH$_4$ (644 mg, 16.9 mmol) at 0° C. The resulting mixture was stirred at 0° C. for 0.5 hr and the reaction was quenched by addition of water (0.7 mL) and 10% NaOH (0.7 mL) successively. The resulting mixture was diluted with EA (100 mL) and filtered. The filtrate was dried over anhydrous Na$_2$SO$_4$ and concentrated in vacuo to give thietan-3-ylmethanol (460 mg) as yellow oil, which was used directly in the next step without any further purification.

Step 4: Preparation of thietan-3-ylmethyl 4-methylbenzenesulfonate

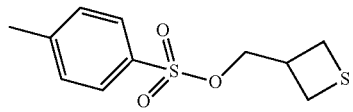 [SMILES: Cc1ccc(S(=O)(=O)OCC2CSC2)cc1]

To a solution of thietan-3-ylmethanol (580 mg, 5.58 mmol) in DCM (10 mL) was added Et$_3$N (1.69 g, 16.7 mmol). Then to the mixture was added a solution of tosyl chloride (1.06 g, 5.58 mmol) in DCM (5 mL) drop wise. The resulting mixture was stirred at 10° C. for 16 hrs, then diluted with DCM (100 mL), and washed with H$_2$O (20 mL), aqueous HCl (20 mL, 1.0 M) and brine (10 mL) successively. The organic layer was dried over anhydrous Na$_2$SO$_4$ and concentrated in vacuo. The residue was purified by column to give thietan-3-ylmethyl 4-methylbenzenesulfonate (600 mg) as yellow oil.

Step 5: Preparation of 6-[3,4-difluoro-5-(thietan-3-ylmethoxy)phenyl]-5-methyl-2-pyrimidin-2-yl-7,8-dihydro-5H-pyrido[4,3-d]pyrimidine

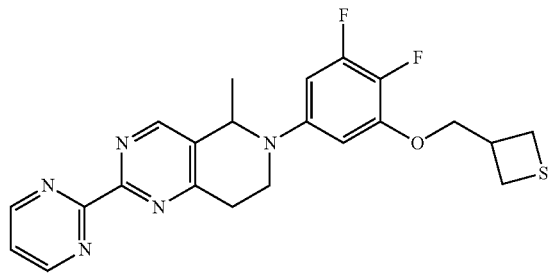 [SMILES: CC1c2cnc(-c3ncccn3)nc2CCN1c1cc(F)c(F)c(OCC2CSC2)c1]

To a mixture of thietan-3-ylmethyl 4-methylbenzenesulfonate (300 mg, 0.85 mmol) in DMF (4 mL) was added Cs$_2$CO$_3$ (831 mg, 2.55 mmol) and 2,3-difluoro-5-(5-methyl-2-pyrimidin-2-yl-7,8-dihydro-5H-pyrido[4,3-d]pyrimidin-6-yl)phenol (229 mg, 0.88 mmol) successively. The resulting mixture was stirred at 50° C. for 16 hrs, then diluted with EA (100 mL), and washed with H$_2$O (30 mL) and brine (30 mL). The organic layer was dried over anhydrous Na$_2$SO$_4$ and concentrated in vacuo. The residue was purified by prep-HPLC to give 6-[3,4-difluoro-5-(thietan-3-ylmethoxy)phenyl]-5-methyl-2-pyrimidin-2-yl-7,8-dihydro-5H-pyrido[4,3-d]pyrimidine (17 mg) as a light yellow solid. $^1$H NMR (400 MHz, CDCl$_3$) δ: 9.04 (d, 2H), 8.79 (s, 1H), 7.44 (t, 1H), 6.34-6.46 (m, 2H), 4.98 (q, 1H), 4.18 (dd, 2H), 3.62-3.77 (m, 2H), 3.45-3.55 (m, 1H), 3.37 (t, 2H), 3.21-3.33 (m, 2H), 3.13 (ddd, 2H), 1.45 (d, 3H). MS obsd (ESI$^+$) [(M+H)$^+$]: 442.

Example 120: 3-[[2,3-difluoro-5-(5-methyl-2-pyrimidin-2-yl-7,8-dihydro-5H-pyrido[4,3-d]pyrimidin-6-yl)phenoxy]methyl]thietane 1,1-dioxide

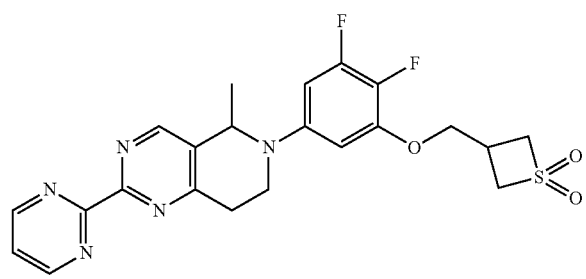 [SMILES: CC1c2cnc(-c3ncccn3)nc2CCN1c1cc(F)c(F)c(OCC2CS(=O)(=O)C2)c1]

To a solution of 6-[3,4-difluoro-5-(thietan-3-ylmethoxy)phenyl]-5-methyl-2-pyrimidin-2-yl-7,8-dihydro-5H-pyrido[4,3-d]pyrimidine (180 mg, 0.41 mmol) in MeOH (8 mL) was added a solution of oxone (125 mg, 0.20 mmol) in water (3 mL) at 0° C. The resulting mixture was stirred at 10° C. for 2 hr. Then the reaction was quenched with aq. Na$_2$SO$_3$ (30 mL) and the resulting mixture was extracted with DCM (100 mL). The organic layer was washed with H$_2$O (30 mL) and brine (30 mL), dried over Na$_2$SO$_4$ and concentrated in vacuo. The residue was purified by prep-HPLC to give 3-[[2,3-difluoro-5-(5-methyl-2-pyrimidin-2-yl-7,8-dihydro-5H-pyrido[4,3-d]pyrimidin-6-yl)phenoxy]methyl]thietane 1,1-dioxide (12.5 mg) as a light yellow solid. $^1$H NMR (400 MHz, CDCl$_3$) δ: 9.04 (d, 1H) 8.80 (s, 1H), 7.45 (t, 1H), 6.45 (ddd, 1H), 6.30-6.40 (m, 1H), 4.98 (q, 1H), 4.21-4.40 (m, 4H), 4.01-4.15 (m, 2H), 3.69-3.79 (m, 1H), 3.43-3.58 (m, 1H), 3.20-3.37 (m, 2H), 3.04 (tot, 1H), 1.46 (d, 3H). MS obsd (ESI$^+$) [(M+H)$^+$]: 474.

Example 121: 6-(3,4-difluoro-5-tetrahydrofuran-3-yloxy-phenyl)-(5R/S)-methyl-2-pyrimidin-2-yl-7,8-dihydro-5H-pyrido[4,3-d]pyrimidine Step 1: Preparation of tetrahydrofuran-3-yl 4-methylbenzenesulfonate

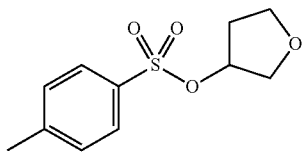 [SMILES: Cc1ccc(S(=O)(=O)OC2CCOC2)cc1]

To a solution of tetrahydrofuran-3-ol (176 mg, 2 mmol), DMAP (24.4 mg, 200 μmol) and DIEA (516 mg, 4 mmol) in DCM (5 mL) was added 4-methylbenzene-1-sulfonyl chloride (381 mg, 2 mmol) at 0° C. After being warmed up to rt and stirred at rt for 5 hrs, the resulting mixture was partitioned between EA and brine. The organic layer was separated, dried over anhydrous Na$_2$SO$_4$ and concentrated in vacuo. The residue was purified by column to give tetrahydrofuran-3-yl 4-methylbenzenesulfonate (80 mg) as yellow oil.

Step 2: Preparation of 6-(3,4-difluoro-5-tetrahydrofuran-3-yloxy-phenyl)-(5R/S)-methyl-2-pyrimidin-2-yl-7,8-dihydro-5H-pyrido[4,3-d]pyrimidine A mixture of (−)-2,3-difluoro-5-(5-methyl-2-pyrimidin-2-yl-7,8-dihydro-5H-pyrido[4,3-d]pyrimidin-6-yl)phenol (30 mg, 84.4 μmol, Example 45), tetrahydrofuran-3-yl 4-methylbenzenesulfonate (30 mg, 124 μmol) and Cs$_2$CO$_3$ (55 mg, 169 μmol) in DMF was heated with stirring at 80° C. for 1 hr. After being cooled rt, the resulting mixture was partitioned between EA and water. The organic layer was washed with brine, dried over anhydrous Na$_2$SO$_4$ and concentrated in vacuo. The residue was purified by flash column chromatography to give 6-(3,4-difluoro-5-tetrahydrofuran-3-yloxy-phenyl)-(5R/S)-methyl-2-pyrimidin-2-yl-7,8-dihydro-5H-pyrido[4,3-d]pyrimidine (12 mg) as a light yellow solid. $^1$H NMR (400 MHz, CDCl$_3$) δ: 8.96-9.16 (m, 2H), 8.71-8.90 (m, 1H), 7.47 (t, 1H), 6.45 (ddd, 1H), 6.32-6.38 (m, 1H), 4.94-5.07 (m, 2H), 3.92-4.09 (m, 4H), 3.64-3.84 (m, 1H), 3.47-3.56 (m, 1H), 3.23-3.38 (m, 2H), 2.16-2.30 (m, 2H), 1.48 (d, 3H). MS obsd. (ESI$^+$) [(M+H)$^+$]: 426.

Example 122: 6-[3,4-difluoro-5-(tetrahydrofuran-2-ylmethoxy)phenyl]-(5R/S)-methyl-2-pyrimidin-2-yl-7,8-dihydro-5H-pyrido[4,3-d]pyrimidine

Step 1: Preparation of (tetrahydrofuran-2-yl)methyl 4-methylbenzenesulfonate

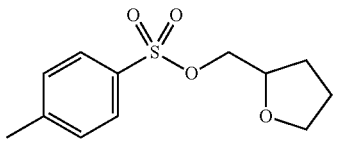 [SMILES: Cc1ccc(S(=O)(=O)OCC2CCCO2)cc1]

To a solution of (tetrahydrofuran-2-yl)methanol (102 mg, 1 mmol), DMAP (12.2 mg, 0.1 mmol) and DIEA (258 mg, 2 mmol) in DCM (2 mL) was added 4-methylbenzene-1-sulfonyl chloride (190 mg, 1 mmol) at 0° C. The resulting mixture was warmed to rt and stirred at rt for 5 hrs. Then the mixture was partitioned between EA and brine. The organic layer was separated, dried over anhydrous $Na_2SO_4$ and concentrated in vacuo. The residue was purified by column chromatography to give (tetrahydrofuran-2-yl)methyl 4-methylbenzenesulfonate (90 mg) as yellow oil.

Step 2: Preparation of 6-[3,4-difluoro-5-(tetrahydrofuran-2-ylmethoxy)phenyl]-(5R/S)-methyl-2-pyrimidin-2-yl-7,8-dihydro-5H-pyrido[4,3-d]pyrimidine A mixture of (−)-2,3-difluoro-5-(5-methyl-2-pyrimidin-2-yl-7,8-dihydro-5H-pyrido[4,3-d]pyrimidin-6-yl)phenol (30 mg, 84.4 μmol, Example 45), (tetrahydrofuran-2-yl)methyl 4-methylbenzenesulfonate (30 mg, 117 μmol) and $Cs_2CO_3$ (55 mg, 169 μmol) in DMF was heated with stirring at 80° C. for 1 hr. After being cooled rt, the resulting mixture was partitioned between EA and water. The organic layer was washed with brine, dried over anhydrous $Na_2SO_4$ and concentrated in vacuo. The residue was purified by flash column chromatography to give 6-[3,4-difluoro-5-(tetrahydrofuran-2-ylmethoxy)phenyl]-(5R/S)-methyl-2-pyrimidin-2-yl-7,8-dihydro-5H-pyrido[4,3-d]pyrimidine (18 mg) as yellow solid. $^1$H NMR (400 MHz, $CDCl_3$) δ: 9.05 (d, 2H), 8.79 (s, 1H), 7.46 (t, 1H), 6.37-6.50 (m, 2H), 4.98 (q, 1H), 4.22-4.40 (m, 1H), 4.03-4.15 (m, 2H), 3.92-4.03 (m, 1H), 3.80-3.90 (m, 1H), 3.73 (ddd, 1H), 3.42-3.60 (m, 1H), 3.22-3.38 (m, 2H), 1.93-2.15 (m, 3H), 1.81-1.91 (m, 1H), 1.46 (d, 3H). MS obsd. (ESI$^+$) [(M+H)$^+$]: 440.

Example 123, 124 and 125: (+)-6-(2,6-dichloro-3-fluoro-5-methoxy-phenyl)-5-methyl-2-pyrimidin-2-yl-7,8-dihydro-5H-pyrido[4,3-d]pyrimidine, (+)-6-(2,4-dichloro-5-fluoro-3-methoxy-phenyl)-5-methyl-2-pyrimidin-2-yl-7,8-dihydro-5H-pyrido[4,3-d]pyrimidine and (+)-6-(2,4-dichloro-3-fluoro-5-methoxy-phenyl)-5-methyl-2-pyrimidin-2-yl-7,8-dihydro-5H-pyrido[4,3-d]pyrimidine To a solution of (−)-6-(3-fluoro-5-methoxy-phenyl)-5-methyl-2-pyrimidin-2-yl-7,8-dihydro-5H-pyrido[4,3-d]pyrimidine (290 mg, 825 μmol, Example 73) in $CH_3CN$ (10 mL) was added N-chlorosuccinimide (121 mg, 908 μmol). The resulting mixture was stirred at rt overnight and purified by prep-HPLC to give (+)-6-(2,6-dichloro-3-fluoro-5-methoxy-phenyl)-5-methyl-2-pyrimidin-2-yl-7,8-dihydro-5H-pyrido[4,3-d]pyrimidine (30 mg) as a yellow solid, (+)-6-(2,4-dichloro-5-fluoro-3-methoxy-phenyl)-5-methyl-2-pyrimidin-2-yl-7,8-dihydro-5H-pyrido[4,3-d]pyrimidine (30 mg) as a yellow solid, and (+)-6-(2,4-dichloro-3-fluoro-5-methoxy-phenyl)-5-methyl-2-pyrimidin-2-yl-7,8-dihydro-5H-pyrido[4,3-d]pyrimidine (30 mg) as a yellow solid.

Example 123: (+)-6-(2,6-dichloro-3-fluoro-5-methoxyphenyl)-5-methyl-2-pyrimidin-2-yl-7,8-dihydro-5H-pyrido[4,3-d]pyrimidine, $^1$H NMR (400 MHz, DMSO-d6) δ: 1.39 (dd, 3H), 2.90-3.16 (m, 2H), 3.40-3.56 (m, 1H), 3.67-3.82 (m, 1H), 3.90 (d, 3H), 4.82-4.94 (m, 1H), 7.21-7.31 (m, 1H), 7.65 (t, 1H), 8.90 (s, 1H), 8.97-9.05 (m, 2H), MS obsd. (ESI$^+$) [(M+H)$^+$]: 420. [a]$_D^{20}$=61.60 (0.05 g/100 mL, MeOH).

Example 124: (+)-6-(2,4-dichloro-5-fluoro-3-methoxyphenyl)-5-methyl-2-pyrimidin-2-yl-7,8-dihydro-5H-pyrido[4,3-d]pyrimidine, $^1$H NMR (400 MHz, DMSO-d6) δ: 1.34 (d, 3H), 2.98-3.18 (m, 2H), 3.35-3.46 (m, 1H), 3.62-3.73 (m, 1H), 3.88 (s, 3H), 4.93-5.05 (m, 1H), 7.16-7.27 (m, 1H), 7.65 (s, 1H), 8.90 (s, 1H), 9.01 (d, 2H), MS obsd. (ESI$^+$) [(M+H)$^+$]: 420. [a]$_D^{20}$=29.10 (0.055 g/100 mL, MeOH).

Example 125: (+)-6-(2,4-dichloro-3-fluoro-5-methoxyphenyl)-5-methyl-2-pyrimidin-2-yl-7,8-dihydro-5H-pyrido[4,3-d]pyrimidine, $^1$H NMR (400 MHz, DMSO-d6) δ: 1.35 (d, 3H), 3.03-3.19 (m, 2H), 3.42-3.53 (m, 1H), 3.64-3.77 (m, 1H), 3.93 (s, 3H), 4.97-5.11 (m, 1H), 6.85 (d, 1H), 7.65 (s, 1H), 8.92 (s, 1H), 9.01 (d, 2H), MS obsd. (ESI$^+$) [(M+H)$^+$]: 420. [a]$_D^{20}$=28.0° (0.05 g/100 mL, MeOH).

Example 126: 6-(6-chloro-4-methoxy-2-pyridyl)-5-methyl-2-(2-pyridyl)-7,8-dihydro-5H-pyrido[4,3-d]pyrimidine

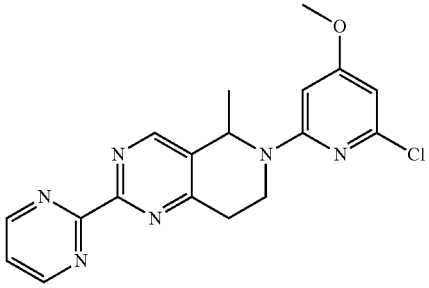 [SMILES: COc1cc(Cl)nc(N2CCc3nc(-c4ncccn4)ncc3C2C)c1]

Step 1: Preparation of tert-butyl 2-pyrimidin-2-yl-7,8-dihydro-5H-pyrido[4,3-d]pyrimidine-6-carboxylate

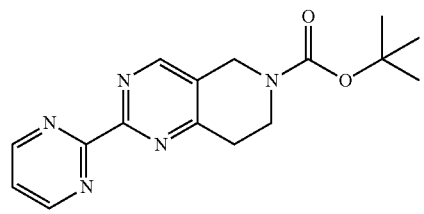 [SMILES: CC(C)(C)OC(=O)N1CCc2nc(-c3ncccn3)ncc2C1]

A solution of N-(tert-butoxycarbonyl)-4-piperidone (100.0 g, 0.50 mol) in DMFDMA (299.0 g, 2.5 mol) was heated with stirring at 120° C. under $N_2$ for 4 hrs. The resulting reaction mixture was concentrated in vacuo. The residue was dissolved in MeOH (2.0 L), and to the resulting solution was added 2-amidinopyrimidine hydrochloride (87.8 g, 0.55 mol) and $K_2CO_3$ (173.9 g, 1.26 mol) successively. The resulting mixture was heated with stirring at 70° C. for 3 hrs. The resulting reaction mixture was cooled to rt and filtered. The filtrate was concentrated in vacuo. The residue was diluted with DCM (2.0 L), washed with $H_2O$ (500 mL) and brine (300 mL), dried over anhydrous $Na_2SO_4$, and concentrated in vacuo. The residue was purified by the flash column chromatography to give tert-butyl 2-pyrimidin-2-yl-7,8-dihydro-5H-pyrido[4,3-d]pyrimidine-6-carboxylate (47.7 g) as a yellow solid.

Step 2: Preparation of 2-pyrimidin-2-yl-5,6,7,8-tetrahydropyrido[4,3-d]pyrimidine

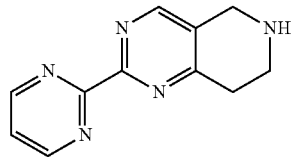 [SMILES: c1cnc(-c2ncc3c(n2)CCNC3)nc1]

To a stirred solution of tert-butyl 2-pyrimidin-2-yl-7,8-dihydro-5H-pyrido[4,3-d]pyrimidine-6-carboxylate (47.7 g, 0.15 mol) in MeOH (500 mL) was added a solution of HCl in MeOH (190 mL, 4.0 M) slowly and the resulting mixture was stirred at 15° C. for 16 hrs. The resulting reaction mixture was concentrated in vacuo. The residue was diluted with MeOH (1.0 L). To the resulting mixture was added basic resin (500 g, AMBERLYST® A21, CAS Number: 9049-93-8, Vendor: Sigma-Aldrich) portion wise. The resulting mixture was stirred at 15° C. until pH>7, and then filtered, and the solid was washed with a mixed solvent of DCM and MeOH (1000 mL, v/v=1:1). The collected filtrate was concentrated in vacuo to afford 2-pyrimidin-2-yl-5,6,7,8-tetrahydropyrido[4,3-d]pyrimidine (39.0 g) as a yellow solid.

Step 3: Preparation of 6-(6-chloro-4-methoxy-2-pyridyl)-2-pyrimidin-2-yl-7,8-dihydro-5H-pyrido[4,3-d]pyrimidine

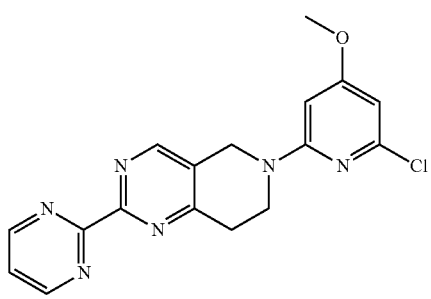 [SMILES: COc1cc(Cl)nc(N2CCc3nc(-c4ncccn4)ncc3C2)c1]

A mixture of 2-pyrimidin-2-yl-5,6,7,8-tetrahydropyrido[4,3-d]pyrimidine (800 mg, 3.75 mmol) and 2,6-dichloro-4-methoxypyridine (668 mg, 3.75 mmol) was heated at 180° C. in a microwave reactor for 30 mins. The resulting mixture was diluted with DCM and purified by column to give 6-(6-chloro-4-methoxy-2-pyridyl)-2-pyrimidin-2-yl-7,8-dihydro-5H-pyrido[4,3-d]pyrimidine (100 mg) as yellow solid.

Step 4: Preparation of 6-(6-chloro-4-methoxy-2-pyridyl)-5-methyl-2-(2-pyridyl)-7,8-dihydro-5H-pyrido[4,3-d]pyrimidine

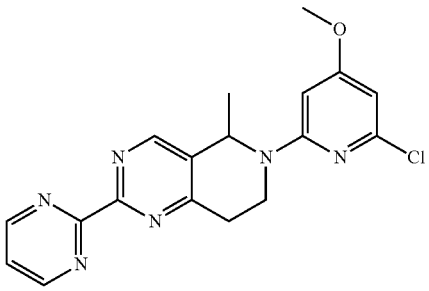 [SMILES: COc1cc(Cl)nc(N2CCc3nc(-c4ncccn4)ncc3C2C)c1]

To a cooled solution of 6-(6-chloro-4-methoxy-2-pyridyl)-2-pyrimidin-2-yl-7,8-dihydro-5H-pyrido[4,3-d]pyrimidine (300 mg, 846 µmol) in MeOH (15 mL) and THF (15 mL) at −70° C. was added $RuCl_3$ hydrate (38.1 mg, 169 µmol) followed by a solution of $NaIO_4$ (362 mg, 1.69 mmol) in $H_2O$ (30 mL). The resulting mixture was warmed to rt and stirred at rt overnight. The reaction was quenched with saturated aqueous $Na_2S_2O_3$ solution. The resulting mixture was extracted with EA (20 mL) for three times. The organic layers were combined, dried over $Na_2SO_4$ and concentrated in vacuo. The residue was dissolved in THF (20 mL) and the solution was cooled to −70° C. To the cooled solution was added borontrifluoride diethyl etherate (212 µl, 1.69 mmol), and the resulting mixture was stirred for 15 mins at −70° C. Then to the resulting mixture was added a solution of dimethylzinc (2.5 mL, 2.5 mmol) in heptane. The resulting mixture was purified by prep-HPLC to give 6-(6-chloro-4-methoxy-2-pyridyl)-5-methyl-2-(2-pyridyl)-7,8-dihydro-5H-pyrido[4,3-d]pyrimidine (19 mg, 51.5 µmol) as pale yellow solid. $^1$H NMR (400 MHz, Methanol-$d_4$) δ: 1.56-1.62 (m, 3H), 3.16 (br. s., 2H), 3.45-3.59 (m, 1H), 3.87 (s, 3H), 4.50-4.62 (m, 1H), 5.73-5.84 (m, 1H), 6.32 (s, 2H), 7.61-7.71 (m, 1H), 8.89 (s, 1H), 9.04 (d, 2H). MS obsd. (ESI$^+$) [(M+H)$^+$]: 369.

Example 127, 128 and 129: 6-(6-fluoro-4-methoxy-2-pyridyl)-5-methyl-2-pyrimidin-2-yl-7,8-dihydro-5H-pyrido[4,3-d]pyrimidine, 6-(6-fluoro-5-iodo-4-methoxy-2-pyridyl)-5-methyl-2-pyrimidin-2-yl-7,8-dihydro-5H-pyrido[4,3-d]pyrimidine and 6-(2-fluoro-6-methoxy-4-pyridyl)-5-methyl-2-pyrimidin-2-yl-7,8-dihydro-5H-pyrido[4,3-d]pyrimidine Example 127

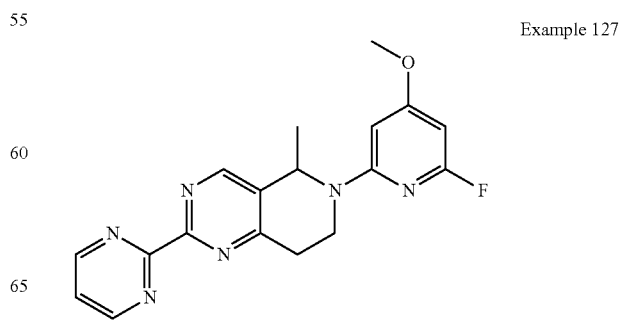

Example 128

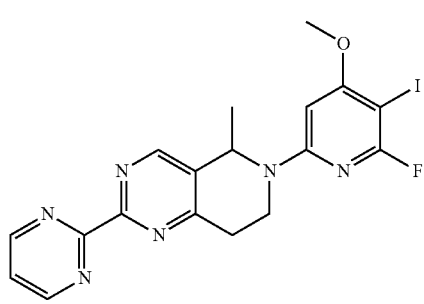

Example 129

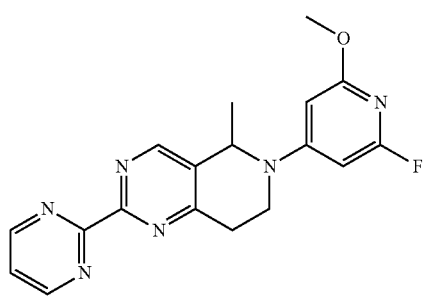

Step 1: Preparation of 2,6-difluoro-4-methoxy-pyridine and 2,4-difluoro-6-methoxy-pyridine

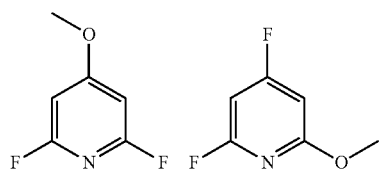

To a stirred solution of 2,4,6-trifluoropyridine (100.0 g, 0.75 mol) in MeOH (1 L) was added MeONa (81.2 g, 1.5 mol) at 0° C. After being stirred at 50° C. for 48 hrs, the resulting mixture was concentrated in vacuo. The residue was diluted with DCM (2 L) and filtered. The filtrate was washed with brine (500 mL) and the organic layer was concentrated in vacuo to give a mixture of 2,6-difluoro-4-methoxy-pyridine and 2,4-difluoro-6-methoxy-pyridine (86.5 g) as colorless oil which was used directly in the next step without any further purification.

Step 2: Preparation of 8-(6-fluoro-4-methoxy-2-pyridyl)-1,4-dioxa-8-azaspiro[4.5]decane and 8-(2-fluoro-6-methoxy-4-pyridyl)-1,4-dioxa-8-azaspiro[4.5]decane

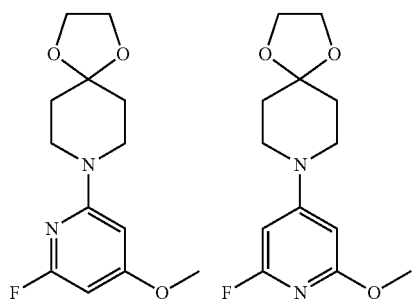

To a stirred solution of 1,4-dioxa-8-azaspiro[4.5]decane hydrochloride (110.0 g, 0.61 mol) in DMF (1 L) was added a mixture of 2,6-difluoro-4-methoxy-pyridine and 2,4-difluoro-6-methoxy-pyridine (93.3 g, 0.64 mol) and $K_2CO_3$ (253.9 g, 1.84 mol). After being stirred at 90° C. for 12 hrs, the resulting mixture was diluted with EA (2.5 L). The organic layer was washed with $H_2O$ (1 L) and brine (1 L). The organic layer was dried over anhydrous $Na_2SO_4$ and concentrated in vacuo to give crude product as a yellow oil. The oil was purified by flash column to give a mixture of 8-(6-fluoro-4-methoxy-2-pyridyl)-1,4-dioxa-8-azaspiro[4.5]decane and 8-(2-fluoro-6-methoxy-4-pyridyl)-1,4-dioxa-8-azaspiro[4.5]decane (150.0 g) as a colorless oil.

Step 3: Preparation of 1-(6-fluoro-4-methoxy-2-pyridyl)piperidin-4-one and 1-(2-fluoro-6-methoxy-4-pyridyl)piperidin-4-one

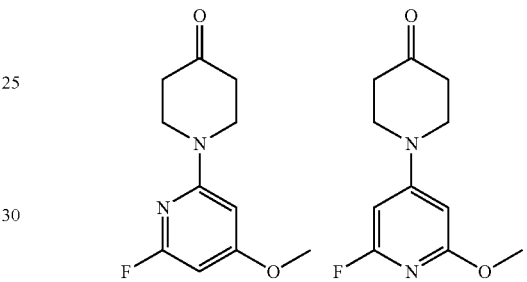

A mixture of 8-(6-fluoro-4-methoxy-2-pyridyl)-1,4-dioxa-8-azaspiro[4.5]decane and 8-(2-fluoro-6-methoxy-4-pyridyl)-1,4-dioxa-8-azaspiro[4.5]decane (150.0 g, 0.56 mol), formic acid (750 mL) and $H_2O$ (750 mL) was stirred at 90° C. for 2 hrs. The resulting mixture was concentrated in vacuo. The residue was diluted with DCM (1.5 L), washed with $H_2O$ (500 mL) and brine (500 mL), dried over anhydrous $Na_2SO_4$ and concentrated in vacuo. The residue was purified by flash column to give 1-(6-fluoro-4-methoxy-2-pyridyl)piperidin-4-one and 1-(2-fluoro-6-methoxy-4-pyridyl)piperidin-4-one (100.0 g) as colorless oil.

Step 4: Preparation of 6-(6-fluoro-4-methoxy-2-pyridyl)-2-pyrimidin-2-yl-7,8-dihydro-5H-pyrido[4,3-d]pyrimidine and 6-(2-fluoro-6-methoxy-4-pyridyl)-2-pyrimidin-2-yl-7,8-dihydro-5H-pyrido[4,3-d]pyrimidine

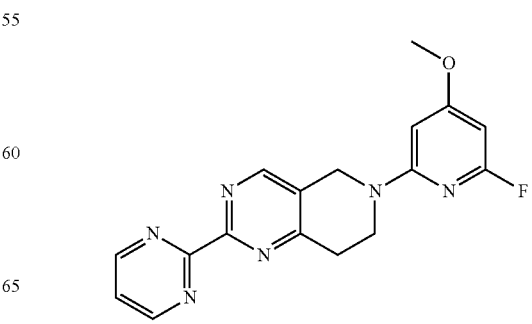

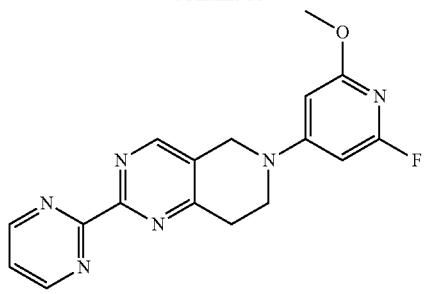

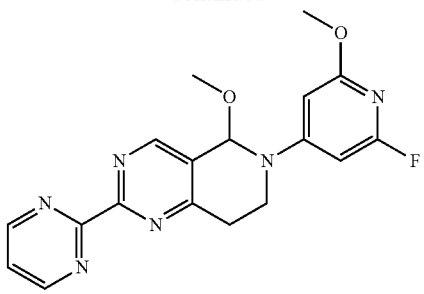

A solution of 1-(6-fluoro-4-methoxy-2-pyridyl)piperidin-4-one and 1-(2-fluoro-6-methoxy-4-pyridyl)piperidin-4-one (100.0 g, 0.44 mol) in DMFDMA (1 L) was heated with stirring at 120° C. for 4 hrs. After being cooled down, the resulting reaction mixture was concentrated in vacuo. The residue was dissolved in MeOH (1.3 L), and then to the solution was added pyrimidine-2-carboximidamide hydrochloride (88.6 g, 0.56 mol) and $K_2CO_3$ (160.8 g, 1.16 mol). After being heated with stirring at 80° C. for 2 hrs, the resulting reaction mixture was diluted with DCM (1.5 L), washed with $H_2O$ (500 mL) and brine (500 mL), dried over anhydrous $Na_2SO_4$ and concentrated in vacuo. The residue was purified by flash column to give a mixture of 6-(6-fluoro-4-methoxy-2-pyridyl)-2-pyrimidin-2-yl-7,8-dihydro-5H-pyrido[4,3-d]pyrimidine and 6-(2-fluoro-6-methoxy-4-pyridyl)-2-pyrimidin-2-yl-7,8-dihydro-5H-pyrido[4,3-d]pyrimidine (105.0 g) as a yellow solid.

Step 5: Preparation of 6-(6-fluoro-4-methoxy-2-pyridyl)-5-methoxy-2-pyrimidin-2-yl-7,8-dihydro-5H-pyrido[4,3-d]pyrimidine and 6-(6-fluoro-5-iodo-4-methoxy-2-pyridyl)-5-methoxy-2-pyrimidin-2-yl-7,8-dihydro-5H-pyrido[4,3-d]pyrimidine and 6-(2-fluoro-6-methoxy-4-pyridyl)-5-methoxy-2-pyrimidin-2-yl-7,8-dihydro-5H-pyrido[4,3-d]pyrimidine A mixture of 6-(6-fluoro-4-methoxy-2-pyridyl)-2-pyrimidin-2-yl-7,8-dihydro-5H-pyrido[4,3-d]pyrimidine and 6-(2-fluoro-6-methoxy-4-pyridyl)-2-pyrimidin-2-yl-7,8-dihydro-5H-pyrido[4,3-d]pyrimidine (210.0 g, 88.7 mmol) in THF (300 mL) and MeOH (900 mL) was cooled to −40° C. To the cooled solution was added $RuCl_3$ hydrate (2.0 g, 8.87 mmol) followed by a solution of $NaIO_4$ (56.9 g, 266.0 mmol) in $H_2O$ (700 mL) slowly. The resulting mixture was stirred for 15 min at −40° C., then warmed to 20° C. and stirred at 20° C. for 12 hrs. The reaction was quenched with a saturated aqueous $Na_2SO_3$ solution (4 L) and the resulting mixture was filtered. The filtrate was extracted with EA (5 L) twice. The organic layers were combined, then washed with aqueous $NaHCO_3$ (2 L) solution and brine (2 L), dried over anhydrous $Na_2SO_4$ and concentrated in vacuo to give a crude mixture of 6-(6-fluoro-4-methoxy-2-pyridyl)-5-methoxy-2-pyrimidin-2-yl-7,8-dihydro-5H-pyrido[4,3-d]pyrimidine, 6-(6-fluoro-5-iodo-4-methoxy-2-pyridyl)-5-methoxy-2-pyrimidin-2-yl-7,8-dihydro-5H-pyrido[4,3-d]pyrimidine and 6-(2-fluoro-6-methoxy-4-pyridyl)-5-methoxy-2-pyrimidin-2-yl-7,8-dihydro-5H-pyrido[4,3-d]pyrimidine (42.0 g, crude), which was used directly in the next step without any further purification.

Step 6: Preparation of 6-(6-fluoro-4-methoxy-2-pyridyl)-5-methyl-2-pyrimidin-2-yl-7,8-dihydro-5H-pyrido[4,3-d]pyrimidine and 6-(6-fluoro-5-iodo-4-methoxy-2-pyridyl)-5-methyl-2-pyrimidin-2-yl-7,8-dihydro-5H-pyrido[4,3-d]pyrimidine and 6-(2-fluoro-6-methoxy-4-pyridyl)-5-methyl-2-pyrimidin-2-yl-7,8-dihydro-5H-pyrido[4,3-d]pyrimidine

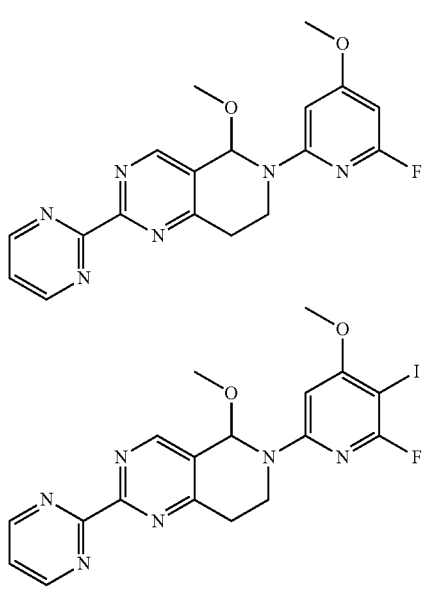

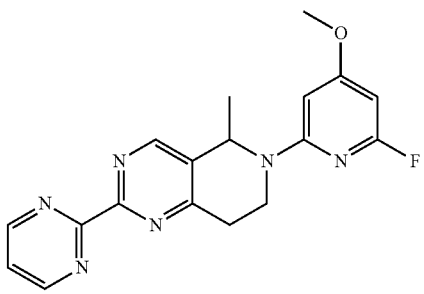

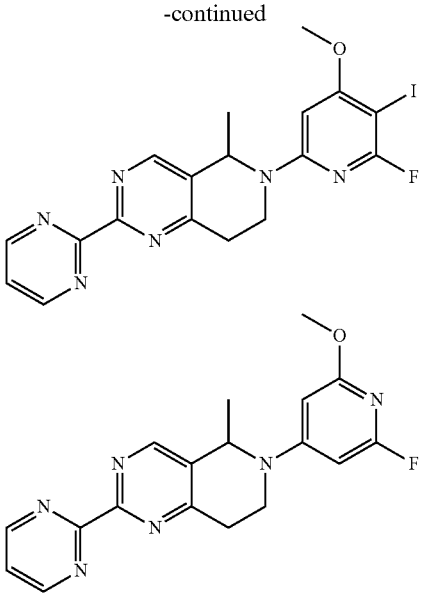

A stirred solution of the mixture of 6-(6-fluoro-4-methoxy-2-pyridyl)-5-methoxy-2-pyrimidin-2-yl-7,8-dihydro-5H-pyrido[4,3-d]pyrimidine, 6-(6-fluoro-5-iodo-4-methoxy-2-pyridyl)-5-methoxy-2-pyrimidin-2-yl-7,8-dihydro-5H-pyrido[4,3-d]pyrimidine and 6-(2-fluoro-6-methoxy-4-pyridyl)-5-methoxy-2-pyrimidin-2-yl-7,8-dihydro-5H-pyrido[4,3-d]pyrimidine (42.0 g, 114.0 mmol) in THF (500 mL) was cooled to −70° C. To the cooled solution was added BF$_3$.Et$_2$O (48.6 g, 342.0 mmol). After the resulting mixture was stirred at −70° C. for 10 mins, to the reaction mixture was added a solution of MeMgBr (114 mL, 342.0 mmol) in Et$_2$O slowly. Then the reaction mixture was stirred at −20° C. for 1 hr. The reaction was quenched by addition of saturated aqueous NH$_4$Cl (60 mL). The resulting mixture was extracted with EA (300 mL) for three times. The organic layers were combined, then washed with brine, dried over anhydrous Na$_2$SO$_4$ and concentrated in vacuo. The residue was purified by prep-HPLC to give 6-(6-fluoro-4-methoxy-2-pyridyl)-5-methyl-2-pyrimidin-2-yl-7,8-dihydro-5H-pyrido[4,3-d]pyrimidine (18.1 g) as a yellow solid, 6-(6-fluoro-5-iodo-4-methoxy-2-pyridyl)-5-methyl-2-pyrimidin-2-yl-7,8-dihydro-5H-pyrido[4,3-d]pyrimidine (21 mg) as a light yellow solid, and 6-(2-fluoro-6-methoxy-4-pyridyl)-5-methyl-2-pyrimidin-2-yl-7,8-dihydro-5H-pyrido[4,3-d]pyrimidine (20 mg) as a light yellow solid.

Example 127: 6-(6-fluoro-4-methoxy-2-pyridyl)-5-methyl-2-pyrimidin-2-yl-7,8-dihydro-5H-pyrido[4,3-d]pyrimidine, $^1$H NMR (400 MHz, DMSO-d$_6$) δ: 9.00 (d, 1H), 8.92 (s, 1H), 7.64 (t, 1H), 6.33 (s, 1H), 5.98 (d, 1H), 5.70 (q, 1H), 4.46 (m, 1H), 3.85 (s, 3H), 3.41-3.54 (m, 1H), 2.93-3.14 (m, 2H), 1.51 (d, 3H), MS obsd. (ESI$^+$) [(M+H$^+$)]: 353.

Example 128: 6-(6-fluoro-5-iodo-4-methoxy-2-pyridyl)-5-methyl-2-pyrimidin-2-yl-7,8-dihydro-5H-pyrido[4,3-d]pyrimidine, $^1$H NMR (400 MHz, CDCl$_3$) δ: 9.04 (d, 2H), 8.84 (s, 1H), 7.45 (t, 1H), 5.97 (s, 1H), 5.71 (d, 1H), 4.32-4.46 (m, 1H), 3.98 (s, 3H), 3.47-3.60 (m, 1H), 3.23-3.34 (m, 2H), 1.60 (d, 3H), MS obsd. (ESI$^+$) [(M+H$^+$)]: 479.

Example 129: 6-(2-fluoro-6-methoxy-4-pyridyl)-5-methyl-2-pyrimidin-2-yl-7,8-dihydro-5H-pyrido[4,3-d]pyrimidine, $^1$H NMR (400 MHz, CDCl$_3$) δ: 9.04 (d, 2H), 8.80 (s, 1H), 7.45 (t, 1H), 6.01 (s, 2H), 5.10 (d, 1H), 3.92-4.03 (m, 1H), 3.89 (s, 3H), 3.51-3.63 (m, 1H), 3.24-3.33 (m, 2H), 1.60 (s, 3H), MS obsd. (ESI$^+$) [(M+H$^+$)]: 353.

Example 130 and 131: (−)-6-(2-chloro-3-fluoro-5-methoxy-phenyl)-5-methyl-2-pyrimidin-2-yl-7,8-dihydro-5H-pyrido[4,3-d]pyrimidine and (−)-6-(2-chloro-5-fluoro-3-methoxy-phenyl)-5-methyl-2-pyrimidin-2-yl-7,8-dihydro-5H-pyrido[4,3-d]pyrimidine (−)-6-(3-Fluoro-5-methoxy-phenyl)-5-methyl-2-pyrimidin-2-yl-7,8-dihydro-5H-pyrido[4,3-d]pyrimidine (130 mg, 370 μmol) was dissolved in acetonitrile (5 mL) and N-chlorosuccinimide (59.3 mg, 444 μmol) was added with stirring. The reaction mixture was stirred at rt overnight. The resulting mixture was purified by prep-HPLC to give (−)-6-(2-chloro-3-fluoro-5-methoxy-phenyl)-5-methyl-2-pyrimidin-2-yl-7,8-dihydro-5H-pyrido[4,3-d]pyrimidine (10 mg) as a light yellow solid and (−)-6-(2-chloro-5-fluoro-3-methoxy-phenyl)-5-methyl-2-pyrimidin-2-yl-7,8-dihydro-5H-pyrido[4,3-d]pyrimidine (20 mg) as a light yellow solid.

Example 130: (−)-6-(2-chloro-3-fluoro-5-methoxy-phenyl)-5-methyl-2-pyrimidin-2-yl-7,8-dihydro-5H-pyrido[4,3-d]pyrimidine, $^1$H NMR (400 MHz, Methanol-d$_4$) δ: 1.40 (d, 3H), 3.17-3.26 (m, 2H), 3.41-3.52 (m, 1H), 3.66-3.75 (m, 2H), 3.81 (s, 3H), 4.98-5.09 (m, 1H), 6.58-6.70 (m, 2H), 7.64-7.70 (m, 1H), 8.87 (s, 1H), 9.05 (d, 2H), MS obsd. (ESI$^+$) [(M+H)$^+$]: 386 [a]$_D^{20}$=−7.2° (0.25 g/100 mL, MeOH);

Example 131: (−)-6-(2-chloro-5-fluoro-3-methoxy-phenyl)-5-methyl-2-pyrimidin-2-yl-7,8-dihydro-5H-pyrido[4,3-d]pyrimidine, $^1$H NMR (400 MHz, Methanol-d$_4$) δ: 1.38 (d, 3H), 3.15-3.27 (m, 2H), 3.28-3.45 (m, 2H), 3.69 (ddd, 1H), 3.90 (s, 3H), 4.90 (s, 4H), 4.95-5.11 (m, 1H), 6.68 (dd, 1H), 6.71 (dd, 1H), 7.66 (t, 1H), 8.87 (s, 1H), 9.05 (d, 2H), MS obsd. (ESI$^+$) [(M+H)$^+$]: 386, [a]$_D^{20}$=−1.5° (0.265 g/100 mL, MeOH).

Example 132: tert-butyl 3-[[2,3-difluoro-5-(5-methyl-2-pyrimidin-2-yl-7,8-dihydro-5H-pyrido[4,3-d]pyrimidin-6-yl)phenoxy]methyl]azetidine-1-carboxylate

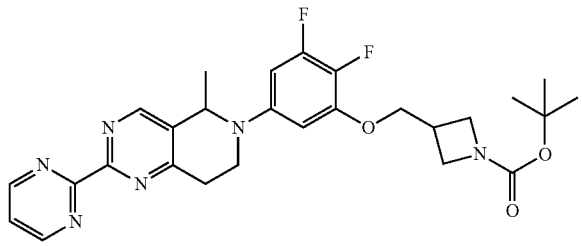 [SMILES: CC1c2cnc(-c3ncccn3)nc2CCN1c1cc(F)c(F)c(OCC2CN(C(=O)OC(C)(C)C)C2)c1]

Step 1: Preparation of tert-butyl 3-(p-tolylsulfonyloxymethyl)azetidine-1-carboxylate

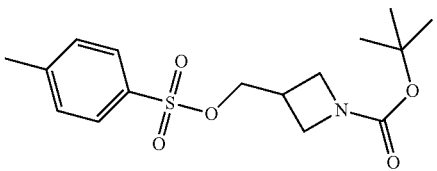 [SMILES: Cc1ccc(S(=O)(=O)OCC2CN(C(=O)OC(C)(C)C)C2)cc1]

To a solution of tert-butyl 3-(hydroxymethyl)azetidine-1-carboxylate (520 mg, 2.78 mmol) in DCM (20 mL) was added tosyl chloride (529 mg, 2.78 mmol) and triethylamine (363 mg, 0.5 mL, 3.59 mmol). After being stirred at rt overnight, the resulting reaction mixture was concentrated in vacuo to give crude tert-butyl 3-(p-tolylsulfonyloxymethyl)azetidine-1-carboxylate (950 mg) as a white solid which was used in the next step directly without any further purification.

Step 2: Preparation of tert-butyl 3-[[2,3-difluoro-5-(5-methyl-2-pyrimidin-2-yl-7,8-dihydro-5H-pyrido[4,3-d]pyrimidin-6-yl)phenoxy]methyl]azetidine-1-carboxylate

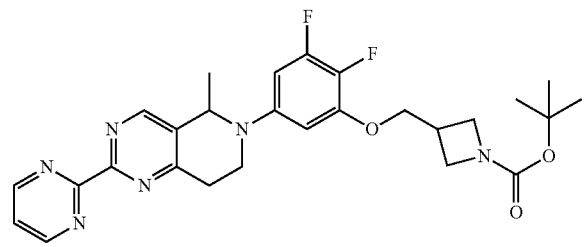 [SMILES: CC1c2cnc(-c3ncccn3)nc2CCN1c1cc(F)c(F)c(OCC2CN(C(=O)OC(C)(C)C)C2)c1]

A mixture of 2,3-difluoro-5-(5-methyl-2-pyrimidin-2-yl-7,8-dihydro-5H-pyrido[4,3-d]pyrimidin-6-yl)phenol (989 mg, 2.78 mmol), tert-butyl 3-(p-tolylsulfonyloxymethyl)-azetidine-1-carboxylate (950 mg, 2.78 mmol) and potassium carbonate (385 mg, 2.78 mmol) in N-methyl-2-pyrrolidinone (20 mL) was heated with stirring at 70° C. overnight. The resulting mixture was purified by prep-HPLC to give tert-butyl 3-[[2,3-difluoro-5-(5-methyl-2-pyrimidin-2-yl-7,8-dihydro-5H-pyrido[4,3-d]pyrimidin-6-yl)phenoxy]methyl]azetidine-1-carboxylate (15 mg) as a light yellow solid. $^1$H NMR (400 MHz, CDCl$_3$) δ: 1.43-1.50 (m, 12H), 2.96-3.08 (m, 1H), 3.29 (s, 2H), 3.46-3.58 (m, 1H), 3.68-3.78 (m, 1H), 3.78-3.87 (m, 2H), 4.12 (t, 2H), 4.21 (d, 2H), 4.99 (d, 1H), 6.36-6.48 (m, 2H), 7.46 (s, 1H), 8.81 (s, 1H), 9.06 (d, 2H). MS obsd. (ESI$^+$) [(M+H)$^+$]: 525.

Example 133: 6-[3-fluoro-5-(trifluoromethoxy)phenyl]-5-methyl-2-pyrimidin-2-yl-7,8-dihydro-5H-pyrido[4,3-d]pyrimidine

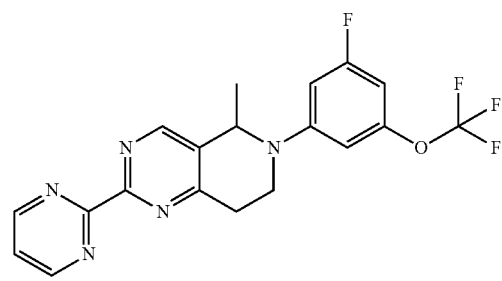 [SMILES: CC1c2cnc(-c3ncccn3)nc2CCN1c1cc(F)cc(OC(F)(F)F)c1]

Step 1: Preparation of 1-bromo-3-fluoro-5-(trifluoromethoxy)benzene

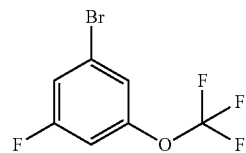 [SMILES: Fc1cc(Br)cc(OC(F)(F)F)c1]

A mixture of 3-fluoro-5-(trifluoromethoxy)aniline (4.0 g, 20.5 mmol) in H$_2$SO$_4$ (90 mL, 30%) was cooled to 0° C., and to the cooled mixture was added NaNO$_2$ (2.83 g, 41.0 mmol). After being stirred at 0° C. for 0.5 hr, the resulting reaction mixture was added to a solution of CuBr (5.86 g, 41.0 mmol) and CuBr$_2$ (9.14 g, 41.0 mmol) in HBr (50 mL). The resulting mixture was then stirred at 10° C. for 16 hrs, diluted with EA (200 mL), washed with water (50 mL) and brine (50 mL), dried over Na$_2$SO$_4$ and concentrated in vacuo to give crude 1-bromo-3-fluoro-5-(trifluoromethoxy)benzene (2.9 g), which was used directly in the next step without any further purification.

Step 2: Preparation of 8-[3-fluoro-5-(trifluoromethoxy)phenyl]-1,4-dioxa-8-azaspiro[4.5]decane

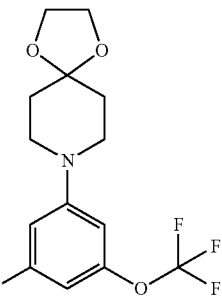

A mixture of 1-bromo-3-fluoro-5-(trifluoromethoxy)benzene (2.9 g, 16.2 mmol), 1,4-dioxa-8-azaspiro[4.5]decane hydrochloride (4.24 g, 16.4 mmol), t-BuONa (3.89 g, 40.5 mmol), Ruphos (120 mg) and Pd$_2$dba$_3$ (80 mg) in dioxane (50 mL) was degassed and heated with stirring at 100° C. under nitrogen for 16 hrs. The mixture was concentrated in vacuo and the residue was diluted with EA (200 mL). The resulting solution was washed with water (50 mL) and brine (50 mL), dried over Na$_2$SO$_4$ and concentrated in vacuo. The residue was purified by flash column to give 8-[3-fluoro-5-(trifluoromethoxy)phenyl]-1,4-dioxa-8-azaspiro[4.5]decane (1.6 g) as a yellow oil.

Step 3: Preparation of 1-[3-fluoro-5-(trifluoromethoxy)phenyl]piperidin-4-one

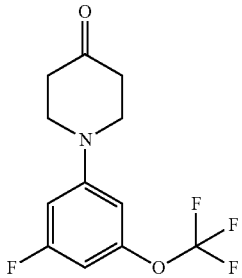 [SMILES: O=C1CCN(c2cc(F)cc(OC(F)(F)F)c2)CC1]

A mixture of 8-[3-fluoro-5-(trifluoromethoxy)phenyl]-1,4-dioxa-8-azaspiro[4.5]decane (1.6 g, 5.0 mol) in formic acid (15 mL) and H$_2$O (15 mL) was heated with stirring at 90° C. for 2 hrs. The resulting mixture was concentrated in vacuo. The residue was diluted with DCM (100 mL), washed with water (30 mL) and brine (30 mL), dried over Na$_2$SO$_4$ and concentrated in vacuo. The residue was purified by flash column to give 1-[3-fluoro-5-(trifluoromethoxy)phenyl]piperidin-4-one (930 mg) as a yellow oil.

Step 4: Preparation of 6-[3-fluoro-5-(trifluoromethoxy)phenyl]-2-pyrimidin-2-yl-7,8-dihydro-5H-pyrido[4,3-d]pyrimidine

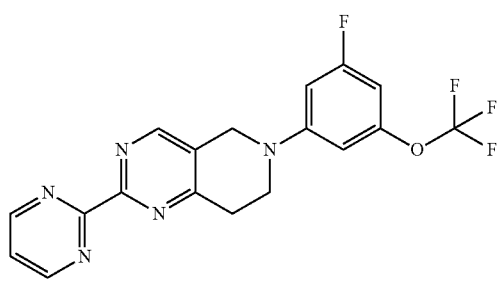

A mixture of 1-[3-fluoro-5-(trifluoromethoxy)phenyl]piperidin-4-one (830 mg. 3.00 mmol) and DMFDMA (10 mL) was heated with stirring at 100° C. for 4 hrs. The resulting mixture was concentrated in vacuo. The residue was dissolved in MeOH (10 mL) and to the solution were added 2-amidinopyrimidine hydrochloride (500 mg, 3.15 mmol) and K$_2$CO$_3$ (911 mg, 6.6 mmol). The resulting mixture was heated with stirring at 60° C. for 2 hrs, and then concentrated in vacuo. The residue was diluted with DCM (100 mL), washed with H$_2$O (30 mL) and brine (30 mL), then dried over Na$_2$SO$_4$ and concentrated in vacuo. The residue was purified by flash column to give 6-[3-fluoro-5-(trifluoromethoxy)phenyl]-2-pyrimidin-2-yl-7,8-dihydro-5H-pyrido[4,3-d]pyrimidine (800 mg) as a light yellow solid.

Step 5: Preparation of 6-[3-fluoro-5-(trifluoromethoxy)phenyl]-5-methoxy-2-pyrimidin-2-yl-7,8-dihydro-5H-pyrido[4,3-d]pyrimidine

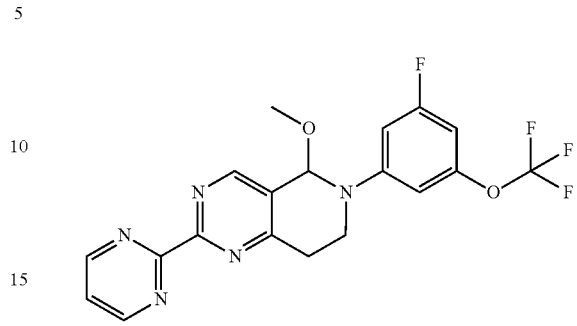

A solution of 6-[3-fluoro-5-(trifluoromethoxy)phenyl]-2-pyrimidin-2-yl-7,8-dihydro-5H-pyrido[4,3-d]pyrimidine (200 mg, 0.511 mmol) in DCM (16 mL) and MeOH (4 mL) was cooled to −50° C. To the cooled solution RuCl$_3$ hydrate (34 mg, 0.153 mmol) was added followed by a solution of NaIO$_4$ (328 mg, 1.533 mmol) in H$_2$O (4 mL) slowly. The resulting mixture was stirred for 15 min and then warmed to 15° C. with stirring for 16 hrs. The reaction was quenched with saturated aqueous Na$_2$SO$_3$ solution (20 mL) and the resulting mixture was filtered. The filtrate was extracted with DCM (50 mL) twice. The organic layers were combined, washed with brine (30 mL), dried over anhydrous Na$_2$SO$_4$ and concentrated in vacuo to give crude 6-[3-fluoro-5-(trifluoromethoxy)phenyl]-5-methoxy-2-pyrimidin-2-yl-7,8-dihydro-5H-pyrido[4,3-d]pyrimidine (190 mg) which was used directly in the next step without any further purification.

Step 6: Preparation of 6-[3-fluoro-5-(trifluoromethoxy)phenyl]-5-methyl-2-pyrimidin-2-yl-7,8-dihydro-5H-pyrido[4,3-d]pyrimidine

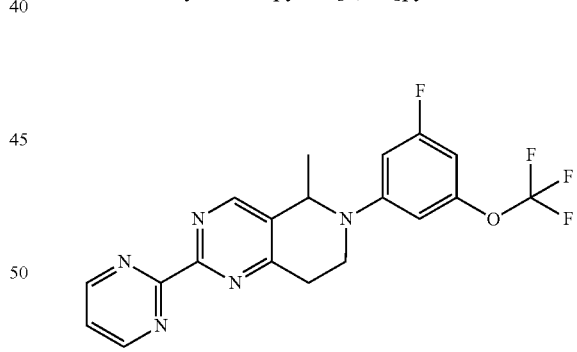

A solution of 6-[3-fluoro-5-(trifluoromethoxy)phenyl]-5-methoxy-2-pyrimidin-2-yl-7,8-dihydro-5H-pyrido[4,3-d]pyrimidine (crude 190 mg, 0.511 mmol) in THF (3 mL) was cooled to −70° C. To the cooled solution were added BF$_3$.Et$_2$O (145 mg, 1.02 mmol) and MeMgBr (0.5 mL, 1.53 mmol) successively. Then the reaction mixture was warmed to 0° C. and stirred for 1 hr. The reaction was quenched with saturated aqueous NH$_4$Cl (100 mL) solution and the resulting mixture was extracted with EA (100 mL). The organic layer was washed with brine (30 mL), dried over anhydrous Na$_2$SO$_4$ and concentrated in vacuo. The residue was purified by prep-HPLC to give 6-[3-fluoro-5-(trifluoromethoxy)phenyl]-5-methyl-2-pyrimidin-2-yl-7,8-dihydro-5H-pyrido[4, 3-d]pyrimidine (46 mg) as a light yellow solid. $^1$H NMR (400 MHz, DMSO-d6) δ: 9.00 (d, 2H), 8.89 (s, 1H), 7.65 (t, 1H), 7.34 (dd, 1H), 7.13 (dd, 1H), 7.00 (d, 1H), 5.03 (q, 1H), 3.57-3.73 (m, 2H), 3.09-3.17 (m, 1H), 2.95-3.03 (m, 1H), 1.39 (d, 3H). MS obsd (ESI) [(M+H)$^+$]: 406.

Example 134: 6-(3-fluoro-5-methyl-phenyl)-5-methyl-2-pyrimidin-2-yl-7,8-dihydro-5H-pyrido[4,3-d]pyrimidine

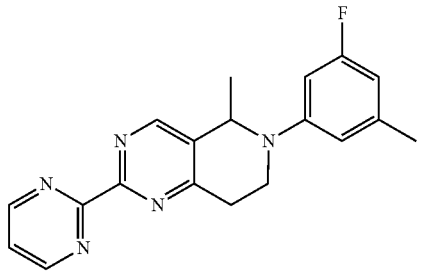 [SMILES: Cc1cc(F)cc(N2CCc3nc(-c4ncccn4)ncc3C2C)c1]

Step 1: Preparation of 8-(3-fluoro-5-methyl-phenyl)-1,4-dioxa-8-azaspiro[4.5]decane

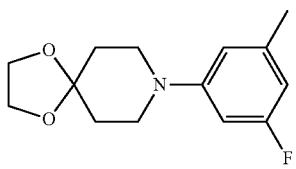 [SMILES: Cc1cc(F)cc(N2CCC3(CC2)OCCO3)c1]

A mixture of 1,4-dioxa-8-azaspiro[4.5]decane hydrochloride (4.0 g, 22.3 mmol), 1-bromo-3-fluoro-5-methylbenzene (5.05 g, 26.7 mmol), Pd$_2$(dba)$_3$ (408 mg, 445 μmol), Ruphos (416 mg, 891 μmol) and Cs$_2$CO$_3$ (18.1 g, 55.7 mmol) in toluene (50 mL) was heated with stirring at 120° C. for 15 hrs. The resulting reaction mixture was filtered through celite and the filtrate was concentrated in vacuo. The residue was purified by flash chromatography to give 8-(3-fluoro-5-methyl-phenyl)-1,4-dioxa-8-azaspiro[4.5]decane (5.0 g) as a yellow oil.

Step 2: Preparation of 1-(3-fluoro-5-methyl-phenyl)piperidin-4-one

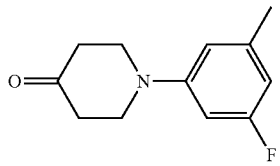

A mixture of 8-(3-fluoro-5-methylphenyl)-1,4-dioxa-8-azaspiro[4.5]decane (5.0 g, 19.9 mmol), formic acid (36 mL) and water (36 mL) was heated with stirring at 90° C. for 10 hrs. The resulting mixture was concentrated in vacuo. The residue was diluted with saturated aqueous NaHCO$_3$ solution and extracted with EA (100 mL) for three times. The combined organic layers were dried over Na$_2$SO$_4$ and concentrated in vacuo to give 1-(3-fluoro-5-methyl-phenyl)piperidin-4-one (4.0 g) as yellow oil, which was used in the next step without any further purification.

Step 3: Preparation of (3E)-3-(dimethylaminomethylene)-1-(3-fluoro-5-methyl-phenyl)piperidin-4-one

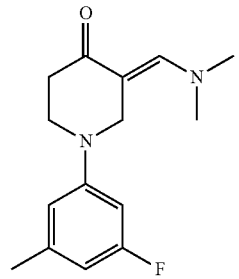

A mixture of 1-(3-fluoro-5-methylphenyl)piperidin-4-one (4 g, 19.3 mmol) and DMFDMA (11.5 g, 96.5 mmol) in DMF (10 mL) was heated with stirring at 90° C. for 2 hrs. The reaction mixture was poured into H$_2$O (20 mL) and the resulting mixture was extracted with DCM (30 mL) twice. The organic layers were combined, dried over Na$_2$SO$_4$ and concentrated in vacuo to give the crude (3E)-3-(dimethylaminomethylene)-1-(3-fluoro-5-methyl-phenyl)piperidin-4-one (4.5 g), which was used in the next step reaction without any further purification.

Step 4: Preparation of 6-(3-fluoro-5-methyl-phenyl)-2-pyrimidin-2-yl-7,8-dihydro-5H-pyrido[4,3-d]pyrimidine

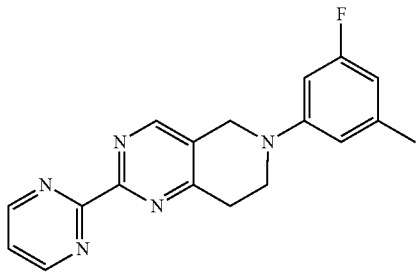 [SMILES: Cc1cc(F)cc(N2CCc3nc(-c4ncccn4)ncc3C2)c1]

A mixture of (3E)-3-(dimethylaminomethylene)-1-(3-fluoro-5-methyl-phenyl)piperidin-4-one (4.5 g, 17.2 mmol), pyrimidine-2-carboximidamide hydrochloride (4.08 g, 25.7 mmol) and K$_2$CO$_3$ (7.11 g, 51.5 mmol) in ethanol (50 mL) was heated with stirring at 90° C. overnight. After being cooled down to rt, the resulting mixture was concentrated in vacuo. The residue was purified by flash chromatography to give 6-(3-fluoro-5-methyl-phenyl)-2-pyrimidin-2-yl-7,8-dihydro-5H-pyrido[4,3-d]pyrimidine (1.7 g) as a brown oil.

Step 5: Preparation of 6-(3-fluoro-5-methyl-phenyl)-5-methoxy-2-pyrimidin-2-yl-7,8-dihydro-5H-pyrido[4,3-d]pyrimidine

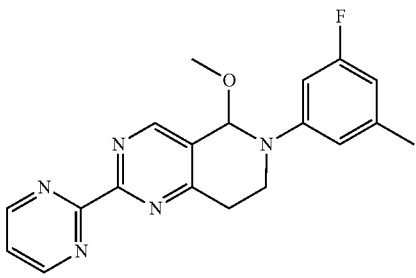 [SMILES: COC1c2cnc(-c3ncccn3)nc2CCN1c1cc(C)cc(F)c1]

To a cooled solution of 6-(3-fluoro-5-methyl-phenyl)-2-pyrimidin-2-yl-7,8-dihydro-5H-pyrido[4,3-d]pyrimidine (400 mg, 1.24 mmol) in DCM (40 mL) and MeOH (10 mL) was added Ruthenium(III) chloride hydrate (28.1 mg, 124 µmol) and a solution of sodium periodate (532 mg, 2.49 mmol) in water (20 mL) successively at −70° C. The resulting mixture was stirred at −70° C. for 5 minutes. Cooling bath was removed and the reaction mixture was warmed naturally to rt and stirred at rt for 2 hrs. The reaction was quenched with saturated aqueous $Na_2S_2O_3$ solution and the resulting mixture was extracted with EA (50 mL) twice. The organic layers were combined, dried over anhydrous $Na_2SO_4$ and concentrated in vacuo to give the crude 6-(3-fluoro-5-methyl-phenyl)-5-methoxy-2-pyrimidin-2-yl-7,8-dihydro-5H-pyrido[4,3-d]pyrimidine (300 mg) as a black oil, which was used in the next step reaction without any further purification.

Step 6: Preparation of 6-(3-fluoro-5-methyl-phenyl)-5-methyl-2-pyrimidin-2-yl-7,8-dihydro-5H-pyrido[4,3-d]pyrimidine

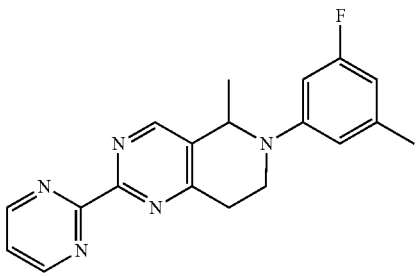 [SMILES: Cc1cc(F)cc(N2CCc3nc(-c4ncccn4)ncc3C2C)c1]

To a solution of 6-(3-fluoro-5-methyl-phenyl)-5-methoxy-2-pyrimidin-2-yl-7,8-dihydro-5H-pyrido[4,3-d]pyrimidine (300 mg, 854 µmol) in THF (10 mL) was added (diethyloxonio)trifluoroborate (242 mg, 1.71 mmol) at −70° C. The reaction mixture was stirred at −70° C. for 15 mins. Then to the reaction mixture was added a solution of methylmagnesium bromide (3.4 mL, 3.4 mmol) in $Et_2O$ at −70° C. The resulting mixture was stirred at −70° C. for 2 hrs. The reaction was then quenched with saturated aqueous $NH_4Cl$ solution and the resulting reaction mixture was extracted with a mixture of $CH_2Cl_2$ and methanol (10 mL, v/v=4/1) twice. The organic layers were combined, washed with brine, dried over $Na_2SO_4$ and concentrated in vacuo. The residue was purified by prep-HPLC to give 6-(3-fluoro-5-methyl-phenyl)-5-methyl-2-pyrimidin-2-yl-7,8-dihydro-5H-pyrido[4,3-d]pyrimidine (26 mg) as a light yellow solid. $^1$H NMR (400 MHz, CDCl$_3$) δ: 9.04 (d, 2H), 8.79 (s, 1H), 7.38-7.52 (m, 1H), 6.32-6.64 (m, 3H), 4.98-5.20 (m, 1H), 3.76-3.94 (m, 1H), 3.46-3.64 (m, 1H), 3.18-3.40 (m, 2H), 2.33 (s, 3H), 1.52 (d, 3H). MS obsd (ESI) [(M+H)$^+$]: 336.

Example 135: 2-(3-fluoro-5-methoxy-phenyl)-1-methyl-6-pyrimidin-2-yl-3,4-dihydro-1H-2,7-naphthyridine

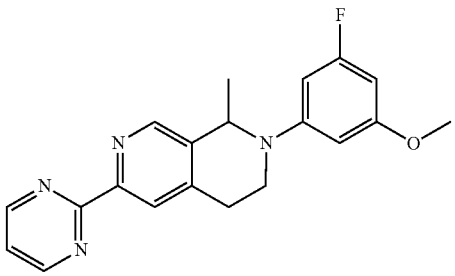 [SMILES: COc1cc(F)cc(N2CCc3cc(-c4ncccn4)ncc3C2C)c1]

Step 1: Preparation of 2-(3-fluoro-5-methoxy-phenyl)-6-methoxy-3,4-dihydro-1H-2,7-naphthyridine

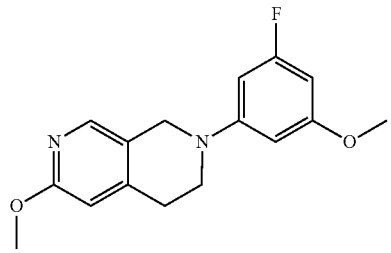 [SMILES: COc1cc(F)cc(N2CCc3cc(OC)ncc3C2)c1]

A mixture of 6-methoxy-1,2,3,4-tetrahydro-2,7-naphthyridine (1.5 g, 9.14 mmol), 3-bromo-5-fluoroanisole (1.88 g, 9.24 mmol), tert-BuONa (2.19 g, 22.85 mmol), Ruphos (220 mg) and $Pd_2dba_3$ (200 mg) in dioxane (20 mL) was degassed, heated with stirring at 100° C. under nitrogen for 16 hrs. The resulting mixture was filtered. The filtrate was diluted with DCM (100 mL), washed with water (30 mL) and brine (30 mL), dried over $Na_2SO_4$ and concentrated in vacuo. The residue was purified by column to give 2-(3-fluoro-5-methoxy-phenyl)-6-methoxy-3,4-dihydro-1H-2,7-naphthyridine (1.2 g) as a light yellow solid.

Step 2: Preparation of 2-(3-fluoro-5-methoxy-phenyl)-1,6-dimethoxy-3,4-dihydro-1H-2,7-naphthyridine

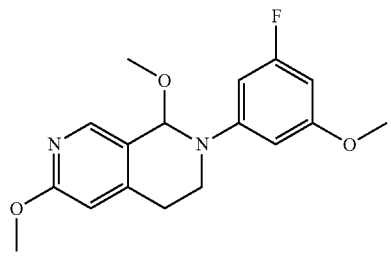 [SMILES: COc1cc(F)cc(N2CCc3cc(OC)ncc3C2OC)c1]

A solution of 2-(3-fluoro-5-methoxy-phenyl)-6-methoxy-3,4-dihydro-1H-2,7-naphthyridine (1.0 g, 3.47 mmol) in THF (7.5 mL) and MeOH (2.5 mL) was cooled to −50° C. To the cooed solution was added $RuCl_3.H_2O$ (24 mg, 0.104 mmol) and a solution of $NaIO_4$ (1.48 g, 6.94 mmol) in $H_2O$ (15 mL) successively. The resulting mixture was stirred at −50° C. for 15 min, then warmed up to 15° C. and stirred further for 3 hrs. The reaction was quenched with saturated aqueous Na₂SO₃ solution (50 mL) and filtered. The filtrate was extracted with EA (50 mL) twice. The organic layers were combined, washed with brine (30 mL), dried over anhydrous Na₂SO₄ and concentrated in vacuo to give crude 2-(3-fluoro-5-methoxy-phenyl)-1,6-dimethoxy-3,4-dihydro-1H-2,7-naphthyridine (900 mg) which was used directly in the next step without any further purification.

Step 3: Preparation of 2-(3-fluoro-5-methoxy-phenyl)-6-methoxy-1-methyl-3,4-dihydro-1H-2,7-naphthyridine

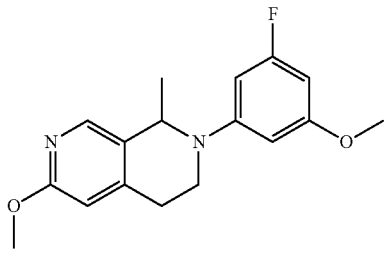 [SMILES: COc1cc(F)cc(N2CCc3cc(OC)ncc3C2C)c1]

To a solution of crude 2-(3-fluoro-5-methoxy-phenyl)-1,6-dimethoxy-3,4-dihydro-1H-2,7-naphthyridine (crude 900 mg, 3.47 mmol) in THF (15 mL) which was cooled to −70° C., was added BF₃.Et₂O (990 mg, 6.94 mmol) and MeMgBr (3.5 mL, 10.4 mmol) successively. Then the reaction mixture was warmed to 0° C. and stirred for 1 hr. The reaction was then quenched with saturated aqueous NH₄Cl (100 mL) solution and the resulting mixture was extracted with EA (100 mL) twice. The organic layers were combined, washed with brine (30 mL), dried over anhydrous Na₂SO₄ and concentrated in vacuo. The residue was purified by column to give 2-(3-fluoro-5-methoxy-phenyl)-6-methoxy-1-methyl-3,4-dihydro-1H-2,7-naphthyridine (300 mg) as a yellow solid.

Step 4: Preparation of 7-(3-fluoro-5-methoxy-phenyl)-8-methyl-6,8-dihydro-5H-2,7-naphthyridin-3-ol

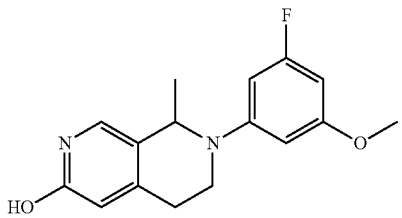 [SMILES: COc1cc(F)cc(N2CCc3cc(O)ncc3C2C)c1]

To a solution of 2-(3-fluoro-5-methoxy-phenyl)-6-methoxy-1-methyl-3,4-dihydro-1H-2,7-naphthyridine (300 mg, 0.993 mmol) in AcOH (10 mL) was added HBr (0.5 mL). The resulting mixture was heated with stirring at 70° C. for 16 hrs and then concentrated in vacuo. The residue was diluted with EA (50 mL), washed with saturated aqueous NaHCO₃ (30 mL) solution and brine (30 mL), dried over Na₂SO₄ and concentrated in vacuo to give crude 7-(3-fluoro-5-methoxy-phenyl)-8-methyl-6,8-dihydro-5H-2,7-naphthyridin-3-ol (250 mg) as a yellow solid which was directly used in the next step without any further purification.

Step 5: Preparation of [7-(3-fluoro-5-methoxy-phenyl)-8-methyl-6,8-dihydro-5H-2,7-naphthyridin-3-yl]trifluoromethanesulfonate

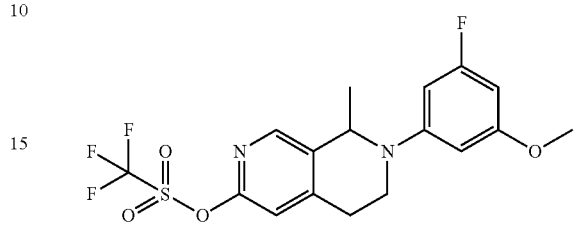

To a solution of 7-(3-fluoro-5-methoxy-phenyl)-8-methyl-6,8-dihydro-5H-2,7-naphthyridin-3-ol (8 mg, 0.028 mmol) in pyridine (0.1 mL) was added Tf₂O (39 mg, 0.14 mmol) at 0° C. Then the mixture was stirred at 15° C. for 16 hrs and concentrated in vacuo. The residue was diluted with EA (50 mL), washed with saturated aqueous NaHCO₃ (30 mL) solution and brine (30 mL), dried over Na₂SO₄ and concentrated in vacuo. The residue was purified by prep-TLC to give [7-(3-fluoro-5-methoxy-phenyl)-8-methyl-6,8-dihydro-5H-2,7-naphthyridin-3-yl]trifluoromethanesulfonate (8 mg) as a yellow solid.

Step 6: Preparation of 2-(3-fluoro-5-methoxy-phenyl)-1-methyl-6-pyrimidin-2-yl-3,4-dihydro-1H-2,7-naphthyridine

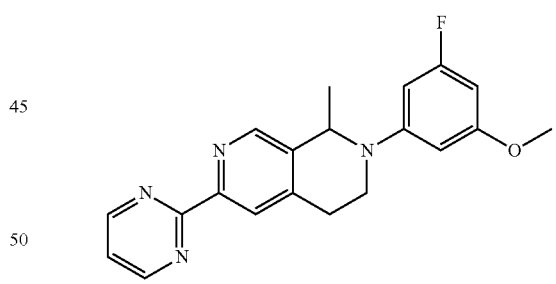

A mixture of [7-(3-fluoro-5-methoxy-phenyl)-8-methyl-6,8-dihydro-5H-2,7-naphthyridin-3-yl]trifluoromethanesulfonate (5 mg, 0.017 mmol), 2-(tributylstannyl)pyrimidine (10 mg, 0.026) and Pd(PPh₃)₄ (1 mg) in dioxane (0.5 mL) was heated with stirring at 130° C. in a microwave reactor for 60 mins. The resulting mixture was concentrated in vacuo and the residue was purified by prep-HPLC to give 2-(3-fluoro-5-methoxy-phenyl)-1-methyl-6-pyrimidin-2-yl-3,4-dihydro-1H-2,7-naphthyridine (3.1 mg) as a pink solid. ¹H NMR (400 MHz, Methanol-d₄) δ: 8.95 (s, 2H), 8.61 (s, 1H), 8.38 (s, 1H), 7.51 (s, 1H), 6.34-6.45 (m, 2H), 6.14 (dt, 1H), 5.20 (d, 1H), 3.76-3.85 (m, 4H), 3.45-3.55 (m, 1H), 2.98-3.22 (m, 2H), 1.51 (d, 3H). MS obsd (ESI) [(M+H)⁺]: 351.

Example 136: 2-[3-fluoro-5-methoxy-4-(4-pyridyl)phenyl]-1-methyl-6-pyrimidin-2-yl-3,4-dihydro-1H-2,7-naphthyridine

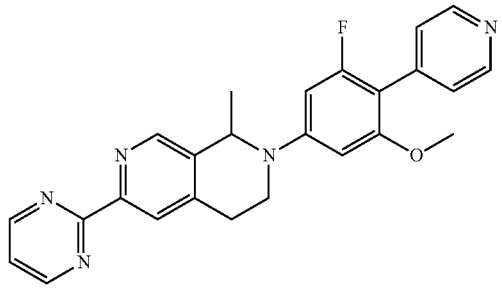 [SMILES: COc1cc(N2CCc3cc(-c4ncccn4)ncc3C2C)cc(F)c1-c1ccncc1]

Step 1: Preparation of [7-[3-fluoro-5-methoxy-4-(4-pyridyl)phenyl]-8-methyl-2-(trifluoromethylsulfonyl)-1,5,6,8-tetrahydro-2,7-naphthyridin-3-yl]trifluoromethanesulfonate

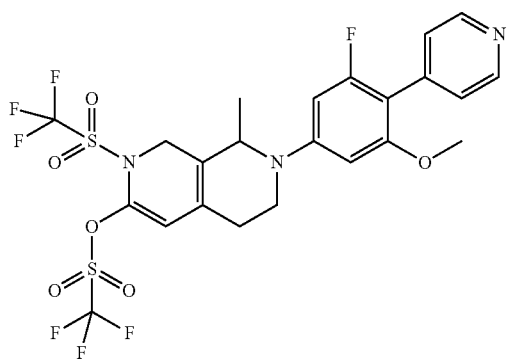 [SMILES: COc1cc(N2CCC3=C(CN(S(=O)(=O)C(F)(F)F)C(OS(=O)(=O)C(F)(F)F)=C3)C2C)cc(F)c1-c1ccncc1]

To a solution of 7-(3-fluoro-5-methoxy-phenyl)-8-methyl-6,8-dihydro-5H-2,7-naphthyridin-3-ol (250 mg, 0.868 mmol) in pyridine (3.0 mL) was added Tf₂O (1.22 g, 4.34 mmol) at 0° C. After being stirred at 25° C. for 16 hrs, the resulting mixture was diluted with EA (100 mL), washed with water (30 mL) and brine (30 mL), dried over Na₂SO₄ and concentrated in vacuo. The residue was purified by column to give [7-[3-fluoro-5-methoxy-4-(4-pyridyl)phenyl]-8-methyl-2-(trifluoromethylsulfonyl)-1,5,6,8-tetrahydro-2,7-naphthyridin-3-yl]trifluoromethanesulfonate (220 mg) as a yellow solid.

Step 2: Preparation of 7-[3-fluoro-5-methoxy-4-(4-pyridyl)phenyl]-8-methyl-6,8-dihydro-5H-2,7-naphthyridin-3-ol

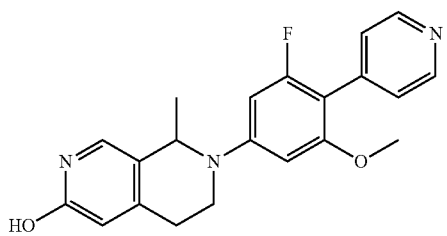 [SMILES: COc1cc(N2CCc3cc(O)ncc3C2C)cc(F)c1-c1ccncc1]

To a solution of [7-[3-fluoro-5-methoxy-4-(4-pyridyl)phenyl]-8-methyl-2-(trifluoromethylsulfonyl)-1,5,6,8-tetrahydro-2,7-naphthyridin-3-yl]trifluoromethanesulfonate (220 mg, 0.348 mmol) in DMSO (4 mL) was added tert-BuOK (112 mg, 1.046 mmol). The resulting mixture was stirred at 25° C. for 30 mins, then diluted with EA (100 mL), and washed with water (30 mL) and brine (30 mL). The organic layer was dried over Na₂SO₄ and concentrated in vacuo to give 7-[3-fluoro-5-methoxy-4-(4-pyridyl)phenyl]-8-methyl-6,8-dihydro-5H-2,7-naphthyridin-3-ol (90 mg) as a yellow solid, which was used directly in the next step without any further purification.

Step 3: Preparation of [7-[3-fluoro-5-methoxy-4-(4-pyridyl)phenyl]-8-methyl-6,8-dihydro-5H-2,7-naphthyridin-3-yl]trifluoromethanesulfonate

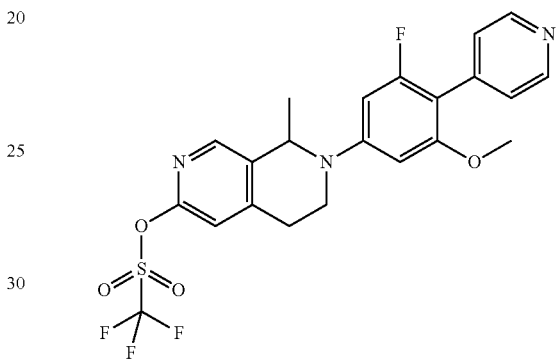

To a solution of 7-[3-fluoro-5-methoxy-4-(4-pyridyl)phenyl]-8-methyl-6,8-dihydro-5H-2,7-naphthyridin-3-ol (80 mg, 0.219 mmol), Et₃N (66 mg, 0.657 mmol) in DCM (1 mL) was added PhNTf₂ (117 mg, 0.329 mmol) at 0° C. After being stirred at 25° C. for 16 hrs, the resulting mixture was diluted with DCM (100 mL), washed with water (30 mL) and brine (30 mL), dried over Na₂SO₄ and concentrated in vacuo. The residue was purified by prep-TLC to give [7-[3-fluoro-5-methoxy-4-(4-pyridyl)phenyl]-8-methyl-6,8-dihydro-5H-2,7-naphthyridin-3-yl]trifluoromethanesulfonate (70 mg) as a yellow solid.

Step 4: Preparation of 2-[3-fluoro-5-methoxy-4-(4-pyridyl)phenyl]-1-methyl-6-pyrimidin-2-yl-3,4-dihydro-1H-2,7-naphthyridine

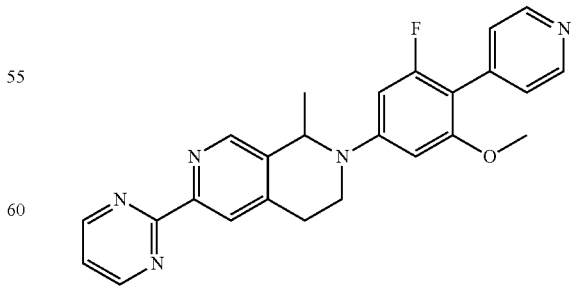

A mixture of [7-[3-fluoro-5-methoxy-4-(4-pyridyl)phenyl]-8-methyl-6,8-dihydro-5H-2,7-naphthyridin-3-yl]trifluoromethanesulfonate (70 mg, 0.141 mmol), 2-(tributylstannyl)pyrimidine (78 mg, 0.211) and Pd(PPh₃)₄ (4 mg) in dioxane (1 mL) was heated with stirring at 130° C. in a microwave reactor for 1 hr. The resulting mixture was concentrated in vacuo. The residue was purified by prep-HPLC to give 2-[3-fluoro-5-methoxy-4-(4-pyridyl)phenyl]-1-methyl-6-pyrimidin-2-yl-3,4-dihydro-1H-2,7-naphthyridine (10.4 mg, yield: 17.3%) as a yellow solid. $^1$H NMR (400 MHz, CDCl₃) δ: 8.93 (d, 2H), 8.69 (s, 1H), 8.60 (d, 2H), 8.37 (s, 1H), 7.50 (d, 2H), 7.34 (t, 1H), 6.35-6.42 (m, 1H), 6.33 (s, 1H), 5.13 (q, 1H), 3.74-3.93 (m, 4H), 3.50-3.65 (m, 1H), 3.01-3.22 (m, 2H), 1.59 (d, 3H).

MS obsd (ESI) [(M+H)⁺]: 428.

Example 137: Preparation of 6-(3-cyclopropyl-5-fluoro-phenyl)-5-methyl-2-pyrimidin-2-yl-7,8-dihydro-5H-pyrido[4,3-d]pyrimidine

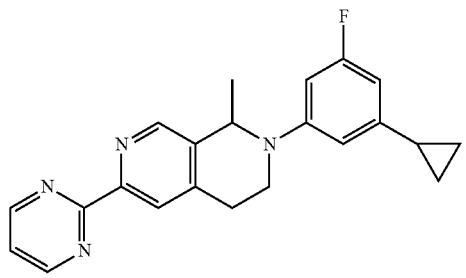 [SMILES: CC1c2cnc(-c3ncccn3)cc2CCN1c1cc(F)cc(C2CC2)c1]

Step 1: Preparation of 8-(3-bromo-5-fluoro-phenyl)-1,4-dioxa-8-azaspiro[4.5]decane

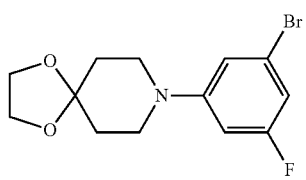 [SMILES: Fc1cc(Br)cc(N2CCC3(CC2)OCCO3)c1]

A mixture of 1,4-dioxa-8-azaspiro[4.5]decane hydrochloride (8 g, 44.5 mmol), 1,3-dibromo-5-fluorobenzene (13.6 g, 53.4 mmol), CuI (1.7 g, 8.91 mmol), L-proline (5.13 g, 44.5 mmol) and K₂CO₃ (18.5 g, 134 mmol) in DMF (50 mL) was heated with stirring at 90° C. for 15 hrs. The resulting reaction mixture was filtered through celite and the filtrate was concentrated in vacuo. The residue was purified by flash chromatography to give 8-(3-bromo-5-fluoro-phenyl)-1,4-dioxa-8-azaspiro[4.5]decane (5.3 g) as a yellow oil.

Step 2: Preparation of 1-(3-bromo-5-fluoro-phenyl)piperidin-4-one

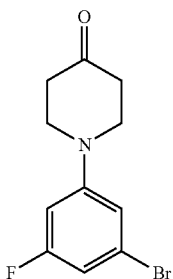

A mixture of 8-(3-bromo-5-fluorophenyl)-1,4-dioxa-8-azaspiro[4.5]decane (5.3 g, 16.8 mmol), formic acid (36 mL) and water (36 mL) was heated with stirring at 90° C. for 10 hrs. Then the mixture was concentrated in vacuo. The residue was diluted with saturated aqueous NaHCO₃ solution, and extracted with EA (100 mL) for three times. The organic layers were combined, dried over Na₂SO₄ and concentrated in vacuo to give 1-(3-bromo-5-fluoro-phenyl)piperidin-4-one (4 g) as yellow oil, which was used in the next step without any further purification.

Step 3: Preparation of (3E)-1-(3-bromo-5-fluoro-phenyl)-3-(dimethylaminomethylene)piperidin-4-one

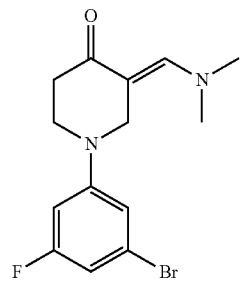 [SMILES: CN(C)/C=C1\CN(c2cc(F)cc(Br)c2)CCC1=O]

A mixture of 1-(3-bromo-5-fluorophenyl)piperidin-4-one (4 g, 14.7 mmol) and DMFDMA (8.76 g, 73.5 mmol) in DMF (10 mL) was heated with stirring at 90° C. for 2 hrs. The reaction mixture was poured into H₂O (20 mL) and extracted with DCM (30 mL) twice. The organic layers were combined, dried over Na₂SO₄ and concentrated in vacuo to give the crude (3E)-1-(3-bromo-5-fluoro-phenyl)-3-(dimethylaminomethylene)piperidin-4-one (4.5 g) which was used into the next step reaction without any further purification.

Step 4: Preparation of 6-(3-bromo-5-fluoro-phenyl)-2-pyrimidin-2-yl-7,8-dihydro-5H-pyrido[4,3-d]pyrimidine

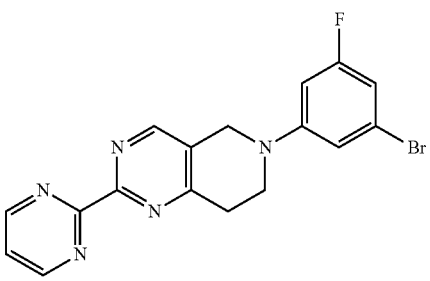 [SMILES: Fc1cc(Br)cc(N2CCc3nc(-c4ncccn4)ncc3C2)c1]

A mixture of (3E)-1-(3-bromo-5-fluoro-phenyl)-3-(dimethylaminomethylene)piperidin-4-one (4.5 g, 13.8 mmol), pyrimidine-2-carboximidamide hydrochloride (2.62 g, 16.5 mmol) and K₂CO₃ (5.7 g, 41.3 mmol) in ethanol (50 mL) was heated with stirring at 90° C. overnight. After being cooled to room temperature, the resulting mixture was concentrated in vacuo. The residue was purified by flash chromatography to give the crude 6-(3-bromo-5-fluorophenyl)-2-pyrimidin-2-yl-7,8-dihydro-5H-pyrido[4,3-d]pyrimidine (4 g) as a brown oil.

Step 5: Preparation of 6-(3-cyclopropyl-5-fluoro-phenyl)-2-pyrimidin-2-yl-7,8-dihydro-5H-pyrido[4,3-d]pyrimidine

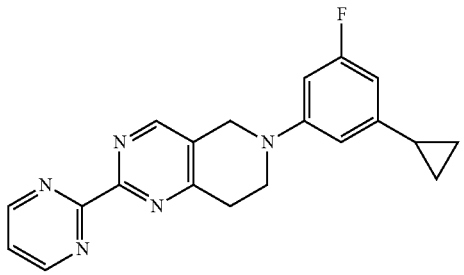 [SMILES: Fc1cc(C2CC2)cc(N2CCc3nc(-c4ncccn4)ncc3C2)c1]

A mixture of 6-(3-bromo-5-fluoro-phenyl)-2-pyrimidin-2-yl-7,8-dihydro-5H-pyrido[4,3-d]pyrimidine (1.5 g, 3.88 mmol), 1,1'-bis(diphenylphosphino)ferrocene-palladium(II) dichloride dichloromethane complex (63.4 mg, 77.7 μmol), potassium cyclopropyltrifluoroborate (862 mg, 5.83 mmol) and $K_2CO_3$ (1.61 g, 11.7 mmol) in toluene (15 ml) and $H_2O$ (1 mL) was heated with stirring at 90° C. overnight. After being cooled to rt, the resulting mixture was concentrated in vacuo. The residue was purified by flash chromatography to give 6-(3-cyclopropyl-5-fluoro-phenyl)-2-pyrimidin-2-yl-7,8-dihydro-5H-pyrido[4,3-d]pyrimidine (100 mg) as a brown oil.

Step 6: Preparation of 6-(3-cyclopropyl-5-fluoro-phenyl)-5-methoxy-2-pyrimidin-2-yl-7,8-dihydro-5H-pyrido[4,3-d]pyrimidine

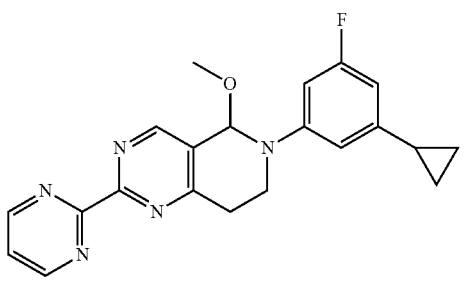 [SMILES: COC1c2cnc(-c3ncccn3)nc2CCN1c1cc(F)cc(C2CC2)c1]

To a solution of 6-(3-cyclopropyl-5-fluoro-phenyl)-2-pyrimidin-2-yl-7,8-dihydro-5H-pyrido[4,3-d]pyrimidine (100 mg, 288 μmol) in THF (4 mL) and MeOH (4 mL) were added ruthenium(III) chloride hydrate (6.49 mg, 28.8 μmol) and a solution of NaIO4 (246 mg, 1.15 mmol) in water (8 mL) successively at −70° C. The resulting mixture was stirred at rt for 1 hr and the reaction was quenched by addition of saturated aqueous $Na_2S_2O_3$ solution. The resulting mixture was then extracted with EA (20 mL) twice. The organic layers were combined, washed with brine, dried over $Na_2SO_4$ and concentrated in vacuo to give the crude product (80 mg) as a brown foam which was directly used in the next step without any further purification.

Step 7: Preparation of 6-(3-cyclopropyl-5-fluoro-phenyl)-5-methyl-2-pyrimidin-2-yl-7,8-dihydro-5H-pyrido[4,3-d]pyrimidine

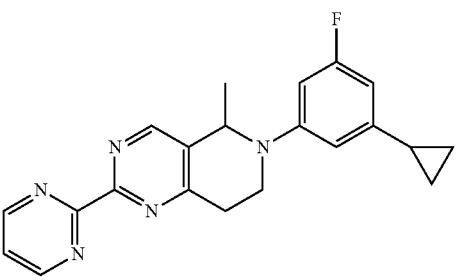 [SMILES: CC1c2cnc(-c3ncccn3)nc2CCN1c1cc(F)cc(C2CC2)c1]

To a solution of 6-(3-cyclopropyl-5-fluoro-phenyl)-5-methoxy-2-pyrimidin-2-yl-7,8-dihydro-5H-pyrido[4,3-d]pyrimidine (80 mg, 212 μmol) in THF (10 mL) was added (diethyloxonio)trifluoroborate (181 mg, 1.27 mmol) at −70° C. The reaction mixture was stirred at −70° C. for 15 min. Then to the reaction mixture was added a solution of methylmagnesium bromide (1.3 mL, 1.3 mmol) in $Et_2O$ at −70° C. The resulting mixture was stirred at −70° C. for 2 hrs. The reaction was quenched by addition of saturated aqueous $NH_4Cl$ solution and the resulting mixture was extracted with a mixture of $CH_2Cl_2$ and methanol (v/v=4:1, 10 mL) twice. Then the organic layers were combined, washed with brine, dried over $Na_2SO_4$ and concentrated in vacuo. The residue was purified by prep-HPLC to give 6-(3-cyclopropyl-5-fluoro-phenyl)-5-methyl-2-pyrimidin-2-yl-7,8-dihydro-5H-pyrido[4,3-d]pyrimidine (2.3 mg). $^1$H NMR (400 MHz, $CDCl_3$) δ: 9.06 (br. s., 2H), 8.83 (br. s., 1H), 7.48 (t, 1H), 6.44-6.63 (m, 2H), 6.25 (d, 1H), 5.10 (d, 1H), 3.79-3.95 (m, 1H), 3.48-3.62 (m, 1H), 3.21-3.38 (m, 2H), 1.84-1.93 (m, 1H), 1.54 (d, 3H), 1.00 (dd, 2H), 0.72 (dd, 2H). MS obsd (ESI) [(M+H)$^+$]: 362.

Example 138 and 139: (−)-6-(6-fluoro-4-methoxy-2-pyridyl)-5-methyl-2-pyrimidin-2-yl-7,8-dihydro-5H-pyrido[4,3-d]pyrimidine and (+)-6-(6-fluoro-4-methoxy-2-pyridyl)-5-methyl-2-pyrimidin-2-yl-7,8-dihydro-5H-pyrido[4,3-d]pyrimidine

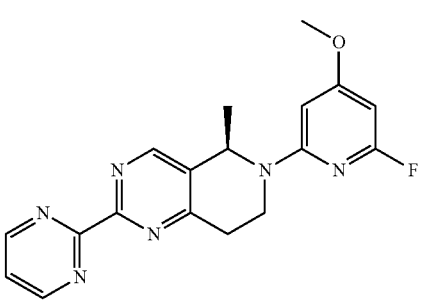

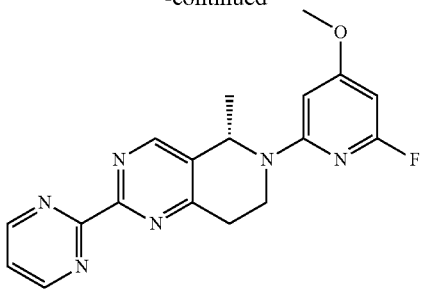

6-(6-Fluoro-4-methoxy-2-pyridyl)-5-methyl-2-pyrimidin-2-yl-7,8-dihydro-5H-pyrido[4,3-d]pyrimidine (300 mg, 851 μmol, Example 127) was chiral separated by SFC to give (−)-6-(6-fluoro-4-methoxy-2-pyridyl)-5-methyl-2-pyrimidin-2-yl-7,8-dihydro-5H-pyrido[4,3-d]pyrimidine (134 mg) as a pale yellow solid and (+)-6-(6-fluoro-4-methoxy-2-pyridyl)-5-methyl-2-pyrimidin-2-yl-7,8-dihydro-5H-pyrido[4,3-d]pyrimidine (131 mg) as a pale yellow solid.

Example 138: (−)-6-(6-fluoro-4-methoxy-2-pyridyl)-5-methyl-2-pyrimidin-2-yl-7,8-dihydro-5H-pyrido[4,3-d]pyrimidine, $^1$H NMR (400 MHz, CDCl$_3$) δ: $^1$H NMR (400 MHz, CDCl$_3$) δ: 1.59 (d, 3H), 3.25-3.32 (m, 2H), 3.44-3.56 (m, 1H), 4.35-4.47 (m, 1H), 5.63-5.76 (m, 1H), 5.84 (s, 1H), 6.02 (s, 1H), 7.45 (s, 1H), 8.78-8.91 (m, 1H), 8.99-9.11 (m, 2H). MS obsd (ESI) [(M+H)$^+$]: 353. [a]$_D^{20}$=−117.2° (0.0614 g/100 mL, MeOH).

Example 139: (+)-6-(6-fluoro-4-methoxy-2-pyridyl)-5-methyl-2-pyrimidin-2-yl-7,8-dihydro-5H-pyrido[4,3-d]pyrimidine, $^1$H NMR (400 MHz, CDCl$_3$) δ: 1.59 (d, 3H), 3.25-3.32 (m, 2H), 3.44-3.57 (m, 1H), 4.35-4.47 (m, 1H), 5.64-5.74 (m, 1H), 5.84 (s, 1H), 6.02 (s, 1H), 7.46 (s, 1H), 8.79-8.89 (m, 1H), 9.05 (d, 2H). MS obsd (ESI) [(M+H)$^+$]: 353.

Example 140: 6-(4-chloro-6-methoxy-2-pyridyl)-5-methyl-2-pyrimidin-2-yl-7,8-dihydro-5H-pyrido[4,3-d]pyrimidine

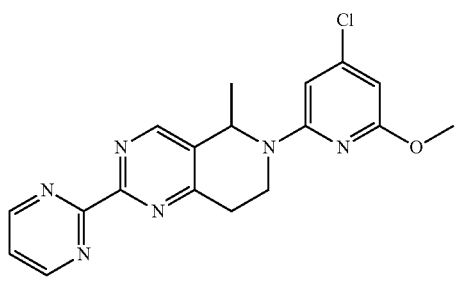

Step 1: Preparation of tert-butyl 2-pyrimidin-2-yl-7,8-dihydro-5H-pyrido[4,3-d]pyrimidine-6-carboxylate

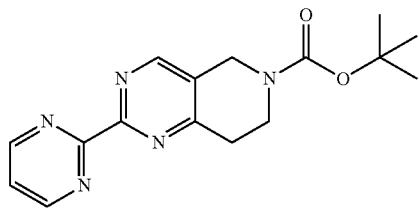 [SMILES: CC(C)(C)OC(=O)N1CCc2nc(-c3ncccn3)ncc2C1]

A solution of N-(tert-butoxycarbonyl)-4-piperidone (100.0 g, 0.50 mol) in DMFDMA (299.0 g, 2.5 mol) was heated with stirring at 120° C. under nitrogen for 4 hrs. The reaction mixture was concentrated in vacuo. The residue was dissolved in MeOH (2.0 L) and to the solution were added 2-amidinopyrimidine hydrochloride (87.8 g, 0.55 mol) and K$_2$CO$_3$ (173.9 g, 1.26 mol) successively. The resulting mixture was heated with stirring at 70° C. for 3 hrs. The resulting reaction mixture was cooled to rt and filtered. The filtrate was concentrated in vacuo. The residue was diluted with DCM (2.0 L), washed with H$_2$O (500 mL) and brine (300 mL), dried over anhydrous Na$_2$SO$_4$ and concentrated in vacuo. The residue was purified by the flash column chromatography to give tert-butyl 2-pyrimidin-2-yl-7,8-dihydro-5H-pyrido[4,3-d]pyrimidine-6-carboxylate (47.7 g) as a yellow solid.

Step 2: Preparation of 2-pyrimidin-2-yl-5,6,7,8-tetrahydropyrido[4,3-d]pyrimidine

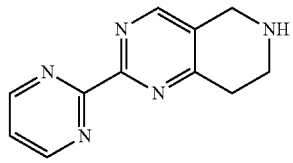 [SMILES: c1cnc(-c2ncc3c(n2)CCNC3)nc1]

To a stirred solution of tert-butyl 2-pyrimidin-2-yl-7,8-dihydro-5H-pyrido[4,3-d]pyrimidine-6-carboxylate (47.7 g, 0.15 mol) in MeOH (500 mL) was added a solution of HCl in MeOH (190 mL, 4.0 M) slowly and the reaction mixture was stirred at 15° C. for 16 hrs. The reaction mixture was concentrated in vacuo and the residue was diluted with MeOH (1.0 L). To the resulting mixture was added basic resin (500 g, AMBERLYST® A21) portion wise. The resulting mixture was stirred at 15° C. until pH>7, and then filtered. The afforded solid was washed with a mixture of DCM and MeOH (1200 mL, v/v=1:1). The collected filtrate was concentrated in vacuo to afford 2-pyrimidin-2-yl-5,6,7,8-tetrahydropyrido[4,3-d]pyrimidine (39.0 g, equal equivalent) as a yellow solid.

Step 3: Preparation of 6-(2-chloro-6-methoxy-4-pyridyl)-2-pyrimidin-2-yl-7,8-dihydro-5H-pyrido[4,3-d]pyrimidine and 6-(4-chloro-6-methoxy-2-pyridyl)-2-pyrimidin-2-yl-7,8-dihydro-5H-pyrido[4,3-d]pyrimidine

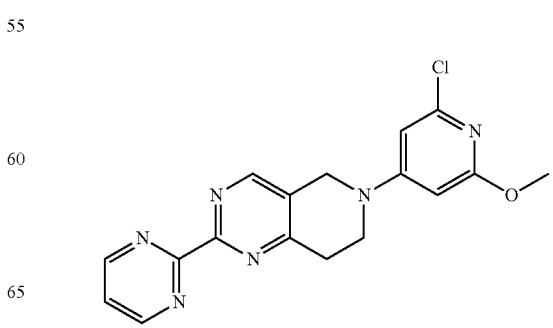

-continued

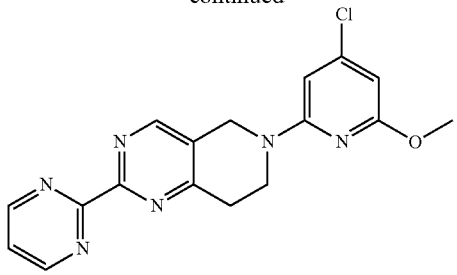

A mixture of 2-pyrimidin-2-yl-5,6,7,8-tetrahydropyrido[4,3-d]pyrimidine (5.6 g, 0.03 mol), 2, 4-dichloro-6-methoxypyridine (6.7 g, 0.03 mol) and $K_2CO_3$ (13.0 g, 0.094 mol) in NMP (100 mL) was heated with stirring at 130° C. under nitrogen for 12 hrs. The reaction mixture was cooled to rt and diluted with $H_2O$ (100 mL). The resulting mixture was extracted with DCM (200 mL) for three times. The organic layers were combined, washed with brine (50 mL), dried over anhydrous $Na_2SO_4$ and concentrated in vacuo. The residue was purified by flash column chromatography and prep-HPLC to give 6-(4-chloro-6-methoxy-2-pyridyl)-2-pyrimidin-2-yl-7,8-dihydro-5H-pyrido[4,3-d]pyrimidine (1.2 g) as a white solid and 6-(2-chloro-6-methoxy-4-pyridyl)-2-pyrimidin-2-yl-7,8-dihydro-5H-pyrido[4,3-d]pyrimidine (450 mg) as a yellow solid.

Step 4: Preparation of 6-(4-chloro-6-methoxy-2-pyridyl)-5-methoxy-2-pyrimidin-2-yl-7,8-dihydro-5H-pyrido[4,3-d]pyrimidine

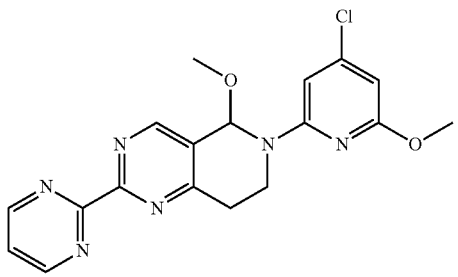

To a solution of 6-(4-chloro-6-methoxy-2-pyridyl)-2-pyrimidin-2-yl-7,8-dihydro-5H-pyrido[4,3-d]pyrimidine (400 mg, 1.13 mmol) in THF (4 mL) and MeOH (4 mL) which was cooled to −70° C., was added $RuCl_3.H_2O$ (25 mg, 0.11 mmol) and a solution of $NaIO_4$ (723 mg, 3.38 mmol) in $H_2O$ (7 mL) successively. The resulting mixture was stirred at −70° C. for 15 min, then warmed up to 25° C. and stirred at 25° C. for 6 hrs. The reaction was quenched with saturated aqueous $Na_2SO_3$ (20 mL) solution. The resulting mixture was filtered. The filtrate was extracted with EA (20 mL) for three times. The organic layers were combined, washed with brine (30 mL), dried over anhydrous $Na_2SO_4$, and concentrated in vacuo to give 6-(4-chloro-6-methoxy-2-pyridyl)-5-methoxy-2-pyrimidin-2-yl-7,8-dihydro-5H-pyrido[4,3-d]pyrimidine (140 mg, crude) as a black oil which was used directly in the next step without any further purification.

Step 5: Preparation of 6-(4-chloro-6-methoxy-2-pyridyl)-5-methyl-2-pyrimidin-2-yl-7,8-dihydro-5H-pyrido[4,3-d]pyrimidine

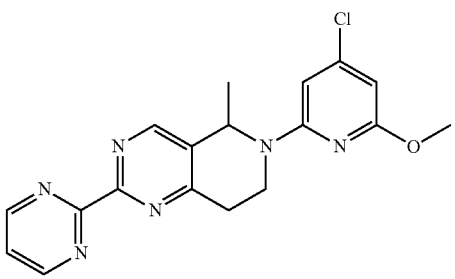

To a stirred solution of 6-(4-chloro-6-methoxy-2-pyridyl)-5-methoxy-2-pyrimidin-2-yl-7,8-dihydro-5H-pyrido[4,3-d]pyrimidine (140 mg, 0.36 mmol) in THF (3 mL) which was cooled to −60° C., were added $BF_3.Et_2O$ (155 mg, 1.09 mmol) and MeMgBr (0.4 mL, 1.09 mmol) successively and slowly. The reaction mixture was warmed up to −30° C. and stirred at −30° C. for 0.5 hr. The reaction was quenched with saturated aqueous $NH_4Cl$ (3 mL) solution and the resulting mixture was extracted with EA (10 mL) for three times. The organic layers were combined, washed with brine (10 mL), dried over anhydrous $Na_2SO_4$ and concentrated in vacuo. The residue was purified by prep-HPLC to give 6-(4-chloro-6-methoxy-2-pyridyl)-5-methyl-2-pyrimidin-2-yl-7,8-dihydro-5H-pyrido[4,3-d]pyrimidine (8 mg) as a yellow solid. $^1$H NMR (400 MHz, Methanol-$d_4$) δ: 9.00-9.06 (m, 2H), 8.89 (s, 1H), 7.64 (t, 1H), 6.42-6.49 (m, 1H), 6.07 (d, 1H), 5.76 (q, 1H), 4.52-4.62 (m, 1H), 3.90 (s, 3H), 3.47-3.58 (m, 1H), 3.13-3.20 (m, 2H). MS obsd. (ESI$^+$) [(M+H)$^+$]: 369.

Example 141: 6-(2-chloro-6-methoxy-4-pyridyl)-5-methyl-2-pyrimidin-2-yl-7,8-dihydro-5H-pyrido[4,3-d]pyrimidine

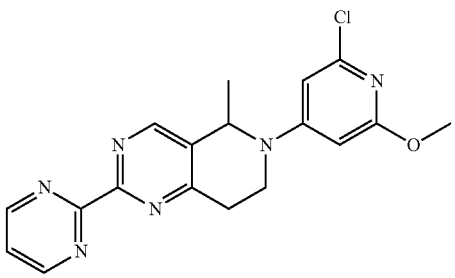

Step 1: Preparation of 6-(2-chloro-6-methoxy-4-pyridyl)-5-methoxy-2-pyrimidin-2-yl-7,8-dihydro-5H-pyrido[4,3-d]pyrimidine

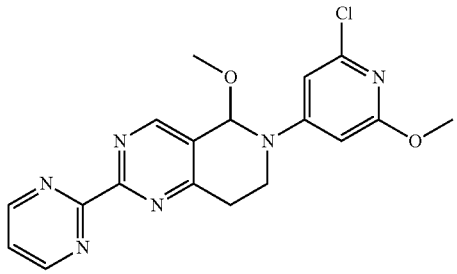

To a solution of 6-(2-chloro-6-methoxy-4-pyridyl)-2-pyrimidin-2-yl-7,8-dihydro-5H-pyrido[4,3-d]pyrimidine (150 mg, 0.42 mmol) in THF (3 mL) and MeOH (3 mL) which was cooled to −70° C., was added RuCl$_3$ hydrate (10 mg, 0.042 mmol) and a solution of NaIO$_4$ (271 mg) in H$_2$O (3 mL) successively and slowly. The resulting mixture was stirred at −70° C. for 15 mins and then warmed to rt and stirred at rt for 6 hrs. The reaction was quenched with saturated aqueous Na$_2$SO$_3$ (20 mL) solution and the mixture was filtered. The filtrate was extracted with EA (20 mL) for three times. The organic layers were combined, washed with brine (30 mL), dried over anhydrous Na$_2$SO$_4$ and concentrated in vacuo to give 6-(2-chloro-6-methoxy-4-pyridyl)-5-methoxy-2-pyrimidin-2-yl-7,8-dihydro-5H-pyrido[4,3-d]pyrimidine (74 mg, crude) as a black oil which was used directly in the next step without any further purification.

Step 2: Preparation of 6-(2-chloro-6-methoxy-4-pyridyl)-5-methyl-2-pyrimidin-2-yl-7,8-dihydro-5H-pyrido[4,3-d]pyrimidine

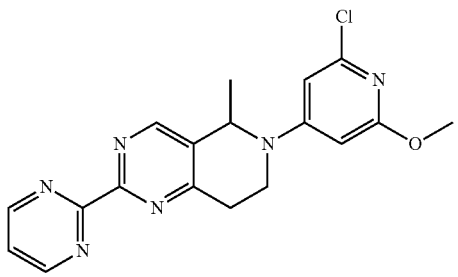

To a stirred solution of 6-(2-chloro-6-methoxy-4-pyridyl)-5-methoxy-2-pyrimidin-2-yl-7,8-dihydro-5H-pyrido[4,3-d]pyrimidine (74 mg, 0.19 mmol) in THF (1 mL) which was cooled to −60° C., was added BF$_3$.Et$_2$O (82 mg, 0.58 mmol) and a solution of MeMgBr (0.2 mL, 0.58 mmol) in Et$_2$O successively and slowly. The reaction mixture was warmed up to −20° C. and stirred for 0.5 hr. The reaction was quenched with saturated aqueous NH$_4$Cl (2 mL) solution and extracted with EA (10 mL) for three times. The organic layers were combined, washed with brine (10 mL), dried over anhydrous Na$_2$SO$_4$ and concentrated in vacuo. The residue was purified by prep-HPLC to give 6-(2-chloro-6-methoxy-4-pyridyl)-5-methyl-2-pyrimidin-2-yl-7,8-dihydro-5H-pyrido[4,3-d]pyrimidine (7 mg) as a white solid.

$^1$H NMR (400 MHz, Methanol-d$_4$) δ: 8.99-9.09 (m, 2H), 8.88 (s, 1H), 7.65 (t, 1H), 6.70 (d, 1H), 6.23 (d, 1H), 5.36 (q, 1H), 4.13 (dt, 1H), 3.85 (s, 3H), 3.52-3.64 (m, 1H), 3.14-3.23 (m, 2H). MS obsd. (ESI$^+$) [(M+H)$^+$]: 369.

Example 142: 6-(4-fluoro-6-methoxy-2-pyridyl)-5-methyl-2-pyrimidin-2-yl-7,8-dihydro-5H-pyrido[4,3-d]pyrimidine

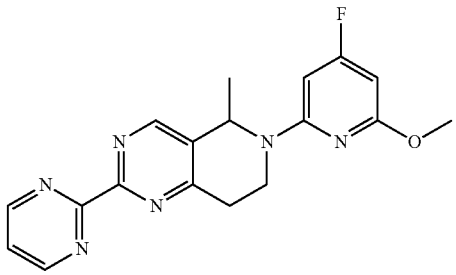

Step 1: Preparation of 6-(4,6-difluoro-2-pyridyl)-2-pyrimidin-2-yl-7,8-dihydro-5H-pyrido[4,3-d]pyrimidine

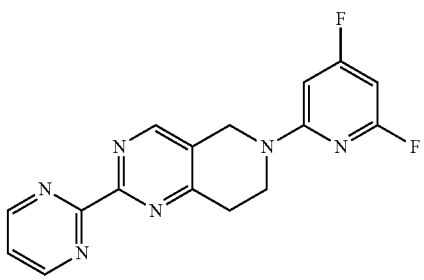 [SMILES: Fc1cc(F)nc(N2CCc3nc(-c4ncccn4)ncc3C2)c1]

To a solution of 2,4,6-trifluoropyridine (1.5 g, 11.4 mmol) in toluene (21 mL) was added K$_2$CO$_3$ (3.3 g, 22.5 mmol) and 2-pyrimidin-2-yl-5,6,7,8-tetrahydropyrido[4,3-d]pyrimidine (3.3 g, 14.7 mmol). Then the reaction vessel was sealed and heated in a microwave reactor at 120° C. for 1 hr. The resulting mixture was cooled down to rt, diluted with EA (50 mL) and washed with brine (50 mL). The organic layer was dried over anhydrous Na$_2$SO$_4$ and concentrated in vacuo. The residue was purified by the flash column to give 6-(4,6-difluoro-2-pyridyl)-2-pyrimidin-2-yl-7,8-dihydro-5H-pyrido[4,3-d]pyrimidine (0.3 g) as a yellow solid.

Step 2: Preparation of 6-(4-fluoro-6-methoxy-2-pyridyl)-2-pyrimidin-2-yl-7,8-dihydro-5H-pyrido[4,3-d]pyrimidine

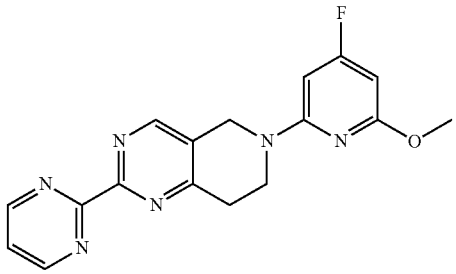

To a solution of 6-(4,6-difluoro-2-pyridyl)-2-pyrimidin-2-yl-7,8-dihydro-5H-pyrido[4,3-d]pyrimidine (1.0 g, 3 mmol) in MeOH (20 mL) was added a freshly prepared NaOMe solution (prepared by dissolving Na (70 mg, 3 mmol) in MeOH (20 mL)). The resulting mixture was stirred at 80° C. on microwave reactor for 1 hr. The mixture was quenched with H₂O (10 mL) and concentrated in vacuo. The residue was purified by prep-HPLC to give 6-(4-fluoro-6-methoxy-2-pyridyl)-2-pyrimidin-2-yl-7,8-dihydro-5H-pyrido[4,3-d]pyrimidine (0.4 g) as a yellow solid.

Step 3: Preparation of 6-(4-fluoro-6-methoxy-2-pyridyl)-5-methoxy-2-pyrimidin-2-yl-7,8-dihydro-5H-pyrido[4,3-d]pyrimidine

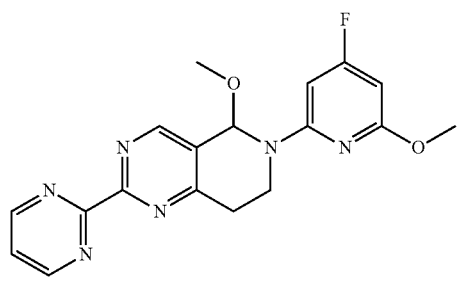 [SMILES: COc1cc(F)cc(N2CCc3nc(-c4ncccn4)ncc3C2OC)n1]

To a solution of 6-(4-fluoro-6-methoxy-2-pyridyl)-2-pyrimidin-2-yl-7,8-dihydro-5H-pyrido[4,3-d]pyrimidine (200 mg, 0.6 mmol) in THF (0.8 mL) and MeOH (6.4 mL) cooled at −40° C., was added RuCl₃ hydrate (13.2 mg, 0.06 mmol) and a solution of NaIO₄ (384 mg, 1.8 mmol) in H₂O (2.4 mL) successively and slowly. The resulting mixture was stirred for 15 min and then warmed to 20° C. with stirring for 6 hrs at 20° C. The reaction was quenched with saturated aqueous Na₂SO₃ solution (30 mL) and filtered. The filtrate was extracted with EA (50 mL) twice. The organic layers were combined, washed with brine (50 mL), dried over anhydrous Na₂SO₄ and concentrated in vacuo to give crude 6-(4-fluoro-6-methoxy-2-pyridyl)-5-methoxy-2-pyrimidin-2-yl-7,8-dihydro-5H-pyrido[4,3-d]pyrimidine (150 mg), which was used directly in the next step without any further purification.

Step 4: Preparation of 6-(4-fluoro-6-methoxy-2-pyridyl)-5-methyl-2-pyrimidin-2-yl-7,8-dihydro-5H-pyrido[4,3-d]pyrimidine

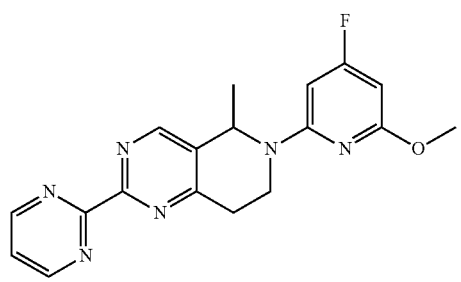 [SMILES: COc1cc(F)cc(N2CCc3nc(-c4ncccn4)ncc3C2C)n1]

To a stirred solution of 6-(4-fluoro-6-methoxy-2-pyridyl)-5-methoxy-2-pyrimidin-2-yl-7,8-dihydro-5H-pyrido[4,3-d]pyrimidine (221 mg, 0.6 mmol) in THF (10 mL) which was cooled to −40° C., was added BF₃.Et₂O (207 mg, 1.8 mmol) and a solution of CH₃MgBr (0.6 mL, 1.8 mmol) in Et₂O successively. Then the reaction mixture was warmed up to 0° C. and stirred at 0° C. for 1 hr. The reaction was quenched by addition of saturated aqueous NH₄Cl (50 mL) and the resulting mixture was extracted with EA (50 mL) twice. The combined organic layers were combined, washed with brine (10 mL), and dried over anhydrous Na₂SO₄ and concentrated in vacuo. The residue was purified by prep-HPLC to give 6-(4-fluoro-6-methoxy-2-pyridyl)-5-methyl-2-pyrimidin-2-yl-7,8-dihydro-5H-pyrido[4,3-d]pyrimidine (14.5 mg) and delivered. ¹H NMR (400 MHz Methanol-d₄) δ: 9.06-9.04 (d, 2H), 8.90 (s, 1H), 7.67 (t, 1H), 6.26 (s, 1H), 6.20 (s, 1H), 5.36 (s, 1H), 4.23-4.25 (m, 1H), 3.85 (s, 3H), 3.65-3.60 (m, 1H), 3.23-3.19 (m, 2H), 1.62-1.60 (d, 3H). MS obsd. (ESI⁺) [(M+H)⁺]: 353.

Example 143: 6-[3-(2,2-difluoroethoxy)-5-fluorophenyl]-5-methyl-2-pyrimidin-2-yl-7,8-dihydro-5H-pyrido[4,3-d]pyrimidine

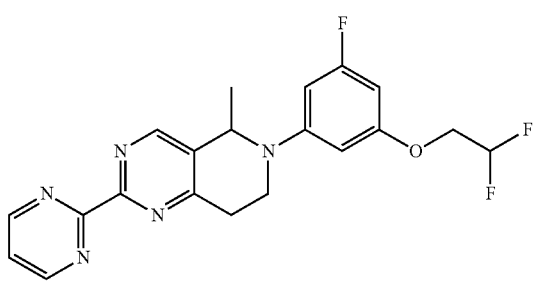 [SMILES: CC1c2cnc(-c3ncccn3)nc2CCN1c1cc(F)cc(OCC(F)F)c1]

Step 1: Preparation of 3-fluoro-5-(5-methyl-2-pyrimidin-2-yl-7,8-dihydro-5H-pyrido[4,3-d]pyrimidin-6-yl)phenol

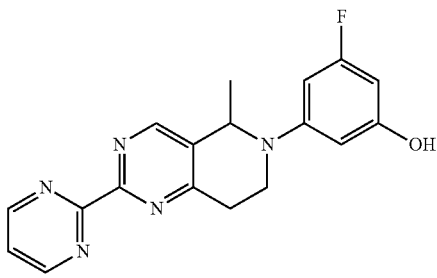 [SMILES: CC1c2cnc(-c3ncccn3)nc2CCN1c1cc(O)cc(F)c1]

To a solution of 6-(3-fluoro-5-methoxy-phenyl)-5-methyl-2-pyrimidin-2-yl-7,8-dihydro-5H-pyrido[4,3-d]pyrimidine (1.2 g, 3.42 mmol) in CH₂Cl₂ (30 mL) was added a solution of boron tribromide (17.1 mL, 17.1 mmol) in DCM. The reaction mixture was stirred at rt overnight and then quenched with MeOH at 0° C. The resulting mixture was concentrated in vacuo, and the residue was diluted with saturated aqueous NaHCO₃ solution. The aqueous layer was separated and extracted with a mixture of DCM and MeOH (v/v=5, 50 mL) for three times. The organic layers were combined, dried over Na₂SO₄ and concentrated in vacuo to give crude 3-fluoro-5-(5-methyl-2-pyrimidin-2-yl-7,8-dihydro-5H-pyrido[4,3-d]pyrimidin-6-yl)phenol (1.2 g) as a brown oil which was used in the next step directly without any further purification.

Step 2: Preparation of 6-[3-(2,2-difluoroethoxy)-5-fluoro-phenyl]-5-methyl-2-pyrimidin-2-yl-7,8-dihydro-5H-pyrido[4,3-d]pyrimidine

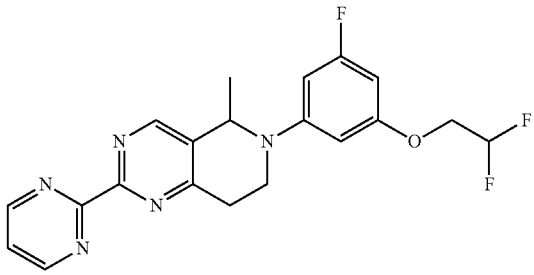 [SMILES: CC1c2cnc(-c3ncccn3)nc2CCN1c1cc(F)cc(OCC(F)F)c1]

A mixture of 3-fluoro-5-(5-methyl-2-pyrimidin-2-yl-7,8-dihydro-5H-pyrido[4,3-d]pyrimidin-6-yl)phenol (400 mg, 1.19 mmol), 2-bromo-1,1-difluoroethane (516 mg, 3.56 mmol) and potassium carbonate (328 mg, 2.37 mmol) in DMF (5 mL) was heated with stirring at 80° C. overnight. The resulting mixture was purified by prep-HPLC to give 6-[3-(2,2-difluoroethoxy)-5-fluoro-phenyl]-5-methyl-2-pyrimidin-2-yl-7,8-dihydro-5H-pyrido[4,3-d]pyrimidine (20 mg) as a light brown solid. $^1$H NMR (400 MHz, Methanol-d$_4$) δ: 1.50 (d, 3H), 3.06-3.28 (m, 2H), 3.45-3.60 (m, 1H), 3.86-4.00 (m, 1H), 4.24 (d, 2H), 5.17-5.33 (m, 1H), 6.18 (s, 2H), 6.45 (s, 2H), 7.55-7.71 (m, 1H), 8.78-8.91 (m, 1H), 8.96-9.10 (m, 2H). MS obsd. (ESI$^+$) [(M+H)$^+$]: 402.

Example 144: 6-[3-fluoro-5-(2,2,2-trifluoroethoxy)phenyl]-5-methyl-2-pyrimidin-2-yl-7,8-dihydro-5H-pyrido[4,3-d]pyrimidine

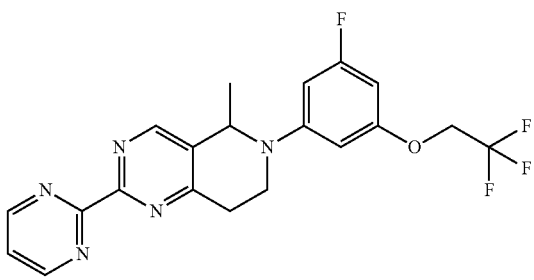 [SMILES: CC1c2cnc(-c3ncccn3)nc2CCN1c1cc(F)cc(OCC(F)(F)F)c1]

A mixture of 3-fluoro-5-(5-methyl-2-pyrimidin-2-yl-7,8-dihydro-5H-pyrido[4,3-d]pyrimidin-6-yl)phenol (400 mg, 1.19 mmol), 1,1,1-trifluoro-2-iodoethane (747 mg, 3.56 mmol) and cesium carbonate (1.16 g, 3.56 mmol) in DMF (5 mL) was heated with stirring at 80° C. overnight. The resulting mixture was purified by prep-HPLC to give 6-[3-fluoro-5-(2,2,2-trifluoroethoxy)phenyl]-5-methyl-2-pyrimidin-2-yl-7,8-dihydro-5H-pyrido[4,3-d]pyrimidine (10 mg) as a light brown solid. $^1$H NMR (400 MHz, Methanol-d$_4$) δ: 1.54 (d, 3H), 3.07-3.27 (m, 2H), 3.48-3.65 (m, 1H), 3.92-4.05 (m, 1H), 4.56 (q, 2H), 5.30 (d, 1H), 6.18-6.29 (m, 1H), 6.51 (s, 2H), 7.60-7.73 (m, 1H), 8.80-8.95 (m, 1H), 8.99-9.12 (m, 2H). MS obsd. (ESI$^+$) [(M+H)$^+$]: 420.

Example 145: 6-[3-(cyclopropylmethoxy)-5-fluoro-phenyl]-5-methyl-2-pyrimidin-2-yl-7,8-dihydro-5H-pyrido[4,3-d]pyrimidine

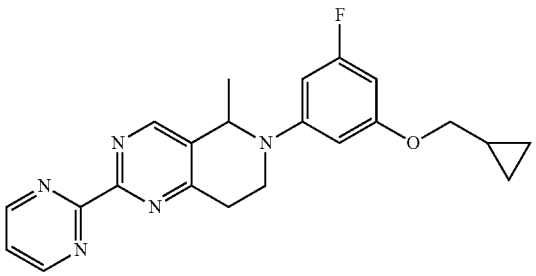 [SMILES: CC1c2cnc(-c3ncccn3)nc2CCN1c1cc(F)cc(OCC2CC2)c1]

A mixture of 3-fluoro-5-(5-methyl-2-pyrimidin-2-yl-7,8-dihydro-5H-pyrido[4,3-d]pyrimidin-6-yl)phenol (400 mg, 1.19 mmol), (bromomethyl)cyclopropane (160 mg, 1.19 mmol) and cesium carbonate (1.16 g, 3.56 mmol) in DMF (5 mL) was heated with stirring at 80° C. overnight. The resulting mixture was purified by prep-HPLC to give 6-[3-(cyclopropylmethoxy)-5-fluoro-phenyl]-5-methyl-2-pyrimidin-2-yl-7,8-dihydro-5H-pyrido[4,3-d]pyrimidine (30 mg) as a light yellow solid. $^1$H NMR (400 MHz, Methanol-d$_4$) δ: 0.04-0.19 (m, 2H), 0.38 (dd, 2H), 0.92-1.09 (m, 1H), 1.26 (d, 3H), 2.83-3.04 (m, 2H), 3.22-3.36 (m, 1H), 3.57 (d, 2H), 3.62-3.75 (m, 1H), 4.92-5.05 (m, 1H), 5.83-5.94 (m, 1H), 6.14 (s, 2H), 7.40 (s, 1H), 8.61 (s, 1H), 8.79 (d, 2H). MS obsd. (ESI$^+$) [(M+H)$^+$]: 392.

Example 146 and 147: (−)-6-(5-chloro-6-fluoro-4-methoxy-2-pyridyl)-5-methyl-2-pyrimidin-2-yl-7,8-dihydro-5H-pyrido[4,3-d]pyrimidine and (−)-6-(3-chloro-6-fluoro-4-methoxy-2-pyridyl)-5-methyl-2-pyrimidin-2-yl-7,8-dihydro-5H-pyrido[4,3-d]pyrimidine To a solution of (−)-6-(6-fluoro-4-methoxy-2-pyridyl)-5-methyl-2-pyrimidin-2-yl-7,8-dihydro-5H-pyrido[4,3-d]pyrimidine (100 mg, 284 μmol, Example 138) in acetonitrile (5 mL) was added N-chlorosuccinate (45.5 mg, 341 μmol). The mixture was heated and stirred at 50° C. overnight. After being cooled to rt, the mixture was purified by prep-HPLC to give (−)-6-(5-chloro-6-fluoro-4-methoxy-2-pyridyl)-5-methyl-2-pyrimidin-2-yl-7,8-dihydro-5H-pyrido[4,3-d]pyrimidine (5 mg) as a pale yellow solid and (−)-6-(3-chloro-6-fluoro-4-methoxy-2-pyridyl)-5-methyl-2-pyrimidin-2-yl-7,8-dihydro-5H-pyrido[4,3-d]pyrimidine (20 mg) as a pale yellow solid.

Example 146: (−)-6-(5-chloro-6-fluoro-4-methoxy-2-pyridyl)-5-methyl-2-pyrimidin-2-yl-7,8-dihydro-5H-pyrido[4,3-d]pyrimidine, $^1$H NMR (400 MHz, Methanol-d$_4$) δ: 1.59-1.66 (m, 3H), 3.12-3.24 (m, 2H), 3.50-3.62 (m, 1H), 3.98-4.06 (m, 3H), 4.50-4.65 (m, 1H), 5.72-5.84 (m, 1H), 6.38-6.44 (m, 1H), 7.63-7.70 (m, 1H), 8.87-8.94 (m, 1H), 9.05 (d, 2H). MS obsd. (ESI$^+$) [(M+H)$^+$]: 387. [α]$_D^{25}$=−57.7° (0.1 g/100 mL, methanol).

Example 147: (−)-6-(3-chloro-6-fluoro-4-methoxy-2-pyridyl)-5-methyl-2-pyrimidin-2-yl-7,8-dihydro-5H-pyrido

[4,3-d]pyrimidine, ¹H NMR (400 MHz, Methanol-d₄) δ: 1.64 (d, 3H), 3.04-3.15 (m, 1H), 3.35-3.46 (m, 1H), 3.63-3.75 (m, 1H), 4.03-4.14 (m, 1H), 5.31-5.42 (m, 1H), 6.38-6.42 (m, 1H), 7.61-7.68 (m, 1H), 8.80-8.86 (m, 1H), 9.03 (d, 2H). MS obsd. (ESI⁺) [(M+H)⁺]: 387. [a]$_D^{25}$=−1.8° (0.1 g/100 mL, methanol).

Example 148, 149 and 150: 6-[6-(2,2-difluoroethoxy)-4-fluoro-2-pyridyl]-5-methyl-2-pyrimidin-2-yl-7,8-dihydro-5H-pyrido[4,3-d]pyrimidine, 6-[4-(2,2-difluoroethoxy)-6-fluoro-2-pyridyl]-5-methyl-2-pyrimidin-2-yl-7,8-dihydro-5H-pyrido[4,3-d]pyrimidine and 6-[2-(2,2-difluoroethoxy)-6-fluoro-4-pyridyl]-5-methyl-2-pyrimidin-2-yl-7,8-dihydro-5H-pyrido[4,3-d]pyrimidine Example 148

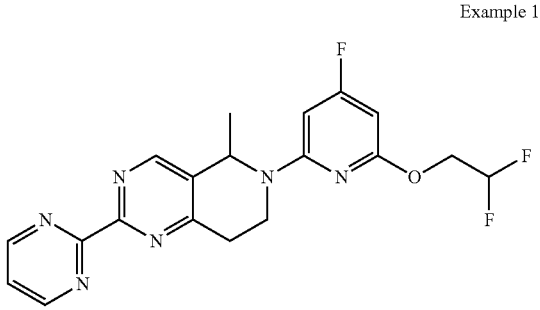

Example 149

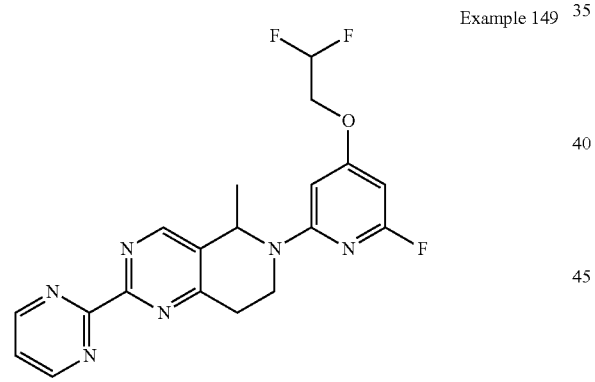

Example 150

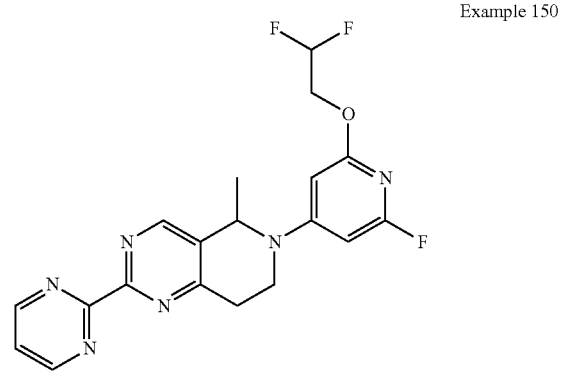

Step 1: Preparation of 2-(2,2-difluoroethoxy)-4,6-difluoro-pyridine and 4-(2,2-difluoroethoxy)-2,6-difluoro-pyridine

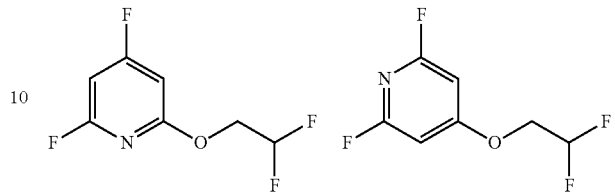

To a solution of 2,2-difluoroethanol (617 mg, 7.51 mmol) in THF was added sodium hydride (301 mg, 7.51 mmol) at 0° C. After the mixture was stirred for 15 mins, to the resulting mixture was added a solution of 2,4,6-trifluoro-pyridine (1.0 g, 7.51 mmol) in THF (20 mL). The resulting reaction mixture was warmed to rt and stirred at rt overnight. Then the reaction was quenched with H₂O and extracted with EA (40 mL) for three times. The combined organic layers were dried over anhydrous Na₂SO₄ and concentrated in vacuo to give a mixture of 4-(2,2-difluoroethoxy)-2,6-difluoropyridine and 2-(2,2-difluoroethoxy)-4,6-difluoropyridine (1.2 g, 6.15 mmol) as light yellow oil which was used in next step directly without any further purification.

Step 2: Preparation of 6-[6-(2,2-difluoroethoxy)-4-fluoro-2-pyridyl]-5-methyl-2-pyrimidin-2-yl-7,8-dihydro-5H-pyrido[4,3-d]pyrimidine and 6-[4-(2,2-difluoroethoxy)-6-fluoro-2-pyridyl]-5-methyl-2-pyrimidin-2-yl-7,8-dihydro-5H-pyrido[4,3-d]pyrimidine and 6-[2-(2,2-difluoroethoxy)-6-fluoro-4-pyridyl]-5-methyl-2-pyrimidin-2-yl-7,8-dihydro-5H-pyrido[4,3-d]pyrimidine Example 148

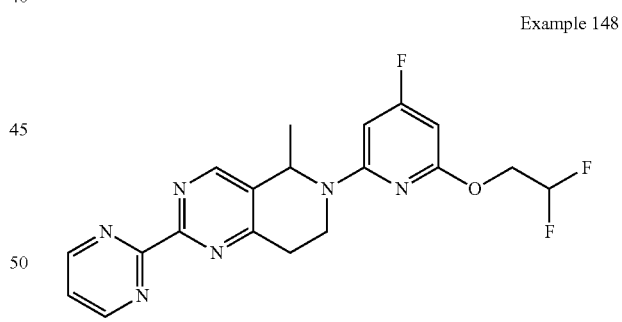

Example 149

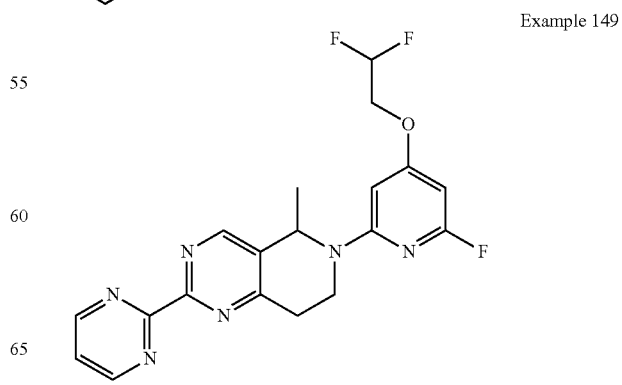

-continued

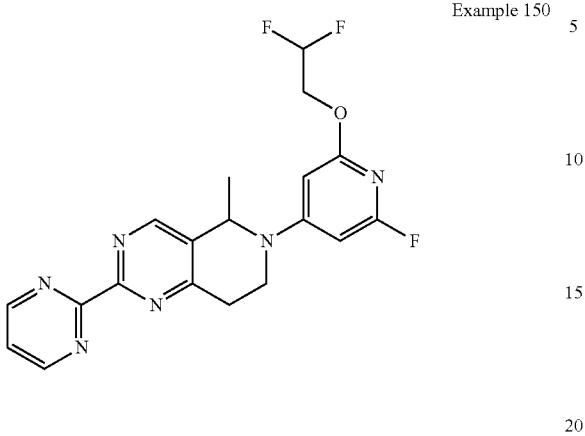

Example 150

A mixture of 5-methyl-2-(pyrimidin-2-yl)-5,6,7,8-tetrahydropyrido[4,3-d]pyrimidine (400 mg, 1.76 mmol), 4-(2,2-difluoroethoxy)-2,6-difluoropyridine and 2-(2,2-difluoroethoxy)-4,6-difluoropyridine (product of Step 1, 1.03 g, 5.28 mmol), and DIPEA (0.8 mL, 1.76 mmol) in DMSO (0.5 mL) was heated to 110° C. and stirred for 15 hrs. The resulting reaction mixture was then concentrated in vacuo. The residue was purified by prep-HPLC to give 6-[6-(2,2-difluoroethoxy)-4-fluoro-2-pyridyl]-5-methyl-2-pyrimidin-2-yl-7,8-dihydro-5H-pyrido[4,3-d]pyrimidine (90 mg) as a light yellow solid and 6-[4-(2,2-difluoroethoxy)-6-fluoro-2-pyridyl]-5-methyl-2-pyrimidin-2-yl-7,8-dihydro-5H-pyrido[4,3-d]pyrimidine (130 mg) as a light yellow solid and 6-[2-(2,2-difluoroethoxy)-6-fluoro-4-pyridyl]-5-methyl-2-pyrimidin-2-yl-7,8-dihydro-5H-pyrido[4,3-d]pyrimidine (90 mg) as a light yellow solid.

Example 148: 6-[6-(2,2-difluoroethoxy)-4-fluoro-2-pyridyl]-5-methyl-2-pyrimidin-2-yl-7,8-dihydro-5H-pyrido[4,3-d]pyrimidine (Example 148), $^1$H NMR (400 MHz, DMSO-$d_6$) δ: 8.82-9.07 (m, 3H), 7.55-7.77 (m, 1H), 6.22-6.58 (m, 2H), 5.95-6.10 (m, 1H), 5.65-5.84 (m, 1H), 4.33-4.71 (m, 3H), 3.41-3.59 (m, 1H), 2.93-3.19 (m, 2H), 1.53 (d, 3H). MS obsd. (ESI$^+$) [(M+H)$^+$]: 403.

Example 149: 6-[4-(2,2-difluoroethoxy)-6-fluoro-2-pyridyl]-5-methyl-2-pyrimidin-2-yl-7,8-dihydro-5H-pyrido[4,3-d]pyrimidine (Example 149), $^1$H NMR (400 MHz, DMSO-$d_6$) δ: 8.84-9.10 (m, 3H), 7.57-7.75 (m, 1H), 6.23-6.64 (m, 2H), 5.98-6.16 (m, 1H), 5.61-5.82 (m, 1H), 4.31-4.58 (m, 3H), 3.38-3.56 (m, 1H), 2.87-3.16 (m, 2H), 1.52 (d, 3H). MS obsd. (ESI$^+$) [(M+H)$^+$]: 403.

Example 150: 6-[2-(2,2-difluoroethoxy)-6-fluoro-4-pyridyl]-5-methyl-2-pyrimidin-2-yl-7,8-dihydro-5H-pyrido[4,3-d]pyrimidine (Example 150), $^1$H NMR (400 MHz, DMSO-$d_6$) δ: 9.00 (d, 2H), 8.84 (s, 1H), 7.64 (t, 1H), 6.12-6.55 (m, 3H), 5.46 (br d, 1H), 4.37-4.58 (m, 2H), 4.08-4.27 (m, 1H), 3.48-3.65 (m, 1H), 2.91-3.19 (m, 2H), 1.52 (d, 3H). MS obsd. (ESI$^+$) [(M+H)$^+$]: 403.

Example 151: 6-[6-fluoro-4-(tetrahydropyran-4-ylmethoxy)-2-pyridyl]-5-methyl-2-pyrimidin-2-yl-7,8-dihydro-5H-pyrido[4,3-d]pyrimidine

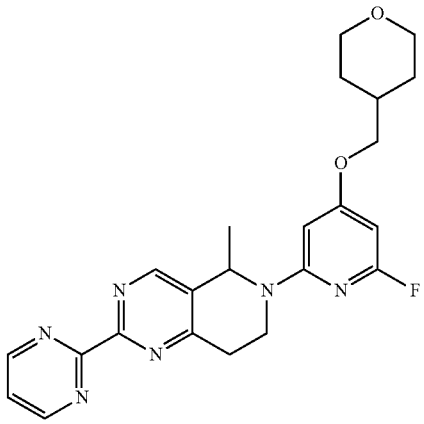 [SMILES: CC1c2cnc(-c3ncccn3)nc2CCN1c1cc(OCC2CCOCC2)cc(F)n1]

Step 1: Preparation of 6-(4,6-difluoro-2-pyridyl)-2-pyrimidin-2-yl-7,8-dihydro-5H-pyrido[4,3-d]pyrimidine

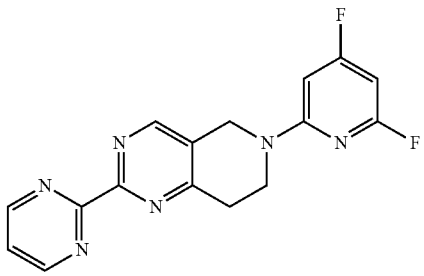 [SMILES: Fc1cc(F)nc(N2CCc3nc(-c4ncccn4)ncc3C2)c1]

To a solution of 2,4,6-trifluoropyridine (1.5 g, 11.4 mmol) in toluene (20 mL) was added K$_2$CO$_3$ (2.8 g, 20.3 mmol) and 2-pyrimidin-2-yl-5,6,7,8-tetrahydropyrido[4,3-d]pyrimidine (3.1 g, 14.7 mmol). The mixture was heated to 130° C. in a microwave reactor for 1 hr. The resulting reaction mixture was diluted with EA (500 mL), washed with brine (100 mL) twice, dried over anhydrous Na$_2$SO$_4$ and concentrated in vacuo. The residue was purified by the column chromatography and prep-HPLC successively to afford 6-(4,6-difluoro-2-pyridyl)-2-pyrimidin-2-yl-7,8-dihydro-5H-pyrido[4,3-d]pyrimidine (650 mg) as a yellow solid.

Step 2: Preparation of 6-(4,6-difluoro-2-pyridyl)-5-methoxy-2-pyrimidin-2-yl-7,8-dihydro-5H-pyrido[4,3-d]pyrimidine

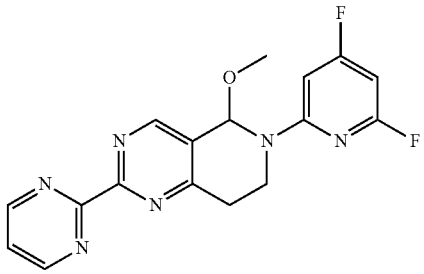 [SMILES: COC1c2cnc(-c3ncccn3)nc2CCN1c1cc(F)cc(F)n1]

To a solution of 6-(4,6-difluoro-2-pyridyl)-2-pyrimidin-2-yl-7,8-dihydro-5H-pyrido[4,3-d]pyrimidine (3.0 g, 9.19 mmol) in THF (40 mL) and MeOH (10 mL), which was cooled to –40° C., was added RuCl₃ hydrate (145 mg, 0.64 mmol) and an solution of NaIO₄ (5.9 g, 27.6 mmol) in H₂O (15 mL) successively at –40° C. The resulting mixture was stirred at the same temperature for 15 mins, and then allowed to warm to 20° C. and stirred at 20° C. for 6 hrs. Then the reaction was quenched with a saturated aqueous solution of Na₂SO₃ (30 mL). The resulting mixture was filtered. The filtrate was diluted with DCM (250 mL), washed with brine (50 mL) twice, dried over anhydrous Na₂SO₄ and then concentrated in vacuo to give crude 6-(4,6-difluoro-2-pyridyl)-5-methoxy-2-pyrimidin-2-yl-7,8-dihydro-5H-pyrido[4,3-d]pyrimidine (2.2 g, crude) as black oil, which was used directly in the next step without any further purification.

Step 3: Preparation of 6-(4,6-difluoro-2-pyridyl)-5-methyl-2-pyrimidin-2-yl-7,8-dihydro-5H-pyrido[4,3-d]pyrimidine

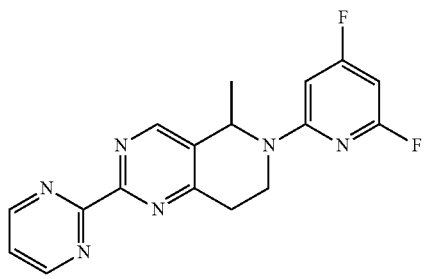 [SMILES: CC1c2cnc(-c3ncccn3)nc2CCN1c1cc(F)cc(F)n1]

To a stirred solution of 6-(4,6-difluoro-2-pyridyl)-5-methoxy-2-pyrimidin-2-yl-7,8-dihydro-5H-pyrido[4,3-d]pyrimidine (3.0 g, 8.4 mmol) in THF (30 mL) was added BF₃.Et₂O (6.0 g, 42.1 mmol) at –70° C. The resulting mixture was stirred at –70° C. for 10 mins, and then to the mixture was added a solution of MeMgBr in THF (14.0 mL, 42.1 mmol). The resulting mixture was allowed to warm to 0° C. and stirred at 0° C. for 1 hr. After the reaction was quenched by addition of a saturated aqueous solution of NH₄Cl (20 mL), the resulting mixture was partitioned between EA (200 mL) and brine (50 mL). The separated organic phase was dried over anhydrous Na₂SO₄ and concentrated in vacuo. The residue was purified by prep-HPLC to afford 6-(4,6-difluoro-2-pyridyl)-5-methyl-2-pyrimidin-2-yl-7,8-dihydro-5H-pyrido[4,3-d]pyrimidine (1.5 g) as a light yellow solid.

Step 4: Preparation of 6-[6-fluoro-4-(tetrahydropyran-4-ylmethoxy)-2-pyridyl]-5-methyl-2-pyrimidin-2-yl-7,8-dihydro-5H-pyrido[4,3-d]pyrimidine

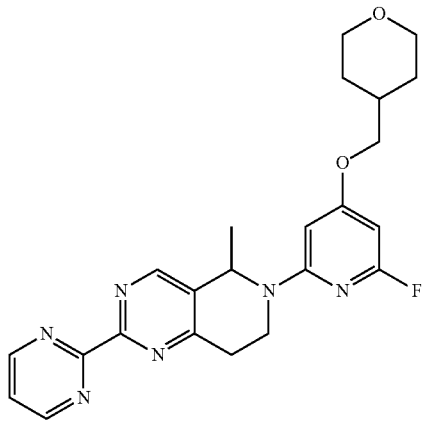 [SMILES: CC1c2cnc(-c3ncccn3)nc2CCN1c1cc(OCC2CCOCC2)cc(F)n1]

To a stirred solution of tetrahydropyran-4-methanol (41 mg, 0.35 mmol) in DMF (1 mL) was added NaH (14 mg, 0.35 mmol) at 0° C. The mixture was stirred at 0° C. for 10 mins, and then to the mixture was added 6-(4,6-difluoro-2-pyridyl)-5-methyl-2-pyrimidin-2-yl-7,8-dihydro-5H-pyrido[4,3-d]pyrimidine (100 mg, 0.29 mmol). After being stirred at 80° C. for 6 hrs, the resulting mixture was partitioned between EA (50 mL) and H₂O (20 mL). The organic layer was separated, washed with brine (20 mL), dried over anhydrous Na₂SO₄ and concentrated in vacuo. The residue was purified by prep-HPLC to afford 6-[6-fluoro-4-(tetrahydropyran-4-ylmethoxy)-2-pyridyl]-5-methyl-2-pyrimidin-2-yl-7,8-dihydro-5H-pyrido[4,3-d]pyrimidine (20 mg) as a light yellow solid. ¹H NMR (400 MHz, CDCl₃) δ: 9.04 (d, 2H), 8.82 (s, 1H), 7.44 (t, 1H), 6.01 (s, 1H), 5.80 (d, 1H), 5.68 (q, 1H), 4.33-4.45 (m, 1H), 4.04 (m, 2H), 3.85 (d, 2H), 3.38-3.55 (m, 3H), 3.22-3.30 (m, 2H), 1.99-2.15 (m, 1H), 1.75 (d, 2H), 1.57 (m., 3H), 1.41-1.53 (m, 2H). MS obsd. (ESI⁺) [(M+H)⁺]: 437.

Example 152: 6-[4-(cyclopropylmethoxy)-6-fluoro-2-pyridyl]-5-methyl-2-pyrimidin-2-yl-7,8-dihydro-5H-pyrido[4,3-d]pyrimidine

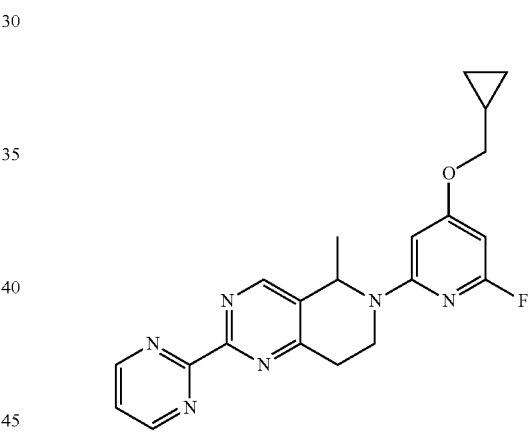

To a stirred solution of cyclopropanemethanol (26 mg, 0.35 mmol) in DMF (1 mL) was added NaH (14 mg, 0.35 mmol) at 0° C. The mixture was stirred at 0° C. for 10 mins. Then to the mixture was added 6-(4,6-difluoro-2-pyridyl)-5-methyl-2-pyrimidin-2-yl-7,8-dihydro-5H-pyrido[4,3-d]pyrimidine (100 mg, 0.29 mmol). The resulting mixture was heated at 80° C. for 6 hrs, and then partitioned between EA (50 mL) and H₂O (20 mL). The organic layer was separated, washed with brine (20 mL), dried over anhydrous Na₂SO₄ and concentrated in vacuo. The residue was purified by prep-HPLC to afford 6-[4-(cyclopropylmethoxy)-6-fluoro-2-pyridyl]-5-methyl-2-pyrimidin-2-yl-7,8-dihydro-5H-pyrido[4,3-d]pyrimidine (55 mg) as a light yellow solid. ¹H NMR (400 MHz, CDCl₃) δ: 9.02 (d, 2H), 8.79 (s, 1H), 7.43 (m, 1H), 6.01 (s, 1H), 5.79 (d, 1H), 5.66 (m, 1H), 4.30-4.45 (m, 1H), 3.84 (d, 2H), 3.40-3.55 (m, 1H), 3.15-3.32 (m, 2H), 1.57 (d, 3H), 1.15-1.35 (m, 1H), 0.62-0.73 (m, 2H), 0.30-0.41 (m, 2H). MS obsd. (ESI⁺) [(M+H)⁺]: 393.

Example 153: 6-(6-fluoro-4-methoxy-2-pyridyl)-5-methyl-2-(2-pyridyl)-7,8-dihydro-5H-pyrido[4,3-d]pyrimidine

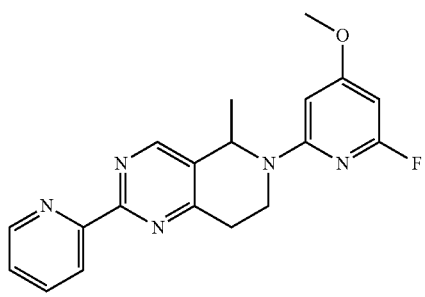 [SMILES: COc1cc(F)nc(N2CCc3nc(-c4ccccn4)ncc3C2C)c1]

A mixture of 5-methyl-2-(2-pyridyl)-5,6,7,8-tetrahydropyrido[4,3-d]pyrimidine (150 mg, 0.663 mmol, see Example 1) and 2,6-difluoro-4-methoxypyridine (385 mg, 2.65 mmol) in DMSO (0.5 mL) and DIPEA (1 mL) was heated and stirred at 110° C. for 15 hrs. The resulting reaction mixture was concentrated in vacuo. The residue was purified by prep-HPLC to give 6-(6-fluoro-4-methoxy-2-pyridyl)-5-methyl-2-(2-pyridyl)-7,8-dihydro-5H-pyrido[4,3-d]pyrimidine (40 mg) as light yellow solid. $^1$H NMR (400 MHz, Methanol-d4) δ: 8.70 (s, 2H), 8.35-8.46 (m, 1H), 7.82-7.98 (m, 1H), 7.33-7.52 (m, 1H), 6.07-6.25 (m, 1H), 5.70-5.85 (m, 1H), 5.47-5.67 (m, 1H), 4.28-4.49 (m, 1H), 3.77 (s, 3H), 3.30-3.50 (m, 1H), 2.90-3.13 (m, 2H), 1.47 (d, 3H). MS obsd. (ESI$^+$) [(M+H)$^+$]: 352.

Example 154: 6-[6-fluoro-4-(tetrahydrofuran-3-ylmethoxy)-2-pyridyl]-5-methyl-2-pyrimidin-2-yl-7,8-dihydro-5H-pyrido[4,3-d]pyrimidine

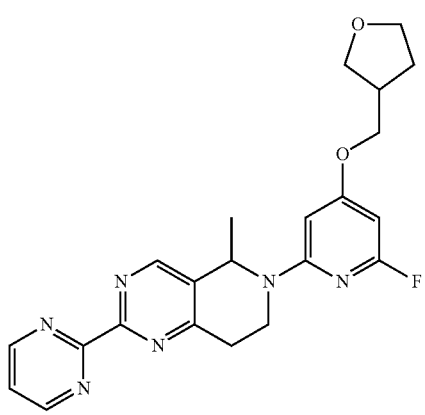 [SMILES: CC1c2cnc(-c3ncccn3)nc2CCN1c1cc(OCC2CCOC2)cc(F)n1]

To a stirred solution of tetrahydro-3-furanmethanol (36 mg, 0.35 mmol) in DMF (1 mL) was added NaH (14 mg, 0.35 mmol) at 0° C. The mixture was stirred at 0° C. for 10 mins, and then to the reaction mixture was added 6-(4,6-difluoro-2-pyridyl)-5-methyl-2-pyrimidin-2-yl-7,8-dihydro-5H-pyrido[4,3-d]pyrimidine (100 mg, 0.29 mmol). The resulting mixture was heated at 80° C. for 6 hrs, and then partitioned between EA (50 mL) and H$_2$O (20 mL). The organic layer was separated, washed with brine (20 mL), dried over anhydrous Na$_2$SO$_4$ and concentrated in vacuo. The residue was purified by prep-HPLC to afford 6-[6-fluoro-4-(tetrahydrofuran-3-ylmethoxy)-2-pyridyl]-5-methyl-2-pyrimidin-2-yl-7,8-dihydro-5H-pyrido[4,3-d]pyrimidine (18 mg) as a white solid. $^1$H NMR (400 MHz, CDCl$_3$) δ: 9.04 (d, 2H), 8.82 (s, 1H), 7.44 (t, 1H), 6.01 (s, 1H), 5.80 (s, 1H), 5.67 (m, 1H), 4.34-4.49 (m, 1H), 3.86-4.05 (m, 4H), 3.65-3.84 (m, 2H), 3.42-3.57 (m, 1H), 3.21-3.31 (m, 2H), 2.66-2.81 (m, 1H), 2.14 (m, 1H), 1.74 (m, 6.27 Hz, 1H), 1.59 (d, 3H). MS obsd. (ESI$^+$) [(M+H)$^+$]: 423.

Example 155: (−)-7-[[2-fluoro-6-[5-methyl-2-pyrimidin-2-yl-7,8-dihydro-5H-pyrido[4,3-d]pyrimidin-6-yl]-4-pyridyl]oxy]heptanoic acid Step 1: Preparation of 2,6-difluoropyridin-4-ol

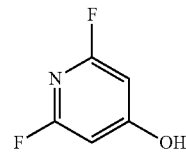

A mixture of 2,6-difluoro-4-methoxypyridine (10 g, 68.9 mmol) and a solution of boron tribromide (1.33 kg, 500 ml, 500 mmol) in DCM was heated at 60° C. with stirring overnight. The resulting reaction mixture was cooled to −70° C. and the reaction was quenched with MeOH. The resulting mixture was concentrated in vacuo to give 2,6-difluoropyridin-4-ol (7.3 g, 55.7 mmol) as a yellow solid which was used in the next step directly without any further purification.

Step 2: Preparation of methyl 7-[(2,6-difluoro-4-pyridyl)oxy]heptanoate

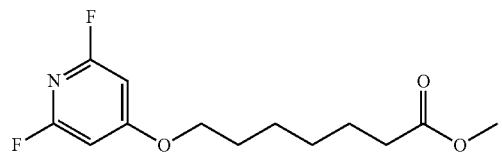 [SMILES: COC(=O)CCCCCCOc1cc(F)nc(F)c1]

A mixture of 2,6-difluoropyridin-4-ol (1.00 g, 7.63 mmol), anhydrous potassium carbonate (2.51 g, 18.2 mmol) and methyl 7-bromopentanoate (1.35 g, 6.05 mmol) was stirred at 100° C. for 10 hrs in DMF (10 mL). The resulting reaction mixture was cooled to rt and extracted with EA (100 mL). The organic layer was washed with brine, dried over MgSO$_4$ and filtered. The filtrate was concentrated in vacuo. The residue was purified by column chromatography to give methyl 7-[(2,6-difluoro-4-pyridyl)oxy]heptanoate (1.2 g) as a yellow oil.

Step 3: Preparation of (+)-5-methyl-2-pyrimidin-2-yl-5,6,7,8-tetrahydropyrido[4,3-d]pyrimidine Chiral separation of 5-methyl-2-pyrimidin-2-yl-5,6,7,8-tetrahydropyrido[4,3-d]pyrimidine (6.0 g) by chiral HPLC provided (+)-5-methyl-2-pyrimidin-2-yl-5,6,7,8-tetrahydropyrido[4,3-d]pyrimidine (2.0 g) as brown solid and (−)-5-methyl-2-pyrimidin-2-yl-5,6,7,8-tetrahydropyrido[4,3-d]pyrimidine (2.1 g) as brown solid. For (+)-5-methyl-2-pyrimidin-2-yl-5,6,7,8-tetrahydropyrido[4,3-d]pyrimidine, [a]$_D^{25}$=94° (0.1 g/100 mL, methanol).

Step 4: Preparation of methyl (+/−)-7-[[2-fluoro-6-[5-methyl-2-pyrimidin-2-yl-7,8-dihydro-5H-pyrido[4,3-d]pyrimidin-6-yl]-4-pyridyl]oxy]heptanoate A mixture of (+)-5-methyl-2-(pyrimidin-2-yl)-5,6,7,8-tetrahydropyrido[4,3-d]pyrimidine (200 mg, 0.880 mmol) and methyl 7-((2,6-difluoropyridin-4-yl)oxy)heptanoate (721 mg, 2.64 mmol) in DMSO (0.5 ml) and DIPEA (1 mL) was heated and stirred at 110° C. for 15 hrs. The resulting reaction mixture was concentrated in vacuo. The residue was purified by flash column to give methyl (+/−)-7-[[2-fluoro-6-[5-methyl-2-pyrimidin-2-yl-7,8-dihydro-5H-pyrido[4,3-d]pyrimidin-6-yl]-4-pyridyl]oxy]heptanoate as yellow oil (280 mg).

Step 5: Preparation of (−)-7-[[2-fluoro-6-[5-methyl-2-pyrimidin-2-yl-7,8-dihydro-5H-pyrido[4,3-d]pyrimidin-6-yl]-4-pyridyl]oxy]heptanoic acid To a solution of methyl (+/−)-7-[[2-fluoro-6-[5-methyl-2-pyrimidin-2-yl-7,8-dihydro-5H-pyrido[4,3-d]pyrimidin-6-yl]-4-pyridyl]oxy]heptanoate (240 mg, 0.499 mmol) in a mixture of methanol (10 mL), THF (5 mL) and water (2 mL) was added LiOH monohydrate (126 mg, 3 mmol). The resulting mixture was stirred overnight at rt and then acidified to pH=6-7 with 1 M HCl. The resulting mixture was extracted with DCM (20 mL) for three times. The combined organic layer was washed with brine, dried over MgSO₄, filtered and concentrated in vacuo. The residue was purified by column chromatography to give the product (220 mg) as a yellow solid. The crude product (70 mg) was purified by prep-HPLC to give (−)-7-[[2-fluoro-6-[5-methyl-2-pyrimidin-2-yl-7,8-dihydro-5H-pyrido[4,3-d]pyrimidin-6-yl]-4-pyridyl]oxy]heptanoic acid (34 mg) as light yellow solid. $^1$H NMR (400 MHz, Methanol-d4) δ: 8.89-9.01 (m, 2H), 8.73-8.85 (m, 1H), 7.42-7.64 (m, 1H), 6.02-6.21 (m, 1H), 5.69-5.84 (m, 1H), 5.53-5.69 (m, 1H), 4.31-4.52 (m, 1H), 3.88-4.11 (m, 2H), 3.32-3.50 (m, 1H), 2.88-3.15 (m, 2H), 2.21 (s, 2H), 1.64-1.76 (m, 2H), 1.48 (d, 9H). MS obsd. (ESI⁺) [(M+H)⁺]: 467. $[a]_D^{25}$=−88.00° (0.05 g/100 mL, methanol).

Example 156: (−)-7-[[2-fluoro-6-[5-methyl-2-pyrimidin-2-yl-7,8-dihydro-5H-pyrido[4,3-d]pyrimidin-6-yl]-4-pyridyl]oxy]heptanamide To a solution of (−)-7-[[2-fluoro-6-[5-methyl-2-pyrimidin-2-yl-7,8-dihydro-5H-pyrido[4,3-d]pyrimidin-6-yl]-4-pyridyl]oxy]heptanoic acid (150 mg, 0.322 mol, Example 155) in DMF (10 mL) was added TEA (65.1 mg, 0.64 mmol) and HATU (245 mg, 0.643 mmol). The resulting mixture was stirred for 10 mins at rt. Then to the reaction mixture was added ammonium chloride (34 mg, 0.643 mmol). After being stirred at rt for 10 hrs, the resulting mixture was poured into water (25 mL) and extracted with EA (50 mL) for three times. The organic layers were combined, washed with brine, dried over anhydrous Na₂SO₄ and concentrated in vacuo to give a red oil, which was purified by prep-HPLC to give (−)-7-[[2-fluoro-6-[5-methyl-2-pyrimidin-2-yl-7,8-dihydro-5H-pyrido[4,3-d]pyrimidin-6-yl]-4-pyridyl]oxy]heptanamide (16 mg) as a light yellow oil. $^1$H NMR (400 MHz, Methanol-d4) δ: 8.89-8.99 (m, 2H), 8.74-8.83 (m, 1H), 7.51-7.64 (m, 1H), 6.10-6.20 (m, 1H), 5.72-5.81 (m, 1H), 5.53-5.66 (m, 1H), 4.35-4.50 (m, 1H), 3.89-4.08 (m, 2H), 3.31-3.49 (m, 1H), 3.00-3.15 (m, 2H), 2.13 (s, 2H), 1.65-1.77 (m, 2H), 1.49 (d, 9H). MS obsd. (ESI⁺) [(M+H)⁺]: 466. $[a]_D^{25}$=−84.00° (0.1 g/100 mL, methanol).

Example 157: (−)-5-[[2-fluoro-6-[5-methyl-2-pyrimidin-2-yl-7,8-dihydro-5H-pyrido[4,3-d]pyrimidin-6-yl]-4-pyridyl]oxy]pentanoic acid Step 1: Preparation of methyl 5-[(2,6-difluoro-4-pyridyl)oxy]pentanoate

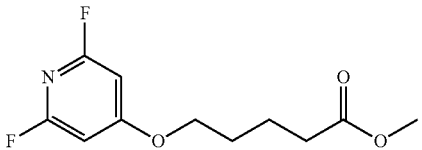 [SMILES: COC(=O)CCCCOc1cc(F)nc(F)c1]

To a solution of 2,6-difluoropyridin-4-ol (786 mg, 6.0 mmol) and methyl 5-bromopentanoate (1.4 g, 7.2 mmol) in DMF (25 mL) was added K₂CO₃ (2.5 g, 18 mmol) and the mixture was stirred at 100° C. for 10 hrs. After being cooled to rt, the reaction mixture was diluted with water (50 mL) and extracted with EA (50 mL) for three times. The combined organic layer was washed with brine, dried over anhydrous Na₂SO₄ and concentrated in vacuo. The residue was purified by flash chromatography to give methyl 5-[(2,6-difluoro-4-pyridyl)oxy]pentanoate as a yellow oil (1.2 g).

Step 2: Preparation of methyl (+/−)-5-[[2-fluoro-6-[5-methyl-2-pyrimidin-2-yl-7,8-dihydro-5H-pyrido[4,3-d]pyrimidin-6-yl]-4-pyridyl]oxy]pentanoate To a solution of (+)-5-methyl-2-pyrimidin-2-yl-5,6,7,8-tetrahydropyrido[4,3-d]pyrimidine (227 mg, 1.0 mmol) in DIPEA (1 mL) and DMSO (0.5 mL) was added methyl 5-((2,6,-difluoropyridin-4-yl)oxy)pentanoate (1.23 g, 5 mmol). The reaction mixture was heated and stirred at 110° C. in a sealed vessel for 50 hrs. After being cooled to rt, the reaction mixture was poured into water (50 mL) and the resulting mixture was extracted with EA (60 mL) twice. The organic layers were combined, washed with brine, dried over anhydrous Na₂SO₄ and concentrated in vacuo to give a red oil, which was purified by flash chromatography to give methyl (+/−)-5-[[2-fluoro-6-[5-methyl-2-pyrimidin-2-yl-7,8-dihydro-5H-pyrido[4,3-d]pyrimidin-6-yl]-4-pyridyl]oxy]pentanoate (362 mg) as a light yellow solid.

Step 3: Preparation of (−)-5-[[2-fluoro-6-[5-methyl-2-pyrimidin-2-yl-7,8-dihydro-5H-pyrido[4,3-d]pyrimidin-6-yl]-4-pyridyl]oxy]pentanoic acid To a solution of methyl (+/−)-5-[[2-fluoro-6-[5-methyl-2-pyrimidin-2-yl-7,8-dihydro-5H-pyrido[4,3-d]pyrimidin-6-yl]-4-pyridyl]oxy]pentanoate (350 mg, 0.8 mol) in methanol (10 mL), THF (5 mL) and water (2 mL) was added LiOH monohydrate (168 mg, 4 mol). The resulting mixture was stirred overnight at rt and then acidified to pH=6-7 with 2 M HCl. The resulting mixture was extracted with DCM (50 mL) twice. The organic layers were combined, washed with brine, dried over anhydrous Na₂SO₄, and filtered. The filtrate was concentrated in vacuo. The residue was purified by prep-HPLC to give (−)-5-[[2-fluoro-6-[5-methyl-2-pyrimidin-2-yl-7,8-dihydro-5H-pyrido[4,3-d]pyrimidin-6-yl]-4-pyridyl]oxy]pentanoic acid (300 mg) as a yellow solid. $^1$H NMR (400 MHz, CDCl₃) δ: 8.99-9.10 (m, 2H), 8.78-8.87 (m, 1H), 7.40-7.52 (m, 1H), 5.97-6.07 (m, 1H), 5.76-5.86 (m, 1H), 5.60-5.73 (m, 1H), 4.37-4.47 (m, 1H), 3.94-4.12 (m, 2H), 3.41-3.57 (m, 1H), 3.19-3.30 (m, 2H), 2.40-2.51

(m, 3H), 1.80-1.94 (m, 4H), 1.54-1.64 (m, 3H). MS obsd. (ESI⁺) [(M+H)⁺]: 439; [a]$_D^{25}$=−51.1° (0.1 g/100 mL, methanol).

Example 158: (−)-5-[[2-fluoro-6-[methyl-2-pyrimidin-2-yl-7,8-dihydro-5H-pyrido[4,3-d]pyrimidin-6-yl]-4-pyridyl]oxy]pentanamide To a solution (−)-5-[[2-fluoro-6-[5-methyl-2-pyrimidin-2-yl-7,8-dihydro-5H-pyrido[4,3-d]pyrimidin-6-yl]-4-pyridyl]oxy]pentanoic acid (175 mg, 0.4 mol, Example 157) in DMF (10 mL) was added TEA (81 mg, 0.8 mmol), HATU (304 mg, 0.8 mmol). The resulting mixture was stirred at rt for 10 mins. To the mixture was added ammonium chloride (42 mg, 0.8 mmol). After being stirred at rt for 10 hrs, the resulting mixture was poured into water (25 mL) and extracted with EA (50 mL) twice. The organic layers were combined, washed with brine, dried over anhydrous Na₂SO₄ and concentrated in vacuo to give a red oil, which was purified by prep-HPLC to give (−)-5-[[2-fluoro-6-[5-methyl-2-pyrimidin-2-yl-7,8-dihydro-5H-pyrido[4,3-d]pyrimidin-6-yl]-4-pyridyl]oxy]pentanamide (32 mg) as a white solid. ¹H NMR (400 MHz, CDCl3): 8.91-8.99 (m, 2H), 8.69-8.78 (m, 1H), 7.31-7.41 (m, 1H), 5.88-5.95 (m, 1H), 5.66-5.76 (m, 1H), 5.52-5.63 (m, 1H), 4.25-4.39 (m, 1H), 3.91-4.02 (m, 2H), 3.35-3.47 (m, 1H), 3.12-3.21 (m, 2H), 2.17-2.32 (m, 2H), 1.71-1.86 (m, 4H), 1.38-1.52 (m, 2H). MS obsd. (ESI⁺) [(M+H)⁺]: 438; [a]$_D^{25}$=−60.7° (0.1 g/100 mL, methanol).

Example 159: 6-[6-fluoro-4-[(1-methylsulfonylazetidin-3-yl)methoxy]-2-pyridyl]-5-methyl-2-pyrimidin-2-yl-7,8-dihydro-5H-pyrido[4,3-d]pyrimidine Step 1: Preparation of tert-butyl 3-[[2-fluoro-6-(5-methyl-2-pyrimidin-2-yl-7,8-dihydro-5H-pyrido[4,3-d]pyrimidin-6-yl)-4-pyridyl]oxymethyl]azetidine-1-carboxylate

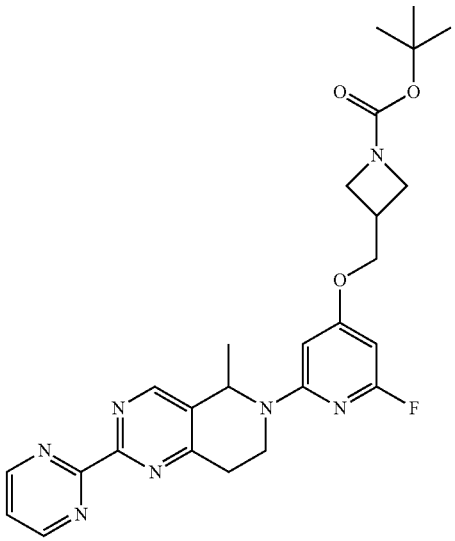 [SMILES: CC1c2cnc(-c3ncccn3)nc2CCN1c1cc(OCC2CN(C(=O)OC(C)(C)C)C2)cc(F)n1]

To a stirred solution of tert-butyl 3-(hydroxymethyl)azetidine-1-carboxylate (66 mg, 0.35 mmol) in DMF (2 mL) was added NaH (14 mg, 0.35 mmol) at 0° C. The mixture was stirred at 0° C. for 10 mins. Then to the reaction mixture was added 6-(4,6-difluoro-2-pyridyl)-5-methyl-2-pyrimidin-2-yl-7,8-dihydro-5H-pyrido[4,3-d]pyrimidine (100 mg, 0.29 mmol). The resulting mixture was heated at 60° C. for 1 hr. The other 2 bathes of this reaction were carried out in parallel. The reaction mixtures of 3 batches were combined and partitioned between EA (200 mL) and H₂O (50 mL). The organic layer was separated, washed with brine (50 mL), dried over anhydrous Na₂SO₄ and concentrated in vacuo to afford tert-butyl 3-[[2-fluoro-6-(5-methyl-2-pyrimidin-2-yl-7,8-dihydro-5H-pyrido[4,3-d]pyrimidin-6-yl)-4-pyridyl]oxymethyl]azetidine-1-carboxylate (500 mg, crude) as a yellow oil, which was used in the next step directly without any further purification.

Step 2: Preparation of 6-[4-(azetidin-3-ylmethoxy)-6-fluoro-2-pyridyl]-5-methyl-2-pyrimidin-2-yl-7,8-dihydro-5H-pyrido[4,3-d]pyrimidine

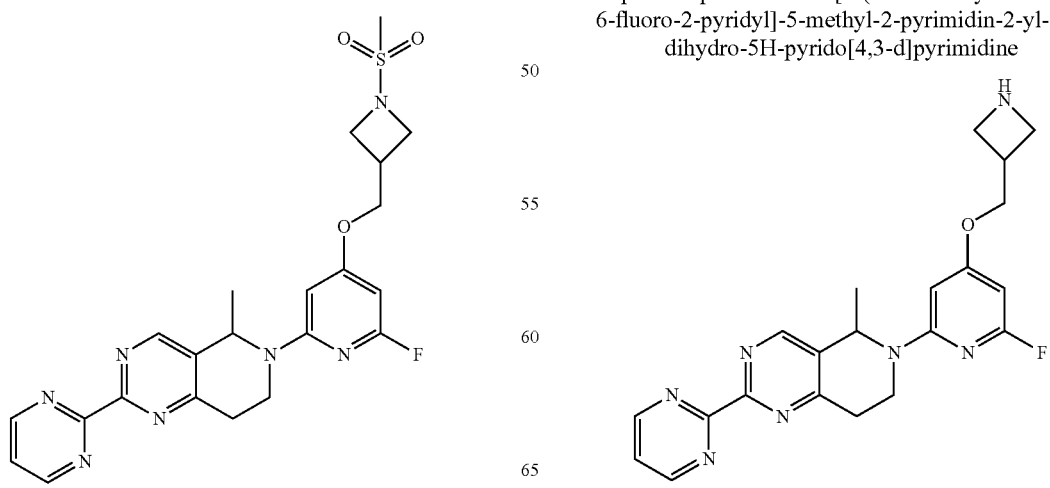

A solution of tert-butyl 3-[[2-fluoro-6-(5-methyl-2-pyrimidin-2-yl-7,8-dihydro-5H-pyrido[4,3-d]pyrimidin-6-yl)-4-pyridyl]oxymethyl]azetidine-1-carboxylate (450 mg, 0.89 mmol) in TFA (1 mL) and DCM (4 mL) was stirred at 20° C. for 12 hrs. The resulting mixture was concentrated in vacuo. The residue was dissolved in MeOH (30 mL). The solution was treated by basic resin, and then filtered. The filtrate was concentrated in vacuo to give 6-[4-(azetidin-3-ylmethoxy)-6-fluoro-2-pyridyl]-5-methyl-2-pyrimidin-2-yl-7,8-dihydro-5H-pyrido[4,3-d]pyrimidine (250 mg, crude) as a yellow oil, which was used in the next step directly without any further purification.

Step 3: Preparation of 6-[6-fluoro-4-[(1-methylsulfonylazetidin-3-yl)methoxy]-2-pyridyl]-5-methyl-2-pyrimidin-2-yl-7,8-dihydro-5H-pyrido[4,3-d]pyrimidine

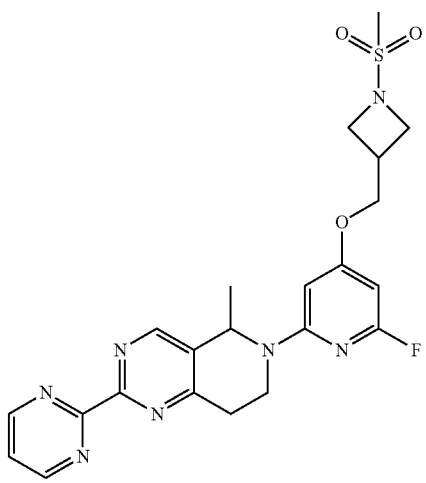 [SMILES: CC1c2cnc(-c3ncccn3)nc2CCN1c1cc(OCC2CN(S(C)(=O)=O)C2)cc(F)n1]

To a stirred solution of 6-[4-(azetidin-3-ylmethoxy)-6-fluoro-2-pyridyl]-5-methyl-2-pyrimidin-2-yl-7,8-dihydro-5H-pyrido[4,3-d]pyrimidine (80 mg, 0.20 mmol) and Et$_3$N (60 mg, 0.59 mmol) in DCM (2 mL) was added methanesulfonyl chloride (34 mg, 0.29 mmol) at 0° C. The resulting mixture was stirred for 0.5 hr at the same temperature, and then partitioned between DCM and H$_2$O. The organic layer was separated, washed with brine, dried over anhydrous Na$_2$SO$_4$ and concentrated in vacuo. The residue was purified by prep-HPLC to afford 6-[6-fluoro-4-[(1-methylsulfonylazetidin-3-yl)methoxy]-2-pyridyl]-5-methyl-2-pyrimidin-2-yl-7,8-dihydro-5H-pyrido[4,3-d]pyrimidine (12 mg) as a white solid. $^1$H NMR (400 MHz, CDCl$_3$) δ: 9.04 (d, 2H), 8.83 (s, 1H), 7.44 (m, 1H), 6.03 (s, 1H), 5.81 (s, 1H), 5.68 (m, 1H), 4.40 (d, 1H), 4.17 (d, 2H), 4.11 (t, 2H), 3.85-3.95 (m, 2H), 3.44-3.57 (m, 1H), 3.21-3.31 (m, 2H), 3.02-3.15 (m, 1H), 2.91 (s, 3H), 1.59 (d, 3H). MS obsd. (ESI$^+$) [(M+H)$^+$]: 486.

Example 160: 1-[3-[[2-fluoro-6-(5-methyl-2-pyrimidin-2-yl-7,8-dihydro-5H-pyrido[4,3-d]pyrimidin-6-yl)-4-pyridyl]oxymethyl]azetidin-1-yl]ethanone

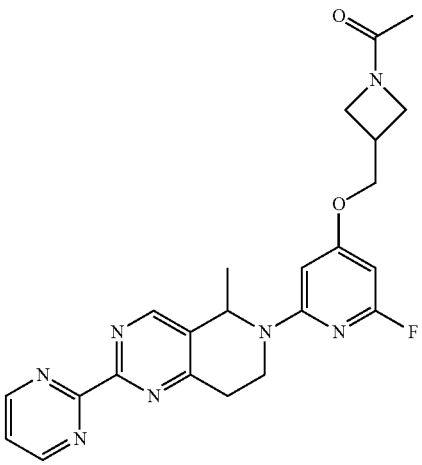 [SMILES: CC(=O)N1CC(COc2cc(F)nc(N3CCc4nc(-c5ncccn5)ncc4C3C)c2)C1]

To a stirred solution of 6-[4-(azetidin-3-ylmethoxy)-6-fluoro-2-pyridyl]-5-methyl-2-pyrimidin-2-yl-7,8-dihydro-5H-pyrido[4,3-d]pyrimidine (100 mg, 0.25 mmol) and Et$_3$N (74 mg, 0.74 mmol) in DCM (2 mL) was added acetyl chloride (29 mg, 0.39 mmol) at 0° C. Then the mixture was allowed to be warmed to 20° C. and stirred at 20° C. for 0.5 hr. The resulting mixture was partitioned between DCM (100 mL) and brine (30 mL). The organic layer was separated, washed with brine (30 mL), dried over anhydrous Na$_2$SO$_4$ and concentrated in vacuo. The residue was purified by prep-HPLC to afford 1-[3-[[2-fluoro-6-(5-methyl-2-pyrimidin-2-yl-7,8-dihydro-5H-pyrido[4,3-d]pyrimidin-6-yl)-4-pyridyl]oxymethyl]azetidin-1-yl]ethanone (5 mg) as a white solid. $^1$H NMR (300 MHz, Methanol-d4) δ: 9.03 (d, 2H), 8.88 (s, 1H), 7.65 (t, 1H), 6.30 (s, 1H), 5.92 (s, 1H), 5.74 (d, 1H), 4.53 (d, 1H), 4.31-4.41 (m, 1H), 4.25 (d, 2H), 4.03-4.18 (m, 2H), 3.86 (m, 1H), 3.44-3.60 (m, 1H), 3.12-3.21 (m, 2H), 3.09 (d, 1H), 1.88 (s, 3H), 1.59 (d, 3H). MS obsd. (ESI$^+$) [(M+H)$^+$]: 450.

Example 161: 6-(4-methoxy-6-methyl-2-pyridyl)-5-methyl-2-pyrimidin-2-yl-7,8-dihydro-5H-pyrido[4,3-d]pyrimidine

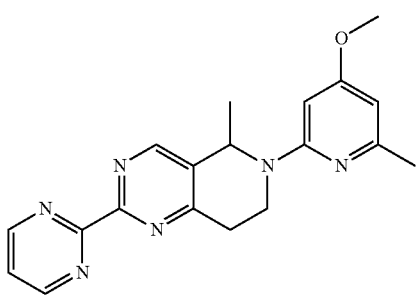 [SMILES: COc1cc(C)nc(N2CCc3nc(-c4ncccn4)ncc3C2C)c1]

To a solution of 6-(6-chloro-4-methoxy-2-pyridyl)-5-methyl-2-(2-pyridyl)-7,8-dihydro-5H-pyrido[4,3-d]pyrimidine (100 mg, 0.27 mmol, Example 126) in DMF (5 mL) was added Pd(PPh$_3$)$_4$ (30 mg, 0.03 mmol) and trimethylaluminium (2 M in toluene, 0.15 mL, 0.30 mmol). The reaction mixture was heated with stirring at 70° C. for 12 hrs. The reaction was then quenched by water (10 mL) and the resulting mixture was extracted with EA (100 mL) twice. The organic layers were combined, washed with brine (50 mL), dried over anhydrous Na$_2$SO$_4$ and concentrated in vacuo. The residue was purified by prep-HPLC to give 6-(4-methoxy-6-methyl-2-pyridyl)-5-methyl-2-pyrimidin-2-yl-7,8-dihydro-5H-pyrido[4,3-d]pyrimidine (11 mg) as a yellow solid. $^1$H NMR (400 MHz, DMSO-d$_6$) δ: 8.99 (d, 2H), 8.90 (s, 1H), 7.63 (t, 1H), 6.25 (s, 1H), 6.18 (s, 1H), 5.80 (q, 1H), 4.58 (dd, 1H), 3.79 (s, 3H), 3.36-3.40 (m, 1H), 2.91-3.12 (m, 2H), 2.28 (s, 3H), 1.49 (d, 3H). MS obsd. (ESI$^+$) [(M+H)$^+$]: 349.

Example 162: 2-[3-[[2-fluoro-6-(5-methyl-2-pyrimidin-2-yl-7,8-dihydro-5H-pyrido[4,3-d]pyrimidin-6-yl)-4-pyridyl]oxy]propoxy]acetic acid

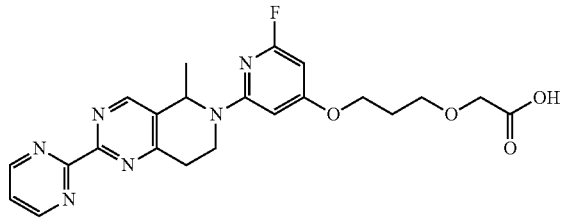 [SMILES: CC1c2cnc(-c3ncccn3)nc2CCN1c1cc(OCCCOCC(=O)O)cc(F)n1]

Step 1: Preparation of 2-(3-benzyloxypropoxy)acetic acid

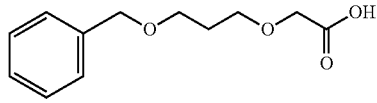 [SMILES: O=C(O)COCCCOCc1ccccc1]

To a solution of 3-(benzyloxy)propan-1-ol (1.6 g, 9.63 mmol) in toluene (20 mL) was added a solution of sodium hydroxide (9.0 g, 225 mmol) in water (9 mL) and tetrabutylammonium bromide (776 mg, 2.41 mmol) successively. The resulting mixture was stirred at rt for 30 mins and then to the resulting mixture was added tert-butyl 2-bromoacetate (5.63 g, 28.9 mmol). After being heated at 90° C. with stirring overnight, the resulting mixture was acidified with 3 M HCl and extracted with EA (100 mL) for three times. The combined organic layer was dried over anhydrous Na$_2$SO$_4$ and concentrated in vacuo to give the crude 2-(3-benzyloxypropoxy)acetic acid which was used in the next step directly without any further purification.

Step 2: preparation of methyl 2-(3-benzyloxypropoxy)acetate

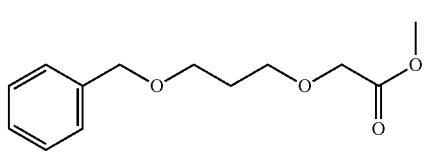 [SMILES: COC(=O)COCCCOCc1ccccc1]

A mixture of 2-(3-(benzyloxy)propoxy)acetic acid (3.3 g, 14.7 mmol), iodomethane (3.13 g, 1.38 mL, 22.1 mmol) and potassium carbonate (4.07 g, 29.4 mmol) in acetonitrile (20 mL) was heated with stirring at 50° C. overnight. The resulting mixture was cooled to rt, acidified with 3M HCl and extracted with EA (50 mL) for three times. The organic layers were combined, dried over anhydrous Na$_2$SO$_4$ and concentrated in vacuo. The residue was purified by flash column to give methyl 2-(3-(benzyloxy)propoxy)acetate (1.8 g) as colorless oil.

Step 3: preparation of methyl 2-(3-hydroxypropoxy)acetate

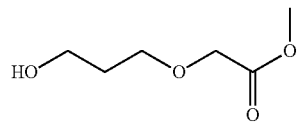

A mixture of methyl 2-(3-(benzyloxy)propoxy)acetate (1.8 g, 7.55 mmol) and palladium on carbon (804 mg, 7.55 mmol, 10%) in MeOH (20 mL) was degassed and filled with hydrogen by using a hydrogen balloon. The resulting mixture was stirred at rt overnight. Then to the resulting mixture was added celite and the solid was filtered off. The filtrate was concentrated in vacuo to give methyl 2-(3-hydroxypropoxy)acetate (1.1 g) as colorless oil.

Step 4: preparation of methyl 2-[3-(p-tolylsulfonyloxy)propoxy]acetate

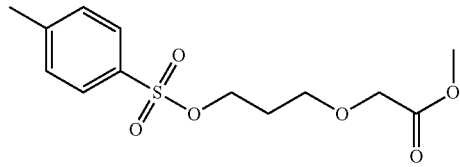

To a solution of methyl 2-(3-hydroxypropoxy)acetate (740 mg) in DCM (20 mL) was added pyridine (1.96 g, 2 mL, 24.7 mmol) and tosyl-Cl (1.9 g, 9.99 mmol) successively. The resulting mixture was stirred at rt. After the reaction was complete, the resulting mixture was concentrated in vacuo, and the residue was purified by flash column to give methyl 2-(3-(tosyloxy)propoxy)acetate (1.0 g) as colorless oil.

Step 5: Preparation of methyl 2-[3-[(2,6-difluoro-4-pyridyl)oxy]propoxy]acetate

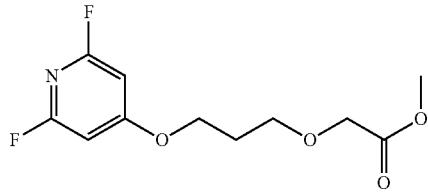 [SMILES: COC(=O)COCCCOc1cc(F)nc(F)c1]

A mixture of 2,6-difluoropyridin-4-ol (434 mg, 3.31 mmol), methyl 2-(3-(tosyloxy)propoxy)acetate (1.0 g, 3.31 mmol) and potassium carbonate (914 mg, 6.61 mmol) in DMF (10 mL) was heated with stirring at 80° C. After the reaction was complete, the reaction mixture was purified by flash column to give methyl 2-(3-((2,6-difluoropyridin-4-yl) oxy)propoxy)acetate (660 mg, 2.53 mmol) as colorless oil.

Step 6: preparation of methyl 2-[3-[[2-fluoro-6-(5-methyl-2-pyrimidin-2-yl-7,8-dihydro-5H-pyrido[4,3-d]pyrimidin-6-yl)-4-pyridyl]oxy]propoxy]acetate

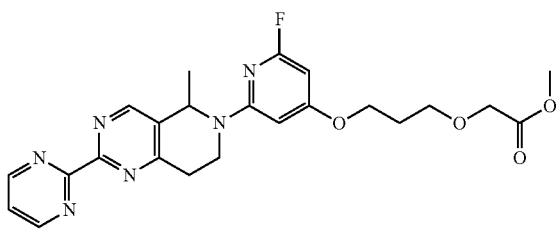 [SMILES: COC(=O)COCCCOc1cc(F)nc(N2CCc3nc(-c4ncccn4)ncc3C2C)c1]

A mixture of methyl 2-(3-((2,6-difluoropyridin-4-yl)oxy) propoxy)acetate (650 mg, 2.49 mmol), 5-methyl-2-(pyrimidin-2-yl)-5,6,7,8-tetrahydropyrido[4,3-d]pyrimidine (300 mg, 1.32 mmol) and DIPEA (740 mg, 1 mL, 5.73 mmol) in DMSO (0.5 mL) was stirred at 110° C. overnight. The mixture was cooled to rt and diluted with water. The resulting mixture was extracted with EA (30 mL) for three times. The combined organic layer was dried over anhydrous Na$_2$SO$_4$ and concentrated in vacuo. The residue was purified by flash column to give methyl 2-[3-[[2-fluoro-6-(5-methyl-2-pyrimidin-2-yl-7,8-dihydro-5H-pyrido[4,3-d] pyrimidin-6-yl)-4-pyridyl]oxy]propoxy]acetate (800 mg) as light yellow oil.

Step 7: Preparation of 2-[3-[[2-fluoro-6-(5-methyl-2-pyrimidin-2-yl-7,8-dihydro-5H-pyrido[4,3-d]pyrimidin-6-yl)-4-pyridyl]oxy]propoxy]acetic acid

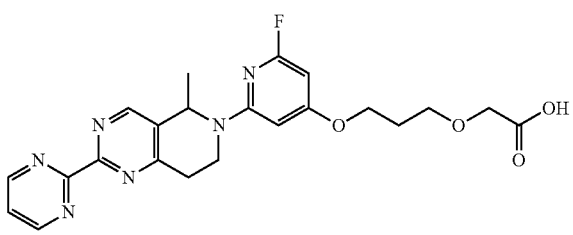 [SMILES: CC1c2cnc(-c3ncccn3)nc2CCN1c1cc(OCCCOCC(=O)O)cc(F)n1]

To a solution of methyl 2-[3-[[2-fluoro-6-(5-methyl-2-pyrimidin-2-yl-7,8-dihydro-5H-pyrido[4,3-d]pyrimidin-6-yl)-4-pyridyl]oxy]propoxy]acetate (800 mg, 1.71 mmol) in THF (15 mL) was added a solution of LiOH (5.12 mL, 5.12 mmol) in water (5 mL). After being stirred at rt for 2 hrs, the resulting mixture was then acidified with 1M HCl and concentrated in vacuo. The residue was purified by prep-HPLC to give 2-[3-[[2-fluoro-6-(5-methyl-2-pyrimidin-2-yl-7,8-dihydro-5H-pyrido[4,3-d]pyrimidin-6-yl)-4-pyridyl] oxy]propoxy]acetic acid (30 mg) as a yellow solid. $^1$H NMR (400 MHz, Methanol-d$_4$) δ: 1.57 (d, 3H), 2.02-2.11 (m, 2H), 3.09-3.21 (m, 2H), 3.37-3.50 (m, 1H), 3.42-3.56 (m, 1H), 3.70 (t, 2H), 4.04-4.12 (m, 2H), 4.19 (t, 2H), 4.51 (br d, 1H), 5.65-5.76 (m, 1H), 5.87 (d, 1H), 6.25 (s, 1H), 7.64 (br s, 1H), 8.88 (s, 1H), 9.02 (br d, 2H). MS obsd. (ESI$^+$) [(M+H)$^+$]: 455.

Example 163: 2-[3-[[2-fluoro-6-(5-methyl-2-pyrimidin-2-yl-7,8-dihydro-5H-pyrido[4,3-d]pyrimidin-6-yl)-4-pyridyl]oxy]propoxy]acetamide

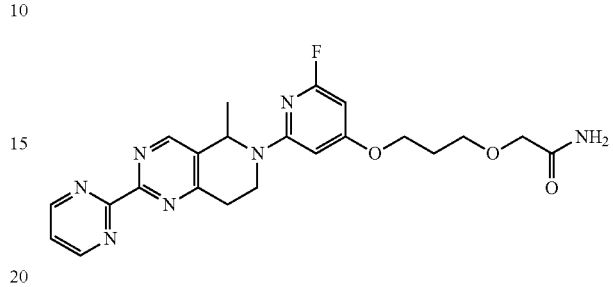

A mixture of 2-[3-[[2-fluoro-6-(5-methyl-2-pyrimidin-2-yl-7,8-dihydro-5H-pyrido[4,3-d]pyrimidin-6-yl)-4-pyridyl] oxy]propoxy]acetic acid (500 mg, 1.1 mmol), ammonium chloride (177 mg, 3.3 mmol), TEA (1.45 g, 2 mL, 14.3 mmol) and HATU (837 mg, 2.2 mmol) in N-methyl-2-pyrrolidinone (5 mL) was stirred at rt overnight. The mixture was purified by prep-HPLC to give 2-[3-[[2-fluoro-6-(5-methyl-2-pyrimidin-2-yl-7,8-dihydro-5H-pyrido[4,3-d]pyrimidin-6-yl)-4-pyridyl]oxy]propoxy]acetamide (15 mg) as light yellow solid. $^1$H NMR (400 MHz, Methanol-d4) δ: 1.60 (d, 3H), 2.12 (t, 2H), 3.12-3.23 (m, 2H), 3.46-3.59 (m, 1H), 3.73 (t, 2H), 3.97 (s, 2H), 4.22 (t, 2H), 4.47-4.59 (m, 1H), 5.69-5.79 (m, 1H), 5.91 (d, 1H), 6.27 (s, 1H), 7.67 (s, 1H), 8.90 (s, 1H), 9.02-9.08 (m, 2H). MS obsd. (ESI$^+$) [(M+H)$^+$]: 454.

Example 164: (−)-6-[[2-fluoro-6-[5-methyl-2-pyrimidin-2-yl-7,8-dihydro-5H-pyrido[4,3-d]pyrimidin-6-yl]-4-pyridyl]oxy]hexanoic acid Step 1: Preparation of methyl 6-[(2,6-difluoro-4-pyridyl)oxy]hexanoate

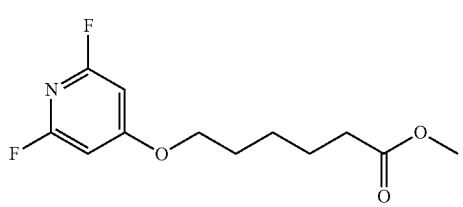 [SMILES: COC(=O)CCCCCOc1cc(F)nc(F)c1]

To a solution of 2,6-difluoropyridin-4-ol (1.0 g, 8.0 mmol) and methyl 6-bromopentanoate (2.1 g, 10 mmol) in DMF (25 mL) was added anhydrous potassium carbonate (3.3 g, 24 mmol) and then the mixture was stirred at 100° C. for 10 hrs. After cooling to rt, the mixture was diluted with water (50 mL) and extracted with EA (50 mL) twice. The organic layer was washed with brine, dried over anhydrous Na$_2$SO$_4$, and concentrated. The residue was purified by flash chromatography to give methyl 6-[(2,6-difluoro-4-pyridyl)oxy] hexanoate (1.3 g).

Step 2: Preparation of methyl (+/−)-6-[[2-fluoro-6-[5-methyl-2-pyrimidin-2-yl-7,8-dihydro-5H-pyrido[4,3-d]pyrimidin-6-yl]-4-pyridyl]oxy]hexanoate To a solution of (+)-5-methyl-2-pyrimidin-2-yl-5,6,7,8-tetrahydropyrido[4,3-d]pyrimidine (227 mg, 1.0 mmol) in DIPEA (1 mL) and DMSO (0.5 mL) was added methyl 6-[(2,6-difluoro-4-pyridyl)oxy]hexanoate (1.3 g, 5 mmol). The resulting mixture is heated and stirred at 110° C. in a sealed vessel for 48 hrs. Then the resulting reaction mixture was cooled to rt, and then poured into water (50 mL) and extracted with EA (60 mL) twice. The organic layers were combined, washed with brine, dried over anhydrous $Na_2SO_4$ and concentrated in vacuo to give a red oil, which was purified by flash chromatography to give methyl (+/−)-6-[[2-fluoro-6-[5-methyl-2-pyrimidin-2-yl-7,8-dihydro-5H-pyrido[4,3-d]pyrimidin-6-yl]-4-pyridyl]oxy]hexanoate (360 mg) as a red solid.

Step 3: Preparation of (−)-6-[[2-fluoro-6-[5-methyl-2-pyrimidin-2-yl-7,8-dihydro-5H-pyrido[4,3-d]pyrimidin-6-yl]-4-pyridyl]oxy]hexanoic acid To a solution of methyl (+/−)-6-[[2-fluoro-6-[5-methyl-2-pyrimidin-2-yl-7,8-dihydro-5H-pyrido[4,3-d]pyrimidin-6-yl]-4-pyridyl]oxy]hexanoate (350 mg, 0.75 mol) in methanol (10 mL), THF (5 mL) and water (2 mL) was added LiOH monohydrate (158 mg, 3.75 mol). The resulting mixture was stirred overnight at rt and then acidified to pH=6-7 with 2M HCl. The reaction mixture was extracted with DCM (50 mL) twice. The organic layer was washed with brine, dried over anhydrous $Na_2SO_4$, and concentrated in vacuo. The residue was purified by prep-HPLC to give (−)-6-[[2-fluoro-6-[5-methyl-2-pyrimidin-2-yl-7,8-dihydro-5H-pyrido[4,3-d]pyrimidin-6-yl]-4-pyridyl]oxy]hexanoic acid (280 mg) as a yellow solid. $^1$H NMR (400 MHz, $CDCl_3$) δ: 8.88-9.01 (m, 2H), 8.69-8.79 (m, 1H), 7.29-7.42 (m, 1H), 5.86-5.98 (m, 1H), 5.62-5.68 (m, 1H), 5.49-5.62 (m, 1H), 4.18-4.37 (m, 1H), 3.74-3.94 (m, 2H), 3.32-3.47 (m, 1H), 3.05-3.24 (m, 2H), 2.26-2.76 (m, 2H), 1.99-2.17 (m, 2H), 1.51-1.65 (m, 2H), 1.41-1.51 (m, 3H), 1.20-1.32 (m, 2H). MS obsd. (ESI$^+$) [(M+H)$^+$]: 453. $[α]_D^{25}$=−49.4° (0.1 g/100 mL, methanol).

Example 165: (−)-6-[[2-fluoro-6-[5-methyl-2-pyrimidin-2-yl-7,8-dihydro-5H-pyrido[4,3-d]pyrimidin-6-yl]-4-pyridyl]oxy]hexanamide To a solution of (−)-6-[[2-fluoro-6-[5-methyl-2-pyrimidin-2-yl-7,8-dihydro-5H-pyrido[4,3-d]pyrimidin-6-yl]-4-pyridyl]oxy]hexanoic acid (226 mg, 0.5 mol) in DMF (10 mL) was added TEA (101 mg, 1.0 mmol) and HATU (380 mg, 1.0 mmol). The resulting mixture was stirred for 10 mins at rt, and then to the resulting mixture was added ammonium chloride (53 mg, 1.0 mmol). After being stirred for 10 hrs at rt, the resulting reaction mixture was poured into water (25 mL) and extracted with DCM (50 mL) twice. The organic layers were combined, washed with brine, dried over anhydrous $Na_2SO_4$ and concentrated in vacuo to give a red oil, which was purified by prep-HPLC to give (−)-6-[[2-fluoro-6-[5-methyl-2-pyrimidin-2-yl-7,8-dihydro-5H-pyrido[4,3-d]pyrimidin-6-yl]-4-pyridyl]oxy]hexanamide (37 mg) as a white solid. $^1$H NMR (400 MHz, Methanol-d4) δ: 8.89-8.98 (m, 2H), 8.74-8.83 (m, 1H), 7.50-7.59 (m, 1H), 6.10-6.19 (m, 1H), 5.73-5.81 (m, 1H), 5.58-5.67 (m, 1H), 4.35-4.47 (m, 1H), 3.94-4.04 (m, 2H), 3.35-3.48 (m, 1H), 2.95-3.10 (m, 2H), 2.09-2.20 (m, 2H), 1.66-1.76 (m, 2H), 1.53-1.65 (m, 2H), 1.47-1.51 (m, 3H), 1.37-1.47 (m, 2H). MS obsd. (ESI$^+$) [(M+H)$^+$]: 452. $[α]_D^{25}$=−40.3° (0.1 g/100 mL, methanol).

Example 166: 6-[6-fluoro-4-(tetrahydrofuran-2-ylmethoxy)-2-pyridyl]-5-methyl-2-pyrimidin-2-yl-7,8-dihydro-5H-pyrido[4,3-d]pyrimidine

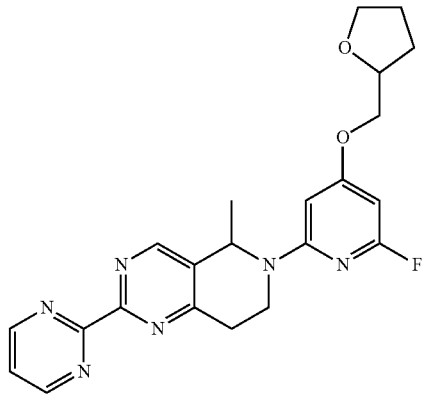 [SMILES: CC1c2cnc(-c3ncccn3)nc2CCN1c1cc(OCC2CCCO2)cc(F)n1]

To a stirred solution of tetrahydrofurfuryl alcohol (36 mg, 0.35 mmol) in DMF (2 mL) was added NaH (14 mg, 0.35 mmol) at 0° C. The mixture was stirred at 0° C. for 10 mins. Then to the reaction mixture was added 6-(4,6-difluoro-2-pyridyl)-5-methyl-2-pyrimidin-2-yl-7,8-dihydro-5H-pyrido[4,3-d]pyrimidine (100 mg, 0.29 mmol). The resulting mixture was heated at 80° C. for 1 hr, and then partitioned between EA (50 mL) and $H_2O$ (20 mL). The organic layer was separated, washed with brine (20 mL), dried over anhydrous $Na_2SO_4$ and concentrated in vacuo. The residue was purified by prep-TLC and prep-HPLC to afford 6-[6-fluoro-4-(tetrahydrofuran-2-ylmethoxy)-2-pyridyl]-5-methyl-2-pyrimidin-2-yl-7,8-dihydro-5H-pyrido[4,3-d]pyrimidine (40 mg) as a light yellow solid. $^1$H NMR (400 MHz, $CDCl_3$) δ: 9.04 (d, 2H), 8.81 (s, 1H), 7.44 (t, 1H), 6.07 (s, 1H), 5.83 (s, 1H), 5.66 (m, 1H), 4.39 (m, 1H), 4.27 (m, 1H), 3.99-4.06 (m, 2H), 3.90-3.98 (m, 1H), 3.85 (m, 1H), 3.43-3.53 (m, 1H), 3.20-3.30 (m, 2H), 2.04-2.18 (m, 1H), 1.92-2.03 (m, 2H), 1.71-1.83 (m, 1H), 1.58-1.59 (m, 3H). MS obsd. (ESI$^+$) [(M+H)$^+$]: 423.

Example 167: methyl 8-[[2-fluoro-6-(5-methyl-2-pyrimidin-2-yl-7,8-dihydro-5H-pyrido[4,3-d]pyrimidin-6-yl)-4-pyridyl]oxy]octanoate

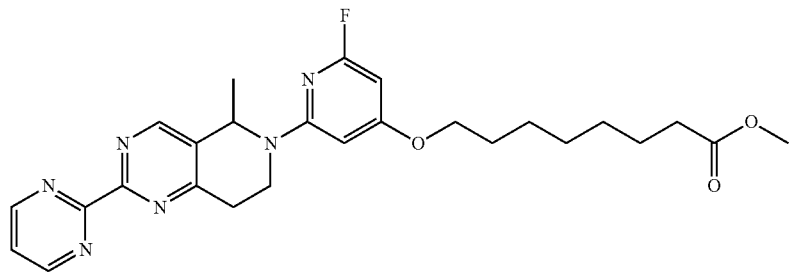 [SMILES: COC(=O)CCCCCCCOc1cc(F)nc(N2CCc3nc(-c4ncccn4)ncc3C2C)c1]

Step 1: Preparation of methyl 8-[(2,6-difluoro-4-pyridyl)oxy]octanoate

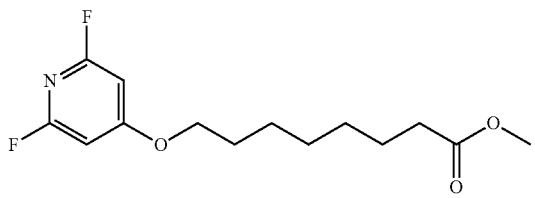 [SMILES: COC(=O)CCCCCCCOc1cc(F)nc(F)c1]

To a solution of 2,6-difluoropyridin-4-ol (1.0 g, 8 mmol) and methyl 8-bromopentanoate (2.4 g, 10 mmol) in DMF (25 mL) was added anhydrous potassium carbonate (3.3 g, 24 mmol) and then the mixture was heated and stirred at 100° C. for 10 hrs. After being cooled to rt, the resulting mixture was diluted with water (50 mL), and then extracted with EA (50 mL) for three times. The organic layers were combined, washed with brine, dried over anhydrous $Na_2SO_4$ and filtered. The filtrate was concentrated in vacuo and the residue was purified by flash chromatography to give methyl 8-[(2,6-difluoro-4-pyridyl)oxy]octanoate as a yellow oil (1.5 g).

Step 2: Preparation of methyl 8-[[2-fluoro-6-(5-methyl-2-pyrimidin-2-yl-7,8-dihydro-5H-pyrido[4,3-d]pyrimidin-6-yl)-4-pyridyl]oxy]octanoate To a solution of 5-methyl-2-(pyrimidin-2-yl)-5,6,7,8-tetrahydropyrido[4,3-d]pyrimidine (227 mg, 1.0 mmol) in DIEA (1 mL) and DMSO (0.5 mL) was added methyl 8-((2,6,-difluoropyridin-4-yl)oxy)pentanoate (1.44 g, 5 mmol). The reaction mixture is heated to 110° C. and stirred in a sealed vessel for 48 hrs. The reaction mixture was poured into water (50 mL) and extracted with EA (60 mL) for three times. The combined organic layer was brine, dried over anhydrous $Na_2SO_4$ and concentrated in vacuo to give a red oil, which was purified by flash chromatography to give methyl 8-[[2-fluoro-6-(5-methyl-2-pyrimidin-2-yl-7,8-dihydro-5H-pyrido[4,3-d]pyrimidin-6-yl)-4-pyridyl]oxy]octanoate (400 mg) as a yellow solid. $^1$H NMR (400 MHz, Methanol-d4) δ: 8.89-8.97 (m, 2H), 8.74-8.81 (m, 1H), 7.50-7.58 (m, 1H), 6.05-6.16 (m, 1H), 5.73-5.82 (m, 1H), 5.57-5.68 (m, 1H), 4.34-4.46 (m, 1H), 3.92-4.00 (m, 2H), 3.55 (s, 3H), 3.32-3.46 (m, 1H), 3.01-3.09 (m, 2H), 2.13-2.31 (m, 2H), 1.63-1.74 (m, 2H), 1.50-1.57 (m, 2H), 1.45-1.50 (m, 3H), 1.35-1.43 (m, 2H), 1.21-1.33 (m, 4H). MS obsd. (ESI$^+$) [(M+H)$^+$]: 495.

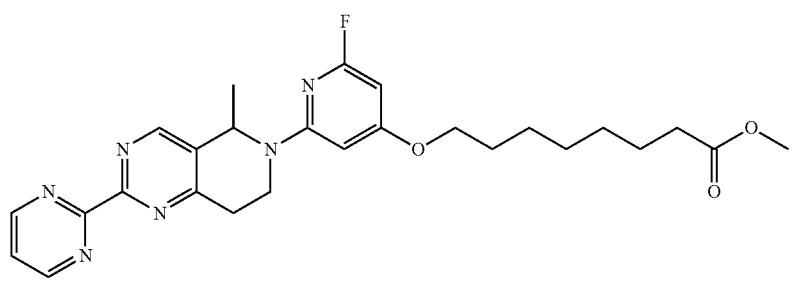 [SMILES: COC(=O)CCCCCCCOc1cc(F)nc(N2CCc3nc(-c4ncccn4)ncc3C2C)c1]

Example 168: 8-[[2-fluoro-6-(5-methyl-2-pyrimidin-2-yl-7,8-dihydro-5H-pyrido[4,3-d]pyrimidin-6-yl)-4-pyridyl]oxy]octanoic acid

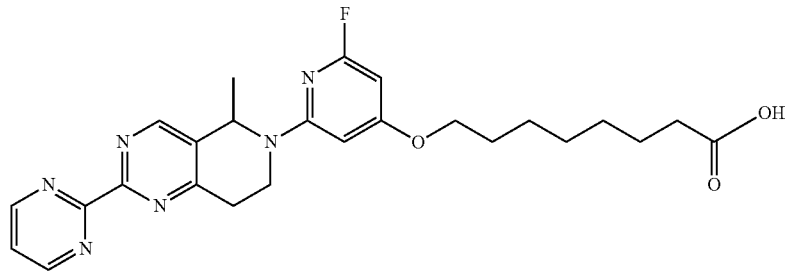 [SMILES: CC1c2cnc(-c3ncccn3)nc2CCN1c1cc(OCCCCCCCC(=O)O)cc(F)n1]

To a solution of methyl 8-[[2-fluoro-6-(5-methyl-2-pyrimidin-2-yl-7,8-dihydro-5H-pyrido[4,3-d]pyrimidin-6-yl)-4-pyridyl]oxy]octanoate (350 mg, 0.70 mol) in methanol (10 mL), THF (5 mL) and water (2 mL) was added LiOH monohydrate (148 mg, 3.5 mol). The resulting mixture was stirred overnight at rt and then acidified to pH=6-7 with 2N HCl. The resulting mixture was extracted with DCM (50 mL) for three times. The combined organic layer was washed with brine, dried over anhydrous $Na_2SO_4$, filtered and concentrated in vacuo. The residue was purified by prep-HPLC to give 8-[[2-fluoro-6-(5-methyl-2-pyrimidin-2-yl-7,8-dihydro-5H-pyrido[4,3-d]pyrimidin-6-yl)-4-pyridyl]oxy]octanoic acid (280 mg) as light yellow solid. $^1$H NMR (400 MHz, $CDCl_3$) δ: 8.90-9.01 (m, 2H), 8.68-8.79 (m, 1H), 7.30-7.41 (m, 1H), 5.88-5.97 (m, 1H), 5.66-5.75 (m, 1H), 5.53-5.64 (m, 1H), 4.22-4.37 (m, 1H), 3.86-3.97 (m, 2H), 3.34-3.46 (m, 1H), 3.10-3.19 (m, 2H), 2.23-2.36 (m, 2H), 1.64-1.76 (m, 2H), 1.53-1.65 (m, 2H), 1.44-1.51 (m, 3H), 1.36-1.43 (m, 2H), 1.25-1.34 (m, 4H). MS obsd. (ESI$^+$) [(M+H)$^+$]: 481.

Example 169: 8-[[2-fluoro-6-(5-methyl-2-pyrimidin-2-yl-7,8-dihydro-5H-pyrido[4,3-d]pyrimidin-6-yl)-4-pyridyl]oxy]octanamide

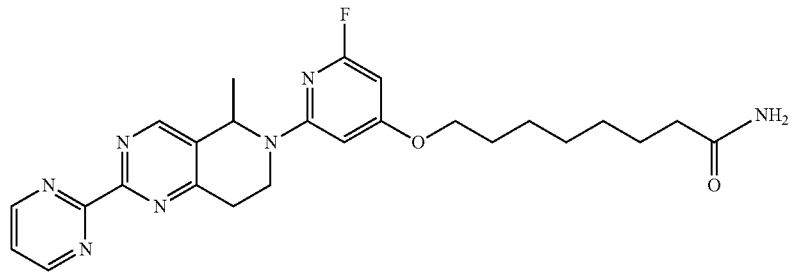 [SMILES: CC1c2cnc(-c3ncccn3)nc2CCN1c1cc(OCCCCCCCC(N)=O)cc(F)n1]

To a solution of 8-[[2-fluoro-6-(5-methyl-2-pyrimidin-2-yl-7,8-dihydro-5H-pyrido[4,3-d]pyrimidin-6-yl)-4-pyridyl]oxy]octanoic acid (240 mg, 0.5 mol) in DMF (10 mL) was added TEA (101 mg, 1.0 mmol) and HATU (380 mg, 1.0 mmol). The resulting mixture was stirred for 10 mins at rt and then to the reaction mixture was added ammonium chloride (53 mg, 1.0 mmol). After being stirred for 10 hrs at rt, the resulting reaction mixture was poured into water (25 mL) and extracted with DCM (50 mL) for three times. The combined organic layer was washed with brine, dried over anhydrous $Na_2SO_4$ and concentrated in vacuo to give a red oil, which was purified by prep-HPLC to give 8-[[2-fluoro-6-(5-methyl-2-pyrimidin-2-yl-7,8-dihydro-5H-pyrido[4,3-d]pyrimidin-6-yl)-4-pyridyl]oxy]octanamide (30 mg) as a light yellow solid. $^1$H NMR (400 MHz, Methanol-d4) δ: 8.88-8.98 (m, 2H), 8.74-8.81 (m, 1H), 7.47-7.59 (m, 1H), 6.04-6.18 (m, 1H), 5.74-5.81 (m, 1H), 5.58-5.66 (m, 1H), 4.37-4.47 (m, 1H), 3.90-4.00 (m, 2H), 3.35-3.47 (m, 1H), 2.95-3.08 (m, 2H), 2.04-2.17 (m, 2H), 1.65-1.75 (m, 2H), 1.51-1.58 (m, 2H), 1.45-1.51 (m, 3H), 1.37-1.44 (m, 2H), 1.26-1.35 (m, 4H). MS obsd. (ESI$^+$) [(M+H)$^+$]: 480.

Example 170: 6-[[2-fluoro-6-[5-methyl-2-(2-pyridyl)-7,8-dihydro-5H-pyrido[4,3-d]pyrimidin-6-yl]-4-pyridyl]oxy]hexanoic acid

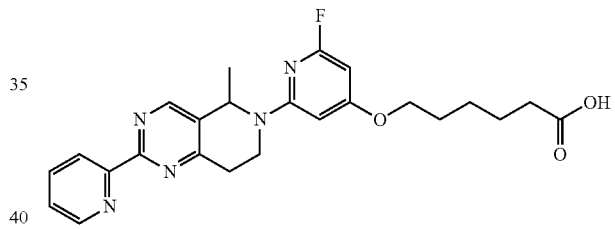

Step 1: Preparation of methyl 6-[(2,6-difluoro-4-pyridyl)oxy]hexanoate

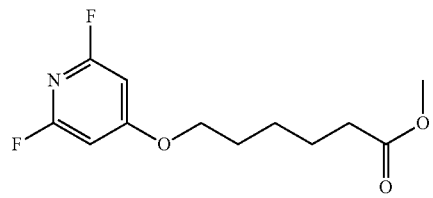 [SMILES: COC(=O)CCCCCOc1cc(F)nc(F)c1]

A mixture of 2,6-difluoropyridin-4-ol (1 g, 7.63 mmol), anhydrous potassium carbonate (3.16 g, 22.9 mmol) and methyl 6-bromopentanoate (1.91 g, 9.15 mmol) in DMF (25 mL) was heated to 100° C. and stirred for 10 hrs. The reaction mixture was allowed to be cooled to rt and extracted with EA (100 mL). The organic layer was washed with brine, dried over MgSO4, and concentrated in vacuo. The residue was purified by column chromatography to give methyl 6-[(2,6-difluoro-4-pyridyl)oxy]hexanoate as a yellow oil (1 g).

Step 2: Preparation of methyl 6-[[2-fluoro-6-[5-methyl-2-(2-pyridyl)-7,8-dihydro-5H-pyrido[4,3-d]pyrimidin-6-yl]-4-pyridyl]oxy]hexanoate

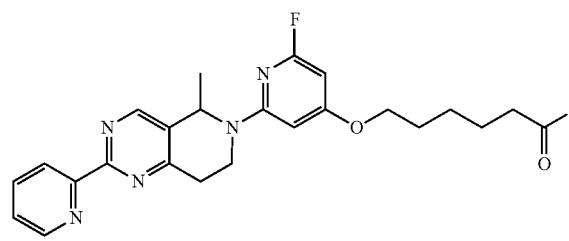

A solution of 5-methyl-2-(2-pyridyl)-5,6,7,8-tetrahydropyrido[4,3-d]pyrimidine (200 mg, 0.884 mmol) and methyl 6-((2,6-difluoropyridin-4-yl)oxy)hexanoate (1.15 g, 4.42 mmol) in DMSO (0.5 mL) and DIEA (1 mL) was heated to 110° C. and stirred for 15 hrs. The resulting reaction mixture was concentrated in vacuo and the residue was purified by flash column to give methyl 6-[[2-fluoro-6-[5-methyl-2-(2-pyridyl)-7,8-dihydro-5H-pyrido[4,3-d]pyrimidin-6-yl]-4-pyridyl]oxy]hexanoate (200 mg) as a yellow oil.

Step 3: Preparation of 6-[[2-fluoro-6-[5-methyl-2-(2-pyridyl)-7,8-dihydro-5H-pyrido[4,3-d]pyrimidin-6-yl]-4-pyridyl]oxy]hexanoic acid

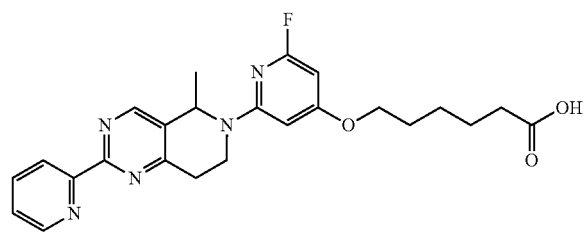 [SMILES: CC1c2cnc(-c3ccccn3)nc2CCN1c1cc(OCCCCCC(=O)O)cc(F)n1]

To a solution of methyl 6-[[2-fluoro-6-[5-methyl-2-(2-pyridyl)-7,8-dihydro-5H-pyrido[4,3-d]pyrimidin-6-yl]-4-pyridyl]oxy]hexanoate (200 mg, 0.43 mmol) in a mixture of methanol (10 mL), THF (5 mL) and water (2 mL) was added LiOH monohydrate (110 mg, 2.58 mmol). After being stirred overnight at rt, the resulting mixture was acidified to pH=6-7 with 1N HCl and then extracted with DCM (20 mL) for 3 times. The combined organic layer was washed with brine, dried over MgSO4, filtered and concentrated in vacuo. The residue was purified by column chromatography to give the crude product (170 mg) as a yellow solid. The crude product (50 mg) was further purified by prep-HPLC to give 6-[[2-fluoro-6-[5-methyl-2-(2-pyridyl)-7,8-dihydro-5H-pyrido[4,3-d]pyrimidin-6-yl]-4-pyridyl]oxy]hexanoic acid (7 mg) as a light yellow solid. $^1$H NMR (400 MHz, Methanol-d4) δ: 8.70 (s, 1H), 8.62 (d, 1H), 8.36-8.47 (m, 1H), 7.78-8.02 (m, 1H), 7.32-7.49 (m, 1H), 6.12 (s, 1H), 5.76 (d, 1H), 5.47-5.64 (m, 1H), 4.32-4.51 (m, 1H), 3.97 (t, 2H), 3.30-3.50 (m, 1H), 2.87-3.11 (m, 2H), 2.15-2.31 (m, 2H), 1.66-1.79 (m, 2H), 1.52-1.66 (m, 2H), 1.46 (d, 5H). MS obsd. (ESI$^+$) [(M+H)$^+$]: 452.

Example 171: 6-[[2-fluoro-6-[5-methyl-2-(2-pyridyl)-7,8-dihydro-5H-pyrido[4,3-d]pyrimidin-6-yl]-4-pyridyl]oxy]hexanamide

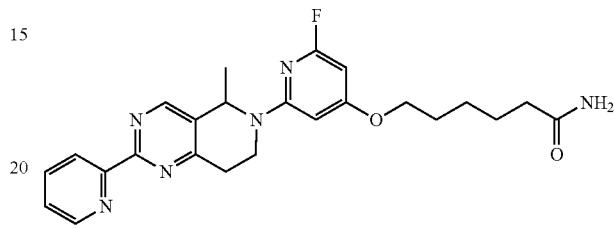

To a solution of 6-[[2-fluoro-6-[5-methyl-2-(2-pyridyl)-7,8-dihydro-5H-pyrido[4,3-d]pyrimidin-6-yl]-4-pyridyl]oxy]hexanoic acid (120 mg, 0.266 mol) in DMF (10 mL) was added TEA (53.8 mg, 0.532 mmol) and HATU (202 mg, 0.532 mmol). The resulting mixture was stirred for 10 mins at rt. Then to the reaction mixture was added ammonium chloride (28.4 mg, 0.532 mmol). After being stirred at rt for 10 hrs, the resulting mixture was poured into water (25 mL) and extracted with DCM (50 mL) for three times. The combined organic layer was washed with brine, dried over anhydrous Na2SO4 and concentrated in vacuo to give a red oil, which was purified by prep-HPLC to give 6-[[2-fluoro-6-[5-methyl-2-(2-pyridyl)-7,8-dihydro-5H-pyrido[4,3-d]pyrimidin-6-yl]-4-pyridyl]oxy]hexanamide (29 mg) as a light yellow solid. $^1$H NMR (400 MHz, Methanol-d4) δ: 8.69-8.77 (m, 1H), 8.60-8.69 (m, 1H), 8.41-8.56 (m, 1H), 7.91-8.08 (m, 1H), 7.46-7.60 (m, 1H), 6.08-6.17 (m, 1H), 5.68-5.79 (m, 1H), 5.50-5.63 (m, 1H), 4.29-4.48 (m, 1H), 3.98 (s, 2H), 3.31-3.47 (m, 1H), 2.91-3.13 (m, 2H), 2.09-2.22 (m, 2H), 1.53-1.78 (m, 4H), 1.34-1.51 (m, 5H). MS obsd. (ESI$^+$) [(M+H)$^+$]: 451.

Example 172 and 173: 6-(6-fluoro-4-tetrahydropyran-4-yloxy-2-pyridyl)-5-methyl-2-pyrimidin-2-yl-7,8-dihydro-5H-pyrido[4,3-d]pyrimidine and 6-(4-fluoro-6-tetrahydropyran-4-yloxy-2-pyridyl)-5-methyl-2-pyrimidin-2-yl-7,8-dihydro-5H-pyrido[4,3-d]pyrimidine Example 172

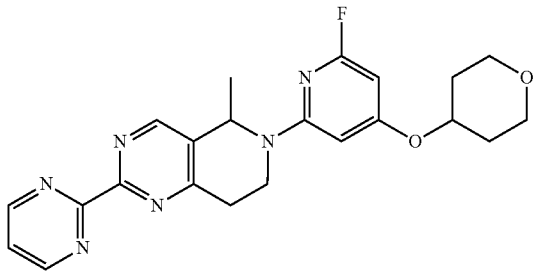

221
-continued

Example 173

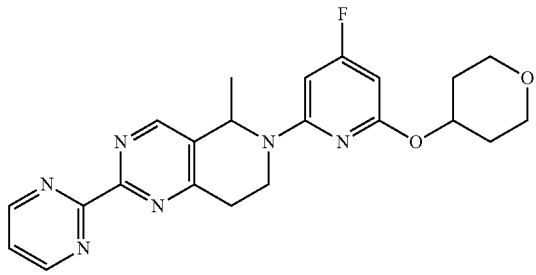

To a solution of tetrahydro-2H-pyran-4-ol (60 mg, 353 µmol) in dioxane (2 mL) was added sodium hydride (7.05 mg, 294 µmol). The mixture was stirred at rt for 20 mins. To the mixture was added 6-(4,6-difluoropyridin-2-yl)-5-methyl-2-(pyrimidin-2-yl)-5,6,7,8-tetrahydropyrido[4,3-d]pyrimidine (100 mg, 294 µmol). After being heated to 50° C. with stirring overnight, the resulting mixture was cooled to rt and purified by prep-HPLC to give 6-(6-fluoro-4-tetrahydropyran-4-yloxy-2-pyridyl)-5-methyl-2-pyrimidin-2-yl-7,8-dihydro-5H-pyrido[4, 3-d]pyrimidine (2 mg) as a light yellow solid and 6-(4-fluoro-6-tetrahydropyran-4-yloxy-2-pyridyl)-5-methyl-2-pyrimidin-2-yl-7,8-dihydro-5H-pyrido[4,3-d]pyrimidine (8 mg) as a light yellow solid.

Example 172: 6-(6-fluoro-4-tetrahydropyran-4-yloxy-2-pyridyl)-5-methyl-2-pyrimidin-2-yl-7,8-dihydro-5H-pyrido[4,3-d]pyrimidine, $^1$H NMR (400 MHz, Methanol-d$_4$) δ: 1.60 (br d, 3H), 1.67-1.81 (m, 2H), 1.98-2.16 (m, 2H), 3.17 (br s, 2H), 3.43-3.56 (m, 1H), 3.57-3.73 (m, 2H), 3.88-4.04 (m, 2H), 4.44-4.61 (m, 1H), 4.66-4.79 (m, 1H), 5.74 (br d, 2H), 5.95 (s, 1H), 6.29 (s, 1H), 7.66 (br t, 1H), 8.90 (s, 1H), 9.05 (br d, 2H). MS obsd. (ESI$^+$) [(M+H)$^+$]: 423.

Example 173: 6-(4-fluoro-6-tetrahydropyran-4-yloxy-2-pyridyl)-5-methyl-2-pyrimidin-2-yl-7,8-dihydro-5H-pyrido[4,3-d]pyrimidine, $^1$H NMR (400 MHz, Methanol-d$_4$) δ: 1.62 (d, 3H), 1.72-1.85 (m, 2H), 2.02-2.18 (m, 2H), 3.08-3.30 (m, 2H), 3.48-3.63 (m, 1H), 3.68 (dddd, 2H), 3.93-4.03 (m, 2H), 4.53 (dt, 1H), 5.28 (tt, 1H), 5.73 (q, 1H), 5.83 (dd, 1H), 6.25 (dd, 1H), 7.63-7.71 (m, 1H), 8.88-8.96 (m, 1H), 9.02-9.11 (m, 2H). MS obsd. (ESI$^+$) [(M+H)$^+$]: 423.

Example 174: 2-[[2-fluoro-6-(5-methyl-2-pyrimidin-2-yl-7,8-dihydro-5H-pyrido[4,3-d]pyrimidin-6-yl)-4-pyridyl]oxy]acetamide

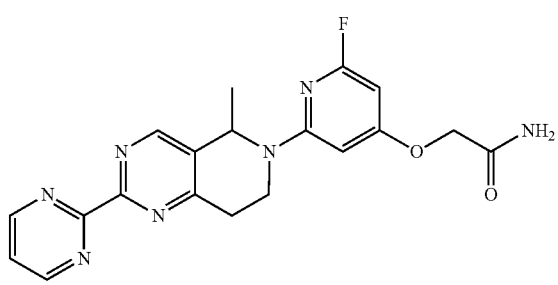 [SMILES: CC1c2cnc(-c3ncccn3)nc2CCN1c1cc(OCC(N)=O)cc(F)n1]

222

To a stirred solution of 2-hydroxyacetamide (26.5 mg, 0.35 mmol) in DMF (1 mL) was added NaH (14 mg, 0.35 mmol) at 0° C. The mixture was stirred at 0° C. for 10 mins, and then to the reaction mixture was added 6-(4,6-difluoro-2-pyridyl)-5-methyl-2-pyrimidin-2-yl-7,8-dihydro-5H-pyrido[4,3-d]pyrimidine (100 mg, 0.29 mmol). After being heated to 80° C. with stirring for 1 hr, the reaction mixture was partitioned between EA (50 mL) and brine (20 mL). The organic layer was separated, washed with brine, dried over anhydrous Na$_2$SO$_4$ and concentrated in vacuo. The residue was purified by prep-HPLC to afford 2-[[2-fluoro-6-(5-methyl-2-pyrimidin-2-yl-7,8-dihydro-5H-pyrido[4,3-d]pyrimidin-6-yl)-4-pyridyl]oxy]acetamide (5 mg) as a light yellow solid. $^1$H NMR (400 MHz, Methanol-d$_4$) δ: 9.03 (d, 2H), 8.90 (s, 1H), 7.65 (t, 1H), 6.29 (m, 1H), 5.96 (m, 1H), 5.77 (m, 1H), 4.75 (d, 2H), 4.46 (d, 1H), 3.44-3.63 (m, 1H), 3.09-3.20 (m, 2H), 1.49-1.65 (m, 3H). MS obsd. (ESI$^+$) [(M+H)$^+$]: 396.

Example 175: methyl 3-fluoro-5-(5-methyl-2-pyrimidin-2-yl-7,8-dihydro-5H-pyrido[4,3-d]pyrimidin-6-yl)benzoate

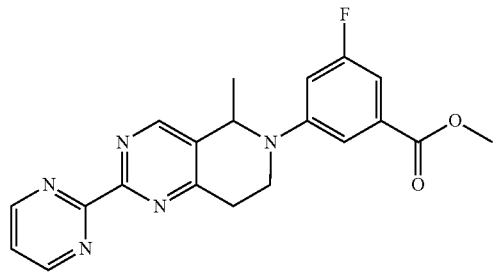 [SMILES: COC(=O)c1cc(F)cc(N2CCc3nc(-c4ncccn4)ncc3C2C)c1]

Step 1: Preparation of methyl 3-bromo-5-fluoro-benzoate

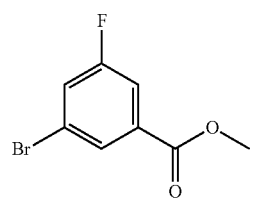

To a solution of 3-bromo-5-fluorobenzoic acid (10.0 g, 45.7 mmol) in MeOH (100 mL) was added SOCl$_2$ (6.6 mL, 91.3 mmol) at 0° C. The reaction mixture was heated to 60° C. and stirred for 2 hrs. The reaction mixture was concentrated in vacuo and the residue was diluted with DCM (250 mL). The resulting mixture was washed with a saturated aqueous solution of NaHCO$_3$ (100 mL), H$_2$O (100 mL) and brine (100 mL) successively, then dried over anhydrous Na$_2$SO$_4$ and concentrated in vacuo. The residue was purified by column chromatography to afford methyl 3-bromo-5-fluoro-benzoate (10.0 g) as colorless oil.

Step 2: Preparation of methyl 3-(1,4-dioxa-8-azaspiro[4.5]decan-8-yl)-5-fluoro-benzoate

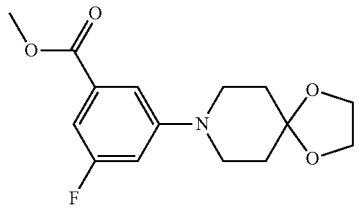 [SMILES: COC(=O)c1cc(F)cc(N2CCC3(CC2)OCCO3)c1]

To a stirred solution of methyl 3-bromo-5-fluoro-benzoate (13.0 g, 55.8 mmol) in dioxane (130 mL) and tert-BuOH (13 mL) was added 1,4-dioxa-8-azaspiro[4.5]decane hydrochloride (11.0 g, 61.4 mmol), $Cs_2CO_3$ (45.4 g, 139.5 mmol), $Pd(OAc)_2$ (250 mg, 1.12 mmol) and XPhos (1.1 g, 2.23 mmol). was After being stirred at 100° C. for 16 hrs under $N_2$, the resulting reaction mixture was cooled to rt, and then partitioned between EA (300 mL) and $H_2O$ (100 mL). The organic layer was washed with brine (100 mL) twice, dried over anhydrous $Na_2SO_4$ and concentrated in vacuo. The residue was purified by column chromatography to give methyl 3-(1,4-dioxa-8-azaspiro[4.5]decan-8-yl)-5-fluoro-benzoate (8.0 g) as a light yellow oil.

Step 3: Preparation of methyl 3-fluoro-5-(4-oxo-1-piperidyl)benzoate

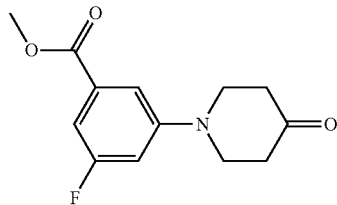 [SMILES: COC(=O)c1cc(F)cc(N2CCC(=O)CC2)c1]

A solution of methyl 3-(1,4-dioxa-8-azaspiro[4.5]decan-8-yl)-5-fluoro-benzoate (9.5 g, 32.1 mmol) in formic acid (90 mL) and $H_2O$ (90 mL) was heated to 90° C. and stirred for 2 hrs. The resulting reaction mixture was concentrated in vacuo and the residue was partitioned between DCM (300 mL) and $H_2O$ (100 mL). The organic layer was washed with $H_2O$ (100 mL), and a saturated aqueous $NaHCO_3$ solution (100 mL) and brine (100 mL) successively, then dried over anhydrous $Na_2SO_4$ and concentrated in vacuo. The residue was purified by column chromatography to give methyl 3-fluoro-5-(4-oxo-1-piperidyl)benzoate (6.5 g) as a light yellow oil.

Step 4: Preparation of 3-fluoro-5-(2-pyrimidin-2-yl-7,8-dihydro-5H-pyrido[4,3-d]pyrimidin-6-yl)benzoic acid

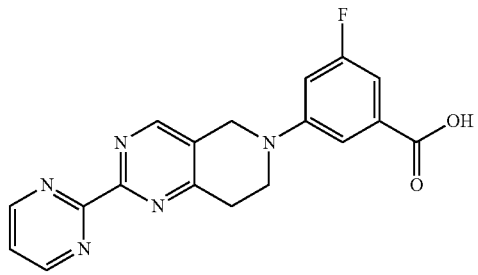 [SMILES: O=C(O)c1cc(F)cc(N2CCc3nc(-c4ncccn4)ncc3C2)c1]

A solution of methyl 3-fluoro-5-(4-oxo-1-piperidyl)benzoate (6.5 g, 25.9 mmol) in DMFDMA (50 mL) was heated to 120° C. and stirred for 12 hrs. After being cooled to rt, the mixture was concentrated in vacuo and the residue was dissolved in MeOH (100 mL). To the solution was added pyrimidine-2-carboximidamide hydrochloride (4.7 g, 29.4 mmol) and $K_2CO_3$ (13.5 g, 97.9 mmol). After being heated to 60° C. and stirred for 2 hrs, the resulting reaction mixture was filtered. The filtrate was concentrated in vacuo to give 3-fluoro-5-(2-pyrimidin-2-yl-7,8-dihydro-5H-pyrido[4,3-d]pyrimidin-6-yl)benzoic acid (14.0 g, crude) as a yellow solid, which was used into the next step without any further purification.

Step 5: Preparation of methyl 3-fluoro-5-(2-pyrimidin-2-yl-7,8-dihydro-5H-pyrido[4,3-d]pyrimidin-6-yl)benzoate

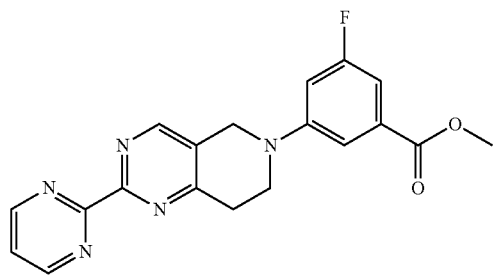

To a stirred solution of 3-fluoro-5-(2-pyrimidin-2-yl-7,8-dihydro-5H-pyrido[4,3-d]pyrimidin-6-yl)benzoic acid (10.0 g, 14.2 mmol) in MeOH (50 mL) was added $SOCl_2$ (6.8 g, 56.9 mmol) at 0° C. The mixture was heated to 60° C. and stirred for 2 hrs, and then partitioned between DCM (500 mL) and $H_2O$ (200 mL). The organic layer was separated, then washed with $H_2O$ (200 mL), a saturated aqueous $NaHCO_3$ solution (200 mL) and brine (200 mL) successively, dried over anhydrous $Na_2SO_4$ and concentrated in vacuo. The residue was purified by column chromatography to give methyl 3-fluoro-5-(2-pyrimidin-2-yl-7,8-dihydro-5H-pyrido[4,3-d]pyrimidin-6-yl)benzoate (3.4 g) as a yellow solid.

Step 6: Preparation of methyl 3-fluoro-5-(5-methoxy-2-pyrimidin-2-yl-7,8-dihydro-5H-pyrido[4,3-d]pyrimidin-6-yl)benzoate

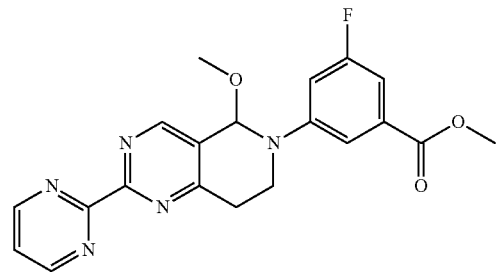 [SMILES: COC(=O)c1cc(F)cc(N2CCc3nc(-c4ncccn4)ncc3C2OC)c1]

To a cooled solution of methyl 3-fluoro-5-(2-pyrimidin-2-yl-7,8-dihydro-5H-pyrido[4,3-d]pyrimidin-6-yl)benzoate (1.5 g, 4.11 mmol) in THF (30 mL) and MeOH (10 mL) was added $RuCl_3$ hydrate (65 mg, 0.29 mmol), followed by the addition of a solution of NaIO₄ (2.63 g, 12.3 mmol) in H₂O (15 mL) at −40° C. After being stirred at −40° C. for 15 mins, the resulting mixture was allowed to be warmed to 20° C. and stirred 12 hrs. The reaction was then quenched with a saturated aqueous Na₂SO₃ solution (20 mL). The resulting mixture was filtered. The filtrate was diluted with DCM (250 mL), then washed with a saturated aqueous NaHCO₃ solution (100 mL) and brine (100 mL), dried over anhydrous Na₂SO₄ and concentrated in vacuo to give methyl 3-fluoro-5-(5-methoxy-2-pyrimidin-2-yl-7,8-dihydro-5H-pyrido[4,3-d]pyrimidin-6-yl)benzoate (1.2 g, crude), which was used directly in the next step without further purification.

Step 7: Preparation of methyl 3-fluoro-5-(5-methyl-2-pyrimidin-2-yl-7,8-dihydro-5H-pyrido[4,3-d]pyrimidin-6-yl)benzoate

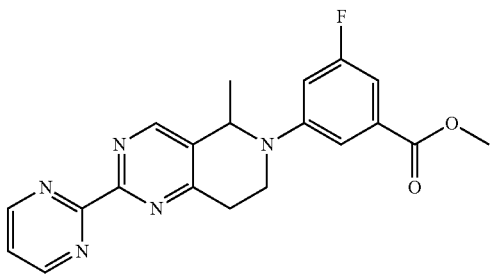 [SMILES: COC(=O)c1cc(F)cc(N2CCc3nc(-c4ncccn4)ncc3C2C)c1]

To a stirred solution of methyl 3-fluoro-5-(5-methoxy-2-pyrimidin-2-yl-7,8-dihydro-5H-pyrido[4,3-d]pyrimidin-6-yl)benzoate (1.2 g, 3.04 mmol) in THF (20 mL) was added BF₃.Et₂O (2.15 g, 15.2 mmol) at −70° C. The mixture was stirred at −70° C. for 10 mins, then to the reaction mixture was added a solution of MeMgBr (5.1 mL, 15.2 mmol) in THF. The resulting mixture was warmed to −20° C. and stirred for 1 hr, and then diluted with saturated aqueous NH₄Cl solution (20 mL). The resulting mixture was extracted with EA (300 mL). The combined organic layers were washed with brine (130 mL) twice and concentrated in vacuo. The residue was purified by column chromatography and prep-HPLC to afford methyl 3-fluoro-5-(5-methyl-2-pyrimidin-2-yl-7,8-dihydro-5H-pyrido[4,3-d]pyrimidin-6-yl)benzoate (290 mg) as a red solid. ¹H NMR (400 MHz, CDCl₃) δ: 9.05 (d, 2H), 8.82 (s, 1H), 7.39-7.49 (m, 2H), 7.18 (d, 1H), 6.84 (m, 1H), 5.16 (q, 1H), 3.95-4.00 (m, 1H), 3.94 (s, 3H), 3.53-3.65 (m, 1H), 3.23-3.42 (m, 2H), 1.55 (d, 3H). MS obsd. (ESI⁺) [(M+H)⁺]: 380.

Example 176: 3-fluoro-5-(5-methyl-2-pyrimidin-2-yl-7,8-dihydro-5H-pyrido[4,3-d]pyrimidin-6-yl)benzoic acid

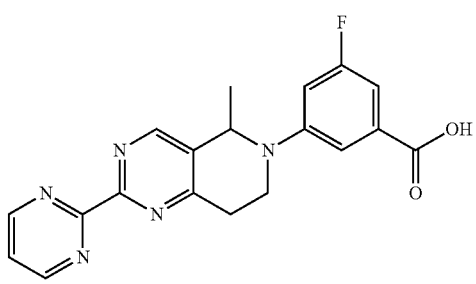 [SMILES: CC1c2cnc(-c3ncccn3)nc2CCN1c1cc(F)cc(C(=O)O)c1]

To a solution of methyl 3-fluoro-5-(5-methyl-2-pyrimidin-2-yl-7,8-dihydro-5H-pyrido[4,3-d]pyrimidin-6-yl)benzoate (100 mg, 0.26 mmol) in MeOH (1 mL) was added aqueous NaOH solution (2 M, 0.8 mL, 1.6 mmol) at 0° C. The mixture was stirred at 20° C. for 1 hr, and then acidified with 2 M HCl (2 mL). The resulting mixture was partitioned between EA (80 mL) and brine (20 mL). The organic layer was separated, washed with brine, dried over anhydrous Na₂SO₄ and concentrated in vacuo. The residue was purified by prep-HPLC to give 3-fluoro-5-(5-methyl-2-pyrimidin-2-yl-7,8-dihydro-5H-pyrido[4,3-d]pyrimidin-6-yl)benzoic acid (10 mg) as a yellow solid. ¹H NMR (400 MHz, CDCl₃) δ: 9.07 (d, 2H), 8.83 (s, 1H), 7.42-7.56 (m, 2H), 7.24 (d, 1H), 6.88 (d, 1H), 5.12-5.24 (m, 1H), 3.98 (d, 1H), 3.55-3.69 (m, 1H), 3.24-3.39 (m, 2H), 1.57 (d, 3H). MS obsd. (ESI⁺) [(M+H)⁺]: 366.

Example 177: 3-fluoro-N-(3-methoxypropyl)-5-(5-methyl-2-pyrimidin-2-yl-7,8-dihydro-5H-pyrido[4,3-d]pyrimidin-6-yl)benzamide

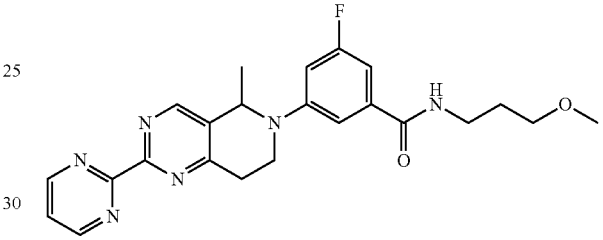

To a stirred solution of 3-fluoro-5-(5-methyl-2-pyrimidin-2-yl-7,8-dihydro-5H-pyrido[4,3-d]pyrimidin-6-yl)benzoic acid (60 mg, 0.16 mmol) in DCM (2 mL) was added HATU (73 mg, 0.19 mmol), 3-methoxypropan-1-amine (22 mg, 0.24 mmol) and DIEA (62 mg, 0.48 mmol). The resulting mixture was stirred at 20° C. for 2 hrs, and then partitioned between DCM (100 mL) and H₂O (30 mL). The organic layer was washed with brine (30 mL), dried over anhydrous Na₂SO₄ and concentrated in vacuo. The residue was purified by prep-HPLC to afford 3-fluoro-N-(3-methoxypropyl)-5-(5-methyl-2-pyrimidin-2-yl-7,8-dihydro-5H-pyrido[4,3-d]pyrimidin-6-yl)benzamide (24 mg) as a light yellow solid. ¹H NMR (400 MHz, CDCl₃) δ: 9.04 (d, 2H), 8.80 (s, 1H), 7.44 (m, 1H), 7.26 (s., 1H), 6.94 (s., 1H), 6.68-6.81 (m, 2H), 5.16 (m, 1H), 3.89-4.05 (m, 1H), 3.52-3.65 (m, 5H), 3.40 (s, 3H), 3.21-3.38 (m, 2H), 1.90 (m, 2H), 1.54 (d, 3H). MS obsd. (ESI⁺) [(M+H)⁺]: 437.

Example 178: 3-fluoro-N-(3-methoxypropyl)-N-methyl-5-(5-methyl-2-pyrimidin-2-yl-7,8-dihydro-5H-pyrido[4,3-d]pyrimidin-6-yl)benzamide

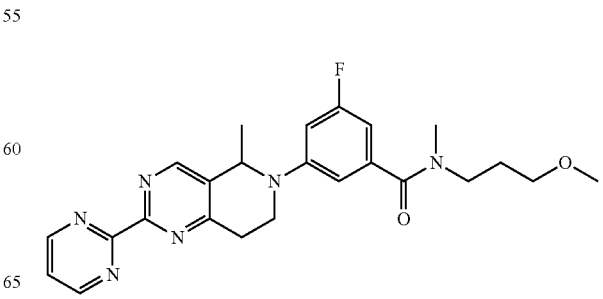

Step 1: Preparation of N-(3-methoxypropyl)-4-nitro-benzenesulfonamide

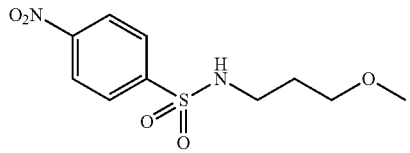 [SMILES: COCCCNS(=O)(=O)c1ccc([N+](=O)[O-])cc1]

A mixture of 3-methoxypropylamine (1.78 g, 20.0 mmol), 4-nitrobenzenesulfonyl chloride (5.3 g, 24.0 mmol) and K₂CO₃ (5.5 g, 40.0 mmol) in MeCN (50.0 mL) was heated to 30° C. and stirred for 4 hrs. The reaction mixture was filtered and the filtrate was concentrated in vacuo to give crude N-(3-methoxypropyl)-4-nitro-benzenesulfonamide (5.0 g), which was used directly in the next step without further purification.

Step 2: Preparation of N-(3-methoxypropyl)-N-methyl-4-nitro-benzenesulfonamide

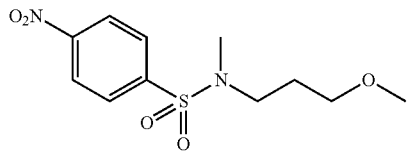 [SMILES: COCCCN(C)S(=O)(=O)c1ccc([N+](=O)[O-])cc1]

To a mixture of N-(3-methoxypropyl)-4-nitro-benzenesulfonamide (5.0 g, 20.0 mmol, crude) in THF (50.0 mL) was added NaH (1.6 g, 40.0 mmol) portion-wise at 0° C. The resulting mixture was warmed to 30° C. and stirred for 1 hr, then to the reaction mixture was added MeI (3.4 g, 24.0 mmol). After being stirred at 30° C. for 3 hrs, the resulting reaction mixture was diluted with water (20.0 mL) and extracted with EA (20.0 mL) for three times. The combined organic layer was concentrated in vacuo and the residue was purified by column chromatography to give N-(3-methoxypropyl)-N-methyl-4-nitro-benzenesulfonamide (2.0 g) as a pale yellow solid.

Step 3: Preparation of 3-methoxy-N-methyl-propan-1-amine

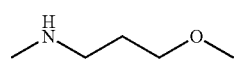

A mixture of N-(3-methoxypropyl)-N-methyl-4-nitro-benzenesulfonamide (2.0 g, 6.9 mmol), K₂CO₃ (1.9 g, 13.8 mmol), and thiophenol (1.52 g, 13.8 mmol) in MeCN (50.0 mL) was heated to 60° C. and stirred for 18 hrs. The reaction mixture was filtered and the filtrate was concentrated in vacuo. The residue was purified by column chromatography to give 3-methoxy-N-methyl-propan-1-amine (60.0 mg) as yellow oil.

Step 4: Preparation of 3-fluoro-N-(3-methoxypropyl)-N-methyl-5-(5-methyl-2-pyrimidin-2-yl-7,8-dihydro-5H-pyrido[4,3-d]pyrimidin-6-yl)benzamide

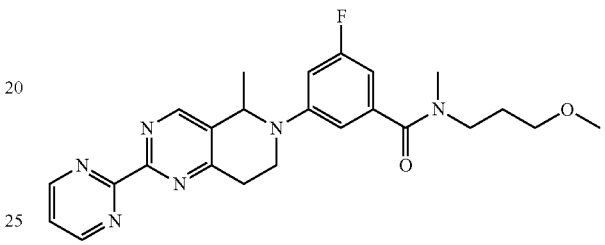

To a stirred solution of 3-fluoro-5-(5-methyl-2-pyrimidin-2-yl-7,8-dihydro-5H-pyrido[4,3-d]pyrimidin-6-yl)benzoic acid (50 mg, 0.14 mmol) in DMF (2 mL) was added HATU (60 mg, 0.16 mmol), 3-methoxy-N-methyl-propan-1-amine (20 mg, 0.20 mmol) and DIEA (50 mg, 0.41 mmol). The mixture was stirred at rt for 2 hrs, and then partitioned between EA (50 mL) and brine (20 mL). The organic layer was separated, washed with brine and concentrated in vacuo. The residue was purified by prep-HPLC to afford 3-fluoro-N-(3-methoxypropyl)-N-methyl-5-(5-methyl-2-pyrimidin-2-yl-7,8-dihydro-5H-pyrido[4,3-d]pyrimidin-6-yl)benzamide (8 mg) as a gray solid. ¹H NMR (400 MHz, CDCl₃) δ: 9.03 (d, 2H), 8.78 (s, 1H), 7.44 (t, 1H), 6.75 (br. s., 1H), 6.66 (d, 1H), 6.52 (d, 1H), 5.10 (q, 1H), 3.91 (d, 1H), 3.45-3.69 (m, 3H) 3.17-3.44 (m, 7H), 2.89-3.13 (m, 3H), 1.79-2.07 (m, 2H), 1.53 (d, 3H). MS obsd. (ESI⁺) [(M+H)⁺]: 451.

Example 179: 7-[[2-fluoro-6-[5-methyl-2-(2-pyridyl)-7,8-dihydro-5H-pyrido[4,3-d]pyrimidin-6-yl]-4-pyridyl]oxy]heptanoic acid

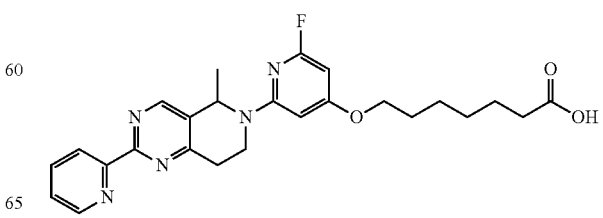

Step 1: Preparation of ethyl 7-[[2-fluoro-6-[5-methyl-2-(2-pyridyl)-7,8-dihydro-5H-pyrido[4,3-d]pyrimidin-6-yl]-4-pyridyl]oxy]heptanoate

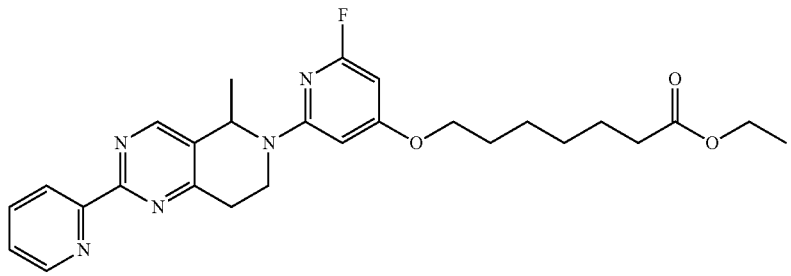 [SMILES: CCOC(=O)CCCCCCOc1cc(F)nc(N2CCc3nc(-c4ccccn4)ncc3C2C)c1]

A mixture of 5-methyl-2-(2-pyridyl)-5,6,7,8-tetrahydropyrido[4,3-d]pyrimidine (200 mg, 884 µmol), ethyl 7-((2,6-difluoropyridin-4-yl)oxy)heptanoate (762 mg, 2.65 mmol), DMSO (0.5 ml) and DIPEA (1 mL) was heated to 110° C. and stirred for 15 hrs. The resulting reaction mixture was concentrated in vacuo and the residue was purified by flash column to give ethyl 7-[[2-fluoro-6-[5-methyl-2-(2-pyridyl)-7,8-dihydro-5H-pyrido[4,3-d]pyrimidin-6-yl]-4-pyridyl]oxy]heptanoate as a yellow oil (300 mg).

Step 2: Preparation of 7-[[2-fluoro-6-[5-methyl-2-(2-pyridyl)-7,8-dihydro-5H-pyrido[4,3-d]pyrimidin-6-yl]-4-pyridyl]oxy]heptanoic acid

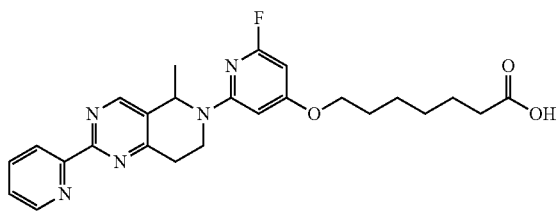 [SMILES: CC1c2cnc(-c3ccccn3)nc2CCN1c1cc(OCCCCCCC(=O)O)cc(F)n1]

To a solution of ethyl 7-[[2-fluoro-6-[5-methyl-2-(2-pyridyl)-7,8-dihydro-5H-pyrido[4,3-d]pyrimidin-6-yl]-4-pyridyl]oxy]heptanoate (300 mg, 0.608 mmol) in a mixture of methanol (10 mL), THF (5 mL) and water (2 mL) was added LiOH monohydrate (110 mg, 2.65 mmol). The resulting mixture was stirred overnight at rt and then acidified to pH=6-7 with 1M HCl. The resulting mixture was extracted with DCM (20 mL) for three times. The combined organic layer was washed with brine, dried over MgSO$_4$, and concentrated in vacuo. The residue was purified by column chromatography to give the crude product as a yellow solid (240 mg). The crude product (80 mg) was purified by prep-HPLC to give 7-[[2-fluoro-6-[5-methyl-2-(2-pyridyl)-7,8-dihydro-5H-pyrido[4,3-d]pyrimidin-6-yl]-4-pyridyl]oxy]heptanoic acid (4 mg) as a light yellow solid. $^1$H NMR (400 MHz, Methanol-d$_4$) δ: 8.65-8.76 (m, 1H), 8.53-8.65 (m, 1H), 8.31-8.45 (m, 1H), 7.78-7.96 (m, 1H), 7.34-7.49 (m, 1H), 6.02-6.19 (m, 1H), 5.75 (s, 1H), 5.43-5.63 (m, 1H), 4.33-4.47 (m, 1H), 3.96 (s, 2H), 3.31-3.47 (m, 1H), 2.89-3.12 (m, 2H), 2.21 (s, 2H), 1.63-1.75 (m, 2H), 1.25-1.62 (m, 9H). MS obsd. (ESI$^+$) [(M+H)$^+$]: 466.

Example 180: 7-[[2-fluoro-6-[5-methyl-2-(2-pyridyl)-7,8-dihydro-5H-pyrido[4,3-d]pyrimidin-6-yl]-4-pyridyl]oxy]heptanamide

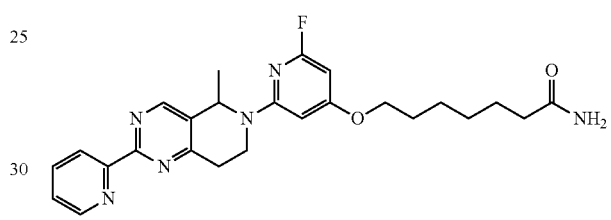

To a solution of 7-((2-fluoro-6-(5-methyl-2-(pyridin-2-yl)-7,8-dihydropyrido[4,3-d]pyrimidin-6(5H)-yl)pyridin-4-yl)oxy)heptanoic acid (200 mg, 0.430 mmol) in DMF (3 mL) was added CDI (104 mg, 0.644 mmol). After the mixture was stirred for 4 hrs at rt, to the mixture was added NH$_3$ (7 mL, ca.4% in isopropyl alcohol, ca.2.0 mol/L). The reaction mixture was stirred at rt overnight and then concentrated in vacuo. The residue was purified by prep-HPLC to give 7-[[2-fluoro-6-[5-methyl-2-(2-pyridyl)-7,8-dihydro-5H-pyrido[4,3-d]pyrimidin-6-yl]-4-pyridyl]oxy]heptanamide (30 mg) as a light yellow solid. $^1$H NMR (400 MHz, Methanol-d$_4$) δ: 8.66-8.74 (m, 1H), 8.56-8.66 (m, 1H), 8.35-8.47 (m, 1H), 7.82-7.93 (m, 1H), 7.37-7.47 (m, 1H), 6.04-6.18 (m, 1H), 5.71-5.84 (m, 1H), 5.45-5.63 (m, 1H), 4.29-4.46 (m, 1H), 3.96 (s, 2H), 3.30-3.45 (m, 1H), 2.88-3.13 (m, 2H), 2.05-2.23 (m, 2H), 1.62-1.79 (m, 2H), 1.51-1.62 (m, 2H), 1.46 (d, 7H). MS obsd. (ESI$^+$) [(M+H)$^+$]: 465.

Example 181: (−)-4-[3-[[2-fluoro-6-[5-methyl-2-pyrimidin-2-yl-7,8-dihydro-5H-pyrido[4,3-d]pyrimidin-6-yl]-4-pyridyl]oxy]propyl]morpholin-3-one Step 1: Preparation of 4-[3-[(2,6-difluoro-4-pyridyl)oxy]propyl]morpholin-3-one

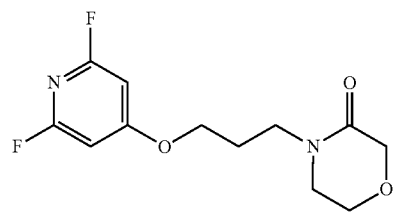 [SMILES: O=C1COCCN1CCCOc1cc(F)nc(F)c1]

A solution of 4-(3-chloropropoxy)-2,6-difluoropyridine (623 mg, 3 mmol) and cesium carbonate (2.0 g, 6 mmol), morpholin-3-one (455 mg, 4.5 mmol) in MeCN (15 mL) was heated to 90° C. and stirred for 10 hrs. The reaction mixture was then allowed to be cooled to rt and diluted with water (50 mL). The resulting mixture was extracted with EA (100 mL). The organic layer was washed with brine, dried over anhydrous $Na_2SO_4$, and concentrated in vacuo. The residue was purified by flash chromatography to give 4-[3-[(2,6-difluoro-4-pyridyl)oxy]propyl]morpholin-3-one as a yellow oil (163 mg).

Step 2: Preparation of (−)-4-[3-[[2-fluoro-6-[5-methyl-2-pyrimidin-2-yl-7,8-dihydro-5H-pyrido[4,3-d]pyrimidin-6-yl]-4-pyridyl]oxy]propyl]morpholin-3-one To a stirred solution of (+)-5-methyl-2-pyrimidin-2-yl-5,6,7,8-tetrahydropyrido[4,3-d]pyrimidine (136 mg, 0.6 mmol) in N,N-diisopropyl ethyl amine (1 mL) and DMSO (1 mL) was added 4-(3-((2,6-difluoropyridin-4-yl)oxy)propyl)morpholin-3-one (163 mg, 0.6 mmol). The reaction mixture is heated to 120° C. and stirred in a sealed vessel for 48 hrs. The reaction mixture was allowed to cool to rt and diluted with $H_2O$ (10 mL). The resulting mixture was extracted with DCM (50 mL). The organic layer was washed with brine, dried over anhydrous $Na_2SO_4$, and concentrated in vacuo. The residue was purified by prep-HPLC to give (−)-4-[3-[[2-fluoro-6-[-5-methyl-2-pyrimidin-2-yl-7,8-dihydro-5H-pyrido[4,3-d]pyrimidin-6-yl]-4-pyridyl]oxy]propyl]morpholin-3-one (40 mg) as a red solid. $^1$H NMR (400 MHz, $CDCl_3$) δ: 8.97-9.11 (m, 2H), 8.81 (s, 1H), 7.38-7.51 (m, 1H), 5.95-6.08 (m, 1H), 5.72-5.86 (m, 1H), 5.57-5.71 (m, 1H), 4.31-4.49 (m, 1H), 4.17 (s, 2H), 4.01-4.11 (m, 2H), 3.85-3.95 (m, 2H), 3.55-3.64 (m, 2H), 3.46-3.53 (m, 1H), 3.38-3.46 (m, 2H), 3.22-3.30 (m, 2H), 2.06-2.15 (m, 2H), 1.72-1.87 (m, 3H). MS obsd. (ESI⁺) [(M+H)⁺]: 480. $[a]_D^{25}$=−52.8° (1 mg/mL, methanol).

Example 182: 3-fluoro-N-(3-methoxypropyl)-5-(5-methyl-2-pyrimidin-2-yl-7,8-dihydro-5H-pyrido[4,3-d]pyrimidin-6-yl)benzenesulfonamide

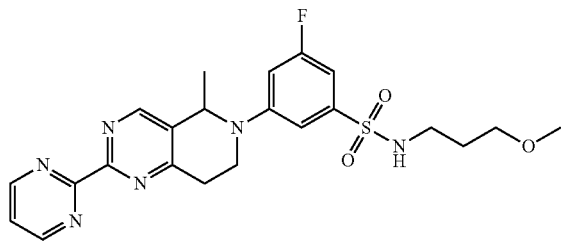

Step 1: Preparation of 1-benzylsulfanyl-3-bromo-5-fluoro-benzene

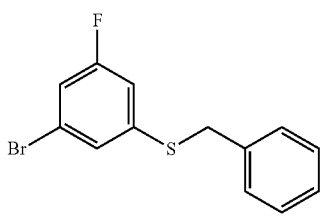 [SMILES: Fc1cc(Br)cc(SCc2ccccc2)c1]

To a solution of 1,3-dibromo-5-fluorobenzene (40.0 g, 157.5 mmol) in dioxane (400 mL) was added benzyl mercaptan (23.27 g, 187.3 mmol), DIEA (40.7 g, 315.1 mmol), $Pd_2(dba)_3$ (4.32 g, 4.72 mmol) and Xantphos (4.56 g, 7.88 mmol). The reaction mixture was heated to 120° C. and stirred for 12 hrs. After being cooled to rt, the resulting reaction mixture was filtered. The filtrate was partitioned between DCM (1 L) and water (300 mL). The organic layer was separated, washed with brine (300 mL), dried over anhydrous $Na_2SO_4$ and concentrated in vacuo. The residue was purified by column chromatography to give 1-benzylsulfanyl-3-bromo-5-fluoro-benzene (45.0 g) as yellow oil.

Step 2: Preparation of 3-bromo-5-fluoro-benzenesulfonyl chloride

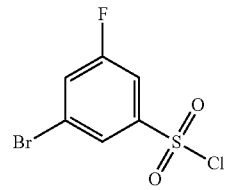 [SMILES: O=S(=O)(Cl)c1cc(F)cc(Br)c1]

To a solution of 1-benzylsulfanyl-3-bromo-5-fluoro-benzene (25.0 g, 84.12 mmol) in MeCN (250 mL) was added 2M HCl (33.6 mL) and NCS (44.9 g, 336.5 mmol) at 0° C. The reaction mixture was stirred at rt for 2 hrs, and then concentrated in vacuo. The residue was partitioned between DCM (500 mL) and water (100 mL). The organic layer was separated, then washed with brine (100 mL), dried over anhydrous $Na_2SO_4$ and concentrated in vacuo to give 3-bromo-5-fluoro-benzenesulfonyl chloride (23.0 g, crude), which was used directly in the next step without further purification.

Step 3: Preparation of 3-bromo-5-fluoro-N-(3-methoxypropyl)benzenesulfonamide

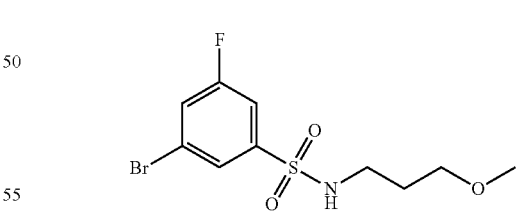

To a solution of 3-bromo-5-fluoro-benzenesulfonyl chloride (23.0 g, 84.12 mmol) in DCM (250 mL) was added 3-methoxypropylamine (8.25 g, 92.53 mmol) and $Et_3N$ (25.5 g, 252.3 mmol). The mixture was stirred at rt for 16 hrs, and then partitioned between DCM (200 mL) and water (200 mL). The organic layer was separated, then washed with brine (200 mL), dried over anhydrous $Na_2SO_4$ and concentrated in vacuo. The residue was purified by column chromatography to give 3-bromo-5-fluoro-N-(3-methoxypropyl)benzenesulfonamide (19.4 g) as a yellow oil.

Step 4: Preparation of 3-(1,4-dioxa-8-azaspiro[4.5]decan-8-yl)-5-fluoro-N-(3-methoxypropyl)benzenesulfonamide

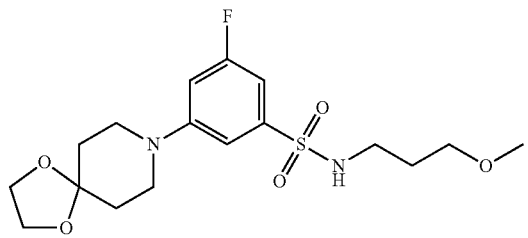 [SMILES: COCCCNS(=O)(=O)c1cc(F)cc(N2CCC3(CC2)OCCO3)c1]

To a solution of 3-bromo-5-fluoro-N-(3-methoxypropyl) benzenesulfonamide (19.4 g, 59.47 mmol) in dioxane (200 mL) was added 1,4-dioxa-8-azaspiro[4.5]decane hydrochloride (12.8 g, 71.37 mmol), Pd$_2$(dba)$_3$ (1.09 g, 1.19 mmol), BINAP (1.48 g, 2.38 mmol) and tert-BuONa (17.14 g, 178.4 mmol). The mixture was heated at 120° C. with stirring for 12 hrs under N$_2$. After being cooled to rt, the reaction mixture was filtered and the filtrate was concentrated in vacuo. The residue was partitioned between DCM (500 mL) and water (100 mL). The organic layer was washed with brine (100 mL), dried over anhydrous Na$_2$SO$_4$ and concentrated in vacuo. The residue was purified by column chromatography to give 3-(1,4-dioxa-8-azaspiro[4.5]decan-8-yl)-5-fluoro-N-(3-methoxypropyl)benzenesulfonamide (15.5 g) as a yellow oil.

Step 5: Preparation of 3-fluoro-N-(3-methoxypropyl)-5-(4-oxo-1-piperidyl)benzenesulfonamide

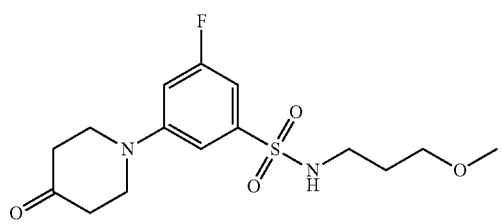 [SMILES: COCCCNS(=O)(=O)c1cc(F)cc(N2CCC(=O)CC2)c1]

A solution of 3-(1,4-dioxa-8-azaspiro[4.5]decan-8-yl)-5-fluoro-N-(3-methoxypropyl)benzenesulfonamide (5.0 g, 12.87 mmol) in formic acid (25 mL) and H$_2$O (25 mL) was heated to 90° C. with stirring for 2 hrs. Then the resulting mixture was concentrated in vacuo. The residue was partitioned between DCM (500 mL) and water (200 mL). The organic layer was washed with a saturated aqueous solution of NaHCO$_3$ (100 mL) and brine (100 mL), then dried over anhydrous Na$_2$SO$_4$ and concentrated in vacuo. The residue was purified by column chromatography to give 3-fluoro-N-(3-methoxypropyl)-5-(4-oxo-1-piperidyl)benzenesulfonamide (4.1 g) as a yellow oil.

Step 6: Preparation of 3-fluoro-N-(3-methoxypropyl)-5-(2-pyrimidin-2-yl-7,8-dihydro-5H-pyrido[4,3-d]pyrimidin-6-yl)benzenesulfonamide

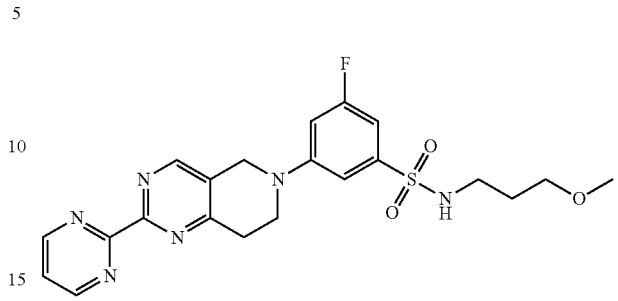

A solution of 3-fluoro-N-(3-methoxypropyl)-5-(4-oxo-1-piperidyl)benzenesulfonamide (4.1 g, 11.90 mmol) in DMFDMA (50 mL) was heated at 120° C. with stirring for 4 hrs. The resulting mixture was concentrated in vacuo and the residue was dissolved in MeOH (50 mL). Then to the solution was added K$_2$CO$_3$ (4.93 g, 35.7 mmol) and pyrimidine-2-carboxamidine hydrochloride (2.26 g, 14.3 mmol). The resulting mixture was heated at 70° C. with stirring for 2 hrs, then cooled to rt, and filtered. The filtrate was concentrated in vacuo. The residue was partitioned between DCM (300 mL) and water (100 mL). The organic layer was separated, washed with brine (100 mL), dried over anhydrous Na$_2$SO$_4$ and concentrated in vacuo. The crude product was purified by column chromatography to give 3-fluoro-N-(3-methoxypropyl)-5-(2-pyrimidin-2-yl-7,8-dihydro-5H-pyrido[4,3-d]pyrimidin-6-yl)benzenesulfonamide (2.5 g) as a yellow solid.

Step 7: Preparation of 3-fluoro-N-(3-methoxypropyl)-5-(5-methoxy-2-pyrimidin-2-yl-7,8-dihydro-5H-pyrido[4,3-d]pyrimidin-6-yl)benzenesulfonamide

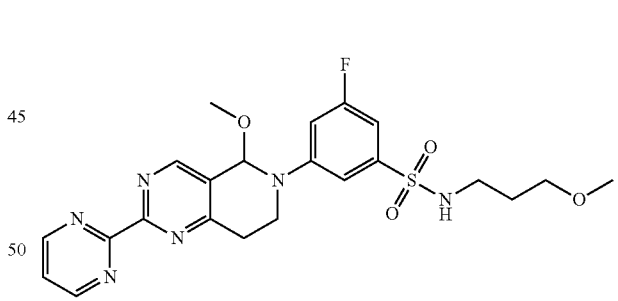

A solution of 3-fluoro-N-(3-methoxypropyl)-5-(2-pyrimidin-2-yl-7,8-dihydro-5H-pyrido[4,3-d]pyrimidin-6-yl)benzenesulfonamide (500 mg, 1.09 mmol) in DCM (40 mL) and MeOH (10 mL) was cooled to −70° C. To the mixture was added RuCl$_3$ hydrate (98 mg, 0.436 mmol) and a solution of NaIO$_4$ (700 mg) in H$_2$O (10 mL) successively. The resulting mixture was stirred at −70° C. for 15 mins, and then allowed to be warmed to 20° C. and stirred further for 16 hrs. The reaction mixture was diluted with a saturated aqueous solution of Na$_2$SO$_3$ (100 mL), and then filtered. The filtrate was washed with brine (100 mL). The organic layer was dried over anhydrous Na$_2$SO$_4$, and then concentrated in vacuo to give 3-fluoro-N-(3-methoxypropyl)-5-(5-methoxy-2-pyrimidin-2-yl-7,8-dihydro-5H-pyrido[4,3-d]pyrimidin-6-yl)

benzenesulfonamide (530 mg, crude) as a black oil which was used directly in the next step without further purification.

Step 8: Preparation of 3-fluoro-N-(3-methoxypropyl)-5-(5-methyl-2-pyrimidin-2-yl-7,8-dihydro-5H-pyrido[4,3-d]pyrimidin-6-yl)benzenesulfonamide

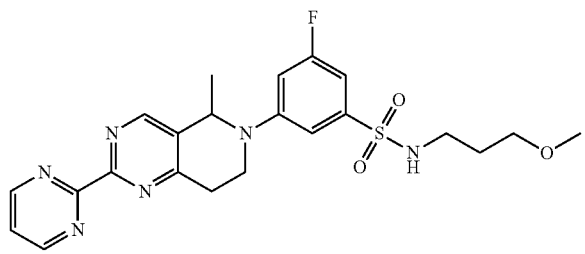 [SMILES: COCCCNS(=O)(=O)c1cc(F)cc(N2CCc3nc(-c4ncccn4)ncc3C2C)c1]

To solution of 3-fluoro-N-(3-methoxypropyl)-5-(5-methoxy-2-pyrimidin-2-yl-7,8-dihydro-5H-pyrido[4,3-d]pyrimidin-6-yl)benzenesulfonamide (530 mg, 1.08 mmol) in THF (50 mL) at −70° C. was added BF$_3$.Et$_2$O (460 mg, 3.24 mmol). After the mixture was stirred at −70° C. for 10 mins, to the resulting mixture was added a solution of MeMgBr (3.2 mmol, 3.2 mL) in THF. After being warmed to −20° C. and stirred for 2 hrs, the reaction was quenched by addition of saturated aqueous solution of NH$_4$Cl (10 mL). Then the resulting mixture was extracted with EA (200 mL) for three times. The combined organic layers were combined, washed with brine (100 mL), dried over anhydrous Na$_2$SO$_4$ and concentrated in vacuo. The residue was purified by the column chromatography and prep-HPLC to give 3-fluoro-N-(3-methoxypropyl)-5-(5-methyl-2-pyrimidin-2-yl-7,8-dihydro-5H-pyrido[4,3-d]pyrimidin-6-yl)benzenesulfonamide (17 mg) as a white solid. $^1$H NMR (400 MHz, CDCl$_3$) δ: 9.09 (d, 2H), 8.86 (s, 1H), 7.44-7.55 (m, 1H), 7.27 (br. s., 1H), 7.00 (d, 1H), 6.83 (d, 1H), 5.14-5.30 (m, 2H), 4.01 (d, 1H), 3.65 (t, 1H), 3.49 (t, 2H), 3.35 (s, 4H), 3.18 (d, 2H), 1.75-1.84 (m, 2H), 1.56-1.62 (m, 3H). MS obsd. (ESI+) [(M+H$^+$)]: 473.

Example 183: 3-fluoro-N-(3-methoxypropyl)-N-methyl-5-(5-methyl-2-pyrimidin-2-yl-7,8-dihydro-5H-pyrido[4,3-d]pyrimidin-6-yl)benzenesulfonamide

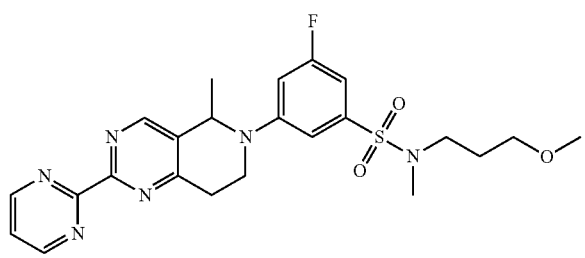 [SMILES: COCCCN(C)S(=O)(=O)c1cc(F)cc(N2CCc3nc(-c4ncccn4)ncc3C2C)c1]

Step 1: Preparation of 3-(1,4-dioxa-8-azaspiro[4.5]decan-8-yl)-5-fluoro-N-(3-methoxypropyl)-N-methyl-benzenesulfonamide

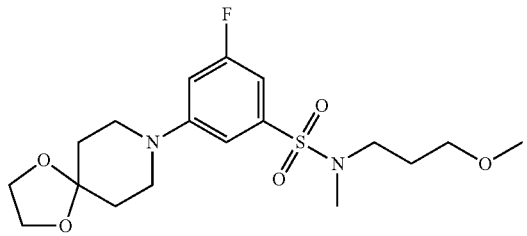 [SMILES: COCCCN(C)S(=O)(=O)c1cc(F)cc(N2CCC3(CC2)OCCO3)c1]

To a solution of 3-(1,4-dioxa-8-azaspiro[4.5]decan-8-yl)-5-fluoro-N-(3-methoxypropyl)benzenesulfonamide (5.0 g, 12.87 mmol) in DMF (50 mL) at 0° C. was added NaH (772 mg, 19.30 mmol, 60% wt) and iodomethane (3.06 g, 21.56 mmol) successively. The resulting mixture was stirred at 20 (for 3 hrs, and then partitioned between EA (200 mL) and water (50 mL). The organic layer was separated, then washed with brine (100 mL) for three times, dried over anhydrous Na$_2$SO$_4$ and concentrated in vacuo to give 3-(1,4-dioxa-8-azaspiro[4.5]decan-8-yl)-5-fluoro-N-(3-methoxypropyl)-N-methyl-benzenesulfonamide (4.90 g) as a yellow oil, which was used in the next step without any further purification.

Step 2: Preparation of 3-fluoro-N-(3-methoxypropyl)-N-methyl-5-(4-oxo-1-piperidyl)benzenesulfonamide

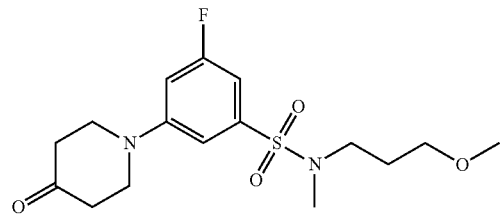 [SMILES: COCCCN(C)S(=O)(=O)c1cc(F)cc(N2CCC(=O)CC2)c1]

A solution of 3-(1,4-dioxa-8-azaspiro[4.5]decan-8-yl)-5-fluoro-N-(3-methoxypropyl)-N-methyl-benzenesulfonamide (4.9 g, 12.17 mmol) in formic acid (25 mL) and H$_2$O (25 mL) was heated to 90° C. and stirred for 2 hrs. After being cooled to rt, the mixture was concentrated in vacuo. The residue was partitioned between DCM (500 mL) and water (200 mL). The organic layer was separated, then washed with a saturated aqueous NaHCO$_3$ solution (100 mL) and brine (100 mL), dried over anhydrous Na$_2$SO$_4$ and concentrated in vacuo. The residue was purified by column chromatography to give 3-fluoro-N-(3-methoxypropyl)-N-methyl-5-(4-oxo-1-piperidyl)benzenesulfonamide (4.1 g) as a yellow oil.

Step 3: Preparation of 3-fluoro-N-(3-methoxypropyl)-N-methyl-5-(2-pyrimidin-2-yl-7,8-dihydro-5H-pyrido[4,3-d]pyrimidin-6-yl)benzenesulfonamide

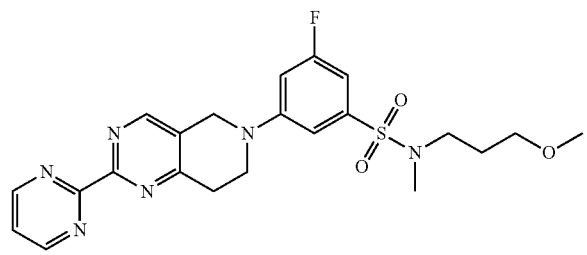 [SMILES: COCCCN(C)S(=O)(=O)c1cc(F)cc(N2CCc3nc(-c4ncccn4)ncc3C2)c1]

A solution of 3-fluoro-N-(3-methoxypropyl)-N-methyl-5-(4-oxo-1-piperidyl)benzenesulfonamide (4.1 g, 11.44 mmol) in DMFDMA (40 mL) was heated to 120° C. and stirred for 4 hrs. After being cooled to rt, the mixture was concentrated in vacuo and the residue was dissolved in MeOH (50 mL). To the solution was added $K_2CO_3$ (5.15 g, 17.26 mmol) and pyrimidine-2-carboxamidine hydrochloride (2.36 g, 14.90 mmol). The resulting mixture was heated at 70° C. for 2 hrs, and then filtered. The filtrate was concentrated in vacuo, and the residue was partitioned between DCM (300 mL) and water (100 mL). The organic layer was separated, then washed with brine (100 mL), dried over anhydrous $Na_2SO_4$ and concentrated in vacuo. The residue was purified by column chromatography to give 3-fluoro-N-(3-methoxypropyl)-N-methyl-5-(2-pyrimidin-2-yl-7,8-dihydro-5H-pyrido[4,3-d]pyrimidin-6-yl)benzenesulfonamide (2.8 g) as a yellow solid.

Step 4: Preparation of 3-fluoro-N-(3-methoxypropyl)-5-(5-methoxy-2-pyrimidin-2-yl-7,8-dihydro-5H-pyrido[4,3-d]pyrimidin-6-yl)-N-methyl-benzenesulfonamide

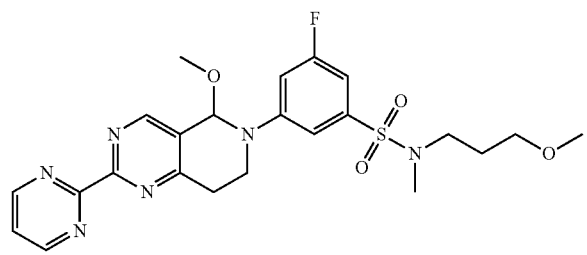 [SMILES: COCCCN(C)S(=O)(=O)c1cc(F)cc(N2CCc3nc(-c4ncccn4)ncc3C2OC)c1]

To a solution of 3-fluoro-N-(3-methoxypropyl)-N-methyl-5-(2-pyrimidin-2-yl-7,8-dihydro-5H-pyrido[4,3-d]pyrimidin-6-yl)benzenesulfonamide (500 mg, 1.058 mmol) in DCM (40 mL) and MeOH (10 mL) at −70° C. was added $RuCl_3$ hydrate (72 mg, 0.317 mmol) and a solution of $NaIO_4$ (679 mg) in $H_2O$ (8 mL) successively. The resulting mixture was stirred at −70° C. for 15 mins, and then allowed to be warmed to rt and stirred for 12 hrs. The reaction mixture was diluted with a saturated aqueous $Na_2SO_3$ solution (100 mL), and then filtered. The filtrate was washed with brine (100 mL). The organic layer was dried over anhydrous $Na_2SO_4$ and concentrated in vacuo to give 3-fluoro-N-(3-methoxypropyl)-5-(5-methoxy-2-pyrimidin-2-yl-7,8-dihydro-5H-pyrido[4,3-d]pyrimidin-6-yl)-N-methyl-benzenesulfonamide (638 mg, crude) as a black solid which was used directly in the next step without further purification.

Step 5: Preparation of 3-fluoro-N-(3-methoxypropyl)-N-methyl-5-(5-methyl-2-pyrimidin-2-yl-7,8-dihydro-5H-pyrido[4,3-d]pyrimidin-6-yl)benzenesulfonamide

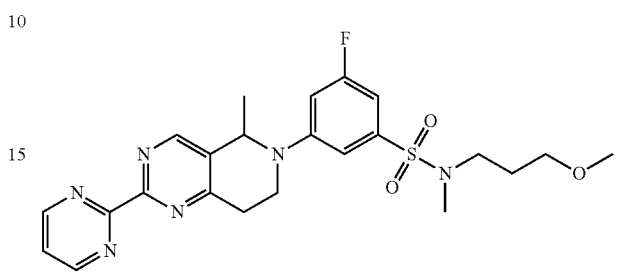

To a cooled solution of 3-fluoro-N-(3-methoxypropyl)-5-(5-methoxy-2-pyrimidin-2-yl-7,8-dihydro-5H-pyrido[4,3-d]pyrimidin-6-yl)-N-methyl-benzenesulfonamide (638 mg, 1.27 mmol) in THF (50 mL) was added $BF_3.Et_2O$ (540 mg, 3.81 mmol) at −70° C. The resulting mixture was stirred at −70° C. for 10 mins, then to the reaction mixture was added a solution of MeMgBr (1.3 mL, 3.81 mmol) in THF. The reaction mixture was then warmed to −20° C. and stirred at this temperature for 2 hrs. The resulting mixture was diluted with a saturated aqueous solution of $NH_4Cl$ (10 mL) and extracted with EA (200 mL) for three times. The combined organic layers were combined, then washed with brine (100 mL), dried over anhydrous $Na_2SO_4$ and concentrated in vacuo. The residue was purified by the flash column chromatography and prep-HPLC to give 3-fluoro-N-(3-methoxypropyl)-N-methyl-5-(5-methyl-2-pyrimidin-2-yl-7,8-dihydro-5H-pyrido[4,3-d]pyrimidin-6-yl)benzenesulfonamide (18 mg) as a white solid. $^1$H NMR (400 MHz, $CDCl_3$) δ: 9.05 (d, 2H), 8.83 (s, 1H), 7.46 (t, 1H), 7.13 (br. s, 1H), 6.89 (d, 1H), 6.80 (d, 1H), 5.14 (d, 1H), 3.95 (d, 1H), 3.55-3.67 (m, 1H), 3.46 (t, 2H), 3.34 (s, 4H), 3.16 (t, 2H), 2.80 (s, 3H), 1.77-1.89 (m, 2H), 1.56 (br. s., 3H). MS obsd. (ESI+) [(M+H$^+$)]: 487.1.

Example 184: (−)-4-[[2-fluoro-6-[5-methyl-2-pyrimidin-2-yl-7,8-dihydro-5H-pyrido[4,3-d]pyrimidin-6-yl]-4-pyridyl]oxy]butanoic acid

Step 1: Preparation of methyl 4-[(2,6-difluoro-4-pyridyl)oxy]butanoate

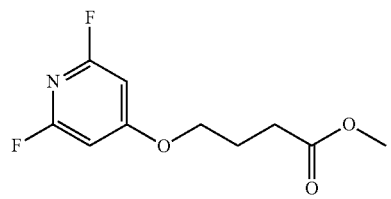 [SMILES: COC(=O)CCCOc1cc(F)nc(F)c1]

A mixture of 2,6-difluoropyridin-4-ol (700 mg, 5.34 mmol), methyl 4-bromobutanoate (1.16 g, 6.41 mmol) and $K_2CO_3$ (2.21 g, 16 mmol) in DMF (10 mL) was heated to 100° C. with stirring for 10 hrs. The reaction mixture was allowed to be cooled to rt and extracted with EA (20 mL).

The organic layer was separated, then washed with water and brine, dried over MgSO₄ and concentrated in vacuo. The residue was purified by column chromatography to give methyl 4-[(2,6-difluoro-4-pyridyl)oxy]butanoate (0.9 g) as an oil.

Step 2: Preparation of methyl (+/−)-4-[[2-fluoro-6-[5-methyl-2-pyrimidin-2-yl-7,8-dihydro-5H-pyrido[4,3-d]pyrimidin-6-yl]-4-pyridyl]oxy]butanoate A solution of (+)-5-methyl-2-(pyrimidin-2-yl)-5,6,7,8-tetrahydropyrido[4,3-d]pyrimidine (200 mg, 0.880 mmol) and methyl 4-((2,6-difluoropyridin-4-yl)oxy)butanoate (900 mg, 3.89 mmol) in DMSO (0.5 ml) and DIPEA (1 mL) was heated to 110° C. and stirred for 15 hrs. The resulting reaction mixture was concentrated in vacuo. The residue was purified by flash column to give methyl (+/−)-4-[[2-fluoro-6-[5-methyl-2-pyrimidin-2-yl-7,8-dihydro-5H-pyrido[4,3-d]pyrimidin-6-yl]-4-pyridyl]oxy]butanoate (200 mg) as brown oil.

Step 3: Preparation of (−)-4-[[2-fluoro-6-[5-methyl-2-pyrimidin-2-yl-7,8-dihydro-5H-pyrido[4,3-d]pyrimidin-6-yl]-4-pyridyl]oxy]butanoic acid To a solution of methyl (+/−)-4-[[2-fluoro-6-[5-methyl-2-pyrimidin-2-yl-7,8-dihydro-5H-pyrido[4,3-d]pyrimidin-6-yl]-4-pyridyl]oxy]butanoate (200 mg, 0.43 mmol) in a mixture of methanol (10 mL), THF (5 mL) and water (2 mL) was added LiOH monohydrate (110 mg, 2.58 mmol). The reaction mixture was stirred overnight at rt and then acidified to pH=6-7 with 1M HCl. The resulting mixture was extracted with DCM (20 mL) for three times. The combined organic mixture was washed with brine, dried over MgSO₄ and concentrated in vacuo. The residue was purified by column chromatography to give the crude product (170 mg) as a yellow solid. 50 mg crude product was further purified by prep-HPLC to give (−)-4-[[2-fluoro-6-[5-methyl-2-pyrimidin-2-yl-7,8-dihydro-5H-pyrido[4,3-d]pyrimidin-6-yl]-4-pyridyl]oxy]butanoic acid (17 mg) as a light yellow solid. ¹H NMR (400 MHz, Methanol-d₄) δ: 8.88-9.00 (m, 2H), 8.68-8.82 (m, 1H), 7.44-7.63 (m, 1H), 6.11-6.23 (m, 1H), 5.71-5.83 (m, 1H), 5.54-5.69 (m, 1H), 4.36-4.51 (m, 1H), 3.96-4.08 (m, 2H), 3.31-3.45 (m, 1H), 2.94-3.15 (m, 2H), 2.34-2.43 (m, 2H), 1.90-2.07 (m, 2H), 1.48 (d, 3H). MS obsd. (ESI⁺) [(M+H)⁺]: 425. $[a]_D^{25}$=−72.00° (0.1 g/100 mL, methanol).

Example 185: (−)-4-[[2-fluoro-6-[5-methyl-2-pyrimidin-2-yl-7,8-dihydro-5H-pyrido[4,3-d]pyrimidin-6-yl]-4-pyridyl]oxy]butanamide A mixture of (−)-4-[[2-fluoro-6-[5-methyl-2-pyrimidin-2-yl-7,8-dihydro-5H-pyrido[4,3-d]pyrimidin-6-yl]-4-pyridyl]oxy]butanoic acid (80 mg, 0.188 mmol) and CDI (45.8 mg, 0.283 mmol) in DMF (3 mL) was stirred for 4 hrs at rt. Then to the reaction mixture was added NH₃ (7 mL, ca.4% in isopropyl alcohol, ca.2.0 mol/L). After being stirred at rt overnight, the resulting reaction mixture was concentrated in vacuo and the residue was purified by prep-HPLC to give (−)-4-[[2-fluoro-6-[5-methyl-2-pyrimidin-2-yl-7,8-dihydro-5H-pyrido[4,3-d]pyrimidin-6-yl]-4-pyridyl]oxy]butanamide (15 mg) as a light yellow solid. ¹H NMR (400 MHz, Methanol-d₄) δ: 8.93 (d, 2H), 8.78 (s, 1H), 7.40-7.61 (m, 1H), 6.16 (s, 1H), 5.77 (d, 1H), 5.53-5.68 (m, 1H), 4.32-4.50 (m, 1H), 3.89-4.12 (m, 2H), 3.31-3.53 (m, 1H), 2.94-3.15 (m, 2H), 2.18-2.39 (m, 2H), 1.99 (br d, 2H), 1.48 (d, 3H). MS obsd. (ESI⁺) [(M+H)⁺]: 424. $[a]_D^{25}$=−84.00° (0.1 g/100 mL, methanol).

Example 186: 5-[[2-fluoro-6-[5-methyl-2-pyrimidin-2-yl-7,8-dihydro-5H-pyrido[4,3-d]pyrimidin-6-yl]-4-pyridyl]oxy]pentanamide

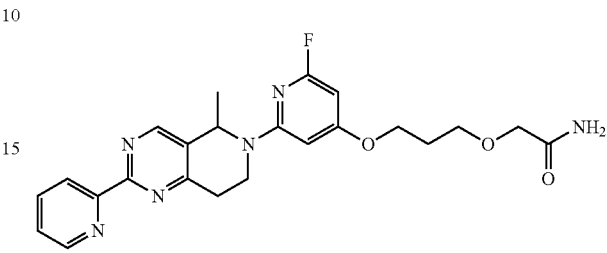

Step 1: Preparation of methyl 2-[3-[[2-fluoro-6-[5-methyl-2-(2-pyridyl)-7,8-dihydro-5H-pyrido[4,3-d]pyrimidin-6-yl]-4-pyridyl]oxy]propoxy]acetate

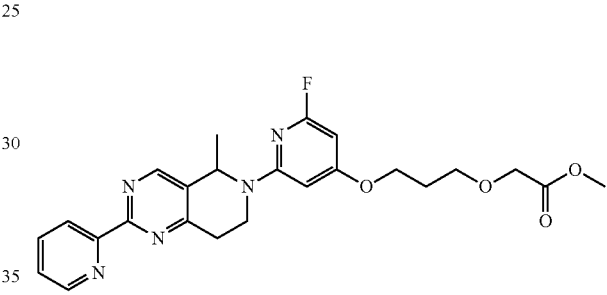

A mixture of methyl 2-[3-[(2,6-difluoro-4-pyridyl)oxy]propoxy]acetate (784 mg, 3 mmol) and 5-methyl-2-(2-pyridyl)-5,6,7,8-tetrahydropyrido[4,3-d]pyrimidine (226 mg, 1.0 mmol) in DIPEA (1 mL) and DMSO (0.5 mL) was heated at 110° C. with stirring in a sealed vessel for 48 hrs. The resulting mixture was poured into water (50 mL) and extracted with EA (60 mL) for three times. The organic layers were combined, then washed with brine, dried over anhydrous Na₂SO₄ and concentrated in vacuo to give a red oil, which was purified by flash chromatography to give methyl 2-[3-[[2-fluoro-6-[5-methyl-2-(2-pyridyl)-7,8-dihydro-5H-pyrido[4,3-d]pyrimidin-6-yl]-4-pyridyl]oxy]propoxy]acetate (234 mg) as a light yellow solid.

Step 2: Preparation of 2-[3-[[2-fluoro-6-[5-methyl-2-(2-pyridyl)-7,8-dihydro-5H-pyrido[4,3-d]pyrimidin-6-yl]-4-pyridyl]oxy]propoxy]acetic acid

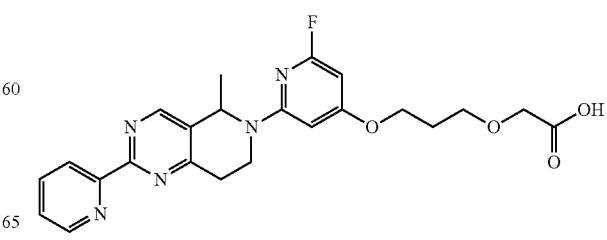

To a solution of methyl 2-[3-[[2-fluoro-6-[5-methyl-2-(2-pyridyl)-7,8-dihydro-5H-pyrido[4,3-d]pyrimidin-6-yl]-4-pyridyl]oxy]propoxy]acetate (234 mg, 0.8 mol) in methanol (5 mL), THF (5 mL) and water (1 mL) was added LiOH monohydrate (84 mg, 2 mol). The resulting mixture was stirred overnight at rt and then acidified to pH=6-7 with 2M HCl. The resulting mixture was extracted with DCM (50 mL) for three times. The combined organic layer was washed with brine, dried over anhydrous $Na_2SO_4$ and concentrated in vacuo to give crude 2-[3-[[2-fluoro-6-[5-methyl-2-(2-pyridyl)-7,8-dihydro-5H-pyrido[4,3-d]pyrimidin-6-yl]-4-pyridyl]oxy]propoxy]acetic acid (180 mg) which was used in next step without further purification.

Step 3: Preparation of 2-[3-[[2-fluoro-6-[5-methyl-2-(2-pyridyl)-7,8-dihydro-5H-pyrido[4,3-d]pyrimidin-6-yl]-4-pyridyl]oxy]propoxy]acetamide

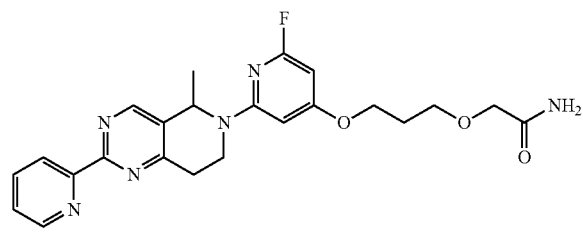 [SMILES: CC1c2cnc(-c3ccccn3)nc2CCN1c1cc(OCCCOCC(N)=O)cc(F)n1]

To a solution of 2-[3-[[2-fluoro-6-[5-methyl-2-(2-pyridyl)-7,8-dihydro-5H-pyrido[4,3-d]pyrimidin-6-yl]-4-pyridyl]oxy]propoxy]acetic acid (180 mg, 0.4 mol) in DMF (10 mL) was added TEA (81 mg, 0.8 mmol) and HATU (304 mg, 0.8 mmol). The resulting mixture was stirred for 10 mins at rt, and then to the resulting mixture was added ammonium chloride (65 mg, 1.2 mmol). was After being stirred at rt for 10 hrs, the resulting reaction mixture was poured into water (25 mL) and extracted with DCM (50 mL) for three times. The organic layers were combined, then washed with brine, dried over anhydrous $Na_2SO_4$ and concentrated in vacuo to give a red oil, which was purified by prep-HPLC to give 2-[3-[[2-fluoro-6-[5-methyl-2-(2-pyridyl)-7,8-dihydro-5H-pyrido[4,3-d]pyrimidin-6-yl]-4-pyridyl]oxy]propoxy]acetamide (58 mg) as a white solid. $^1$H NMR (400 MHz, Methanol-$d_4$) δ: 8.61-8.77 (m, 2H), 8.48-8.57 (m, 1H), 8.04-8.16 (m, 1H), 7.53-7.67 (m, 1H), 6.10-6.16 (m, 1H), 6.03-6.09 (m, 1H), 5.50-5.61 (m, 1H), 4.33-4.46 (m, 1H), 4.01-4.13 (m, 2H), 3.73 (s, 2H), 3.54-3.65 (m, 2H), 3.19-3.24 (m, 1H), 2.91-3.08 (m, 2H), 1.95-2.05 (m, 2H), 1.39-1.51 (m, 3H). MS obsd. (ESI$^+$) [(M+H)$^+$]:453.

Example 187: 6-[3-fluoro-5-(3-methoxypropylsulfonyl)phenyl]-5-methyl-2-pyrimidin-2-yl-7,8-dihydro-5H-pyrido[4,3-d]pyrimidine

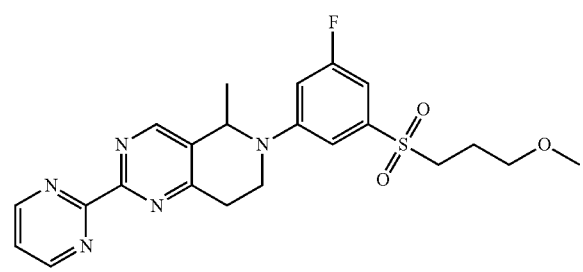 [SMILES: COCCCS(=O)(=O)c1cc(F)cc(N2CCc3nc(-c4ncccn4)ncc3C2C)c1]

Step 1: Preparation of 8-(3-bromo-5-fluoro-phenyl)-1,4-dioxa-8-azaspiro[4.5]decane

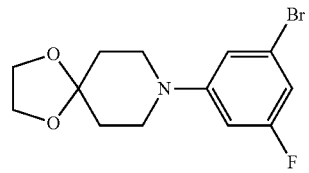 [SMILES: Fc1cc(Br)cc(N2CCC3(CC2)OCCO3)c1]

To a stirred solution of 1,3-dibromo-5-fluorobenzene (40.0 g, 157.5 mmol) in dioxane (600.0 mL) was added 1,4-dioxa-8-azaspiro[4.5]decane hydrochloride (22.6 g, 126.0 mmol), tert-BuONa (37.8 g, 393.8 mmol), $Pd_2(dba)_3$ (2.88 g, 3.15 mmol) and BINAP (3.92 g, 6.30 mmol). The resulting mixture was heated to 80° C. and stirred for 16 hrs under $N_2$ and then partitioned between EA (1 L) and $H_2O$ (100 mL). The organic layer was separated, then washed with brine (100 mL) twice, dried over anhydrous $Na_2SO_4$ and concentrated in vacuo. The residue was purified by column chromatography to give 8-(3-bromo-5-fluoro-phenyl)-1,4-dioxa-8-azaspiro[4.5]decane (20.0 g) as a light yellow oil.

Step 2: Preparation of 2-ethylhexyl 3-[3-(1,4-dioxa-8-azaspiro[4.5]decan-8-yl)-5-fluoro-phenyl]sulfanyl-propanoate

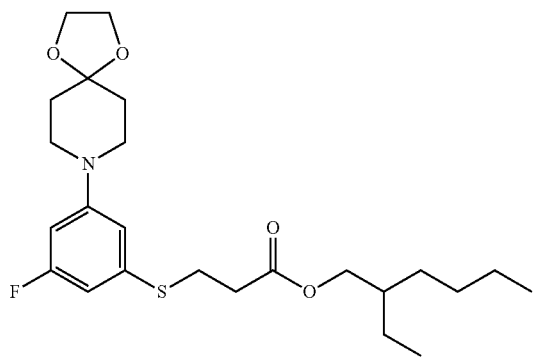 [SMILES: CCCCC(CC)COC(=O)CCSc1cc(F)cc(N2CCC3(CC2)OCCO3)c1]

To a stirred solution of 8-(3-bromo-5-fluoro-phenyl)-1,4-dioxa-8-azaspiro[4.5]decane (20.0 g, 63.2 mmol) in dioxane (600 mL) was added 3-mercaptopropionic acid 2-ethylhexyl ester (20.7 g, 94.8 mmol), DIEA (16.33 g, 126.4 mmol), $Pd_2(dba)_3$ (2.89 g, 3.16 mmol) and Xantphos (3.70 g, 6.40 mmol). The reaction mixture was heated to 90° C. and stirred for 16 hrs, and then partitioned between EA (500 mL) and $H_2O$ (200 mL). The organic layer was separated, washed with brine (200 mL) twice, dried over anhydrous $Na_2SO_4$ and concentrated in vacuo. The residue was purified by column chromatography to give 2-ethylhexyl 3-[3-(1,4-dioxa-8-azaspiro[4.5]decan-8-yl)-5-fluoro-phenyl]sulfanyl-propanoate (20.0 g) as a yellow oil.

Step 3: Preparation of sodium 3-(1,4-dioxa-8-azaspiro[4.5]decan-8-yl)-5-fluoro-benzenethiolate

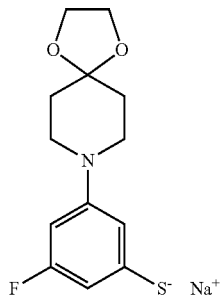 [SMILES: Fc1cc([S-])cc(N2CCC3(CC2)OCCO3)c1 ; [Na+]]

To a solution of 2-ethylhexyl 3-[3-(1,4-dioxa-8-azaspiro[4.5]decan-8-yl)-5-fluoro-phenyl]sulfanylpropanoate (20.0 g, 44.0 mmol) in EtOH (500 mL) was added Na (2.02 g, 88.0 mmol). The resulting mixture was stirred at rt for 18 hrs, and then concentrated in vacuo to give crude sodium 3-(1,4-dioxa-8-azaspiro[4.5]decan-8-yl)-5-fluoro-benzenethiolate (13.0 g) as a yellow oil, which was used in next step directly without further purification.

Step 4: Preparation of 8-[3-fluoro-5-(3-methoxypropylsulfanyl)phenyl]-1,4-dioxa-8-azaspiro[4.5]decane

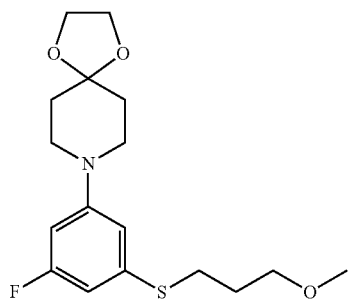 [SMILES: COCCCSc1cc(F)cc(N2CCC3(CC2)OCCO3)c1]

To a solution of sodium 3-(1,4-dioxa-8-azaspiro[4.5]decan-8-yl)-5-fluoro-benzenethiolate (13.0 g, 44.0 mmol) in DMF (200 mL) was added 1-bromo-3-methoxypropane (6.73 g, 44.0 mmol). After being stirred at rt for 2 hrs, the resulting reaction was diluted with water and extracted with EA (200 mL) for three times. The organic layers were combined, then washed with brine (200 mL), dried over anhydrous Na₂SO₄, and concentrated in vacuo. The residue was purified by column chromatography to give 8-[3-fluoro-5-(3-methoxypropylsulfanyl)phenyl]-1,4-dioxa-8-azaspiro[4.5]decane (10.0 g) as a yellow oil.

Step 5: Preparation of 8-[3-fluoro-5-(3-methoxypropylsulfonyl)phenyl]-1,4-dioxa-8-azaspiro[4.5]decane

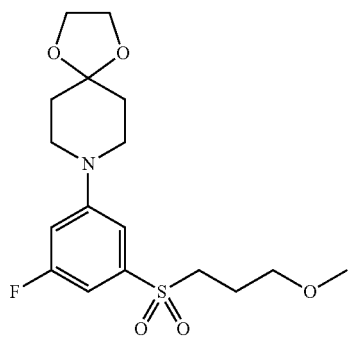 [SMILES: COCCCS(=O)(=O)c1cc(F)cc(N2CCC3(CC2)OCCO3)c1]

To a solution of 8-[3-fluoro-5-(3-methoxypropylsulfanyl)phenyl]-1,4-dioxa-8-azaspiro[4.5]decane (7.0 g, 20.5 mmol) in DCM (70 mL) was added m-CPBA (8.84 g, 51.2 mmol) at rt. The reaction mixture was stirred at rt for 12 hrs, and then the reaction was quenched by a saturated aqueous Na₂SO₃ solution (80 mL). The resulting mixture was extracted with DCM (300 mL). The organic layer was washed with a saturated aqueous Na₂CO₃ solution (80 mL) and brine (100 mL) successively, dried over anhydrous Na₂SO₄ and concentrated in vacuo. The residue was dissolved in EtOH (70 mL) and water (20 mL), then to the solution was added NH₄Cl (9.6 g, 179.3 mmol) and Fe (10.0 g, 179.3 mmol). The resulting mixture was heated at 60° C. with stirring for 2 hrs, and then partitioned between DCM (500 mL) and water (200 mL). The organic layer was separated, then washed with brine, dried over anhydrous Na₂SO₄ and concentrated in vacuo. The residue was purified by column chromatography to give 8-[3-fluoro-5-(3-methoxypropylsulfonyl)phenyl]-1,4-dioxa-8-azaspiro[4.5]decane (4.5 g) as yellow oil.

Step 6: Preparation of 1-[3-fluoro-5-(3-methoxypropylsulfonyl)phenyl]piperidin-4-one

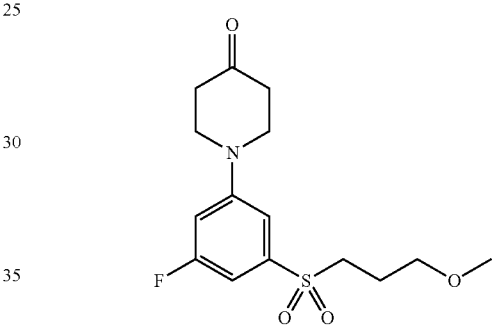

A solution of 8-[3-fluoro-5-(3-methoxypropylsulfonyl)phenyl]-1,4-dioxa-8-azaspiro[4.5]decane (6.0 g, 12.0 mmol) in formic acid (25 mL) and H₂O (25 mL) was heated to 90° C. and stirred for 2 hrs. The reaction mixture was diluted with EA (400 mL). The resulting mixture was washed with a saturated aqueous Na₂CO₃ solution (100 mL), H₂O (100 mL) and brine (100 mL) successively, then dried over anhydrous Na₂SO₄ and concentrated in vacuo. The residue was purified by column chromatography to give 1-[3-fluoro-5-(3-methoxypropylsulfonyl)phenyl]piperidin-4-one (4.8 g) as a light yellow oil.

Step 7: Preparation of 6-[3-fluoro-5-(3-methoxypropylsulfonyl)phenyl]-2-pyrimidin-2-yl-7,8-dihydro-5H-pyrido[4,3-d]pyrimidine

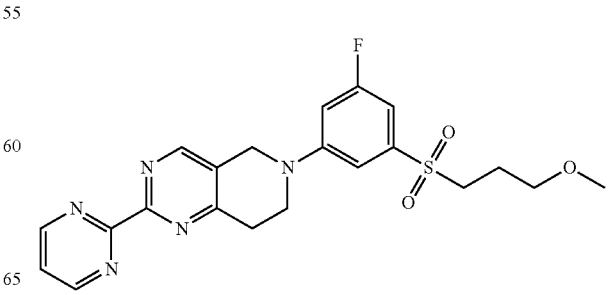

A solution of 1-[3-fluoro-5-(3-methoxypropylsulfonyl)phenyl]piperidin-4-one (4.0 g, 12.1 mmol) in DMFDMA (25 mL) was heated to 120° C. and stirred for 4 hrs. After being cooled to rt, the mixture was concentrated in vacuo and the residue was dissolved in MeOH (70 mL). To the solution was added 2-amidinopyrimidine hydrochloride (2.94 g, 18.6 mmol) and K₂CO₃ (5.57 g, 40.3 mmol). The resulting reaction mixture was heated with stirring at 60° C. for 2 hrs, and then filtered. The filtrate was concentrated in vacuo. The residue was partitioned between DCM (300 mL) and brine (100 mL). The organic layer was separated, then washed with brine, dried over anhydrous Na₂SO₄ and concentrated in vacuo. The residue was purified by column chromatography to give 6-[3-fluoro-5-(3-methoxypropylsulfonyl)phenyl]-2-pyrimidin-2-yl-7,8-dihydro-5H-pyrido[4,3-d]pyrimidine (3.0 g) as a yellow oil.

Step 8: Preparation of 6-[3-fluoro-5-(3-methoxypropylsulfonyl)phenyl]-5-methoxy-2-pyrimidin-2-yl-7,8-dihydro-5H-pyrido[4,3-d]pyrimidine

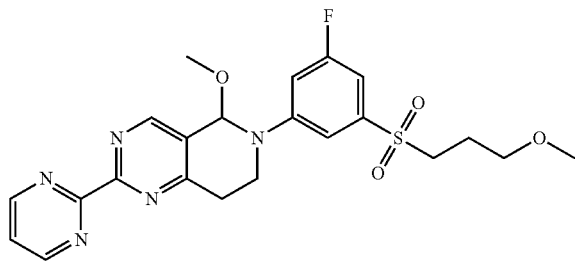 [SMILES: COCCCS(=O)(=O)c1cc(F)cc(N2CCc3nc(-c4ncccn4)ncc3C2OC)c1]

To a solution of 6-[3-fluoro-5-(3-methoxypropyl sulfonyl)phenyl]-2-pyrimidin-2-yl-7,8-dihydro-5H-pyrido[4,3-d]pyrimidine (500 mg, 1.13 mmol) in THF (8 mL) and MeOH (2 mL) at −40° C. was added RuCl₃ hydrate (20 mg, 0.09 mmol) and a solution of NaIO₄ (723 mg, 3.38 mmol) in H₂O (10 mL) successively. The resulting mixture was stirred at −40° C. for 15 mins, and then allowed to be warmed to rt and stirred at rt for 12 hrs. The resulting reaction mixture was diluted with a saturated aqueous Na₂SO₃ solution (20 mL) and filtered. The filtrate was partitioned between DCM (200 mL) and brine (80 mL). The organic layer was separated, then washed with brine, dried over anhydrous Na₂SO₄ and concentrated in vacuo to give 6-[3-fluoro-5-(3-methoxypropylsulfonyl)phenyl]-5-methoxy-2-pyrimidin-2-yl-7,8-dihydro-5H-pyrido[4,3-d]pyrimidine (300 mg, crude) which was used directly in the next step without further purification.

Step 9: Preparation of 6-[3-fluoro-5-(3-methoxypropylsulfonyl)phenyl]-5-methyl-2-pyrimidin-2-yl-7,8-dihydro-5H-pyrido[4,3-d]pyrimidine

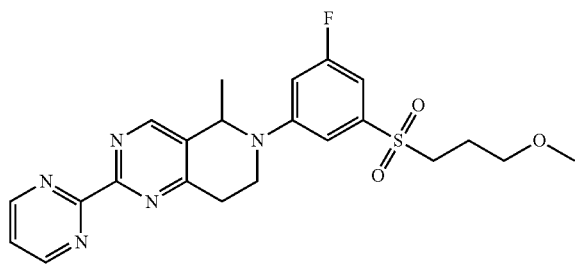 [SMILES: COCCCS(=O)(=O)c1cc(F)cc(N2CCc3nc(-c4ncccn4)ncc3C2C)c1]

To a stirred solution of 6-[3-fluoro-5-(3-methoxypropylsulfonyl)phenyl]-5-methoxy-2-pyrimidin-2-yl-7,8-dihydro-5H-pyrido[4,3-d]pyrimidine (300 mg, 0.63 mmol) in THF (15 mL) at −70° C. was added BF₃.Et₂O (449 mg, 3.17 mmol). The mixture was stirred at −70° C. for 10 mins, then to the resulting mixture was added a solution of MeMgBr (1.1 mL, 3.17 mmol) in THF. The resulting mixture was allowed to be warmed to −20° C. and stirred for 1 hr. The resulting reaction mixture was diluted with EA (100 mL), then washed with brine (20 mL) twice and concentrated in vacuo. The residue was purified by column chromatography and prep-HPLC to afford 6-[3-fluoro-5-(3-methoxypropylsulfonyl)phenyl]-5-methyl-2-pyrimidin-2-yl-7,8-dihydro-5H-pyrido[4,3-d]pyrimidine (60 mg) as a white solid. ¹H NMR (400 MHz, CDCl₃) δ: 9.05 (d, 2H), 8.83 (s, 1H), 7.46 (t, 1H), 7.23 (s, 1H), 7.01 (d, 1H), 6.85 (d, 1H), 5.16 (m, 1H), 3.98 (m, 1H), 3.55-3.69 (m, 1H), 3.39-3.50 (m, 2H), 3.31-3.38 (m, 2H), 3.30 (s, 3H), 3.18-3.26 (m, 2H), 1.95-2.09 (m, 2H), 1.58 (d, 3H). MS obsd. (ESI⁺) [(M+H)⁺]: 458.

Example 188: 6-[6-fluoro-4-(tetrahydrofuran-3-ylmethoxy)-2-pyridyl]-5-methyl-2-(2-pyridyl)-7,8-dihydro-5H-pyrido[4,3-d]pyrimidine

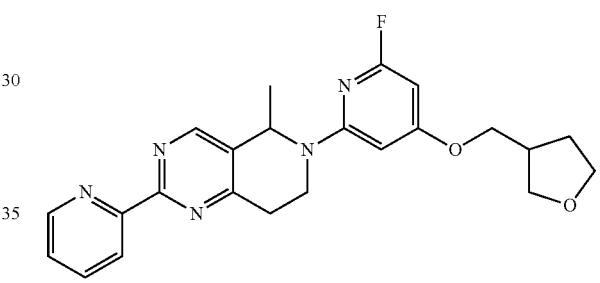

Step 1: Preparation of 6-(4,6-difluoro-2-pyridyl)-5-methyl-2-(2-pyridyl)-7,8-dihydro-5H-pyrido[4,3-d]pyrimidine

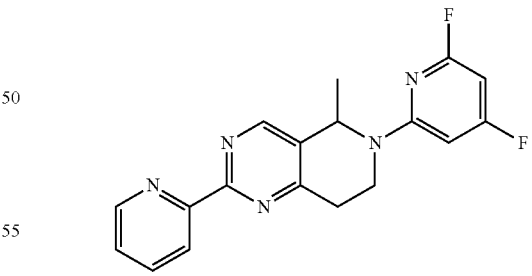

To a solution of 5-methyl-2-(2-pyridyl)-5,6,7,8-tetrahydropyrido[4,3-d]pyrimidine (1.5 g, 6.6 mmol, see Example 1) in NMP (15 mL) was added 2,4,6-trifluoropyridine (1.1 g, 8.0 mmol) and DIPEA (2.6 g, 19.8 mmol). The reaction mixture was heated at 150° C. in a microwave reactor for 1 hr. The reaction mixture was diluted with H₂O (50 mL) and extracted with DCM (50 mL) twice. The combined organic layer was washed with brine and dried over anhydrous Na₂SO₄, and concentrated in vacuo. The residue was purified by prep-HPLC to 6-(4,6-difluoro-2-pyridyl)-5-methyl-2-(2-pyridyl)-7,8-dihydro-5H-pyrido[4,3-d]pyrimidine (400 mg) as a yellow solid.

Step 2: Preparation of 6-[6-fluoro-4-(tetrahydrofuran-3-ylmethoxy)-2-pyridyl]-5-methyl-2-(2-pyridyl)-7,8-dihydro-5H-pyrido[4,3-d]pyrimidine

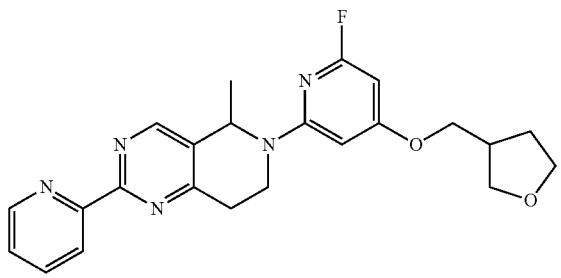 [SMILES: CC1c2cnc(-c3ccccn3)nc2CCN1c1cc(OCC2CCOC2)cc(F)n1]

To a solution of (tetrahydrofuran-3-yl)methanol (36.1 mg, 354 μmol) in anhydrous DMF (2 mL) was added sodium hydride (23.6 mg, 589 μmol) at 0° C. The mixture was stirred for 30 mins at 0° C., then to the reaction mixture was added 6-(4,6-difluoro-2-pyridyl)-5-methyl-2-(2-pyridyl)-7,8-dihydro-5H-pyrido[4,3-d]pyrimidine (100 mg, 295 μmol). The resulting mixture was then heated to 80° C. and stirred for 10 hrs. After being cooled to rt, the resulting reaction mixture was diluted with water, then washed with brine and extracted with DCM (30 mL) for three times. The combined organic layer was concentrated in vacuo and the residue was purified by prep-HPLC to give 6-[6-fluoro-4-(tetrahydrofuran-3-ylmethoxy)-2-pyridyl]-5-methyl-2-(2-pyridyl)-7,8-dihydro-5H-pyrido[4,3-d]pyrimidine (52 mg) as a light yellow solid. $^1$H NMR (400 MHz, DMSO-d$_6$) δ: 8.88 (s, 1H), 8.74-8.72 (m, 1H), 8.35 (d, 1H), 7.97-7.95 (m, 1H), 7.53-7.50 (m, 1H), 6.33 (s, 1H), 5.98 (s, 1H), 5.67-5.65 (m, 1H), 4.54-4.39 (m, 1H), 4.05-3.95 (m, 2H), 3.81-3.76 (m, 2H), 3.67-3.63 (m, 1H), 3.60-3.40 (m, 2H), 3.10-2.94 (m, 2H), 2.70-2.55 (m, 1H), 2.10-1.95 (m, 1H), 1.75-1.55 (m, 1H), 1.49 (d, 3H). MS obsd. (ESI$^+$) [(M+H)$^+$]: 422.

Example 189: 6-[6-fluoro-4-(tetrahydrofuran-2-ylmethoxy)-2-pyridyl]-5-methyl-2-(2-pyridyl)-7,8-dihydro-5H-pyrido[4,3-d]pyrimidine

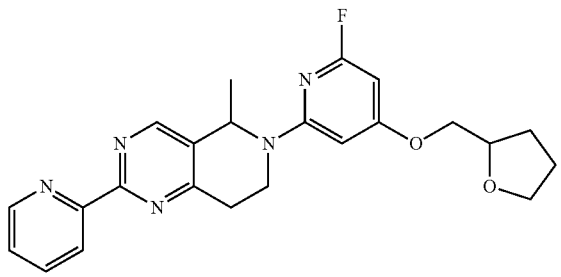 [SMILES: CC1c2cnc(-c3ccccn3)nc2CCN1c1cc(OCC2CCCO2)cc(F)n1]

To a solution of (tetrahydrofuran-2-yl)methanol (36.1 mg, 354 μmol) in anhydrous DMF (2 mL) was added sodium hydride (23.6 mg, 589 μmol) at 0° C. The mixture was stirred for 30 mins at 0° C., then to the reaction mixture was added 6-(4,6-difluoro-2-pyridyl)-5-methyl-2-(2-pyridyl)-7,8-dihydro-5H-pyrido[4,3-d]pyrimidine (100 mg, 295 μmol). The reaction mixture was then heated to 80° C. and stirred for 10 hrs. After being cooled to rt, the mixture was diluted with water. The resulting mixture was extracted with DCM (30 mL) for three times. The combined organic layer was concentrated in vacuo and the residue was purified by prep-HPLC to give 6-[6-fluoro-4-(tetrahydrofuran-2-ylmethoxy)-2-pyridyl]-5-methyl-2-(2-pyridyl)-7,8-dihydro-5H-pyrido[4,3-d]pyrimidine (54 mg) as a light yellow solid. $^1$HNMR (400 MHz, DMSO-d$_6$) δ: 8.88 (s, 1H), 8.78-8.68 (m, 1H), 8.35 (d, 1H), 7.99-7.92 (m, 1H), 7.55-7.48 (m, 1H), 6.33 (s, 1H), 5.98 (s, 1H), 5.70-5.60 (m, 1H), 4.54-4.39 (m, 1H), 4.18-3.98 (m, 3H), 3.83-3.74 (m, 1H), 3.71-3.63 (m, 1H), 3.49-3.37 (m, 1H), 3.10-2.94 (m, 2H), 2.09-1.96 (m, 1H), 1.92-1.77 (m, 2H), 1.71-1.58 (m, 1H), 1.49 (d, 3H). MS obsd. (ESI$^+$) [(M+H)$^+$]: 422.

Example 190: 6-[6-fluoro-4-(tetrahydropyran-4-ylmethoxy)-2-pyridyl]-5-methyl-2-(2-pyridyl)-7,8-dihydro-5H-pyrido[4,3-d]pyrimidine

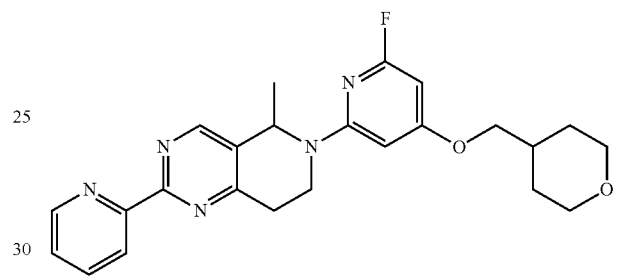

To a solution of (tetrahydro-2H-pyran-4-yl)methanol (41.8 mg, 360 μmol) in DMF (1 mL) was added NaH (8.64 mg, 360 μmol) at 0° C. The mixture was stirred at 0° C. for 30 min. then to the reaction mixture was added 6-(4,6-difluoro-2-pyridyl)-5-methyl-2-(2-pyridyl)-7,8-dihydro-5H-pyrido[4,3-d]pyrimidine (102 mg, 0.3 mmol). The resulting reaction mixture was heated with stirring at 70° C. overnight. After being cooled to rt, the reaction mixture was purified by prep-HPLC to afford 6-[6-fluoro-4-(tetrahydropyran-4-ylmethoxy)-2-pyridyl]-5-methyl-2-(2-pyridyl)-7,8-dihydro-5H-pyrido[4,3-d]pyrimidine (15 mg) as a brown solid. $^1$H NMR (400 MHz, CDCl$_3$) δ: 9.63 (br s, 2H), 9.07 (d, 1H), 8.83 (d, 1H), 8.74 (s, 1H), 8.40 (dt, 1H), 7.92-7.85 (m, 1H), 6.01 (s, 1H), 5.80 (d, 1H), 5.73 (q, 1H), 4.33 (br dd, 1H), 4.04 (dd, 2H), 3.85 (d, 2H), 3.53-3.40 (m, 3H), 3.22-3.13 (m, 2H), 2.15-2.01 (m, 1H), 1.75 (br dd, 2H), 1.57 (d, 3H), 1.47 (dq, 2H). MS obsd. (ESI$^+$) [(M+H)$^+$]: 436.

Example 191: 6-[4-(cyclopropylmethoxy)-6-fluoro-2-pyridyl]-5-methyl-2-(2-pyridyl)-7,8-dihydro-5H-pyrido[4,3-d]pyrimidine

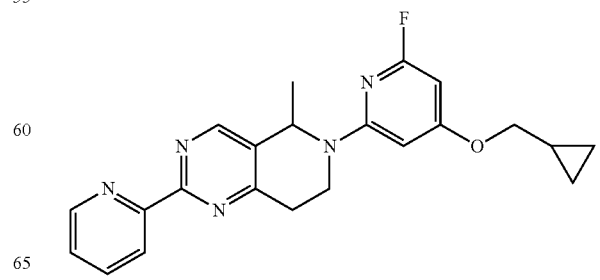

To a solution of cyclopropylmethanol (25.5 mg, 354 μmol) in anhydrous DMF (2 mL) was added sodium hydride (23.6 mg, 589 μmol) at 0° C. The resulting mixture was stirred for 30 mins then to the reaction mixture was added 6-(4,6-difluoro-2-pyridyl)-5-methyl-2-(2-pyridyl)-7,8-dihydro-5H-pyrido[4,3-d]pyrimidine (100 mg, 295 μmol). The resulting mixture was heated and stirred at 80° C. for 10 hrs. After being cooled to rt and diluted with water, the resulting mixture was washed brine and extracted with DCM (30 ml) for three times. The combined organic layer was concentrated in vacuo and the residue was purified by prep-HPLC to give 6-[4-(cyclopropylmethoxy)-6-fluoro-2-pyridyl]-5-methyl-2-(2-pyridyl)-7,8-dihydro-5H-pyrido[4,3-d]pyrimidine (48 mg) as a light yellow solid. $^1$H NMR (400 MHz, DMSO-$d_6$) δ: 8.87 (s, 1H), 8.77-8.69 (m, 1H), 8.35 (d, 1H), 7.99-7.94 (m, 1H), 7.53-7.50 (m, 1H), 6.31 (s, 1H), 5.95 (s, 1H), 5.72-5.66 (m, 1H), 4.50-4.38 (m, 1H), 3.93 (d, 2H), 3.47-3.38 (m, 1H), 3.11-2.93 (m, 2H), 1.49 (d, 3H), 1.30-1.16 (m, 1H), 0.64-0.54 (m, 2H), 0.36-0.27 (m, 2H). MS obsd. (ESI$^+$) [(M+H)$^+$]: 392.

Example 192 and 193: 6-[4-(2,2-difluoroethoxy)-6-fluoro-2-pyridyl]-5-methyl-2-(2-pyridyl)-7,8-dihydro-5H-pyrido[4,3-d]pyrimidine and 6-[6-(2,2-difluoroethoxy)-4-fluoro-2-pyridyl]-5-methyl-2-(2-pyridyl)-7,8-dihydro-5H-pyrido[4,3-d]pyrimidine

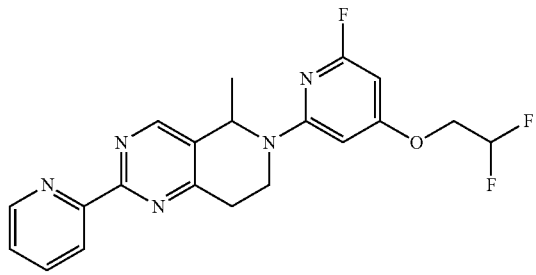 [SMILES: CC1c2cnc(-c3ccccn3)nc2CCN1c1cc(OCC2CC2)cc(F)n1]

Example 192

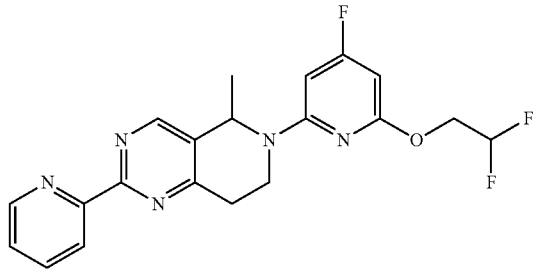

Example 193

To a solution of 2,2-difluoroethanol (88.6 mg, 1.08 mmol) in DMF (3 ml) was added NaH (43.2 mg, 1.8 mmol) at 0° C. The resulting mixture was stirred at 0° C. for 30 mins, then to the reaction mixture was added 6-(4,6-difluoro-2-pyridyl)-5-methyl-2-(2-pyridyl)-7,8-dihydro-5H-pyrido[4,3-d]pyrimidine (305 mg, 0.9 mmol). The resulting reaction mixture was heated with stirring at 70° C. overnight. After being cooled to rt, the resulting reaction mixture was purified by prep-HPLC to afford 6-[4-(2,2-difluoroethoxy)-6-fluoro-2-pyridyl]-5-methyl-2-(2-pyridyl)-7,8-dihydro-5H-pyrido[4,3-d]pyrimidine (215 mg) as a brown solid and 6-[6-(2,2-difluoroethoxy)-4-fluoro-2-pyridyl]-5-methyl-2-(2-pyridyl)-7,8-dihydro-5H-pyrido[4,3-d]pyrimidine (15 mg) as a brown solid.

Example 192: 6-[4-(2,2-difluoroethoxy)-6-fluoro-2-pyridyl]-5-methyl-2-(2-pyridyl)-7,8-dihydro-5H-pyrido[4,3-d]pyrimidine, $^1$H NMR (400 MHz, CDCl$_3$) δ: 9.92 (br s, 2H), 9.06 (br d, 1H), 8.79 (d, 1H), 8.74 (s, 1H), 8.34 (dt, 1H), 7.83 (t, 1H), 6.22-5.95 (m, 2H), 5.81 (s, 1H), 5.70 (q, 1H), 4.41-4.31 (m, 1H), 4.23 (dt, 2H), 3.54-3.43 (m, 1H), 3.22-3.14 (m, 2H), 1.57 (d, 3H). MS obsd. (ESI$^+$) [(M+H)$^+$]: 402.

Example 193: 6-[6-(2,2-difluoroethoxy)-4-fluoro-2-pyridyl]-5-methyl-2-(2-pyridyl)-7,8-dihydro-5H-pyrido[4,3-d]pyrimidine, $^1$H NMR (400 MHz, CDCl$_3$) δ: 10.45 (br s, 2H), 9.08 (d, 1H), 8.85 (d, 1H), 8.77 (s, 1H), 8.42 (dt, 1H), 7.96-7.85 (m, 1H), 6.24 (t, 1H), 6.10-5.96 (m, 2H), 5.91 (dd, 1H), 5.60 (q, 1H), 4.58-4.46 (m, 2H), 4.37 (td, 1H), 3.54-3.42 (m, 1H), 3.22-3.13 (m, 2H), 1.59 (d, 3H). MS obsd. (ESI+) [(M+H)+]: 402.

Example 194: 6-[6-fluoro-4-(thietan-3-ylmethoxy)-2-pyridyl]-5-methyl-2-pyrimidin-2-yl-7,8-dihydro-5H-pyrido[4,3-d]pyrimidine

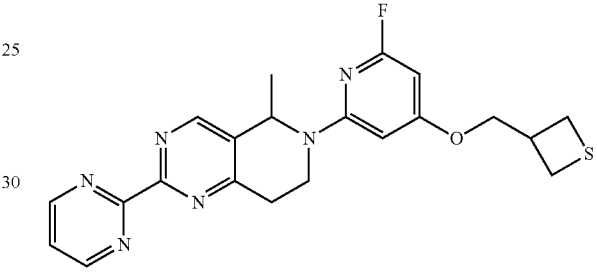

Step 1: Preparation of 2-fluoro-6-(5-methyl-2-pyrimidin-2-yl-7,8-dihydro-5H-pyrido[4,3-d]pyrimidin-6-yl)pyridin-4-ol

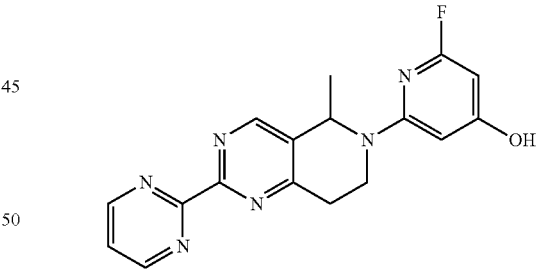

To a solution of 6-(6-fluoro-4-methoxy-2-pyridyl)-5-methyl-2-pyrimidin-2-yl-7,8-dihydro-5H-pyrido[4,3-d]pyrimidine (400 mg, 1.14 mmol) in DCE (10 mL) which was cooled to 0° C. was added BBr$_3$ (1.42 g, 5.68 mmol) slowly. The resulting mixture was heated to 80° C. and stirred for 8 hrs. The reaction was then quenched with MeOH (100 mL) and the resulting mixture was concentrated in vacuo. The residue was diluted with a saturated aqueous NaHCO$_3$ solution and extracted with a mixture of DCM and MeOH (200 mL, v/v=5/1). The organic layer was dried over Na$_2$SO$_4$ and concentrated in vacuo. The residue was purified by column chromatography to give 2-fluoro-6-(5-methyl-2-pyrimidin-2-yl-7,8-dihydro-5H-pyrido[4,3-d]pyrimidin-6-yl)pyridin-4-ol (350 mg) as a brown solid.

Step 2: Preparation of 6-[6-fluoro-4-(thietan-3-yl-methoxy)-2-pyridyl]-5-methyl-2-pyrimidin-2-yl-7,8-dihydro-5H-pyrido[4,3-d]pyrimidine

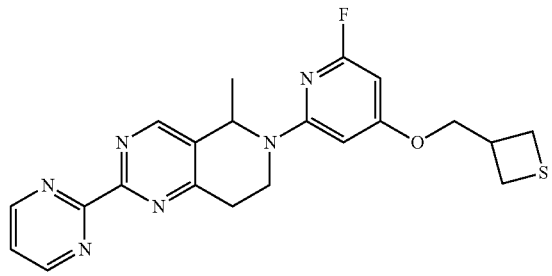 [SMILES: CC1c2cnc(-c3ncccn3)nc2CCN1c1cc(OCC2CSC2)cc(F)n1]

To a solution of 2-fluoro-6-(5-methyl-2-pyrimidin-2-yl-7,8-dihydro-5H-pyrido[4,3-d]pyrimidin-6-yl)pyridin-4-ol (110 mg, 0.325 mmol) in DMF (5 mL) was added Cs$_2$CO$_3$ (318 mg, 0.975 mmol) and thietan-3-ylmethyl 4-methylbenzenesulfonate (109 mg, 0.423 mmol). After being heated to 50° C. and stirred for 16 hrs, the resulting mixture was filtered. The filtrate was diluted with EA (200 mL), then washed with brine (200 mL), dried over with anhydrous Na$_2$SO$_4$ and concentrated in vacuo. The residue was purified by prep-HPLC to give 6-[6-fluoro-4-(thietan-3-ylmethoxy)-2-pyridyl]-5-methyl-2-pyrimidin-2-yl-7,8-dihydro-5H-pyrido[4,3-d]pyrimidine (15 mg) as a light yellow solid. $^1$H NMR (400 MHz, CDCl$_3$) δ: 9.04 (d, 2H), 8.82 (s, 1H), 7.44 (t, 1H), 6.04 (s, 1H), 5.82 (s, 1H), 5.68 (d, 1H), 4.41 (d, 1H), 4.12 (d, 2H), 3.64-3.69 (m, 1H), 3.47-3.53 (m, 1H), 3.35 (t, 2H), 3.27 (dd, 2H), 3.11-3.19 (m, 2H), 1.60 (br. s., 3H). MS obsd. (ESI$^+$) [(M+H)$^+$]: 425.

Example 195: 3-[[2-fluoro-6-(5-methyl-2-pyrimidin-2-yl-7,8-dihydro-5H-pyrido[4,3-d]pyrimidin-6-yl)-4-pyridyl]oxymethyl]thietane 1,1-dioxide

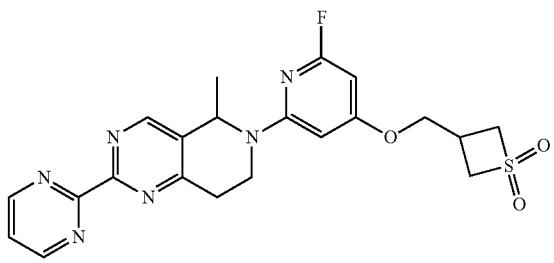 [SMILES: CC1c2cnc(-c3ncccn3)nc2CCN1c1cc(OCC2CS(=O)(=O)C2)cc(F)n1]

To a solution of 6-[6-fluoro-4-(thietan-3-ylmethoxy)-2-pyridyl]-5-methyl-2-pyrimidin-2-yl-7,8-dihydro-5H-pyrido[4,3-d]pyrimidine (190 mg, 0.448 mmol) in MeOH (10 mL) was added a solution of oxone (2.2 g, 3.58 mmol) in H$_2$O (3 mL) slowly at 0° C. After the mixture was stirred at 10° C. for 2 hrs, the reaction was quenched with a saturated aqueous Na$_2$SO$_3$ solution (50 mL) and the resulting mixture was extracted with DCM (100 mL). The organic layer was washed with brine (100 mL), dried over with anhydrous Na$_2$SO$_4$ and concentrated in vacuo. The residue was purified by prep-HPLC to give 3-[[2-fluoro-6-(5-methyl-2-pyrimidin-2-yl-7,8-dihydro-5H-pyrido[4,3-d]pyrimidin-6-yl)-4-pyridyl]oxymethyl]thietane 1,1-dioxide (10 mg) as a yellow solid. $^1$H NMR (400 MHz, CDCl$_3$) δ: 9.04 (d, 2H), 8.83 (s, 1H), 7.45 (t, 1H), 6.04 (s, 1H), 5.80 (s, 1H), 5.67 (d, 1H), 4.41 (d, 1H), 4.32 (dd, 2H), 4.21 (d, 2H), 4.09 (dd, 2H), 3.46-3.56 (m, 1H), 3.27 (dd, 2H), 2.98-3.08 (m, 1H), 1.58-1.61 (m, 3H). MS obsd. (ESI$^+$) [(M+H)$^+$]: 457.

Example 196 and 197: 2-fluoro-N,N-dimethyl-6-(5-methyl-2-pyrimidin-2-yl-7,8-dihydro-5H-pyrido[4,3-d]pyrimidin-6-yl)pyridin-4-amine and 4-fluoro-N,N-dimethyl-6-(5-methyl-2-pyrimidin-2-yl-7,8-dihydro-5H-pyrido[4,3-d]pyrimidin-6-yl)pyridin-2-amine Example 196

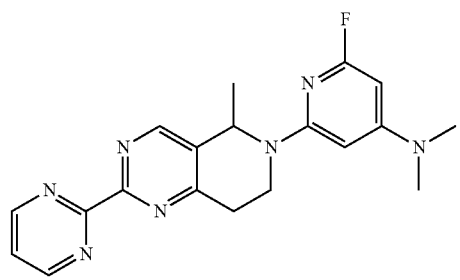

Example 197

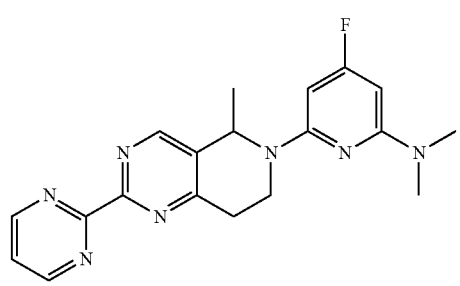

A mixture of 6-(4,6-difluoro-2-pyridyl)-5-methyl-2-pyrimidin-2-yl-7,8-dihydro-5H-pyrido[4,3-d]pyrimidine (35 mg, 103 μmol, the product of step 3 in Example 151), dimethylamine hydrochloride (17 mg, 208 μmol) and cesium carbonate (67 mg, 206 μmol) in DMF (2 mL) was heated to 110° C. and stirred overnight. The resulting mixture was cooled and then purified by prep-HPLC to give 2-fluoro-N,N-dimethyl-6-(5-methyl-2-pyrimidin-2-yl-7,8-dihydro-5H-pyrido[4,3-d]pyrimidin-6-yl)pyridin-4-amine (20 mg) and 4-fluoro-N,N-dimethyl-6-(5-methyl-2-pyrimidin-2-yl-7,8-dihydro-5H-pyrido[4,3-d]pyrimidin-6-yl)pyridin-2-amine (10 mg).

Example 196: 2-fluoro-N,N-dimethyl-6-(5-methyl-2-pyrimidin-2-yl-7,8-dihydro-5H-pyrido[4,3-d]pyrimidin-6-yl)pyridin-4-amine, light yellow solid, $^1$H NMR (400 MHz, Methanol-d4) δ: 1.55 (d, 3H), 3.01 (s, 6H), 3.09-3.23 (m, 2H), 3.39-3.53 (m, 1H), 4.39-4.53 (m, 1H), 5.59-5.65 (m, 1H), 5.65-5.74 (m, 1H), 5.79-5.87 (m, 1H), 7.60-7.67 (m, 1H), 8.82-8.88 (m, 1H), 8.98-9.06 (m, 2H). MS obsd. (ESI$^+$) [(M+H)$^+$]: 366.

Example 197: 4-fluoro-N,N-dimethyl-6-(5-methyl-2-pyrimidin-2-yl-7,8-dihydro-5H-pyrido[4,3-d]pyrimidin-6-yl)pyridin-2-amine, light yellow solid, $^1$H NMR (400 MHz, Methanol-d4) δ: 1.58 (d, 3H), 3.04 (s, 6H), 3.12 (br s, 2H), 3.39-3.52 (m, 1H), 4.47-4.58 (m, 1H), 5.65 (d, 1H), 5.70-5.80 (m, 1H), 5.85-5.95 (m, 1H), 7.60-7.68 (m, 1H), 8.84-8.90 (m, 1H), 9.03 (d, 2H). MS obsd. (ESI$^+$) [(M+H)$^+$]: 366.

Example 198 and 199: 6-(6-fluoro-4-pyrrolidin-1-yl-2-pyridyl)-5-methyl-2-pyrimidin-2-yl-7,8-dihydro-5H-pyrido[4,3-d]pyrimidine and 6-(4-fluoro-6-pyrrolidin-1-yl-2-pyridyl)-5-methyl-2-pyrimidin-2-yl-7,8-dihydro-5H-pyrido[4,3-d]pyrimidine Example 200 and 201: (−)-6-(6-fluoro-4-pyrrolidin-1-yl-2-pyridyl)-5-methyl-2-pyrimidin-2-yl-7,8-dihydro-5H-pyrido[4,3-d]pyrimidine and (+)-6-(6-fluoro-4-pyrrolidin-1-yl-2-pyridyl)-5-methyl-2-pyrimidin-2-yl-7,8-dihydro-5H-pyrido[4,3-d]pyrimidine

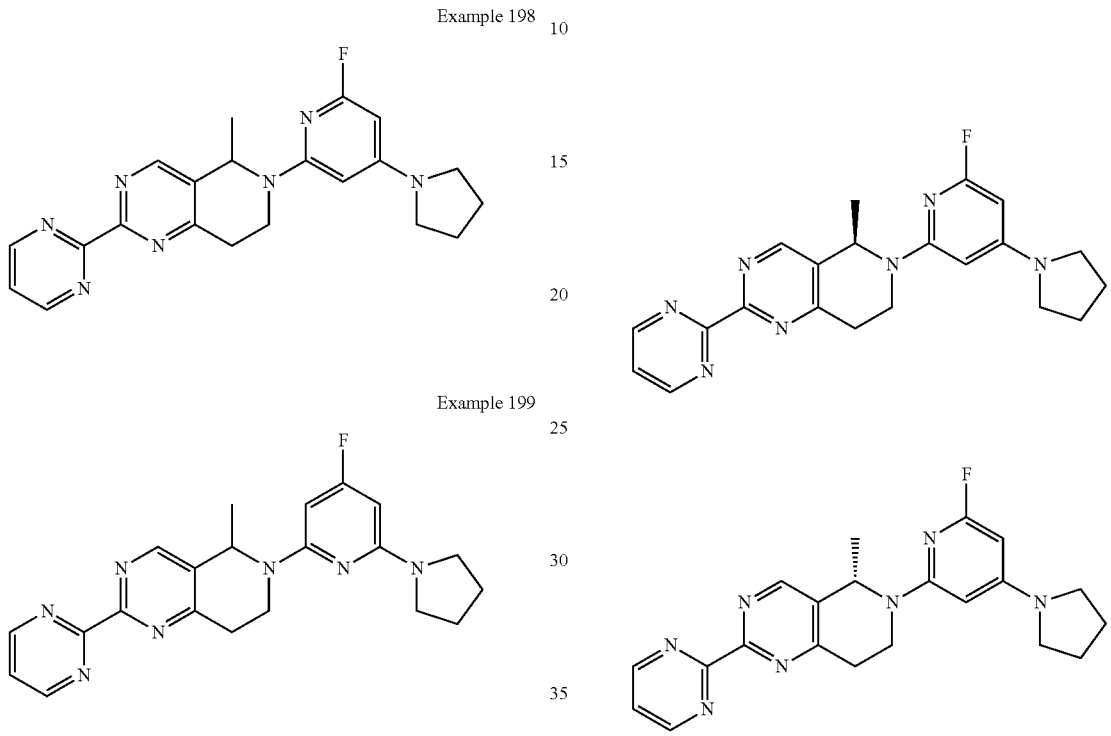

A mixture of 6-(4,6-difluoro-2-pyridyl)-5-methyl-2-pyrimidin-2-yl-7,8-dihydro-5H-pyrido[4,3-d]pyrimidine (100 mg, 294 μmol), pyrrolidine (42 mg, 588 μmol) and potassium carbonate (81 mg, 588 μmol) in DMSO (2 mL) was heated at 50° C. with stirring for 2 hrs. The resulting mixture was cooled and purified by prep-HPLC to give 6-(6-fluoro-4-pyrrolidin-1-yl-2-pyridyl)-5-methyl-2-pyrimidin-2-yl-7,8-dihydro-5H-pyrido[4,3-d]pyrimidine (77 mg) and 6-(4-fluoro-6-pyrrolidin-1-yl-2-pyridyl)-5-methyl-2-pyrimidin-2-yl-7,8-dihydro-5H-pyrido[4,3-d]pyrimidine (20 mg).

Example 198: 6-(6-fluoro-4-pyrrolidin-1-yl-2-pyridyl)-5-methyl-2-pyrimidin-2-yl-7,8-dihydro-5H-pyrido[4,3-d]pyrimidine, light yellow solid $^1$H NMR (400 MHz, Methanol-d4) δ: 1.53 (d, 3H), 1.91-2.02 (m, 4H), 3.01-3.21 (m, 2H), 3.26-3.45 (m, 5H), 3.31-3.47 (m, 2H), 4.42 (br dd, 1H), 5.45 (s, 1H), 5.59-5.71 (m, 2H), 7.61 (t, 1H), 8.82 (s, 1H), 9.00 (d, 2H). MS obsd. (ESI$^+$) [(M+H)$^+$]: 392.

Example 199: 6-(4-fluoro-6-pyrrolidin-1-yl-2-pyridyl)-5-methyl-2-pyrimidin-2-yl-7,8-dihydro-5H-pyrido[4,3-d]pyrimidine, light yellow solid, $^1$H NMR (400 MHz, Methanol-d4) δ: 1.58 (d, 3H), 1.89-2.07 (m, 4H), 3.13 (br s, 2H), 3.36-3.52 (m, 5H), 4.54 (br dd, 1H), 5.49 (d, 1H), 5.78 (br d, 1H), 5.87 (d, 1H), 7.64 (br t, 1H), 8.80-8.93 (m, 1H), 9.03 (br d, 2H). MS obsd. (ESI$^+$) [(M+H)$^+$]: 392.

6-(6-fluoro-4-pyrrolidin-1-yl-2-pyridyl)-5-methyl-2-pyrimidin-2-yl-7,8-dihydro-5H-pyrido[4,3-d]pyrimidine (59 mg, Example 198) was chiral separated using SFC to give (−)-6-(6-fluoro-4-pyrrolidin-1-yl-2-pyridyl)-5-methyl-2-pyrimidin-2-yl-7,8-dihydro-5H-pyrido[4,3-d]pyrimidine (20 mg) and (−)-6-(6-fluoro-4-pyrrolidin-1-yl-2-pyridyl)-5-methyl-2-pyrimidin-2-yl-7,8-dihydro-5H-pyrido[4,3-d]pyrimidine (20 mg). Both compounds are light yellow solid.

Example 200: (−)-6-(6-fluoro-4-pyrrolidin-1-yl-2-pyridyl)-5-methyl-2-pyrimidin-2-yl-7,8-dihydro-5H-pyrido[4,3-d]pyrimidine, $^1$H NMR (400 MHz, DMSO-d$_6$) δ ppm 1.48 (d, 3H) 1.90-1.97 (m, 4H), 2.98-3.10 (m, 2H), 3.25-3.30 (m, 3H), 3.38 (m, 1H), 4.43 (br dd, 1H), 5.52 (s, 1H), 5.67 (br d, 1H), 5.74 (s, 1H), 7.63 (t, 1H), 8.91 (s, 1H), 8.99 (d, 2H). MS obsd. (ESI$^+$) [(M+H)$^+$]: 392.

Example 201: (+)-6-(6-fluoro-4-pyrrolidin-1-yl-2-pyridyl)-5-methyl-2-pyrimidin-2-yl-7,8-dihydro-5H-pyrido[4,3-d]pyrimidine, $^1$H NMR (400 MHz, DMSO-d$_6$) δ ppm 1.48 (d, 3H) 1.90-1.97 (m, 4H), 2.98-3.10 (m, 2H), 3.25-3.30 (m, 3H), 3.38 (m, 1H), 4.43 (br dd, 1H), 5.52 (s, 1H), 5.67 (br d, 1H), 5.74 (s, 1H), 7.63 (t, 1H), 8.91 (s, 1H), 8.99 (d, 2H). MS obsd. (ESI$^+$) [(M+H)$^+$]: 392. [a]$_D^{20}$=105.1° (0.055 g/100 mL, methanol).

Example 202: 4-[2-fluoro-6-(5-methyl-2-pyrimidin-2-yl-7,8-dihydro-5H-pyrido[4,3-d]pyrimidin-6-yl)-4-pyridyl]morpholine

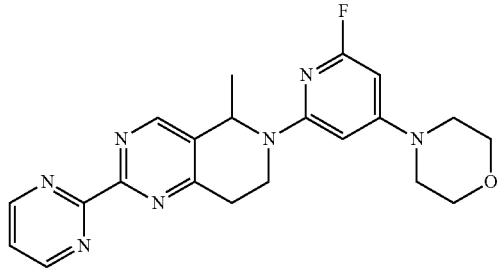 [SMILES: CC1c2cnc(-c3ncccn3)nc2CCN1c1cc(N2CCOCC2)cc(F)n1]

A mixture of 6-(4,6-difluoro-2-pyridyl)-5-methyl-2-pyrimidin-2-yl-7,8-dihydro-5H-pyrido[4,3-d]pyrimidine (100.0 mg, 0.29 mmol), morpholine (76.6 mg, 0.88 mmol) and K$_2$CO$_3$ (121.8 mg, 0.88 mmol) in DMA (3 mL) was heated at 110° C. with stirring for 16 hrs. The resulting mixture was partitioned between brine (4 mL) and DCM (3 mL). The aqueous layer was separated and extracted with DCM for three times. The combined organic layer was washed with water and brine, then dried over anhydrous Na$_2$SO$_4$ and concentrated in vacuo. The residue was purified by prep-HPLC to afford (21.0 mg) as a red brown solid. $^1$H NMR (400 MHz CDCl$_3$) δ: 9.02 (d, 2H), 8.80 (s, 1H), 7.39-7.45 (m, 1H), 5.79-5.86 (m, 1H), 5.62-5.75 (m, 2H), 4.32-4.45 (m, 1H), 3.82 (d, 4H), 3.42-3.55 (m, 1H), 3.28 (br. s., 6H), 1.56 (d, 3H). MS obsd. (ESI$^+$) [(M+H)$^+$]: 408.

Example 203: (−)-2-fluoro-N-methyl-6-[5-methyl-2-pyrimidin-2-yl-7,8-dihydro-5H-pyrido[4,3-d]pyrimidin-6-yl]pyridin-4-amine

Step 1: Preparation of 2,6-difluoro-N-methyl-pyridin-4-amine

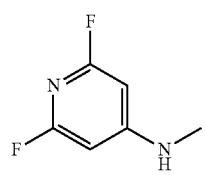

A mixture of 2,4,6-trifluoropyridine (5.0 g, 37.6 mmol) and an aqueous solution of methylamine (10.7 g, 10 mL, 138 mmol) was stirred at rt overnight. The resulting mixture was extracted with EA (100 mL) for three times. The combined organic layer was dried over anhydrous Na$_2$SO$_4$ and concentrated in vacuo to give a crude 2,6-difluoro-N-methyl-pyridin-4-amine (3.6 g), which was used in the next step directly without any further purification.

Step 2: Preparation of methyl 5-[(2,6-difluoro-4-pyridyl)-methyl-amino]-5-oxo-pentanoate

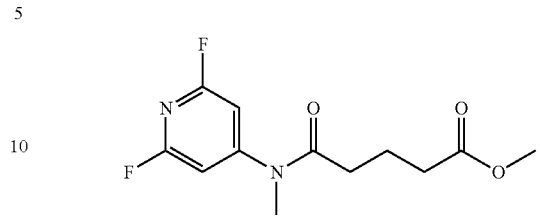

A mixture of glutaric anhydride (950 mg, 8.33 mmol) and 2,6-difluoro-N-methylpyridin-4-amine (600 mg, 4.16 mmol) was heated at 150° C. for 2 hrs in a microwave reactor. The reaction mixture was cooled to rt and diluted with acetone (20 mL), to the resulting mixture were added potassium carbonate (1.73 g, 12.5 mmol) and iodomethane (1.77 g, 781 μl, 12.5 mmol) successively. The resulting mixture was stirred at rt for 3 hrs and then filtered. The filtrate was concentrated in vacuo. The residue was purified by column to give methyl 5-((2,6-difluoropyridin-4-yl)(methyl)amino)-5-oxopentanoate (560 mg) as light yellow oil.

Step 3: Preparation of methyl (+/−)-5-[[2-fluoro-6-[5-methyl-2-pyrimidin-2-yl-7,8-dihydro-5H-pyrido[4,3-d]pyrimidin-6-yl]-4-pyridyl]-methyl-amino]-5-oxo-pentanoate A mixture of (+)-5-methyl-2-pyrimidin-2-yl-5,6,7,8-tetrahydropyrido[4,3-d]pyrimidine (310 mg, 1.36 mmol) and methyl 5-[(2,6-difluoro-4-pyridyl)-methyl-amino]-5-oxo-pentanoate (560 mg, 2.06 mmol) in DMSO (2 mL) and DIPEA (6 mL) was heated at 120° C. with stirring overnight. The resulting mixture was diluted with H$_2$O (20 mL) and extracted with EA (50 mL) for three times. The combined organic layer was dried over anhydrous Na$_2$SO$_4$ and concentrated in vacuo to give methyl (+/−)-5-[[2-fluoro-6-[5-methyl-2-pyrimidin-2-yl-7,8-dihydro-5H-pyrido[4,3-d]pyrimidin-6-yl]-4-pyridyl]-methyl-amino]-5-oxo-pentanoate (490 mg) as yellow oil.

Step 4: Preparation (−)-2-fluoro-N-methyl-6-[5-methyl-2-pyrimidin-2-yl-7,8-dihydro-5H-pyrido[4,3-d]pyrimidin-6-yl]pyridin-4-amine To a solution of methyl (+/−)-5-[[2-fluoro-6-[5-methyl-2-pyrimidin-2-yl-7,8-dihydro-5H-pyrido[4,3-d]pyrimidin-6-yl]-4-pyridyl]-methyl-amino]-5-oxo-pentanoate (490 mg, 1.02 mmol) in THF (10 mL) was added a solution of lithium hydroxide (48.9 mg, 2.04 mmol) in water (2 mL). The mixture was stirred at rt overnight. The mixture acidified by 1M HCl and concentrated in vacuo. The residue was purified by prep-HPLC to give (−)-2-fluoro-N-methyl-6-[5-methyl-2-pyrimidin-2-yl-7,8-dihydro-5H-pyrido[4,3-d]pyrimidin-6-yl]pyridin-4-amine (10 mg) as light yellow solid. $^1$H NMR (400 MHz, Methanol-d4) δ: 1.49 (d, 3H), 2.78 (s, 3H), 2.93-3.21 (m, 2H), 3.35-3.42 (m, 1H), 4.36 (br dd, 1H), 5.47 (s, 1H), 5.52-5.65 (m, 1H), 5.75 (s, 1H), 7.59 (t, 1H), 8.77 (s, 1H), 8.98 (d, 2H). MS obsd. (ESI$^+$) [(M+H)$^+$]: 352. [a]$_D^{20}$=−170.6° (0.05 g/100 mL, methanol).

Example 204 and 205: (+)-4-fluoro-N,N-dimethyl-6-[5-methyl-2-pyrimidin-2-yl-7,8-dihydro-5H-pyrido[4,3-d]pyrimidin-6-yl]pyridin-2-amine and (−)-4-fluoro-N,N-dimethyl-6-[5-methyl-2-pyrimidin-2-yl-7,8-dihydro-5H-pyrido[4,3-d]pyrimidin-6-yl]pyridin-2-amine Example 206 and 207: (+)-2-fluoro-N,N-dimethyl-6-[5-methyl-2-pyrimidin-2-yl-7,8-dihydro-5H-pyrido[4,3-d]pyrimidin-6-yl]pyridin-4-amine and (−)-2-fluoro-N,N-dimethyl-6-[5-methyl-2-pyrimidin-2-yl-7,8-dihydro-5H-pyrido[4,3-d]pyrimidin-6-yl]pyridin-4-amine

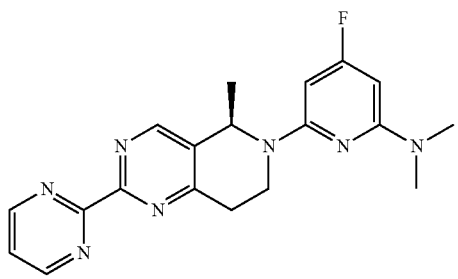

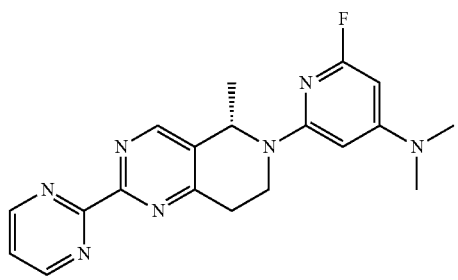

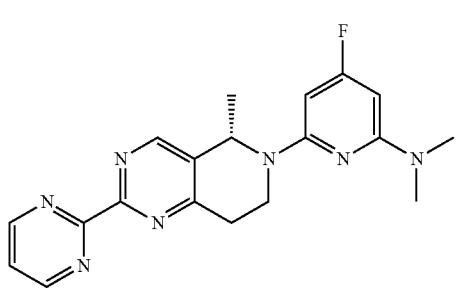

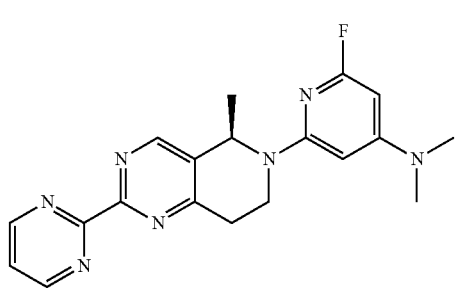

4-Fluoro-N,N-dimethyl-6-[5-methyl-2-pyrimidin-2-yl-7,8-dihydro-5H-pyrido[4,3-d]pyrimidin-6-yl]pyridin-2-amine (190 mg, Example 197) was chiral separated by SFC to give (+)-4-fluoro-N,N-dimethyl-6-[5-methyl-2-pyrimidin-2-yl-7,8-dihydro-5H-pyrido[4,3-d]pyrimidin-6-yl]pyridin-2-amine (40 mg) and (+)-4-fluoro-N,N-dimethyl-6-[5-methyl-2-pyrimidin-2-yl-7,8-dihydro-5H-pyrido[4,3-d]pyrimidin-6-yl]pyridin-2-amine (40 mg).

Example 204: (+)-4-fluoro-N,N-dimethyl-6-[5-methyl-2-pyrimidin-2-yl-7,8-dihydro-5H-pyrido[4,3-d]pyrimidin-6-yl]pyridin-2-amine, light yellow solid, $^1$H NMR (400 MHz, Methanol-d4) δ: 1.58 (d, 3H), 3.04 (s, 6H), 3.12 (br s, 2H), 3.39-3.52 (m, 1H), 4.47-4.58 (m, 1H), 5.65 (d, 1H), 5.70-5.80 (m, 1H), 5.85-5.95 (m, 1H), 7.60-7.68 (m, 1H), 8.84-8.90 (m, 1H), 9.03 (d, 2H). MS obsd. (ESI$^+$) [(M+H)$^+$]: 366. $[a]_D^{20}$=92.1° (0.1 g/100 mL, methanol).

Example 205: (−)-4-fluoro-N,N-dimethyl-6-[5-methyl-2-pyrimidin-2-yl-7,8-dihydro-5H-pyrido[4,3-d]pyrimidin-6-yl]pyridin-2-amine, light yellow solid, $^1$H NMR (400 MHz, Methanol-d4) δ: 1.58 (d, 3H), 3.04 (s, 6H), 3.12 (br s, 2H), 3.39-3.52 (m, 1H), 4.47-4.58 (m, 1H), 5.65 (d, 1H), 5.70-5.80 (m, 1H), 5.85-5.95 (m, 1H), 7.60-7.68 (m, 1H), 8.84-8.90 (m, 1H), 9.03 (d, 2H). MS obsd. (ESI$^+$) [(M+H)$^+$]: 366. $[a]_D^{20}$=−103.7° (0.1 g/100 mL, methanol).

2-Fluoro-N,N-dimethyl-6-[5-methyl-2-pyrimidin-2-yl-7,8-dihydro-5H-pyrido[4,3-d]pyrimidin-6-yl]pyridin-4-amine (190 mg, Example 196) was chiral separated by SFC to give (+)-2-fluoro-N,N-dimethyl-6-[5-methyl-2-pyrimidin-2-yl-7,8-dihydro-5H-pyrido[4,3-d]pyrimidin-6-yl]pyridin-4-amine (46 mg) and (−)-2-fluoro-N,N-dimethyl-6-[5-methyl-2-pyrimidin-2-yl-7,8-dihydro-5H-pyrido[4,3-d]pyrimidin-6-yl]pyridin-4-amine (54 mg).

Example 206: (+)-2-fluoro-N,N-dimethyl-6-[5-methyl-2-pyrimidin-2-yl-7,8-dihydro-5H-pyrido[4,3-d]pyrimidin-6-yl]pyridin-4-amine, light yellow solid, $^1$H NMR (400 MHz, DMSO-d6) δ: 8.92 (d, 2H), 8.84 (s, 1H), 7.51-7.61 (m, 1H), 5.77-5.84 (m, 1H), 5.55-5.68 (m, 2H), 4.29-4.43 (m, 1H), 3.28-3.39 (m, 1H), 2.91 (s, 8H), 1.38-1.46 (m, 3H). MS obsd. (ESI$^+$) [(M+H)$^+$]: 366. $[a]_D^{25}$=+134.0° (0.1 g/100 mL, methanol).

Example 207: (−)-2-fluoro-N,N-dimethyl-6-[5-methyl-2-pyrimidin-2-yl-7,8-dihydro-5H-pyrido[4,3-d]pyrimidin-6-yl]pyridin-4-amine, light yellow solid, $^1$H NMR (400 MHz, DMSO-d6) δ: 8.90-8.97 (m, 2H), 8.79-8.88 (m, 1H), 7.51-7.63 (m, 1H), 5.74-5.84 (m, 1H), 5.52-5.67 (m, 2H), 4.30-4.45 (m, 1H), 3.27-3.40 (m, 1H), 2.91 (s, 8H), 1.35-1.47 (m, 3H). MS obsd. (ESI$^+$) [(M+H)$^+$]: 366. $[a]_D^{25}$=−110.0° (0.1 g/100 mL, methanol).

Example 208 and 209: 6-(6-fluoro-4-piperazin-1-yl-2-pyridyl)-5-methyl-2-pyrimidin-2-yl-7,8-dihydro-5H-pyrido[4,3-d]pyrimidine and 6-(4-fluoro-6-piperazin-1-yl-2-pyridyl)-5-methyl-2-pyrimidin-2-yl-7,8-dihydro-5H-pyrido[4,3-d]pyrimidine Example 208

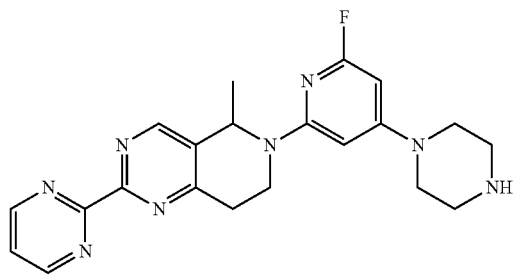

Example 209

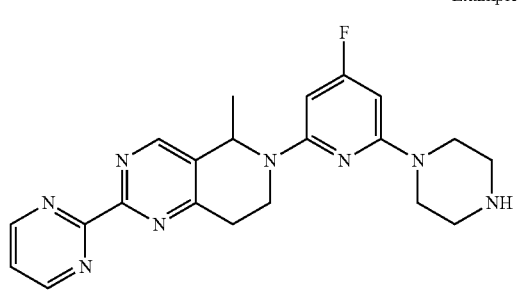

A mixture of 6-(4, 6-difluoro-2-pyridyl)-5-methyl-2-pyrimidin-2-yl-7,8-dihydro-5H-pyrido[4,3-d]pyrimidine (80 mg, 0.23 mmol), piperazine (60 mg, 0.70 mmol) and K$_2$CO$_3$ (97 mg, 0.70 mmol) in DMA (1 mL) was heated at 110° C. with stirring for 12 hrs. The resulting mixture was concentrated in vacuo. The residue was partitioned between DCM (20 mL) and H$_2$O (10 mL). The organic layer was separated and concentrated in vacuo. The residue was purified by prep-HPLC to afford 6-(6-fluoro-4-piperazin-1-yl-2-pyridyl)-5-methyl-2-pyrimidin-2-yl-7,8-dihydro-5H-pyrido[4,3-d]pyrimidine (20.6 mg) as a white solid and 6-(4-fluoro-6-piperazin-1-yl-2-pyridyl)-5-methyl-2-pyrimidin-2-yl-7,8-dihydro-5H-pyrido[4,3-d]pyrimidine (8.8 mg) as a white solid.

Example 208: 6-(6-fluoro-4-piperazin-1-yl-2-pyridyl)-5-methyl-2-pyrimidin-2-yl-7,8-dihydro-5H-pyrido[4,3-d]pyrimidine, $^1$H NMR (400 MHz, CDCl$_3$) δ: 9.05 (d, 2H), 8.84 (s, 1H), 7.46 (t, 1H), 5.86 (s, 1H), 5.78-5.63 (m, 2H), 4.46-4.32 (m, 1H), 3.59-3.41 (m, 5H), 3.35-3.15 (m, 6H), 1.59 (d, 3H). MS obsd. (ESI$^+$) [(M+H)$^+$]: 407.

Example 209: 6-(4-fluoro-6-piperazin-1-yl-2-pyridyl)-5-methyl-2-pyrimidin-2-yl-7,8-dihydro-5H-pyrido[4,3-d]pyrimidine, $^1$H NMR (400 MHz, CDCl$_3$) δ: 9.06 (d, 2H), 8.84 (s, 1H), 7.46 (t, 1H), 5.89 (d, 1H), 5.77 (d, 1H), 5.62 (d, 1H), 4.43 (d, 1H), 3.72 (br. s., 4H), 3.53-3.44 (m, 1H), 3.33-3.10 (m, 6H), 1.59 (d, 4H). MS obsd. (ESI$^+$) [(M+H)$^+$]: 407.

Example 210: 2-fluoro-6-(5-methyl-2-pyrimidin-2-yl-7,8-dihydro-5H-pyrido[4,3-d]pyrimidin-6-yl)pyridin-4-amine

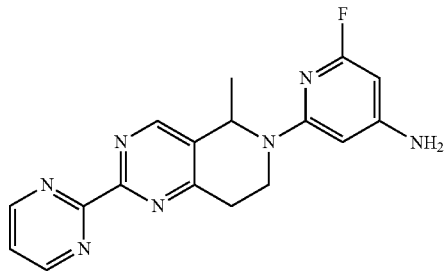 [SMILES: CC1c2cnc(-c3ncccn3)nc2CCN1c1cc(N)cc(F)n1]

A mixture of 6-(4,6-difluoro-2-pyridyl)-5-methyl-2-pyrimidin-2-yl-7,8-dihydro-5H-pyrido[4,3-d]pyrimidine (100 mg, 0.29 mmol) in EtOH (3 mL) and concentrated NH$_3$.H$_2$O (7 mL) was heated at 90° C. with stirring for 16 hrs. The mixture was cooled to rt and concentrated in vacuo. The residue was purified by prep-HPLC to give 2-fluoro-6-(5-methyl-2-pyrimidin-2-yl-7,8-dihydro-5H-pyrido[4,3-d]pyrimidin-6-yl)pyridin-4-amine (10 mg) as a yellow solid. $^1$H NMR (400 MHz, Methanol-d4) δ: 9.03 (s, 2H), 8.85 (s, 1H), 7.64 (t, 1H), 5.91 (s, 1H), 5.61 (q, 1H), 5.55 (d, 1H), 4.37 (dd, 1H), 3.38-3.53 (m, 1H), 3.03-3.25 (m, 2H), 1.55 (d, 3H). MS obsd. (ESI$^+$) [(M+H)$^+$]: 338.

Example 211 and 212: N-[2-fluoro-6-(5-methyl-2-pyrimidin-2-yl-7,8-dihydro-5H-pyrido[4,3-d]pyrimidin-6-yl)-4-pyridyl]methanesulfonamide and N-[4-fluoro-6-(5-methyl-2-pyrimidin-2-yl-7,8-dihydro-5H-pyrido[4,3-d]pyrimidin-6-yl)-2-pyridyl]methanesulfonamide Example 211

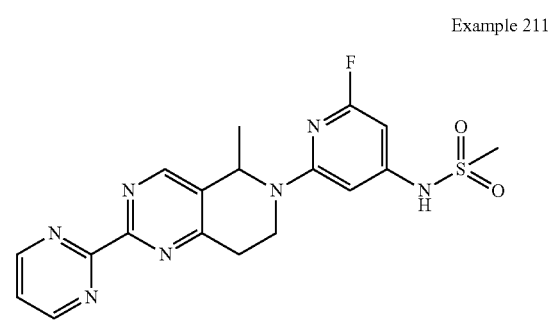

Example 212

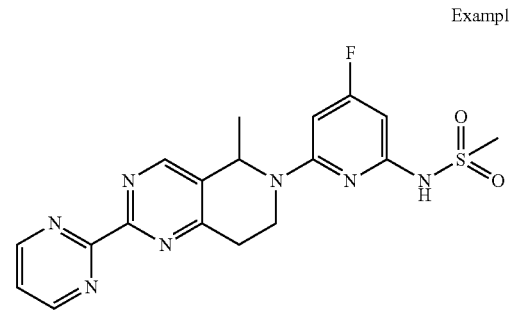

A mixture of 6-(4,6-difluoro-2-pyridyl)-5-methyl-2-pyrimidin-2-yl-7,8-dihydro-5H-pyrido[4,3-d]pyrimidine (100 mg, 0.30 mmol), methanesulfonamide (140 mg, 1.47 mmol) and K₂CO₃ (200 mg, 1.47 mmol) in NMP (2 mL) was heated at 120° C. with stirring for 16 hrs. The mixture was cooled to rt, and partitioned between H₂O (5 mL) and EA (20 mL). The aqueous layer was separated and extracted with EA twice. The combined organic layers were washed with brine, dried over anhydrous Na₂SO₄, and concentrated in vacuo. The residue was purified by prep-HPLC to give N-[2-fluoro-6-(5-methyl-2-pyrimidin-2-yl-7,8-dihydro-5H-pyrido[4,3-d]pyrimidin-6-yl)-4-pyridyl]methanesulfonamide (8 mg) as a light yellow solid and N-[4-fluoro-6-(5-methyl-2-pyrimidin-2-yl-7,8-dihydro-5H-pyrido[4,3-d]pyrimidin-6-yl)-2-pyridyl]methanesulfonamide (4 mg) as a light yellow solid.

Example 211: N-[2-fluoro-6-(5-methyl-2-pyrimidin-2-yl-7,8-dihydro-5H-pyrido[4,3-d]pyrimidin-6-yl)-4-pyridyl]methanesulfonamide, ¹H NMR (400 MHz, Methanol-d4) δ: 9.03 (d, 2H), 8.90 (s, 1H), 7.65 (s, 1H), 6.44 (s, 1H), 6.13 (s, 1H), 5.70 (d, 1H), 4.46 (d, 1H), 3.48-3.64 (m, 1H), 3.17 (m, 2H), 3.12 (s, 3H), 1.60 (d, 3H). MS obsd. (ESI⁺) [(M+H)⁺]: 416.

Example 212: N-[4-fluoro-6-(5-methyl-2-pyrimidin-2-yl-7,8-dihydro-5H-pyrido[4,3-d]pyrimidin-6-yl)-2-pyridyl]methanesulfonamide, ¹H NMR (400 MHz, Methanol-d4) δ: 9.03 (m, 2H), 8.89 (s, 1H), 7.66 (s, 1H), 6.37 (d, 1H), 6.05 (d, 1H), 5.76 (d, 1H), 4.56 (d, 2H), 3.50-3.61 (m, 1H), 3.31 (s, 3H), 3.17 (m, 2H), 1.62 (d, 3H). MS obsd. (ESI⁺) [(M+H)⁺]: 416.

Example 213: (−)-N,N,6-trimethyl-2-[5-methyl-2-pyrimidin-2-yl-7,8-dihydro-5H-pyrido[4,3-d]pyrimidin-6-yl]pyrimidin-4-amine

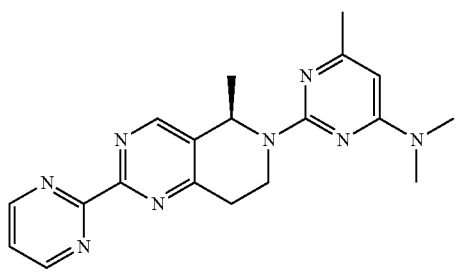

Step 1: Preparation of 2-chloro-N,N,6-trimethyl-pyrimidin-4-amine

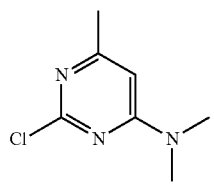

To a solution of 2,4-dichloro-6-methylpyrimidine (2.1 g, 12.9 mmol) in THF (50 mL) cooled to 0° C. was added a solution of dimethylamine (11.5 g, 12.9 mL) in THF. The mixture was stirred at 10° C. for 1 hr and the mixture was then concentrated in vacuo. The residue was purified by column to give 2-chloro-N,N,6-trimethylpyrimidin-4-amine (730 mg) as white solid.

Step 2: Preparation of (−)-N,N,6-trimethyl-2-[5-methyl-2-pyrimidin-2-yl-7,8-dihydro-5H-pyrido[4,3-d]pyrimidin-6-yl]pyrimidin-4-amine

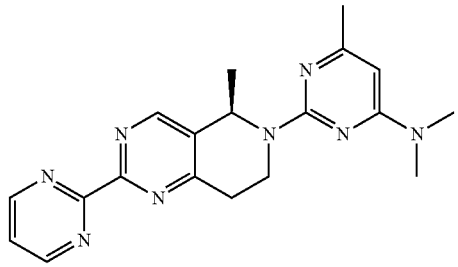 [SMILES: Cc1cc(N(C)C)nc(N2CCc3nc(-c4ncccn4)ncc3[C@H]2C)n1]

A mixture of (+)-5-methyl-2-(pyrimidin-2-yl)-5,6,7,8-tetrahydropyrido[4,3-d]pyrimidine (110 mg, 484 μmol) and 2-chloro-N,N,6-trimethylpyrimidin-4-amine (83.1 mg, 484 μmol) in NMP (3 mL) was heated at 200° C. in a microwave reactor for 1 hr. The resulting mixture was cooled and purified by prep-HPLC to give (−)-N,N,6-trimethyl-2-[5-methyl-2-pyrimidin-2-yl-7,8-dihydro-5H-pyrido[4,3-d]pyrimidin-6-yl]pyrimidin-4-amine (30 mg) as light brown solid. ¹H NMR (400 MHz, CDCl₃) δ: 1.63 (d, 3H), 2.37 (s, 3H), 3.17 (s, 6H), 3.22-3.33 (m, 2H), 3.42-3.53 (m, 1H), 5.03 (br dd, 1H), 5.84 (s, 1H), 6.05 (q, 1H), 7.41-7.49 (m, 1H), 8.84 (s, 1H), 9.03 (d, 2H). MS obsd. (ESI⁺) [(M+H)⁺]: 363. [a]_D^{20}=−84.0° (0.1 g/100 mL, methanol).

Example 214 and 215: 4-[4-fluoro-6-(5-methyl-2-pyrimidin-2-yl-7,8-dihydro-5H-pyrido[4,3-d]pyrimidin-6-yl)-2-pyridyl]piperazin-2-one and 4-[2-fluoro-6-(5-methyl-2-pyrimidin-2-yl-7,8-dihydro-5H-pyrido[4,3-d]pyrimidin-6-yl)-4-pyridyl]piperazin-2-one Example 214

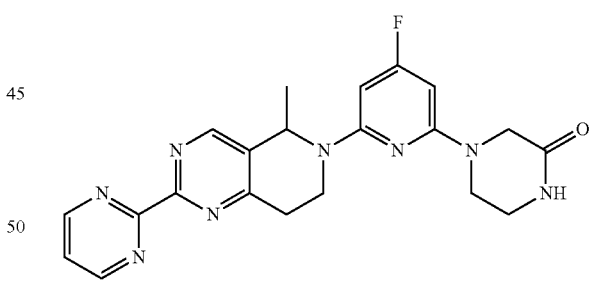

Example 215

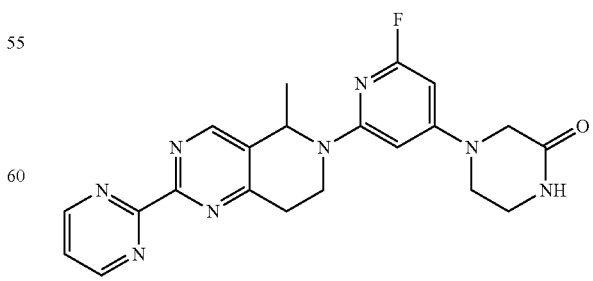

A mixture of 6-(4,6-difluoro-2-pyridyl)-5-methyl-2-pyrimidin-2-yl-7,8-dihydro-5H-pyrido[4,3-d]pyrimidine (100 mg, 0.29 mmol, the product of step 3 in Example 151), piperazin-2-one (88 mg, 0.88 mmol) and K₂CO₃ (73 mg, 0.53 mmol) in NMP (2 mL) was heated at 170° C. in a microwave reactor for 2 hrs. The resulting mixture was diluted with DCM (10 mL) and then filtered. The filtrated was concentrated in vacuo and the residue was purified by prep-HPLC to give 4-[4-fluoro-6-(5-methyl-2-pyrimidin-2-yl-7,8-dihydro-5H-pyrido[4,3-d]pyrimidin-6-yl)-2-pyridyl] piperazin-2-one (21 mg) and 4-[2-fluoro-6-(5-methyl-2-pyrimidin-2-yl-7,8-dihydro-5H-pyrido[4,3-d]pyrimidin-6-yl)-4-pyridyl]piperazin-2-one (20 mg).

Example 214: 4-[4-fluoro-6-(5-methyl-2-pyrimidin-2-yl-7,8-dihydro-5H-pyrido[4,3-d]pyrimidin-6-yl)-2-pyridyl]piperazin-2-one, light yellow solid, ¹H NMR (400 MHz, Methanol-d4) δ: 9.03 (d, 2H), 8.91 (s, 1H), 7.65 (t, 1H), 6.07 (d, 1H), 5.87 (d, 1H), 5.78 (q, 1H), 4.52 (d, 1H), 4.15 (s, 2H), 3.73-3.83 (m, 2H), 3.46-3.55 (m, 1H), 3.43 (t, 2H), 3.14 (d, 2H), 1.59 (d, 3H). MS obsd. (ESI⁺) [(M+H)⁺]: 421.

Example 215: 4-[2-fluoro-6-(5-methyl-2-pyrimidin-2-yl-7,8-dihydro-5H-pyrido[4,3-d]pyrimidin-6-yl)-4-pyridyl]piperazin-2-one, light yellow solid, ¹H NMR (400 MHz, Methanol-d4) δ: 9.03 (d, 2H), 8.88 (s, 1H), 7.64 (t, 1H), 6.03 (s, 1H), 5.82 (s, 1H), 5.75 (q, 1H), 4.47-4.58 (m, 1H), 4.00 (s, 2H), 3.58-3.65 (m, 2H), 3.43-3.54 (m, 3H), 3.07-3.24 (m, 2H), 1.58 (d, 3H). MS obsd. (ESI⁺) [(M+H)⁺]: 421.

Example 216 and 217: 2-fluoro-N,N-dimethyl-6-[5-methyl-2-(2-pyridyl)-7,8-dihydro-5H-pyrido[4,3-d]pyrimidin-6-yl]pyridin-4-amine and 4-fluoro-N,N-dimethyl-6-[5-methyl-2-(2-pyridyl)-7,8-dihydro-5H-pyrido[4,3-d]pyrimidin-6-yl]pyridin-2-amine Example 216

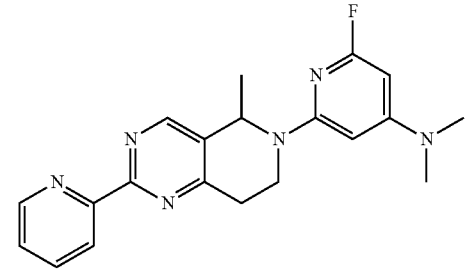

Example 217

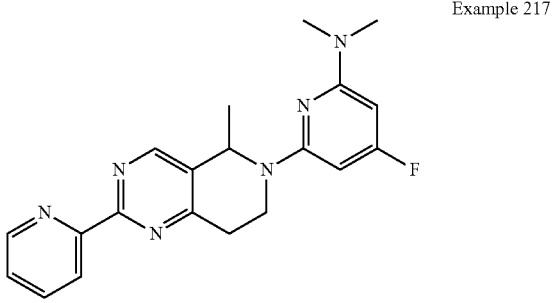

A mixture of 6-(4,6-difluoro-2-pyridyl)-5-methyl-2-(2-pyridyl)-7,8-dihydro-5H-pyrido[4,3-d]pyrimidine (160 mg, 472 μmol), dimethylamine hydrochloride (115 mg, 1.41 mmol) and potassium carbonate (195 mg, 1.41 mmol) in NMP (5 mL) was heated at 100° C. with stirring for 5 hrs. The resulting mixture was purified by prep-HPLC to give 2-fluoro-N,N-dimethyl-6-[5-methyl-2-(2-pyridyl)-7,8-dihydro-5H-pyrido[4,3-d]pyrimidin-6-yl]pyridin-4-amine (70 mg) and 4-fluoro-N,N-dimethyl-6-[5-methyl-2-(2-pyridyl)-7,8-dihydro-5H-pyrido[4,3-d]pyrimidin-6-yl]pyridin-2-amine (20 mg). Both two compounds are light yellow solid.

Example 216: 2-fluoro-N,N-dimethyl-6-[5-methyl-2-(2-pyridyl)-7,8-dihydro-5H-pyrido[4,3-d]pyrimidin-6-yl]pyridin-4-amine, light yellow solid, ¹H NMR (400 MHz, CDCl₃) δ: 1.54 (d, 3H), 3.01 (s, 6H), 3.08-3.29 (m, 2H), 3.41-3.49 (m, 1H), 4.34-4.43 (m, 1H), 5.57 (s, 1H), 5.60-5.71 (m, 2H), 7.39-7.47 (m, 1H), 7.89 (td, 1H), 8.50 (d, 1H), 8.71 (s, 1H), 8.80-8.86 (m, 1H). MS obsd. (ESI⁺) [(M+H)⁺]: 363.

Example 217: 4-fluoro-N,N-dimethyl-6-[5-methyl-2-(2-pyridyl)-7,8-dihydro-5H-pyrido[4,3-d]pyrimidin-6-yl]pyridin-2-amine, light yellow solid, ¹H NMR (400 MHz, CDCl₃) δ: 1.55 (d, 3H), 3.05 (s, 6H), 3.11-3.27 (m, 2H), 3.38-3.47 (m, 1H), 3.41-3.48 (s, 1H), 4.37-4.49 (m, 1H), 5.57-5.67 (m, 2H), 5.73 (dd, 1H), 7.40 (ddd, 1H), 7.86 (td, 1H), 8.47-8.52 (m, 1H), 8.70 (s, 1H), 8.83 (d, 1H). MS obsd. (ESI⁺) [(M+H)⁺]: 363.

Example 218 and 219: 6-[6-fluoro-4-(1-piperidyl)-2-pyridyl]-5-methyl-2-(2-pyridyl)-7,8-dihydro-5H-pyrido[4,3-d]pyrimidine and 6-[4-fluoro-6-(1-piperidyl)-2-pyridyl]-5-methyl-2-(2-pyridyl)-7,8-dihydro-5H-pyrido[4,3-d]pyrimidine Example 218

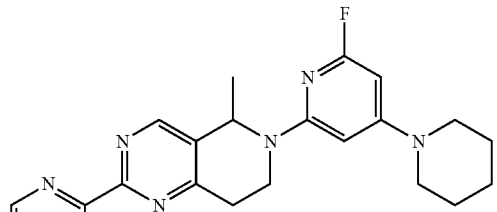

Example 219

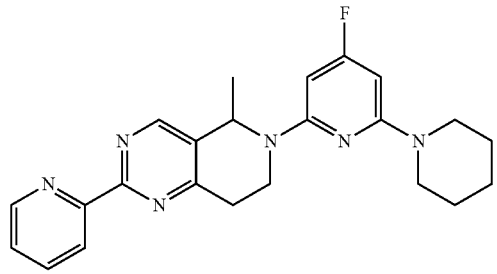

A mixture of 6-(4,6-difluoro-2-pyridyl)-5-methyl-2-(2-pyridyl)-7,8-dihydro-5H-pyrido[4,3-d]pyrimidine (136 mg, 0.4 mmol), piperidine (102 mg, 1.2 mmol) and K₂CO₃ (166 mg, 1.2 mmol) in DMA (1 mL) was heated at 110° C. for 20 hrs. The reaction mixture was filtered and the filtrate was purified by prep-HPLC to afford 6-[6-fluoro-4-(1-piperidyl)-2-pyridyl]-5-methyl-2-(2-pyridyl)-7,8-dihydro-5H-pyrido[4,3-d]pyrimidine (65 mg) and 6-[4-fluoro-6-(1-piperidyl)-2-pyridyl]-5-methyl-2-(2-pyridyl)-7,8-dihydro-5H-pyrido[4,3-d]pyrimidine (16 mg).

Example 218: 6-(6-fluoro-4-(piperidin-1-yl)pyridin-2-yl)-5-methyl-2-(pyridin-2-yl)-5,6,7,8-tetrahydropyrido[4,3-d]pyrimidine, yellow powder, ¹H NMR (400 MHz, CDCl₃) δ: 8.87-8.80 (m, 1H), 8.70 (s, 1H), 8.49 (td, 1H), 7.85 (dt, 1H), 7.39 (ddd, 1H), 5.83 (s, 1H), 5.71 (s, 1H), 5.64 (q, 1H), 4.40-4.34 (m, 1H), 3.51-3.39 (m, 1H), 3.37-3.28 (m, 4H), 3.27-3.10 (m, 2H), 1.72-1.58 (m, 6H), 1.54 (d, 3H). MS obsd. (ESI⁺) [(M+H)⁺]: 405.

Example 219: 6-[4-fluoro-6-(1-piperidyl)-2-pyridyl]-5-methyl-2-(2-pyridyl)-7,8-dihydro-5H-pyrido[4,3-d]pyrimidine, yellow powder, ¹H NMR (400 MHz, CDCl₃) δ: 8.88-8.82 (m, 1H), 8.72 (s, 1H), 8.51 (d, 1H), 7.87 (dt, 1H), 7.41 (ddd, 1H), 5.80-5.70 (m, 2H), 5.60 (q, 1H), 4.47-4.38 (m, 1H), 3.59-3.49 (m, 4H), 3.46-3.39 (m, 1H), 3.28-3.11 (m, 2H), 1.74-1.60 (m, 6H), 1.56 (d, 3H). MS obsd. (ESI⁺) [(M+H)⁺]: 405.

Example 220 and 221: 4-[2-fluoro-6-[5-methyl-2-(2-pyridyl)-7,8-dihydro-5H-pyrido[4,3-d]pyrimidin-6-yl]-4-pyridyl]morpholine and 4-[4-fluoro-6-[5-methyl-2-(2-pyridyl)-7,8-dihydro-5H-pyrido[4,3-d]pyrimidin-6-yl]-2-pyridyl]morpholine Example 220

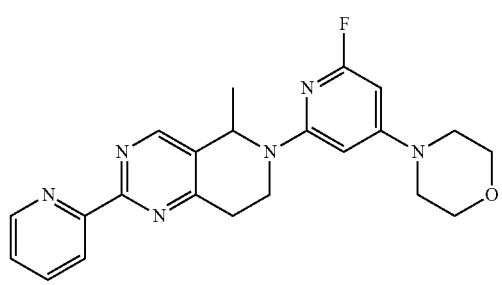

Example 221

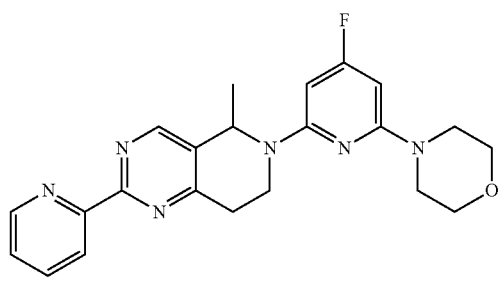

A mixture of 6-(4,6-difluoro-2-pyridyl)-5-methyl-2-(2-pyridyl)-7,8-dihydro-5H-pyrido[4,3-d]pyrimidine (136 mg, 0.4 mmol), morpholine (105 mg, 1.2 mmol) and K₂CO₃ (166 mg, 1.2 mmol) in DMA (1 mL) was heated at 110° C. for 20 hrs. The reaction mixture was filtered and the filtrate was purified by prep-HPLC to afford 4-[2-fluoro-6-[5-methyl-2-(2-pyridyl)-7,8-dihydro-5H-pyrido[4,3-d]pyrimidin-6-yl]-4-pyridyl]morpholine (46 mg) and 4-[4-fluoro-6-[5-methyl-2-(2-pyridyl)-7,8-dihydro-5H-pyrido[4,3-d]pyrimidin-6-yl]-2-pyridyl]morpholine (15 mg).

Example 220: 4-[2-fluoro-6-[5-methyl-2-(2-pyridyl)-7,8-dihydro-5H-pyrido[4,3-d]pyrimidin-6-yl]-4-pyridyl]morpholine, yellow powder, ¹H NMR (400 MHz, CDCl₃) δ: 8.85 (dd, 1H), 8.71 (s, 1H), 8.50 (d, 1H), 7.86 (dt, 1H), 7.40 (ddd, 1H), 5.84 (s, 1H), 5.71 (d, 1H), 5.64 (q, 1H), 4.43-4.33 (m, 1H), 3.89-3.79 (m, 4H), 3.52-3.41 (m, 1H), 3.33-3.27 (m, 4H), 3.26-3.11 (m, 2H), 1.56 (d, 3H). MS obsd. (ESI⁺) [(M+H)⁺]: 407.

Example 221: 4-[4-fluoro-6-[5-methyl-2-(2-pyridyl)-7,8-dihydro-5H-pyrido[4,3-d]pyrimidin-6-yl]-2-pyridyl]morpholine, yellow powder, ¹H NMR (400 MHz, CDCl₃) δ: 8.90-8.81 (m, 1H), 8.72 (s, 1H), 8.51 (d, 1H), 7.87 (dt, 1H), 7.41 (ddd, 1H), 5.85 (dd, 1H), 5.72 (dd, 1H), 5.58 (q, 1H), 4.47-4.38 (m, 1H), 3.84 (t, 4H), 3.56-3.40 (m, 5H), 3.27-3.11 (m, 2H), 1.57 (d, 3H). MS obsd. (ESI⁺) [(M+H)⁺]: 407.

Example 222 and 223: 4-[2-fluoro-6-[5-methyl-2-(2-pyridyl)-7,8-dihydro-5H-pyrido[4,3-d]pyrimidin-6-yl]-4-pyridyl]piperazin-2-one and 4-[4-fluoro-6-[5-methyl-2-(2-pyridyl)-7,8-dihydro-5H-pyrido[4,3-d]pyrimidin-6-yl]-2-pyridyl]piperazin-2-one Example 222

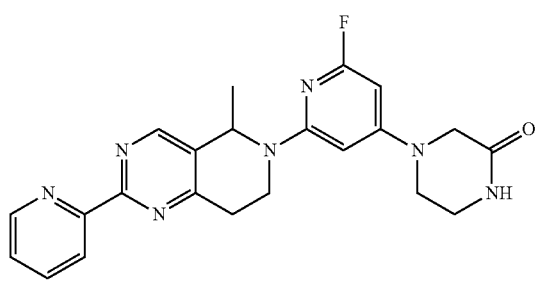

Example 223

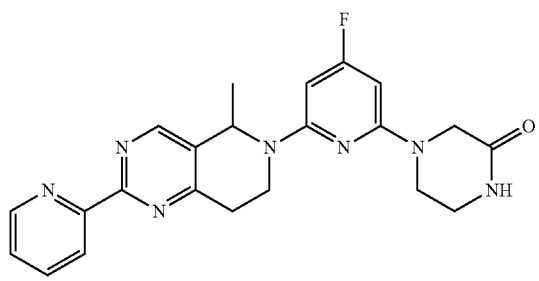

A mixture of 6-(4,6-difluoro-2-pyridyl)-5-methyl-2-(2-pyridyl)-7,8-dihydro-5H-pyrido[4,3-d]pyrimidine (136 mg, 0.4 mmol), piperazin-2-one (120 mg, 1.2 mmol) and K₂CO₃ (166 mg, 1.2 mmol) in DMA (1 mL) was heated at 110° C. for 20 hrs. The reaction mixture was filtered and the filtrate was purified by prep-HPLC to afford 4-[2-fluoro-6-[5-methyl-2-(2-pyridyl)-7,8-dihydro-5H-pyrido[4,3-d]pyrimidin-6-yl]-4-pyridyl]piperazin-2-one (17 mg) and 4-[4-fluoro-6-[5-methyl-2-(2-pyridyl)-7,8-dihydro-5H-pyrido[4,3-d]pyrimidin-6-yl]-2-pyridyl]piperazin-2-one (8 mg).

Example 222: 4-[2-fluoro-6-[5-methyl-2-(2-pyridyl)-7,8-dihydro-5H-pyrido[4,3-d]pyrimidin-6-yl]-4-pyridyl]piperazin-2-one, yellow powder, ¹H NMR (400 MHz, CDCl₃) δ: 8.92-8.80 (m, 1H), 8.73 (s, 1H), 8.51 (d, 1H), 7.87 (dt, 1H), 7.41 (ddd, 1H), 6.61 (br s, 1H), 5.76 (s, 1H), 5.71-5.59 (m, 2H), 4.47-4.36 (m, 1H), 4.04 (s, 2H), 3.64-3.42 (m, 5H), 3.31-3.13 (m, 2H), 1.57 (d, 3H). MS obsd. (ESI⁺) [(M+H)⁺]: 420.

Example 223: 4-[4-fluoro-6-[5-methyl-2-(2-pyridyl)-7,8-dihydro-5H-pyrido[4,3-d]pyrimidin-6-yl]-2-pyridyl]piperazin-2-one, yellow powder, ¹H NMR (400 MHz, CDCl₃) δ: 8.86 (d, 1H), 8.74 (s, 1H), 8.52 (d, 1H), 7.88 (dt, 1H), 7.42 (ddd, 1H), 6.30 (br s, 1H), 5.88 (dd, 1H), 5.71 (dd, 1H), 5.60 (q, 1H), 4.49-4.37 (m, 1H), 4.21 (s, 2H), 3.86-3.76 (m, 2H), 3.59-3.40 (m, 3H), 3.28-3.14 (m, 2H), 1.58 (d, 3H). MS obsd. (ESI⁺) [(M+H)⁺]: 420.

Example 224: 6-(6-fluoro-4-pyrrolidin-1-yl-2-pyridyl)-5-methyl-2-(2-pyridyl)-7,8-dihydro-5H-pyrido[4,3-d]pyrimidine

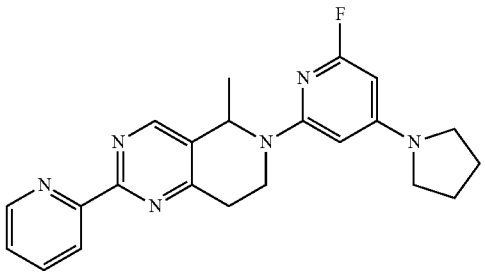 [SMILES: CC1c2cnc(-c3ccccn3)nc2CCN1c1cc(N2CCCC2)cc(F)n1]

To a solution of 6-(4,6-difluoro-2-pyridyl)-5-methyl-2-(2-pyridyl)-7,8-dihydro-5H-pyrido[4,3-d]pyrimidine (170 mg, 0.5 mmol) in NMP (5 mL) was added potassium carbonate (207 mg, 1.5 mmol) and pyrrolidine (107 mg, 1.5 mmol). After being heated and stirred at 110° C. for 5 hrs, the resulting mixture was poured into water (20 mL) and the aqueous solution was extracted with DCM (50 mL) twice. The organic layers were combined, then washed with water and brine, dried over anhydrous $Na_2SO_4$ and concentrated in vacuo. The residue was purified by prep-HPLC to give 6-(6-fluoro-4-pyrrolidin-1-yl-2-pyridyl)-5-methyl-2-(2-pyridyl)-7,8-dihydro-5H-pyrido[4,3-d]pyrimidine (95 mg) as a yellow powder. $^1$H NMR (400 MHz, CDCl$_3$) δ: 8.80-8.92 (m, 1H), 8.68-8.79 (m, 1H), 8.47-8.58 (m, 1H), 7.82-7.96 (m, 1H), 7.35-7.49 (m, 1H), 5.62-5.75 (m, 1H), 5.54-5.57 (m, 1H), 5.49 (d, 1H), 4.36-4.45 (m, 1H), 3.42-3.51 (m, 1H), 3.30-3.39 (m, 4H), 3.12-3.29 (m, 2H), 2.00-2.09 (m, 4H), 1.53-1.58 (m, 3H). MS obsd. (ESI$^+$) [(M+H)$^+$]: 391.

Example 225: (−)-4-[4-fluoro-6-(5-methyl-2-pyrimidin-2-yl-7,8-dihydro-5H-pyrido[4,3-d]pyrimidin-6-yl)-2-pyridyl]piperazin-2-one

Step 1: Preparation of (+/−)-6-(4,6-difluoro-2-pyridyl)-5-methyl-2-pyrimidin-2-yl-7,8-dihydro-5H-pyrido[4,3-d]pyrimidine To a solution of (+)-5-methyl-2-pyrimidin-2-yl-5,6,7,8-tetrahydropyrido[4,3-d]pyrimidine (2.27 g, 10 mmol) in DMSO (10 mL) and DIEA (10 mL) was added 2,4,6-trifluoropyridine (1.46 g, 11 mmol). The reaction mixture is heated to 150° C. for 1 hour in a microwave reactor. After the reaction was complete, the reaction mixture was cooled to rt, poured into water (50 mL) and extracted with DCM (50 mL) twice. The organic layers were combined, then washed with water and brine, dried over anhydrous $Na_2SO_4$ and concentrated in vacuo. The residue was purified by prep-HPLC to give (+/−)-6-(4,6-difluoro-2-pyridyl)-5-methyl-2-pyrimidin-2-yl-7,8-dihydro-5H-pyrido[4,3-d]pyrimidine (1.2 g) as a yellow solid.

Step 2: Preparation of (−)-4-[4-fluoro-6-(5-methyl-2-pyrimidin-2-yl-7,8-dihydro-5H-pyrido[4,3-d]pyrimidin-6-yl)-2-pyridyl]piperazin-2-one To a mixture of (+/−)-6-(4,6-difluoro-2-pyridyl)-5-methyl-2-pyrimidin-2-yl-7,8-dihydro-5H-pyrido[4,3-d]pyrimidine (340 mg, 1 mmol) and potassium carbonate (276 mg, 2 mmol) in NMP (5 mL) was added piperazin-2-one (125 mg, 1.25 mmol). The resulting mixture was stirred for 10 min at rt and then heated to 180° C. in a closed vessel for 2 hrs in a microwave reactor. The resulting reaction mixture was poured into water (50 mL) and extracted with EA (50 mL) for three times. The organic layers were combined, then washed with water and brine, dried over anhydrous $Na_2SO_4$ and concentrated in vacuo. The residue was purified by prep-HPLC and chiral SFC to give (−)-4-[4-fluoro-6-(5-methyl-2-pyrimidin-2-yl-7,8-dihydro-5H-pyrido[4,3-d]pyrimidin-6-yl)-2-pyridyl]piperazin-2-one (100 mg) as a yellow powder. $^1$H NMR (400 MHz, Methanol-d) δ: 9.03 (d, 2H), 8.88 (s, 1H), 7.64 (t, 1H), 6.03 (s, 1H), 5.82 (s, 1H), 5.75 (q, 1H), 4.47-4.58 (m, 1H), 4.00 (s, 2H), 3.58-3.65 (m, 2H), 3.43-3.54 (m, 3H), 3.07-3.24 (m, 2H), 1.58 (d, 3H). MS obsd. (ESI$^+$) [(M+H)$^+$]: 421. $[a]_D^{25}$=−93.1° (0.1 g/100 mL, methanol).

BIOLOGICAL EXAMPLES

Example 226: Materials and Methods

HBV Cell Line

HepG2.2.15 cells (Acs et al. *Proc Natl Acad Sci USA*, 84, (1987), 4641-4), a constitutively HBV-expressing cell line were cultured in DMEM+Glutamax-I medium (Invitrogen, Carlsbad, Calif., USA), supplemented with 10% fetal bovine serum (Invitrogen) and G418 (Invitrogen) at a final concentration of 200 mg/L and maintained in 5% $CO_2$ at 37° C.

HBsAg Assay

HepG2.2.15 cells were seeded in duplicate into white, 96-well plates at 1.5×10$^4$ cells/well. The cells were treated with a three-fold serial dilution series of the compounds in DMSO. The final DMSO concentration in all wells was 1% and DMSO was used as no drug control.

The HBsAg chemiluminescence immunoassay (CLIA) kit (Autobio Diagnostics Co., Zhengzhou, China, Catalog number: CL0310-2) was used to measure the levels of secreted HBV antigens semi-quantitatively. For the detection 50 μL/well culture supernatant was used and HBsAg was quantified using HBsAg chemiluminescence immunoassay (CLIA) kit (Autobio Diagnostics Co., Zhengzhou, China, Catalog number: CL0310-2), 50 μL of the supernatant was transferred to the CLIA assay plate and 50 μL of enzyme conjugate reagent was added into each well. The plates were sealed and gently agitated for 1 hour at room temperature. The supernatant-enzyme-mixture was discarded and wells were washed 6 times with 300 μL of PBS. The residual liquid was removed by plating the CLIA plate right side down on absorbent tissue paper. 25 μL of substrates A and B were added to each well. Luminance was measured using a luminometer (Mithras LB 940 Multimode Microplate Reader) after 10 minutes incubation. Dose-response curves were generated and the IC$_{50}$ value was extrapolated by using the E-WorkBook Suite (ID Business Solutions Ltd., Guildford, UK). The IC$_{50}$ was defined as the compound concentration (or conditioned media log dilution) at which HBsAg secretion was reduced by 50% compared to the no drug control.

The compounds according to formula I were tested for their capacity to inhibit HBsAg as described herein. The Examples were tested in the above assay and found to have IC$_{50}$ below 50 μM. Particular compounds of formula I were found to have IC$_{50}$ below 0.50 μM. More Particular compounds of formula I were found to have IC$_{50}$ below 0.100 μM. Results of HBsAg assay are given in Table 1.

TABLE 1

Activity data in HBsAg assay

| Example No. | IC$_{50}$ (μM) |
|---|---|
| 1 | 0.186 |
| 2 | 2.063 |
| 3 | 0.115 |
| 4 | 1.924 |
| 5 | 0.038 |
| 6 | 8.066 |
| 7 | 0.012 |
| 8 | 19.61 |
| 9 | 0.183 |
| 10 | 21.865 |
| 11 | 0.085 |
| 12 | 7.488 |
| 13 | 14.392 |
| 14 | 2.974 |
| 15 | 0.015 |
| 16 | 1.516 |
| 17 | 0.008 |
| 18 | 0.363 |
| 19 | 0.042 |
| 20 | 5.007 |
| 21 | 0.05 |
| 22 | 0.027 |
| 23 | 1.491 |
| 24 | 0.029 |
| 25 | 0.033 |
| 26 | 0.078 |
| 27 | 3.431 |
| 28 | 3.079 |
| 29 | 0.05 |
| 30 | 0.096 |
| 31 | 0.156 |
| 32 | 0.074 |
| 33 | 0.048 |
| 34 | 1.711 |
| 35 | 0.046 |
| 36 | 39.778 |
| 37 | 4.856 |
| 38 | 3.364 |
| 39 | 1.339 |
| 40 | 4.863 |
| 41 | 0.038 |
| 42 | 3.252 |
| 43 | 0.018 |
| 44 | 0.494 |
| 45 | 0.176 |
| 46 | 8.169 |
| 47 | 0.036 |
| 48 | 0.184 |
| 49 | 0.034 |
| 50 | 1.131 |
| 51 | 2.67 |
| 52 | 0.11 |
| 53 | 0.103 |
| 54 | 0.146 |
| 55 | 0.113 |
| 56 | 0.055 |
| 57 | 0.11 |
| 58 | 0.193 |
| 59 | 0.075 |
| 60 | 0.022 |
| 61 | 3.323 |
| 62 | 0.494 |
| 63 | 0.447 |
| 64 | 0.062 |
| 65 | 16.677 |
| 66 | 0.168 |
| 67 | 32.331 |
| 68 | 0.074 |
| 69 | 0.033 |
| 70 | 0.026 |
| 71 | 0.068 |
| 72 | 0.022 |
| 73 | 0.018 |
| 74 | 2.249 |
| 75 | 0.021 |
| 76 | 0.028 |
| 77 | 0.105 |
| 78 | 0.976 |
| 79 | 0.015 |
| 80 | 0.071 |
| 81 | 0.131 |
| 82 | 0.03 |
| 83 | 0.19 |
| 84 | 0.266 |
| 85 | 0.156 |
| 86 | 0.1 |
| 87 | 0.073 |
| 88 | 0.027 |
| 89 | 0.021 |
| 90 | 0.022 |
| 91 | 0.483 |
| 92 | 0.054 |
| 93 | 0.061 |
| 94 | 0.07 |
| 95 | 0.724 |
| 96 | 0.094 |
| 97 | 0.154 |
| 98 | 0.372 |
| 99 | 1.271 |
| 100 | 0.096 |
| 101 | 0.113 |
| 102 | 0.249 |
| 103 | 2.164 |
| 104 | 19.031 |
| 105 | 0.023 |
| 106 | 0.208 |
| 107 | 0.171 |
| 108 | 0.084 |
| 109 | 0.08 |
| 110 | 0.079 |
| 111 | 0.041 |
| 112 | 0.084 |
| 113 | 0.094 |
| 114 | 0.018 |
| 115 | 0.012 |
| 116 | 0.902 |
| 117 | 0.072 |
| 118 | 0.013 |
| 119 | 0.051 |
| 120 | 0.096 |
| 121 | 0.042 |
| 122 | 0.016 |
| 123 | 1.143 |
| 124 | 1.248 |
| 125 | 1.117 |
| 126 | 0.008 |
| 127 | 0.024 |
| 128 | 0.005 |
| 129 | 0.018 |
| 130 | 0.679 |
| 131 | 0.002 |
| 132 | 0.03 |
| 133 | 1.758 |
| 134 | 0.048 |
| 135 | 0.015 |
| 136 | 0.357 |
| 137 | 0.124 |
| 138 | 0.011 |
| 139 | 1.59 |
| 140 | 0.024 |
| 141 | 0.113 |
| 142 | 0.04 |
| 143 | 0.022 |
| 144 | 0.048 |
| 145 | 0.014 |
| 146 | 0.002 |
| 147 | 0.021 |
| 148 | 0.017 |
| 149 | 0.01 |
| 150 | 0.049 |

TABLE 1-continued

Activity data in HBsAg assay

| Example No. | IC$_{50}$ (μM) |
|---|---|
| 151 | 0.012 |
| 152 | 0.011 |
| 153 | 0.022 |
| 154 | 0.007 |
| 155 | 0.012 |
| 156 | 0.006 |
| 157 | 0.047 |
| 158 | 0.016 |
| 159 | 0.056 |
| 160 | 0.196 |
| 161 | 0.095 |
| 162 | 1.779 |
| 163 | 0.035 |
| 164 | 0.022 |
| 165 | 0.013 |
| 166 | 0.019 |
| 167 | 0.026 |
| 168 | 0.021 |
| 169 | 0.018 |
| 170 | 0.016 |
| 171 | 0.018 |
| 172 | 0.056 |
| 173 | 0.132 |
| 174 | 0.66 |
| 175 | 1.465 |
| 176 | 27.754 |
| 177 | 0.29 |
| 178 | 0.123 |
| 179 | 0.029 |
| 180 | 0.027 |
| 181 | 0.012 |
| 182 | 2.239 |
| 183 | 0.838 |
| 184 | 0.182 |
| 185 | 0.014 |
| 186 | 0.018 |
| 187 | 0.613 |
| 188 | 0.029 |
| 189 | 0.04 |
| 190 | 0.024 |
| 191 | 0.035 |
| 192 | 0.03 |
| 193 | 0.083 |
| 194 | 0.043 |
| 195 | 0.055 |
| 196 | 0.002 |
| 197 | 0.006 |
| 198 | 0.004 |
| 199 | 0.018 |
| 200 | 0.002 |
| 201 | 0.124 |
| 202 | 0.013 |
| 203 | 0.006 |
| 204 | 0.113 |
| 205 | 0.005 |
| 206 | 0.285 |
| 207 | 0.002 |
| 208 | 0.186 |
| 209 | 0.649 |
| 210 | 0.065 |
| 211 | 0.27 |
| 212 | 0.837 |
| 213 | 0.065 |
| 214 | 0.022 |
| 215 | 0.064 |
| 216 | 0.013 |
| 217 | 0.028 |
| 218 | 0.022 |
| 219 | 0.11 |
| 220 | 0.021 |
| 221 | 0.034 |
| 222 | 0.016 |
| 223 | 0.015 |
| 224 | 0.013 |
| 225 | 0.013 |

HBV DNA Assay

The assay employs real-time qPCR (TaqMan) to directly measure extracellular HBV DNA copy number in the cell supernatant. HepG2.2.15 cells were plated in 96-well microtiter plates before treatment with complete medium (DMEM, Glutamax, 10% FBS, 1% Penicillin/Streptomycin, 250 μg/mL Genetycin, final DMSO concentration is 1%). Only the interior wells were utilized to reduce "edge effects" observed during cell culture, the exterior wells were filled with complete medium to help minimize sample evaporation. The HepG2.2.15 cells were treated 1 h later with various concentrations of a test compound in duplicate (top concentration used at 5 μM, 2 μM or 0.5 μM according to the HBsAg IC50 observed, with ⅓ successive dilutions (total of 10 dilutions). Six days following the initial administration of the test compound, the cell culture supernatant was collected; DNA extraction was performed by automated system (Magnapure) and then used in a real-time qPCR/TaqMan assay to determine HBV DNA copy numbers. Antiviral activity was calculated from the reduction in HBV DNA levels (IC$_{50}$). The compounds of the present invention were tested for their capacity to inhibit HBV DNA as described herein. The Examples were tested in the above assay and found to have IC$_{50}$ below 50 μM. Results of HBV DNA assay are given in Table 2.

TABLE 2

Anti HBV DNA production activity in HepG2.2.15 cells

| Example No. | IC$_{50}$ (μM) |
|---|---|
| 17 | 0.002 |
| 43 | 0.008 |
| 64 | 0.004 |
| 73 | 0.005 |
| 86 | 0.001 |
| 87 | 0.01 |
| 149 | 0.001 |
| 165 | <0.001 |
| 200 | <0.001 |
| 203 | 0.00016 |
| 207 | 0.00034 |
| 214 | 0.0072 |
| 215 | 0.00081 |

The invention claimed is:
1. A compound of formula I,

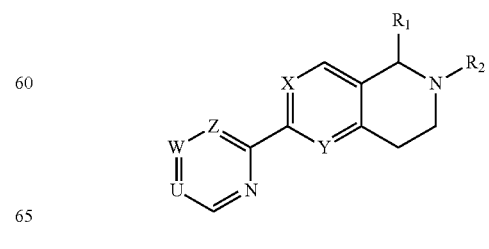

wherein
- $R^1$ is $C_{1-6}$alkyl, $C_{3-7}$cycloalkyl, halo$C_{1-6}$alkyl, hydroxy$C_{1-6}$alkyl, nitro$C_{1-6}$alkyl, $C_{1-6}$alkoxycarbonyl$C_{1-6}$alkyl, carboxy$C_{1-6}$alkyl, di($C_{1-6}$alkoxycarbonyl)methylenyl, cyano$C_{1-6}$alkyl, $C_{3-7}$cycloalkyl $C_{1-6}$alkyl, phenyl$C_{1-6}$alkyl, $C_{1-6}$alkylsulfanyl $C_{1-6}$alkyl, $C_{1-6}$alkylsufonyl$C_{1-6}$alkyl, amino$C_{1-6}$alkyl, $C_{1-6}$alkylcarbonylamino$C_{1-6}$alkyl, $C_{1-6}$alkylsufonylamino$C_{1-6}$alkyl, $C_{1-6}$alkoxycarbonyl amino$C_{1-6}$alkyl, aminocarbonyl$C_{1-6}$alkyl, di$C_{1-6}$alkylaminocarbonyl$C_{1-6}$alkyl, monocyclic heterocycloalkyl$C_{1-6}$alkyl or imidazolyl$C_{1-6}$alkyl;
- $R^2$ is aryl or heteroaryl, said aryl or heteroaryl being unsubstituted, or substituted by one, two, three or four substituents independently selected from $C_{1-6}$alkyl, $C_{3-7}$cycloalkyl, halogen, halo$C_{1-6}$alkyl, cyano, nitro, hydroxy, halo$C_{1-6}$alkoxy, —O—$C_xH_{2x}$—$R^3$, —O—$C_y$—$H_{2y}$—$NHR^6$, —$NR^9R^{10}$, —$SO_2$—$R^{11}$, —$SO_2$—$NR^{12}R^{13}$, carboxy, $C_{1-6}$alkoxycarbonyl, —C(=O)—$NR^{12}R^{13}$, aryl, heteroaryl, monocyclic heterocycloalkyl and —O-monocyclic heterocycloalkyl; wherein monocyclic heterocycloalkyl is unsubstituted or substituted by $C_{1-6}$alkyl, $C_{3-7}$cycloalkyl, $C_{1-6}$alkylcarbonyl, $C_{1-6}$alkylsufonyl or $C_{1-6}$alkoxycarbonyl;
- $R^3$ is hydrogen; $C_{3-7}$cycloalkyl; halo$C_{3-7}$cycloalkyl; hydroxy; hydroxy$C_{1-6}$alkyl$C_{3-7}$cycloalkyl; $C_{1-6}$alkoxy; monocyclic heterocycloalkyl; monocyclic heterocycloalkyl substituted by $C_{1-6}$alkyl, $C_{1-6}$alkylcarbonyl, $C_{1-6}$alkylsufonyl, $C_{3-7}$cycloalkyl or $C_{1-6}$alkoxycarbonyl; —C(=O)—$R^4$; $C_{1-6}$alkylsulfinyl; —$SO_2$—$R^5$; —C($NHR^7$)—C(=O)—$R^8$; carboxy$C_{1-6}$alkoxy or aminocarbonyl$C_{1-6}$alkoxy; wherein
- $R^4$ is hydroxy, $C_{1-6}$alkoxy, amino, $C_{1-6}$alkylamino, di$C_{1-6}$alkylamino, tetrahydrofuranylamino, pyrrolidinyl or morpholinyl;
- $R^5$ is $C_{1-6}$alkyl, $C_{3-7}$cycloalkyl, hydroxy, amino, $C_{1-6}$alkylamino or di$C_{1-6}$alkylamino;
- $R^7$ is hydrogen or $C_{1-6}$alkoxycarbonyl;
- $R^8$ is hydroxy or $C_{1-6}$alkoxy;
- $R^6$ is hydrogen, $C_{1-6}$alkylcarbonyl, halo$C_{1-6}$alkylcarbonyl, $C_{1-6}$alkoxycarbonyl, $C_{1-6}$alkylsulfonyl, $C_{3-7}$cycloalkylsulfonyl or $C_{1-6}$alkoxy$C_{1-6}$alkylsulfonyl;
- $R^9$ and $R^{10}$ are independently selected from hydrogen, $C_{1-6}$alkyl, $C_{3-7}$cycloalkyl, $C_{1-6}$alkylcarbonyl, $C_{1-6}$alkylsulfonyl, $C_{3-7}$cycloalkylcarbonyl and $C_{3-7}$cycloalkylsulfonyl; or
- $R^9$ and $R^{10}$ together with the nitrogen to which they are attached form monocyclic heterocycloalkyl;
- $R^{11}$ is $C_{1-6}$alkyl, halo$C_{1-6}$alkyl, $C_{3-7}$cycloalkyl, halo$C_{3-7}$cycloalkyl, hydroxy$C_{1-6}$alkyl, $C_{1-6}$alkoxy$C_{1-6}$alkyl, halo$C_{1-6}$alkoxy$C_{1-6}$alkyl, $C_{3-7}$cycloalkyl$C_{1-6}$alkyl, amino$C_{1-6}$alkyl, $C_{1-6}$alkylamino$C_{1-6}$alkyl, di$C_{1-6}$alkylamino$C_{1-6}$alkyl, $C_{1-6}$alkylcarbonylamino$C_{1-6}$alkyl, $C_{1-6}$alkylsulfonylamino$C_{1-6}$alkyl, $C_{1-6}$alkoxycarbonylamino $C_{1-6}$alkyl, $C_{1-6}$alkylsulfenyl$C_{1-6}$alkyl, $C_{1-6}$alkylsulfanyl$C_{1-6}$alkyl or $C_{1-6}$alkylsulfonyl$C_{1-6}$alkyl;
- $R^{12}$ and $R^{13}$ are independently selected from hydrogen, $C_{1-6}$alkyl, $C_{1-6}$alkoxy$C_{1-6}$alkyl, halo$C_{1-6}$alkyl, $C_{3-7}$cycloalkyl and halo$C_{3-7}$cycloalkyl; or
- $R^{12}$ and $R^{13}$ together with the nitrogen to which they are attached form monocyclic heterocycloalkyl;
- x is 1, 2, 3, 4, 5, 6, 7 or 8;
- y is 1, 2, 3, 4, 5, 6, 7 or 8;
- U, W and Z are independently selected from CH and N; one of X and Y is N, and the other one is N;

or a pharmaceutically acceptable salt, enantiomer, or diastereomer thereof.

2. A compound according to claim 1, wherein,
- $R^1$ is $C_{1-6}$alkyl, $C_{3-7}$cycloalkyl, hydroxy$C_{1-6}$alkyl, $C_{1-6}$alkoxycarbonyl$C_{1-6}$alkyl or carboxy$C_{1-6}$alkyl;
- $R^2$ is phenyl substituted by one, two, three or four groups independently selected from $C_{1-6}$alkyl, $C_{3-7}$cycloalkyl, halogen, halo$C_{1-6}$alkyl, cyano, nitro, hydroxy, halo$C_{1-6}$alkoxy, tetrahydrofuranyloxy, —O—$C_xH_{2x}$—$R^3$, —O—$C_y$—$H_{2y}$—$NHR^6$, $SO_2$—$R^{11}$, —$SO_2$—$NR^{12}R^{13}$, carboxy, $C_{1-6}$alkoxycarbonyl and —C(=O)—$NR^{12}R^{13}$; pyridinyl substituted by one, two or three groups independently selected from halogen, $C_{1-6}$alkyl, halo$C_{1-6}$alkoxy, tetrahydropyranyloxy, —O—$C_xH_{2x}$—$R^3$ and $NR^9R^{10}$; or pyrimidinyl substituted by $C_{1-6}$alkyl and di$C_{1-6}$alkylamino; wherein
- $R^3$ is hydrogen, $C_{3-7}$cycloalkyl, halo$C_{3-7}$cycloalkyl, hydroxy, hydroxy$C_{1-6}$alkyl$C_{3-7}$cycloalkyl, $C_{1-6}$alkoxy, oxetanyl, tetrahydrofuranyl, tetrahydropyranyl, thietanyl, 1,1-dioxothietanyl, 1,1-dioxothiolanyl, morpholinyl, oxopyrrolidinyl, oxomorpholinyl, oxopiperazinyl, $C_{1-6}$alkoxycarbonyloxopiperazinyl, oxoimidazolidinyl, $C_{1-6}$alkylpiperazinyl, $C_{1-6}$alkylcarbonylpiperazinyl, $C_{1-6}$alkylsulfonylpiperazinyl, $C_{1-6}$alkoxycarbonylpiperazinyl, azetidinyl, $C_{1-6}$alkylcarbonylazetidinyl, $C_{1-6}$alkylsulfonylazetidinyl, $C_{1-6}$alkoxycarbonylazetidinyl, —C(=O)—$R^4$, $C_{1-6}$alkylsulfinyl, —$SO_2$—$R^5$, —C($NHR^7$)—C(=O)—$R^8$, carboxy$C_{1-6}$alkoxy or aminocarbonyl$C_{1-6}$alkoxy; wherein
- $R^4$ is hydroxy, $C_{1-6}$alkoxy, amino, $C_{1-6}$alkylamino, di$C_{1-6}$alkylamino, tetrahydrofuranylamino, pyrrolidinyl or morpholinyl;
- $R^5$ is $C_{1-6}$alkyl, hydroxy or amino;
- $R^7$ is hydrogen or $C_{1-6}$alkoxycarbonyl;
- $R^8$ is hydroxy or $C_{1-6}$alkoxy;
- $R^6$ is hydrogen, $C_{1-6}$alkylcarbonyl, halo$C_{1-6}$alkylcarbonyl, $C_{1-6}$alkoxycarbonyl, $C_{1-6}$alkylsulfonyl, $C_{3-7}$cycloalkylsulfonyl or $C_{1-6}$alkoxy$C_{1-6}$alkylsulfonyl;
- $R^9$ and $R^{10}$ are independently selected from hydrogen, $C_{1-6}$alkyl and $C_{1-6}$alkylsulfonyl; or
- $R^9$ and $R^{10}$ together with the nitrogen to which they are attached form pyrrolidinyl, morpholinyl, piperidinyl, piperazinyl and oxopiperazinyl;
- $R^{11}$ is $C_{1-6}$alkyl or $C_{1-6}$alkoxy$C_{1-6}$alkyl;
- $R^{12}$ and $R^{13}$ are independently selected from hydrogen, $C_{1-6}$alkyl and $C_{1-6}$alkoxy$C_{1-6}$alkyl;
- x is 1, 2, 3, 4, 5, 6, 7 or 8;
- y is 1, 2, 3, 4, 5, 6, 7 or 8;
- U is CH;
- W is CH;
- Z is CH or N;
- X is N;
- Y is N;

or a pharmaceutically acceptable salt, enantiomer, or diastereomer thereof.

3. A compound according to claim 1, wherein,
- $R^1$ is $C_{1-6}$alkyl;
- $R^2$ is phenyl substituted by one, two, three or four groups independently selected from $C_{1-6}$alkyl, $C_{3-7}$cycloalkyl, halogen, halo$C_{1-6}$alkyl, cyano, hydroxy, halo$C_{1-6}$alkoxy, tetrahydrofuranyloxy, —O—$C_xH_{2x}$—

$R^3$, —O—$C_yH_{2y}$—$NHR^6$, $SO_2$—$R^{11}$, —$SO_2$—$NR^{12}R^{13}$, carboxy, $C_{1-6}$alkoxycarbonyl and —C(=O)—$NR^{12}R^{13}$; pyridinyl substituted by one, two or three groups independently selected from halogen, $C_{1-6}$alkyl, halo$C_{1-6}$alkoxy, tetrahydropyranyloxy, —O—$C_xH_{2x}$—$R^3$ and $NR^9R^{10}$; or pyrimidinyl substituted by $C_{1-6}$alkyl and di$C_{1-6}$alkylamino; wherein $R^3$ is hydrogen, $C_{3-7}$cycloalkyl, halo$C_{3-7}$cycloalkyl, hydroxy$C_{1-6}$alkyl$C_{3-7}$cycloalkyl, oxetanyl, tetrahydrofuranyl, tetrahydropyranyl, thietanyl, 1,1-dioxothietanyl, 1,1-dioxothiolanyl, oxopyrrolidinyl, oxomorpholinyl, oxopiperazinyl, $C_{1-6}$alkoxycarbonyloxopiperazinyl, oxoimidazolidinyl, $C_{1-6}$alkylpiperazinyl, $C_{1-6}$alkylcarbonylpiperazinyl, $C_{1-6}$alkylsulfonylpiperazinyl, $C_{1-6}$alkoxycarbonylpiperazinyl, azetidinyl, $C_{1-6}$alkylcarbonylazetidinyl, $C_{1-6}$alkylsulfonylazetidinyl, $C_{1-6}$alkoxycarbonylazetidinyl, —C(=O)—$R^4$, $C_{1-6}$alkylsulfinyl, —$SO_2$—$R^5$, —C($NHR^7$)—C(=O)—$R^8$, carboxy$C_{1-6}$alkoxy or aminocarbonyl$C_{1-6}$alkoxy; wherein $R^4$ is hydroxy, $C_{1-6}$alkoxy, amino, $C_{1-6}$alkylamino, tetrahydrofuranylamino, or morpholinyl;

$R^5$ is $C_{1-6}$alkyl, hydroxy or amino;

$R^7$ is hydrogen or $C_{1-6}$alkoxycarbonyl;

$R^8$ is hydroxy or $C_{1-6}$alkoxy;

$R^6$ is hydrogen, $C_{1-6}$alkylcarbonyl, halo$C_{1-6}$alkylcarbonyl, $C_{1-6}$alkoxycarbonyl, $C_{3-7}$cycloalkylsulfonyl or $C_{1-6}$alkoxy$C_{1-6}$alkylsulfonyl;

$R^9$ and $R^{10}$ are independently selected from hydrogen, $C_{1-6}$alkyl and $C_{1-6}$alkylsulfonyl; or $R^9$ and $R^{10}$ together with the nitrogen to which they are attached form pyrrolidinyl, morpholinyl, piperazinyl and oxopiperazinyl;

$R^{11}$ is $C_{1-6}$alkoxy$C_{1-6}$alkyl;

$R^{12}$ and $R^{13}$ are independently selected from hydrogen, $C_{1-6}$alkyl and $C_{1-6}$alkoxy$C_{1-6}$alkyl;

x is 1, 2, 3, 4, 5, 6, 7 or 8;

y is 1, 2, 3, 4, 5, 6, 7 or 8;

U is CH;

W is CH;

Z is N;

X is N;

Y is N;

or a pharmaceutically acceptable salt, enantiomer, or diastereomer thereof.

4. A compound according to claim 1, or a pharmaceutically acceptable salt, enantiomer, or diastereomer thereof, wherein $R^1$ is methyl.

5. A compound according to claim 1, wherein $R^1$ is $C_{1-6}$alkyl;

$R^2$ is phenyl substituted by one, two, three or four groups independently selected from $C_{1-6}$alkyl, $C_{3-7}$cycloalkyl, halogen, halo$C_{1-6}$alkyl, cyano, hydroxy, halo$C_{1-6}$alkoxy, tetrahydrofuranyloxy, —O—$C_xH_{2x}$—$R^3$, —O—$C_yH_{2y}$—$NHR^6$, $SO_2$—$R^{11}$, —$SO_2$—$NR^{12}R^{13}$, carboxy, $C_{1-6}$alkoxycarbonyl and —C(=O)—$NR^{12}R^{13}$;

$R^3$ is hydrogen, $C_{3-7}$cycloalkyl, halo$C_{3-7}$cycloalkyl, hydroxy$C_{1-6}$alkyl$C_{3-7}$cycloalkyl, oxetanyl, tetrahydrofuranyl, tetrahydropyranyl, thietanyl, 1,1-dioxothietanyl, 1,1-dioxothiolanyl, oxopyrrolidinyl, oxomorpholinyl, oxopiperazinyl, $C_{1-6}$alkoxycarbonyloxopiperazinyl, oxoimidazolidinyl, $C_{1-6}$alkylpiperazinyl, $C_{1-6}$alkylcarbonylpiperazinyl, $C_{1-6}$alkylsulfonylpiperazinyl, $C_{1-6}$alkoxycarbonylpiperazinyl, azetidinyl, $C_{1-6}$alkylcarbonylazetidinyl, $C_{1-6}$alkylsulfonylazetidinyl, $C_{1-6}$alkoxycarbonylazetidinyl, —C(=O)—$R^4$, $C_{1-6}$alkylsulfinyl, —$SO_2$—$R^5$ or —C($NHR^7$)—C(=O)—$R^8$; wherein $R^4$ is hydroxy, $C_{1-6}$alkoxy, amino, $C_{1-6}$alkylamino, tetrahydrofuranylamino, or morpholinyl;

$R^5$ is $C_{1-6}$alkyl, hydroxy or amino;

$R^7$ is hydrogen or $C_{1-6}$alkoxycarbonyl;

$R^8$ is hydroxy or $C_{1-6}$alkoxy;

$R^6$ is hydrogen, $C_{1-6}$alkylcarbonyl, halo$C_{1-6}$alkylcarbonyl, $C_{1-6}$alkoxycarbonyl, $C_{3-7}$cycloalkylsulfonyl or $C_{1-6}$alkoxy$C_{1-6}$alkylsulfonyl;

$R^{11}$ is $C_{1-6}$alkoxy$C_{1-6}$alkyl;

$R^{12}$ and $R^{13}$ are independently selected from hydrogen, $C_{1-6}$alkyl and $C_{1-6}$alkoxy$C_{1-6}$alkyl;

x is 1, 2, 3, 4, 5 or 6;

y is 1, 2, 3, 4, 5, 6, 7 or 8;

U is CH;

W is CH;

Z is N;

X is N;

Y is N;

or a pharmaceutically acceptable salt, enantiomer, or diastereomer thereof.

6. A compound according to claim 1, wherein $R^1$ is methyl;

$R^2$ is phenyl substituted by one, two, three or four groups independently selected from methyl, cyclopropyl, fluoro, chloro, iodo, trifluoromethyl, cyano, hydroxy, methoxy, difluoroethoxy, difluoromethoxy, trifluoroethoxy, trifluoromethoxy, cyclopropylmethoxy, difluorocyclopropylmethoxy, hydroxymethylcyclopropylmethoxy, oxetanylethoxy, oxetanylmethoxy, tetrahydrofuranylethoxy, tetrahydrofuranylmethoxy, tetrahydropyranylmethoxy, thietanylmethoxy, (1,1-dioxothietanyl)methoxy, (1,1-dioxothiolanyl)methoxy, oxopyrrolidinylpropoxy, oxomorpholinylpropoxy, oxopiperazinylpropoxy, (tert-butoxycarbonyloxopiperazinyl)propoxy, oxoimidazolidinylpropoxy, methylpiperazinylpropoxy, acetylpiperazinylpropoxy, methylsulfonylpiperazinylpropoxy, (tert-butoxycarbonylpiperazinyl)propoxy, azetidinylethoxy, acetylazetidinylethoxy, methylsulfonylazetidinylethoxy, (tert-butoxycarbonylazetidinyl)ethoxy, (tert-butoxycarbonylazetidinyl)methoxy, carboxybutoxy, carboxyethoxy, carboxyhexyloxy, carboxymethoxy, carboxypropoxy, methoxycarbonylbutoxy, ethoxycarbonylhexyloxy, aminocarbonylbutoxy, aminocarbonylhexyloxy, aminocarbonylmethoxy, aminocarbonylpropoxy, methylaminocarbonylpropoxy, tetrahydrofuranylaminocarbonylmethoxy, morpholinylcarbonylmethoxy, methylsulfinylpropoxy, methylsulfonylpropoxy, sulfopropoxy, aminosulfonylpropoxy, amino-carboxy-propoxy, (tert-butoxycarbonylamino)-carboxy-propoxy, (tert-butoxycarbonylamino)-(methoxycarbonyl)-propoxy, aminopropoxy, aminopentoxy, aminohexyloxy, aminooctyloxy, methylcarbonylaminopropoxy, chloropropylcarbonylaminopropoxy, (tert-butoxycarbonylamino)hexyloxy, (tert-butoxycarbonylamino)octyloxy, (tert-butoxycarbonylamino)pentoxy, (tert-butoxycarbonylamino)propoxy, cyclopropylsulfonylaminopropoxy, methoxyethylsulfonylaminopropoxy, methoxypropylsulfonyl, methoxypropylaminosulfonyl, N-methoxypropyl-N-methylaminosulfonyl, carboxy, methoxycarbonyl, methoxypropylaminocarbonyl, N-methoxypropyl-N-methyl-aminocarbonyl and tetrahydrofuranyloxy;

U is CH;
W is CH;
Z is N;
X is N;
Y is N;
or a pharmaceutically acceptable salt, enantiomer, or diastereomer thereof.

7. A compound according to claim 1, or a pharmaceutically acceptable salt, enantiomer, or diastereomer thereof, wherein $R^2$ is phenyl substituted by one, two or three groups independently selected from halogen, $C_{1-6}$alkoxy, halo$C_{1-6}$alkoxy, $C_{3-7}$cycloalkyl$C_{1-6}$alkoxy and halo$C_{3-7}$cycloalkyl$C_{1-6}$alkoxy.

8. A compound according to claim 1, or a pharmaceutically acceptable salt, enantiomer, or diastereomer thereof, wherein $R^2$ is phenyl substituted by one, two or three groups independently selected from fluoro, chloro, methoxy, difluoroethoxy, trifluoroethoxy, cyclopropylmethoxy and difluorocyclopropylmethoxy.

9. A compound according to claim 1, wherein
$R^1$ is $C_{1-6}$alkyl;
$R^2$ is phenyl substituted by two or three groups independently selected from halogen, cyano, halo$C_{1-6}$alkoxy, —O—$C_xH_{2x}$—$R^3$ and —O—$C_xH_{2x}$—NHR$^6$;
$R^3$ is hydrogen, $C_{3-7}$cycloalkyl, halo$C_{3-7}$cycloalkyl, oxetanyl, tetrahydrofuranyl, tetrahydropyranyl, $C_{1-6}$alkylsulfonylazetidinyl, aminocarbonyl or $C_{1-6}$alkylsulfonyl;
$R^6$ is hydrogen or $C_{1-6}$alkoxycarbonyl;
x is 1, 2, 3, 4, 5 or 6;
y is 1, 2, 3, 4, 5 or 6;
U is CH;
W is CH;
Z is N;
X is N;
Y is N;
or a pharmaceutically acceptable salt, enantiomer, or diastereomer thereof.

10. A compound according to claim 1, wherein
$R^1$ is methyl;
$R^2$ is phenyl substituted by two or three groups independently selected from fluoro, chloro, cyano, methoxy, difluoroethoxy, trifluoroethoxy, cyclopropylmethoxy, difluorocyclopropylmethoxy, methylsulfonylpropoxy, aminocarbonylmethoxy, oxetanylmethoxy, oxetanylethoxy, tetrahydrofuranylmethoxy, tetrahydropyranylmethoxy, methylsulfonylazetidinylethoxy, aminohexyloxy and (tert-butoxycarbonylamino)propoxy;
U is CH;
W is CH;
Z is N;
X is N;
Y is N;
or a pharmaceutically acceptable salt, enantiomer, or diastereomer thereof.

11. A compound according to claim 1, wherein
$R^1$ is $C_{1-6}$alkyl;
$R^2$ is pyridinyl substituted by one, two or three groups independently selected from halogen, $C_{1-6}$alkyl, halo$C_{1-6}$alkoxy, tetrahydropyranyloxy, —O—$C_xH_{2x}$—$R^3$ and NR$^9$R$^{10}$;
$R^3$ is hydrogen, $C_{3-7}$cycloalkyl, thietanyl, tetrahydrofuranyl, tetrahydropyranyl, oxomorpholinyl, 1,1-dioxo-thietanyl, $C_{1-6}$alkylcarbonylazetidinyl, $C_{1-6}$alkylsulfonylazetidinyl, —C(=O)—R$^4$, carboxy$C_{1-6}$alkoxy or aminocarbonyl$C_{1-6}$alkoxy; wherein $R^4$ is hydroxy, $C_{1-6}$alkoxy or amino;
$R^9$ and $R^{10}$ are independently selected from hydrogen, $C_{1-6}$alkyl and $C_{1-6}$alkylsulfonyl; or
$R^9$ and $R^{10}$ together with the nitrogen to which they are attached form pyrrolidinyl, morpholinyl, piperazinyl and oxopiperazinyl;
x is 1, 2, 3, 4, 5, 6, 7 or 8;
U is CH;
W is CH;
Z is N;
X is N;
Y is N;
or a pharmaceutically acceptable salt, enantiomer, or diastereomer thereof.

12. A compound according to claim 1, wherein
$R^1$ is methyl;
$R^2$ is pyridinyl substituted by one, two or three groups independently selected from fluoro, chloro, iodo, methoxy, methyl, difluoroethoxy, tetrahydropyranyloxy, cyclopropylmethoxy, thietanylmethoxy, tetrahydropyranylmethyl, tetrahydropyranylmethoxy, oxomorpholinylpropoxy, (1,1-dioxo-thietanyl)methoxy, acetylazetidinylmethoxy, methylsulfonylazetidinylmethoxy, carboxybutoxy, carboxyheptyloxy, carboxyhexyloxy, carboxypentyloxy, carboxypropoxy, methoxycarbonylheptyloxy, aminocarbonylbutoxy, aminocarbonylheptyloxy, aminocarbonylhexyloxy, aminocarbonylmethoxy, aminocarbonylpentyloxy, aminocarbonylpropoxy, carboxymethoxypropoxy, aminocarbonylmethoxypropoxy, amino, methylamino, dimethylamino, methylsulfonylamino, pyrrolidinyl, morpholinyl, piperazinyl and oxopiperazinyl;
U is CH;
W is CH;
Z is N;
X is N;
Y is N;
or a pharmaceutically acceptable salt, enantiomer, or diastereomer thereof.

13. A compound according to claim 1, or a pharmaceutically acceptable salt, enantiomer, or diastereomer thereof, wherein $R^2$ is pyridinyl substituted by one, two or three groups independently selected from halogen, $C_{1-6}$alkoxy, halo$C_{1-6}$alkoxy, $C_{1-6}$alkylamino, di$C_{1-6}$alkylamino, pyrrolidinyl and oxopiperazinyl.

14. A compound according to claim 1, or a pharmaceutically acceptable salt, enantiomer, or diastereomer thereof, wherein $R^2$ is pyridinyl substituted by one, two or three groups independently selected from fluoro, chloro, methoxy, difluoroethoxy, methylamino, dimethylamino, pyrrolidinyl and oxopiperazinyl.

15. A compound according to claim 1, wherein
$R^1$ is $C_{1-6}$alkyl;
$R^2$ is pyridinyl substituted by two or three groups independently selected from halogen, halo$C_{1-6}$alkoxy, —O—$C_xH_{2x}$—$R^3$ and NR$^9$R$^{10}$;
$R^3$ is hydrogen, tetrahydropyranyl, tetrahydropyranyl, oxomorpholinyl or aminocarbonyl;
$R^9$ and $R^{10}$ are independently selected from hydrogen and $C_{1-6}$alkyl; or
$R^9$ and $R^{10}$ together with the nitrogen to which they are attached form pyrrolidinyl and oxopiperazinyl;
x is 1, 2, 3, 4, 5 or 6;
U is CH;
W is CH;
Z is N;
X is N;
Y is N;

or a pharmaceutically acceptable salt, enantiomer, or diastereomer thereof.

16. A compound according to claim 1, wherein
$R^1$ is methyl;
$R^2$ is pyridinyl substituted by two or three groups independently selected from fluoro, chloro, methoxy, difluoroethoxy, tetrahydropyranylmethoxy, tetrahydropyranylmethoxy, oxomorpholinylpropoxy, aminocarbonylhexyloxy, methylamino, dimethylamino, pyrrolidinyl and oxopiperazinyl;
U is CH;
W is CH;
Z is N;
X is N;
Y is N;
or a pharmaceutically acceptable salt, enantiomer, or diastereomer thereof.

17. A compound according to claim 1, wherein
$R^1$ is $C_{1-6}$alkyl, $C_{3-7}$cycloalkyl, hydroxy$C_{1-6}$alkyl, $C_{1-6}$alkoxycarbonyl$C_{1-6}$alkyl, or carboxy$C_{1-6}$alkyl;
$R^2$ is phenyl substituted by one, two or three groups independently selected from halogen, nitro, $C_{1-6}$alkylsulfonyl, —O—$C_xH_{2x}$—$R^3$ and —O—$C_yH_{2y}$—$NHR^6$; or pyridinyl substituted by two groups independently selected from halogen, halo$C_{1-6}$alkoxy, —O—$C_xH_{2x}$—$R^3$ and $NR^9R^{10}$; wherein
$R^3$ is hydrogen, $C_{3-7}$cycloalkyl, hydroxy, $C_{1-6}$alkoxy, tetrahydrofuranyl, tetrahydropyranyl, morpholinyl, —C(=O)—$R^4$, —SO$_2$—$R^5$ or aminocarbonyl $C_{1-6}$alkoxy; wherein
$R^4$ is hydroxy, $C_{1-6}$alkoxy, amino, di$C_{1-6}$alkylamino or pyrrolidinyl;
$R^5$ is $C_{1-6}$alkyl;
$R^6$ is hydrogen or $C_{1-6}$alkylsulfonyl;
$R^9$ and $R^{10}$ are $C_{1-6}$alkyl; or
$R^9$ and $R^{10}$ together with the nitrogen to which they are attached form pyrrolidinyl, morpholinyl, piperidinyl and oxopiperazinyl;
x is 1, 2, 3, 4, 5 or 6;
y is 1, 2, 3, 4, 5 or 6;
U is CH;
W is CH;
Z is CH;
X is N;
Y is N;
or a pharmaceutically acceptable salt, enantiomer, or diastereomer thereof.

18. A compound according to claim 17, or a pharmaceutically acceptable salt, enantiomer, or diastereomer thereof, wherein $R^1$ is $C_{1-6}$alkyl.

19. A compound according to claim 18, or a pharmaceutically acceptable salt, enantiomer, or diastereomer thereof, wherein $R^1$ is methyl.

20. A compound according to claim 1, or a pharmaceutically acceptable salt, enantiomer, or diastereomer thereof, wherein $R^2$ is phenyl substituted by one, two or three groups independently selected from halogen and $C_{1-6}$alkoxy; or pyridinyl substituted by two groups independently selected from halogen, di$C_{1-6}$alkylamino, pyrrolidinyl, and oxopiperazinyl.

21. A compound according to claim 1, or a pharmaceutically acceptable salt, enantiomer, or diastereomer thereof, wherein $R^2$ is phenyl substituted by one, two or three groups independently selected from fluoro and methoxy; or pyridinyl substituted by two groups independently selected from fluoro, dimethylamino, pyrrolidinyl and oxopiperazinyl.

22. A compound according to claim 1, selected from
5-methyl-6-(4-nitrophenyl)-2-(2-pyridyl)-7,8-dihydro-5H-pyrido[4,3-d]pyrimidine;
(+)-5-methyl-6-(4-nitrophenyl)-2-(2-pyridyl)-7,8-dihydro-5H-pyrido[4,3-d]pyrimidine;
(−)-5-methyl-6-(4-nitrophenyl)-2-(2-pyridyl)-7,8-dihydro-5H-pyrido[4,3-d]pyrimidine;
5-ethyl-6-(4-methylsulfonylphenyl)-2-(2-pyridyl)-7,8-dihydro-5H-pyrido[4,3-d]pyrimidine;
6-(3,4-difluoro-5-methoxy-phenyl)-5-methyl-2-(2-pyridyl)-7,8-dihydro-5H-pyrido[4,3-d]pyrimidine;
(+)-6-(3,4-difluoro-5-methoxy-phenyl)-5-methyl-2-(2-pyridyl)-7,8-dihydro-5H-pyrido[4,3-d]pyrimidine;
(−)-6-(3,4-difluoro-5-methoxy-phenyl)-5-methyl-2-(2-pyridyl)-7,8-dihydro-5H-pyrido[4,3-d]pyrimidine;
dimethyl 2-[6-(4-methylsulfonylphenyl)-2-(2-pyridyl)-7,8-dihydro-5H-pyrido[4,3-d]pyrimidin-5-yl]propanedioate;
6-(3,4-difluoro-5-methoxy-phenyl)-5-ethyl-2-(2-pyridyl)-7,8-dihydro-5H-pyrido[4,3-d]pyrimidine;
(+)-6-(3,4-difluoro-5-methoxy-phenyl)-5-ethyl-2-(2-pyridyl)-7,8-dihydro-5H-pyrido[4,3-d]pyrimidine;
(−)-6-(3,4-difluoro-5-methoxy-phenyl)-5-ethyl-2-(2-pyridyl)-7,8-dihydro-5H-pyrido[4,3-d]pyrimidine;
6-(3,4-difluoro-5-methoxy-phenyl)-5-propyl-2-(2-pyridyl)-7,8-dihydro-5H-pyrido[4,3-d]pyrimidine;
(+)-6-(3,4-difluoro-5-methoxy-phenyl)-5-propyl-2-(2-pyridyl)-7,8-dihydro-5H-pyrido[4,3-d]pyrimidine;
(−)-6-(3,4-difluoro-5-methoxy-phenyl)-5-propyl-2-(2-pyridyl)-7,8-dihydro-5H-pyrido[4,3-d]pyrimidine;
6-(3,4-difluoro-5-methoxy-phenyl)-5-methyl-2-pyrimidin-2-yl-7,8-dihydro-5H-pyrido[4,3-d]pyrimidine;
(+)-6-(3,4-difluoro-5-methoxy-phenyl)-5-methyl-2-pyrimidin-2-yl-7,8-dihydro-5H-pyrido[4,3-d]pyrimidine;
(−)-6-(3,4-difluoro-5-methoxy-phenyl)-5-methyl-2-pyrimidin-2-yl-7,8-dihydro-5H-pyrido[4,3-d]pyrimidine;
5-cyclopropyl-6-(3,4-difluoro-5-methoxy-phenyl)-2-(2-pyridyl)-7,8-dihydro-5H-pyrido[4,3-d]pyrimidine;
6-[3,4-difluoro-5-(2-methoxyethoxy)phenyl]-5-methyl-2-(2-pyridyl)-7,8-dihydro-5H-pyrido[4,3-d]pyrimidine;
(+)-6-[3,4-difluoro-5-(2-methoxyethoxy)phenyl]-5-methyl-2-(2-pyridyl)-7,8-dihydro-5H-pyrido[4,3-d]pyrimidine;
(−)-6-[3,4-difluoro-5-(2-methoxyethoxy)phenyl]-5-methyl-2-(2-pyridyl)-7,8-dihydro-5H-pyrido[4,3-d]pyrimidine;
2-fluoro-6-methoxy-4-(5-methyl-2-pyrimidin-2-yl-7,8-dihydro-5H-pyrido[4,3-d]pyrimidin-6-yl)benzonitrile;
5-methyl-6-(4-methylsulfonylphenyl)-2-(2-pyridyl)-7,8-dihydro-5H-pyrido[4,3-d]pyrimidine;
4-[2,3-difluoro-5-[5-methyl-2-(2-pyridyl)-7,8-dihydro-5H-pyrido[4,3-d]pyrimidin-6-yl]phenoxy]butan-1-ol;
5-[2,3-difluoro-5-[5-methyl-2-(2-pyridyl)-7,8-dihydro-5H-pyrido[4,3-d]pyrimidin-6-yl]phenoxy]pentan-1-ol;
6-[3,4-difluoro-5-(2-methylsulfonylethoxy)phenyl]-5-methyl-2-(2-pyridyl)-7,8-dihydro-5H-pyrido[4,3-d]pyrimidine;
methyl 2-[2,3-difluoro-5-[5-methyl-2-(2-pyridyl)-7,8-dihydro-5H-pyrido[4,3-d]pyrimidin-6-yl]phenoxy]acetate;
2-[2,3-difluoro-5-[5-methyl-2-(2-pyridyl)-7,8-dihydro-5H-pyrido[4,3-d]pyrimidin-6-yl]phenoxy]acetic acid;
2-[2,3-difluoro-5-[5-methyl-2-(2-pyridyl)-7,8-dihydro-5H-pyrido[4,3-d]pyrimidin-6-yl]phenoxy]acetamide;
2-[2,3-difluoro-5-[5-methyl-2-(2-pyridyl)-7,8-dihydro-5H-pyrido[4,3-d]pyrimidin-6-yl]phenoxy]-N,N-dimethyl-acetamide;

2-[2,3-difluoro-5-[5-methyl-2-(2-pyridyl)-7,8-dihydro-5H-pyrido[4,3-d]pyrimidin-6-yl]phenoxy]-1-pyrrolidin-1-yl-ethanone;
4-[3-[2,3-difluoro-5-[5-methyl-2-(2-pyridyl)-7,8-dihydro-5H-pyrido[4,3-d]pyrimidin-6-yl]phenoxy]propyl]morpholine;
6-[3,4-difluoro-5-(3-methylsulfonylpropoxy)phenyl]-5-methyl-2-(2-pyridyl)-7,8-dihydro-5H-pyrido[4,3-d]pyrimidine;
3-[2,3-difluoro-5-[5-methyl-2-(2-pyridyl)-7,8-dihydro-5H-pyrido[4,3-d]pyrimidin-6-yl]phenoxy]propan-1-amine;
N-[3-[2,3-difluoro-5-[5-methyl-2-(2-pyridyl)-7,8-dihydro-5H-pyrido[4,3-d]pyrimidin-6-yl]phenoxy]propyl]methanesulfonamide;
ethyl 2-[6-(3,4-difluoro-5-methoxy-phenyl)-2-(2-pyridyl)-7,8-dihydro-5H-pyrido[4,3-d]pyrimidin-5-yl]acetate;
2-[6-(3,4-difluoro-5-methoxy-phenyl)-2-(2-pyridyl)-7,8-dihydro-5H-pyrido[4,3-d]pyrimidin-5-yl]acetic acid;
2-[6-(3,4-difluoro-5-methoxy-phenyl)-2-(2-pyridyl)-7,8-dihydro-5H-pyrido[4,3-d]pyrimidin-5-yl]ethanol;
6-(3,4-difluoro-5-methoxy-phenyl)-5-(nitromethyl)-2-(2-pyridyl)-7,8-dihydro-5H-pyrido[4,3-d]pyrimidine;
6-(4-chloro-3-fluoro-5-methoxy-phenyl)-5-methyl-2-pyrimidin-2-yl-7,8-dihydro-5H-pyrido[4,3-d]pyrimidine;
6-(3-chloro-4-fluoro-5-methoxy-phenyl)-5-methyl-2-pyrimidin-2-yl-7,8-dihydro-5H-pyrido[4,3-d]pyrimidine;
(+)-6-(3-chloro-4-fluoro-5-methoxy-phenyl)-5-methyl-2-pyrimidin-2-yl-7,8-dihydro-5H-pyrido[4,3-d]pyrimidine;
(−)-6-(3-chloro-4-fluoro-5-methoxy-phenyl)-5-methyl-2-pyrimidin-2-yl-7,8-dihydro-5H-pyrido[4,3-d]pyrimidine;
2,3-difluoro-5-(5-methyl-2-pyrimidin-2-yl-7,8-dihydro-5H-pyrido[4,3-d]pyrimidin-6-yl)phenol;
(−)-2,3-difluoro-5-(5-methyl-2-pyrimidin-2-yl-7,8-dihydro-5H-pyrido[4,3-d]pyrimidin-6-yl)phenol;
(+)-2,3-difluoro-5-(5-methyl-2-pyrimidin-2-yl-7,8-dihydro-5H-pyrido[4,3-d]pyrimidin-6-yl)phenol;
6-[3,4-difluoro-5-(3-methylsulfonylpropoxy)phenyl]-5-methyl-2-pyrimidin-2-yl-7,8-dihydro-5H-pyrido[4,3-d]pyrimidine;
(+)-6-[3,4-difluoro-5-(3-methylsulfonylpropoxy)phenyl]-5-methyl-2-pyrimidin-2-yl-7,8-dihydro-5H-pyrido[4,3-d]pyrimidine;
(−)-6-[3,4-difluoro-5-(3-methylsulfonylpropoxy)phenyl]-5-methyl-2-pyrimidin-2-yl-7,8-dihydro-5H-pyrido[4,3-d]pyrimidine;
4-[2,3-difluoro-5-(5-methyl-2-pyrimidin-2-yl-7,8-dihydro-5H-pyrido[4,3-d]pyrimidin-6-yl)phenoxy]butanoic acid;
3-[2,3-difluoro-5-(5-methyl-2-pyrimidin-2-yl-7,8-dihydro-5H-pyrido[4,3-d]pyrimidin-6-yl)phenoxy]propanoic acid;
4-[2,3-difluoro-5-(5-methyl-2-pyrimidin-2-yl-7,8-dihydro-5H-pyrido[4,3-d]pyrimidin-6-yl)phenoxy]butanamide;
4-[2,3-difluoro-5-(5-methyl-2-pyrimidin-2-yl-7,8-dihydro-5H-pyrido[4,3-d]pyrimidin-6-yl)phenoxy]-N-methyl-butanamide;
tert-butyl N-[8-[2,3-difluoro-5-(5-methyl-2-pyrimidin-2-yl-7,8-dihydro-5H-pyrido[4,3-d]pyrimidin-6-yl)phenoxy]octyl]carbamate;
8-[2,3-difluoro-5-(5-methyl-2-pyrimidin-2-yl-7,8-dihydro-5H-pyrido[4,3-d]pyrimidin-6-yl)phenoxy]octan-1-amine;
tert-butyl N-[5-[2,3-difluoro-5-(5-methyl-2-pyrimidin-2-yl-7,8-dihydro-5H-pyrido[4,3-d]pyrimidin-6-yl)phenoxy]pentyl]carbamate;
5-[2,3-difluoro-5-(5-methyl-2-pyrimidin-2-yl-7,8-dihydro-5H-pyrido[4,3-d]pyrimidin-6-yl)phenoxy]pentan-1-amine;
tert-butyl N-[6-[2,3-difluoro-5-(5-methyl-2-pyrimidin-2-yl-7,8-dihydro-5H-pyrido[4,3-d]pyrimidin-6-yl)phenoxy]hexyl]carbamate;
6-[2,3-difluoro-5-(5-methyl-2-pyrimidin-2-yl-7,8-dihydro-5H-pyrido[4,3-d]pyrimidin-6-yl)phenoxy]hexan-1-amine;
(−)-6-[2,3-difluoro-5-[5-methyl-2-pyrimidin-2-yl-7,8-dihydro-5H-pyrido[4,3-d]pyrimidin-6-yl]phenoxy]hexan-1-amine;
(+)-6-[2,3-difluoro-5-[5-methyl-2-pyrimidin-2-yl-7,8-dihydro-5H-pyrido[4,3-d]pyrimidin-6-yl]phenoxy]hexan-1-amine;
methyl 5-[2,3-difluoro-5-(5-methyl-2-pyrimidin-2-yl-7,8-dihydro-5H-pyrido[4,3-d]pyrimidin-6-yl)phenoxy]pentanoate;
5-[2,3-difluoro-5-(5-methyl-2-pyrimidin-2-yl-7,8-dihydro-5H-pyrido[4,3-d]pyrimidin-6-yl)phenoxy]pentanoic acid;
5-[2,3-difluoro-5-(5-methyl-2-pyrimidin-2-yl-7,8-dihydro-5H-pyrido[4,3-d]pyrimidin-6-yl)phenoxy]pentanamide;
2-[2,3-difluoro-5-(5-methyl-2-pyrimidin-2-yl-7,8-dihydro-5H-pyrido[4,3-d]pyrimidin-6-yl)phenoxy]acetic acid;
2-[2,3-difluoro-5-(5-methyl-2-pyrimidin-2-yl-7,8-dihydro-5H-pyrido[4,3-d]pyrimidin-6-yl)phenoxy]acetamide;
(+)-2-[2,3-difluoro-5-[5-methyl-2-pyrimidin-2-yl-7,8-dihydro-5H-pyrido[4,3-d]pyrimidin-6-yl]phenoxy]acetamide;
(−)-2-[2,3-difluoro-5-[5-methyl-2-pyrimidin-2-yl-7,8-dihydro-5H-pyrido[4,3-d]pyrimidin-6-yl]phenoxy]acetamide;
6-[3,4-difluoro-5-(2,2,2-trifluoroethoxy)phenyl]-5-methyl-2-pyrimidin-2-yl-7,8-dihydro-5H-pyrido[4,3-d]pyrimidine;
6-[3-(2,2-difluoroethoxy)-4,5-difluoro-phenyl]-5-methyl-2-pyrimidin-2-yl-7,8-dihydro-5H-pyrido[4,3-d]pyrimidine;
6-[3-(difluoromethoxy)-4,5-difluoro-phenyl]-5-methyl-2-pyrimidin-2-yl-7,8-dihydro-5H-pyrido[4,3-d]pyrimidine;
(6-(3-fluoro-5-methoxy-phenyl)-5-methyl-2-pyrimidin-2-yl-7,8-dihydro-5H-pyrido[4,3-d]pyrimidine;
(−)-6-(3-fluoro-5-methoxy-phenyl)-5-methyl-2-pyrimidin-2-yl-7,8-dihydro-5H-pyrido[4,3-d]pyrimidine;
(+)-6-(3-fluoro-5-methoxy-phenyl)-5-methyl-2-pyrimidin-2-yl-7,8-dihydro-5H-pyrido[4,3-d]pyrimidine;
6-[3,4-difluoro-5-(tetrahydrofuran-3-ylmethoxy)phenyl]-5-methyl-2-pyrimidin-2-yl-7,8-dihydro-5H-pyrido[4,3-d]pyrimidine;
6-[3,4-difluoro-5-(oxetan-3-ylmethoxy)phenyl]-5-methyl-2-pyrimidin-2-yl-7,8-dihydro-5H-pyrido[4,3-d]pyrimidine;
[1-[[2,3-difluoro-5-(5-methyl-2-pyrimidin-2-yl-7,8-dihydro-5H-pyrido[4,3-d]pyrimidin-6-yl)phenoxy]methyl]cyclopropyl]methanol;
3-[2,3-difluoro-5-(5-methyl-2-pyrimidin-2-yl-7,8-dihydro-5H-pyrido[4,3-d]pyrimidin-6-yl)phenoxy]propane-1-sulfonic acid;

6-[3,4-difluoro-5-[2-(oxetan-3-yl)ethoxy]phenyl]-5-methyl-2-pyrimidin-2-yl-7,8-dihydro-5H-pyrido[4,3-d]pyrimidine;

4-[3-[2,3-difluoro-5-(5-methyl-2-pyrimidin-2-yl-7,8-dihydro-5H-pyrido[4,3-d]pyrimidin-6-yl)phenoxy]propyl]morpholin-3-one;

6-[3-fluoro-5-(trifluoromethyl)phenyl]-5-methyl-2-pyrimidin-2-yl-7,8-dihydro-5H-pyrido[4,3-d]pyrimidine;

6-[3-[(2,2-difluorocyclopropyl)methoxy]-5-fluoro-phenyl]-5-methyl-2-pyrimidin-2-yl-7,8-dihydro-5H-pyrido[4,3-d]pyrimidine;

2-[2,3-difluoro-5-(5-methyl-2-pyrimidin-2-yl-7,8-dihydro-5H-pyrido[4,3-d]pyrimidin-6-yl)phenoxy]-N-tetrahydrofuran-3-yl-acetamide;

2-[2,3-difluoro-5-(5-methyl-2-pyrimidin-2-yl-7,8-dihydro-5H-pyrido[4,3-d]pyrimidin-6-yl)phenoxy]-1-morpholino-ethanone;

ethyl 7-[2,3-difluoro-5-(5-methyl-2-pyrimidin-2-yl-7,8-dihydro-5H-pyrido[4,3-d]pyrimidin-6-yl)phenoxy]heptanoate;

7-[2,3-difluoro-5-(5-methyl-2-pyrimidin-2-yl-7,8-dihydro-5H-pyrido[4,3-d]pyrimidin-6-yl)phenoxy]heptanoic acid;

7-[2,3-difluoro-5-(5-methyl-2-pyrimidin-2-yl-7,8-dihydro-5H-pyrido[4,3-d]pyrimidin-6-yl)phenoxy]heptanamide;

6-[3-(cyclopropylmethoxy)-4,5-difluoro-phenyl]-5-methyl-2-pyrimidin-2-yl-7,8-dihydro-5H-pyrido[4,3-d]pyrimidine;

6-[3,4-difluoro-5-(tetrahydropyran-4-ylmethoxy)phenyl]-5-methyl-2-pyrimidin-2-yl-7,8-dihydro-5H-pyrido[4,3-d]pyrimidine;

tert-butyl N-[3-[2,3-difluoro-5-(5-methyl-2-pyrimidin-2-yl-7,8-dihydro-5H-pyrido[4,3-d]pyrimidin-6-yl)phenoxy]propyl]carbamate;

3-[2,3-difluoro-5-(5-methyl-2-pyrimidin-2-yl-7,8-dihydro-5H-pyrido[4,3-d]pyrimidin-6-yl)phenoxy]propan-1-amine;

N-[3-[2,3-difluoro-5-(5-methyl-2-pyrimidin-2-yl-7,8-dihydro-5H-pyrido[4,3-d]pyrimidin-6-yl)phenoxy]propyl]acetamide;

N-[3-[2,3-difluoro-5-(5-methyl-2-pyrimidin-2-yl-7,8-dihydro-5H-pyrido[4,3-d]pyrimidin-6-yl)phenoxy]propyl]cyclopropane sulfonamide;

N-[3-[2,3-difluoro-5-(5-methyl-2-pyrimidin-2-yl-7,8-dihydro-5H-pyrido[4,3-d]pyrimidin-6-yl)phenoxy]propyl]-2-methoxy-ethane sulfonamide;

4-chloro-N-[3-[2,3-difluoro-5-(5-methyl-2-pyrimidin-2-yl-7,8-dihydro-5H-pyrido[4,3-d]pyrimidin-6-yl)phenoxy]propyl]butanamide;

1-[3-[2,3-difluoro-5-(5-methyl-2-pyrimidin-2-yl-7,8-dihydro-5H-pyrido[4,3-d]pyrimidin-6-yl)phenoxy]propyl]pyrrolidin-2-one;

3-[2,3-difluoro-5-(5-methyl-2-pyrimidin-2-yl-7,8-dihydro-5H-pyrido[4,3-d]pyrimidin-6-yl)phenoxy]propane-1-sulfonamide;

tert-butyl 4-[3-[2,3-difluoro-5-(5-methyl-2-pyrimidin-2-yl-7,8-dihydro-5H-pyrido[4,3-d]pyrimidin-6-yl)phenoxy]propyl]-3-oxo-piperazine-1-carboxylate;

1-[3-[2,3-difluoro-5-(5-methyl-2-pyrimidin-2-yl-7,8-dihydro-5H-pyrido[4,3-d]pyrimidin-6-yl)phenoxy]propyl]piperazin-2-one;

3-[[3-fluoro-5-(5-methyl-2-pyrimidin-2-yl-7,8-dihydro-5H-pyrido[4,3-d]pyrimidin-6-yl)phenoxy]methyl]thiolane 1,1-dioxide;

6-[3,4-difluoro-5-[3-(4-methylpiperazin-1-yl)propoxy]phenyl]-5-methyl-2-pyrimidin-2-yl-7,8-dihydro-5H-pyrido[4,3-d]pyrimidine;

methyl 2-(tert-butoxycarbonylamino)-4-[2,3-difluoro-5-(5-methyl-2-pyrimidin-2-yl-7,8-dihydro-5H-pyrido[4,3-d]pyrimidin-6-yl)phenoxy]butanoate;

2-(tert-butoxycarbonylamino)-4-[2,3-difluoro-5-(5-methyl-2-pyrimidin-2-yl-7,8-dihydro-5H-pyrido[4,3-d]pyrimidin-6-yl)phenoxy]butanoic acid;

2-amino-4-[2,3-difluoro-5-(5-methyl-2-pyrimidin-2-yl-7,8-dihydro-5H-pyrido[4,3-d]pyrimidin-6-yl)phenoxy]butanoic acid;

6-[3,4-difluoro-5-(2-tetrahydrofuran-2-ylethoxy)phenyl]-5-methyl-2-pyrimidin-2-yl-7,8-dihydro-5H-pyrido[4,3-d]pyrimidine;

6-[3,4-difluoro-5-(3-methyl sulfinylpropoxy)phenyl]-5-methyl-2-pyrimidin-2-yl-7,8-dihydro-5H-pyrido[4,3-d]pyrimidine;

4-[3-[2,3-difluoro-5-(5-methyl-2-pyrimidin-2-yl-7,8-dihydro-5H-pyrido[4,3-d]pyrimidin-6-yl)phenoxy]propyl]piperazin-2-one;

tert-butyl 4-[3-[2,3-difluoro-5-(5-methyl-2-pyrimidin-2-yl-7,8-dihydro-5H-pyrido[4,3-d]pyrimidin-6-yl)phenoxy]propyl]piperazine-1-carboxylate;

1-[4-[3-[2,3-difluoro-5-(5-methyl-2-pyrimidin-2-yl-7,8-dihydro-5H-pyrido[4,3-d]pyrimidin-6-yl)phenoxy]propyl]piperazin-1-yl]ethanone;

6-[3,4-difluoro-5-[3-(4-methylsulfonylpiperazin-1-yl)propoxy]phenyl]-5-methyl-2-pyrimidin-2-yl-7,8-dihydro-5H-pyrido[4,3-d]pyrimidine;

6-(3-fluoro-4-iodo-5-methoxy-phenyl)-5-methyl-2-pyrimidin-2-yl-7,8-dihydro-5H-pyrido[4,3-d]pyrimidine;

6-[3-methoxy-5-(trifluoromethyl)phenyl]-5-methyl-2-pyrimidin-2-yl-7,8-dihydro-5H-pyrido[4,3-d]pyrimidine;

1-[3-[2,3-difluoro-5-(5-methyl-2-pyrimidin-2-yl-7,8-dihydro-5H-pyrido[4,3-d]pyrimidin-6-yl)phenoxy]propyl]imidazolidin-2-one;

6-[3,4-difluoro-5-(2-tetrahydrofuran-3-ylethoxy)phenyl]-5-methyl-2-pyrimidin-2-yl-7,8-dihydro-5H-pyrido[4,3-d]pyrimidine;

tert-butyl 3-[2-[2,3-difluoro-5-(5-methyl-2-pyrimidin-2-yl-7,8-dihydro-5H-pyrido[4,3-d]pyrimidin-6-yl)phenoxy]ethyl]azetidine-1-carboxylate;

6-[3-[2-(azetidin-3-yl)ethoxy]-4,5-difluoro-phenyl]-5-methyl-2-pyrimidin-2-yl-7,8-dihydro-5H-pyrido[4,3-d]pyrimidine;

1-[3-[2-[2,3-difluoro-5-(5-methyl-2-pyrimidin-2-yl-7,8-dihydro-5H-pyrido[4,3-d]pyrimidin-6-yl)phenoxy]ethyl]azetidin-1-yl]ethanone;

6-[3,4-difluoro-5-[2-(1-methylsulfonylazetidin-3-yl)ethoxy]phenyl]-5-methyl-2-pyrimidin-2-yl-7,8-dihydro-5H-pyrido[4,3-d]pyrimidine;

6-[3,4-difluoro-5-(thietan-3-ylmethoxy)phenyl]-5-methyl-2-pyrimidin-2-yl-7,8-dihydro-5H-pyrido[4,3-d]pyrimidine;

3-[[2,3-difluoro-5-(5-methyl-2-pyrimidin-2-yl-7,8-dihydro-5H-pyrido[4,3-d]pyrimidin-6-yl)phenoxy]methyl]thietane 1,1-dioxide;

6-(3,4-difluoro-5-tetrahydrofuran-3-yloxy-phenyl)-(5R/S)-methyl-2-pyrimidin-2-yl-7,8-dihydro-5H-pyrido[4,3-d]pyrimidine;

6-[3,4-difluoro-5-(tetrahydrofuran-2-ylmethoxy)phenyl]-(5R/S)-methyl-2-pyrimidin-2-yl-7,8-dihydro-5H-pyrido[4,3-d]pyrimidine;

(+)-6-(2,6-dichloro-3-fluoro-5-methoxy-phenyl)-5-methyl-2-pyrimidin-2-yl-7,8-dihydro-5H-pyrido[4,3-d]pyrimidine;

(+)-6-(2,4-dichloro-5-fluoro-3-methoxy-phenyl)-5-methyl-2-pyrimidin-2-yl-7,8-dihydro-5H-pyrido[4,3-d]pyrimidine;
(+)-6-(2,4-dichloro-3-fluoro-5-methoxy-phenyl)-5-methyl-2-pyrimidin-2-yl-7,8-dihydro-5H-pyrido[4,3-d]pyrimidine;
6-(6-chloro-4-methoxy-2-pyridyl)-5-methyl-2-(2-pyridyl)-7,8-dihydro-5H-pyrido[4,3-d]pyrimidine;
6-(6-fluoro-4-methoxy-2-pyridyl)-5-methyl-2-pyrimidin-2-yl-7,8-dihydro-5H-pyrido[4,3-d]pyrimidine;
6-(6-fluoro-5-iodo-4-methoxy-2-pyridyl)-5-methyl-2-pyrimidin-2-yl-7,8-dihydro-5H-pyrido[4,3-d]pyrimidine;
6-(2-fluoro-6-methoxy-4-pyridyl)-5-methyl-2-pyrimidin-2-yl-7,8-dihydro-5H-pyrido[4,3-d]pyrimidine;
(−)-6-(2-chloro-3-fluoro-5-methoxy-phenyl)-5-methyl-2-pyrimidin-2-yl-7,8-dihydro-5H-pyrido[4,3-d]pyrimidine;
(−)-6-(2-chloro-5-fluoro-3-methoxy-phenyl)-5-methyl-2-pyrimidin-2-yl-7,8-dihydro-5H-pyrido[4,3-d]pyrimidine;
tert-butyl 3-[[2,3-difluoro-5-(5-methyl-2-pyrimidin-2-yl-7,8-dihydro-5H-pyrido[4,3-d]pyrimidin-6-yl)phenoxy]methyl]azetidine-1-carboxylate;
6-[3-fluoro-5-(trifluoromethoxy)phenyl]-5-methyl-2-pyrimidin-2-yl-7,8-dihydro-5H-pyrido[4,3-d]pyrimidine;
6-(3-fluoro-5-methyl-phenyl)-5-methyl-2-pyrimidin-2-yl-7,8-dihydro-5H-pyrido[4,3-d]pyrimidine;
6-(3-cyclopropyl-5-fluoro-phenyl)-5-methyl-2-pyrimidin-2-yl-7,8-dihydro-5H-pyrido[4,3-d]pyrimidine;
(−)-6-(6-fluoro-4-methoxy-2-pyridyl)-5-methyl-2-pyrimidin-2-yl-7,8-dihydro-5H-pyrido[4,3-d]pyrimidine;
(+)-6-(6-fluoro-4-methoxy-2-pyridyl)-5-methyl-2-pyrimidin-2-yl-7,8-dihydro-5H-pyrido[4,3-d]pyrimidine;
6-(4-chloro-6-methoxy-2-pyridyl)-5-methyl-2-pyrimidin-2-yl-7,8-dihydro-5H-pyrido[4,3-d]pyrimidine;
6-(2-chloro-6-methoxy-4-pyridyl)-5-methyl-2-pyrimidin-2-yl-7,8-dihydro-5H-pyrido[4,3-d]pyrimidine;
6-(4-fluoro-6-methoxy-2-pyridyl)-5-methyl-2-pyrimidin-2-yl-7,8-dihydro-5H-pyrido[4,3-d]pyrimidine;
6-[3-(2,2-difluoroethoxy)-5-fluoro-phenyl]-5-methyl-2-pyrimidin-2-yl-7,8-dihydro-5H-pyrido[4,3-d]pyrimidine;
6-[3-fluoro-5-(2,2,2-trifluoroethoxy)phenyl]-5-methyl-2-pyrimidin-2-yl-7,8-dihydro-5H-pyrido[4,3-d]pyrimidine;
6-[3-(cyclopropylmethoxy)-5-fluoro-phenyl]-5-methyl-2-pyrimidin-2-yl-7,8-dihydro-5H-pyrido[4,3-d]pyrimidine;
(−)-6-(5-chloro-6-fluoro-4-methoxy-2-pyridyl)-5-methyl-2-pyrimidin-2-yl-7,8-dihydro-5H-pyrido[4,3-d]pyrimidine;
(−)-6-(3-chloro-6-fluoro-4-methoxy-2-pyridyl)-5-methyl-2-pyrimidin-2-yl-7,8-dihydro-5H-pyrido[4,3-d]pyrimidine;
6-[6-(2,2-difluoroethoxy)-4-fluoro-2-pyridyl]-5-methyl-2-pyrimidin-2-yl-7,8-dihydro-5H-pyrido[4,3-d]pyrimidine;
6-[4-(2,2-difluoroethoxy)-6-fluoro-2-pyridyl]-5-methyl-2-pyrimidin-2-yl-7,8-dihydro-5H-pyrido[4,3-d]pyrimidine;
6-[2-(2,2-difluoroethoxy)-6-fluoro-4-pyridyl]-5-methyl-2-pyrimidin-2-yl-7,8-dihydro-5H-pyrido[4,3-d]pyrimidine;
6-[6-fluoro-4-(tetrahydropyran-4-ylmethoxy)-2-pyridyl]-5-methyl-2-pyrimidin-2-yl-7,8-dihydro-5H-pyrido[4,3-d]pyrimidine;
6-[4-(cyclopropylmethoxy)-6-fluoro-2-pyridyl]-5-methyl-2-pyrimidin-2-yl-7,8-dihydro-5H-pyrido[4,3-d]pyrimidine;
6-(6-fluoro-4-methoxy-2-pyridyl)-5-methyl-2-(2-pyridyl)-7,8-dihydro-5H-pyrido[4,3-d]pyrimidine;
6-[6-fluoro-4-(tetrahydrofuran-3-ylmethoxy)-2-pyridyl]-5-methyl-2-pyrimidin-2-yl-7,8-dihydro-5H-pyrido[4,3-d]pyrimidine;
(−)-7-[[2-fluoro-6-[5-methyl-2-pyrimidin-2-yl-7,8-dihydro-5H-pyrido[4,3-d]pyrimidin-6-yl]-4-pyridyl]oxy]heptanoic acid;
(−)-7-[[2-fluoro-6-[5-methyl-2-pyrimidin-2-yl-7,8-dihydro-5H-pyrido[4,3-d]pyrimidin-6-yl]-4-pyridyl]oxy]heptanamide;
(−)-5-[[2-fluoro-6-[5-methyl-2-pyrimidin-2-yl-7,8-dihydro-5H-pyrido[4,3-d]pyrimidin-6-yl]-4-pyridyl]oxy]pentanoic acid;
(−)-5-[[2-fluoro-6-[5-methyl-2-pyrimidin-2-yl-7,8-dihydro-5H-pyrido[4,3-d]pyrimidin-6-yl]-4-pyridyl]oxy]pentanamide;
6-[6-fluoro-4-[(1-methylsulfonylazetidin-3-yl)methoxy]-2-pyridyl]-5-methyl-2-pyrimidin-2-yl-7,8-dihydro-5H-pyrido[4,3-d]pyrimidine;
1-[3-[[2-fluoro-6-(5-methyl-2-pyrimidin-2-yl-7,8-dihydro-5H-pyrido[4,3-d]pyrimidin-6-yl)-4-pyridyl]oxymethyl]azetidin-1-yl]ethanone;
6-(4-methoxy-6-methyl-2-pyridyl)-5-methyl-2-pyrimidin-2-yl-7,8-dihydro-5H-pyrido[4,3-d]pyrimidine;
2-[3-[[2-fluoro-6-(5-methyl-2-pyrimidin-2-yl-7,8-dihydro-5H-pyrido[4,3-d]pyrimidin-6-yl)-4-pyridyl]oxy]propoxy]acetic acid;
2-[3-[[2-fluoro-6-(5-methyl-2-pyrimidin-2-yl-7,8-dihydro-5H-pyrido[4,3-d]pyrimidin-6-yl)-4-pyridyl]oxy]propoxy]acetamide;
(−)-6-[[2-fluoro-6-[5-methyl-2-pyrimidin-2-yl-7,8-dihydro-5H-pyrido[4,3-d]pyrimidin-6-yl]-4-pyridyl]oxy]hexanoic acid;
(−)-6-[[2-fluoro-6-[5-methyl-2-pyrimidin-2-yl-7,8-dihydro-5H-pyrido[4,3-d]pyrimidin-6-yl]-4-pyridyl]oxy]hexanamide;
6-[6-fluoro-4-(tetrahydrofuran-2-ylmethoxy)-2-pyridyl]-5-methyl-2-pyrimidin-2-yl-7,8-dihydro-5H-pyrido[4,3-d]pyrimidine;
methyl 8-[[2-fluoro-6-(5-methyl-2-pyrimidin-2-yl-7,8-dihydro-5H-pyrido[4,3-d]pyrimidin-6-yl)-4-pyridyl]oxy]octanoate;
8-[[2-fluoro-6-(5-methyl-2-pyrimidin-2-yl-7,8-dihydro-5H-pyrido[4,3-d]pyrimidin-6-yl)-4-pyridyl]oxy]octanoic acid;
8-[[2-fluoro-6-(5-methyl-2-pyrimidin-2-yl-7,8-dihydro-5H-pyrido[4,3-d]pyrimidin-6-yl)-4-pyridyl]oxy]octanamide;
6-[[2-fluoro-6-[5-methyl-2-(2-pyridyl)-7,8-dihydro-5H-pyrido[4,3-d]pyrimidin-6-yl]-4-pyridyl]oxy]hexanoic acid;
6-[[2-fluoro-6-[5-methyl-2-(2-pyridyl)-7,8-dihydro-5H-pyrido[4,3-d]pyrimidin-6-yl]-4-pyridyl]oxy]hexanamide;
6-(6-fluoro-4-tetrahydropyran-4-yloxy-2-pyridyl)-5-methyl-2-pyrimidin-2-yl-7,8-dihydro-5H-pyrido[4,3-d]pyrimidine;
6-(4-fluoro-6-tetrahydropyran-4-yloxy-2-pyridyl)-5-methyl-2-pyrimidin-2-yl-7,8-dihydro-5H-pyrido[4,3-d]pyrimidine;
2-[[2-fluoro-6-(5-methyl-2-pyrimidin-2-yl-7,8-dihydro-5H-pyrido[4,3-d]pyrimidin-6-yl)-4-pyridyl]oxy]acetamide;

methyl 3-fluoro-5-(5-methyl-2-pyrimidin-2-yl-7,8-dihydro-5H-pyrido[4,3-d]pyrimidin-6-yl)benzoate;

3-fluoro-5-(5-methyl-2-pyrimidin-2-yl-7,8-dihydro-5H-pyrido[4,3-d]pyrimidin-6-yl)benzoic acid;

3-fluoro-N-(3-methoxypropyl)-5-(5-methyl-2-pyrimidin-2-yl-7,8-dihydro-5H-pyrido[4,3-d]pyrimidin-6-yl)benzamide;

3-fluoro-N-(3-methoxypropyl)-N-methyl-5-(5-methyl-2-pyrimidin-2-yl-7,8-dihydro-5H-pyrido[4,3-d]pyrimidin-6-yl)benzamide;

7-[[2-fluoro-6-[5-methyl-2-(2-pyridyl)-7,8-dihydro-5H-pyrido[4,3-d]pyrimidin-6-yl]-4-pyridyl]oxy]heptanoic acid;

7-[[2-fluoro-6-[5-methyl-2-(2-pyridyl)-7,8-dihydro-5H-pyrido[4,3-d]pyrimidin-6-yl]-4-pyridyl]oxy]heptanamide;

(+)-4-[3-[[2-fluoro-6-[5-methyl-2-pyrimidin-2-yl-7,8-dihydro-5H-pyrido[4,3-d]pyrimidin-6-yl]-4-pyridyl]oxy]propyl]morpholin-3-one;

3-fluoro-N-(3-methoxypropyl)-5-(5-methyl-2-pyrimidin-2-yl-7,8-dihydro-5H-pyrido[4,3-d]pyrimidin-6-yl)benzenesulfonamide;

3-fluoro-N-(3-methoxypropyl)-N-methyl-5-(5-methyl-2-pyrimidin-2-yl-7,8-dihydro-5H-pyrido[4,3-d]pyrimidin-6-yl)benzenesulfonamide;

(−)-4-[[2-fluoro-6-[5-methyl-2-pyrimidin-2-yl-7,8-dihydro-5H-pyrido[4,3-d]pyrimidin-6-yl]-4-pyridyl]oxy]butanoic acid;

(−)-4-[[2-fluoro-6-[5-methyl-2-pyrimidin-2-yl-7,8-dihydro-5H-pyrido[4,3-d]pyrimidin-6-yl]-4-pyridyl]oxy]butanamide;

2-[3-[[2-fluoro-6-[5-methyl-2-(2-pyridyl)-7,8-dihydro-5H-pyrido[4,3-d]pyrimidin-6-yl]-4-pyridyl]oxy]propoxy]acetamide;

6-[3-fluoro-5-(3-methoxypropylsulfonyl)phenyl]-5-methyl-2-pyrimidin-2-yl-7,8-dihydro-5H-pyrido[4,3-d]pyrimidine;

6-[6-fluoro-4-(tetrahydrofuran-3-ylmethoxy)-2-pyridyl]-5-methyl-2-(2-pyridyl)-7,8-dihydro-5H-pyrido[4,3-d]pyrimidine;

6-[6-fluoro-4-(tetrahydrofuran-2-ylmethoxy)-2-pyridyl]-5-methyl-2-(2-pyridyl)-7,8-dihydro-5H-pyrido[4,3-d]pyrimidine;

6-[6-fluoro-4-(tetrahydropyran-4-ylmethoxy)-2-pyridyl]-5-methyl-2-(2-pyridyl)-7,8-dihydro-5H-pyrido[4,3-d]pyrimidine;

6-[4-(cyclopropylmethoxy)-6-fluoro-2-pyridyl]-5-methyl-2-(2-pyridyl)-7,8-dihydro-5H-pyrido[4,3-d]pyrimidine;

6-[4-(2,2-difluoroethoxy)-6-fluoro-2-pyridyl]-5-methyl-2-(2-pyridyl)-7,8-dihydro-5H-pyrido[4,3-d]pyrimidine;

6-[6-(2,2-difluoroethoxy)-4-fluoro-2-pyridyl]-5-methyl-2-(2-pyridyl)-7,8-dihydro-5H-pyrido[4,3-d]pyrimidine;

6-[6-fluoro-4-(thietan-3-ylmethoxy)-2-pyridyl]-5-methyl-2-(2-pyridyl)-7,8-dihydro-5H-pyrido[4,3-d]pyrimidine;

3-[[2-fluoro-6-(5-methyl-2-pyrimidin-2-yl-7,8-dihydro-5H-pyrido[4,3-d]pyrimidin-6-yl)-4-pyridyl]oxymethyl]thietane 1,1-dioxide;

2-fluoro-N,N-dimethyl-6-(5-methyl-2-pyrimidin-2-yl-7,8-dihydro-5H-pyrido[4,3-d]pyrimidin-6-yl)pyridin-4-amine;

4-fluoro-N,N-dimethyl-6-(5-methyl-2-pyrimidin-2-yl-7,8-dihydro-5H-pyrido[4,3-d]pyrimidin-6-yl)pyridin-2-amine;

6-(6-fluoro-4-pyrrolidin-1-yl-2-pyridyl)-5-methyl-2-pyrimidin-2-yl-7,8-dihydro-5H-pyrido[4,3-d]pyrimidine;

6-(4-fluoro-6-pyrrolidin-1-yl-2-pyridyl)-5-methyl-2-pyrimidin-2-yl-7,8-dihydro-5H-pyrido[4,3-d]pyrimidine;

(−)-6-(6-fluoro-4-pyrrolidin-1-yl-2-pyridyl)-5-methyl-2-pyrimidin-2-yl-7,8-dihydro-5H-pyrido[4,3-d]pyrimidine;

(+)-6-(6-fluoro-4-pyrrolidin-1-yl-2-pyridyl)-5-methyl-2-pyrimidin-2-yl-7,8-dihydro-5H-pyrido[4,3-d]pyrimidine;

4-[2-fluoro-6-(5-methyl-2-pyrimidin-2-yl-7,8-dihydro-5H-pyrido[4,3-d]pyrimidin-6-yl)-4-pyridyl]morpholine;

(−)-2-fluoro-N-methyl-6-[5-methyl-2-pyrimidin-2-yl-7,8-dihydro-5H-pyrido[4,3-d]pyrimidin-6-yl]pyridin-4-amine;

(+)-4-fluoro-N,N-dimethyl-6-[5-methyl-2-pyrimidin-2-yl-7,8-dihydro-5H-pyrido[4,3-d]pyrimidin-6-yl]pyridin-2-amine;

(−)-4-fluoro-N,N-dimethyl-6-[5-methyl-2-pyrimidin-2-yl-7,8-dihydro-5H-pyrido[4,3-d]pyrimidin-6-yl]pyridin-2-amine;

(+)-2-fluoro-N,N-dimethyl-6-[5-methyl-2-pyrimidin-2-yl-7,8-dihydro-5H-pyrido[4,3-d]pyrimidin-6-yl]pyridin-4-amine;

(−)-2-fluoro-N,N-dimethyl-6-[5-methyl-2-pyrimidin-2-yl-7,8-dihydro-5H-pyrido[4,3-d]pyrimidin-6-yl]pyridin-4-amine;

6-(6-fluoro-4-piperazin-1-yl-2-pyridyl)-5-methyl-2-pyrimidin-2-yl-7,8-dihydro-5H-pyrido[4,3-d]pyrimidine;

6-(4-fluoro-6-piperazin-1-yl-2-pyridyl)-5-methyl-2-pyrimidin-2-yl-7,8-dihydro-5H-pyrido[4,3-d]pyrimidine;

2-fluoro-6-(5-methyl-2-pyrimidin-2-yl-7,8-dihydro-5H-pyrido[4,3-d]pyrimidin-6-yl)pyridin-4-amine;

N-[2-fluoro-6-(5-methyl-2-pyrimidin-2-yl-7,8-dihydro-5H-pyrido[4,3-d]pyrimidin-6-yl)-4-pyridyl]methanesulfonamide;

N-[4-fluoro-6-(5-methyl-2-pyrimidin-2-yl-7,8-dihydro-5H-pyrido[4,3-d]pyrimidin-6-yl)-2-pyridyl]methanesulfonamide;

(−)-N,N,6-trimethyl-2-[5-methyl-2-pyrimidin-2-yl-7,8-dihydro-5H-pyrido[4,3-d]pyrimidin-6-yl]pyrimidin-4-amine;

4-[4-fluoro-6-(5-methyl-2-pyrimidin-2-yl-7,8-dihydro-5H-pyrido[4,3-d]pyrimidin-6-yl)-2-pyridyl]piperazin-2-one;

4-[2-fluoro-6-(5-methyl-2-pyrimidin-2-yl-7,8-dihydro-5H-pyrido[4,3-d]pyrimidin-6-yl)-4-pyridyl]piperazin-2-one;

2-fluoro-N,N-dimethyl-6-[5-methyl-2-(2-pyridyl)-7,8-dihydro-5H-pyrido[4,3-d]pyrimidin-6-yl]pyridin-4-amine;

4-fluoro-N,N-dimethyl-6-[5-methyl-2-(2-pyridyl)-7,8-dihydro-5H-pyrido[4,3-d]pyrimidin-6-yl]pyridin-2-amine;

6-[6-fluoro-4-(1-piperidyl)-2-pyridyl]-5-methyl-2-(2-pyridyl)-7,8-dihydro-5H-pyrido[4,3-d]pyrimidine;

6-[4-fluoro-6-(1-piperidyl)-2-pyridyl]-5-methyl-2-(2-pyridyl)-7,8-dihydro-5H-pyrido[4,3-d]pyrimidine;

4-[2-fluoro-6-[5-methyl-2-(2-pyridyl)-7,8-dihydro-5H-pyrido[4,3-d]pyrimidin-6-yl]-4-pyridyl]morpholine;

4-[4-fluoro-6-[5-methyl-2-(2-pyridyl)-7,8-dihydro-5H-pyrido[4,3-d]pyrimidin-6-yl]-2-pyridyl]morpholine;

4-[2-fluoro-6-[5-methyl-2-(2-pyridyl)-7,8-dihydro-5H-pyrido[4,3-d]pyrimidin-6-yl]-4-pyridyl]piperazin-2-one;

4-[4-fluoro-6-[5-methyl-2-(2-pyridyl)-7,8-dihydro-5H-pyrido[4,3-d]pyrimidin-6-yl]-2-pyridyl]piperazin-2-one;
6-(6-fluoro-4-pyrrolidin-1-yl-2-pyridyl)-5-methyl-2-(2-pyridyl)-7,8-dihydro-5H-pyrido[4,3-d]pyrimidine; and
(+)-4-[4-fluoro-6-(5-methyl-2-pyrimidin-2-yl-7,8-dihydro-5H-pyrido[4,3-d]pyrimidin-6-yl)-2-pyridyl]piperazin-2-one;
or a pharmaceutically acceptable salt, enantiomer, or diastereomer thereof.

23. A compound according to claim 1, selected from
(−)-6-(3,4-difluoro-5-methoxy-phenyl)-5-methyl-2-(2-pyridyl)-7,8-dihydro-5H-pyrido[4,3-d]pyrimidine;
6-(3,4-difluoro-5-methoxy-phenyl)-5-methyl-2-pyrimidin-2-yl-7,8-dihydro-5H-pyrido[4,3-d]pyrimidine;
(−)-6-(3,4-difluoro-5-methoxy-phenyl)-5-methyl-2-pyrimidin-2-yl-7,8-dihydro-5H-pyrido[4,3-d]pyrimidine;
2-fluoro-6-methoxy-4-(5-methyl-2-pyrimidin-2-yl-7,8-dihydro-5H-pyrido[4,3-d]pyrimidin-6-yl)benzonitrile;
6-(3-chloro-4-fluoro-5-methoxy-phenyl)-5-methyl-2-pyrimidin-2-yl-7,8-dihydro-5H-pyrido[4,3-d]pyrimidine;
(−)-6-(3-chloro-4-fluoro-5-methoxy-phenyl)-5-methyl-2-pyrimidin-2-yl-7,8-dihydro-5H-pyrido[4,3-d]pyrimidine;
(−)-6-[3,4-difluoro-5-(3-methyl sulfonylpropoxy)phenyl]-5-methyl-2-pyrimidin-2-yl-7,8-dihydro-5H-pyrido[4,3-d]pyrimidine;
(−)-6-[2,3-difluoro-5-[5-methyl-2-pyrimidin-2-yl-7,8-dihydro-5H-pyrido[4,3-d]pyrimidin-6-yl]phenoxy]hexan-1-amine;
(−)-2-[2,3-difluoro-5-[5-methyl-2-pyrimidin-2-yl-7,8-dihydro-5H-pyrido[4,3-d]pyrimidin-6-yl]phenoxy]acetamide;
6-[3,4-difluoro-5-(2,2,2-trifluoroethoxy)phenyl]-5-methyl-2-pyrimidin-2-yl-7,8-dihydro-5H-pyrido[4,3-d]pyrimidine;
6-[3-(2,2-difluoroethoxy)-4,5-difluoro-phenyl]-5-methyl-2-pyrimidin-2-yl-7,8-dihydro-5H-pyrido[4,3-d]pyrimidine;
6-(3-fluoro-5-methoxy-phenyl)-5-methyl-2-pyrimidin-2-yl-7,8-dihydro-5H-pyrido[4,3-d]pyrimidine;
(−)-6-(3-fluoro-5-methoxy-phenyl)-5-methyl-2-pyrimidin-2-yl-7,8-dihydro-5H-pyrido[4,3-d]pyrimidine;
6-[3,4-difluoro-5-(tetrahydrofuran-3-ylmethoxy)phenyl]-5-methyl-2-pyrimidin-2-yl-7,8-dihydro-5H-pyrido[4,3-d]pyrimidine;
6-[3,4-difluoro-5-(oxetan-3-ylmethoxy)phenyl]-5-methyl-2-pyrimidin-2-yl-7,8-dihydro-5H-pyrido[4,3-d]pyrimidine;
6-[3,4-difluoro-5-[2-(oxetan-3-yl)ethoxy]phenyl]-5-methyl-2-pyrimidin-2-yl-7,8-dihydro-5H-pyrido[4,3-d]pyrimidine;
6-[3-[(2,2-difluorocyclopropyl)methoxy]-5-fluoro-phenyl]-5-methyl-2-pyrimidin-2-yl-7,8-dihydro-5H-pyrido[4,3-d]pyrimidine;
6-[3-(cyclopropylmethoxy)-4,5-difluoro-phenyl]-5-methyl-2-pyrimidin-2-yl-7,8-dihydro-5H-pyrido[4,3-d]pyrimidine;
6-[3,4-difluoro-5-(tetrahydropyran-4-ylmethoxy)phenyl]-5-methyl-2-pyrimidin-2-yl-7,8-dihydro-5H-pyrido[4,3-d]pyrimidine;
tert-butyl N-[3-[2,3-difluoro-5-(5-methyl-2-pyrimidin-2-yl-7,8-dihydro-5H-pyrido[4,3-d]pyrimidin-6-yl)phenoxy]propyl]carbamate;
6-[3,4-difluoro-5-[2-(1-methylsulfonylazetidin-3-yl)ethoxy]phenyl]-5-methyl-2-pyrimidin-2-yl-7,8-dihydro-5H-pyrido[4,3-d]pyrimidine;
6-[3,4-difluoro-5-(tetrahydrofuran-2-ylmethoxy)phenyl]-(5R/S)-methyl-2-pyrimidin-2-yl-7,8-dihydro-5H-pyrido[4,3-d]pyrimidine;
6-(6-chloro-4-methoxy-2-pyridyl)-5-methyl-2-(2-pyridyl)-7,8-dihydro-5H-pyrido[4,3-d]pyrimidine;
6-(6-fluoro-4-methoxy-2-pyridyl)-5-methyl-2-pyrimidin-2-yl-7,8-dihydro-5H-pyrido[4,3-d]pyrimidine;
6-(2-fluoro-6-methoxy-4-pyridyl)-5-methyl-2-pyrimidin-2-yl-7,8-dihydro-5H-pyrido[4,3-d]pyrimidine;
(−)-6-(2-chloro-5-fluoro-3-methoxy-phenyl)-5-methyl-2-pyrimidin-2-yl-7,8-dihydro-5H-pyrido[4,3-d]pyrimidine;
(−)-6-(6-fluoro-4-methoxy-2-pyridyl)-5-methyl-2-pyrimidin-2-yl-7,8-dihydro-5H-pyrido[4,3-d]pyrimidine;
6-(4-chloro-6-methoxy-2-pyridyl)-5-methyl-2-pyrimidin-2-yl-7,8-dihydro-5H-pyrido[4,3-d]pyrimidine;
6-(4-fluoro-6-methoxy-2-pyridyl)-5-methyl-2-pyrimidin-2-yl-7,8-dihydro-5H-pyrido[4,3-d]pyrimidine;
6-[3-(2,2-difluoroethoxy)-5-fluoro-phenyl]-5-methyl-2-pyrimidin-2-yl-7,8-dihydro-5H-pyrido[4,3-d]pyrimidine;
6-[3-(cyclopropylmethoxy)-5-fluoro-phenyl]-5-methyl-2-pyrimidin-2-yl-7,8-dihydro-5H-pyrido[4,3-d]pyrimidine;
(−)-6-(5-chloro-6-fluoro-4-methoxy-2-pyridyl)-5-methyl-2-pyrimidin-2-yl-7,8-dihydro-5H-pyrido[4,3-d]pyrimidine;
6-[6-(2,2-difluoroethoxy)-4-fluoro-2-pyridyl]-5-methyl-2-pyrimidin-2-yl-7,8-dihydro-5H-pyrido[4,3-d]pyrimidine;
6-[4-(2,2-difluoroethoxy)-6-fluoro-2-pyridyl]-5-methyl-2-pyrimidin-2-yl-7,8-dihydro-5H-pyrido[4,3-d]pyrimidine;
6-[6-fluoro-4-(tetrahydropyran-4-ylmethoxy)-2-pyridyl]-5-methyl-2-pyrimidin-2-yl-7,8-dihydro-5H-pyrido[4,3-d]pyrimidine;
6-[6-fluoro-4-(tetrahydrofuran-3-ylmethoxy)-2-pyridyl]-5-methyl-2-pyrimidin-2-yl-7,8-dihydro-5H-pyrido[4,3-d]pyrimidine;
(−)-7-[[2-fluoro-6-[5-methyl-2-pyrimidin-2-yl-7,8-dihydro-5H-pyrido[4,3-d]pyrimidin-6-yl]-4-pyridyl]oxy]heptanamide;
(−)-4-[3-[[2-fluoro-6-[5-methyl-2-pyrimidin-2-yl-7,8-dihydro-5H-pyrido[4,3-d]pyrimidin-6-yl]-4-pyridyl]oxy]propyl]morpholin-3-one;
2-fluoro-N,N-dimethyl-6-[5-methyl-2-pyrimidin-2-yl-7,8-dihydro-5H-pyrido[4,3-d]pyrimidin-6-yl]pyridin-4-amine;
(−)-6-(6-fluoro-4-pyrrolidin-1-yl-2-pyridyl)-5-methyl-2-pyrimidin-2-yl-7,8-dihydro-5H-pyrido[4,3-d]pyrimidine;
(−)-2-fluoro-N-methyl-6-[5-methyl-2-pyrimidin-2-yl-7,8-dihydro-5H-pyrido[4,3-d]pyrimidin-6-yl]pyridin-4-amine;
(−)-2-fluoro-N,N-dimethyl-6-[5-methyl-2-pyrimidin-2-yl-7,8-dihydro-5H-pyrido[4,3-d]pyrimidin-6-yl]pyridin-4-amine;
4-[4-fluoro-6-(5-methyl-2-pyrimidin-2-yl-7,8-dihydro-5H-pyrido[4,3-d]pyrimidin-6-yl)-2-pyridyl]piperazin-2-one;
4-[2-fluoro-6-(5-methyl-2-pyrimidin-2-yl-7,8-dihydro-5H-pyrido[4,3-d]pyrimidin-6-yl)-4-pyridyl]piperazin-2-one; and
(−)-4-[4-fluoro-6-(5-methyl-2-pyrimidin-2-yl-7,8-dihydro-5H-pyrido[4,3-d]pyrimidin-6-yl)-2-pyridyl]piperazin-2-one;

or a pharmaceutically acceptable salt, enantiomer, or diastereomer thereof.

24. A process for the preparation of a compound of formula I according to claim 1, or a pharmaceutically acceptable salt, enantiomer, or diastereomer thereof, comprising coupling of a compound of formula (A)

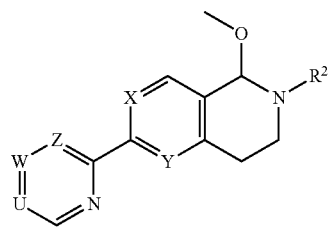

(A)

with a compound of formula (B)

R¹M                                    (B)

in the presence of a Lewis acid;
wherein M is H, Mg, Zn or Na.

25. A pharmaceutical composition comprising an effective amount of a compound according to claim 1, or a pharmaceutically acceptable salt, enantiomer, or diastereomer thereof, and a therapeutically inert carrier.

26. A method for the treatment of HBV infection in a patient in need thereof, which method comprises administering to the patient an effective amount of a compound according to claim 1, or a pharmaceutically acceptable salt, enantiomer, or diastereomer thereof.

27. A process for the preparation of a first compound of formula I according to claim 1, or a pharmaceutically acceptable salt, enantiomer, or diastereomer thereof, comprising coupling of a second compound of formula I of formula (C)

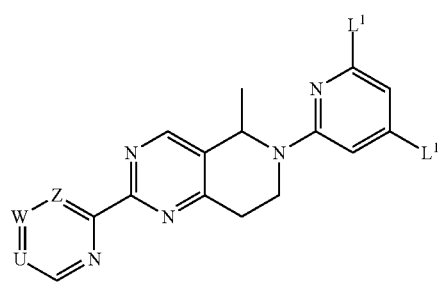

(C)

with a compound of formula (D)

NHR⁹R¹⁰                                (D)

in the presence of a base;
wherein L¹ is F, Cl or Br.

28. A process for the preparation of a compound of formula I according to claim 1, or a pharmaceutically acceptable salt, enantiomer, or diastereomer thereof, comprising coupling of a compound of formula (E)

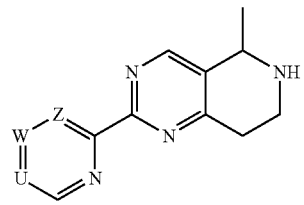

(E)

with a compound of formula (F)

R²-L²                                  (F);

wherein L² is F, Cl or Br.

29. A compound which is 6-(3,4-difluoro-5-methoxy-phenyl)-5-methyl-2-pyrimidin-2-yl-7,8-dihydro-5H-pyrido[4,3-d]pyrimidine, or a pharmaceutically acceptable salt thereof.

30. A compound which is (−)-6-(3,4-difluoro-5-methoxy-phenyl)-5-methyl-2-pyrimidin-2-yl-7,8-dihydro-5H-pyrido[4,3-d]pyrimidine, or a pharmaceutically acceptable salt thereof.

31. A compound which is (+)-6-(3,4-difluoro-5-methoxy-phenyl)-5-methyl-2-pyrimidin-2-yl-7,8-dihydro-5H-pyrido[4,3-d]pyrimidine, or a pharmaceutically acceptable salt thereof.

32. A compound which is 6-(3-chloro-4-fluoro-5-methoxy-phenyl)-5-methyl-2-pyrimidin-2-yl-7,8-dihydro-5H-pyrido[4,3-d]pyrimidine, or a pharmaceutically acceptable salt thereof.

33. A compound which is (+)-6-(3-chloro-4-fluoro-5-methoxy-phenyl)-5-methyl-2-pyrimidin-2-yl-7,8-dihydro-5H-pyrido[4,3-d]pyrimidine, or a pharmaceutically acceptable salt thereof.

34. A compound which is (−)-6-(3-chloro-4-fluoro-5-methoxy-phenyl)-5-methyl-2-pyrimidin-2-yl-7,8-dihydro-5H-pyrido[4,3-d]pyrimidine, or a pharmaceutically acceptable salt thereof.

35. A compound which is (−)-6-[2,3-difluoro-5-[5-methyl-2-pyrimidin-2-yl-7,8-dihydro-5H-pyrido[4,3-d]pyrimidin-6-yl]phenoxy]hexan-1-amine, or a pharmaceutically acceptable salt thereof.

36. A compound which is (+)-6-[2,3-difluoro-5-[5-methyl-2-pyrimidin-2-yl-7,8-dihydro-5H-pyrido[4,3-d]pyrimidin-6-yl]phenoxy]hexan-1-amine, or a pharmaceutically acceptable salt thereof.

37. A compound which is 6-(3-fluoro-5-methoxy-phenyl)-5-methyl-2-pyrimidin-2-yl-7,8-dihydro-5H-pyrido[4,3-d]pyrimidine, or a pharmaceutically acceptable salt thereof.

38. A compound which is (−)-6-(3-fluoro-5-methoxy-phenyl)-5-methyl-2-pyrimidin-2-yl-7,8-dihydro-5H-pyrido[4,3-d]pyrimidine, or a pharmaceutically acceptable salt thereof.

39. A compound which is (+)-6-(3-fluoro-5-methoxy-phenyl)-5-methyl-2-pyrimidin-2-yl-7,8-dihydro-5H-pyrido[4,3-d]pyrimidine, or a pharmaceutically acceptable salt thereof.

40. A compound which is 6-(6-fluoro-4-methoxy-2-pyridyl)-5-methyl-2-pyrimidin-2-yl-7,8-dihydro-5H-pyrido[4,3-d]pyrimidine, or a pharmaceutically acceptable salt thereof.

41. A compound which is (−)-6-(6-fluoro-4-methoxy-2-pyridyl)-5-methyl-2-pyrimidin-2-yl-7,8-dihydro-5H-pyrido[4,3-d]pyrimidine, or a pharmaceutically acceptable salt thereof.

42. A compound which is (+)-6-(6-fluoro-4-methoxy-2-pyridyl)-5-methyl-2-pyrimidin-2-yl-7,8-dihydro-5H-pyrido[4,3-d]pyrimidine, or a pharmaceutically acceptable salt thereof.

43. A compound which is 6-[3-(2,2-difluoroethoxy)-5-fluoro-phenyl]-5-methyl-2-pyrimidin-2-yl-7,8-dihydro-5H-pyrido[4,3-d]pyrimidine, or a pharmaceutically acceptable salt thereof.

44. A compound which is 6-[4-(cyclopropylmethoxy)-6-fluoro-2-pyridyl]-5-methyl-2-pyrimidin-2-yl-7,8-dihydro-5H-pyrido[4,3-d]pyrimidine, or a pharmaceutically acceptable salt thereof.

45. A compound which is (−)-6-(6-fluoro-4-pyrrolidin-1-yl-2-pyridyl)-5-methyl-2-pyrimidin-2-yl-7,8-dihydro-5H-pyrido[4,3-d]pyrimidine, or a pharmaceutically acceptable salt thereof.

46. A compound which is (+)-6-(6-fluoro-4-pyrrolidin-1-yl-2-pyridyl)-5-methyl-2-pyrimidin-2-yl-7,8-dihydro-5H-pyrido[4,3-d]pyrimidine, or a pharmaceutically acceptable salt thereof.

* * * * *